United States Patent
Jin

(10) Patent No.: US 12,150,378 B2
(45) Date of Patent: Nov. 19, 2024

(54) LUMINESCENCE DEVICE AND POLYCYCLIC COMPOUND FOR LUMINESCENCE DEVICE

(71) Applicant: Samsung Display Co., LTD., Yongin-si (KR)

(72) Inventor: XiuLan Jin, Yokohama (JP)

(73) Assignee: SAMSUNG DISPLAY CO., LTD., Gyeonggi-Do (KR)

( * ) Notice: Subject to any disclaimer, the term of this patent is extended or adjusted under 35 U.S.C. 154(b) by 685 days.

(21) Appl. No.: 17/062,817

(22) Filed: Oct. 5, 2020

(65) Prior Publication Data

US 2021/0104676 A1  Apr. 8, 2021

(30) Foreign Application Priority Data

Oct. 7, 2019 (KR) .................. 10-2019-0123810
Sep. 29, 2020 (KR) .................. 10-2020-0126642

(51) Int. Cl.
*H01L 51/00* (2006.01)
*C07D 491/048* (2006.01)
(Continued)

(52) U.S. Cl.
CPC ....... *H10K 85/636* (2023.02); *C07D 491/048* (2013.01); *C07D 495/04* (2013.01);
(Continued)

(58) Field of Classification Search
None
See application file for complete search history.

(56) References Cited

U.S. PATENT DOCUMENTS 9,893,293 B2   2/2018   Sasaki et al.
10,115,907 B2  10/2018  Shin et al.
(Continued)

FOREIGN PATENT DOCUMENTS

CN   105655492 A   6/2016
CN   108774236 A   11/2018
(Continued)

OTHER PUBLICATIONS

Machine English translation of KR 10-2014-0046771. Mar. 15, 2023.*
(Continued)

*Primary Examiner* — Jay Yang
(74) *Attorney, Agent, or Firm* — CANTOR COLBURN LLP

(57) ABSTRACT

The present disclosure herein relates to a luminescence device including a polycyclic compound represented by Formula 1 in at least one functional layer and achieving a low driving voltage, high efficiency, and long life, and a polycyclic compound represented by Formula 1 below.

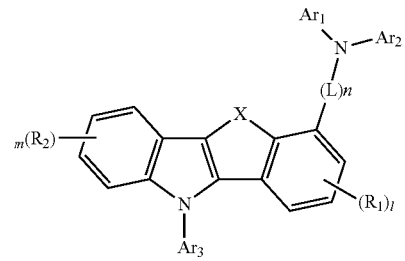

Formula 1

18 Claims, 2 Drawing Sheets

(51) Int. Cl.
*C07D 495/04* (2006.01)
*H10K 85/60* (2023.01)
*H10K 50/15* (2023.01)

(52) U.S. Cl.
CPC ........... *H10K 50/15* (2023.02); *H10K 85/657* (2023.02); *H10K 85/6574* (2023.02); *H10K 85/6576* (2023.02)

(56) References Cited

U.S. PATENT DOCUMENTS

| | | | |
|---|---|---|---|
| 2013/0200350 A1 | 8/2013 | Sawada et al. | |
| 2021/0104676 A1 | 4/2021 | Jin | |

FOREIGN PATENT DOCUMENTS

| | | | |
|---|---|---|---|
| EP | 3029752 | A2 | 6/2016 |
| JP | 2016111065 | A | 6/2016 |
| KR | 1020140046771 | A | 4/2014 |
| KR | 20150042386 | A | 4/2015 |
| KR | 1020150058625 | A | 5/2015 |
| KR | 1020150145131 | A | 12/2015 |
| KR | 1020150145463 | A | 12/2015 |
| KR | 1020160082209 | A | 7/2016 |
| KR | 20160122974 | A | 10/2016 |
| KR | 1020170091470 | A | 8/2017 |
| KR | 1020190011463 | A | 2/2019 |
| WO | 2012035934 | A1 | 3/2012 |
| WO | 2014058183 | A1 | 4/2014 |
| WO | 2019022435 | A1 | 1/2019 |

OTHER PUBLICATIONS

Machine English translation of KR 10-2016-0122974. Mar. 15, 2023.*
General synthesis, structure, and optical properties of benzothiophene-fused benzoheteroles containing Group 15 and 16 elements, Tetrahedron 72 (2016) 8085-8090, Aichi Gakuin University.
Extended European Search Report dated Jan. 22, 2021, issued from the European Patent Office in respect of European Patent Application No. 20193076 which corresponds to the U.S. application.
Examination report Aug. 5, 2023 from the Chinese Patent Office in respect of the Chinese Patent Application.

* cited by examiner

LUMINESCENCE DEVICE AND POLYCYCLIC COMPOUND FOR LUMINESCENCE DEVICE

CROSS-REFERENCE TO RELATED APPLICATIONS

This U.S. non-provisional patent application claims priority under 35 U.S.C. § 119 to Korean Patent Application No. 10-2019-0123810, filed on Oct. 7, 2019, and Korean Patent Application No. 10-2020-0126642, filed on Sep. 29, 2020, the entire contents of which are hereby incorporated by reference.

BACKGROUND

The present disclosure relates to a luminescence device and a polycyclic compound used therein.

There has been an increased interest in the development of an electroluminescence display as an image display. The electroluminescence display may include an organic electroluminescence display as an example. The organic electroluminescence display is different from a liquid crystal display and is a self-luminescent display in which a light-emitting material included in an emission layer emits light to produce a display by recombining holes and electrons injected from a first electrode and a second electrode in an emission layer.

In the application of a luminescence device to a display, an increase of the efficiency and life of the luminescence device is desirable. Therefore, there is a need for materials with improved properties such as driving voltage and emission efficiency for a luminescence device.

SUMMARY

The present disclosure provides a luminescence device having a low driving voltage, high efficiency, and long life.

The present disclosure also provides a polycyclic compound which may be applied to a luminescence device to accomplish a low driving voltage, high efficiency, and long life.

A luminescence device according to an embodiment may include a first electrode, a second electrode disposed on the first electrode, and at least one functional layer disposed between the first electrode and the second electrode. The at least one functional layer may include a polycyclic compound represented by the following Formula 1:

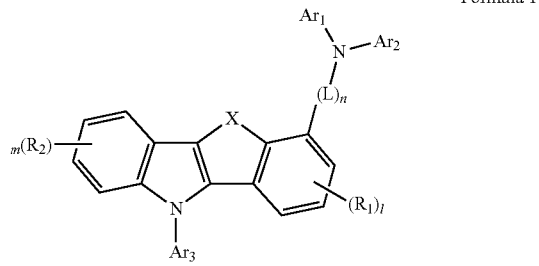

Formula 1

In Formula 1, X may be O, or S. R1 and R2 may each independently be a hydrogen atom, a deuterium atom, a halogen atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms. Ar1 to Ar3 may be each independently a substituted or unsubstituted aryl group of 6 to 30 ring carbon atoms, or a substituted or unsubstituted heteroaryl group of 2 to 30 ring carbon atoms. L may be a direct linkage, a substituted or unsubstituted arylene group of 6 to 30 ring carbon atoms, or a substituted or unsubstituted heteroarylene group of 2 to 30 ring carbon atoms. l may be an integer of 0 to 3. m may be an integer of 0 to 4. n may be an integer of 0 to 3.

In an embodiment, the at least one functional layer may include a hole transport region disposed on the first electrode, an emission layer disposed on the hole transport region, and an electron transport region disposed on the emission layer. The hole transport region may include the polycyclic compound.

In an embodiment, the hole transport region may further include a hole injection layer disposed on the first electrode, and a hole transport layer disposed between the hole injection layer and the emission layer. The hole transport layer may include the polycyclic compound.

In an embodiment, Formula 1 may include one acyclic amine.

In an embodiment, Formula 1 may be represented by the following Formula 1-1 or Formula 1-2:

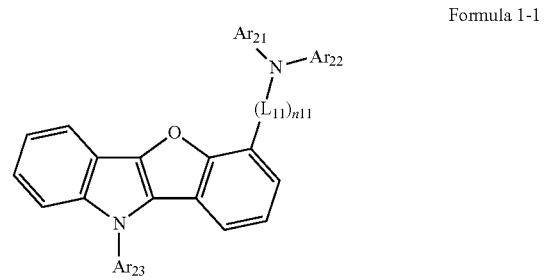

Formula 1-1

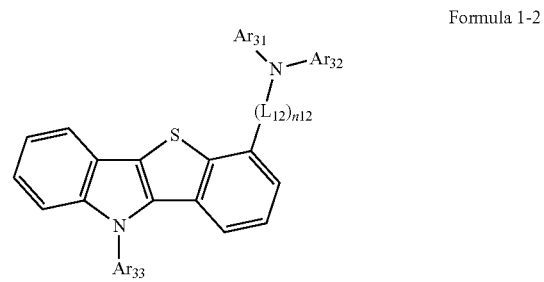

Formula 1-2

In Formula 1-1 and Formula 1-2, Ar21 to Ar23, and Ar31 to Ar33 may be each independently a substituted or unsubstituted aryl group of 6 to 30 ring carbon atoms, or a substituted or unsubstituted heteroaryl group of 2 to 30 ring carbon atoms. L11, and L12 may be each independently a direct linkage, a substituted or unsubstituted arylene group of 6 to 30 ring carbon atoms, or a substituted or unsubstituted heteroarylene group of 2 to 30 ring carbon atoms. n11, and n12 may be each independently an integer of 0 to 3.

In an embodiment, Formula 1 may be represented by the following Formula 1-3:

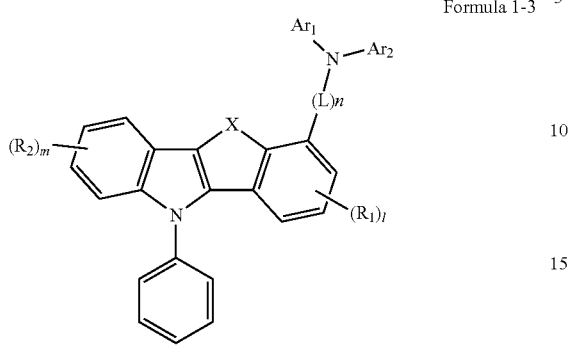

Formula 1-3

In Formula 1-3, X, R1, R2, Ar1, Ar2, L, and l to n may be the same as defined in Formula 1.

In an embodiment, Formula 1 may be represented by the following Formula 1-4:

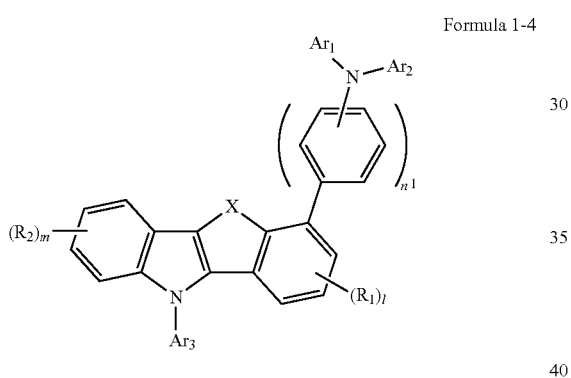

Formula 1-4

In Formula 1-4, n1 may be 0 or 1. X, R1, R2, Ar1 to Ar3, l, and m may be the same as defined in Formula 1.

In an embodiment, Ar1 and Ar2 may be each independently represented by the following Formula 2:

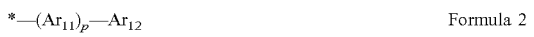

Formula 2

In Formula 2, Ar11 may be a substituted or unsubstituted phenylene group, a substituted or unsubstituted divalent biphenyl group, a substituted or unsubstituted divalent terphenyl group, a substituted or unsubstituted phenanthrylene group, a substituted or unsubstituted fluorenylene group, a substituted or unsubstituted naphthylene group, a substituted or unsubstituted carbazolylene group, a substituted or unsubstituted dibenzofuranylene group, or a substituted or unsubstituted dibenzothiophenylene group. Ar12 may be a substituted or unsubstituted phenyl group, a substituted or unsubstituted biphenyl group, a substituted or unsubstituted terphenyl group, a substituted or unsubstituted phenanthryl group, a substituted or unsubstituted fluorenyl group, a substituted or unsubstituted naphthyl group, a substituted or unsubstituted carbazolyl group, a substituted or unsubstituted dibenzofuranyl group, or a substituted or unsubstituted dibenzothiophenyl group. p may be 0 or 1.

In an embodiment, Ar1 and Ar2 may be each independently represented by the following 1-1 to 1-10:

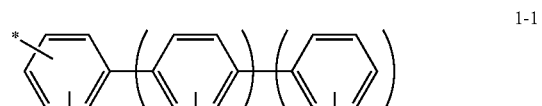

1-1

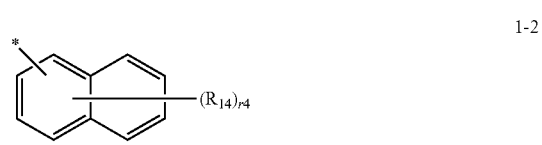

1-2

1-3

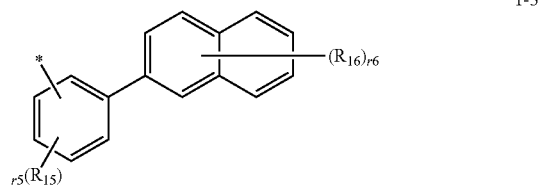

1-4

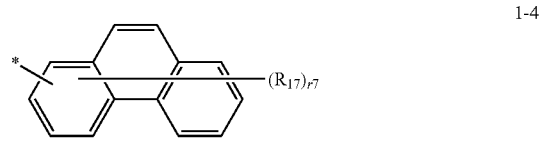

1-5

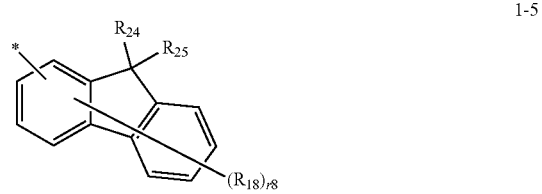

1-6

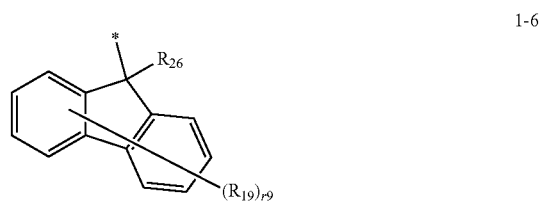

1-7

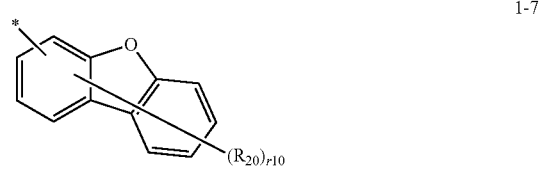

1-8

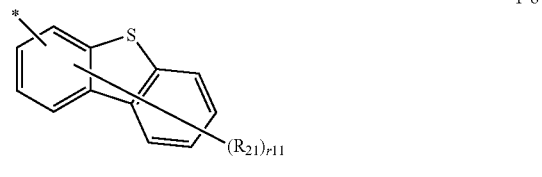

1-9

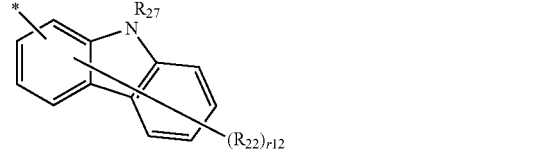

-continued 1-10

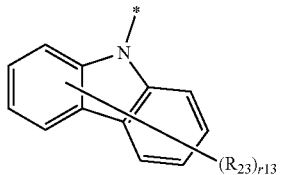

In 1-1 to 1-10 above, R11 to R27 may be each independently a hydrogen atom, a deuterium atom, a halogen atom, a substituted or unsubstituted alkyl group of 1 to 20 carbon atoms a substituted or unsubstituted aryl group of 6 to 30 ring carbon atoms, or a substituted or unsubstituted heteroaryl group of 2 to 30 ring carbon atoms. r1, r2, and r5 may be each independently an integer of 0 to 4. r3 may be an integer of 0 to 5. r4, r6, r8, and r10 to r12 may be each independently an integer of 0 to 7. r7 may be an integer of 0 to 9. r9 and r13 may be each independently an integer of 0 to 8. q1 and q2 may be each independently 0 or 1.

In an embodiment, Formula 1 may be represented by the following Formula 1-5:

Formula 1-5

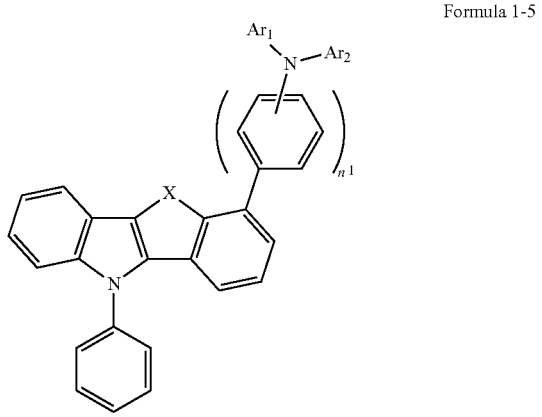

In Formula 1-5, n1 may be 0 or 1. X, Ar1, and Ar2 may be the same as defined in Formula 1.

According to an embodiment, a polycyclic compound represented by Formula 1 above may be provided.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1:
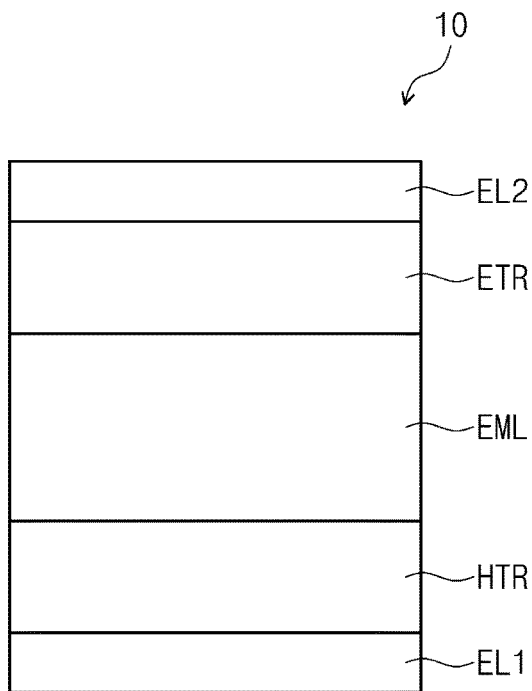
FIG. 1 is a cross-sectional view schematically illustrating a luminescence device according to an exemplary embodiment of the inventive concept.

The inventive concept may have various modifications and may be embodied in different forms, and example embodiments will be explained in detail with reference to the accompany drawings. The inventive concept may, however, be embodied in different forms and should not be construed as limited to the embodiments set forth herein. Rather, all modifications, equivalents, and substituents which are included in the spirit and technical scope of the inventive concept should be included in the inventive concept.

Like reference numerals refer to like elements throughout. In the drawings, the dimensions of structures are exaggerated for clarity of illustration. It will be understood that, although the terms first, second, etc. may be used herein to describe various elements, these elements should not be limited by these terms. These terms are only used to distinguish one element from another element. Thus, a first element could be termed a second element without departing from the teachings of the present invention. Similarly, a second element could be termed a first element. As used herein, the singular forms are intended to include the plural forms as well, unless the context clearly indicates otherwise.

It will be further understood that the terms "comprises" and/or "comprising," when used in this specification, specify the presence of stated features, numerals, steps, operations, elements, parts, or the combination thereof, but do not preclude the presence or addition of one or more other features, numerals, steps, operations, elements, parts, or the combination thereof.

It will also be understood that when a layer, a film, a region, a plate, etc. is referred to as being "on" or "above" another part, it can be "directly on" the other part, or intervening layers may also be present. On the contrary, it will also be understood that when a layer, a film, a region, a plate, etc. is referred to as being "under" or "below" another part, it can be "directly under" the other part, or intervening layers may also be present. Also, when an element is referred to as being disposed "on" another element, it can be disposed under the other element.

In the description, a substituent of a substituted group is at least one of a deuterium atom, a halogen atom, a cyano group, a nitro group, an amino group, a silyl group, an alkoxy group, an aryloxy group, an alkylthio group, an arylthio group, a sulfinyl group, a sulfonyl group, a carbonyl group, a boron group, a phosphine oxide group, a phosphine sulfide group, an alkyl group, an alkenyl group, an alkoxy group, a hydrocarbon ring group, an aryl group, and a heterocyclic group. In addition, each of the substituents may be substituted or unsubstituted. For example, a biphenyl group may be interpreted as an aryl group or a phenyl group substituted with a phenyl group.

In the description, the term "adjacent group" means a pair of substituent groups where the first substituent is connected to an atom that is directly connected to another atom substituted with the second substituent, a pair of substituent groups connected to the same atom and different from each other, or a substituent sterically positioned at the nearest position to a corresponding substituent. For example, in 1,2-dimethylbenzene, two methyl groups may be interpreted as "adjacent groups" to each other, and in 1,1-diethylcyclopentane, two ethyl groups may be interpreted as "adjacent groups" to each other.

In the description, the halogen atom may be a fluorine atom, a chlorine atom, a bromine atom or an iodine atom.

In the description, the alkyl may be a linear, branched or cyclic type. The carbon number of the alkyl may be 1 to 50, 1 to 30, 1 to 20, 1 to 10, or 1 to 6. Examples of the alkyl may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the description, the hydrocarbon ring group means an optional functional group or substituent derived from an aliphatic hydrocarbon ring. The hydrocarbon ring group may be a saturated hydrocarbon ring group of 5 to 20 ring carbon atoms.

In the description, the aryl group means an optional functional group or substituent derived from an aromatic hydrocarbon ring. The aryl group may be a monocyclic aryl group or a polycyclic aryl group. The ring carbon number in the aryl group may be 6 to 30, 6 to 20, or 6 to 15. Examples of the aryl group may include phenyl, naphthyl, fluorenyl, anthracenyl, phenanthryl, biphenyl, terphenyl, quaterphenyl, quinquephenyl, sexiphenyl, triphenylenyl, pyrenyl, benzofluoranthenyl, chrysenyl, etc., without limitation.

In the description, the fluorenyl group may be substituted, and two substituents may be combined with each other to form a spiro structure. Examples of a substituted fluorenyl group are as follows. However, an embodiment of the inventive concept is not limited thereto.

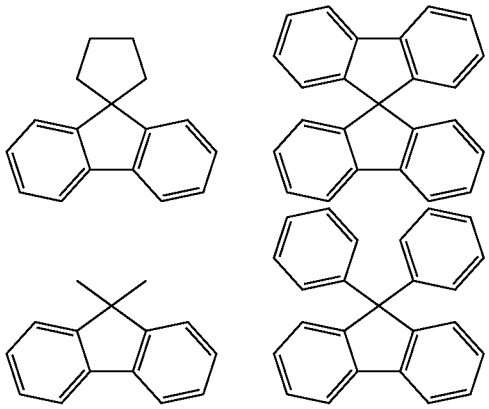

In the description, the heterocyclic group may include one or more among B, O, N, P, Si, Se, Ge, and S as heteroatoms. If the heterocyclic group includes two or more heteroatoms, two or more heteroatoms may be the same or different. The heterocyclic group may be a monocyclic heterocyclic group or a polycyclic heterocyclic group, and has a concept including a heteroaryl group. The ring carbon number of the heteroaryl group may be 2 to 30, 2 to 20, or 2 to 10.

In the description, the aliphatic heterocyclic group may include one or more among B, O, N, P, Si, Se, Ge, and S as heteroatoms. The ring carbon of the aliphatic heterocyclic group may be 2 to 30, 2 to 20, or 2 to 10. Examples of the aliphatic heterocyclic group may include an oxirane group, a thiirane group, a pyrrolidine group, a piperidine group, a tetrahydrofuran group, a tetrahydrothiophene group, a thiane group, a tetrahydropyran group, a 1,4-dioxane group, etc., without limitation.

In the description, the heteroaryl group may include one or more among B, O, N, P, Si, Se, Ge, and S as heteroatoms. If the heteroaryl group includes two or more heteroatoms, two or more heteroatoms may be the same or different. The heteroaryl group may be a monocyclic heteroaryl group or polycyclic heteroaryl group. The carbon number for forming a ring of the heteroaryl group may be 2 to 30, 2 to 20, or 2 to 10. Examples of the heteroaryl group may include thiophene, furan, pyrrole, imidazole, thiazole, oxazole, oxadiazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuran, phenanthroline, isooxazole, oxadiazole, thiadiazole, phenothiazine, dibenzosilole, dibenzofuran, etc., without limitation.

In the description, the aryl group may be applied to the arylene group except that the arylene group is a divalent group. The explanation on the heteroaryl group may be applied to the heteroarylene group except that the heteroarylene group is a divalent group.

In the description, the alkenyl group may be a linear chain or a branched chain. The carbon number is not specifically limited but may be 2 to 30, 2 to 20, or 2 to 10. Examples of the alkenyl group may include a vinyl group, a 1-butenyl group, a 1-pentenyl group, a 1,3-butadienyl aryl group, a styrenyl group, a styrylvinyl group, etc., without limitation.

In the description, the alkoxy group may be a linear, branched or cyclic chain. The carbon number of the alkoxy group is not specifically limited but may be, for example, 1 to 20 or 1 to 10. Examples of the alkoxy group may include methoxy, ethoxy, n-propoxy, isopropoxy, butoxy, pentyloxy, hexyloxy, octyloxy, nonyloxy, decyloxy, etc. However, an embodiment of the inventive concept is not limited thereto.

In the description, the carbon number for forming a ring of the aryl oxy group is not specifically limited, bur for example, may be 6 to 30, 6 to 20, or 6 to 15.

In the description, the alkylthio group may be a linear, branched or cyclic chain. The carbon number of the alkylthio group is not specifically limited but may be, for example, 1 to 20 or 1 to 10. Examples of the alkylthio group may include —S-methyl, —S-ethyl, —S-n-propyl, —S-isopropyl, and the like. However, an embodiment of the inventive concept is not limited thereto.

In the description, the carbon number for forming a ring of the aryl thio group is not specifically limited, bur for example, may be 6 to 30, 6 to 20, or 6 to 15.

In the description, the carbon number of the amine group is not specifically limited, but may be 1 to 30. The amine group may include an alkyl amine group and an aryl amine group. Examples of the amine group include a methylamine group, a dimethylamine group, a phenylamine group, a diphenylamine group, a naphthylamine group, a 9-methyl-anthracenylamine group, a triphenylamine group, etc., without limitation.

The aryl amine group is defined as an amine group in which at least one of an aryl group or a heteroaryl group is substituted at a nitrogen atom.

In the description, the direct linkage may mean a single bond.

Meanwhile, in the description, "*⎯⎯" means a connected position.

FIG. 1 is a cross-sectional view schematically showing a luminescence device 10 according to an embodiment of the inventive concept. The luminescence device 10 according to an embodiment may include a first electrode EL1, a hole transport region HTR, an emission layer EML, an electron transport region ETR, and a second electrode EL2 stacked in order. The luminescence device 10 may be an organic electroluminescence device including an organic light-emitting material, but an embodiment of the inventive concept is not limited thereto. Hereinafter, the explanation will be based on that the luminescence device 10 is an organic electroluminescence device.

FIGS. 1 to 4 are cross-sectional views schematically showing luminescence devices 10 according to exemplary embodiments of the inventive concept. Referring to FIGS. 1 to 4, in a luminescence device 10 according to an embodiment, a first electrode EL1 and a second electrode EL2 are oppositely disposed, and between the first electrode EL1 and the second electrode EL2, an emission layer EML may be disposed.

In addition, the luminescence device 10 of an embodiment further includes a plurality of functional layers between the first electrode EL1 and the second electrode EL2 in addition to the emission layer EML. The plurality of the functional layers may include a hole transport region HTR and an electron transport region ETR. That is, the luminescence device 10 of an embodiment may include a first electrode EL1, a hole transport region HTR, an emission layer EML, an electron transport region ETR, and a second electrode, stacked in order. In addition, the luminescence device 10 of an embodiment may include a capping layer CPL which is disposed on the second electrode EL2.

The luminescence device 10 of an embodiment may include a compound of an embodiment, which will be explained later, in the emission layer EML which is disposed between the first electrode EL1 and the second electrode EL2. However, an embodiment of the inventive concept is not limited thereto, and the luminescence device 10 of an embodiment may include a polycyclic compound of an embodiment, which will be explained later, in the hole transport region HTR or the electron transport region ETR, which are functional layers disposed between the first electrode EL1 and the second electrode EL2, or include a polycyclic compound of an embodiment, which will be explained later, in the capping layer CPL disposed on the second electrode EL2, in addition to the emission layer EML.

Figure 2:
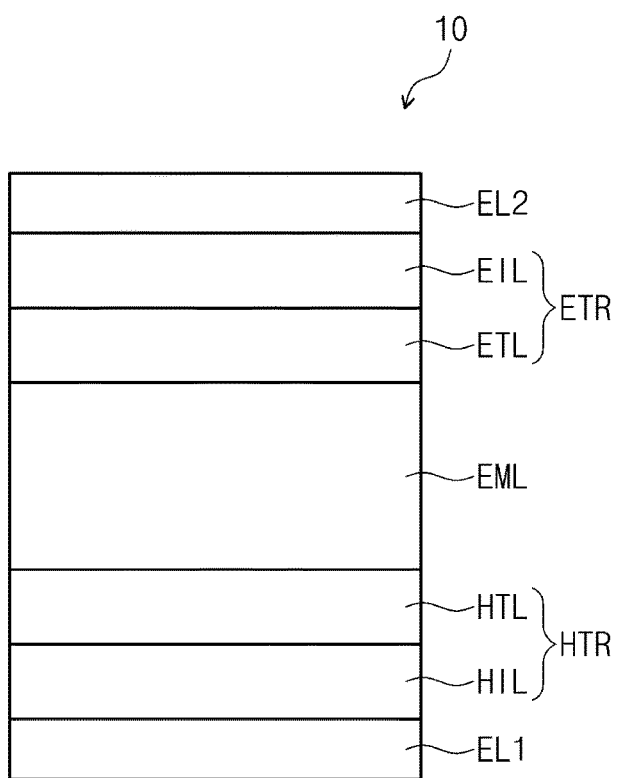
FIG. 2 is a cross-sectional view schematically illustrating a luminescence device according to an embodiment of the inventive concept.
Figure 3:
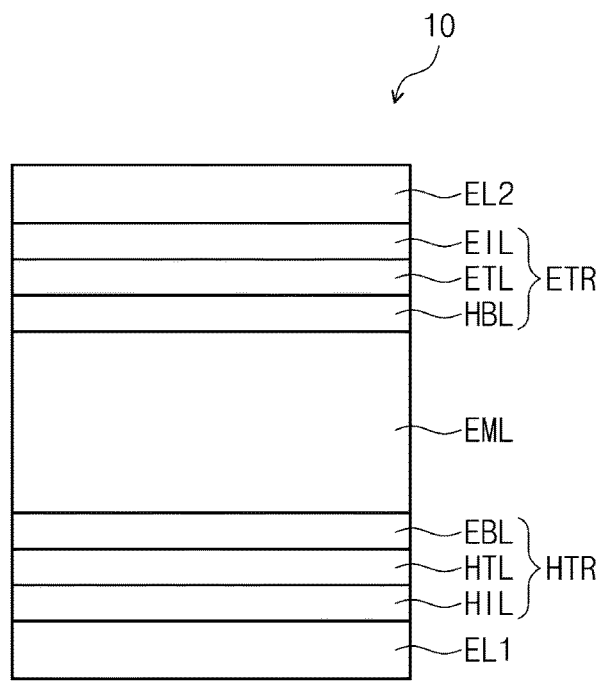
FIG. 3 is a cross-sectional view schematically illustrating a luminescence device according to an embodiment of the inventive concept.
Figure 4:
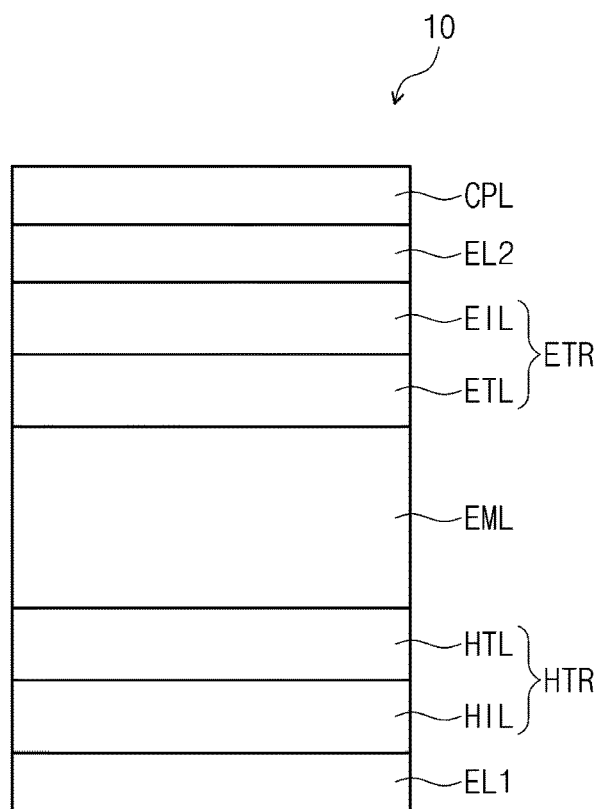
FIG. 4 is a cross-sectional view schematically illustrating a luminescence device according to an embodiment of the inventive concept.

Meanwhile, when compared with FIG. 1, FIG. 2 shows the cross-sectional view of a luminescence device 10 of an embodiment, wherein a hole transport region HTR includes a hole injection layer HIL and a hole transport layer HTL, and an electron transport region ETR includes an electron injection layer EIL and an electron transport layer ETL. In addition, when compared with FIG. 1, FIG. 3 shows the cross-sectional view of a luminescence device 10 of an embodiment, wherein a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. When compared with FIG. 2, FIG. 4 shows the cross-sectional view of a luminescence device 10 of an embodiment, including a capping layer CPL disposed on the second electrode EL2.

At least one functional layer may include a polycyclic compound represented by the following Formula 1:

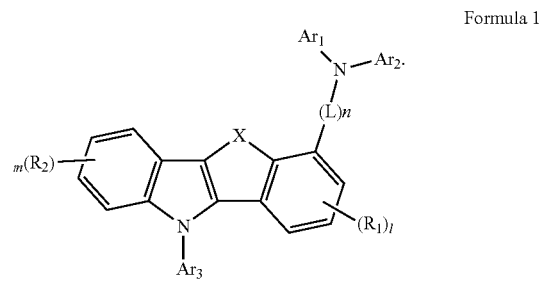

Formula 1

In Formula 1, X may be O, or S. $R_1$ and $R_2$ may be each independently a hydrogen atom, a deuterium atom, a halogen atom, an alkyl group, an aryl group, or a heteroaryl group. The alkyl group may be a substituted or unsubstituted alkyl group of 1 to 20 carbon atoms. The aryl group may be a substituted or unsubstituted aryl group of 6 to 30 ring carbon atoms. The heteroaryl group may be a substituted or unsubstituted heteroaryl group of 2 to 30 ring carbon atoms.

$Ar_1$ to $Ar_3$ may be each independently an aryl group, or a heteroaryl group. The aryl group may be a substituted or unsubstituted aryl group of 6 to 30 ring carbon atoms. The heteroaryl group may be a substituted or unsubstituted heteroaryl group of 2 to 30 ring carbon atoms.

For example, $Ar_3$ may be a substituted or unsubstituted phenyl group.

L may be a direct linkage, an arylene group, or a heteroarylene group. The arylene group may be a substituted or unsubstituted arylene group of 6 to 30 ring carbon atoms. The heteroarylene group may be a substituted or unsubstituted heteroarylene group of 2 to 30 ring carbon atoms. For example, L may be a substituted or unsubstituted phenylene group.

In case where $Ar_1$ to $Ar_3$, and L are substituted groups, they may be substituted with, for example, halogen atoms. The halogen atom may be, for example, a fluorine atom which has high inductive effect and small electron donor properties because of the resonance effect.

l may be an integer of 0 to 3. m may be an integer of 0 to 4. n may be an integer of 0 to 3. If l is an integer of 2 or more, a plurality of $R_1$ groups may be the same or different. If l is an integer of 2 or more, at least one $R_1$ may not be a hydrogen atom. If m is an integer of 2 or more, a plurality of $R_2$ groups may be the same or different. If m is an integer of 2 or more, at least one $R_2$ may not be a hydrogen atom. If n is an integer of 2 or more, a plurality of L groups may be the same or different. If n is an integer of 2 or more, at least one L may not be a direct linkage.

The polycyclic compound of an embodiment may include one acyclic amine. The polycyclic compound of an embodiment may not include a cyclic amine. That is, the polycyclic compound represented by Formula 1 may not include any acyclic amine excluding *—$NAr_1Ar_2$.

$Ar_1$ and $Ar_2$ may be each independently represented by the following Formula 2:

*—(Ar$_{11}$)$_p$—Ar$_{12}$   Formula 2

In Formula 2, $Ar_{11}$ may be a substituted or unsubstituted phenylene group, a substituted or unsubstituted divalent biphenyl group, a substituted or unsubstituted divalent terphenyl group, a substituted or unsubstituted phenanthrylene group, a substituted or unsubstituted fluorenylene group, a substituted or unsubstituted naphthylene group, a substituted or unsubstituted carbazolylene group, a substituted or unsubstituted dibenzofuranylene group, or a substituted or unsubstituted dibenzothiophenylene group.

$Ar_{12}$ may be a substituted or unsubstituted phenyl group, a substituted or unsubstituted biphenyl group, a substituted or unsubstituted terphenyl group, a substituted or unsubstituted phenanthryl group, a substituted or unsubstituted fluorenyl group, a substituted or unsubstituted naphthyl group, a substituted or unsubstituted carbazolyl group, a substituted or unsubstituted dibenzofuranyl group, or a substituted or unsubstituted dibenzothiophenyl group.

Further, p may be 0 or 1.

$Ar_1$ and $Ar_2$ may be each independently represented by the following 1-1 to 1-10:

1-1
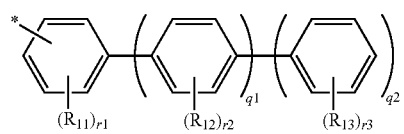

1-2
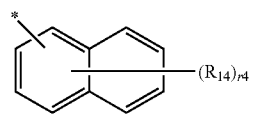

1-3
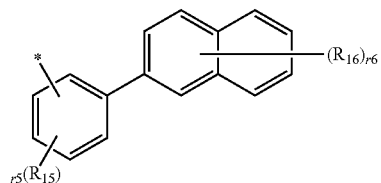

1-4
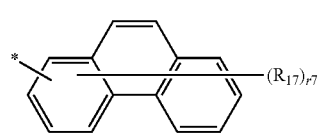

1-5
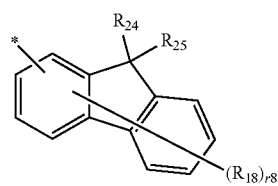

1-6
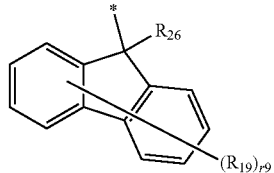

1-7
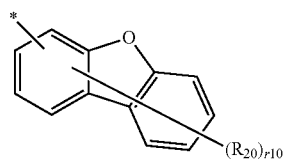

1-8
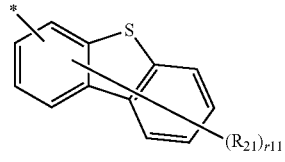

1-9
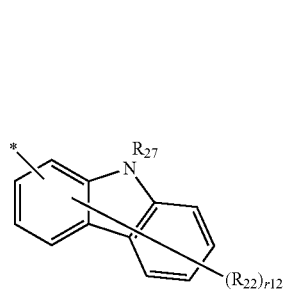

1-10
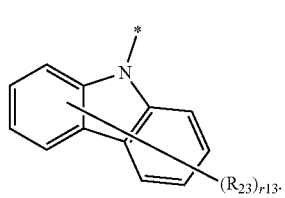

In 1-1 to 1-10 above, $R_{11}$ to $R_{27}$ may be each independently a hydrogen atom, a deuterium atom, an alkyl group, a halogen atom, an aryl group, or a heteroaryl group. The alkyl group may be a substituted or unsubstituted alkyl group of 1 to 20 carbon atoms. The aryl group may be a substituted or unsubstituted aryl group of 6 to 30 ring carbon atoms. The heteroaryl group may be a substituted or unsubstituted heteroaryl group of 2 to 30 ring carbon atoms. For example, $R_{11}$ to $R_{27}$ may be each independently a hydrogen atom, a halogen atom, or a substituted unsubstituted phenyl group.

Further, r1, r2, and r5 may be each independently an integer of 0 to 4; r3 may be an integer of 0 to 5. r4, r6, r8 and r0 to r12 may be each independently an integer of 0 to 7. r7 may be an integer of 0 to 9. r9 and r13 may be each independently an integer of 0 to 8. q1 and q2 may be each independently 0 or 1. For example, r1 to r13 may be each independently 0, or 1. Otherwise, all r1 to R13 may be 0.

If r1 is an integer of 2 or more, a plurality of Rn groups may be the same or different. The same explanation may be applied to r2 to r13.

Formula 1 may be represented by the following Formula 1-1 or Formula 1-2:

Formula 1-1

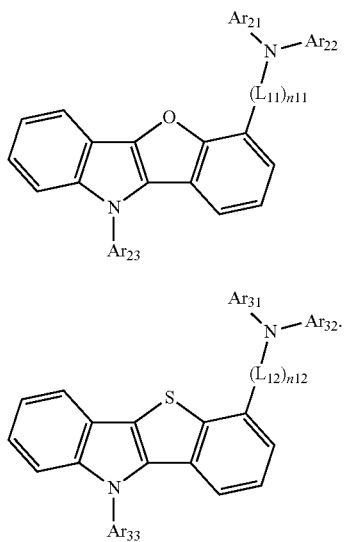

Formula 1-2

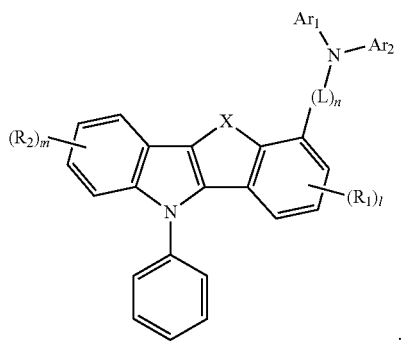

Formula 1-1 corresponds to Formula 1, wherein X, and l are embodied. Formula 1-2 corresponds to Formula 1, wherein X, and m are embodied.

$Ar_{21}$ to $Ar_{23}$, and $Ar_{31}$ to $Ar_{33}$ may be each independently an aryl group, or a heteroaryl group. The aryl group may be a substituted or unsubstituted aryl group of 6 to 30 ring carbon atoms. The heteroaryl group may be a substituted or unsubstituted heteroaryl group of 2 to 30 ring carbon atoms.

$L_{11}$, and $L_{12}$ may be each independently a direct linkage, an arylene group, or a heteroarylene group. The arylene group may be a substituted or unsubstituted arylene group of 6 to 30 ring carbon atoms. The heteroarylene group may be a substituted or unsubstituted heteroarylene group of 2 to 30 ring carbon atoms.

Further, n11, and n12 may be each independently an integer of 0 to 3.

Formula 1 may be represented by the following Formula 1-3:

Formula 1-3

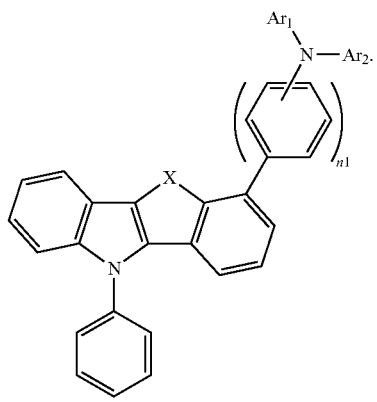

Formula 1-3 corresponds to Formula 1, wherein $Ar_3$ is an unsubstituted phenyl group. In Formula 1-3, X, $R_1$, $R_2$, $Ar_1$, $Ar_2$, L, and l to n may be the same as defined in Formula 1.

Formula 1 may be represented by the following Formula 1-4:

Formula 1-4

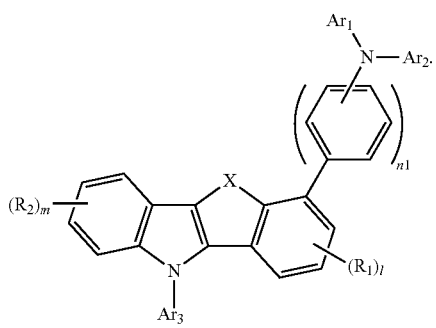

Formula 1-4 corresponds to Formula 1, wherein L is a direct linkage, or an unsubstituted phenylene group. In Formula 1-4, n1 may be 0 or 1. In Formula 1-4, X, $R_1$, $R_2$, $Ar_1$ to $Ar_3$, l, and m may be the same as defined in Formula 1.

Formula 1 may be represented by the following Formula 1-5:

Formula 1-5

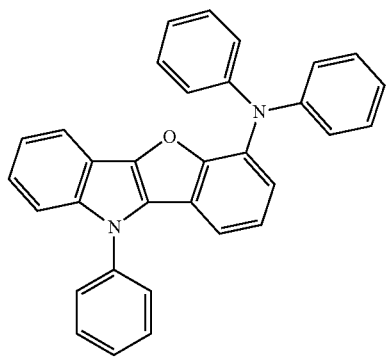

Formula 1-5 corresponds to Formula 1, wherein $Ar_3$ is an unsubstituted phenyl group, and L is a direct linkage, or an unsubstituted phenylene group. In Formula 1-5, n1 may be 0 or 1. X, $Ar_1$, and $Ar_2$ may be the same as defined in Formula 1.

The polycyclic compound of an embodiment may be any one among Compound Group 1 and Compound Group 2:

Compound Group 1

A1

A2
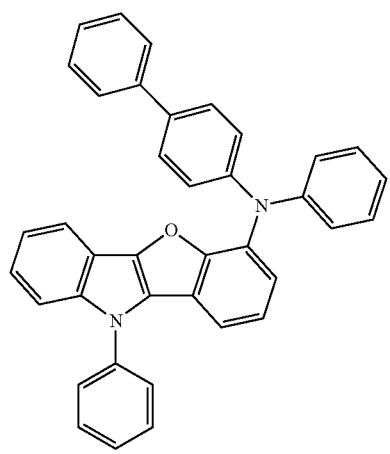
A3
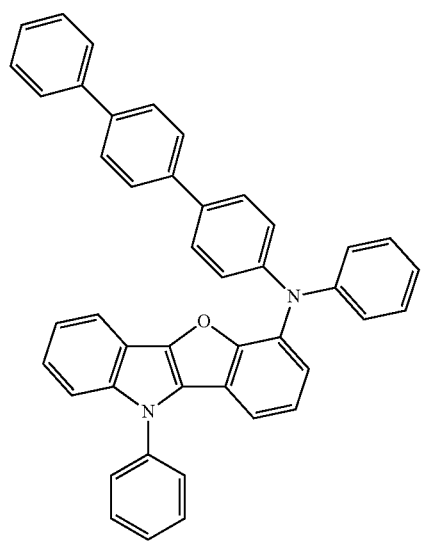
A4
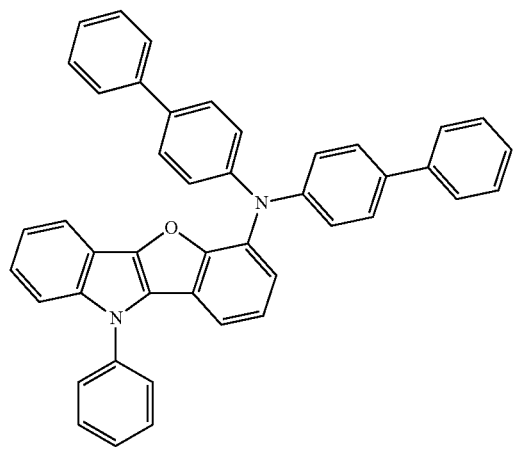
A5
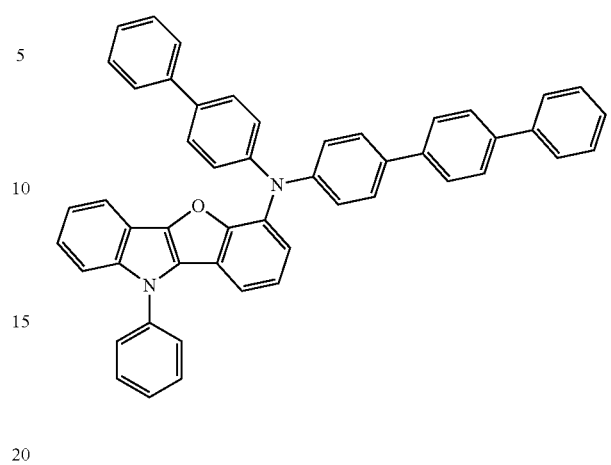
A6
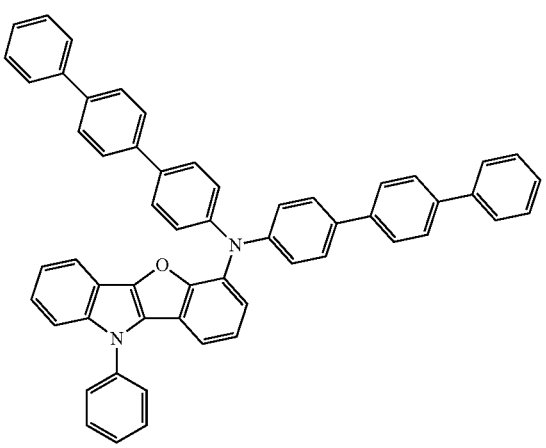
A7
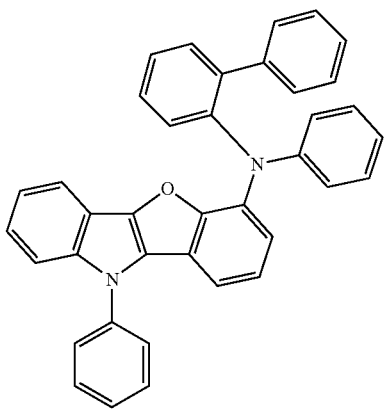

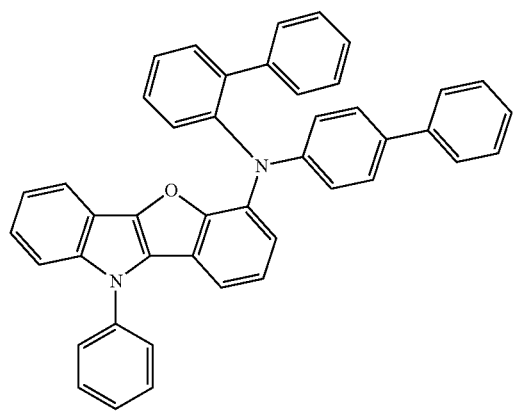
A8
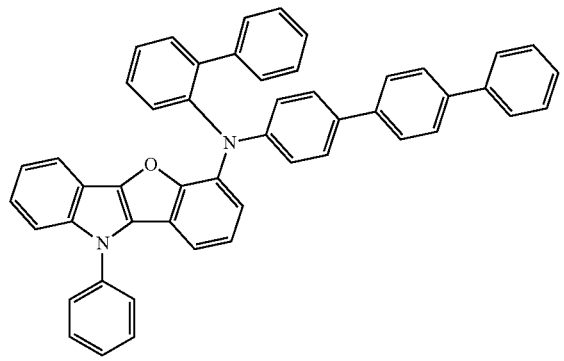
A9
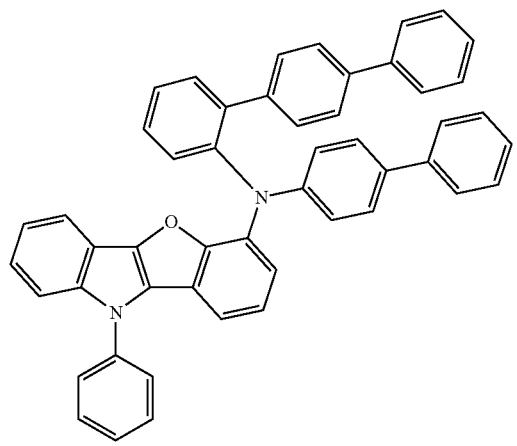
A10
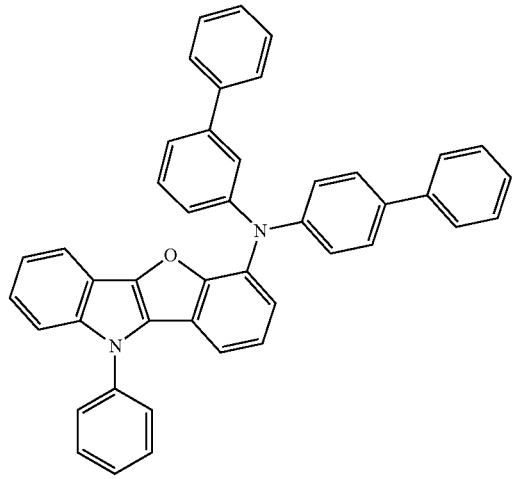
A11
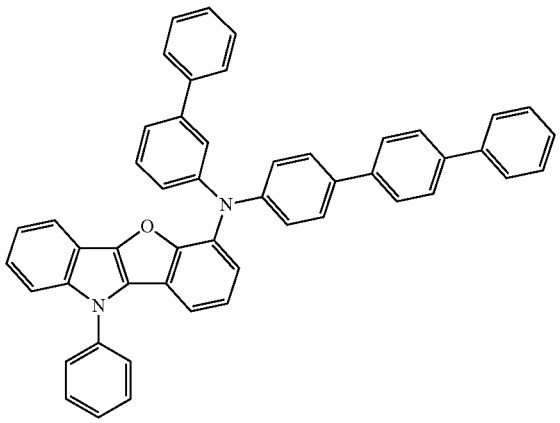
A12
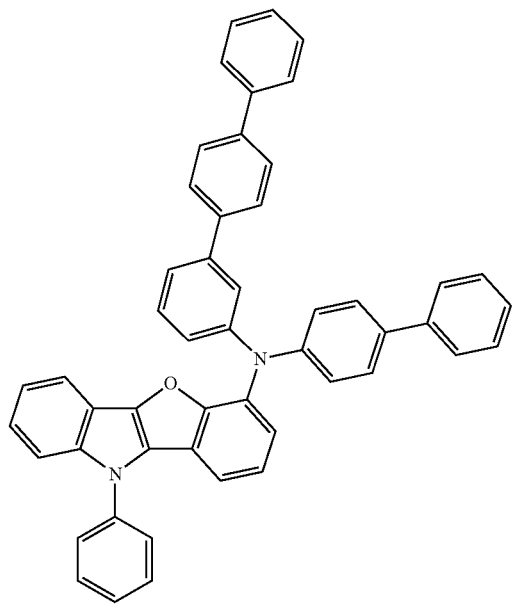
A13

-continued
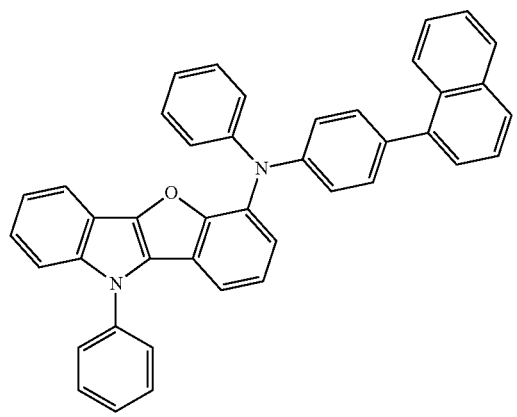
A14
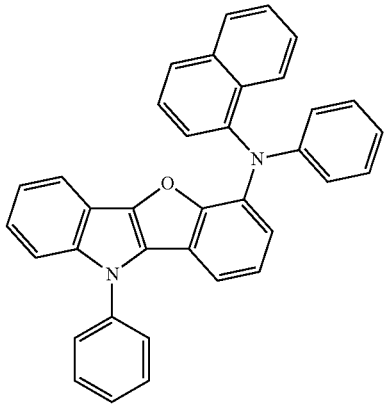
A17
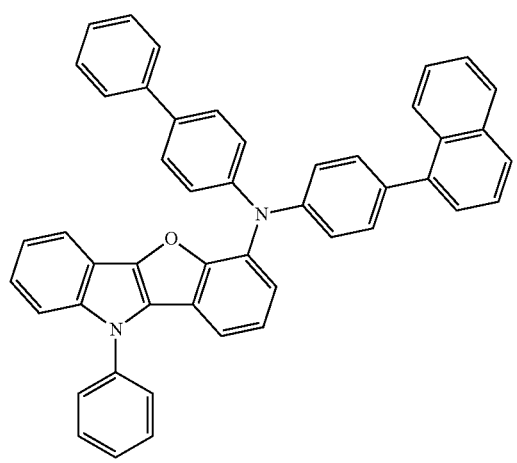
A15
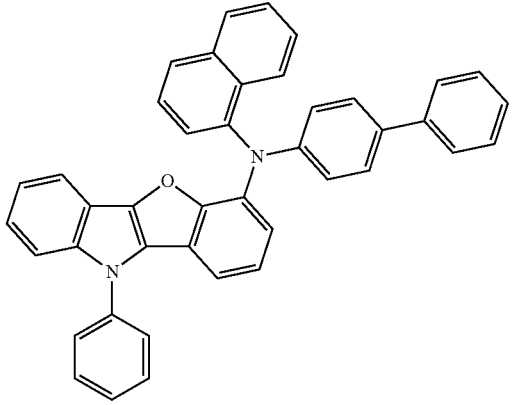
A18
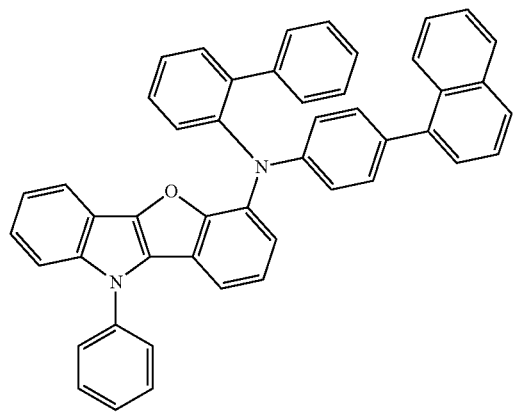
A16
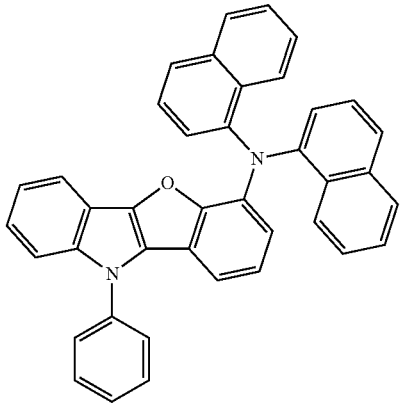
A19

A20
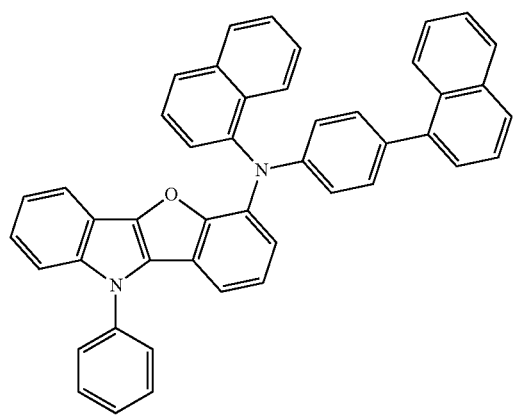
A21
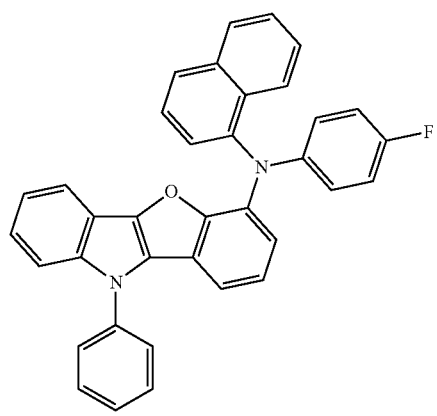
A22
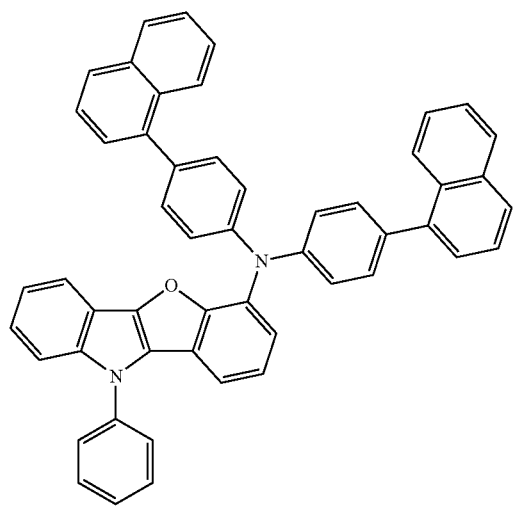
A23
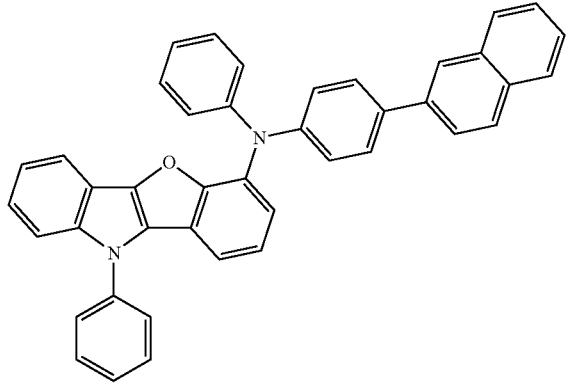
A24
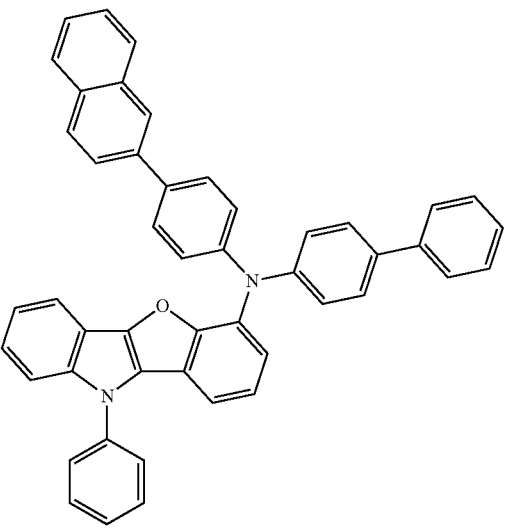
A25
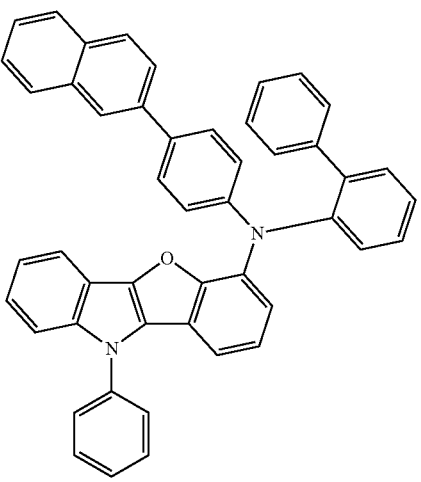

A26
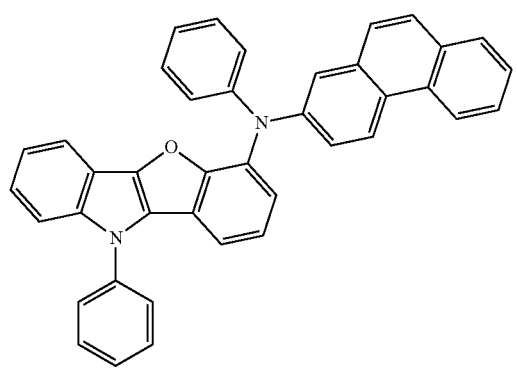
A27
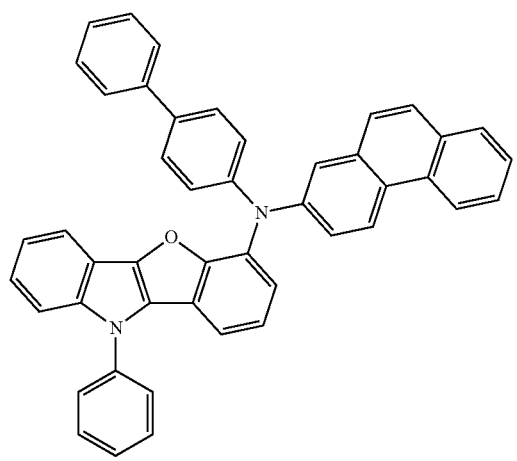
A28
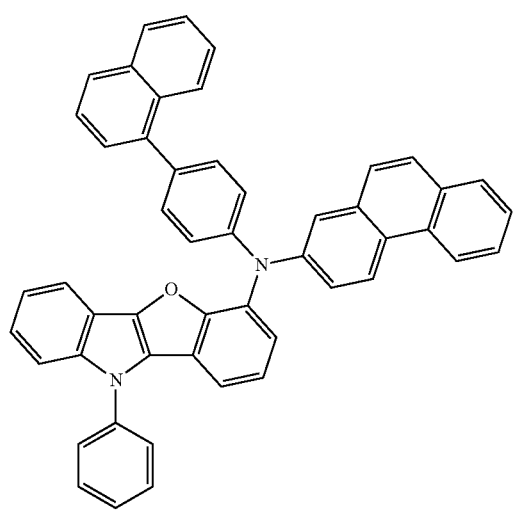
A29
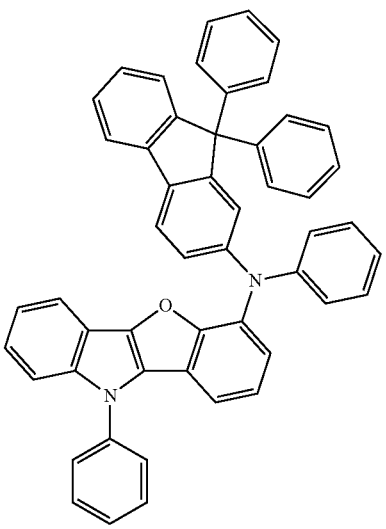
A30
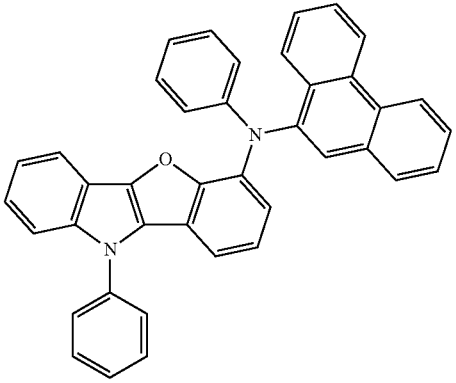
A31
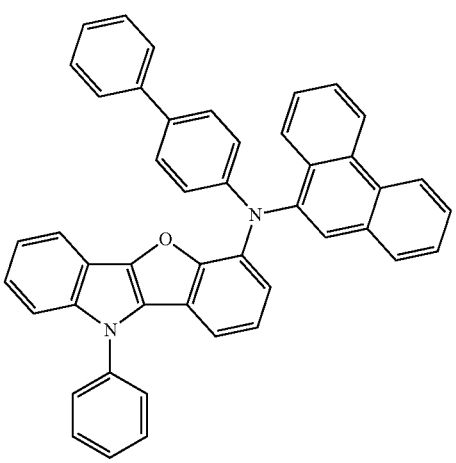

A32
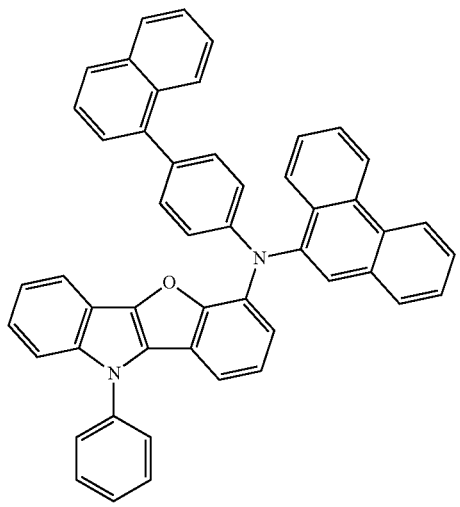
A33
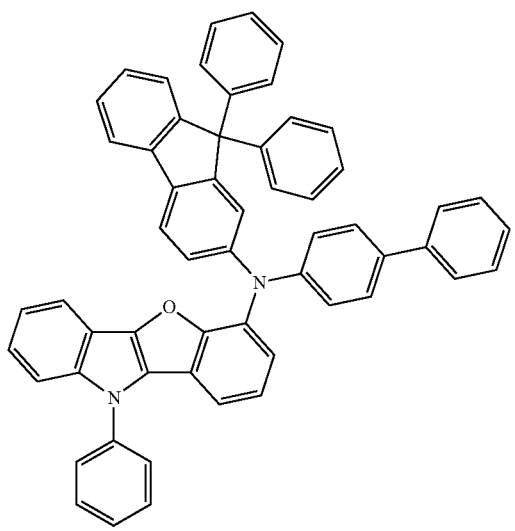
A34
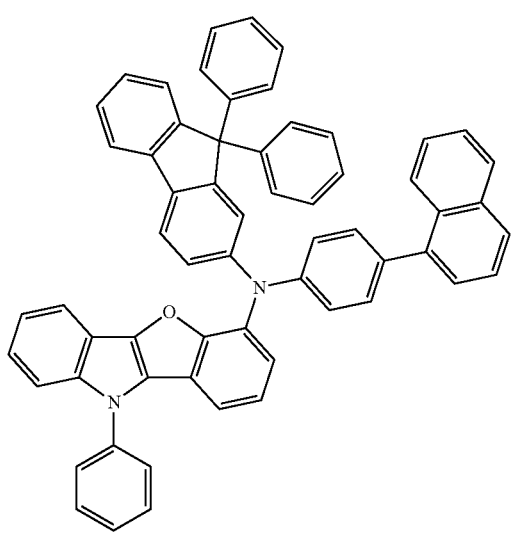
A35
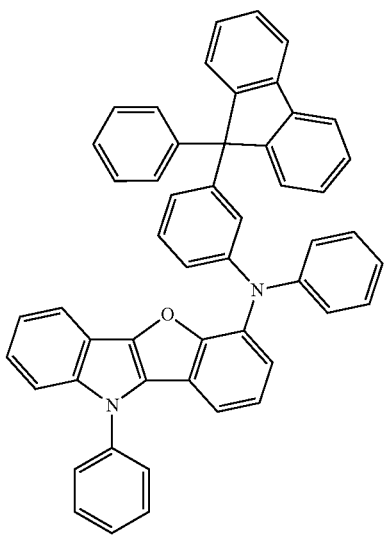
A36
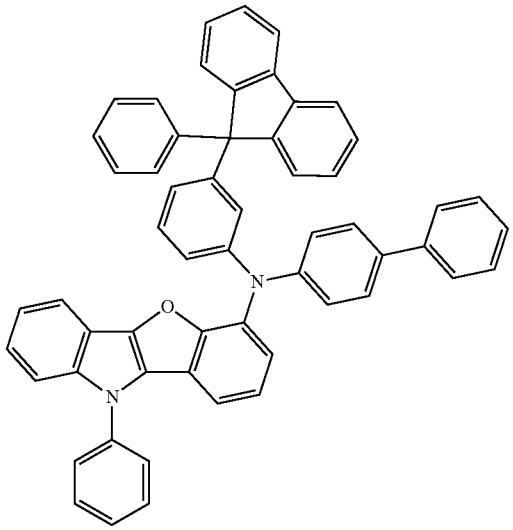
A37
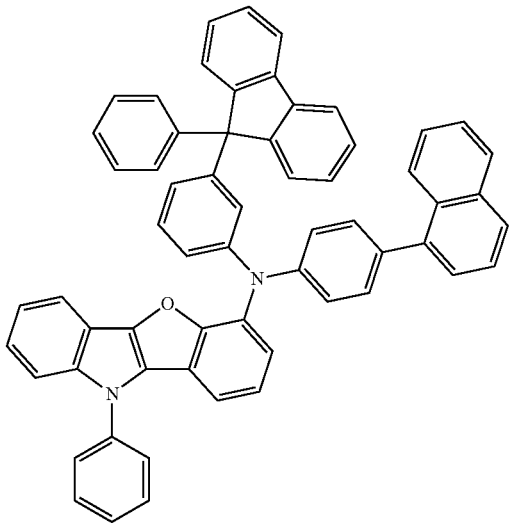

A38
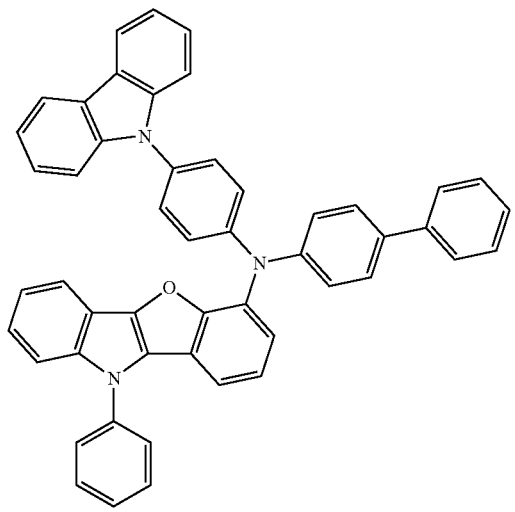
A39
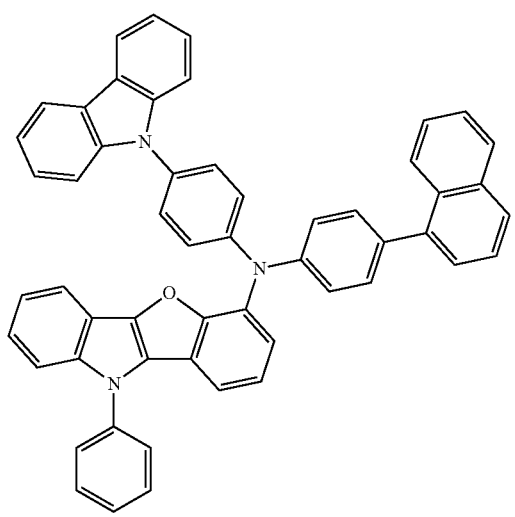
A40
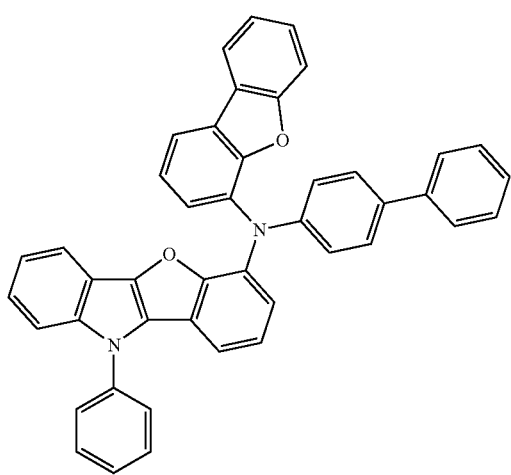
A41
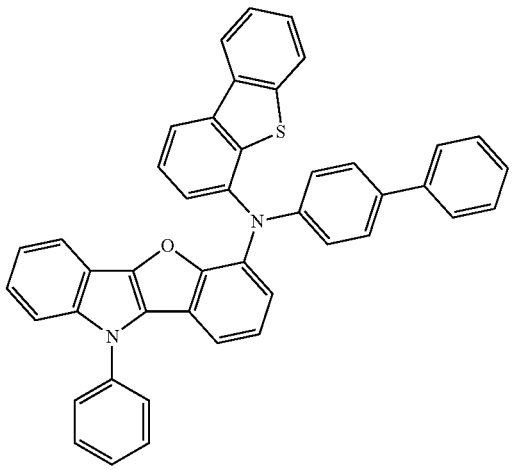
A42
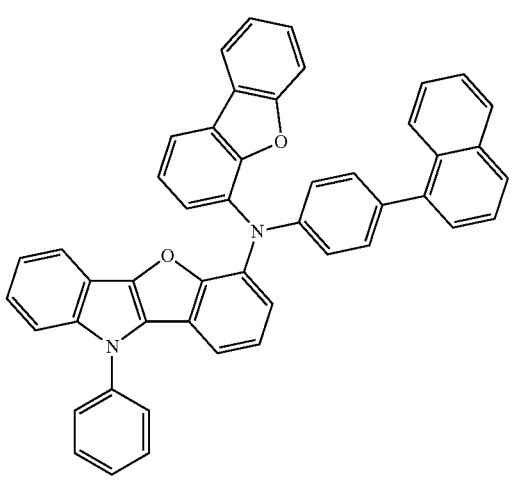
A43
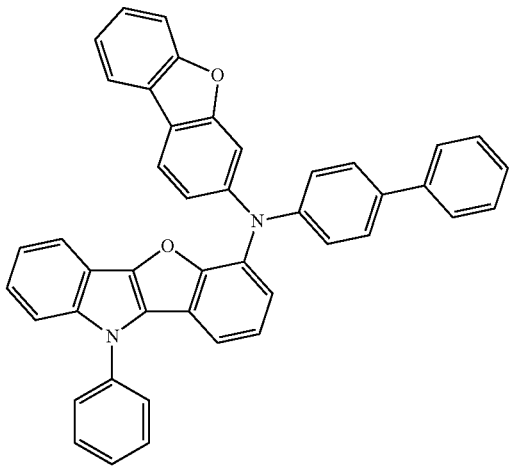

A44
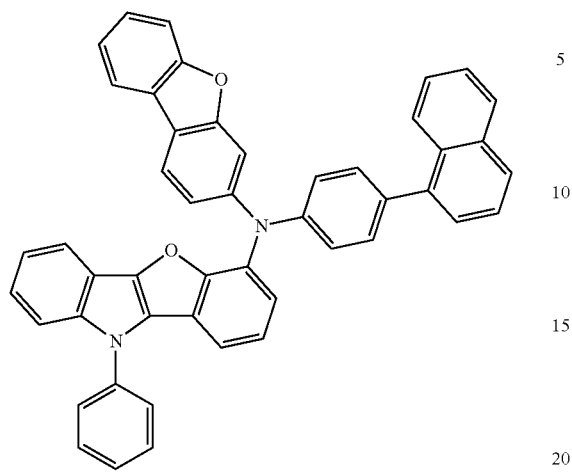
A45
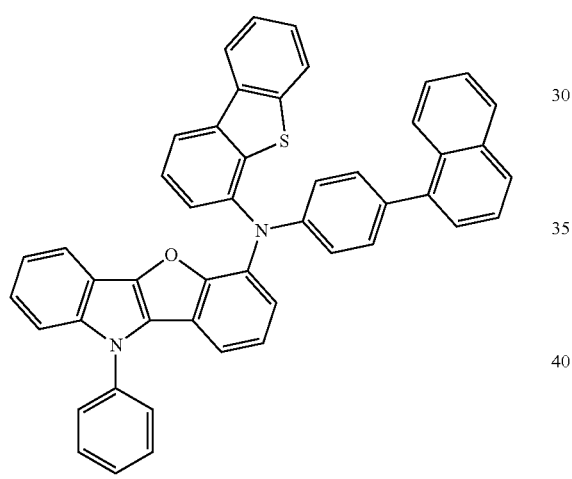
A46
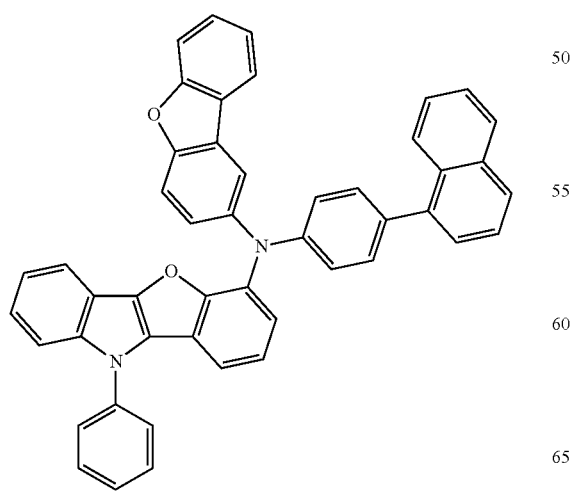
A47
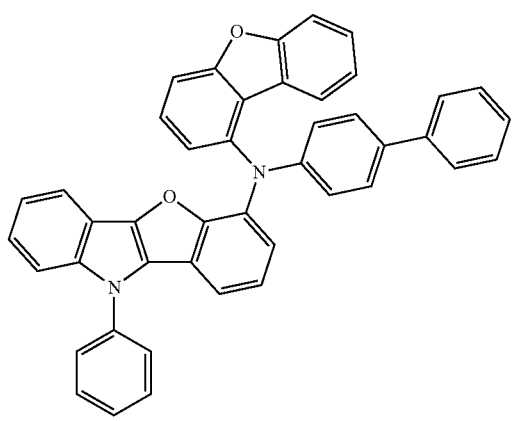
A48
A49
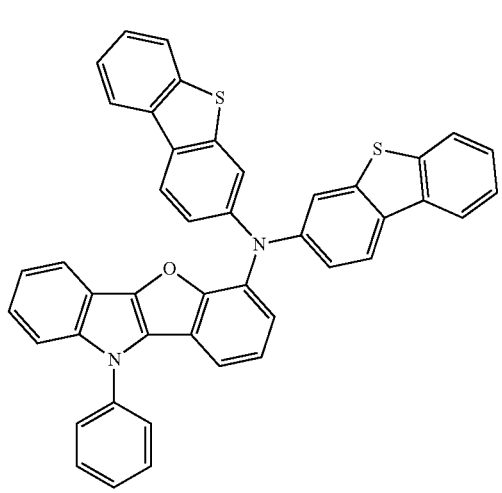

A50
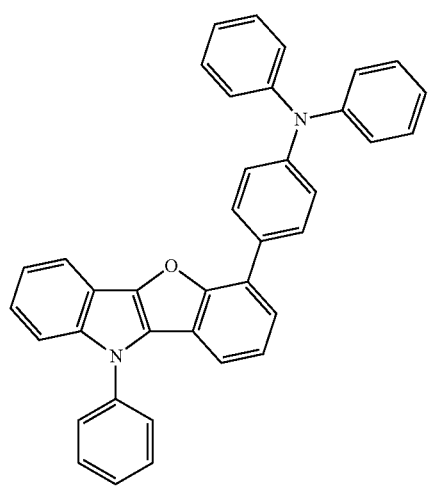
A52
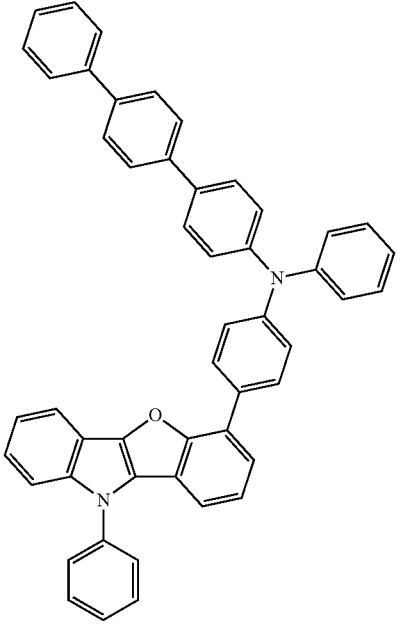
A51
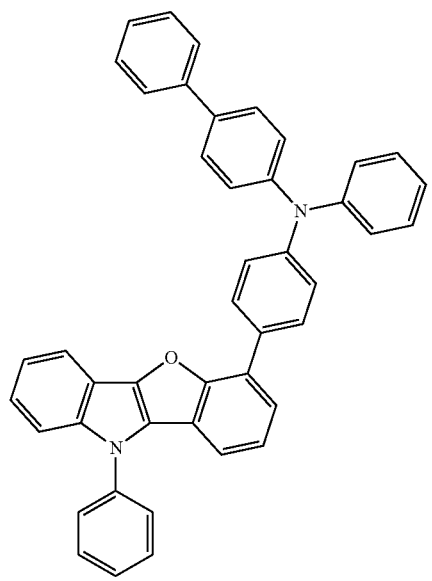
A53
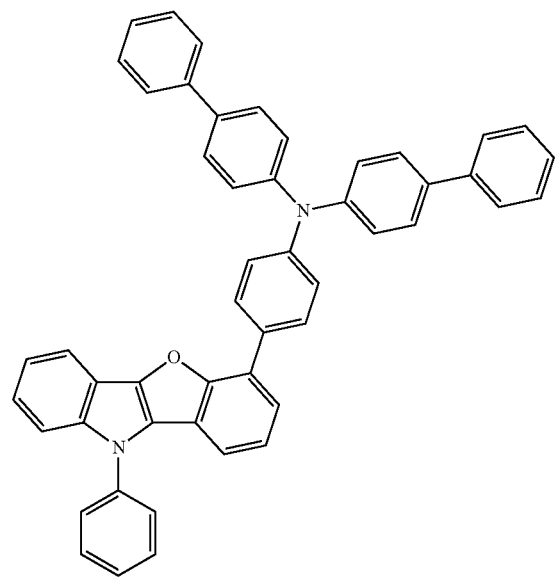

A54
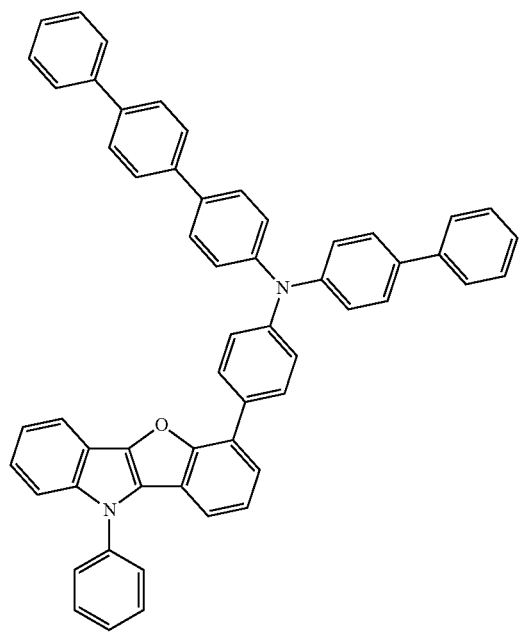
A55
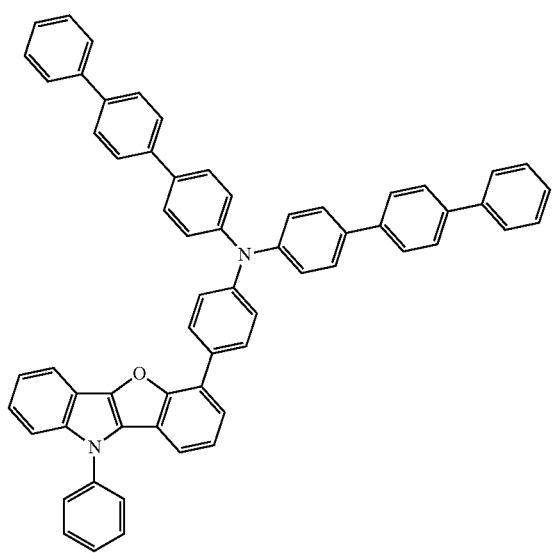
A56
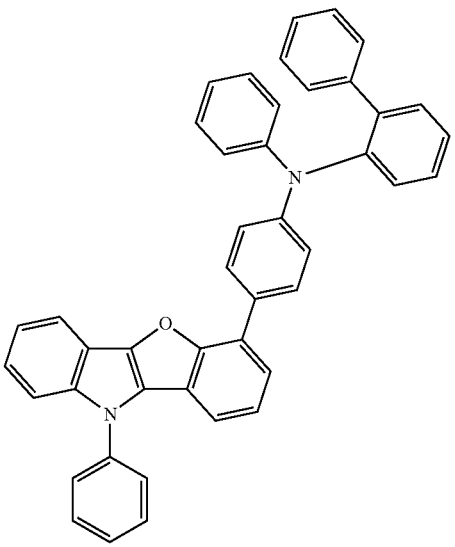
A57
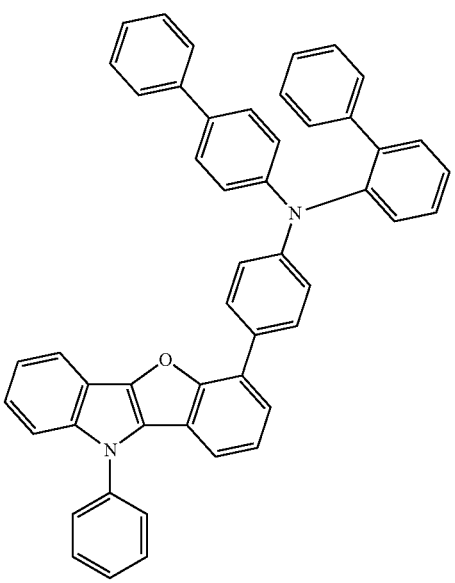
A58
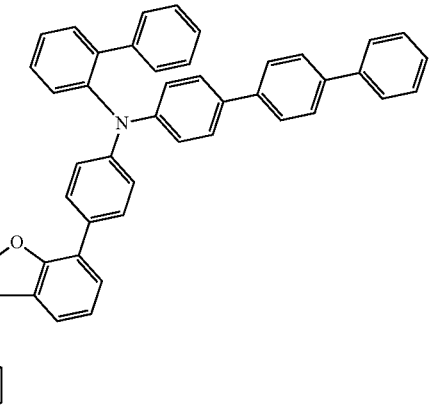

A59
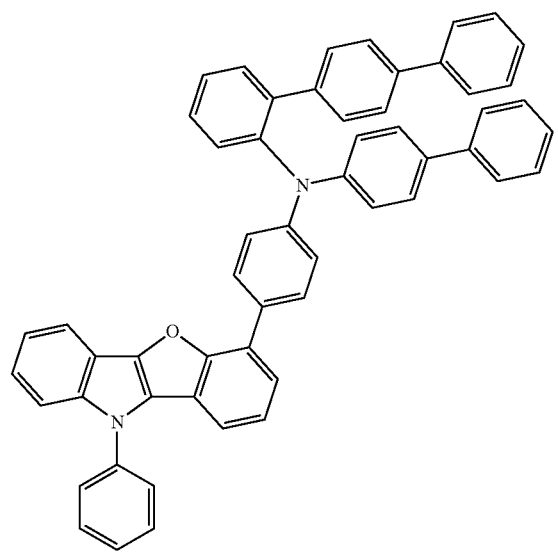
A60
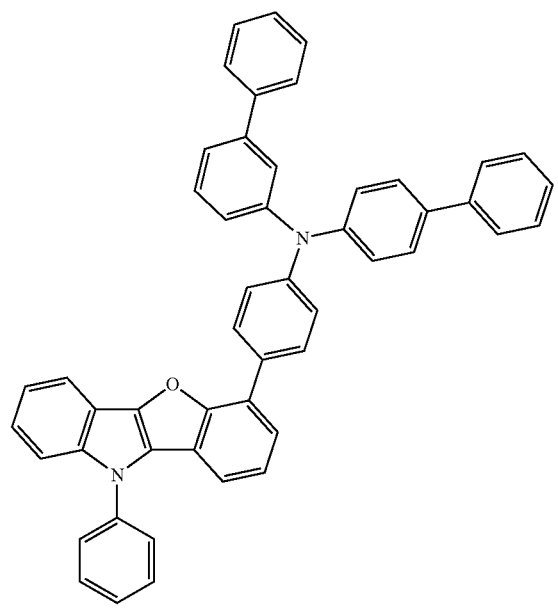
A61
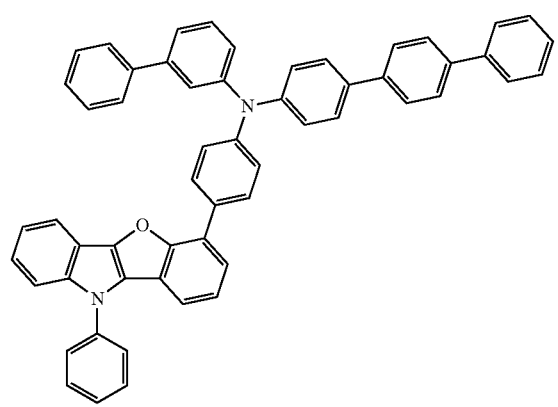
A62
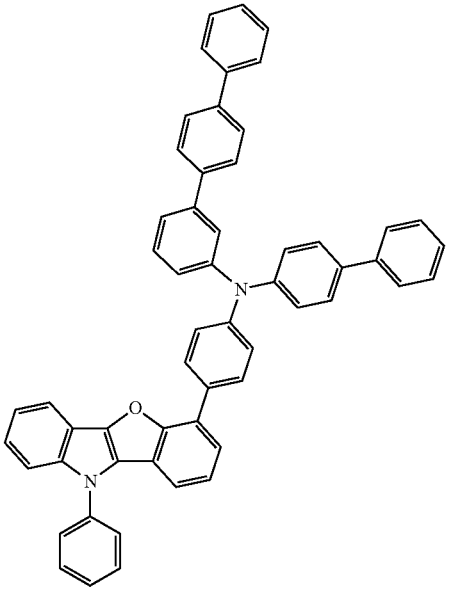
A63
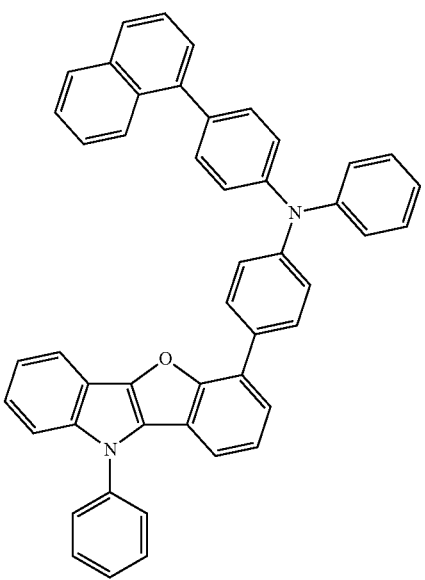

A64
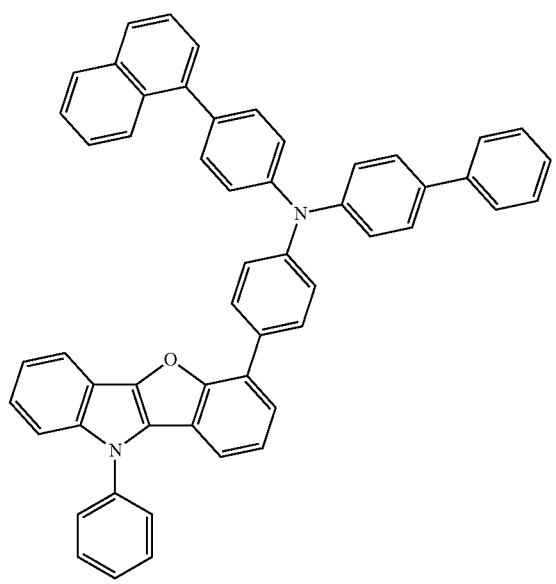
A65
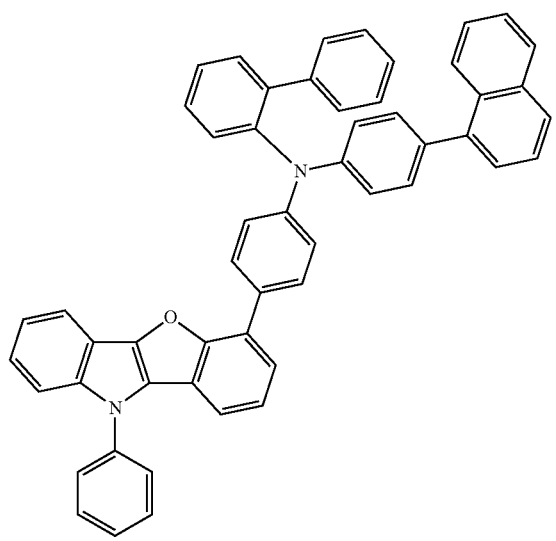
A66
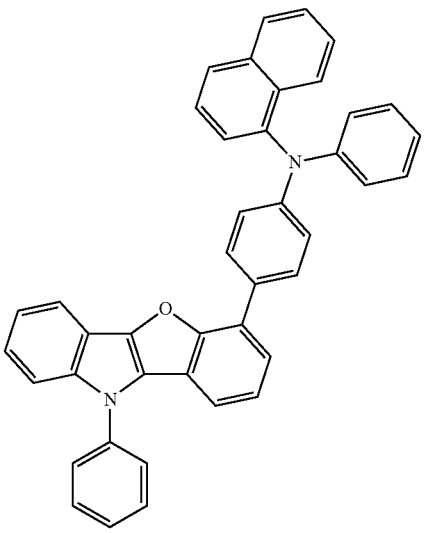
A67
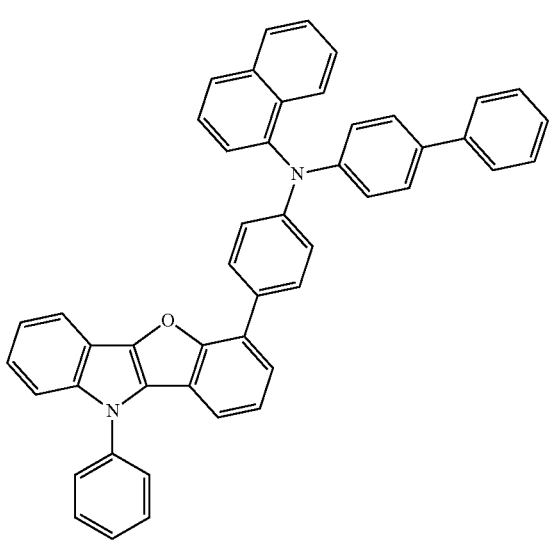
A68
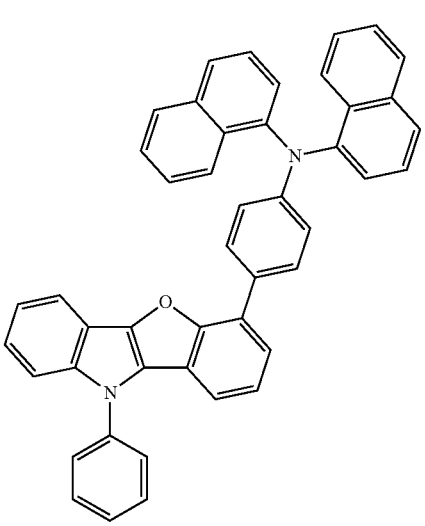

-continued
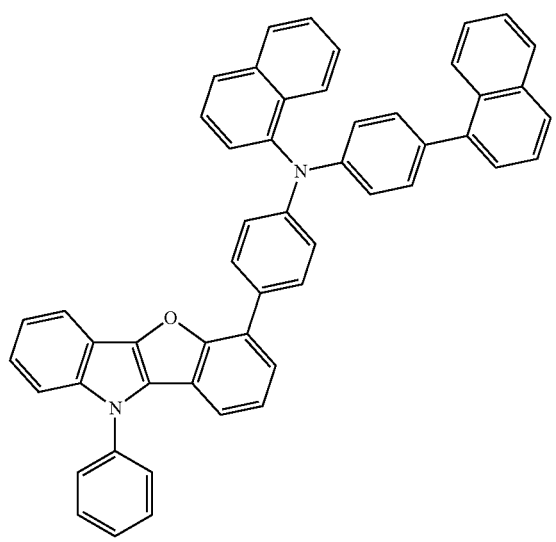
A69
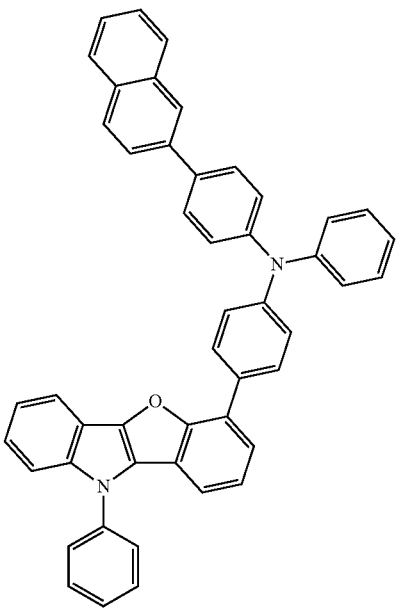
A71
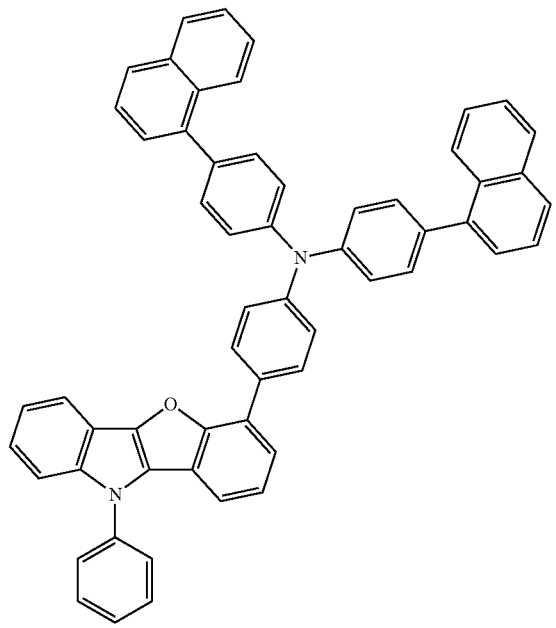
A70
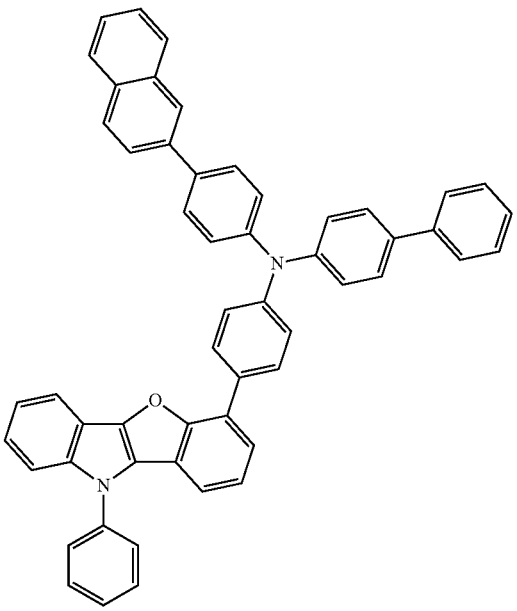
A72

A73
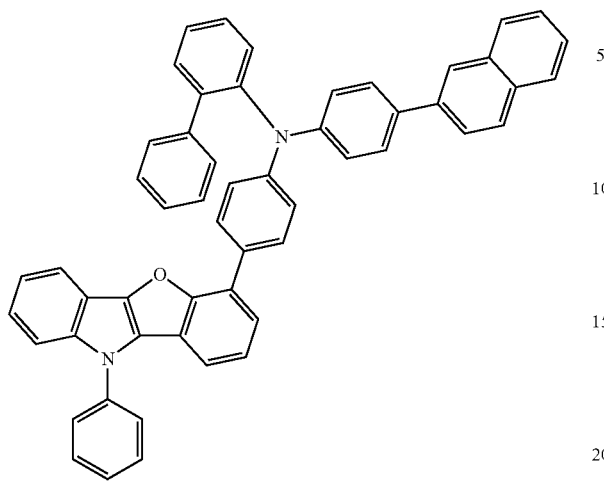
A74
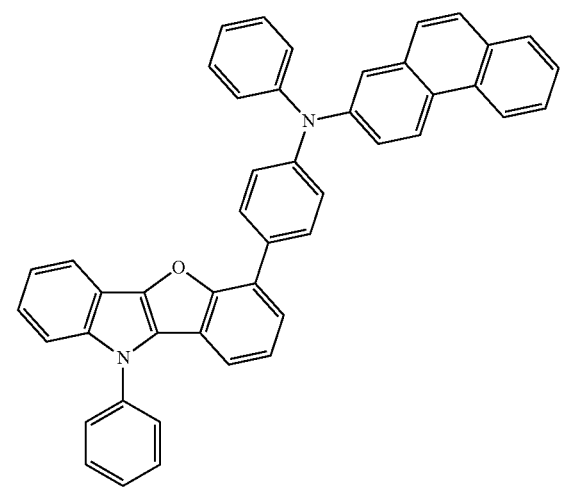
A75
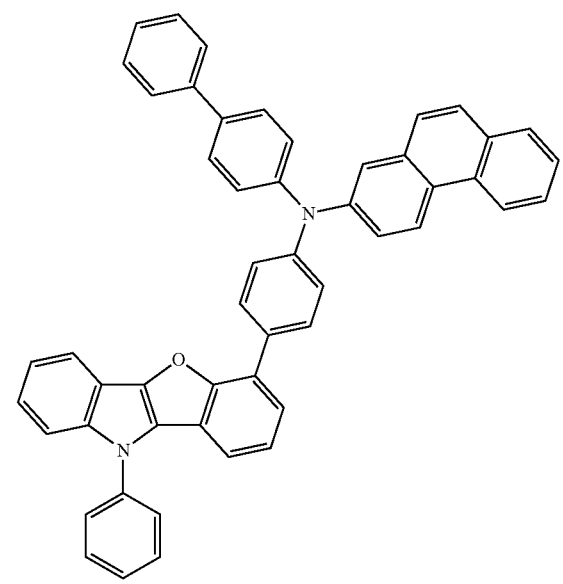
A76
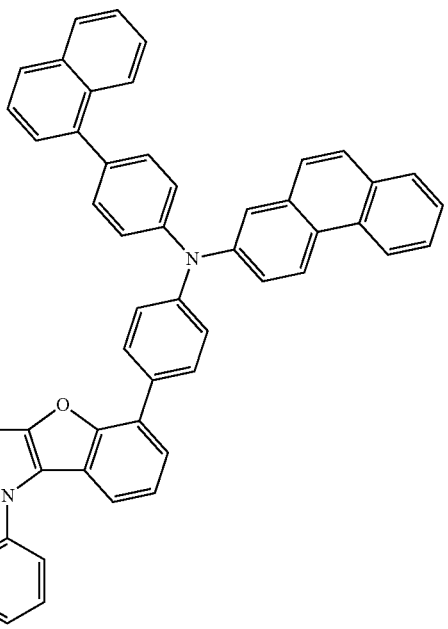
A77
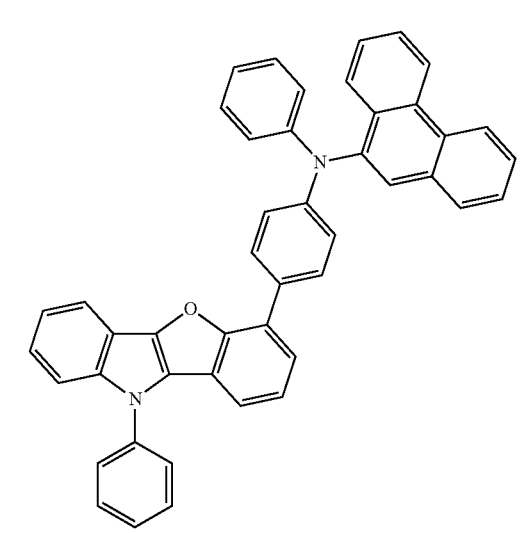

A78
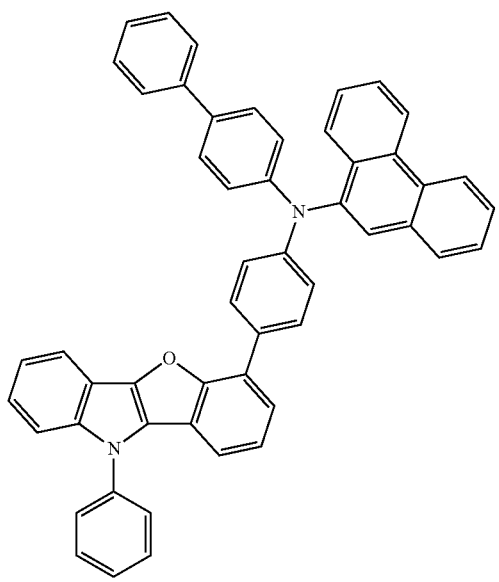
A79
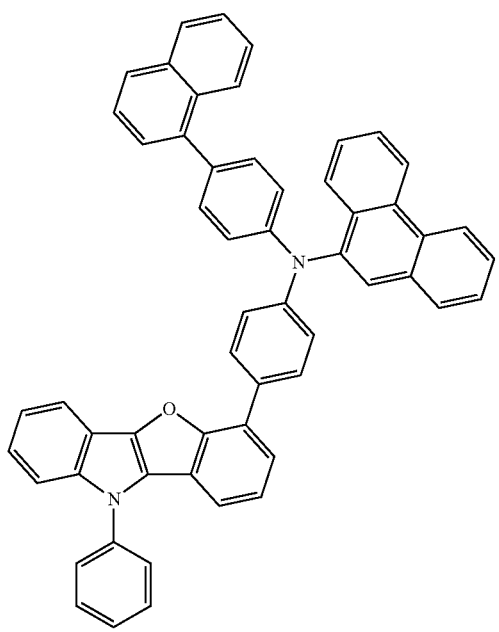
A80
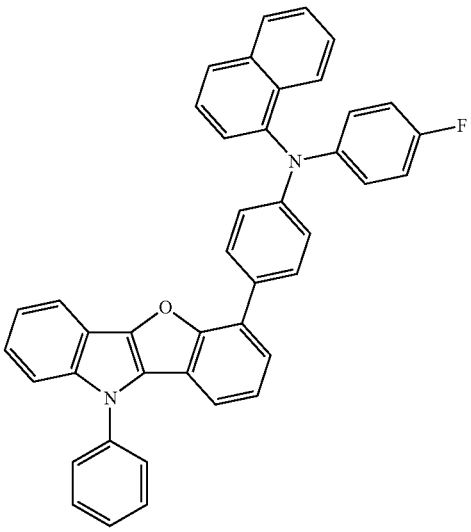
A81
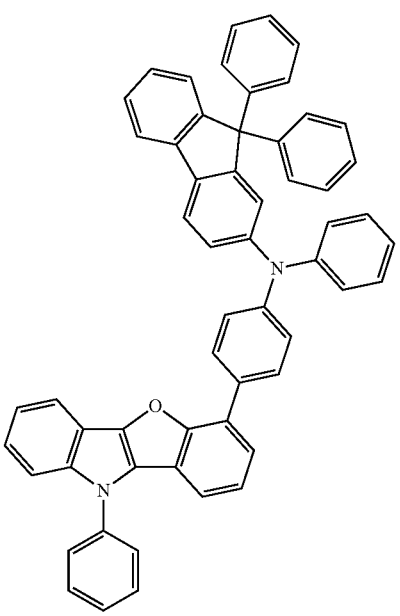

A82
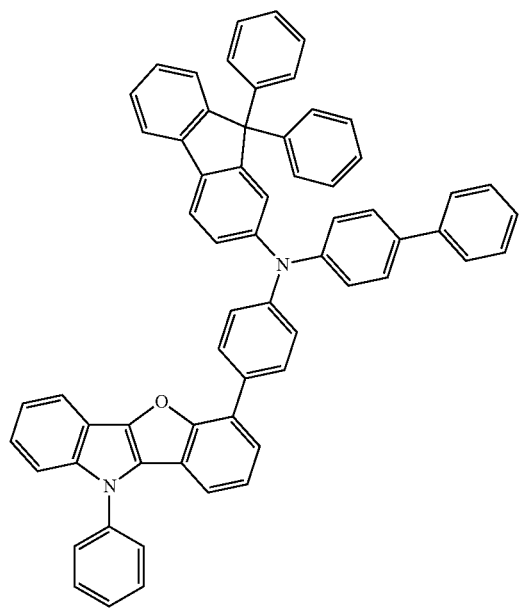
A84
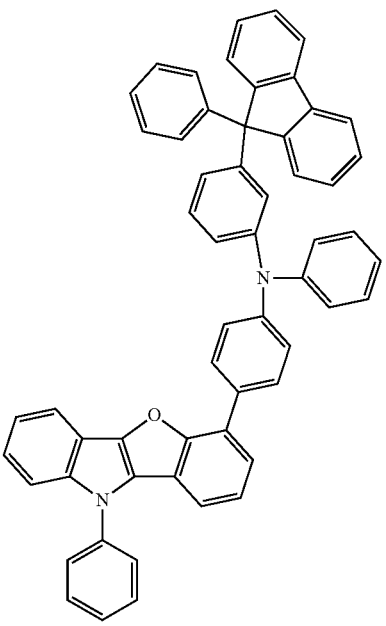
A83
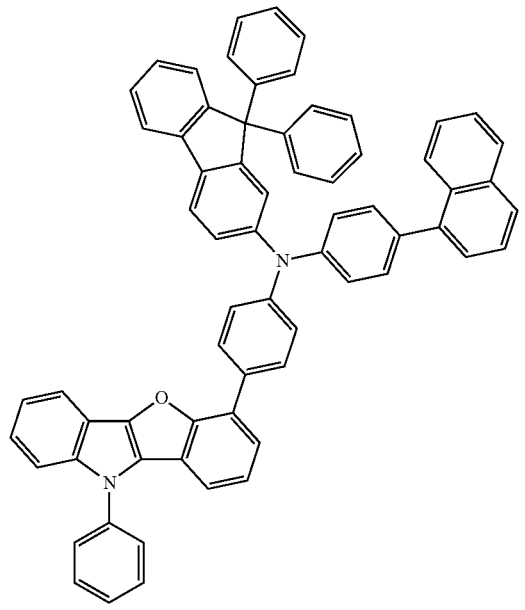
A85
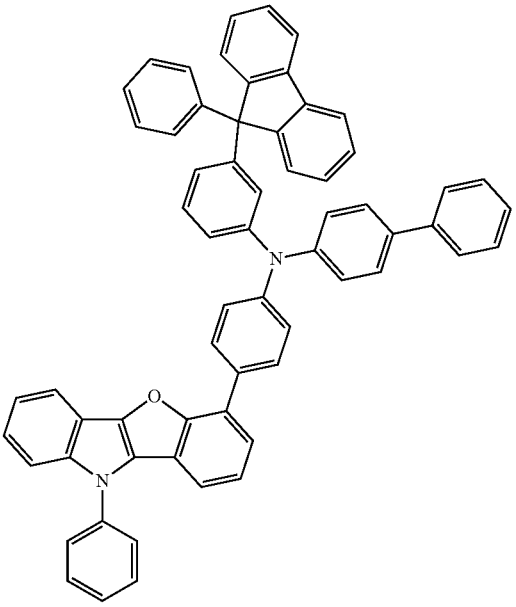

A86
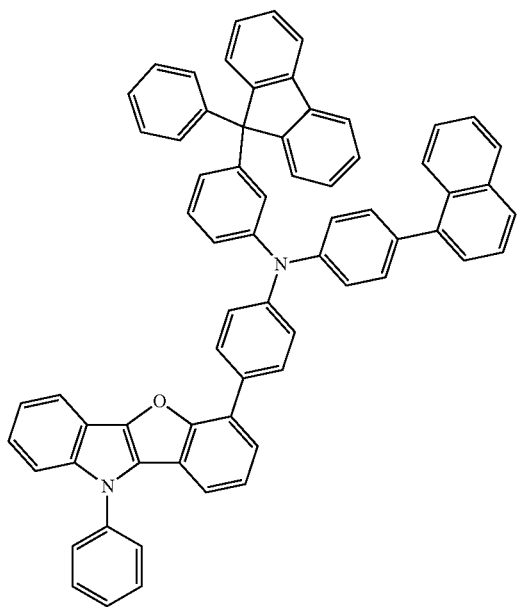
A88
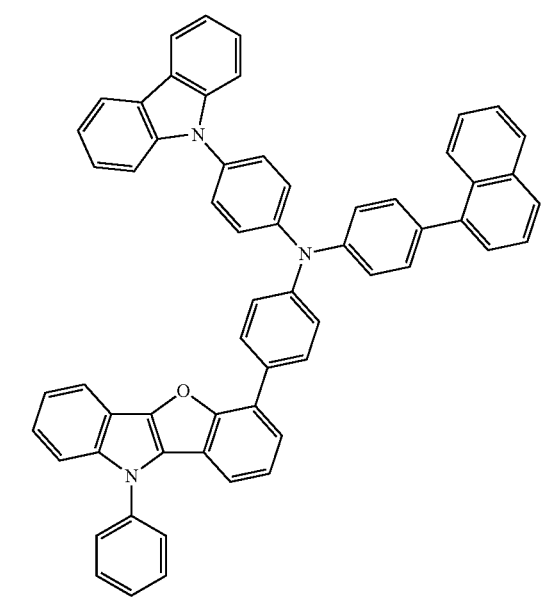
A87
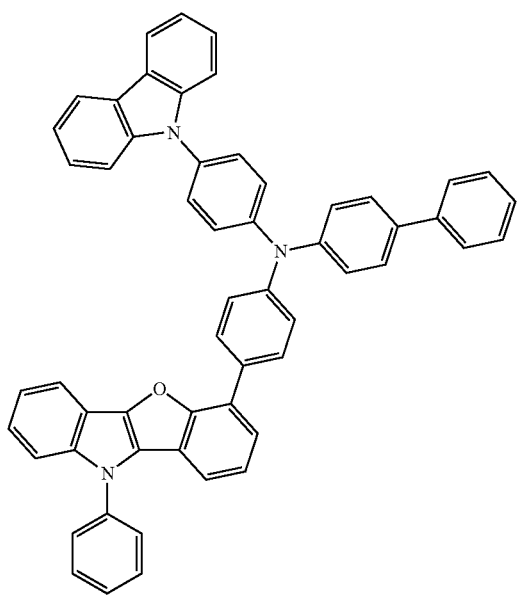
A89
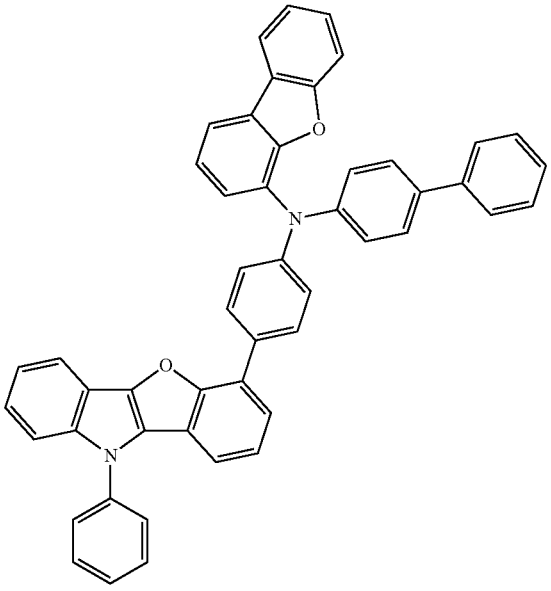

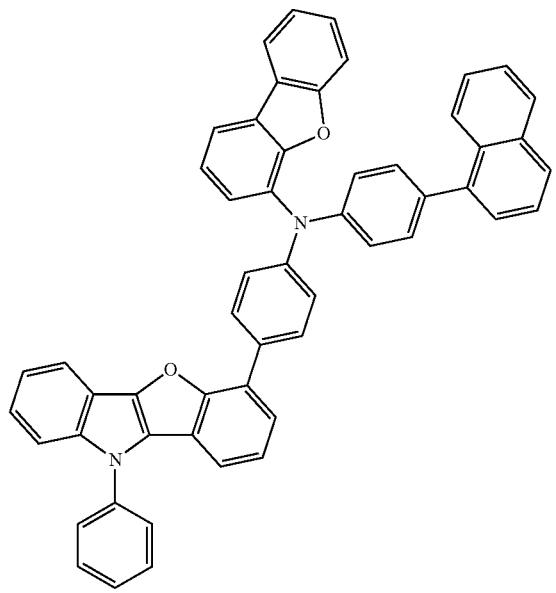
A90
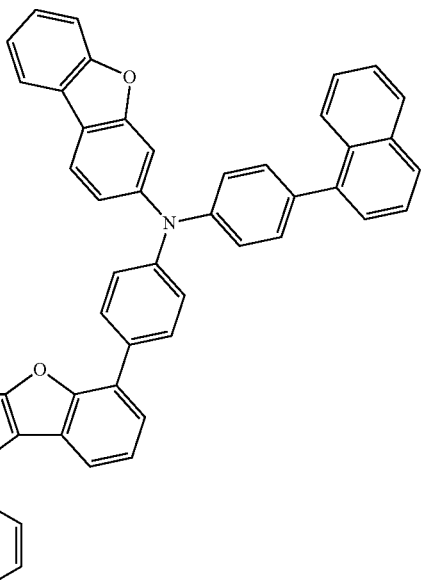
A92
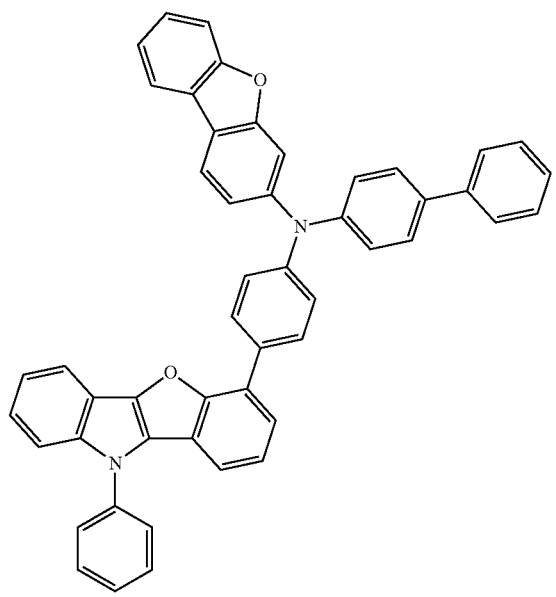
A91
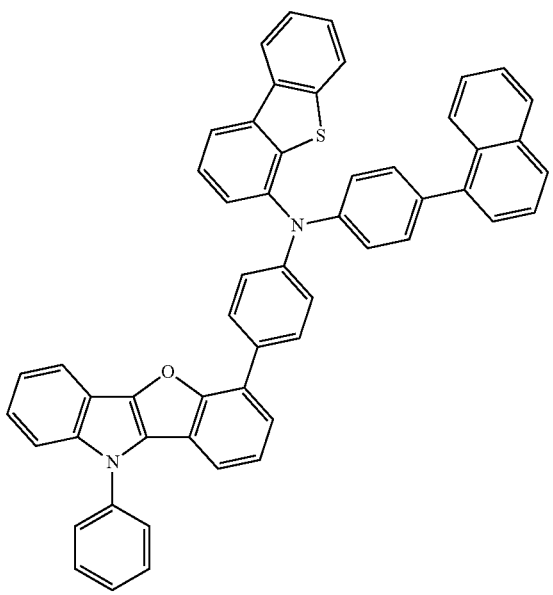
A93

A94
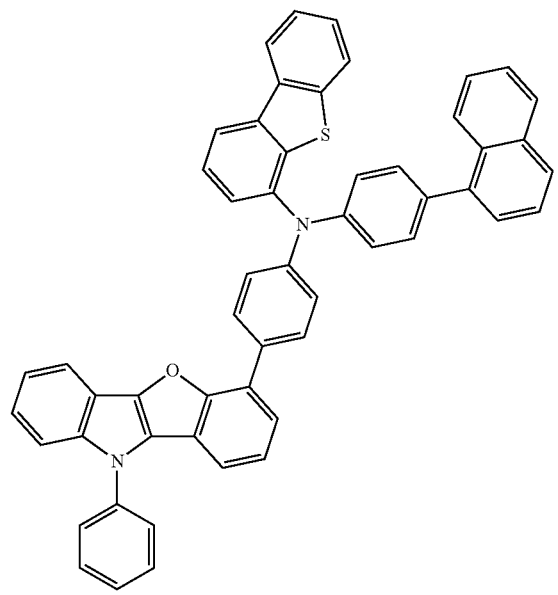
A95
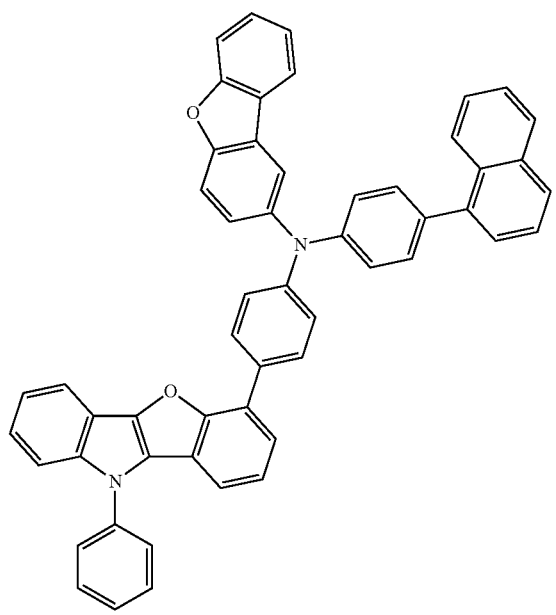
A96
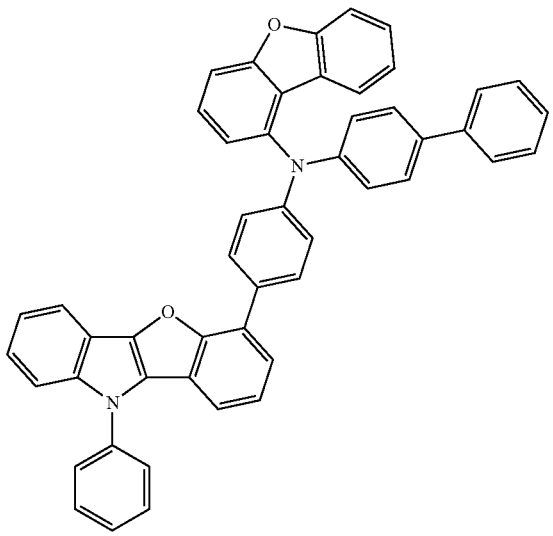
A97
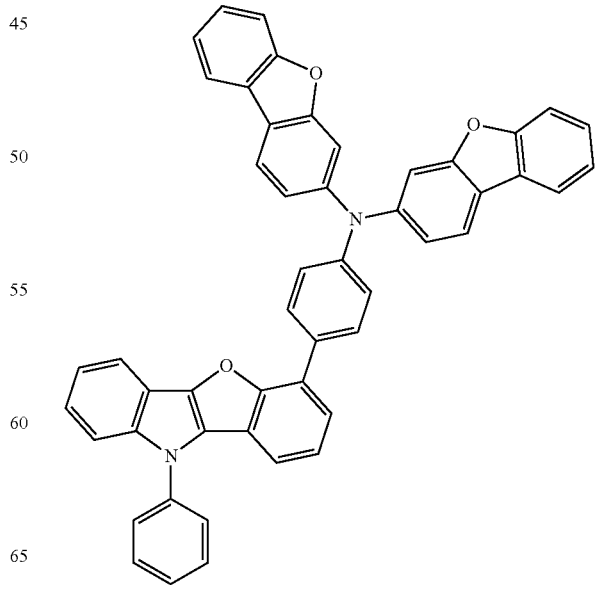

A98
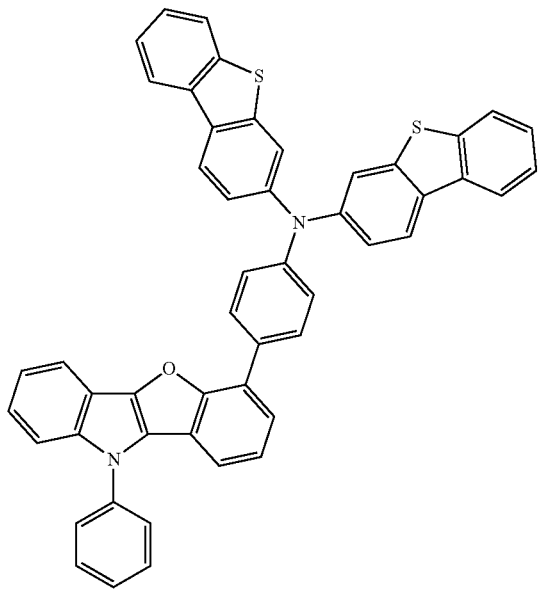
A99
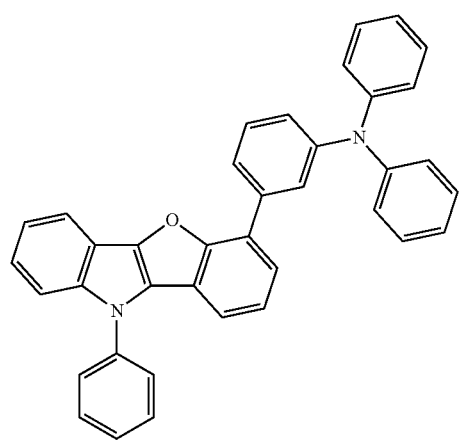
A100
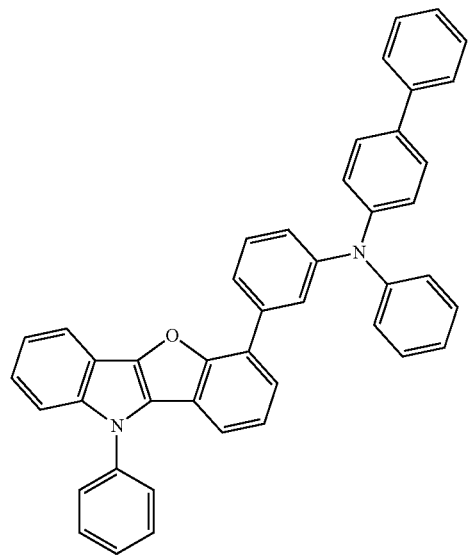
A101
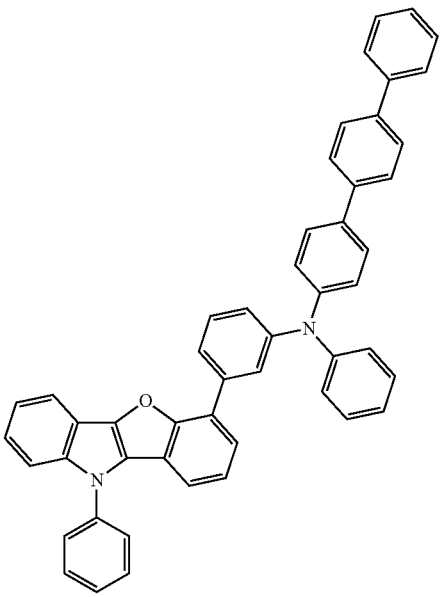
A102
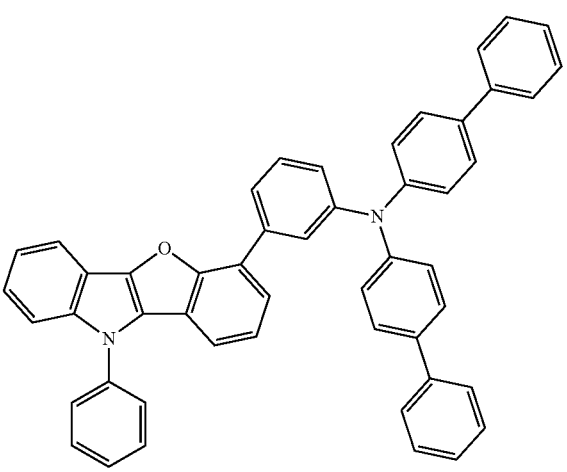

A103
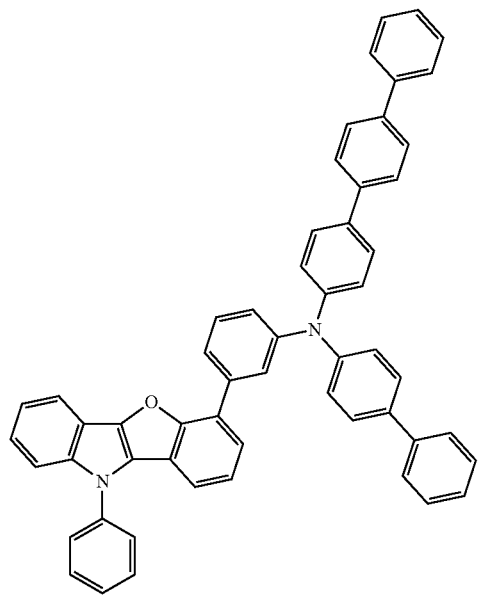
A105
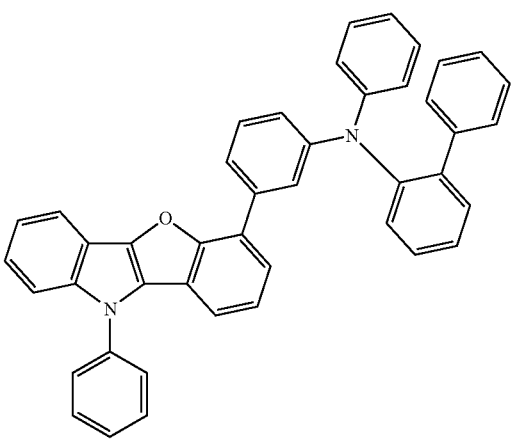
A106
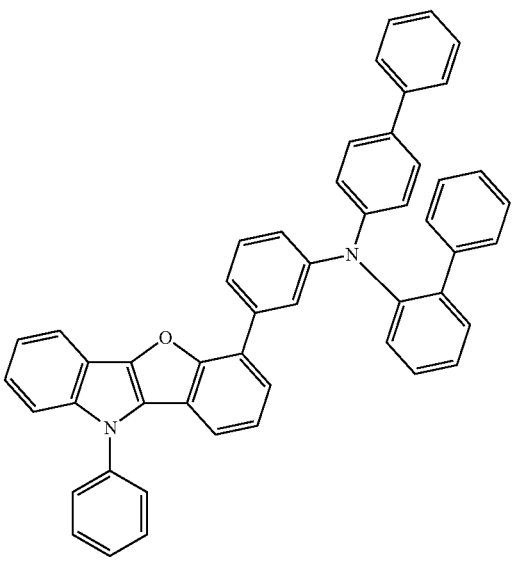
A104
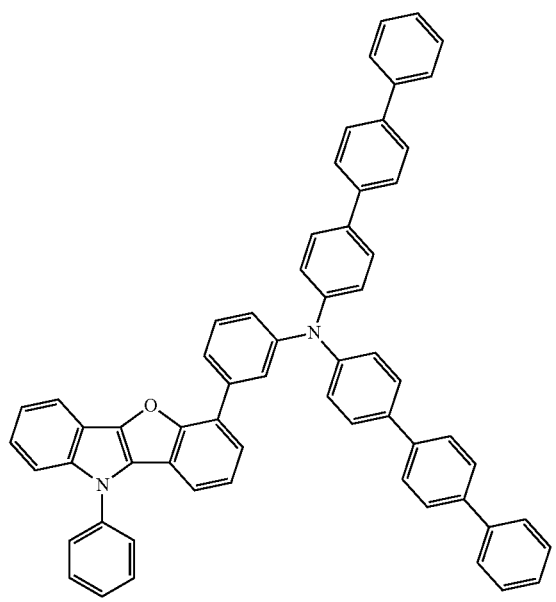
A107
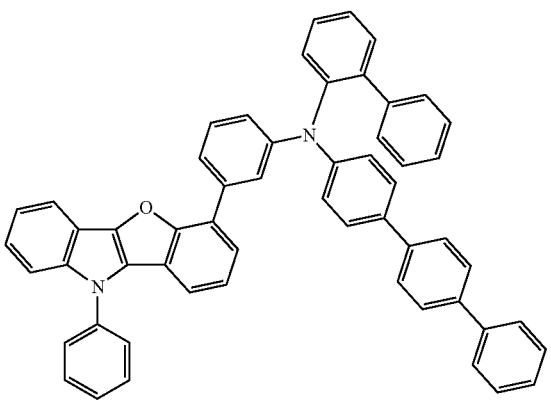

A108
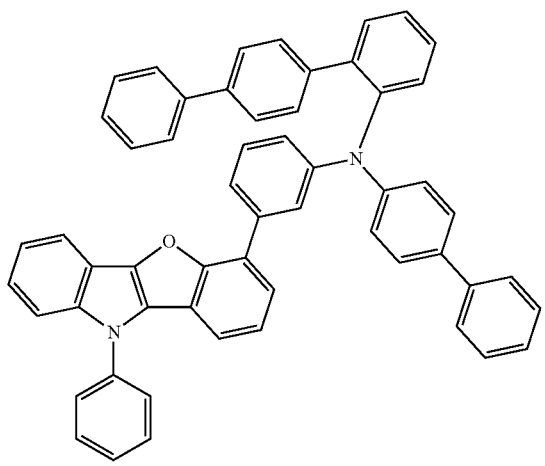
A109
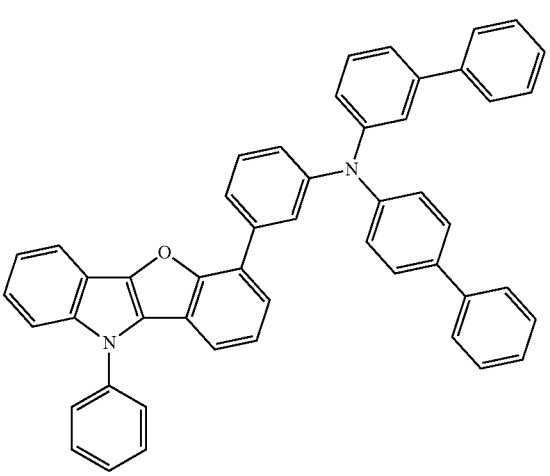
A110
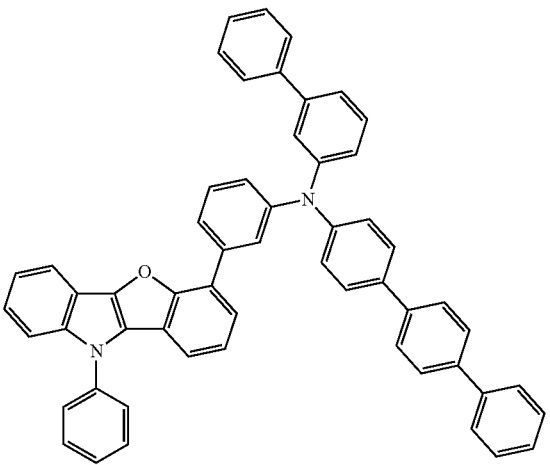
A111
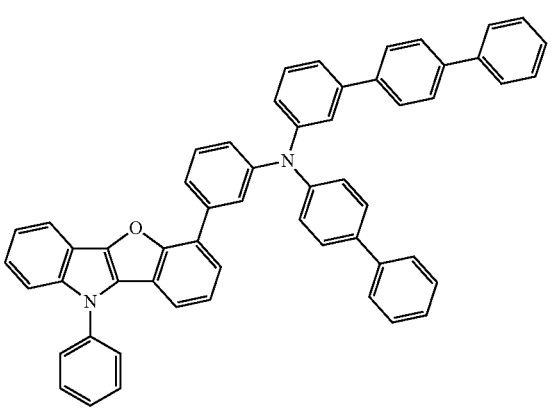
A112
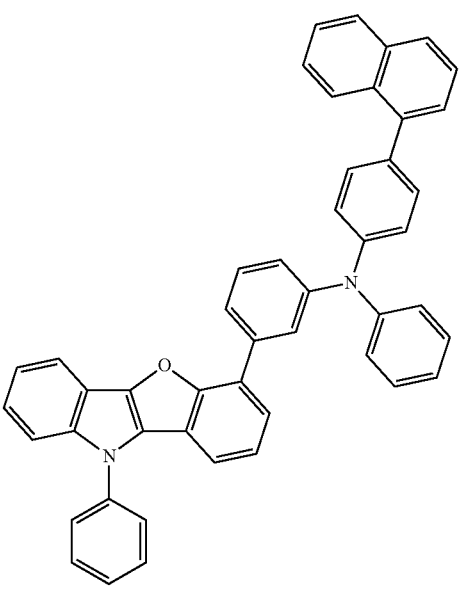
A113
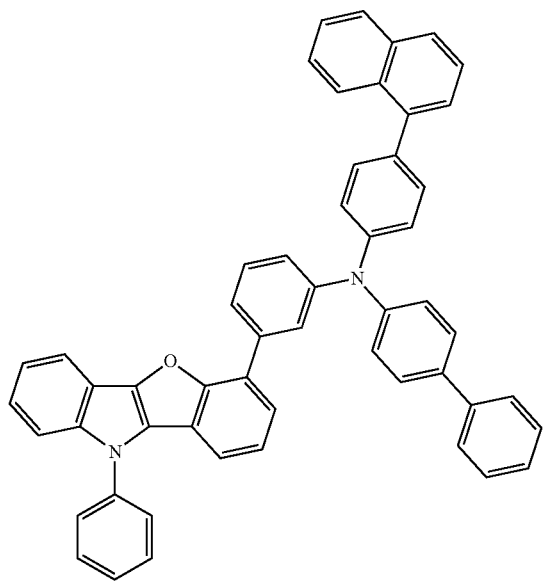

A114
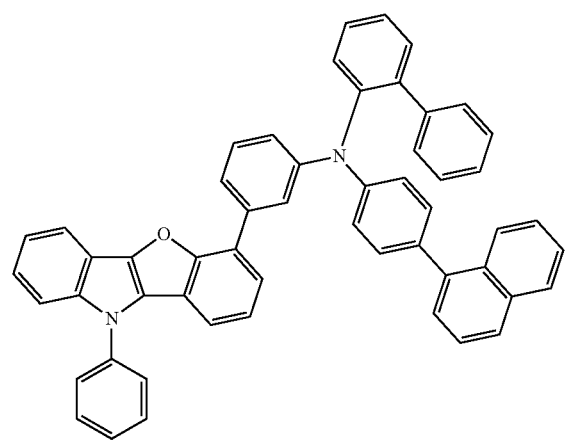
A115
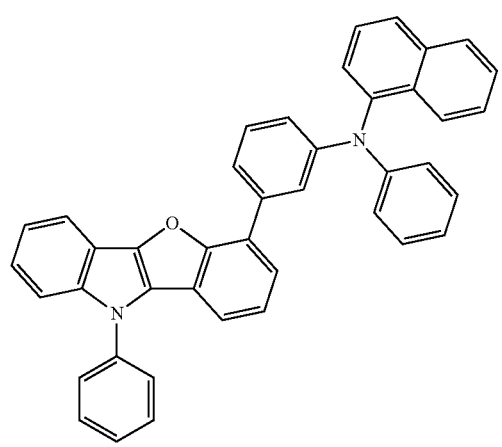
A116
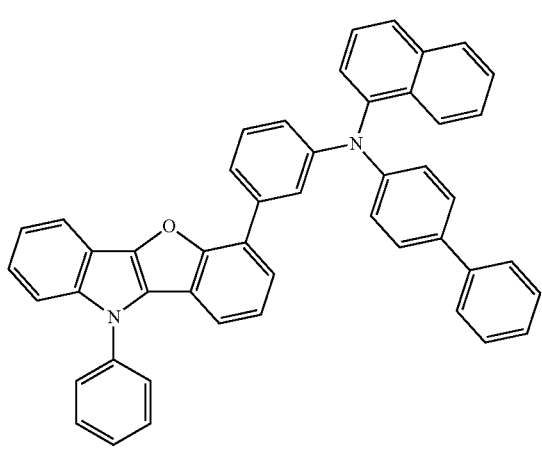
A117
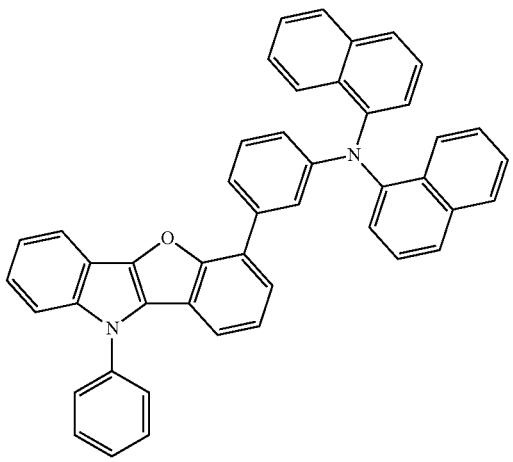
A118
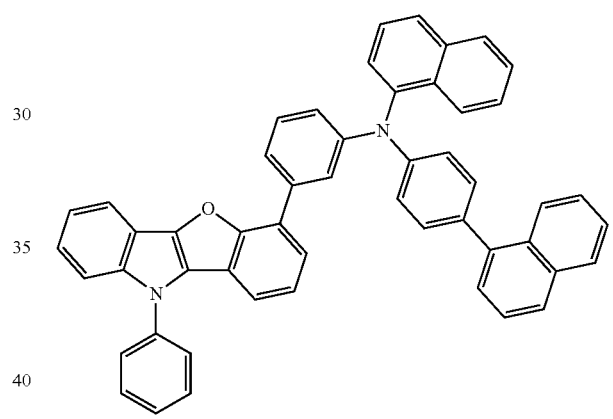
A119
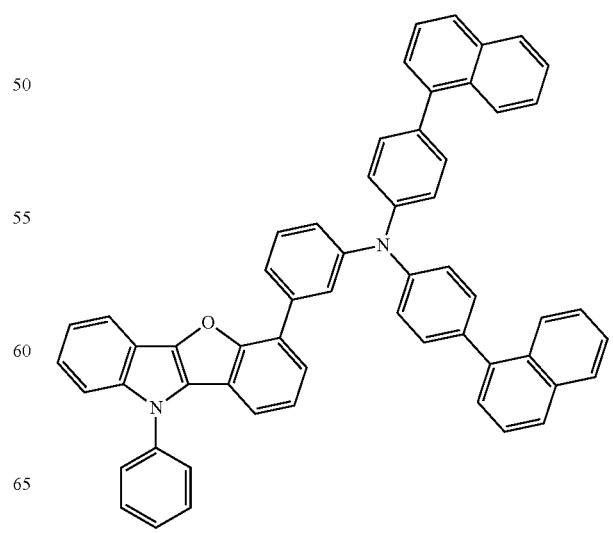

A120
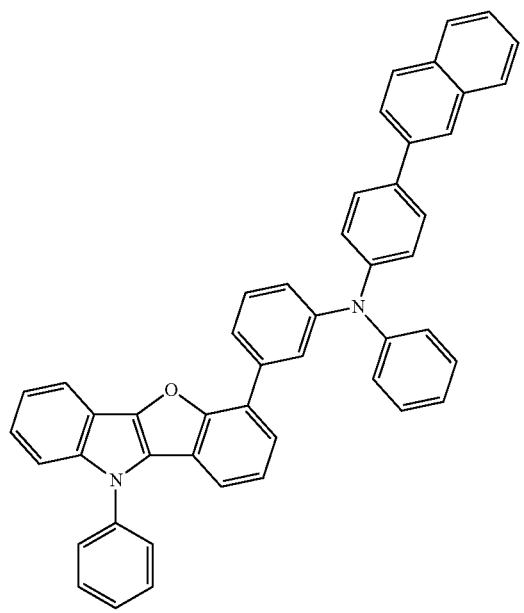
A122
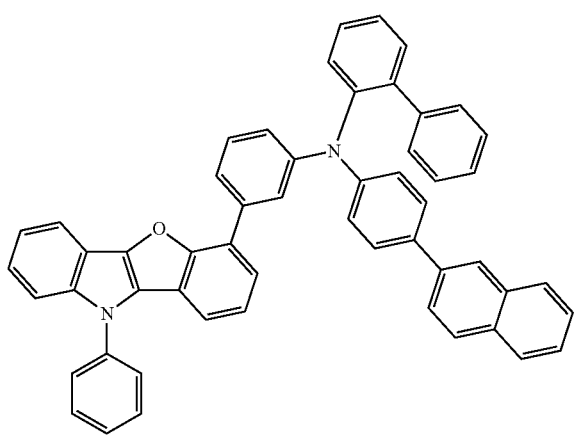
A123
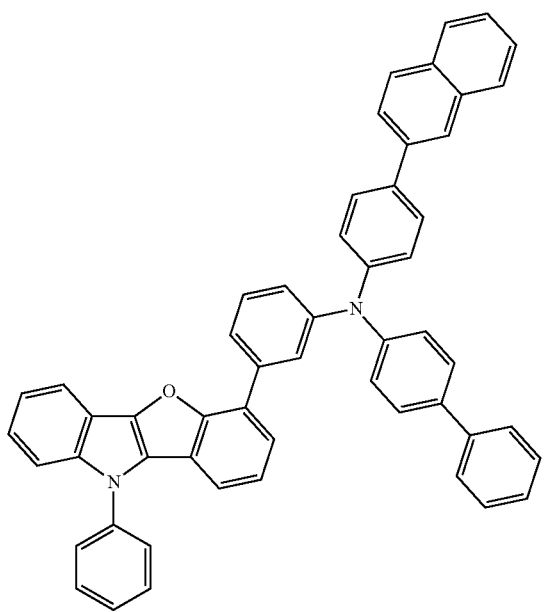
A121
A124
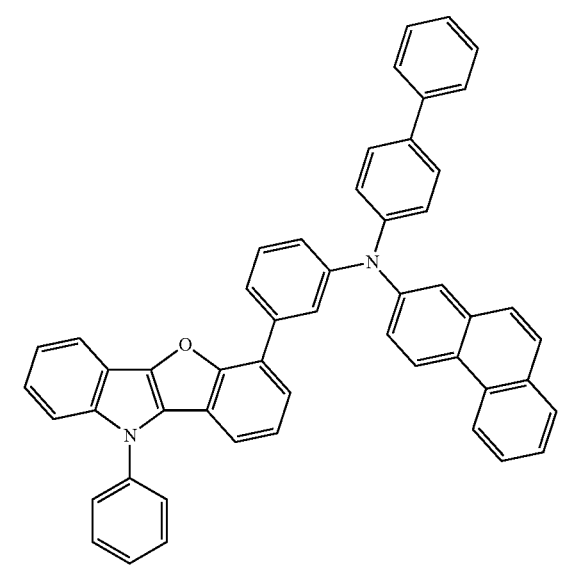

A125
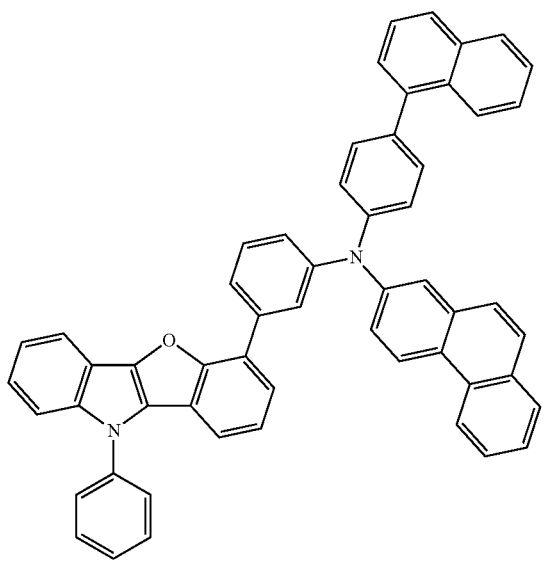
A126
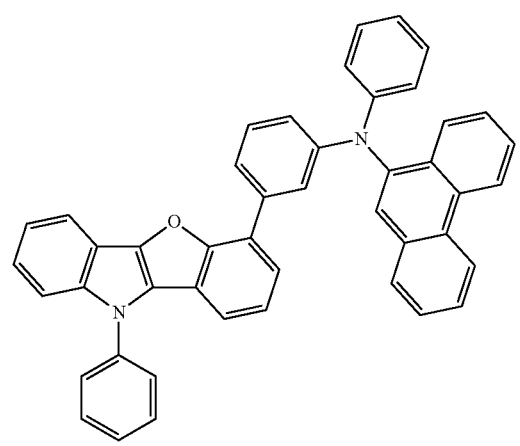
A127
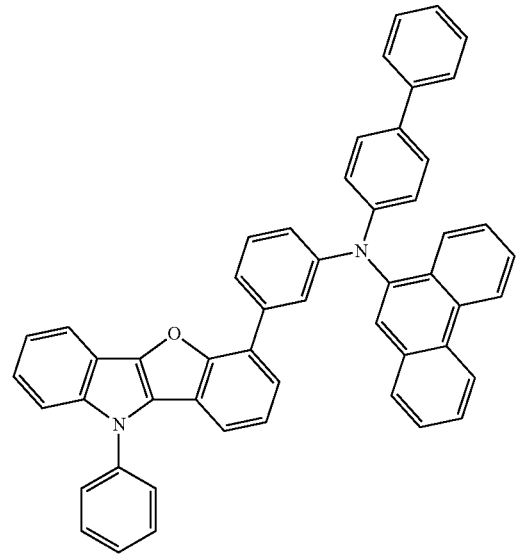
A128
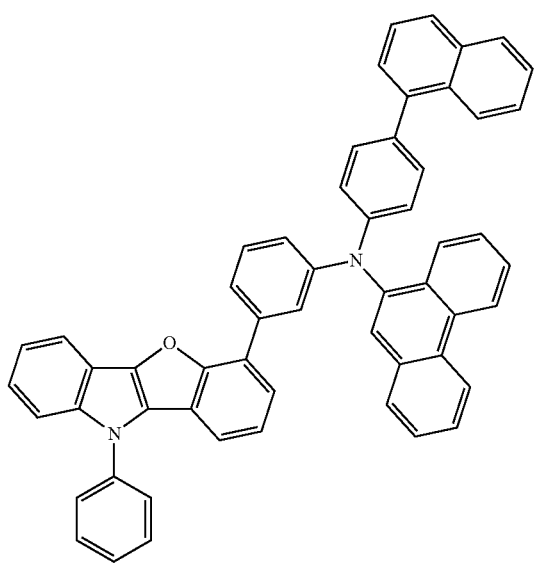
A129
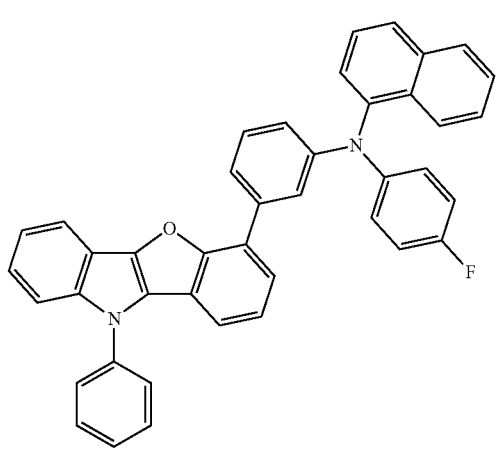
A130
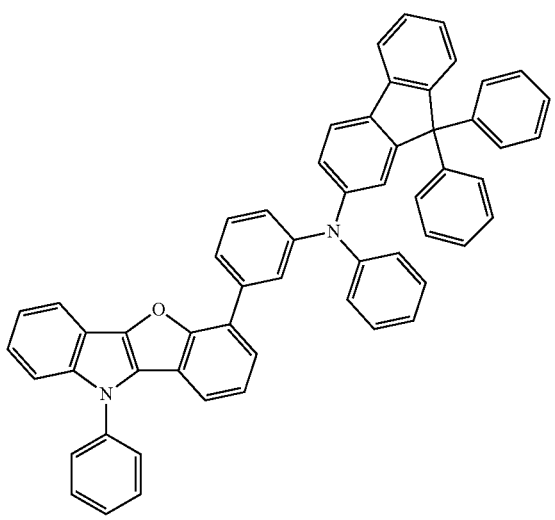

A131
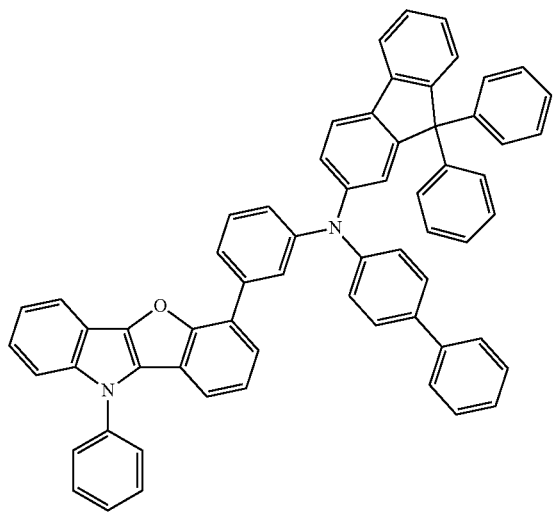
A132
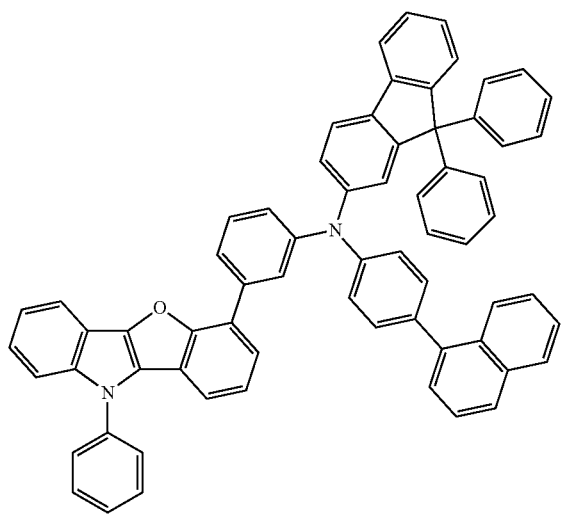
A133
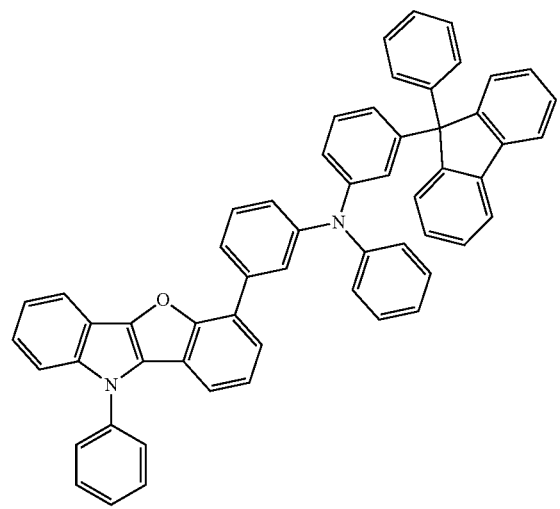
A134
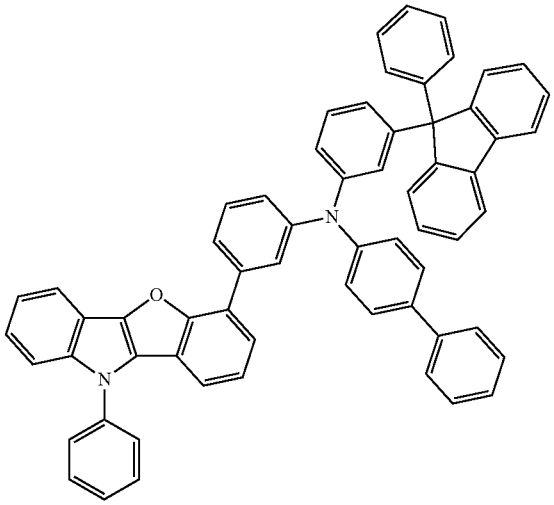
A135
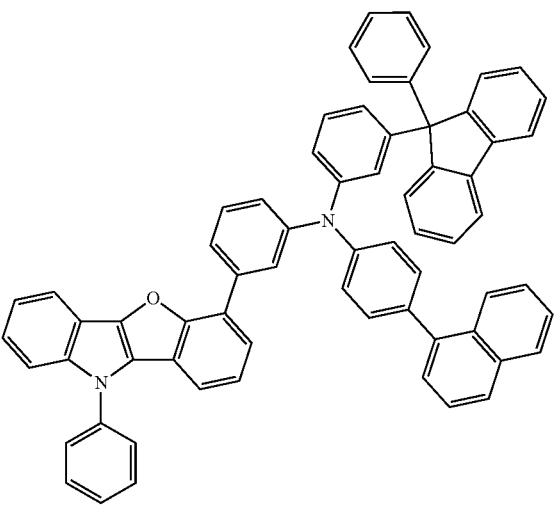
A136
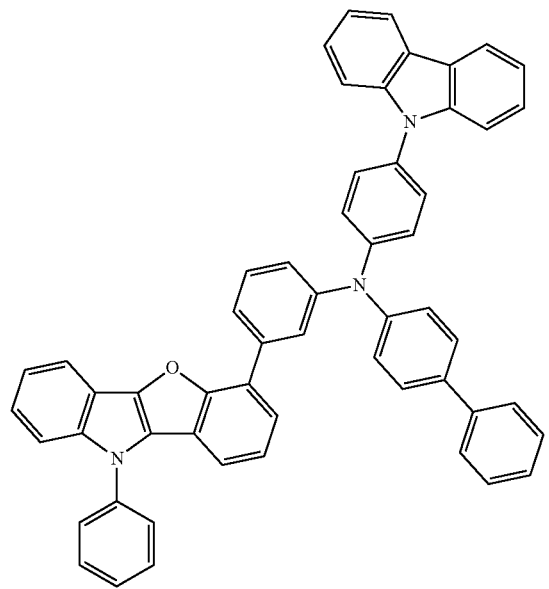

A137
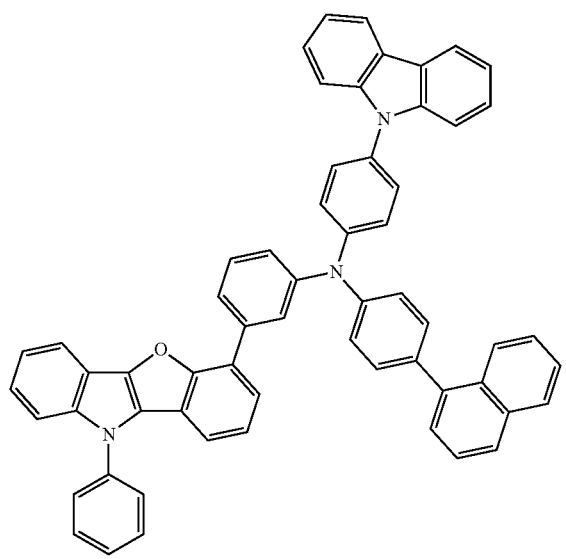
A138
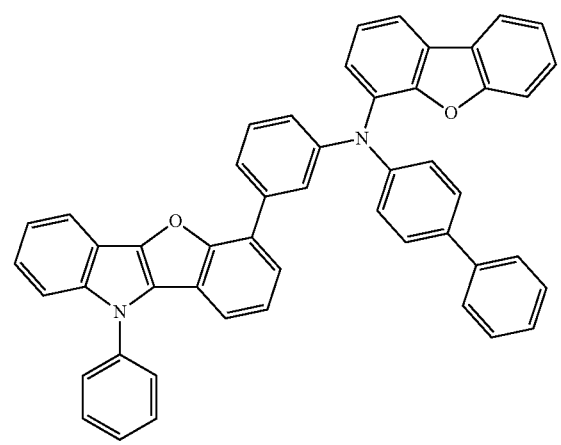
A139
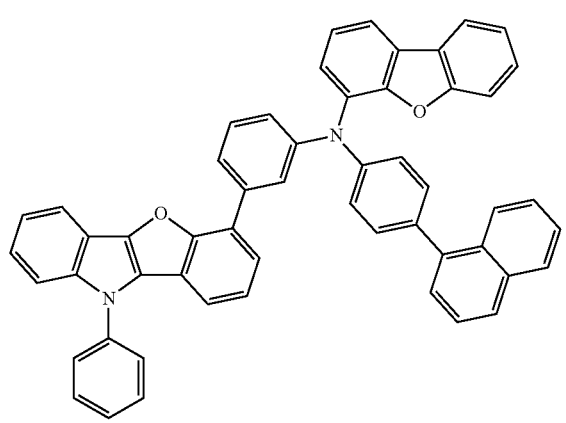
A140
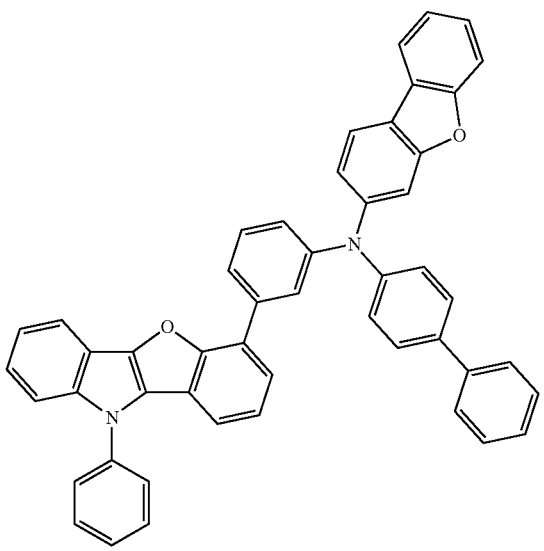
A141
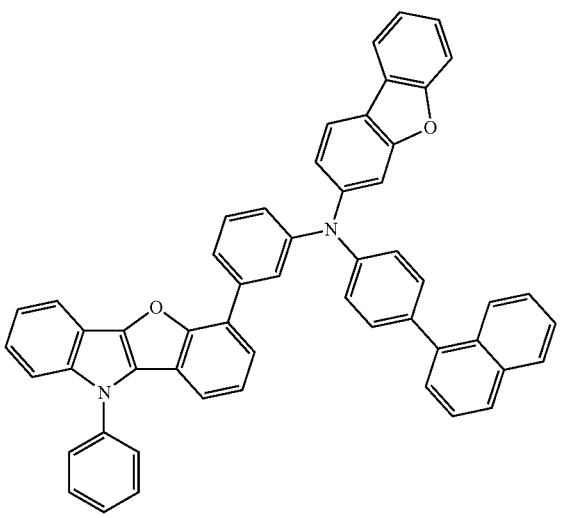
A142
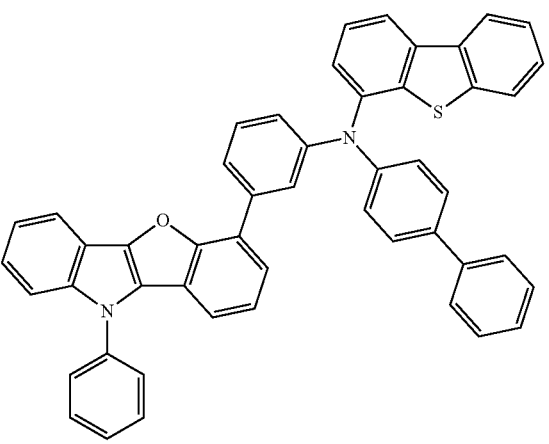

A143
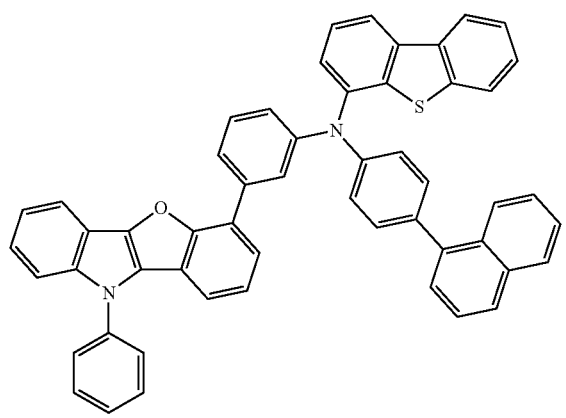
A144
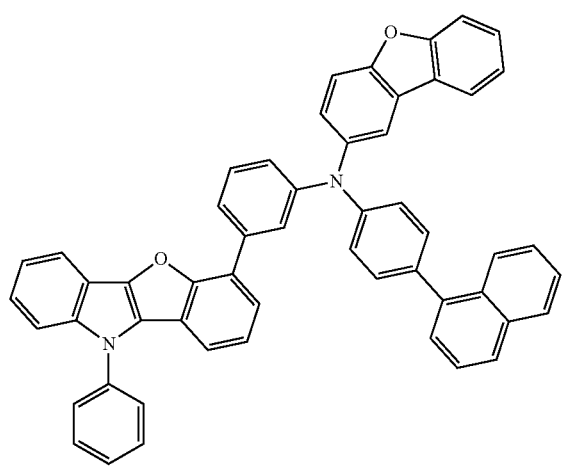
A145
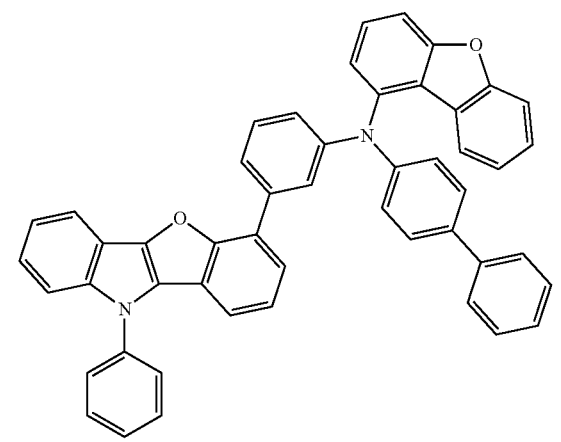
A146
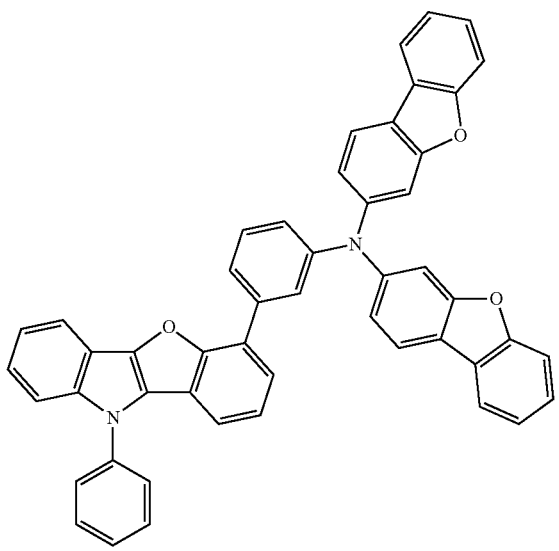
A147
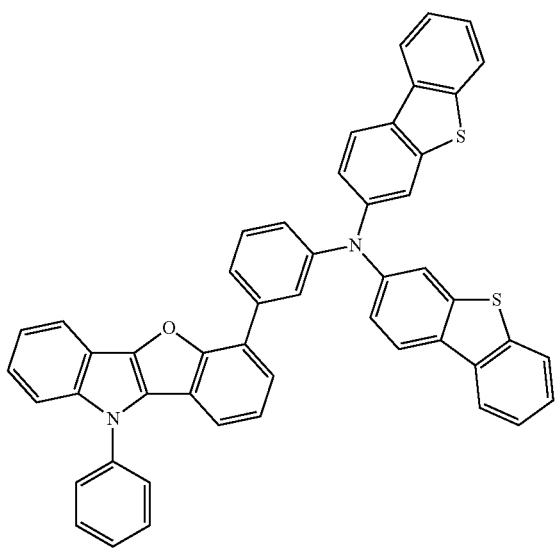
A148
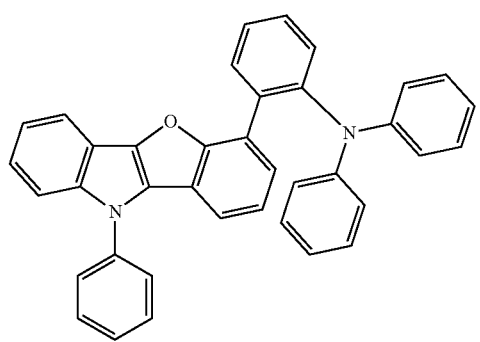

A149
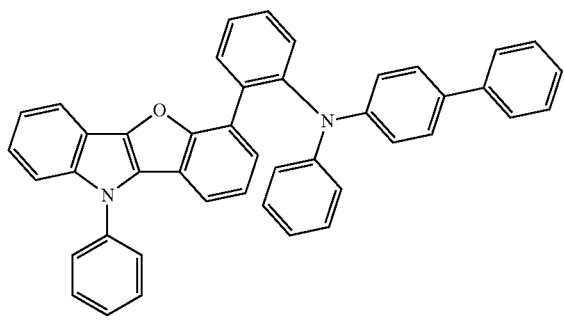
A153
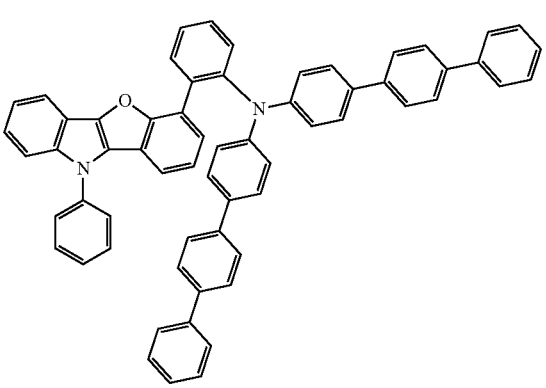
A150
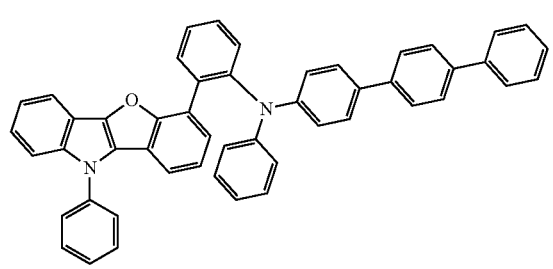
A154
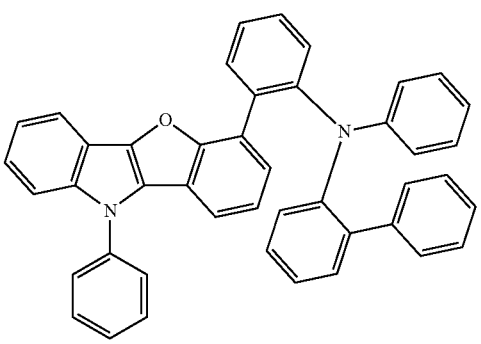
A151
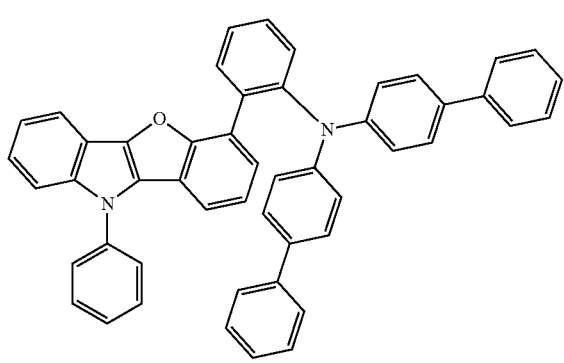
A155
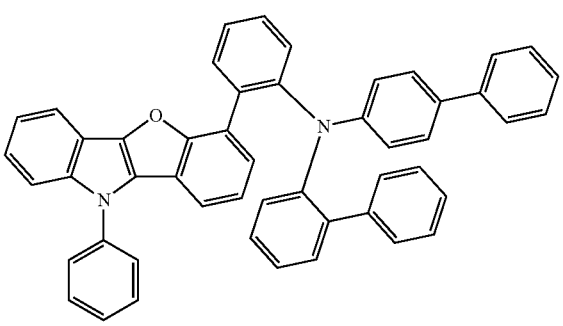
A152
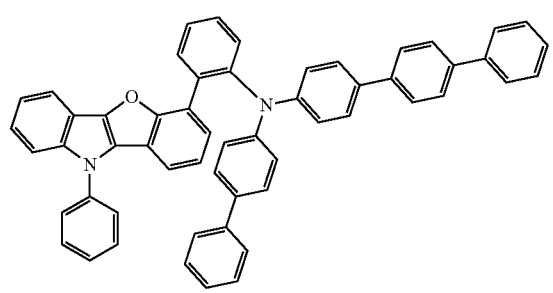
A156
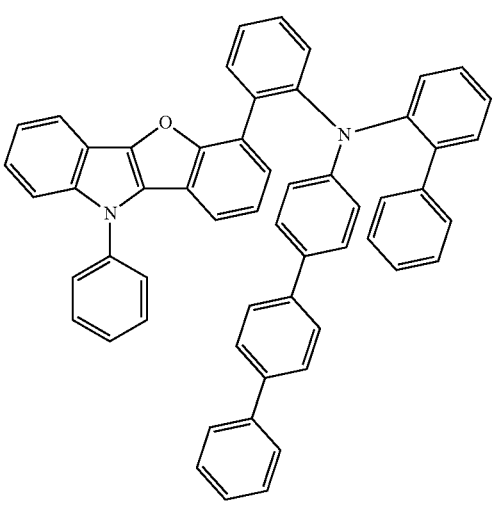

A157
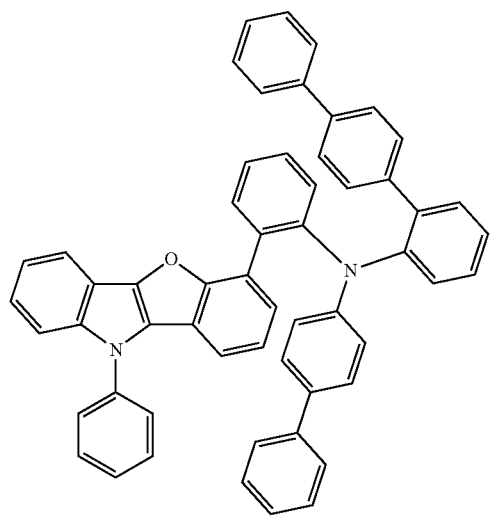
A158
A159
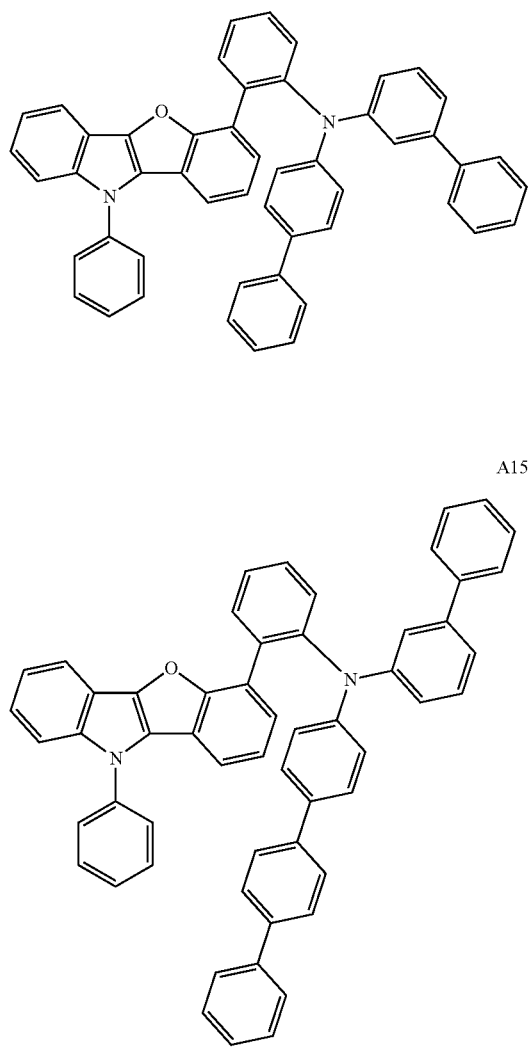
A160
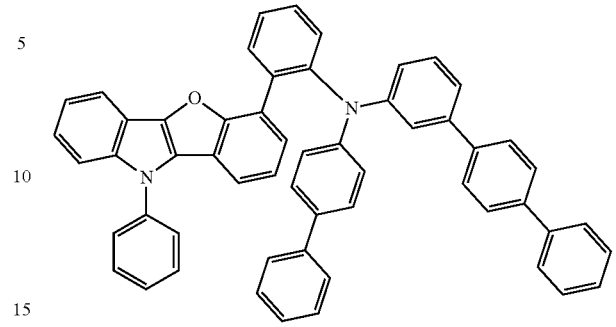
A161
A162
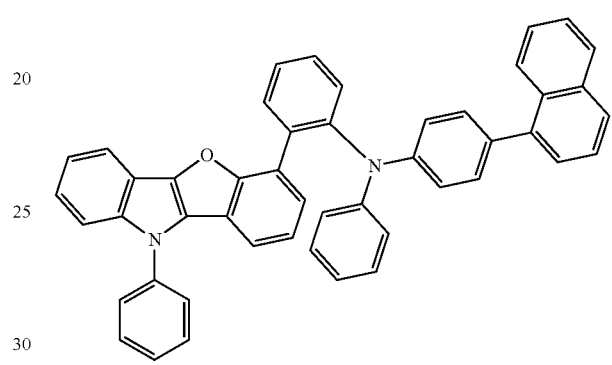
A163
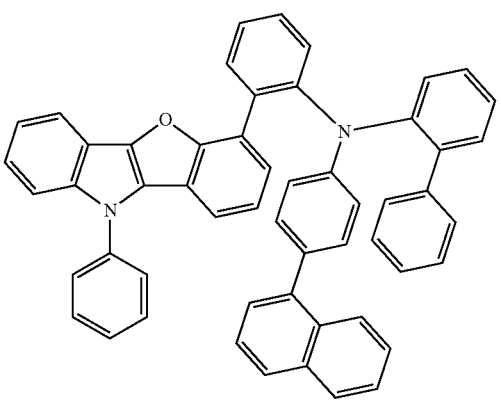

A164
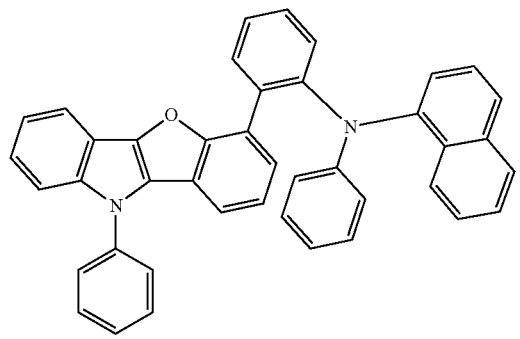
A165
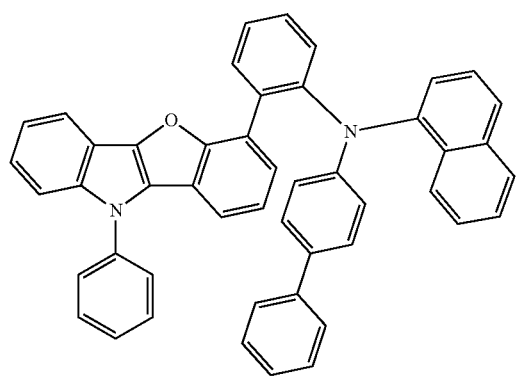
A166
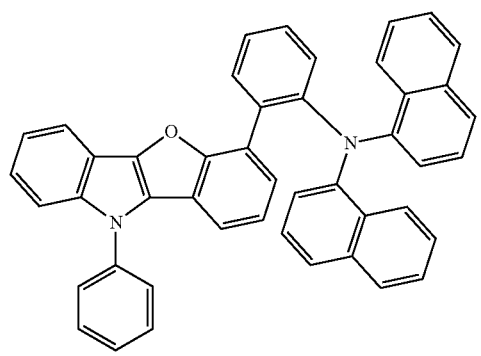
A167
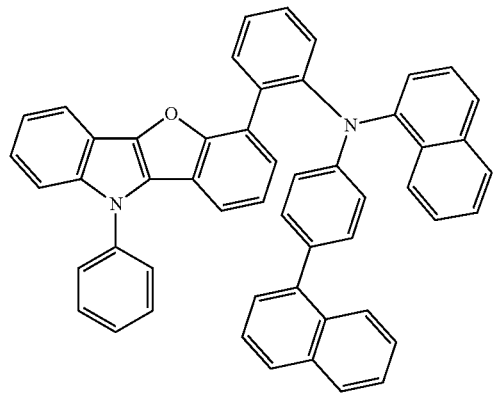
A168
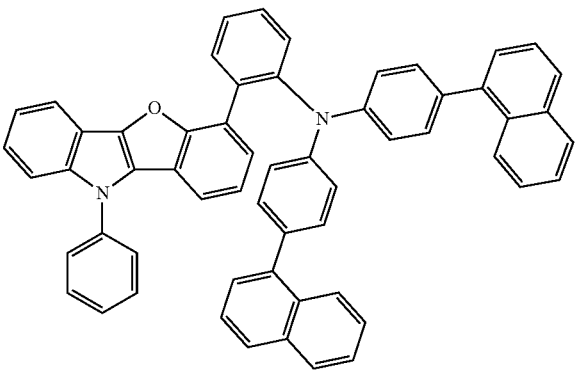
A169
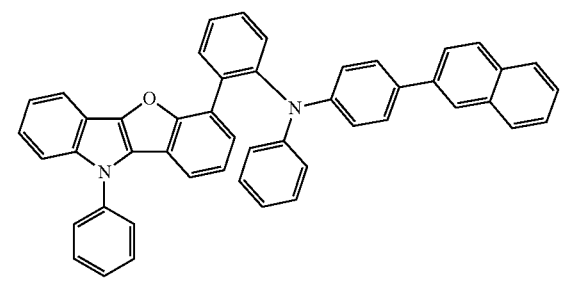
A170
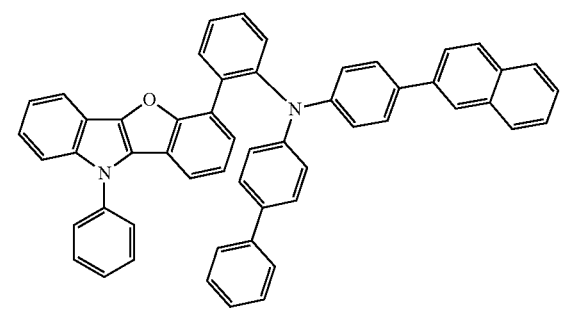
A171
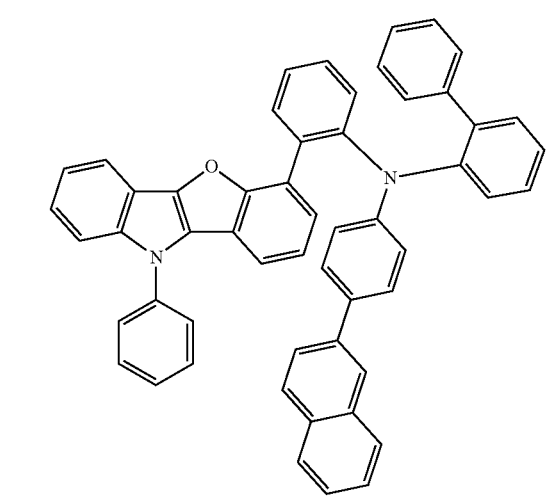

-continued
A172
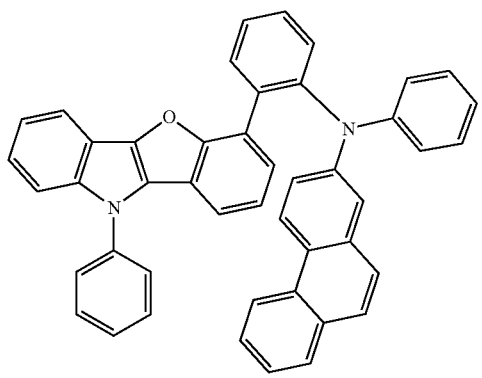
A176
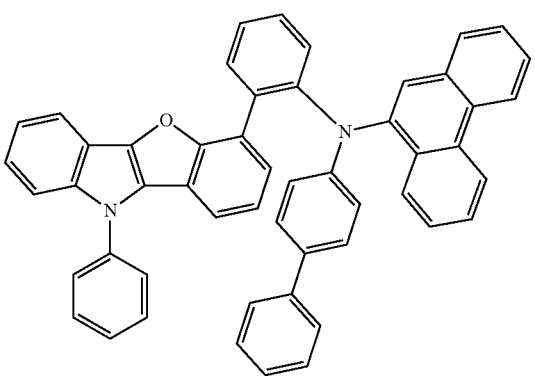
A173
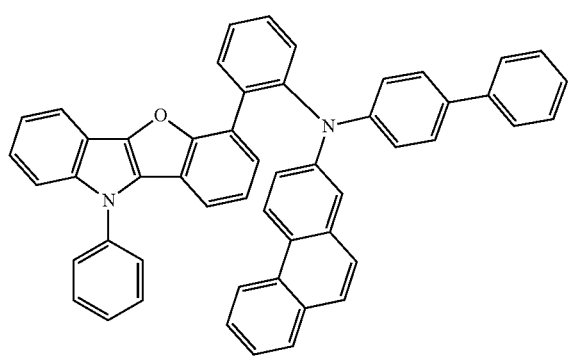
A177
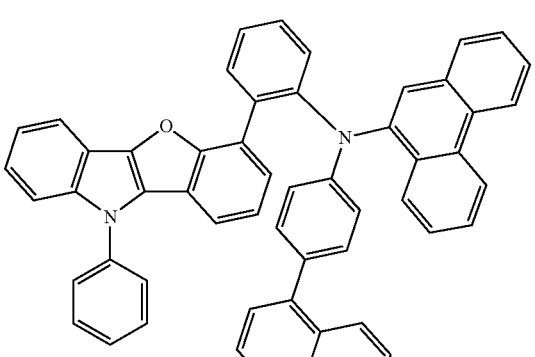
A174
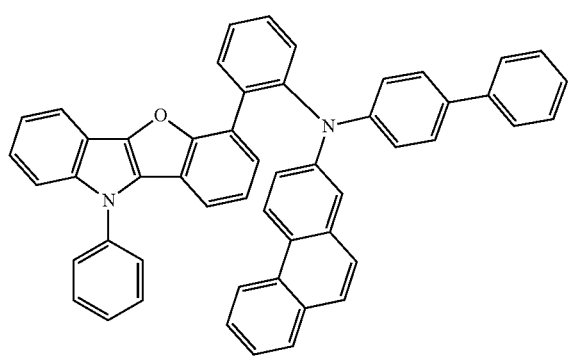
A178
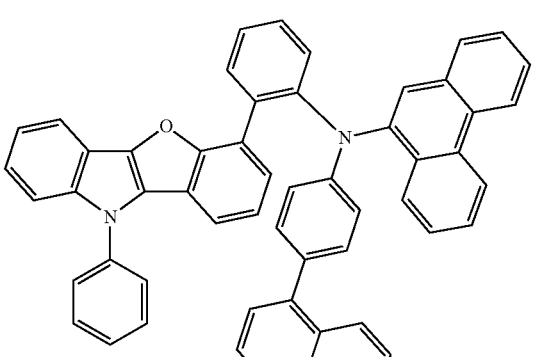
A175
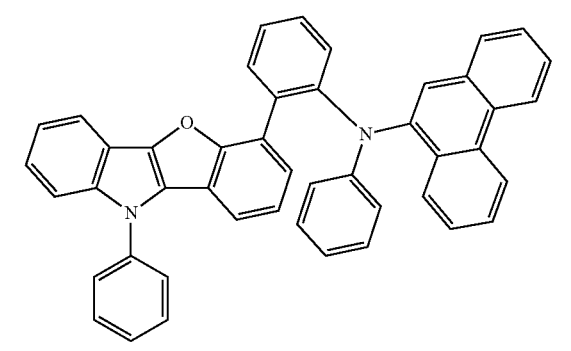
A179
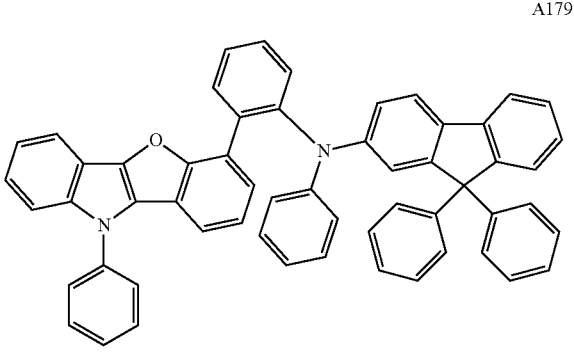

A180
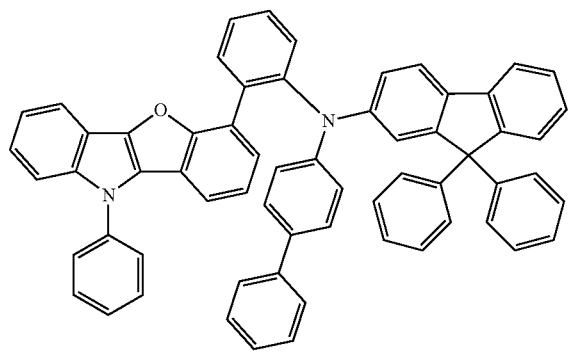
A184
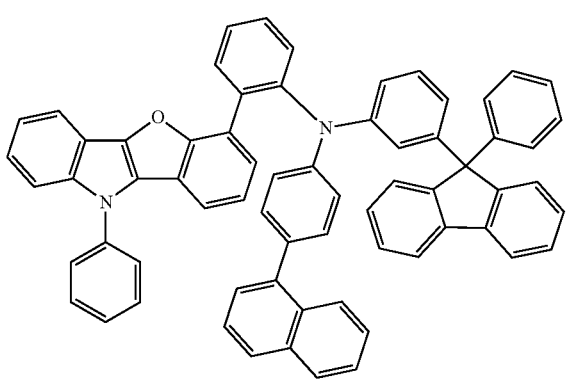
A181
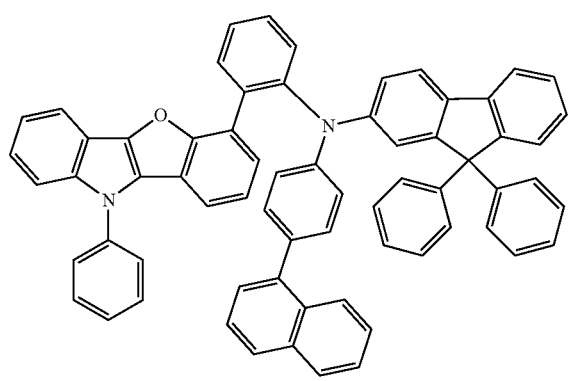
A185
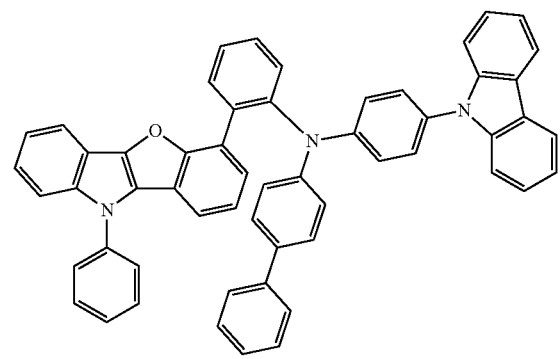
A182
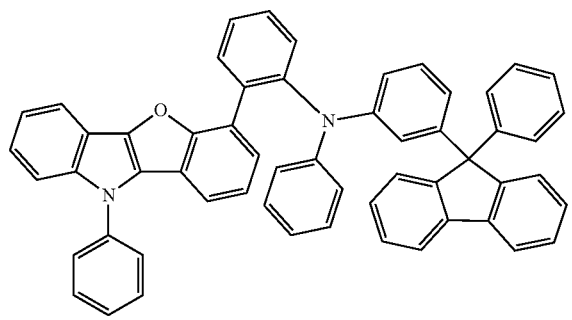
A186
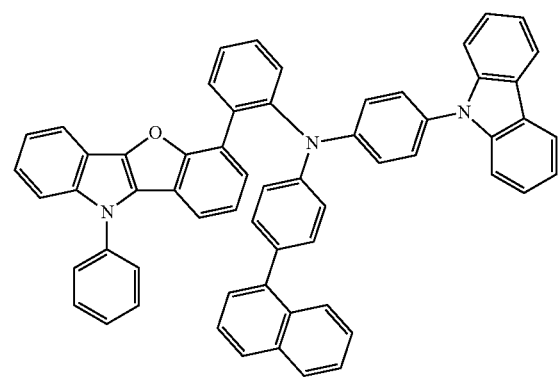
A183
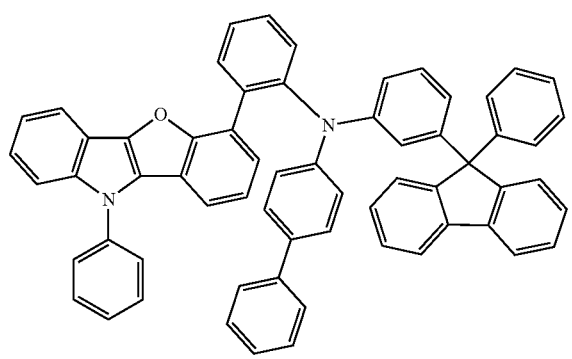
A187
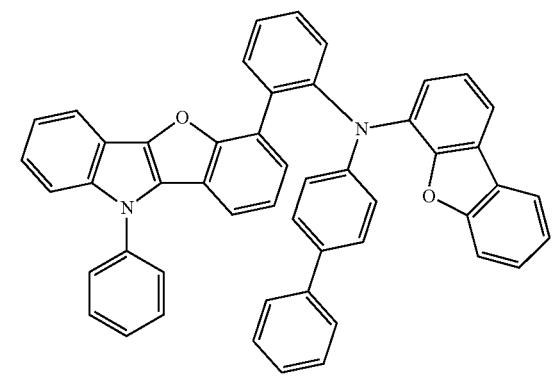

A188
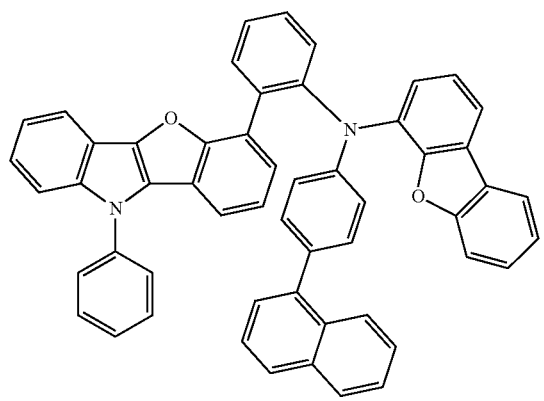
A189
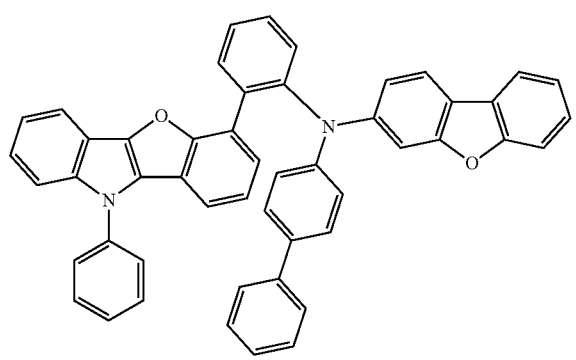
A190
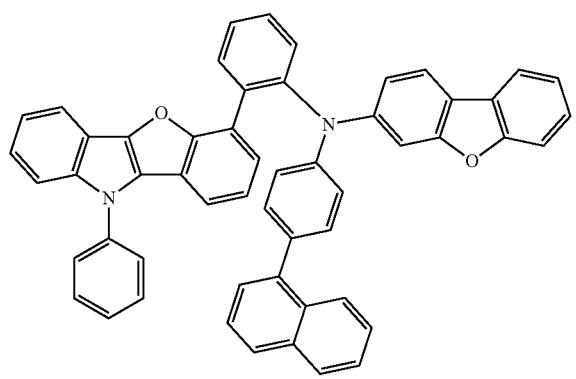
A191
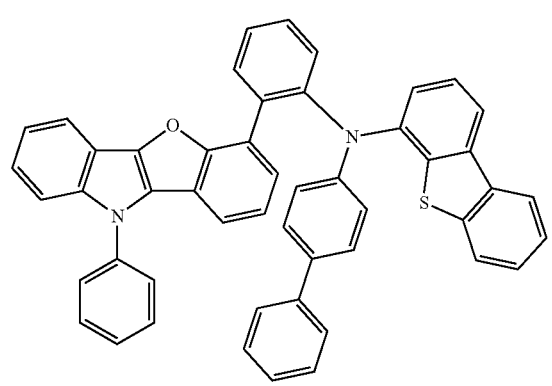
A192
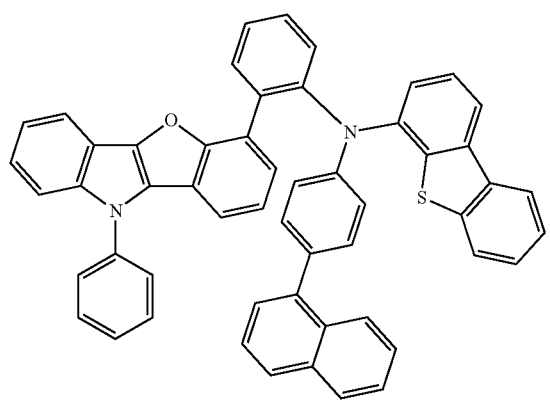
A193
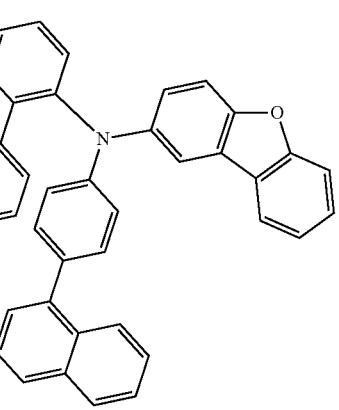
A194
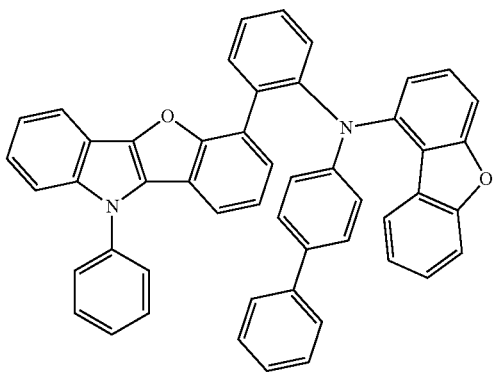
A195
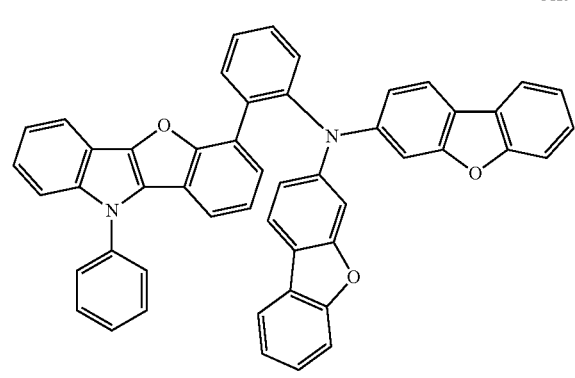

A196
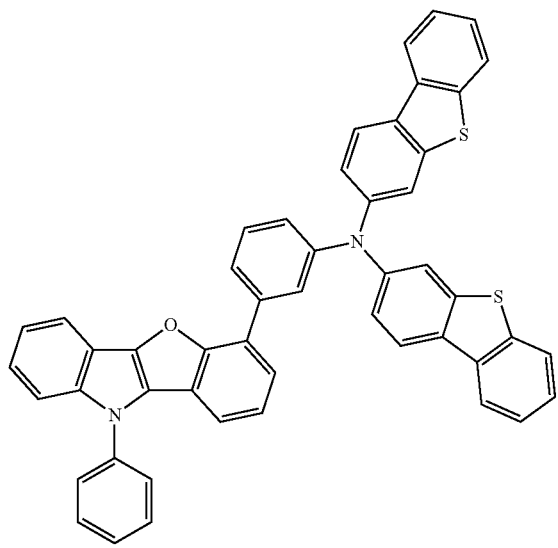
A197
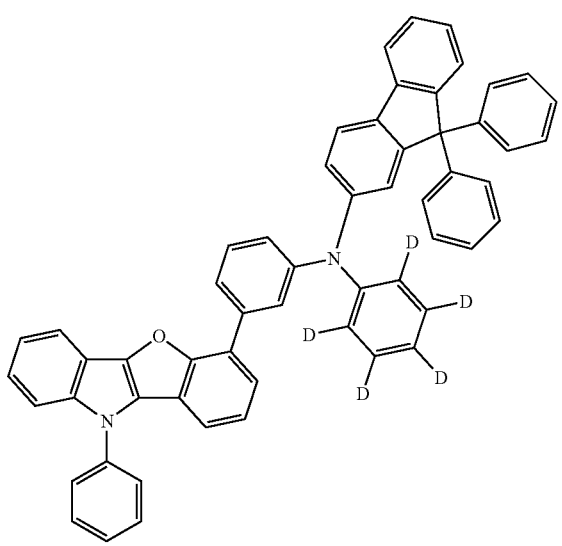
A198
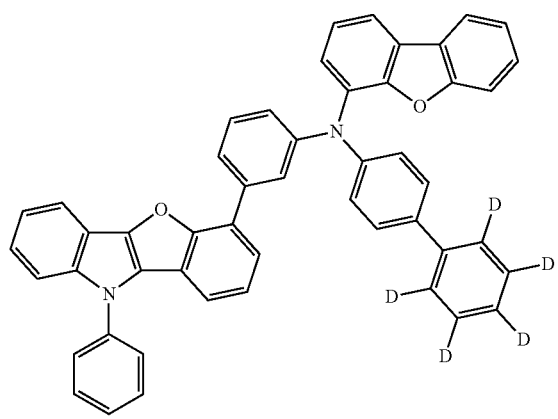
A199
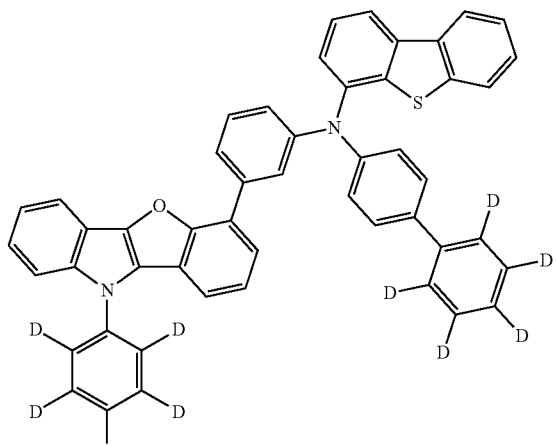
A200
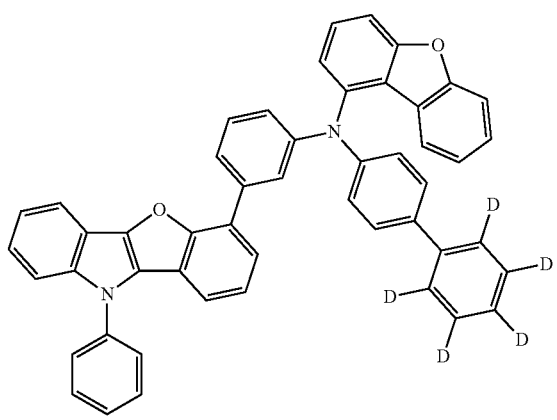
A201
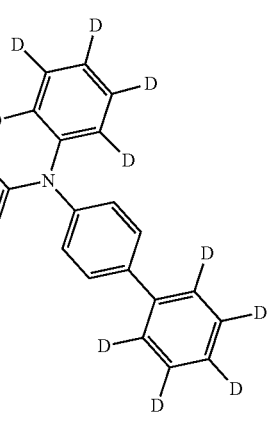

Compound Group 2
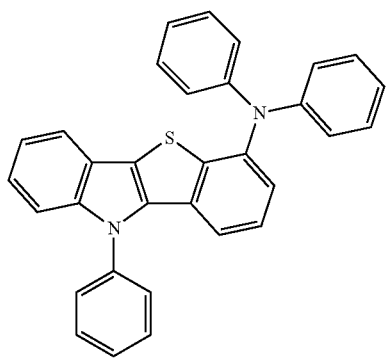
B1
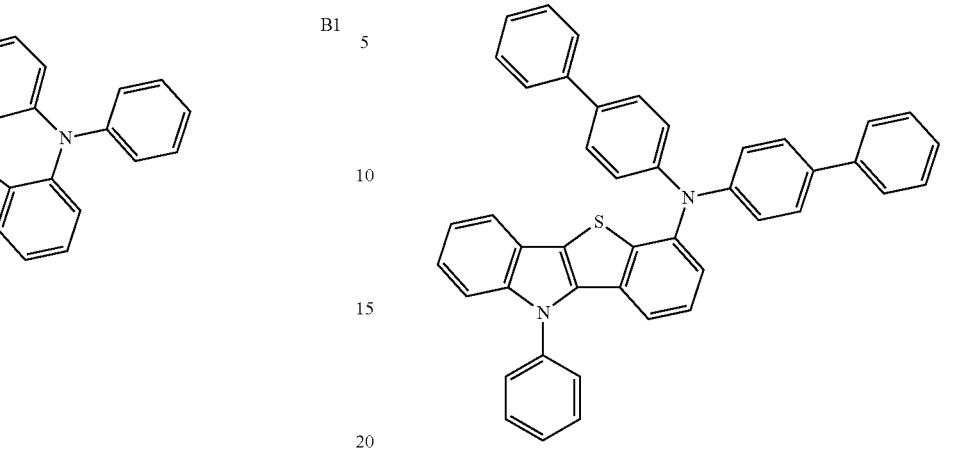
B4
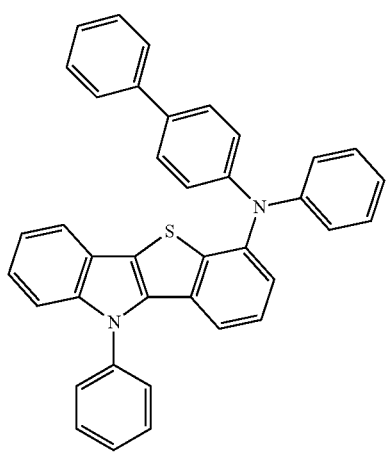
B2
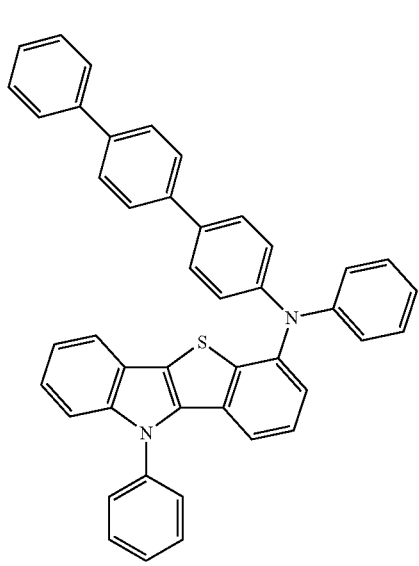
B3
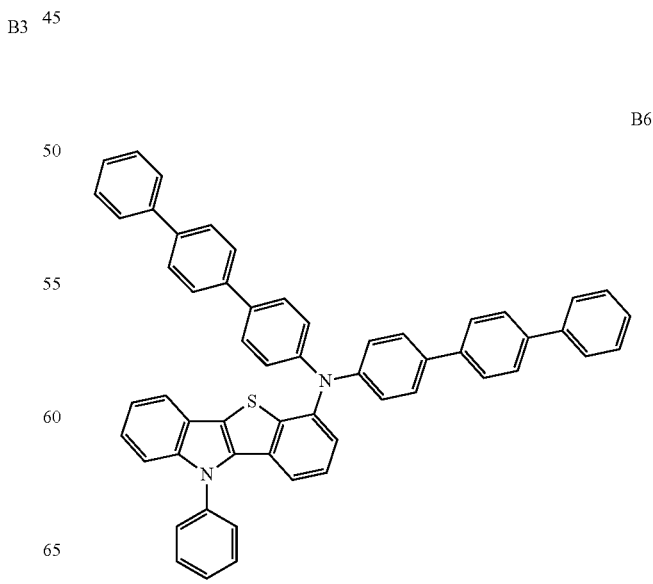
B5
B6

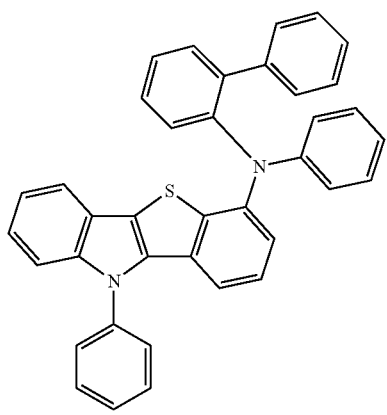
B7
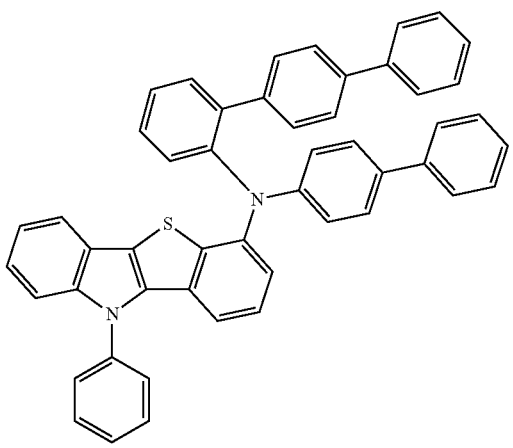
B10
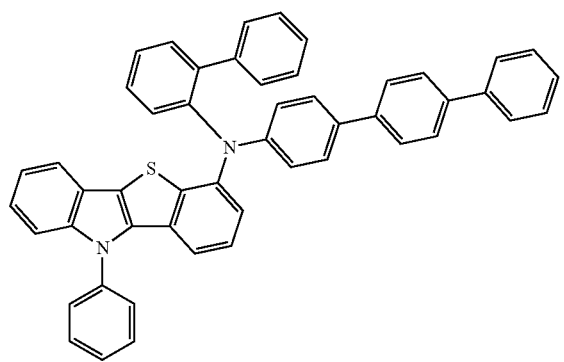
B8
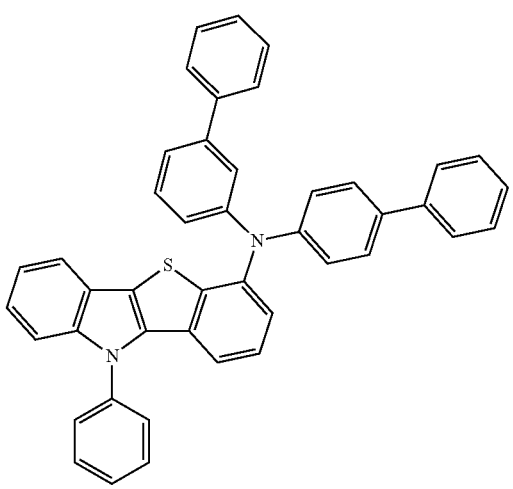
B11
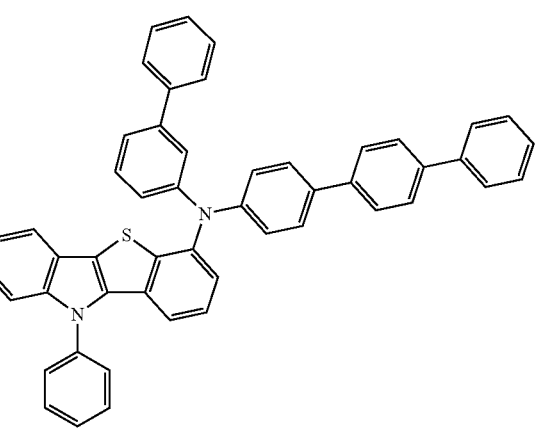
B12
B9

B13
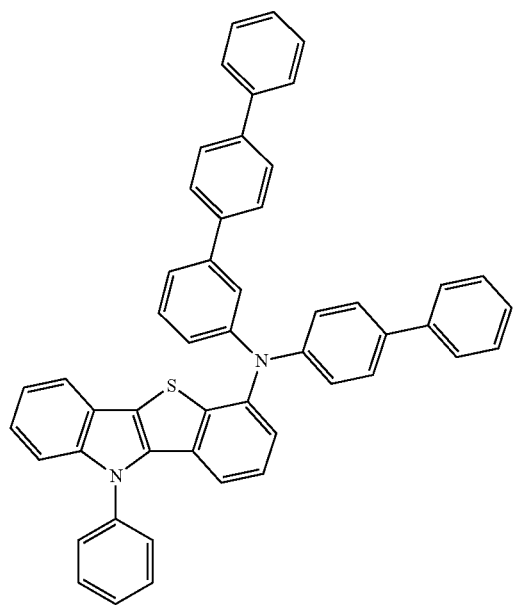
B14
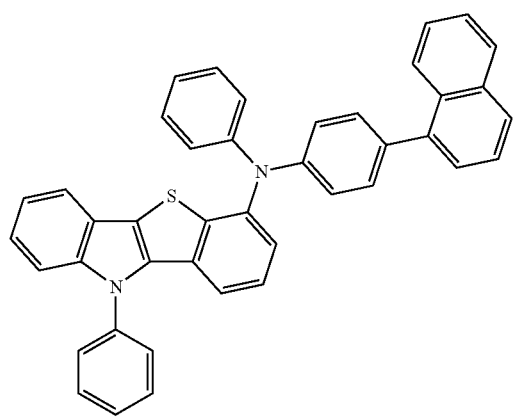
B15
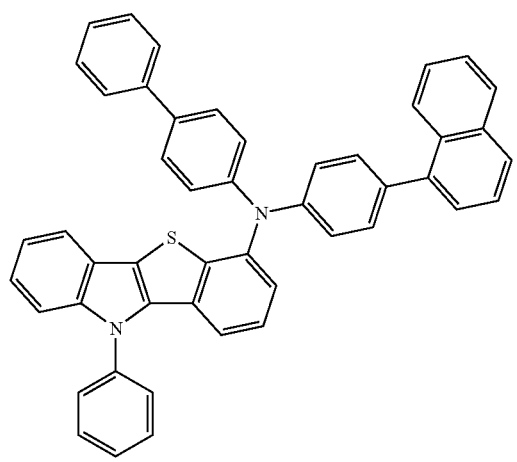
B16
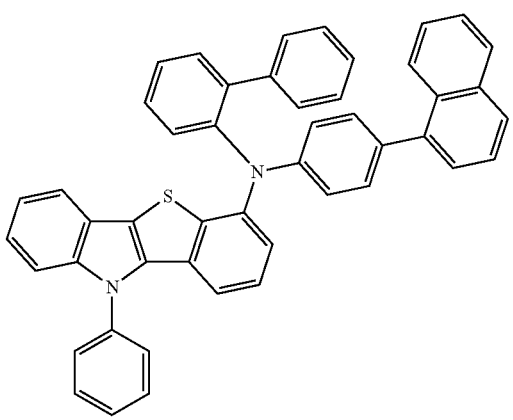
B17
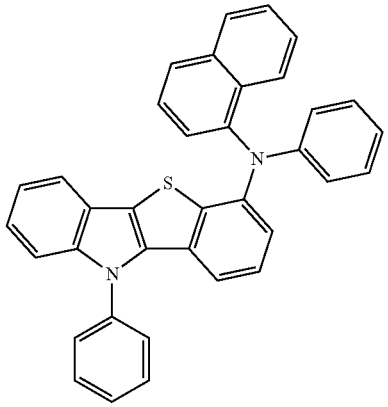
B18
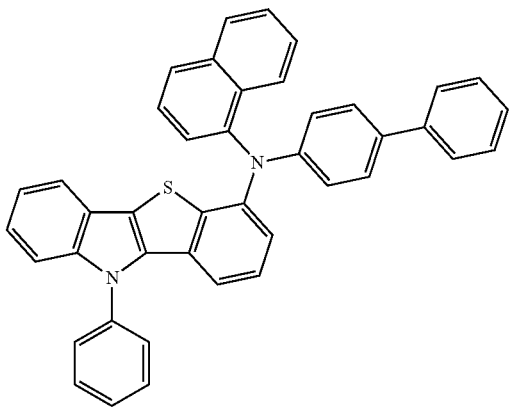

B19
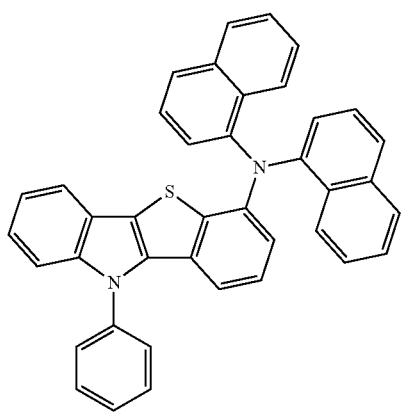
B20
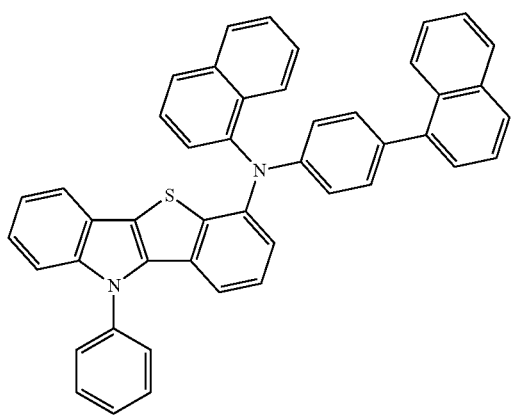
B21
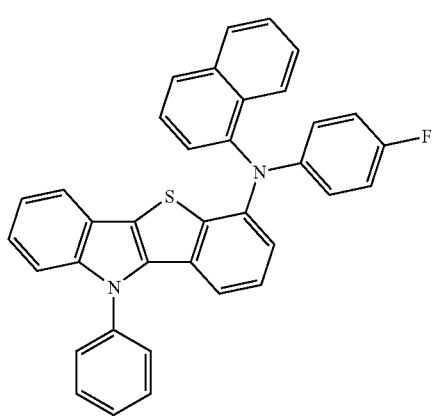
B22
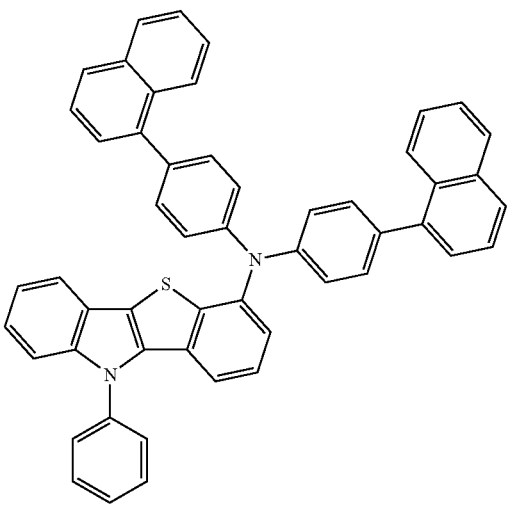
B23
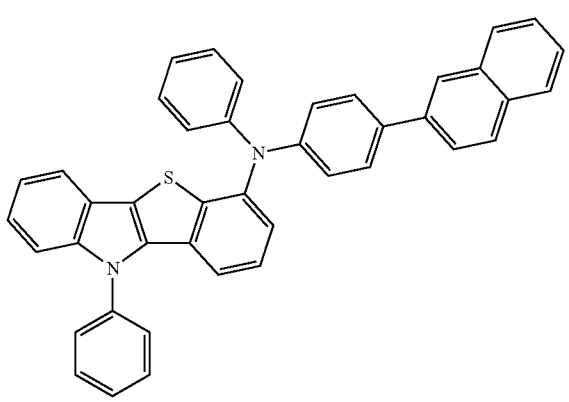
B24
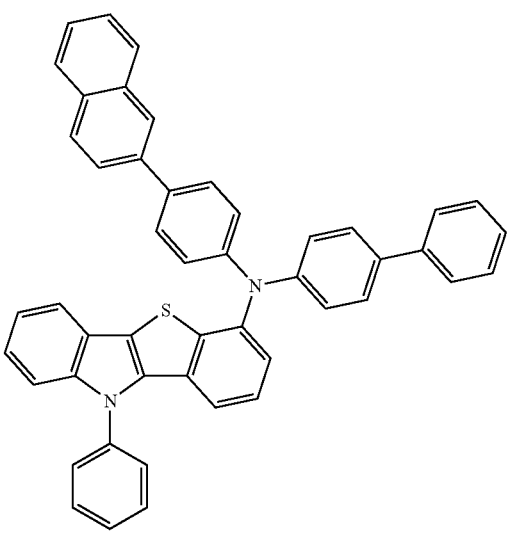

B25
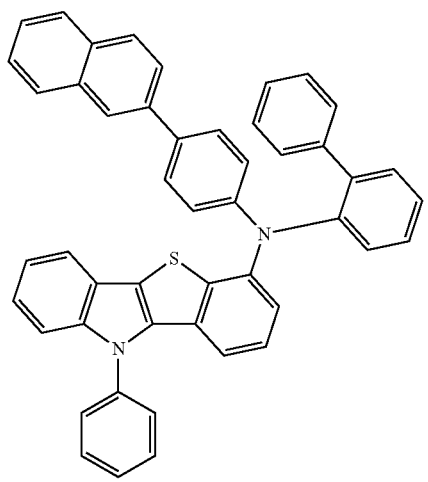
B28
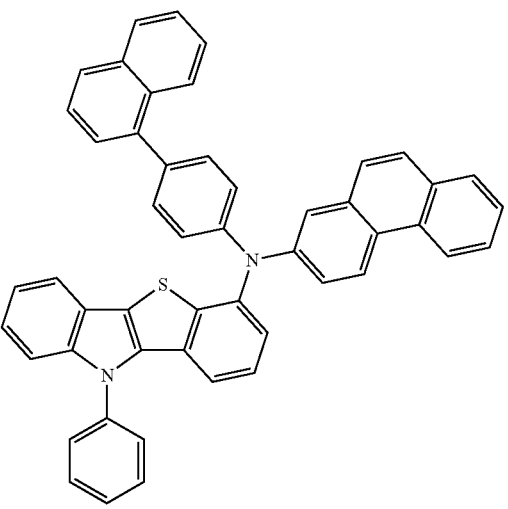
B26
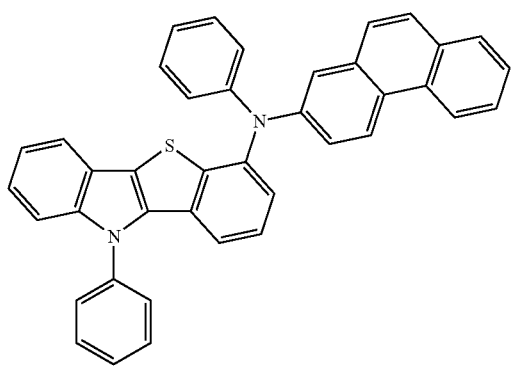
B29
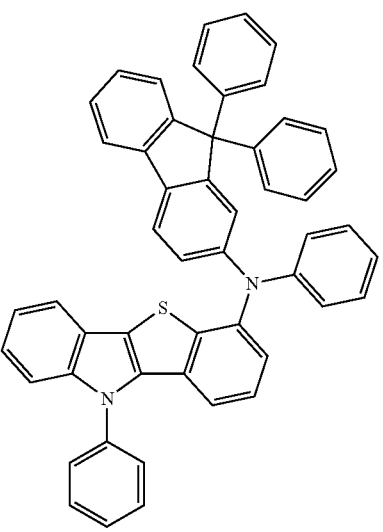
B27
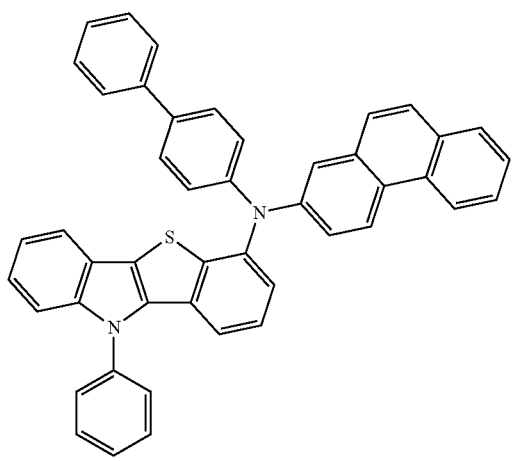
B30
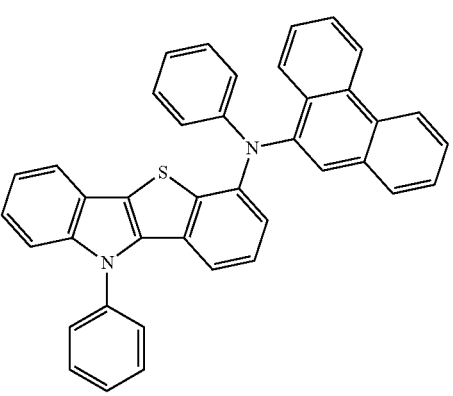

B31
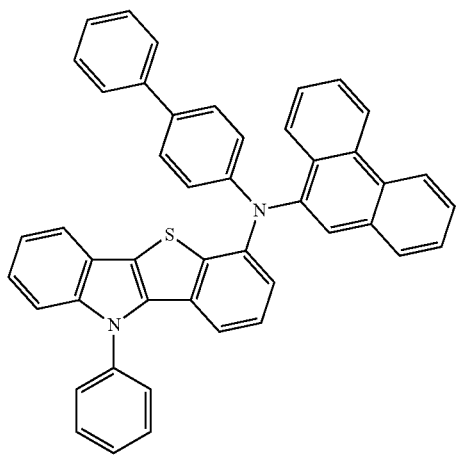
B32
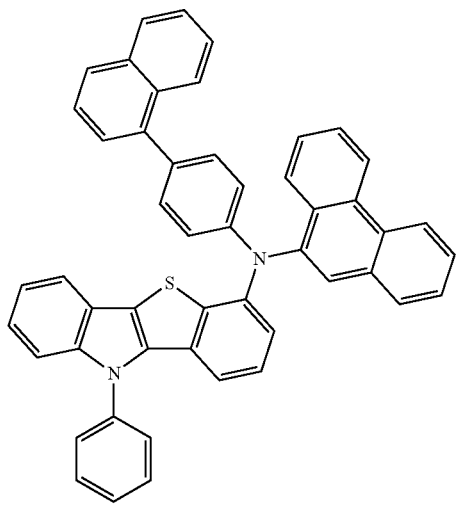
B33
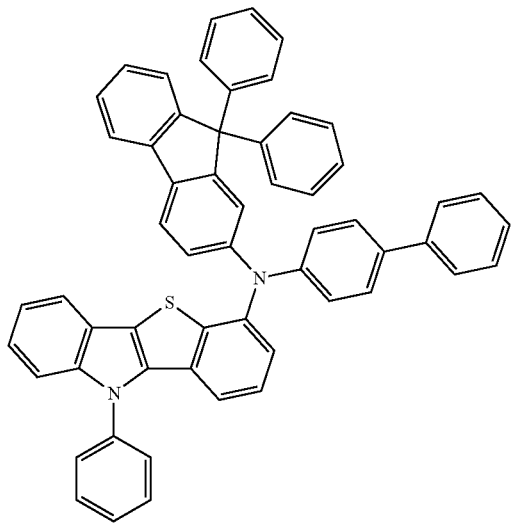
B34
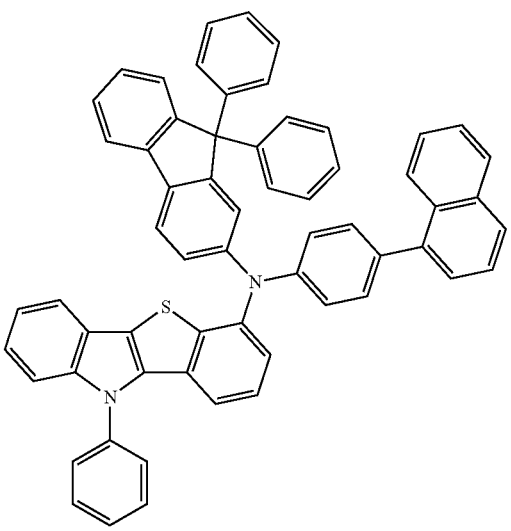
B35
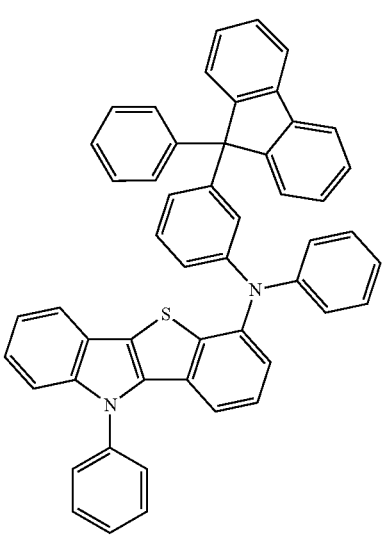
B36
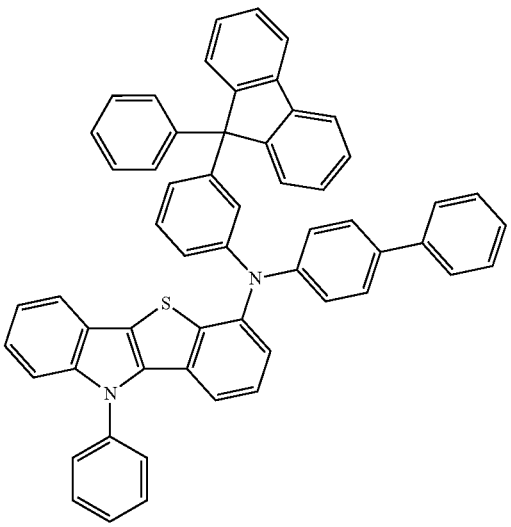

B37
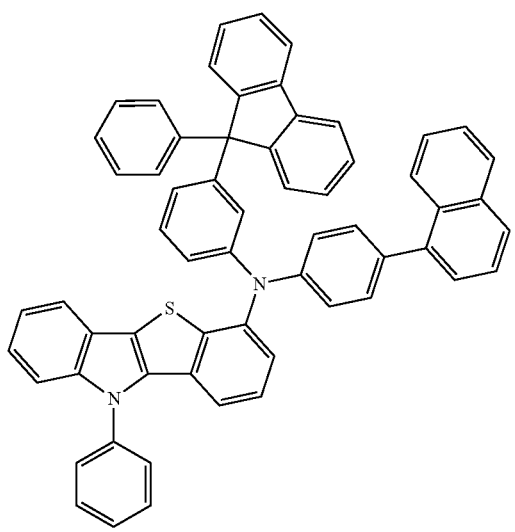
B38
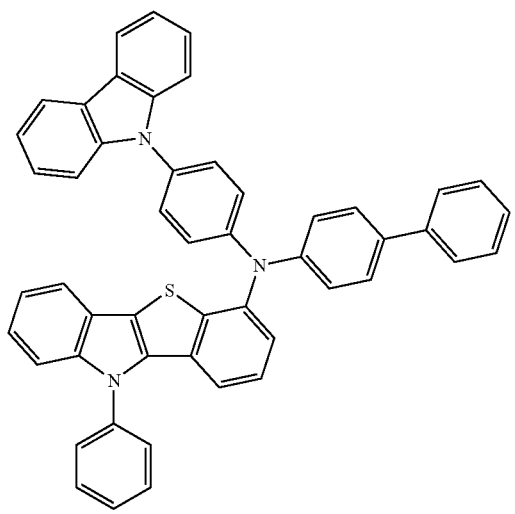
B39
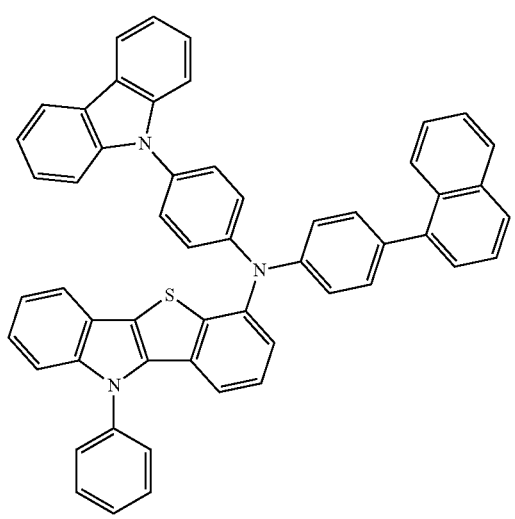
B40
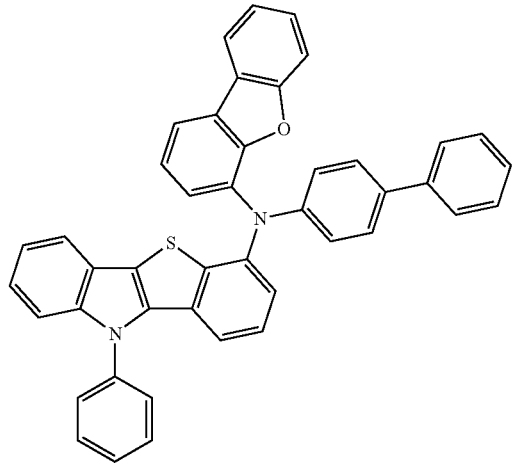
B41
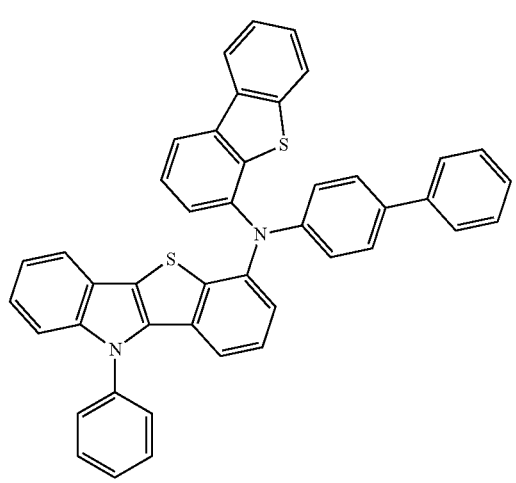
B42
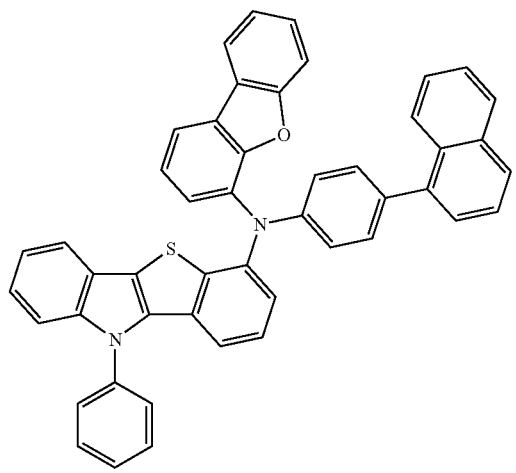

B43
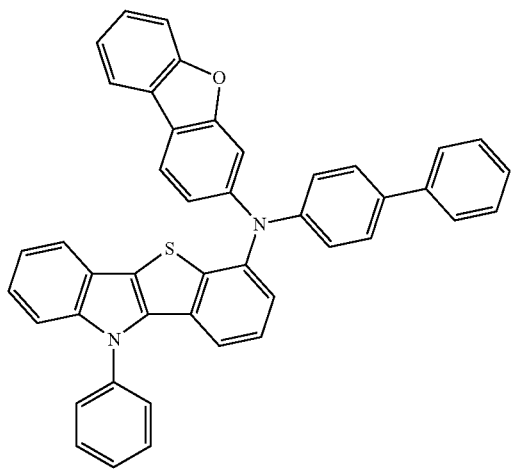
B44
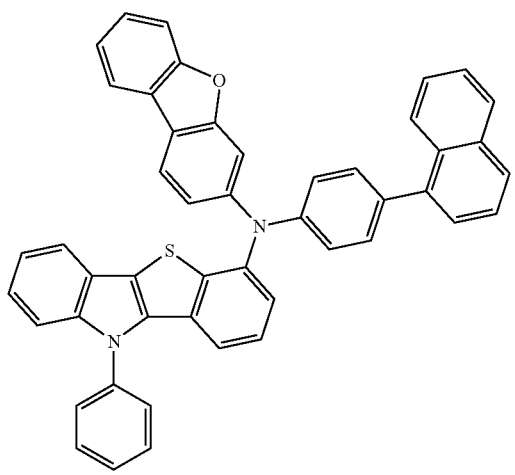
B45
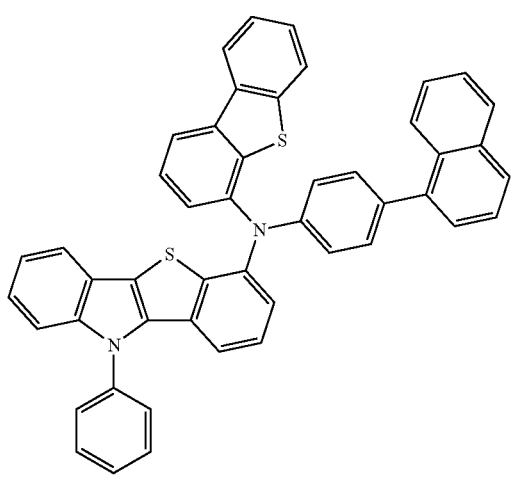
B46
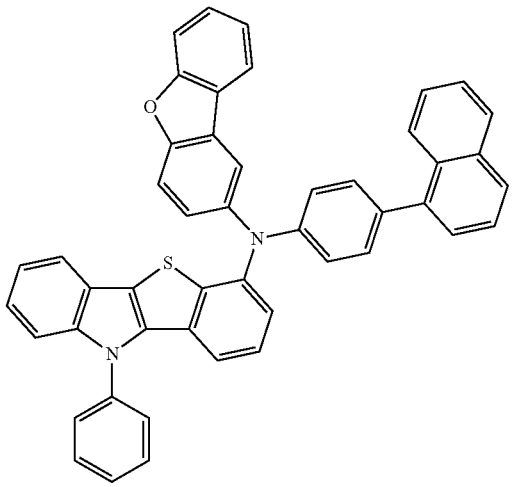
B47
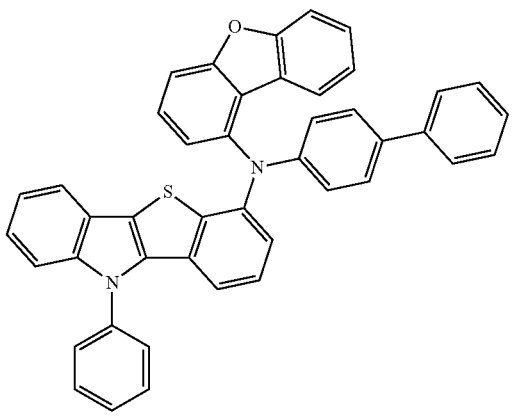
B48
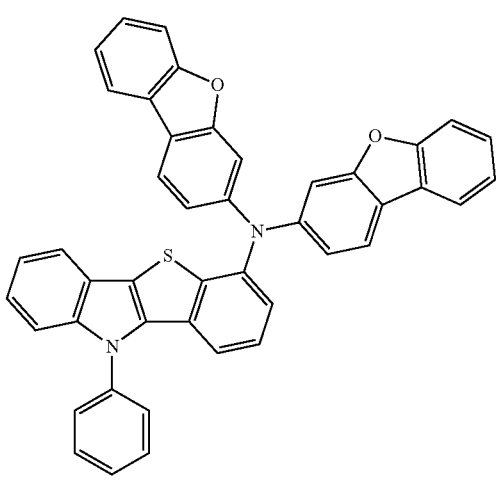

B49
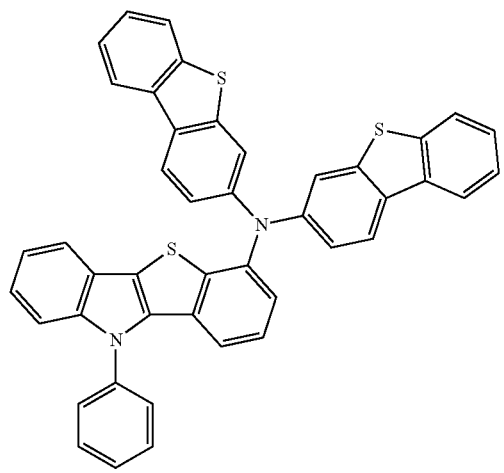
B50
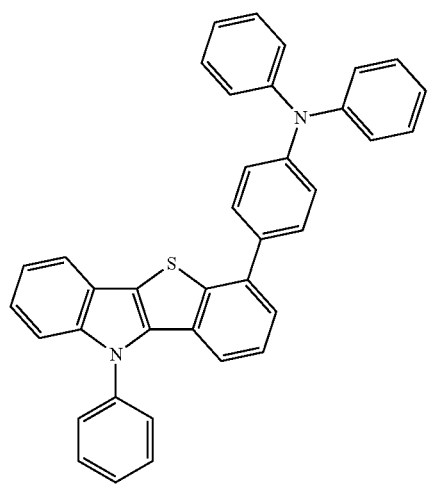
B51
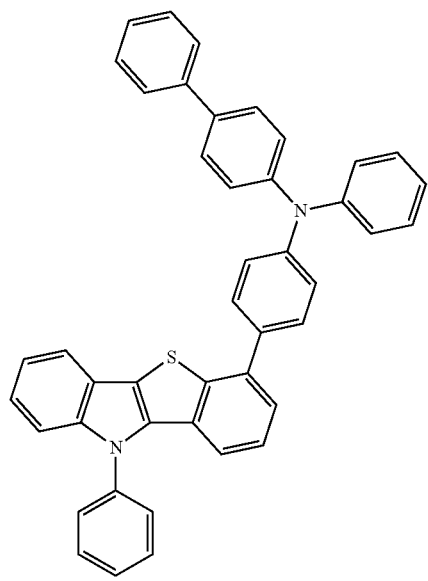
B52
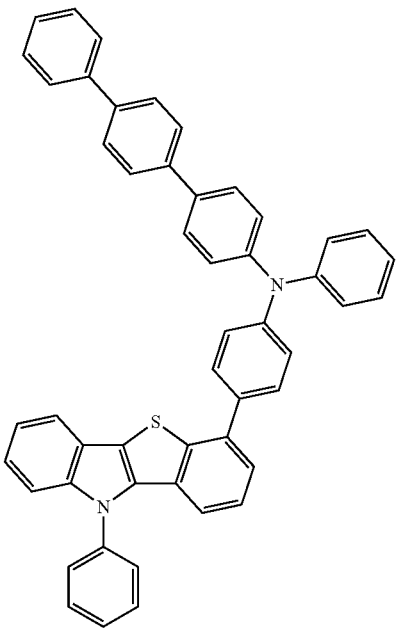
B53
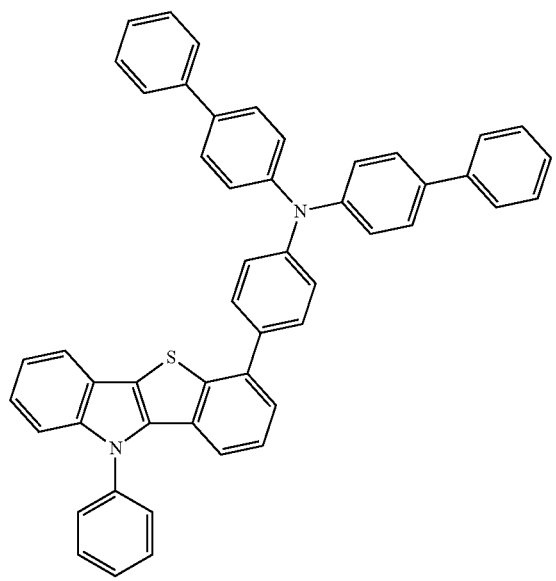

B54
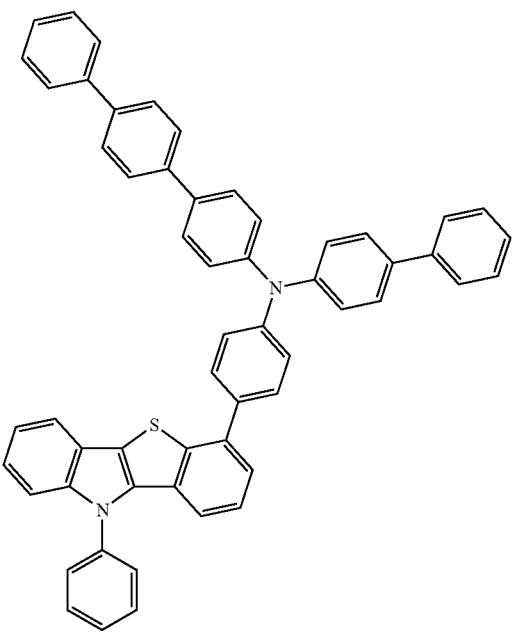
B55
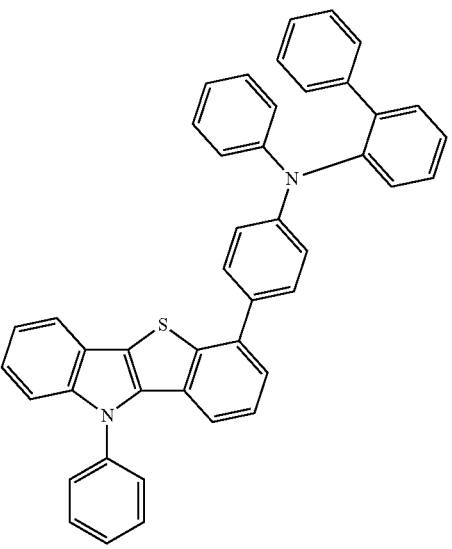
B56
B57
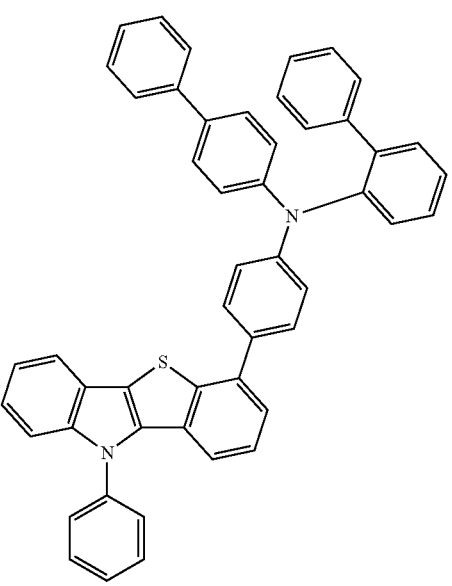
B58

-continued
B59
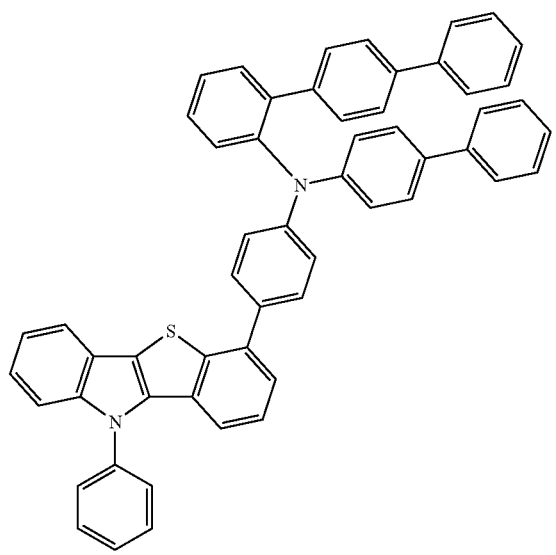
B60
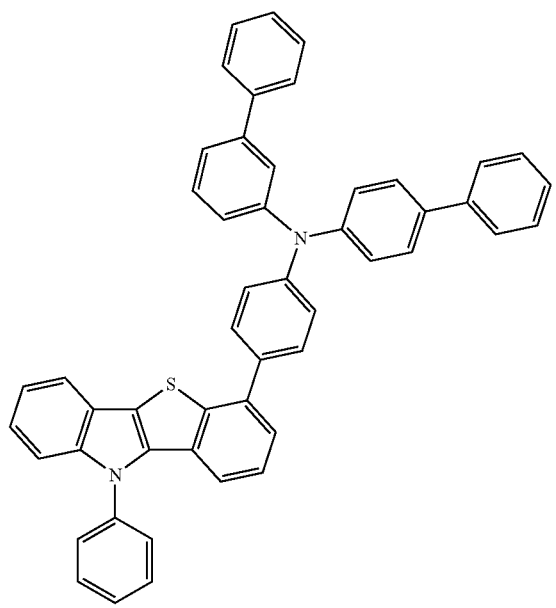
B61
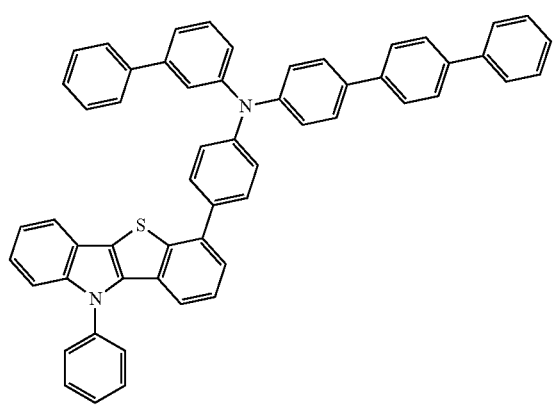
B62
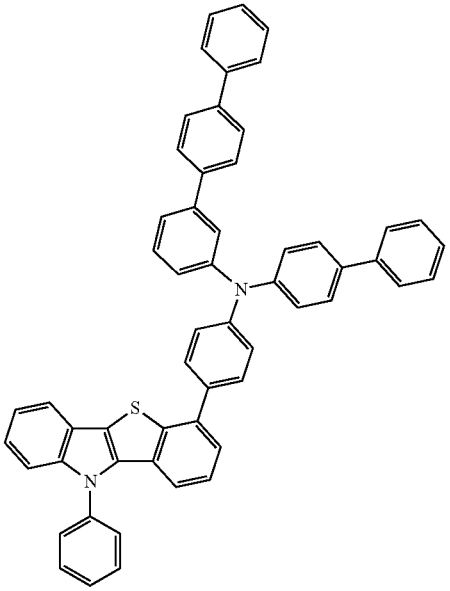
B63
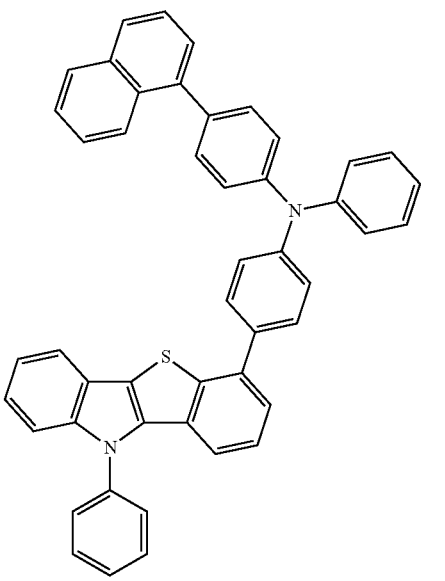

B64
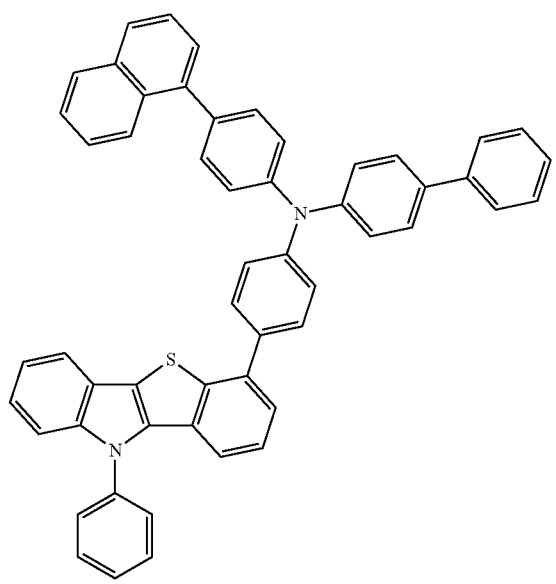
B65
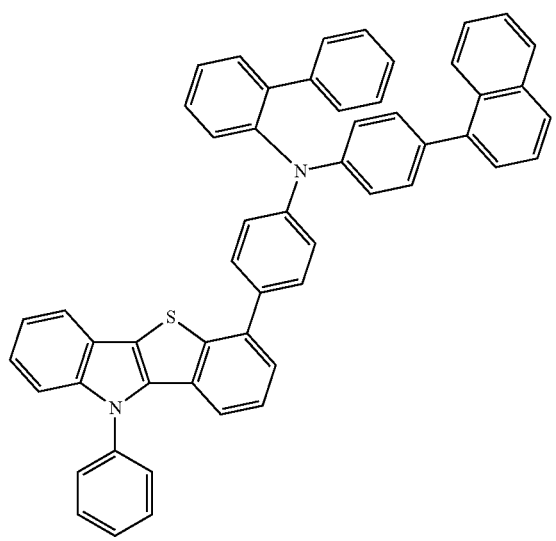
B66
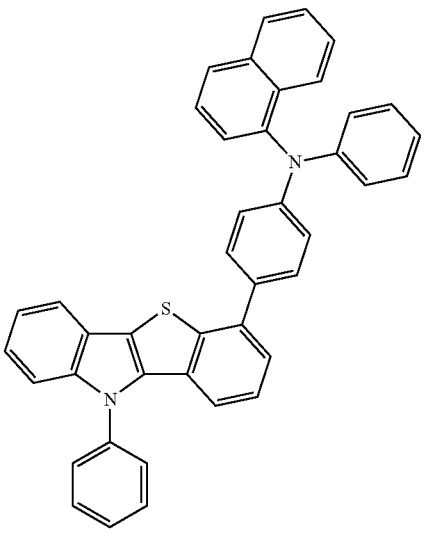
B67
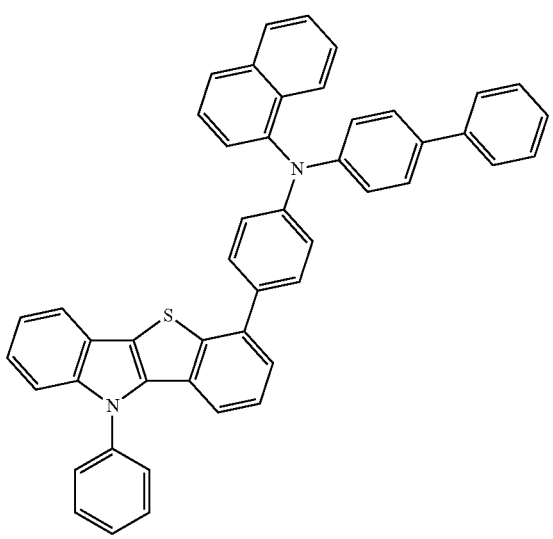
B68
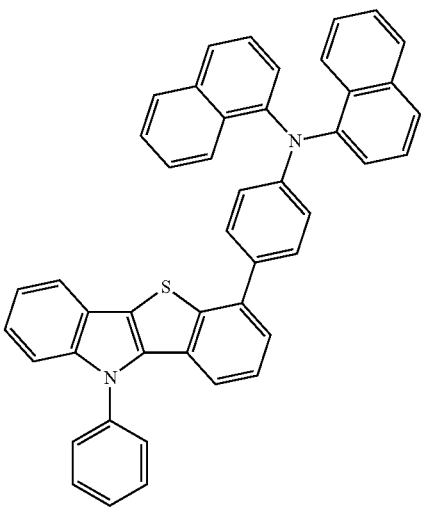

B69
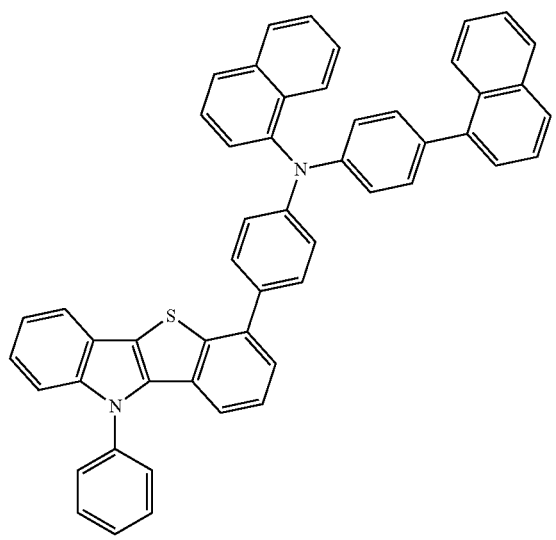
B70
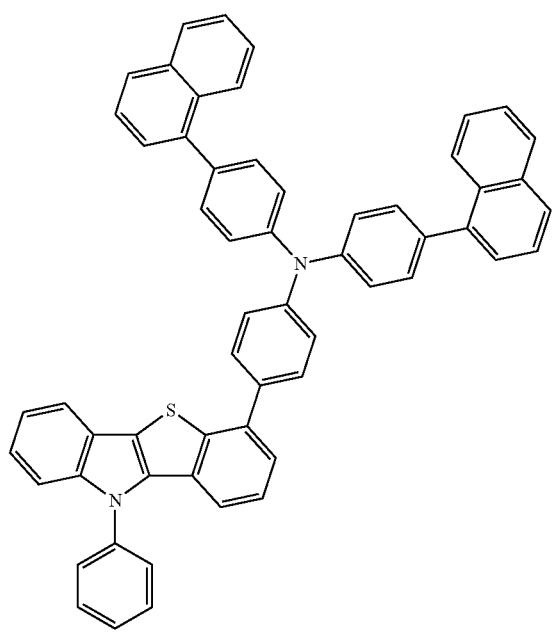
B71
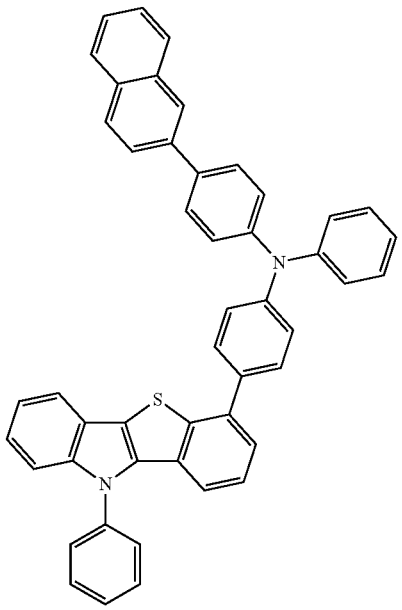
B72
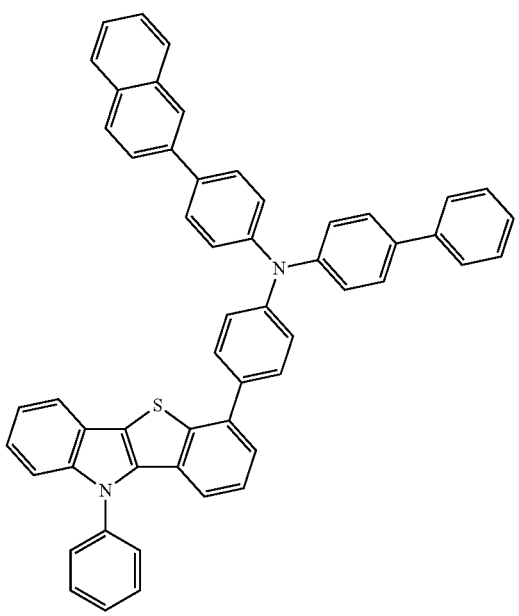

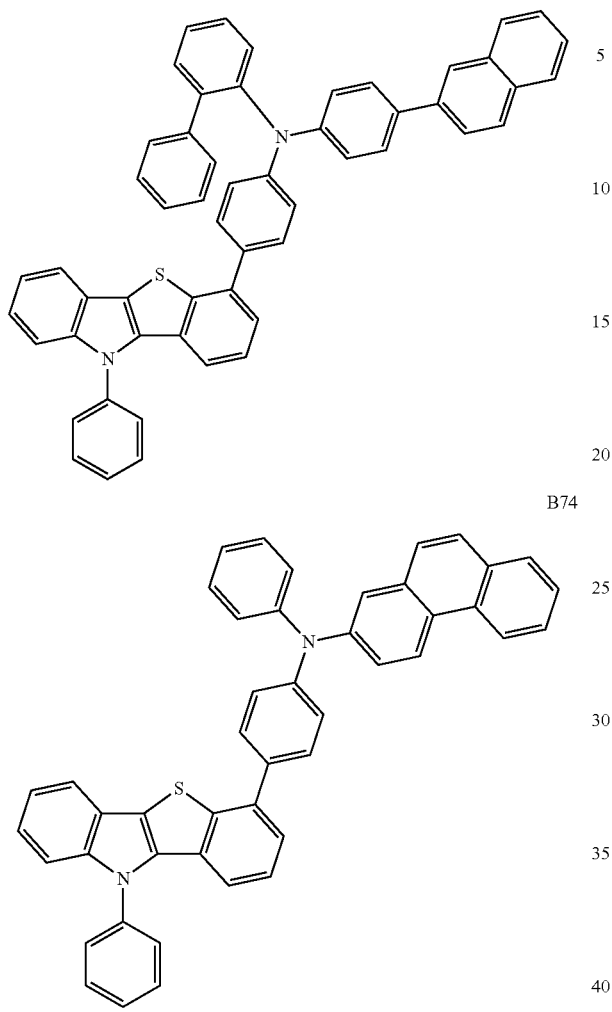
B73
B74
B75
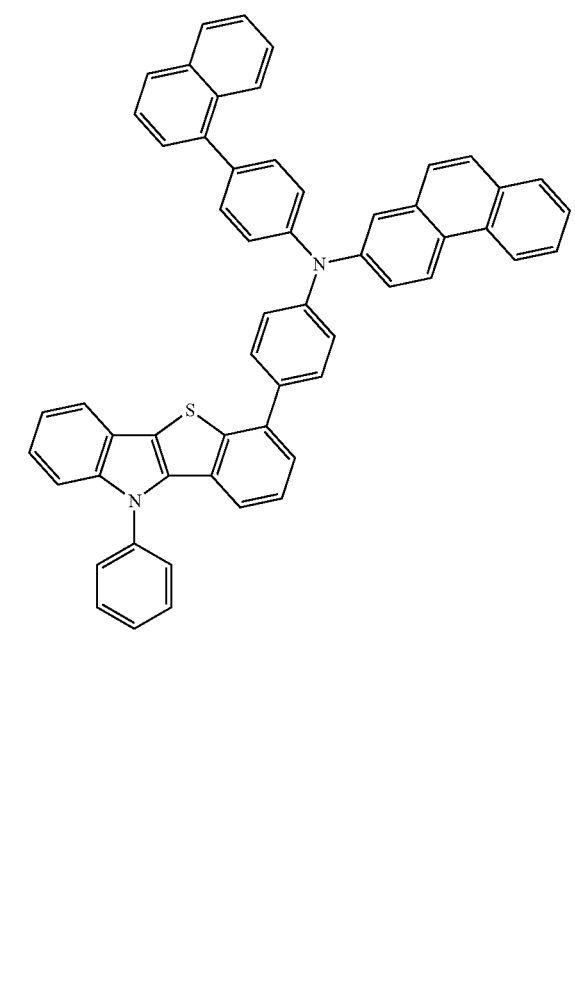
B76
B77

B78
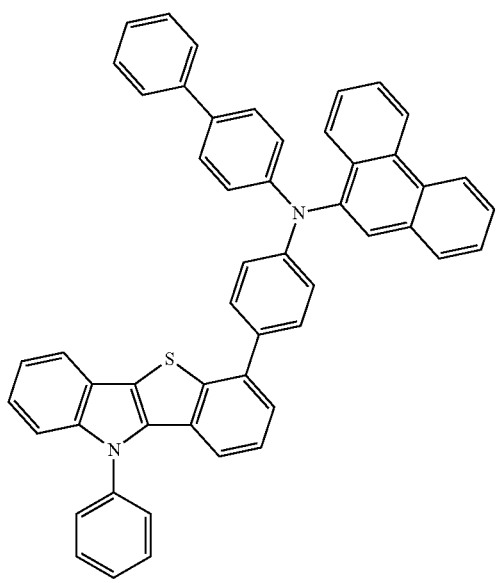
B79
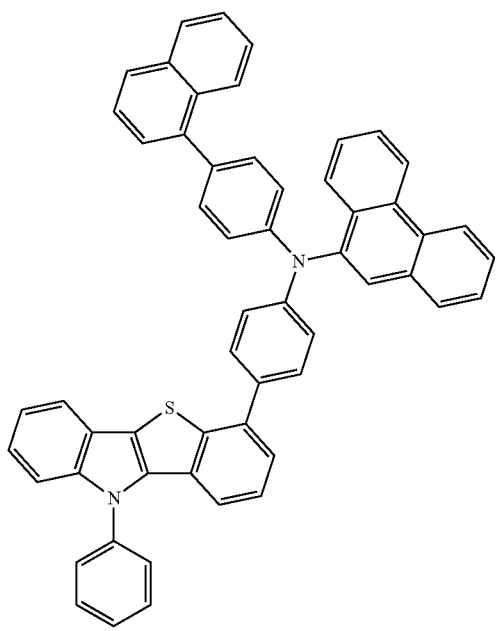
B80
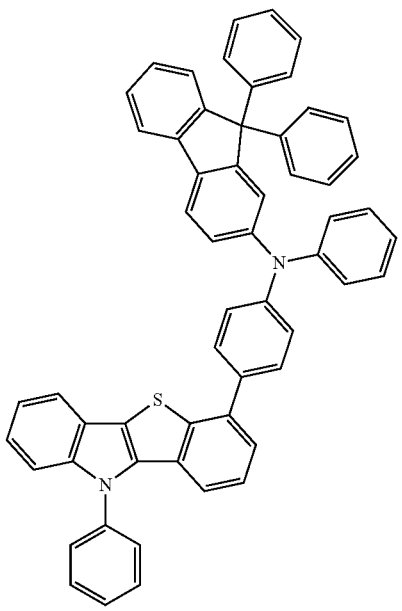
B81

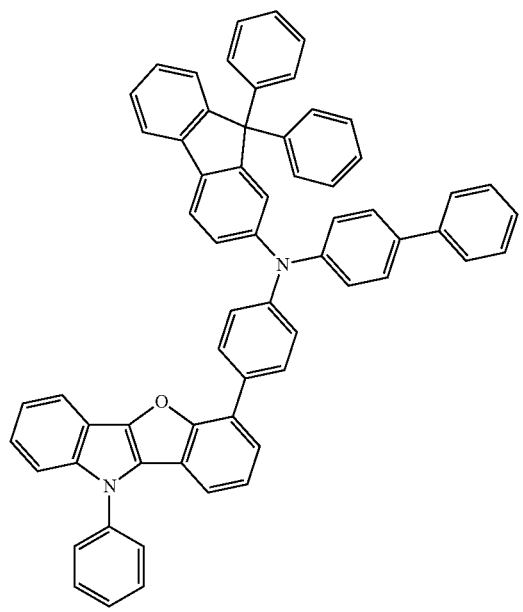
B82
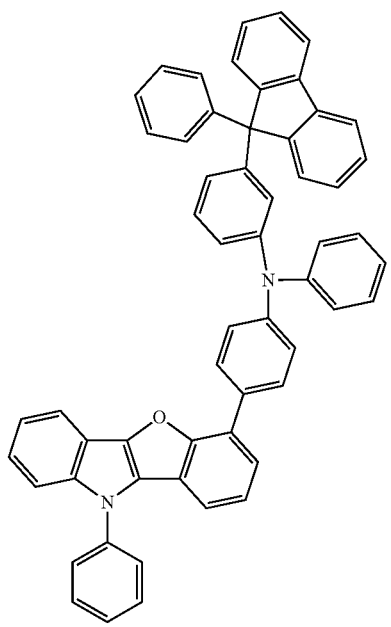
B84
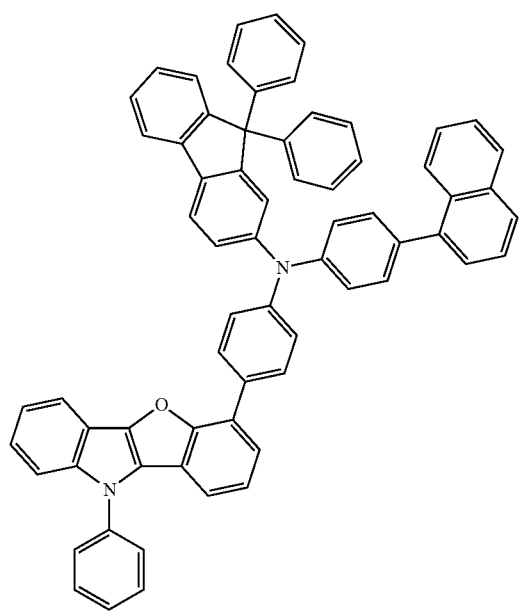
B83
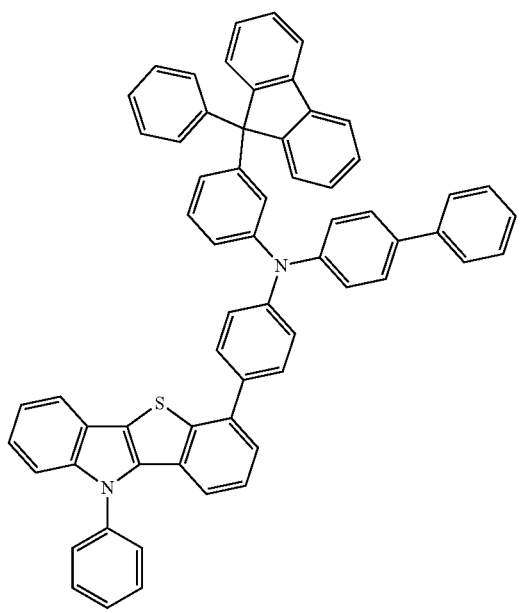
B85

B86
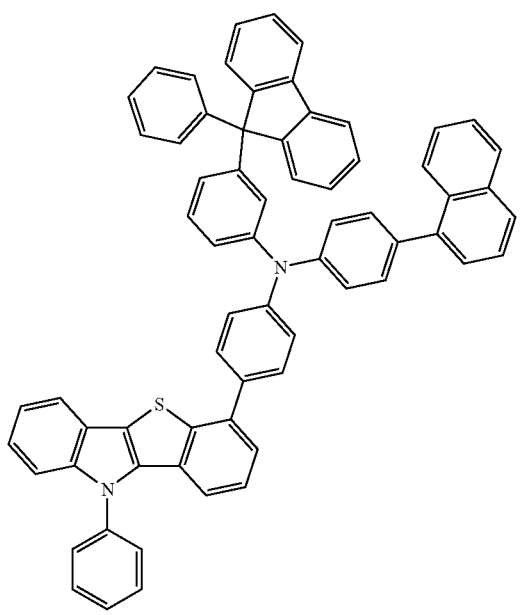
B88
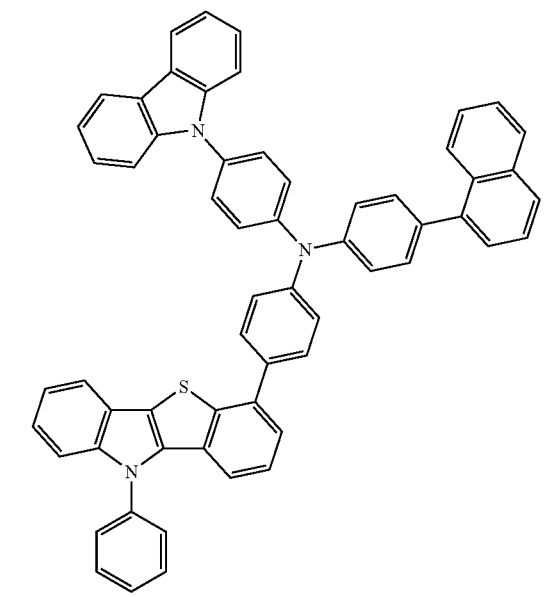
B87
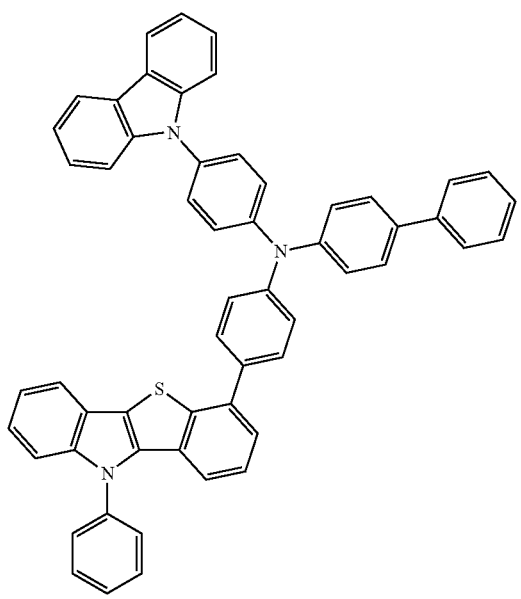
B89
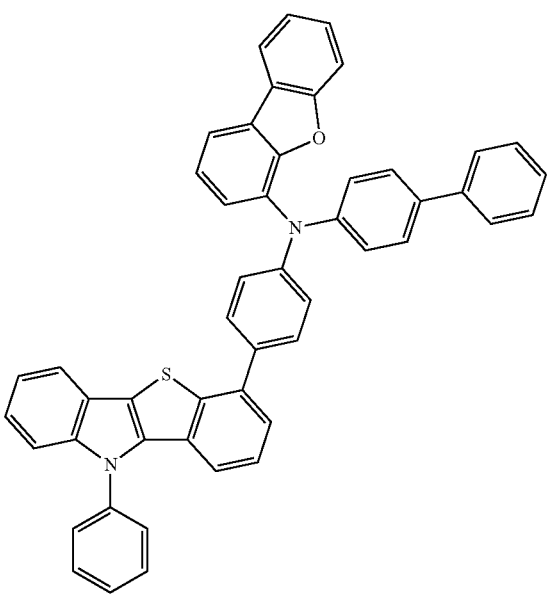

-continued
B90
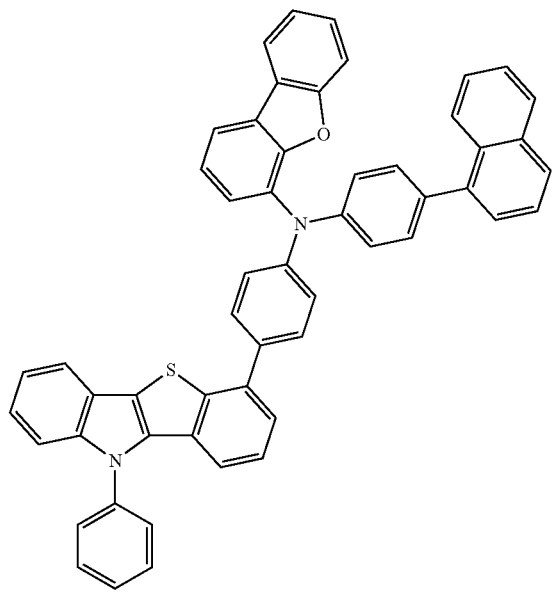
B92
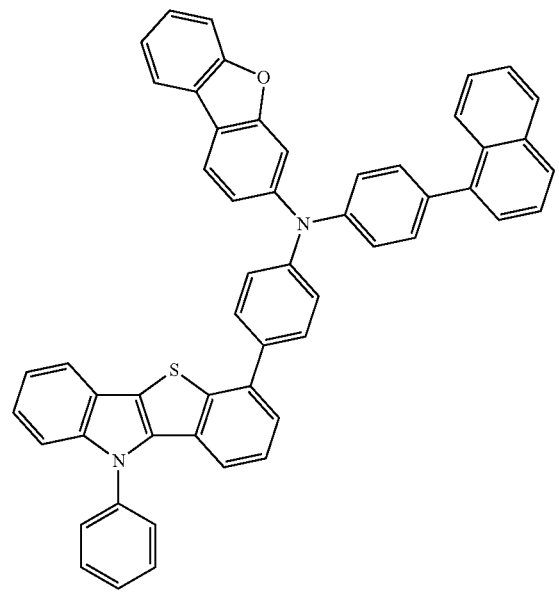
B91
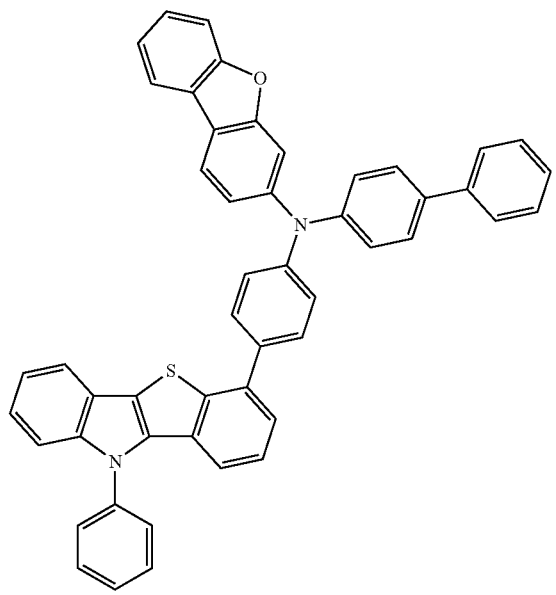
B93
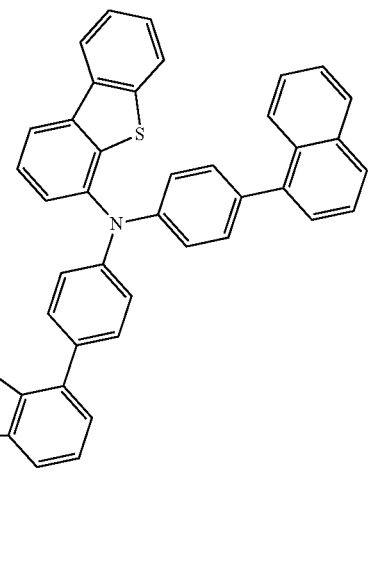

-continued
B94
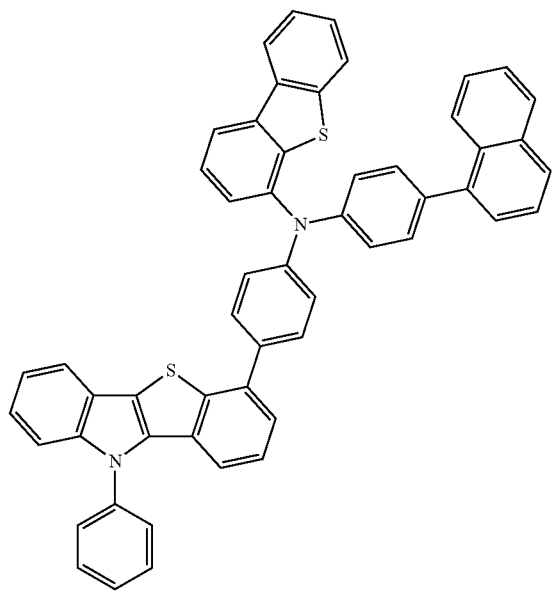
B96
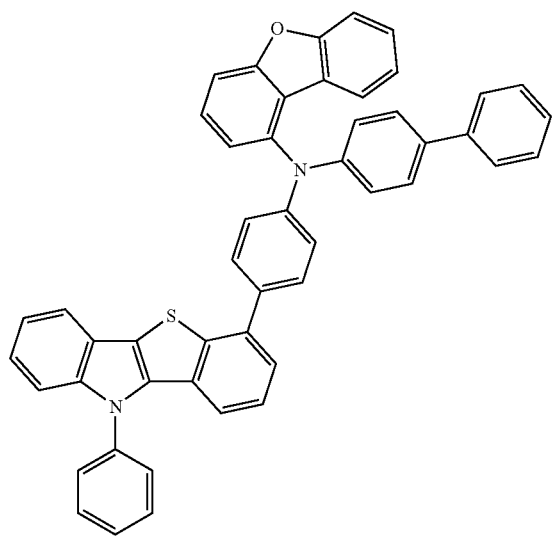
B95
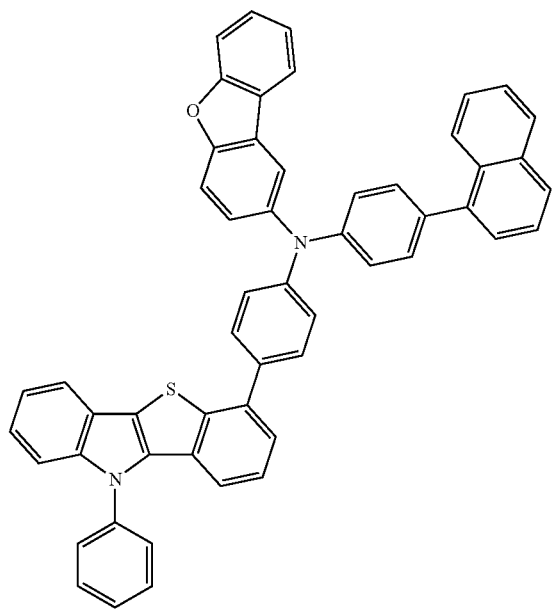
B97
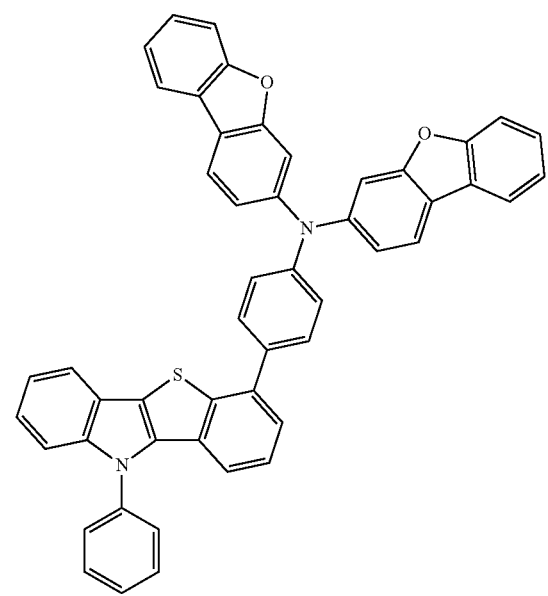

B98
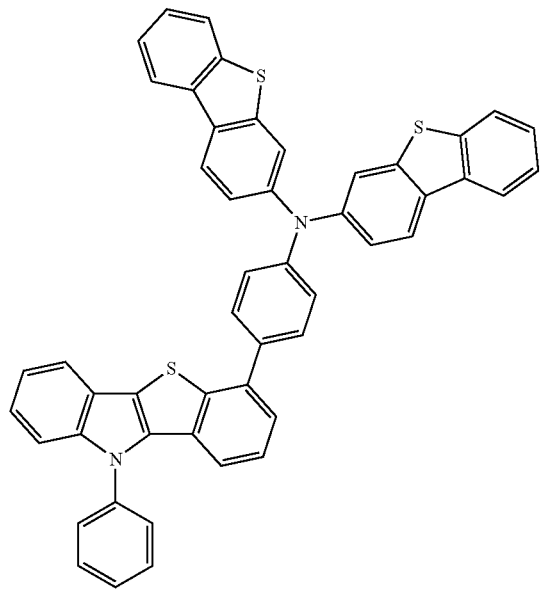
B99
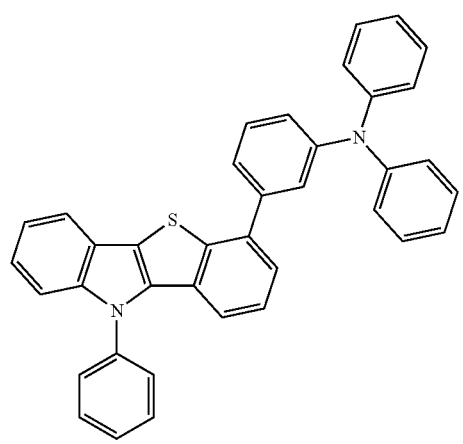
B100
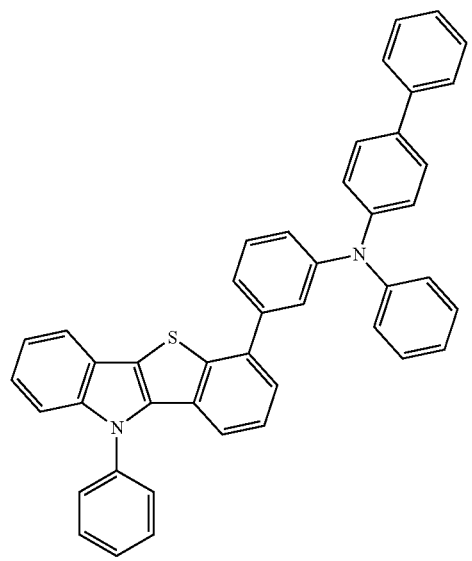
B101
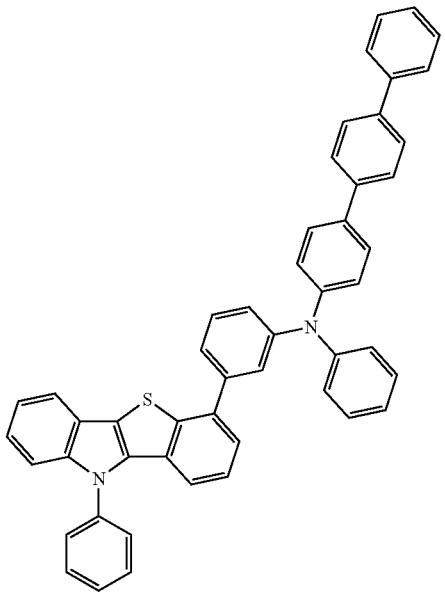
B102
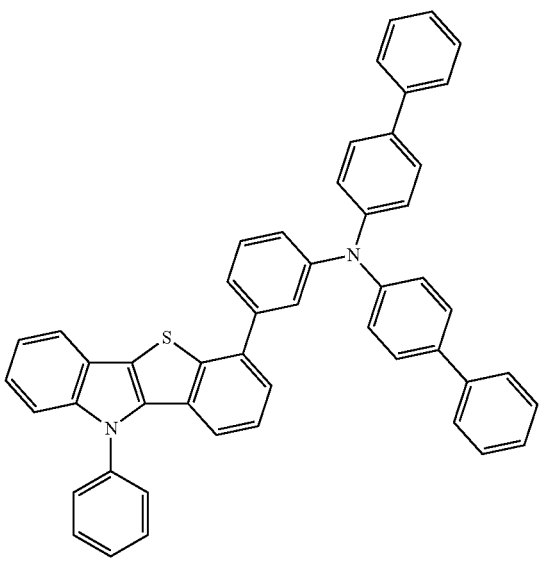

B103
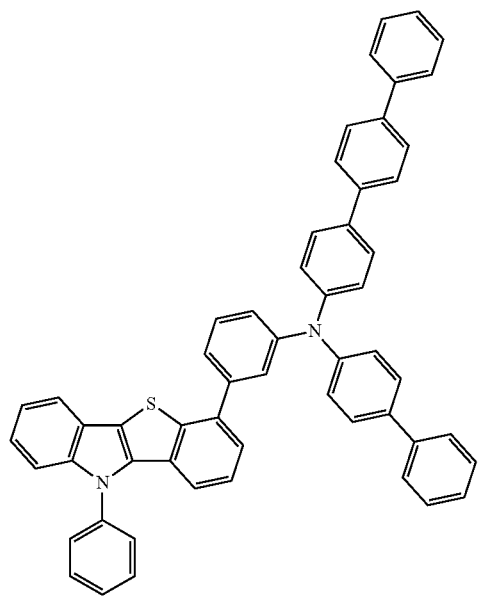
B104
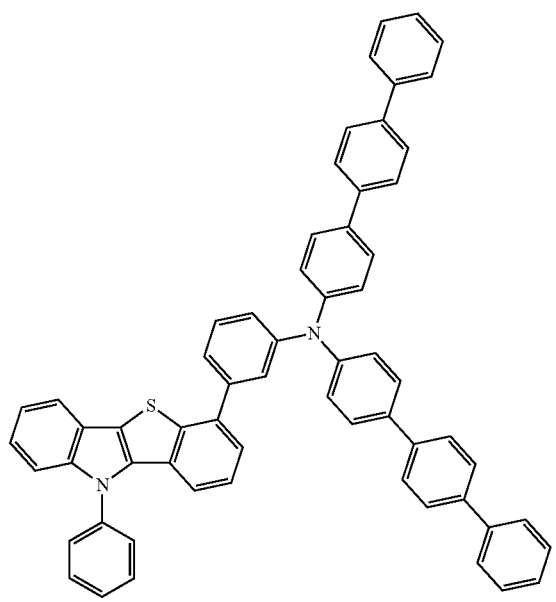
B105
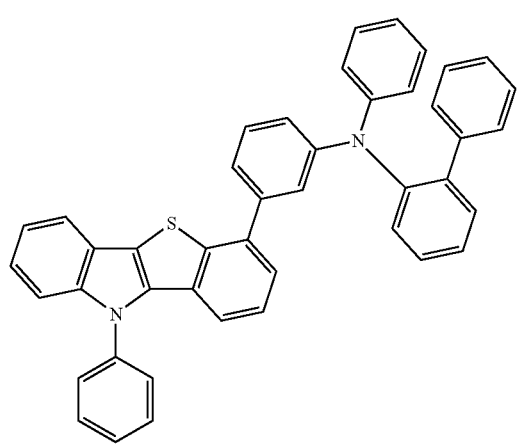
B106
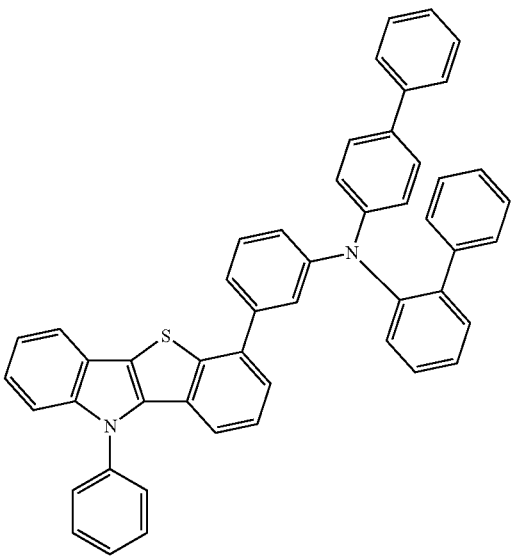
B107
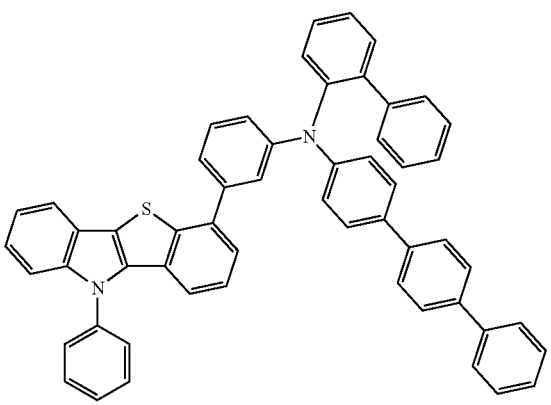
B108
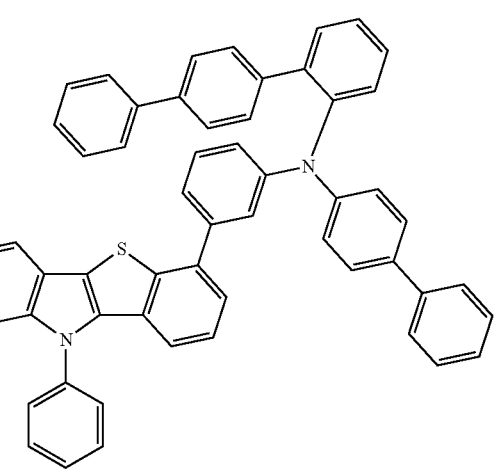

B109

B110
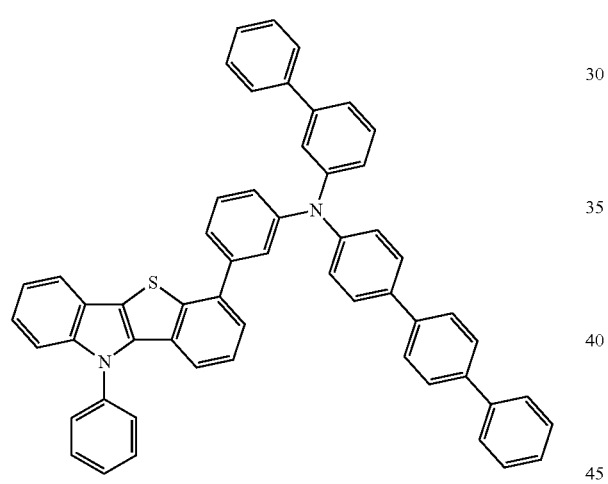
B111
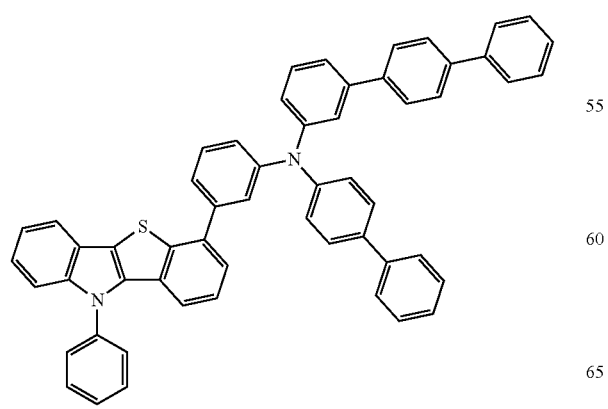
B112
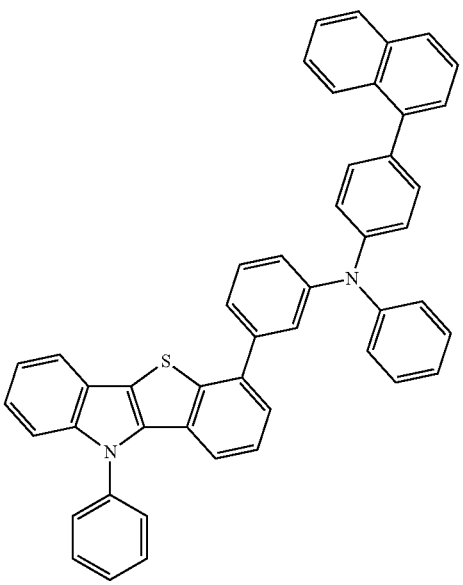
B113
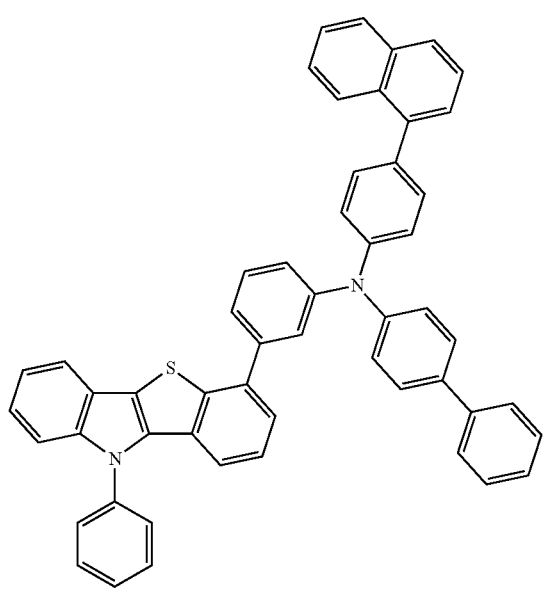
B114
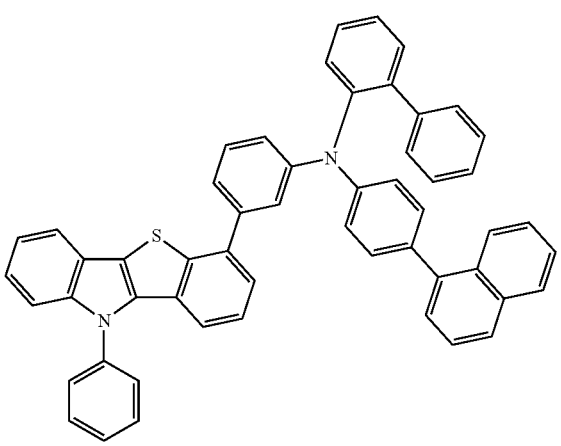

B115
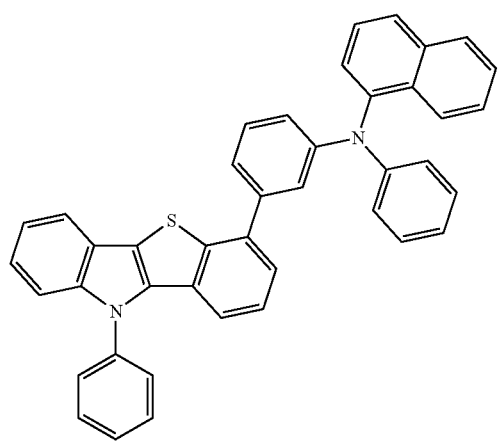
B116
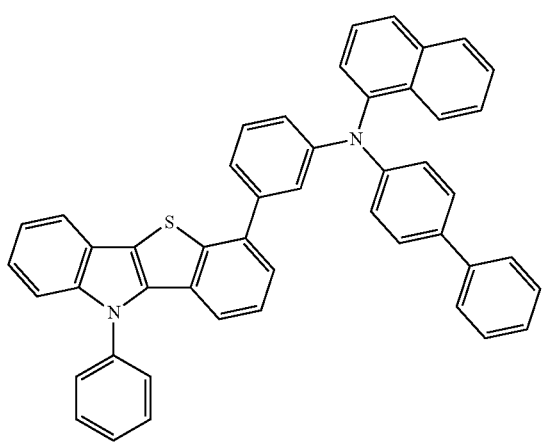
B117
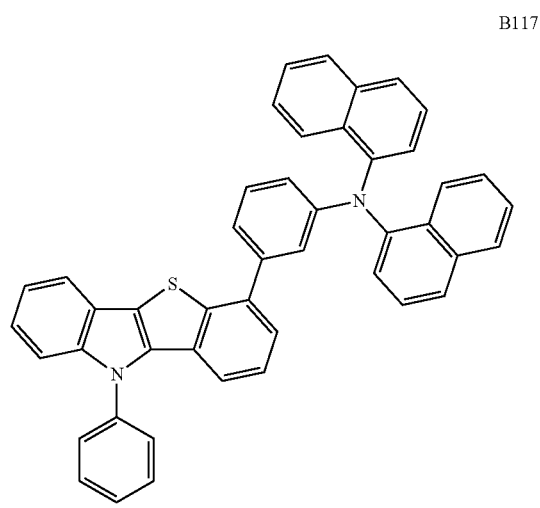
B118
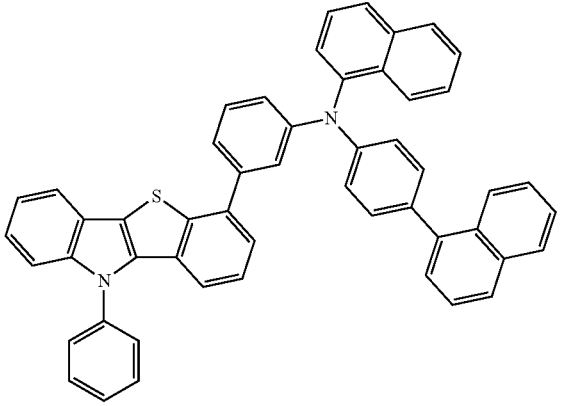
B119
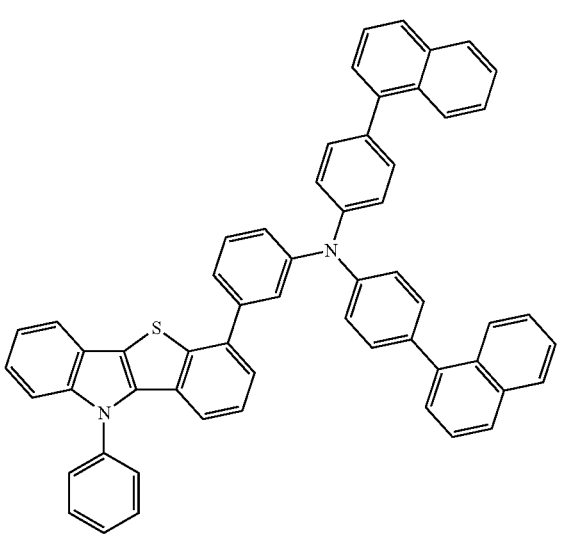
B120
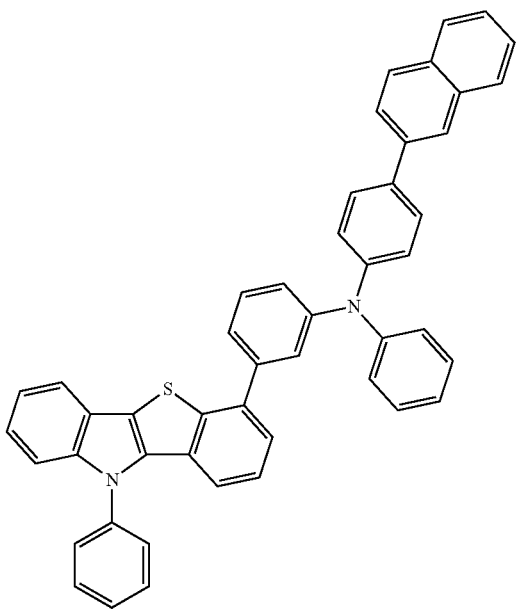

B121
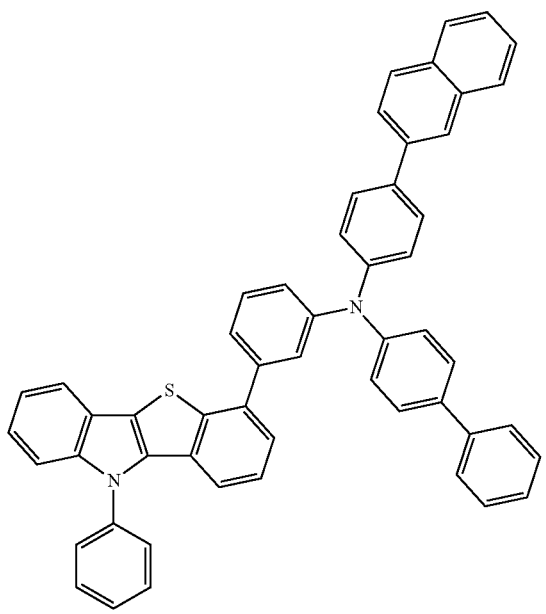
B122
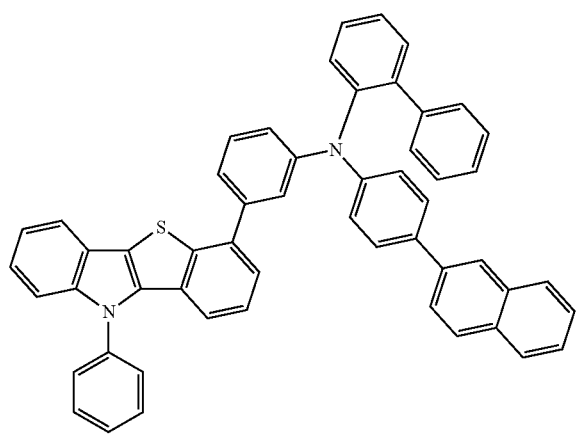
B123
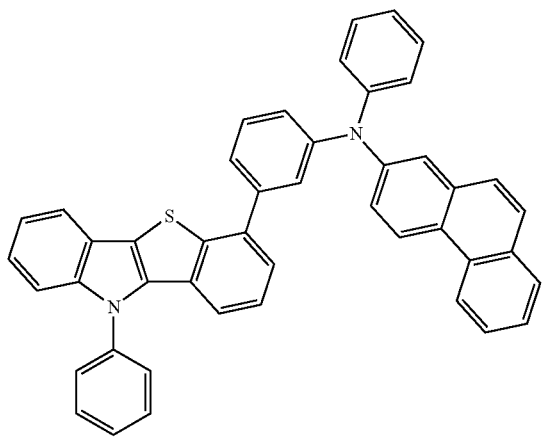
B124
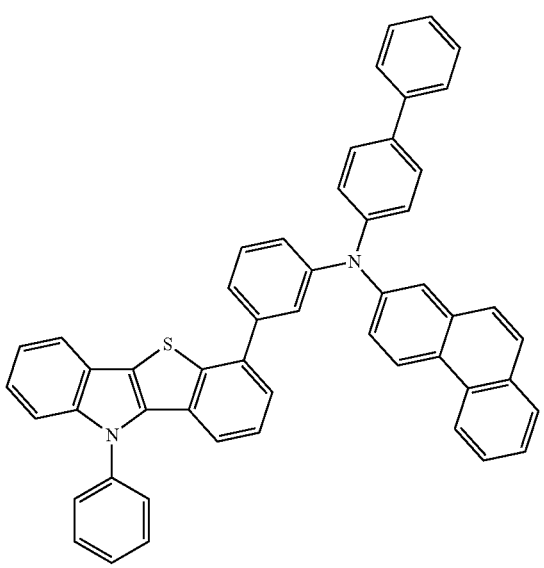
B125
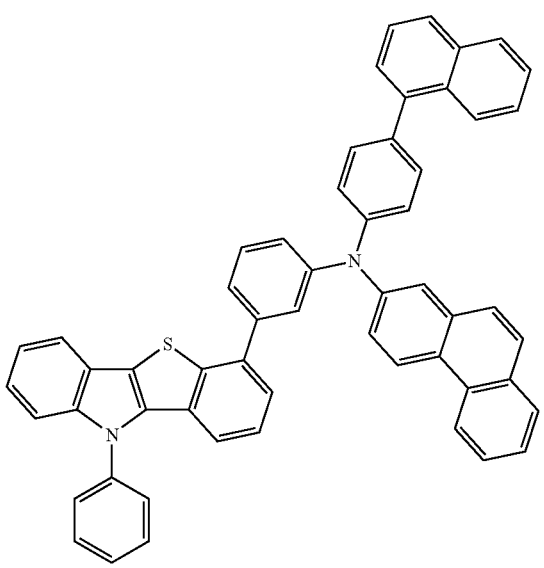
B126
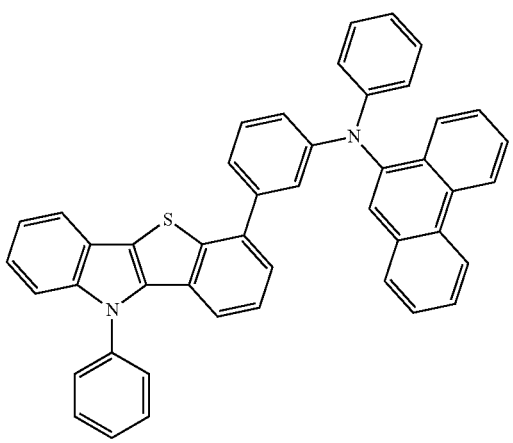

B127
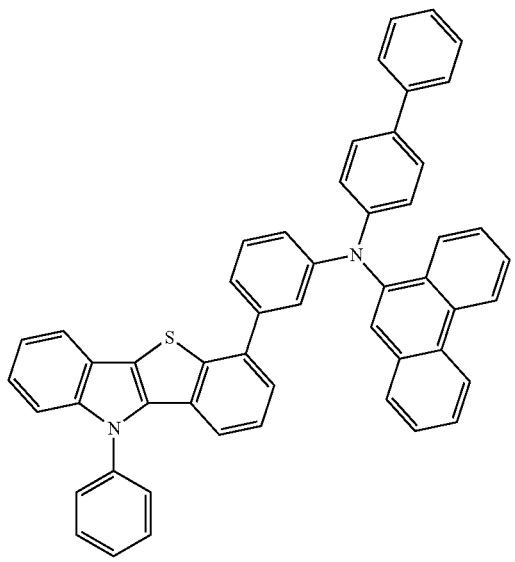
B128
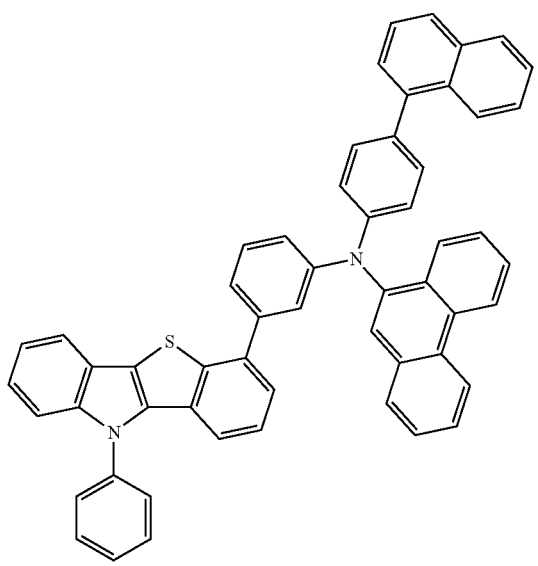
B129
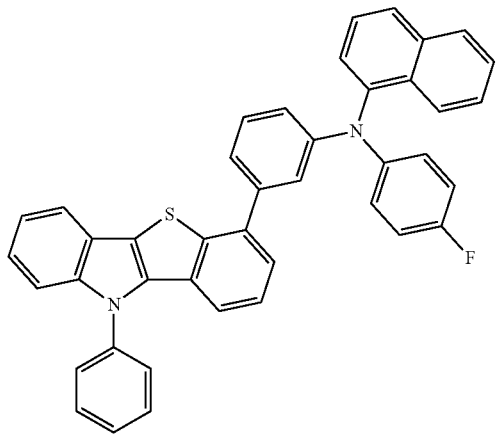
B130
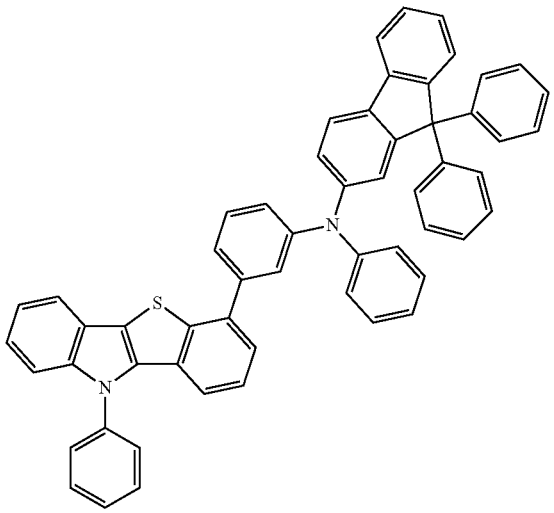
B131
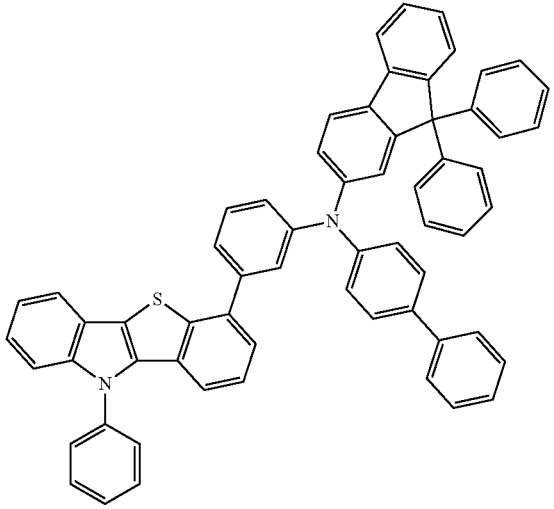
B132
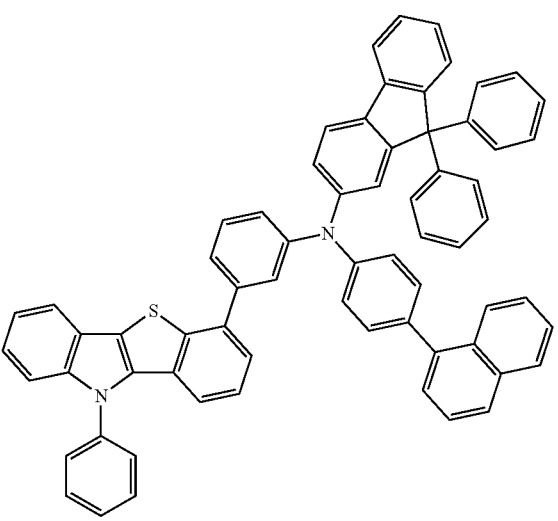

B133
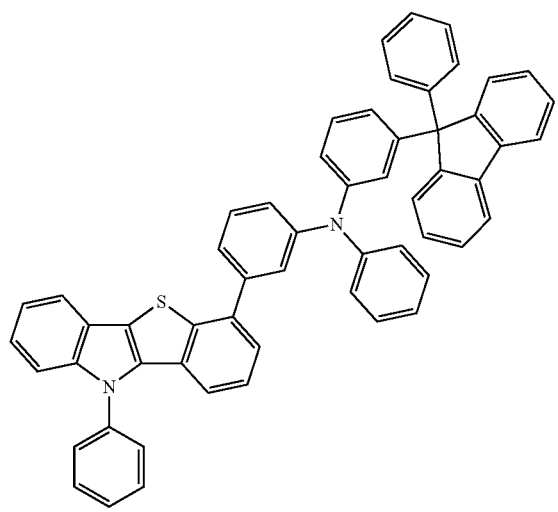
B134
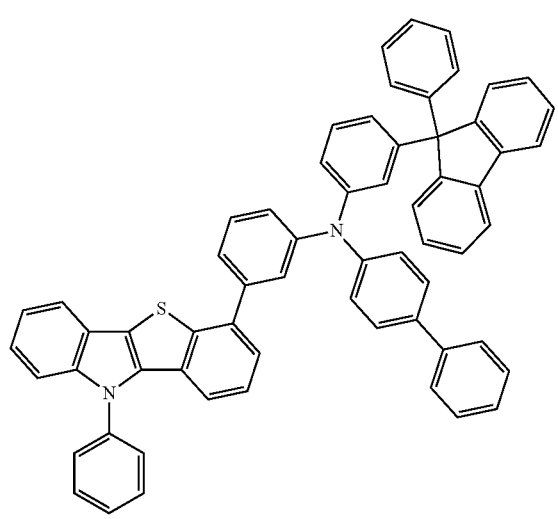
B135
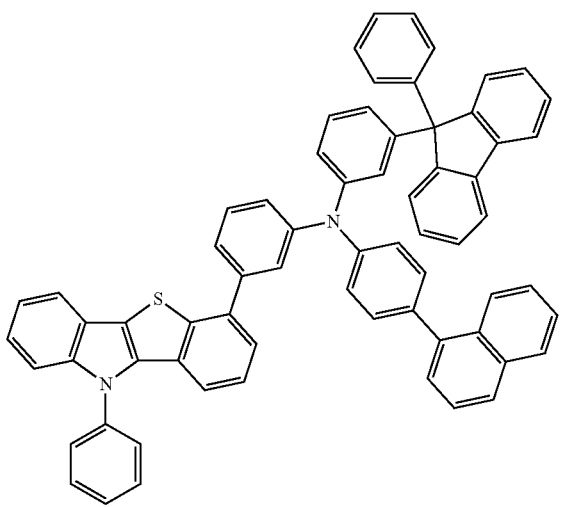
B136
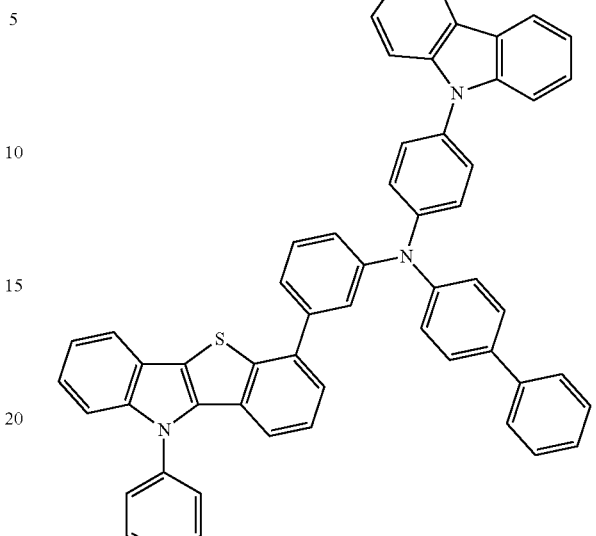
B137
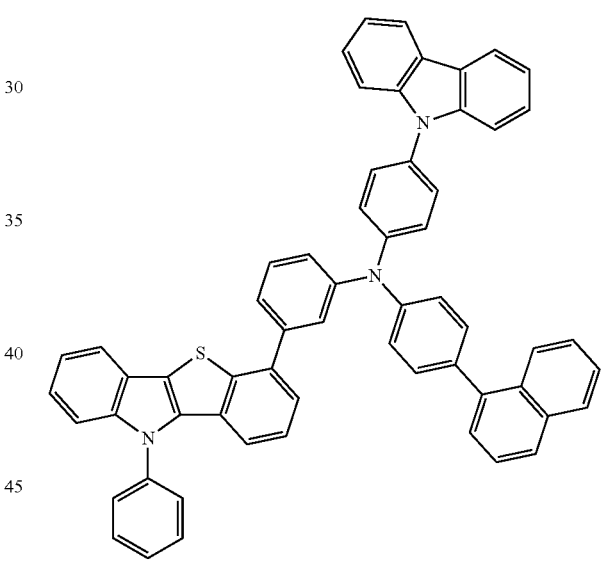
B138
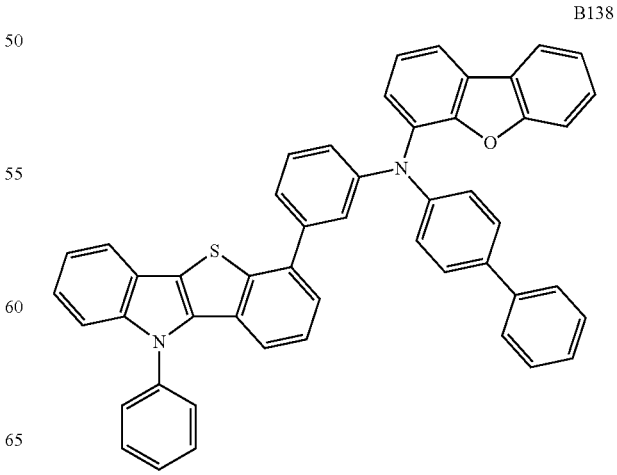

B139
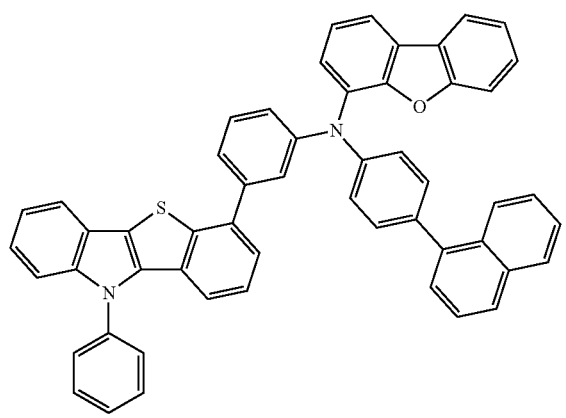
B140
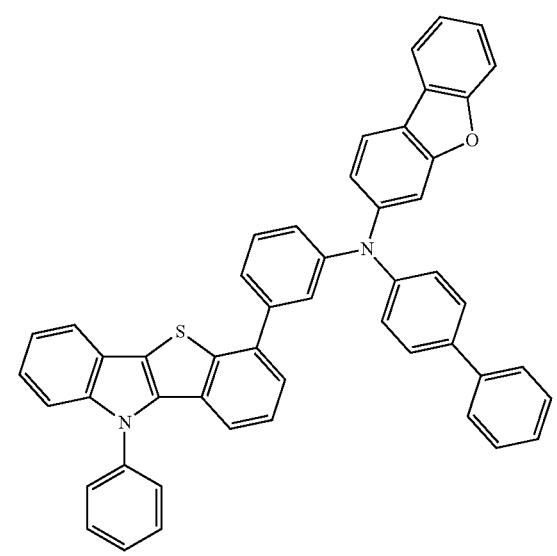
B141
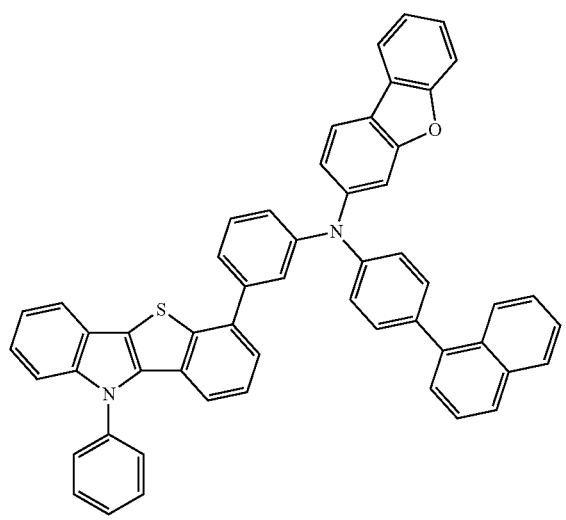
B142
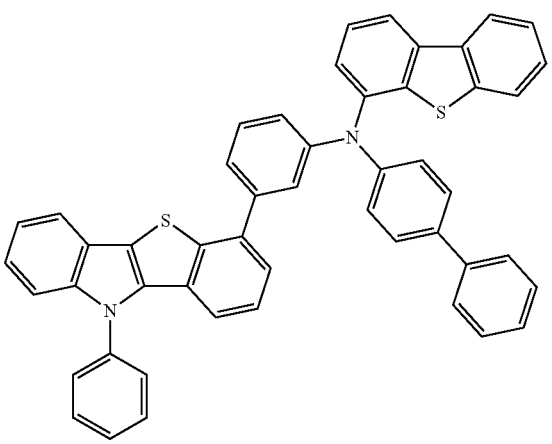
B143
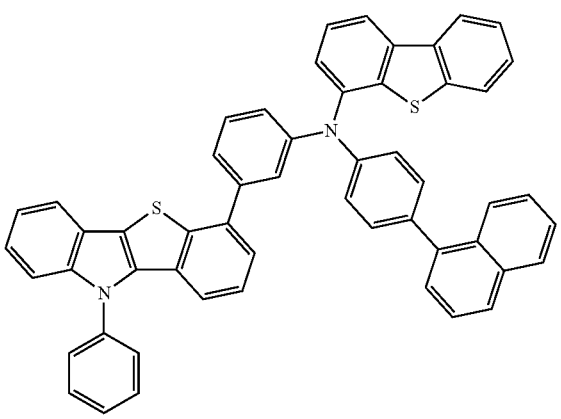
B144
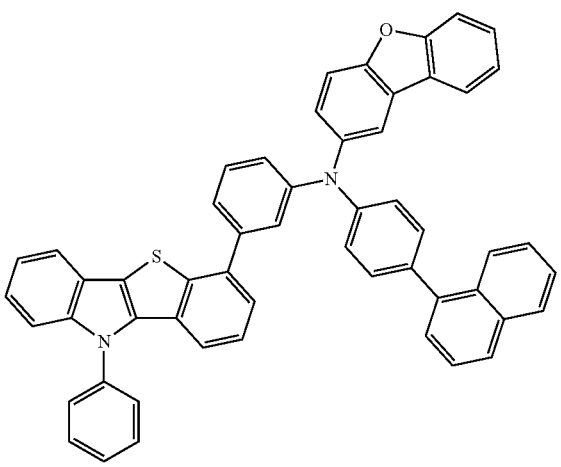

B145
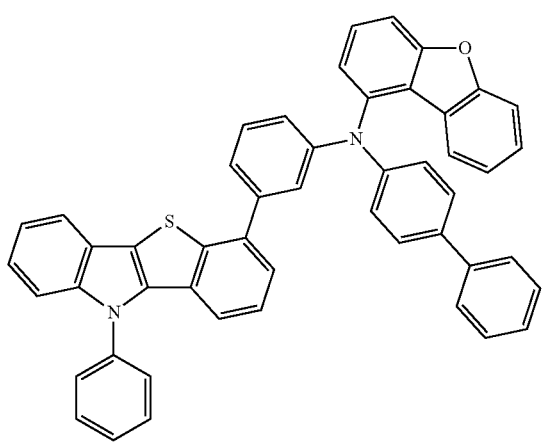
B146
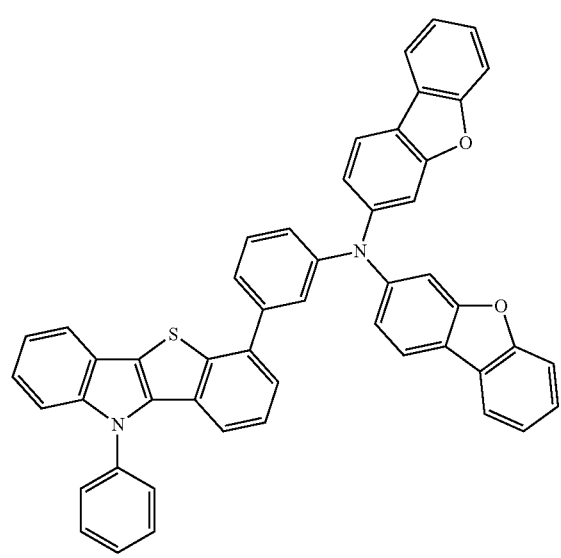
B147
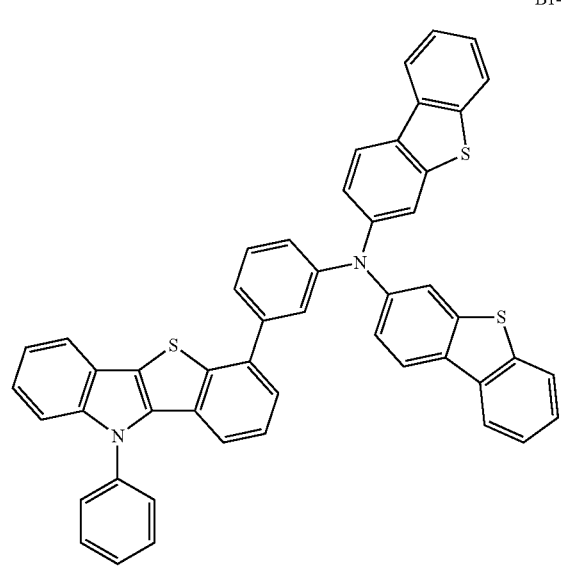
B148
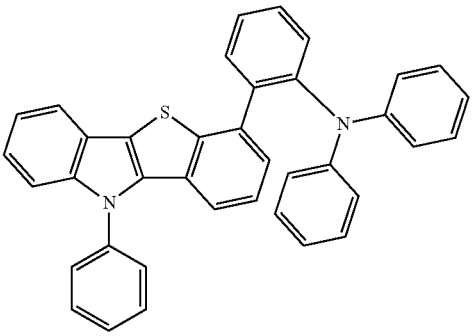
B149
B150
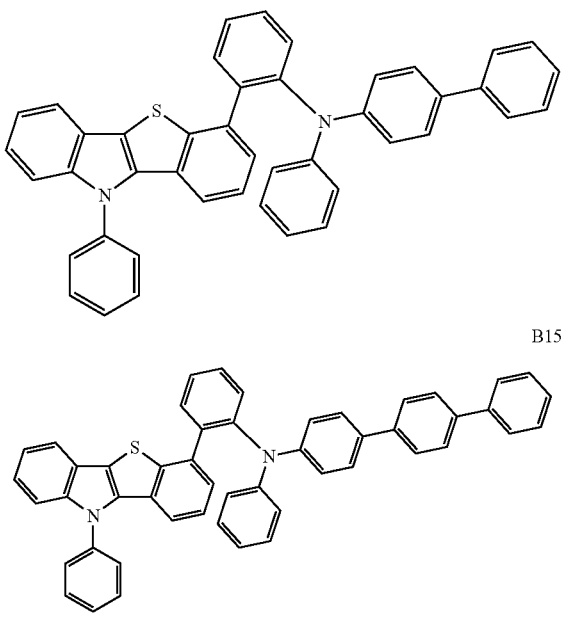
B151
B152
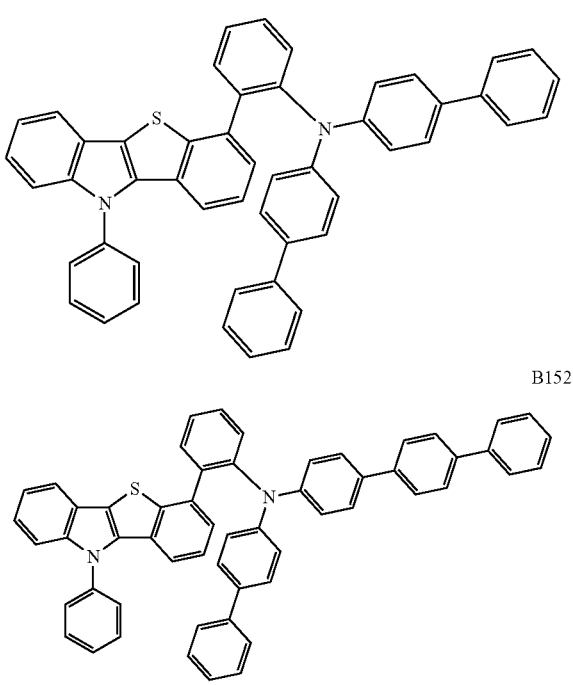

B153
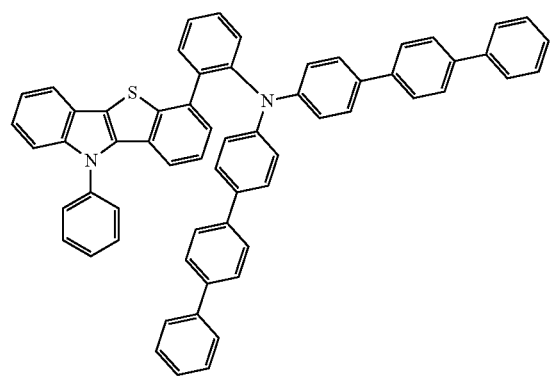
B154
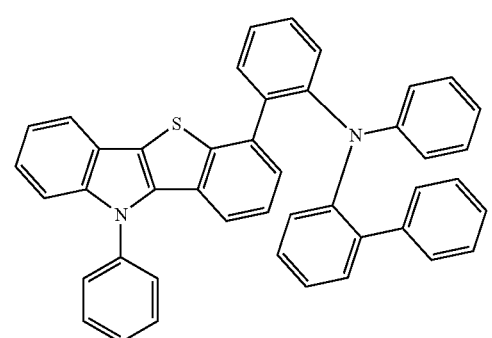
B155
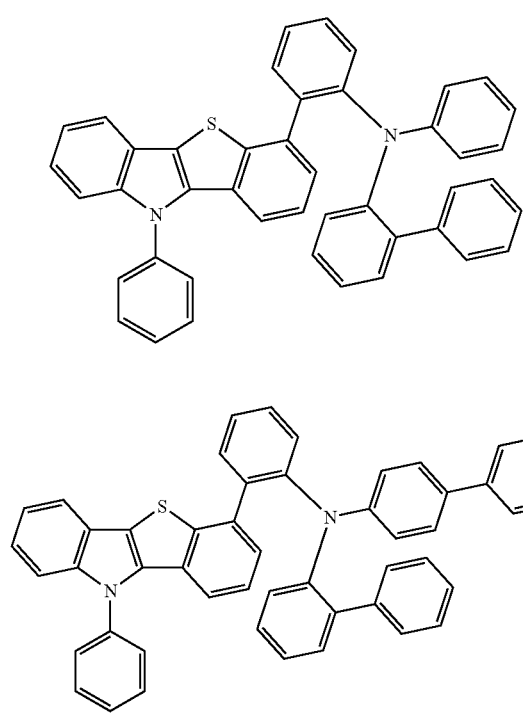
B156

B157
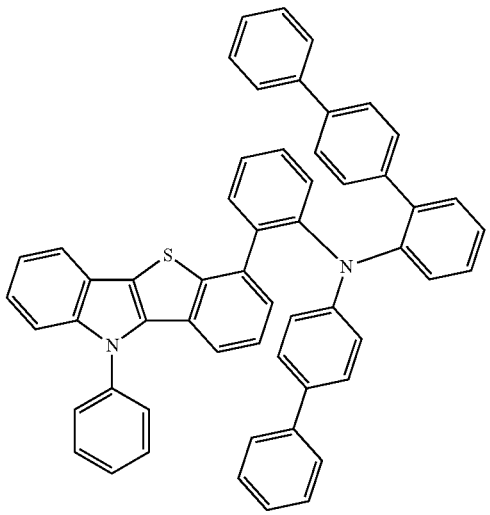
B158
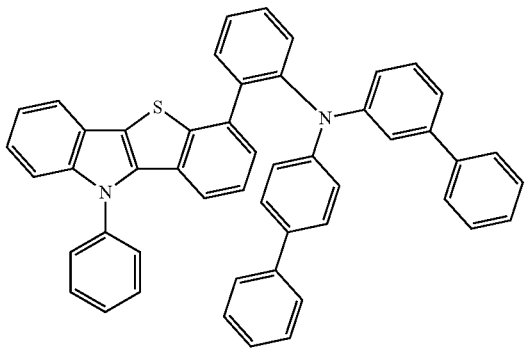
B159
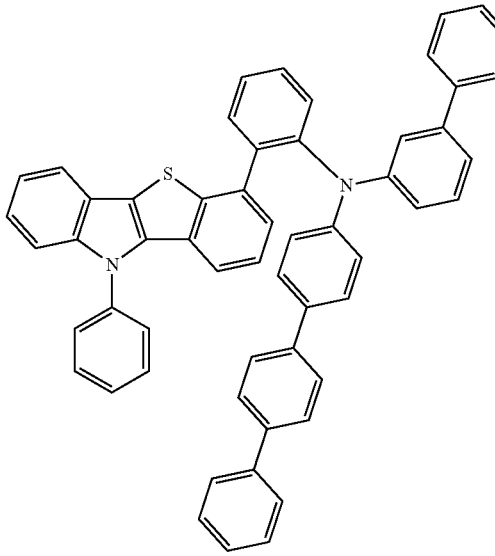

B160
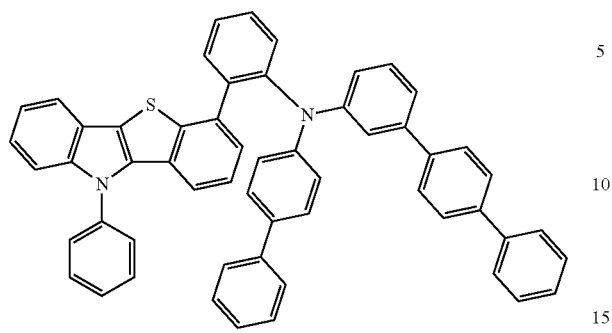
B161
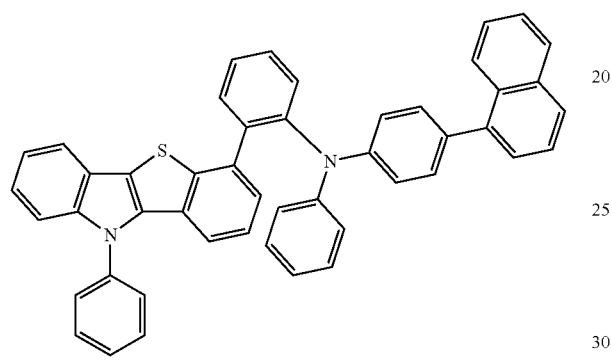
B162
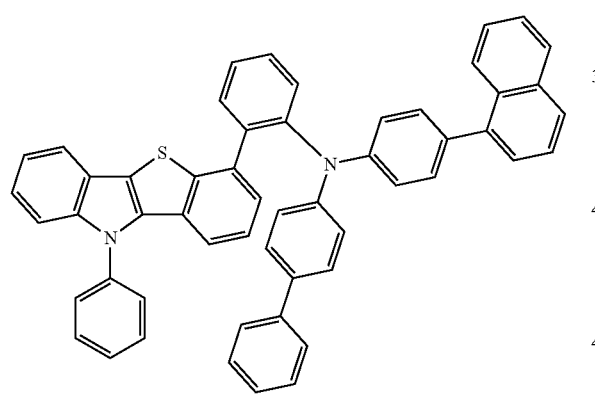
B163
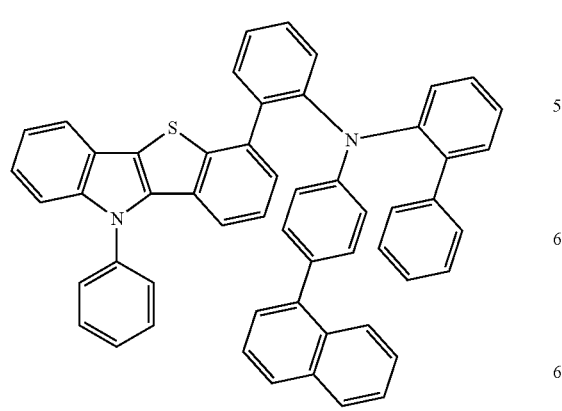
B164
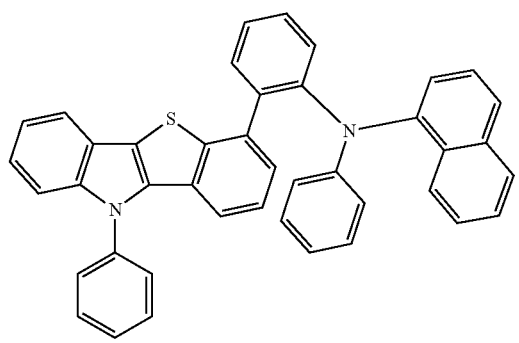
B165
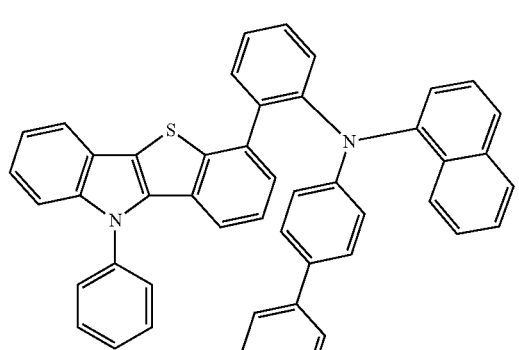
B166
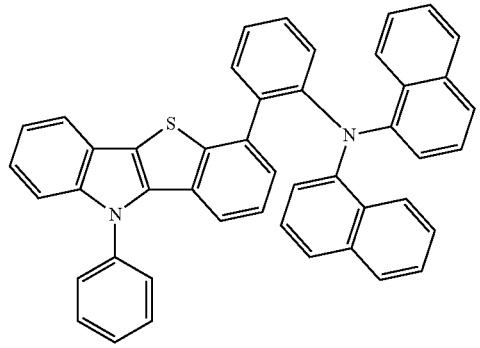
B167
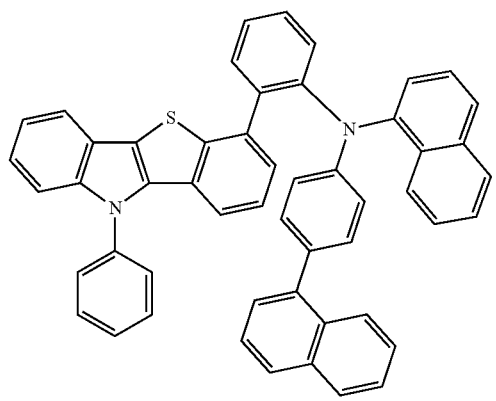

B168
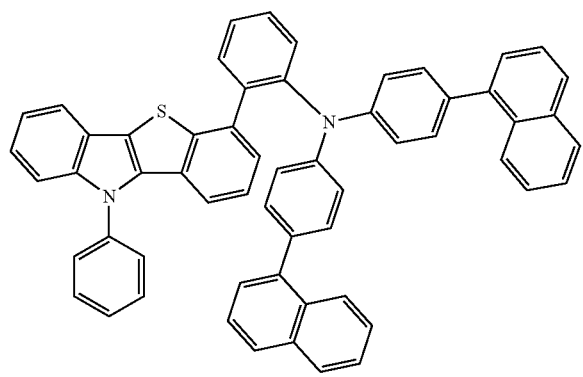
B172
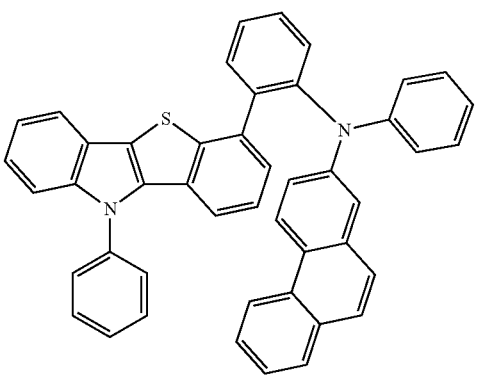
B169
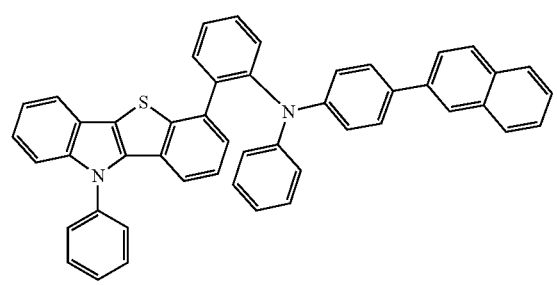
B173
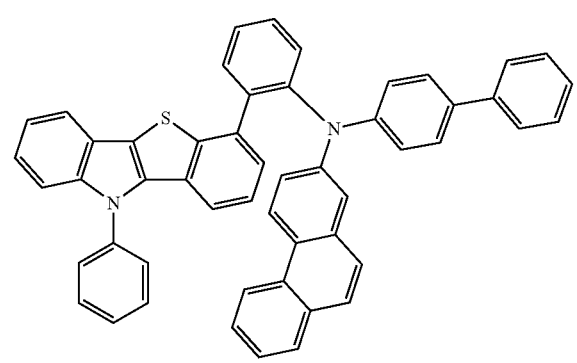
B170
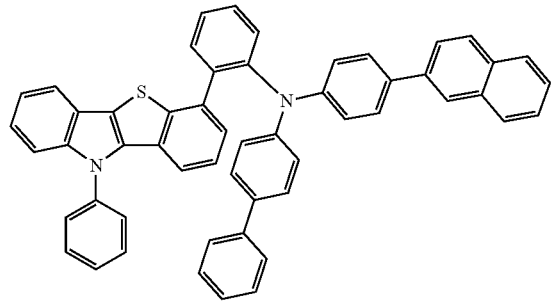
B174
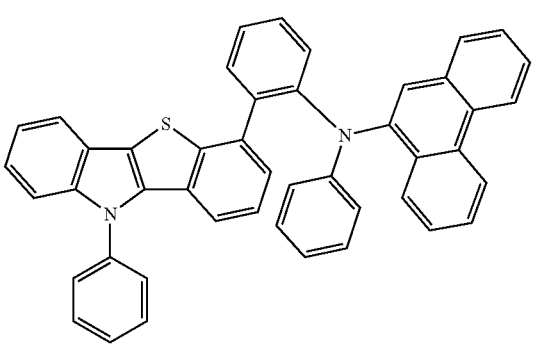
B171
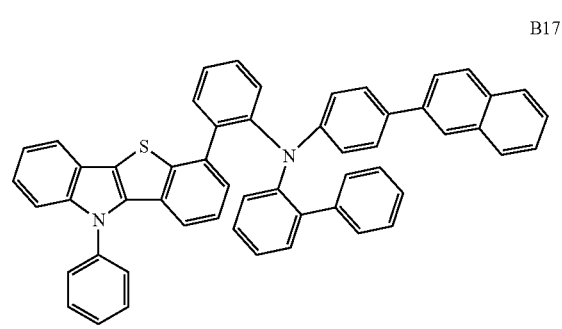
B175

B176
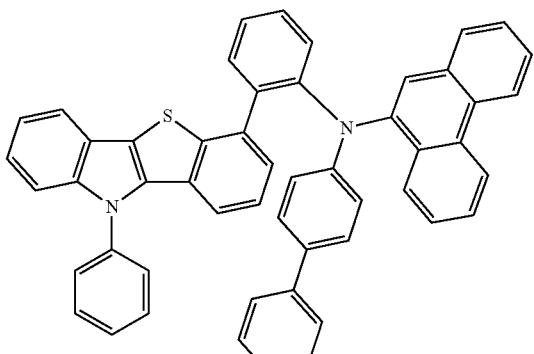
B177
B178
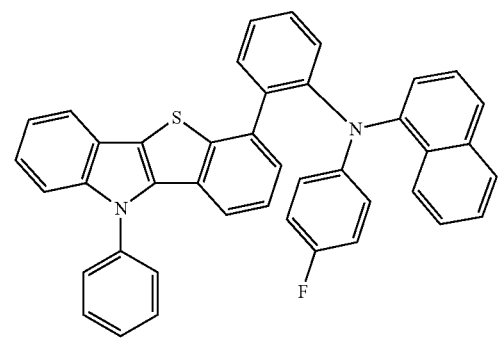
B179
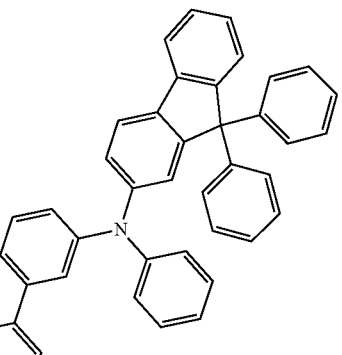
B180
B181
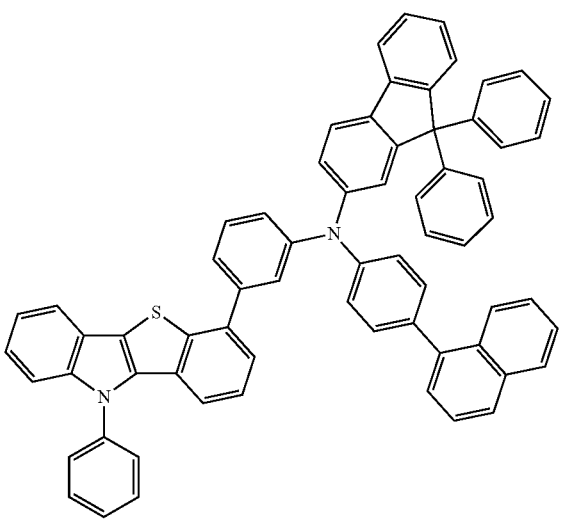

B182
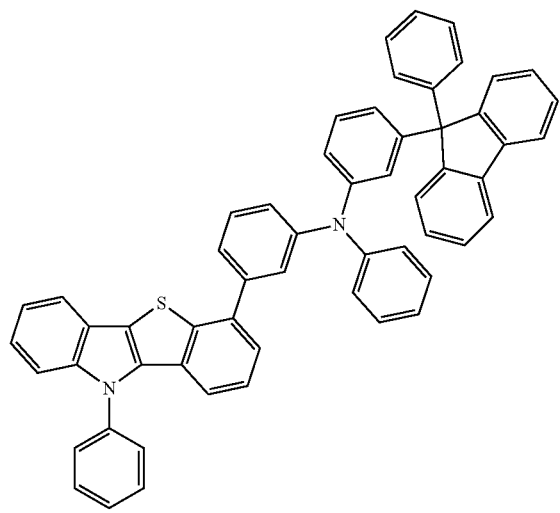
B183
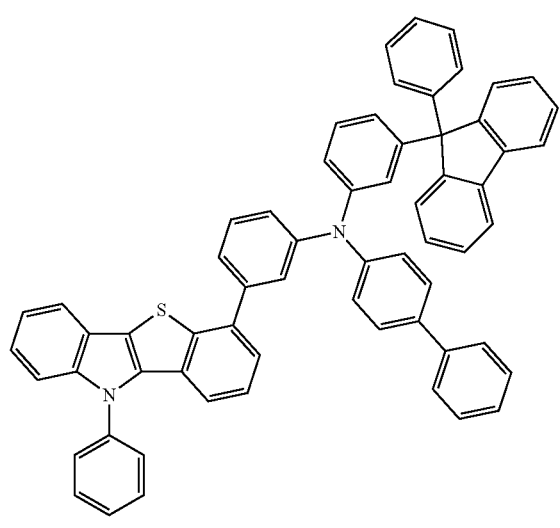
B184
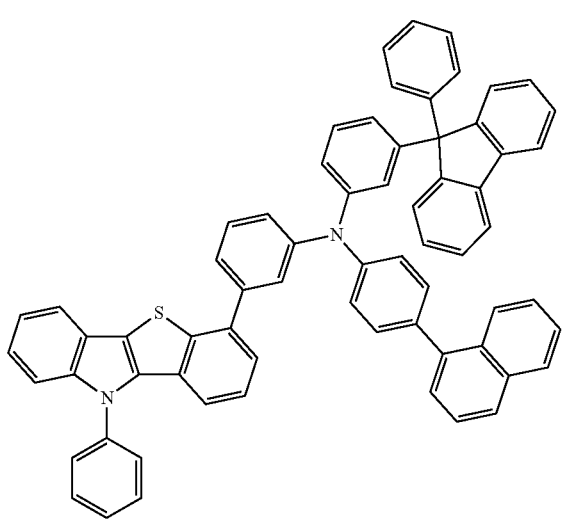
B185
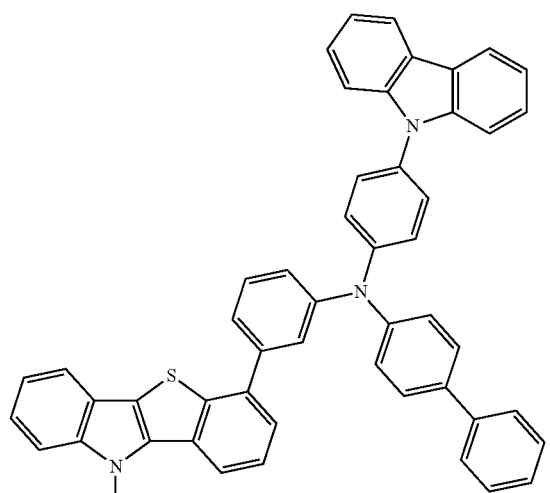
B186
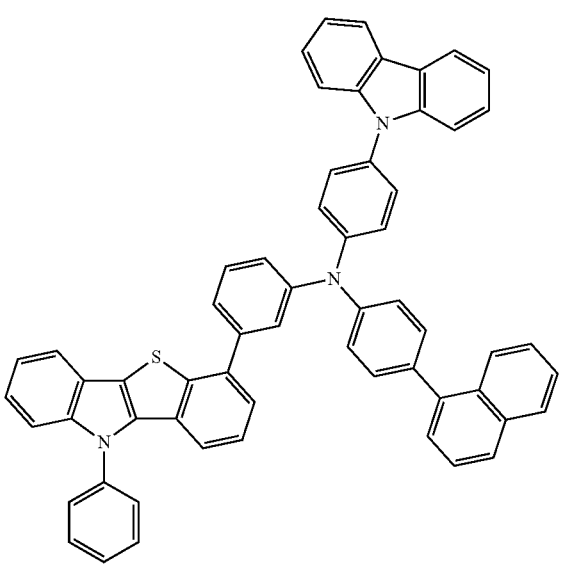
B187
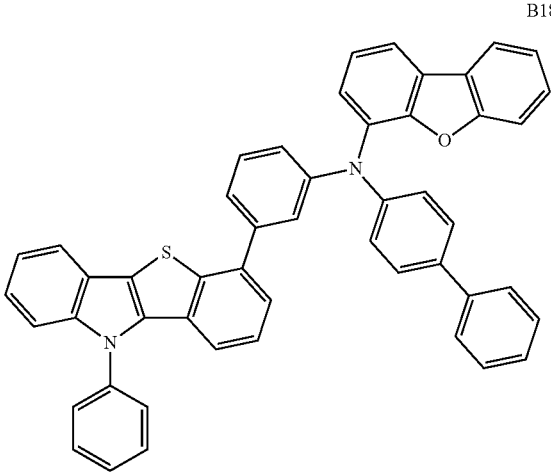

B188

B189

B190

B191

B192

B193

B194
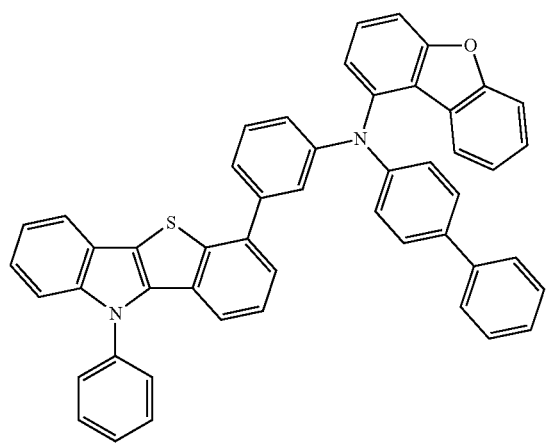
B195
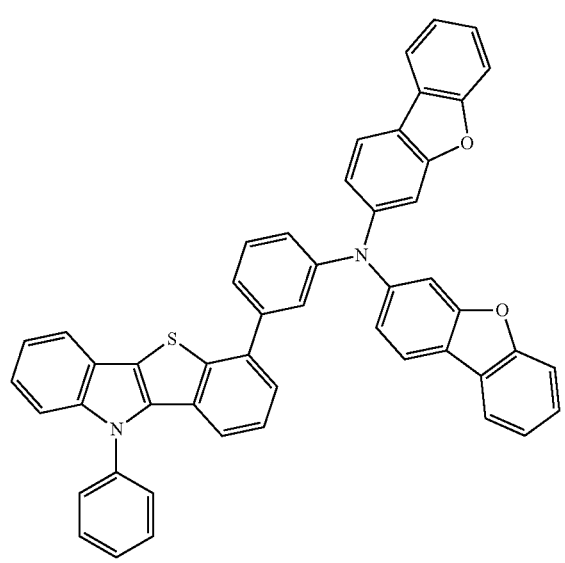
B196
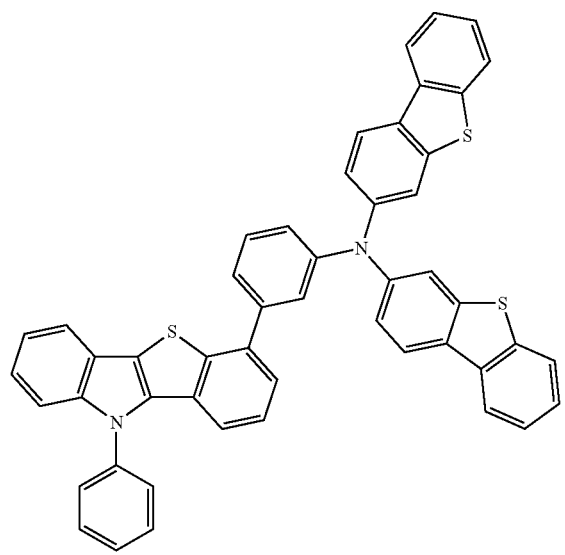
B197
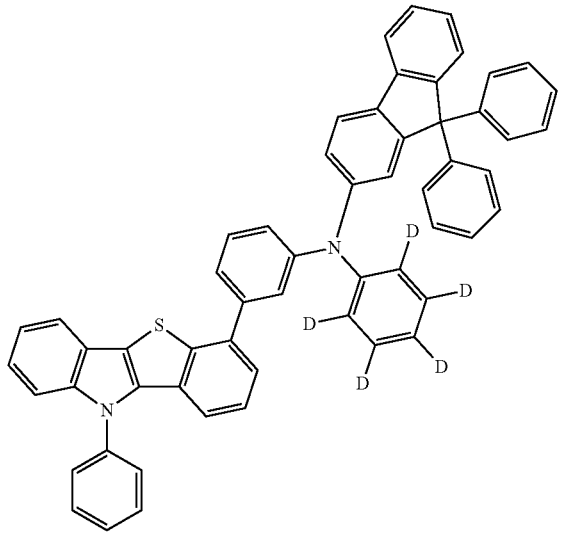
B198
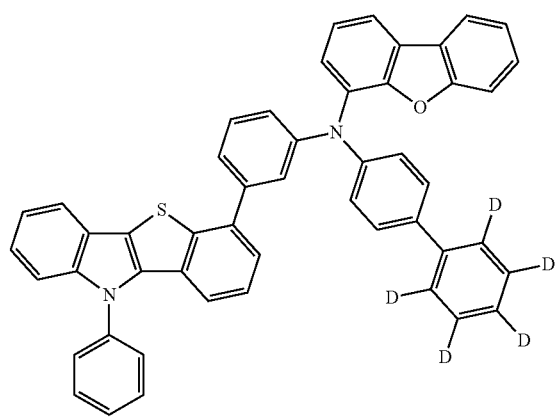
B199
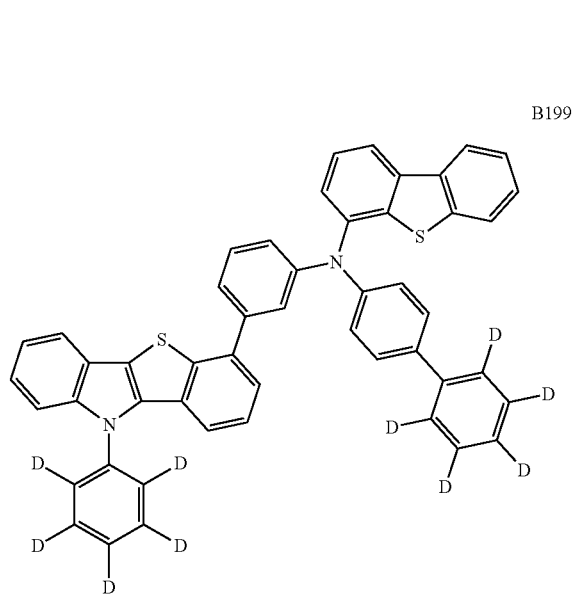

-continued

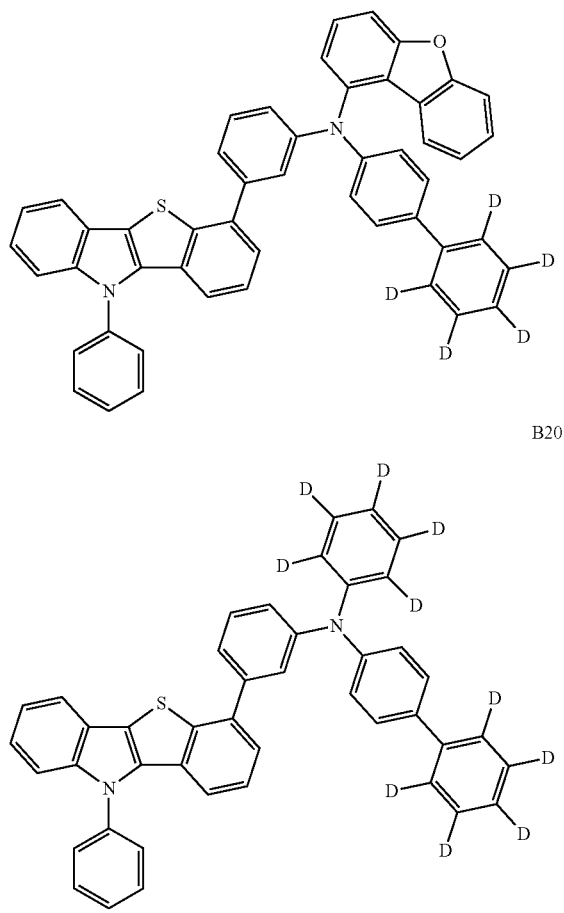

A hole transport region of an embodiment may include the above-described polycyclic compound of an embodiment, as explained later.

The first electrode EL1 has conductivity. The first electrode EL1 may be formed using a metal alloy or a conductive compound. The first electrode EL1 may be an anode. Also, the first electrode EL1 may be a pixel electrode. The first electrode EL1 may be a transmissive electrode, a transflective electrode, or a reflective electrode. If the first electrode EL1 is a transmissive electrode, the first electrode EL1 may include a transparent metal oxide, for example, indium tin oxide (ITO), indium zinc oxide (IZO), zinc oxide (ZnO), and indium tin zinc oxide (ITZO), etc. If the first electrode EL1 is a transflective electrode or a reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Alternatively, the first electrode EL1 may have a structure including a plurality of layers including a reflective layer or a transflective layer formed using the above materials, and a transmissive conductive layer formed using ITO, IZO, ZnO, ITZO, etc. For example, the first electrode EL1 may include a three-layer structure of ITO/Ag/ITO. However, an embodiment of the inventive concept is not limited thereto. The thickness of the first electrode EL1 may be from about 1,000 Å to about 10,000 Å, for example, from about 1,000 Å to about 3,000 Å.

The hole transport region HTR is disposed on the first electrode EL1. The hole transport region HTR may include at least one of a hole injection layer HIL, a hole transport layer HTL, a hole buffer layer (not shown), or an electron blocking layer EBL.

The hole transport region HTR may have a single layer formed using a single material, a single layer formed using a plurality of different materials, or a multilayer structure including a plurality of layers formed using a plurality of different materials.

For example, the hole transport region HTR may have a single layer structure of the hole injection layer HIL or the hole transport layer HTL, or a single layer structure formed using a hole injection material and a hole transport material. In addition, the hole transport region HTR may have a structure of a single layer formed using a plurality of different materials, or a structure stacked from the first electrode EL1 of hole injection layer HIL/hole transport layer HTL, hole injection layer HIL/hole transport layer HTL/hole buffer layer (not shown), hole injection layer HIL/hole buffer layer (not shown), hole transport layer HTL/hole buffer layer, or hole injection layer HIL/hole transport layer HTL/electron blocking layer EBL, without limitation.

The hole transport region HTR may include the polycyclic compound in an embodiment. For example, at least one layer among a hole injection layer HIL, a hole transport layer HTL, a hole buffer layer (not shown), or an electron blocking layer EBL may include the polycyclic compound in an embodiment.

In the polycyclic compound of an embodiment, an aryl amine group which has high hole tolerance is connected with a benzofuranoindole skeleton, or a benzothienoindole skeleton. Accordingly, the polycyclic compound of an embodiment may maintain long life.

Particularly, in the polycyclic compound of an embodiment, the aryl amine group may be substituted at an ortho position with respect to an oxygen atom of the benzofuranoindole skeleton, or substituted at an ortho position with respect to a sulfur atom of the benzothienoindole skeleton. Accordingly, structural asymmetric properties in a molecule may increase, the crystallinity of the molecule may be restrained, and hole transport capacity may be improved.

In the polycyclic compound of an embodiment, an aryl amine group is in an ortho position with respect to a sulfur atom or an oxygen atom, and the disposition of partial negative charge in a resonance structure is different when the aryl amine group is in a meta position with respect to a sulfur atom or an oxygen atom. Accordingly, the polycyclic compound of an embodiment has specific electrical properties according to the substitution position of the aryl amine group. Due to such specific electrical properties of the compound of an embodiment, improved hole transport capacity may be achieved.

In conclusion, the polycyclic compound of an embodiment may be included in a hole transport region to show excellent hole transport capacity. The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole injection layer HIL may include in addition to the polycyclic compound of an embodiment, for example, a phthalocyanine compound such as copper phthalocyanine, N,N'-diphenyl-N,N'-bis-[4-(phenyl-m-tolyl-amino)-phenyl]-biphenyl-4,4'-diamine (DNTPD), 4,4',4"-tris(3-methylphenylphenylamino) triphenylamine (m-MTDATA), 4,4', 4"-tris(N,N-diphenylamino)triphenylamine (TDATA), 4,4', 4"-tris{N,-2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(1-naphthalene-1-yl)-N,N'-diphenyl-benzidine (NPB), triphenylamine-containing polyetherketone (TPAPEK), 4-isopropyl-4'-methyldiphenyliodonium tetrakis(pentafluorophenyl)borate, and dipyrazino[2,3-f:2',3'-h]quinoxaline-2,3,6,7,10,11-hexacarbonitrile (HAT-CN).

The hole transport layer HTL may include in addition to the polycyclic compound of an embodiment, for example, carbazole derivatives such as N-phenyl carbazole and polyvinyl carbazole, fluorine-based derivatives, N,N'-bis(3-methylphenyl)-N,N'-diphenyl-[1,1-biphenyl]-4,4'-diamine (TPD), triphenylamine-based derivatives such as 4,4',4"-tris(carbazol-9-yl)triphenylamine (TCTA), N,N'-di(naphthalene-1-yl)-N,N'-diphenyl-benzidine (NPB), 4,4'-bis[N,N-bis(4-methylphenyl)benzeneamine] (TAPC), 4,4'-bis[N,N'-(3-tolyl)amino]-3,3'-dimethylbiphenyl (HMTPD), 1,3-bis(N-carbazolyl)benzene (mCP), 9-(4-tert-butylphenyl)-3,6-bis(triphenylsilyl)-9H-carbazole (CzSi), etc.

The thickness of the hole transport region HTR may be from about 100 Å to about 10,000 Å, for example, from about 100 Å to about 5,000 Å. The thickness of the hole injection region HIL may be, for example, from about 30 Å to about 1,000 Å, and the thickness of the hole transport layer HTL may be from about 30 Å to about 1,000 Å. For example, the thickness of the electron blocking layer EBL may be from about 10 Å to about 1,000 Å. If the thicknesses of the hole transport region HTR, the hole injection layer HIL, the hole transport layer HTL and the electron blocking layer EBL satisfy the above-described ranges, satisfactory hole transport properties may be achieved without substantial increase of a driving voltage.

The hole transport region HTR may further include a charge generating material to increase conductivity in addition to the above-described materials. The charge generating material may be dispersed uniformly or non-uniformly in the hole transport region HTR. The charge generating material may be, for example, a p-dopant. The p-dopant may be one of quinone derivatives, metal oxides, or cyano group-containing compounds, without limitation. For example, non-limiting examples of the p-dopant may include quinone derivatives such as tetracyanoquinodimethane (TCNQ) and 2,3,5,6-tetrafluoro-7,7,8,8-tetracyanoquinodimethane (F4-TCNQ), metal oxides such as tungsten oxide and molybdenum oxide, etc., without limitation.

As described above, the hole transport region HTR may further include at least one of a hole buffer layer (now shown) or an electron blocking layer EBL in addition to the hole injection layer HIL and the hole transport layer HTL. The hole buffer layer (not shown) may compensate an optical resonance distance according to the wavelength of light emitted from an emission layer EML to increase light emission efficiency. Materials which may be included in the hole transport region HTR may be used as materials included in the hole buffer layer (not shown). The electron blocking layer EBL is a layer playing the role of preventing the electron injection from the electron transport region ETR to the hole transport region HTR.

The emission layer EML is disposed on the hole transport region HTR. The emission layer EML may have a thickness of, for example, about 100 Å to about 1,000 Å or about 100 Å to about 300 Å. The emission layer EML may have a single layer formed using a single material, a single layer formed using a plurality of different materials, or a multi-layer structure having a plurality of layers formed using a plurality of different materials.

In the luminescence device 10 of an embodiment, the emission layer EML may include anthracene derivatives, pyrene derivatives, fluoranthene derivatives, chrysene derivatives, dihydrobenzanthracene derivatives, or triphenylene derivatives. Particularly, the emission layer EML may include anthracene derivatives or pyrene derivatives.

The emission layer EML may include an anthracene derivative represented by the following Formula A:

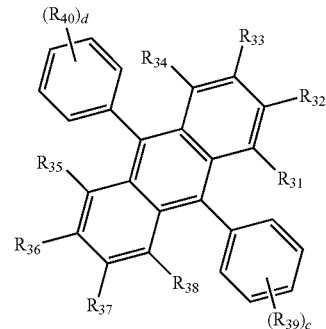

Formula A

In the above formula, $R_{31}$ to $R_{40}$ may be each independently a hydrogen atom, a deuterium atom, a halogen atom, a substituted or unsubstituted silyl group, a substituted or unsubstituted alkyl group of 1 to 10 carbon atoms, a substituted or unsubstituted aryl group of 6 to 30 ring carbon atoms, or a substituted or unsubstituted heteroaryl group of 2 to 30 ring carbon atoms, or combined with an adjacent group to form a ring. Meanwhile, $R_{31}$ to $R_{40}$ may be combined with adjacent groups from each other to form saturated hydrocarbon rings or unsaturated hydrocarbon ring.

In the above formula, c and d may be each independently an integer of 0 to 5.

The above formula may be represented by any one among Compound 3-1 to Compound 3-12:

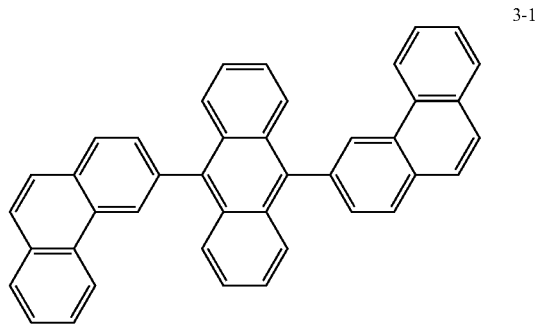

3-1

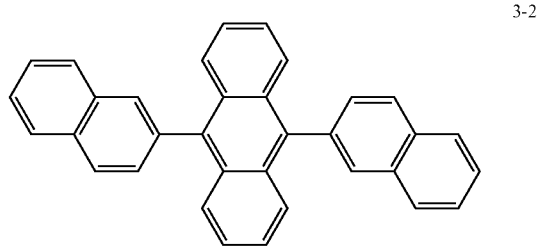

3-2

-continued
3-3
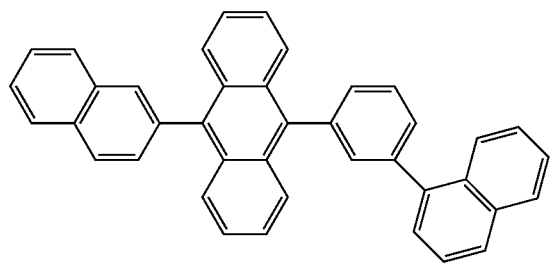
3-4
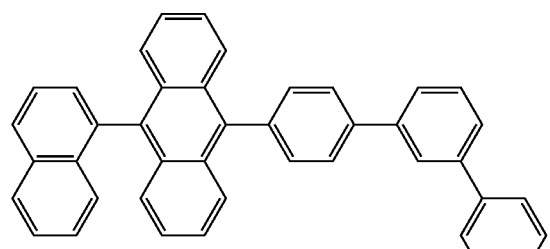
3-5
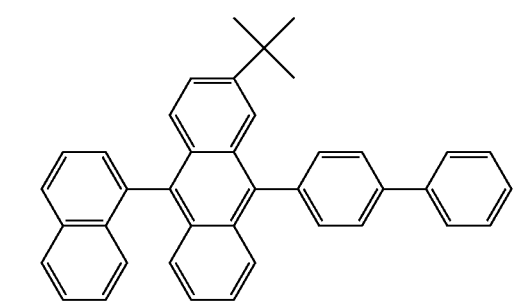
3-6
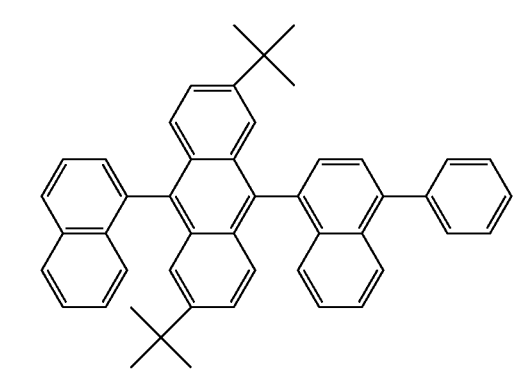
3-7
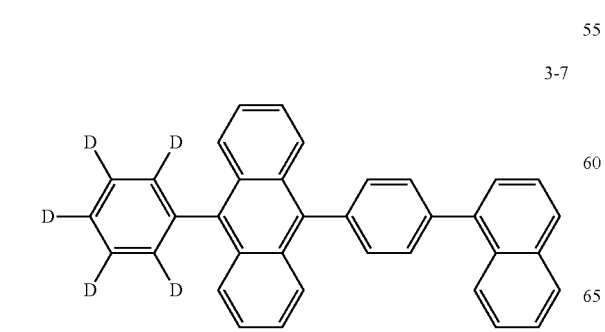
-continued
3-8
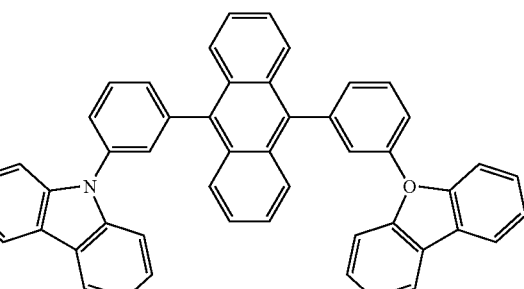
3-9
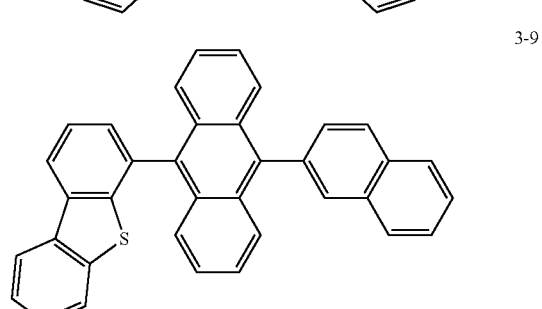
3-10
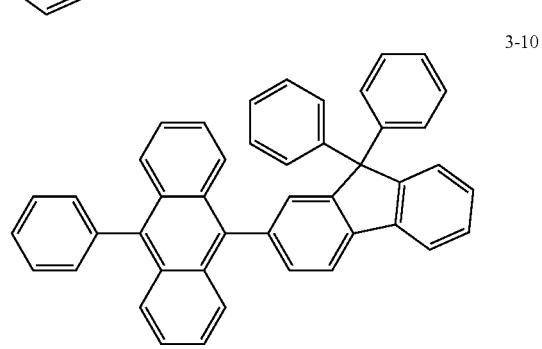
3-11
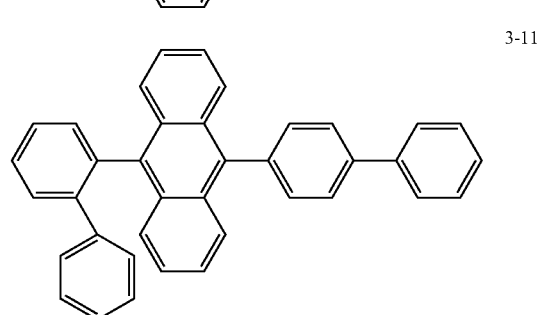
3-12

-continued 3-13
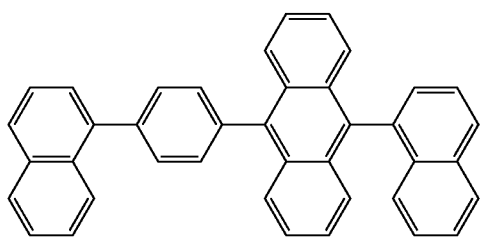

3-14
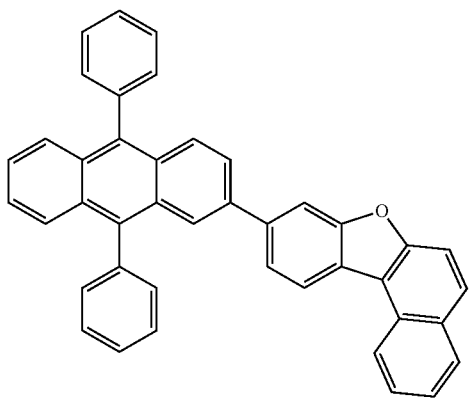

3-15
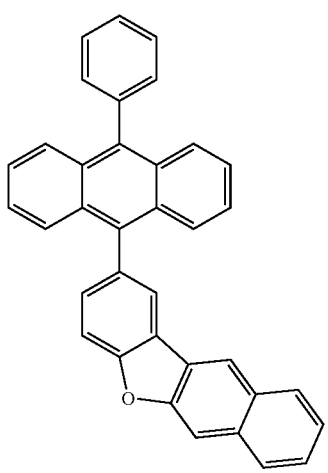

3-16
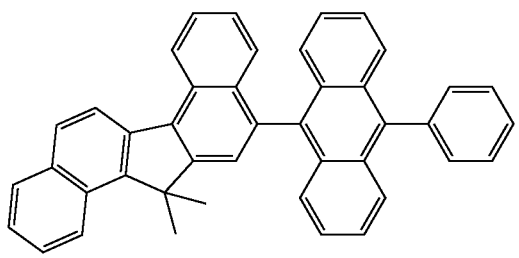

In the luminescence devices 10 of exemplary embodiments as shown in FIG. 1 to FIG. 4, the emission layer EML may include a host and a dopant, and the emission layer EML may include the compounds represented by the above-described chemical formulae as host or dopant materials.

The emission layer EML may further include commonly used materials well known as the host material in the art. For example, the emission layer EML may include as a host material, at least one of bis[2-(diphenylphosphino)phenyl] ether oxide (DPEPO), 4,4'-bis(carbazol-9-yl)biphenyl (CBP), 1,3-bis(carbazol-9-yl)benzene (mCP), 2,8-bis(diphenylphosphoryl)dibenzo[b,d]furan (PPF), 4,4',4''-tris (carbazol-9-yl) triphenylamine or 1,3,5-tris(1-phenyl-1H-benzo[d] imidazol-2-yl)benzene (TPBi). However, an embodiment of the inventive concept is not limited thereto. For example, tris(8-hydroxyquinolino)aluminum ($Alq_3$), 4,4'-bis(N-carbazolyl)-1,1'-biphenyl (CBP), poly(N-vinylcarbazole) (PVK), 9,10-di(naphthalene-2-yl)anthracene (ADN), 2-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis (triphenylsilyl)benzene (UGH2), hexaphenylcyclotrisiloxane ($DPSiO_3$), octaphenylcyclotetrasiloxane ($DPSiO_4$), 2,8-bis(diphenylphosphoryl)dibenzofuran (PPF), 9-(4-tert-butylphenyl)-3,6-bis(triphenylsilyl)-9H-carbazole (CzSi), etc. may be used as the host material.

In an embodiment, the emission layer EML may include as the dopant material, styryl derivatives (for example, 1,4-bis[2-(3-N-ethylcarbazoryl)vinyl]benzene (BCzVB), 4-(di-p-tolylamino)-4'-[(di-p-tolylamino)styryl]stilbene (DPAVB), and N-(4-((E)-2-(6-((E)-4-(diphenylamino) styryl)naphthalen-2-yl)vinyl)phenyl)-N-phenylbenzenamine (N-BDAVBi)), perylene and the derivatives thereof (for example, 2,5,8,11-tetra-t-butylperylene (TBP)), pyrene and the derivatives thereof (for example, 1,1-dipyrene, 1,4-dipyrenylbenzene, 1,4-bis(N,N-diphenylamino)pyrene), etc.

The explanation has been based on that the emission layer EML included an organic light-emitting material, but an embodiment of the inventive concept is not limited thereto. For example, the emission layer EML may include an inorganic material of a quantum dot, or a quantum rod.

In the luminescence devices 10 of embodiments as shown in FIGS. 1 to 4, the electron transport region ETR is disposed on the emission layer EML. The electron transport region ETR may include at least one of a hole blocking layer HBL, an electron transport layer ETL or an electron injection layer EIL. However, an embodiment is not limited thereto.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of an electron injection layer EIL or an electron transport layer ETL, or a single layer structure formed using an electron injection material or an electron transport material. Also, the electron transport region ETR may have a single layer structure formed using a plurality of different materials, or a structure stacked from the emission layer EML of electron transport layer ETL/electron injection layer EIL, or hole blocking layer HBL/electron transport layer ETL/electron injection layer EIL, without limitation. The thickness of the electron transport region ETR may be, for example, from about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

If the electron transport region ETR includes an electron transport layer ETL, the electron transport region ETR may include an anthracene-based compound. An embodiment of the inventive concept is not limited thereto, but the electron transport region ETR may include, for example, tris(8- hydroxyquinolinato)aluminum (Alq₃), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazole-1-ylphenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate (Bebg₂), 9,10-di(naphthalene-2-yl)anthracene (ADN), 1,3-bis[3,5-di(pyridine-3-yl)phenyl]benzene (BmPyPhB), or a mixture thereof. The thickness of the electron transport layer ETL may be from about 100 Å to about 1,000 Å and may be, for example, from about 150 Å to about 500 Å. If the thickness of the electron transport layer ETL satisfies the above-described range, satisfactory electron transport properties may be obtained without substantial increase of a driving voltage.

If the electron transport region ETR includes the electron injection layer EIL, the electron transport region ETR may use a metal halide such as LiF, NaCl, CsF, RbCl, RbI, and CuI, a metal in lanthanoides such as Yb, a metal oxide such as Li₂O and BaO, or lithium quinolate (LiQ). However, an embodiment of the inventive concept is not limited thereto. The electron injection layer EIL may also be formed using a mixture material of an electron transport material and an insulating organometal salt. The organometal salt may be a material having an energy band gap of about 4 eV or more. Particularly, the organometal salt may include, for example, metal acetates, metal benzoates, metal acetoacetates, metal acetylacetonates, or metal stearates. The thickness of the electron injection layer EIL may be from about 1 Å to about 100 Å, and from about 3 Å to about 90 Å. If the thickness of the electron injection layer EIL satisfies the above described range, satisfactory electron injection properties may be obtained without inducing substantial increase of a driving voltage.

The electron transport region ETR may include a hole blocking layer HBL as described above. The hole blocking layer HBL may include, for example, at least one of 2,9-dimethyl-4,7-diphenyl-1,10-phenanthroline (BCP), or 4,7-diphenyl-1,10-phenanthroline (Bphen). However, an embodiment of the inventive concept is not limited thereto.

The second electrode EL2 is disposed on the electron transport region ETR. The second electrode EL2 may be a common electrode or a cathode. The second electrode EL2 may be a transmissive electrode, a transflective electrode or a reflective electrode. If the second electrode EL2 is the transmissive electrode, the second electrode EL2 may be formed using a transparent metal oxide, for example, ITO, IZO, ZnO, ITZO, etc.

If the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Alternatively, the second electrode EL2 may have a multilayered structure including a reflective layer or a transflective layer formed using the above-described materials and a transparent conductive layer formed using ITO, IZO, ZnO, ITZO, etc.

Though not shown, the second electrode EL2 may be connected with an auxiliary electrode. If the second electrode EL2 is connected with the auxiliary electrode, the resistance of the second electrode EL2 may decrease.

A capping layer (CPL) may be further disposed on the second electrode EL2 of the luminescence device 10 of an embodiment. Meanwhile, though not shown in the drawings, a capping layer (CPL) may be disposed on the second electrode EL2 of the luminescence device 10 of an embodiment. The capping layer CPL may include, for example, α-NPD, NPB, TPD, m-MTDATA, Alq₃, CuPc, N4,N4,N4',N4'-tetra(biphenyl-4-yl) biphenyl-4,4'-diamine (TPD15), 4,4',4''-tris(carbazol-9-yl)triphenylamine (TCTA), etc.

The above-described compound of an embodiment may be included in a functional layer other than the hole transport region HTR as a material for the luminescence device 10. The luminescence device 10 according to an embodiment of the inventive concept may include the above-described compound in at least one functional layer disposed between the first electrode EL1 and the second electrode EL2, or in the capping layer (CPL) disposed on the second electrode EL2.

In the luminescence device 10, according to the application of voltages to the first electrode EL1 and second electrode EL2, respectively, holes injected from the first electrode EL1 may move via the hole transport region HTR to the emission layer EML, and electrons injected from the second electrode EL2 may move via the electron transport region ETR to the emission layer EML. The electrons and the holes are recombined in the emission layer EML to produce excitons, and the excitons may emit light via transition from an excited state to a ground state.

Hereinafter, the compound according to an embodiment of the inventive concept and the luminescence device 10 of an embodiment including the compound of an embodiment will be particularly explained referring to embodiments and comparative embodiments. The following embodiments are only illustrations to assist the understanding of the inventive concept, and the scope of the inventive concept is not limited thereto.

EXAMPLES

1. Synthetic Examples

The polycyclic compound of an embodiment may be synthesized, for example, by the following. However, the synthetic method of the polycyclic compound of an embodiment is not limited thereto.

1-1. Synthesis of Intermediate A-4

Intermediate A-4 for synthesizing the compound of an embodiment may be synthesized, for example, by the following Scheme 1:

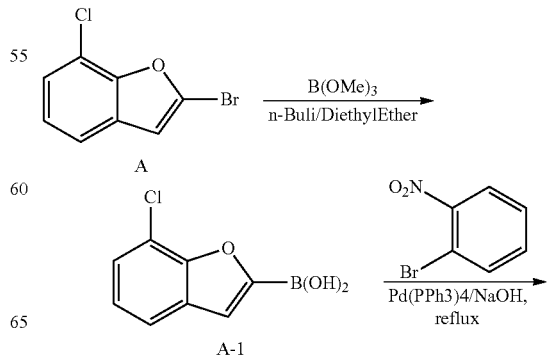

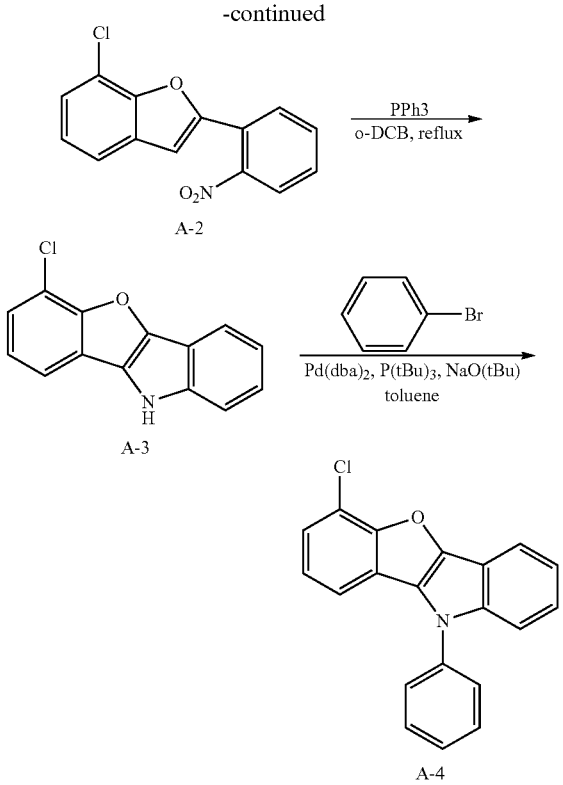

Synthesis of Intermediate A-1

Under an argon atmosphere, to a 500 ml, three-neck flask, Reactant A (11.57 g, 50 mmol), and diethyl ether (250 ml) were added, and the temperature was decreased to about −78° C. Then, n-BuLi (74.07 g, 120 mmol) was added thereto dropwise and stirred for about 1 hour. After that, B(OMe)₃ (15.59 g, 150 mmol) was added thereto dropwise, and the reaction temperature was elevated back to room temperature, followed by stirring for about 3 hours. Then, the reaction solution was neutralized with 1 M (1 molar concentration) HCl, extracted with CH$_2$Cl$_2$, dried with MgSO$_4$, and concentrated. The crude product thus obtained was separated by silica gel column chromatography to obtain a white solid compound (7.07 g, yield 72%).

The molecular ion peak (m/z) of Intermediate A-1 measured by a FAB-MS measurement method was 196.

Synthesis of Intermediate A-2

Under an argon atmosphere, to a 500 ml, three-neck flask, 2-nitrobromobenzene (6.0 g, 29.6 mmol), Intermediate A-1 (7.00 g, 35.6 mmol), K$_3$PO$_4$ (12.8 g, 60.5 mmol), toluene (138.6 ml), ethanol (69.3 ml), and H$_2$O (34.6 ml) were added in order and then completely mixed. Then, Pd(PPh$_3$)$_4$ (1.2 g, 1.07 mmol) was added thereto, followed by heating and stirring at about 80° C. for about 4 hours. After cooling to room temperature in the air, reaction solvents were removed by distillation. The crude product thus obtained was separated by silica gel column chromatography to obtain Intermediate A-2 (6.32 g, yield 78%) as a white solid.

The molecular ion peak (m/z) of Intermediate A-2 measured by a FAB-MS measurement method was 273.

Synthesis of Intermediate A-3

Under an argon atmosphere, to a 500 ml, three-neck flask, A-2 (6.2 g, 22.6 mmol), PPh$_3$ (14.8 g, 56.5 mmol), and o-dichlorobenzene (105 ml) were added, followed by refluxing and stirring for about 24 hours. After cooling to room temperature in the air, the reaction product was filtered. The filtrate was concentrated and separated by silica gel column chromatography to obtain Intermediate A-3 (2.5 g, yield 45%).

The molecular ion peak (m/z) of Intermediate A-3 measured by a FAB-MS measurement method was 241.

Synthesis of Intermediate A-4

Under an argon atmosphere, to a 500 ml, three-neck flask, Intermediate A-3 (5.0 g, 20.7 mmol), Pd(dba)$_2$ (0.59 g, 0.05 eq, 1.03 mmol), NaOtBu (1.99 g, 1 eq, 20.7 mmol), toluene (194 ml), bromobenzene (4.64 g, 1.1 eq, 22.77 mmol) and tBu$_3$P (0.79 g, 0.2 eq, 4.14 mmol) were added in order, followed by heating, refluxing and stirring for about 6 hours. After cooling in the air to room temperature, water was added to the reaction solvent, and the organic layer separated. The aqueous layer was extracted with toluene. The combined organic layers were washed with a saline solution and dried with MgSO$_4$. MgSO$_4$ was filtered and removed, and the filtrate was concentrated to obtain a crude product. The crude product thus obtained was separated by silica gel column chromatography to obtain Intermediate A-4 (5.72 g, yield 87%) as a white solid.

The molecular ion peak (m/z) of Intermediate A-4 measured by a FAB-MS measurement method was 317.

1-2. Synthesis of Compound A15

Polycyclic Compound A15 of an embodiment may be synthesized, for example, by the following Scheme 2:

Scheme 2

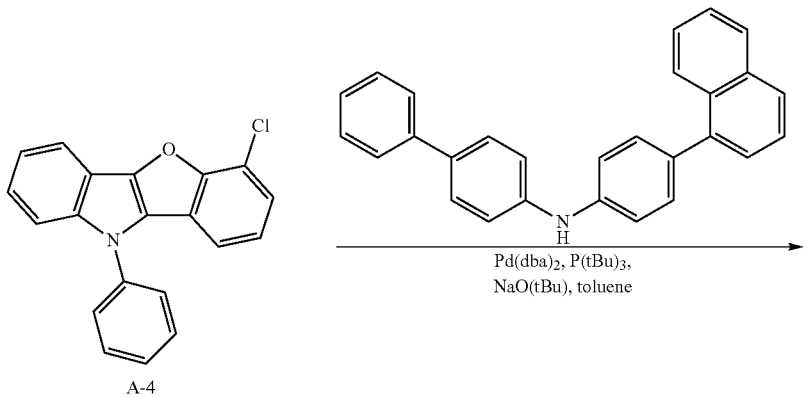

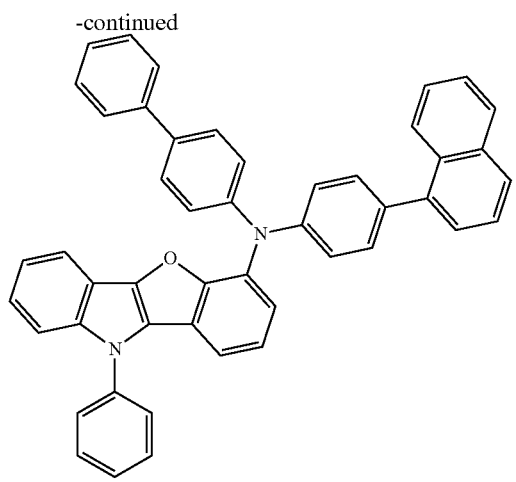

A15

Synthesis of Compound 15

Under an argon atmosphere, to a 300 ml, three-neck flask, Intermediate A-4 (4.8 g, 14.98 mmol), Pd(dba)$_2$ (0.43 g, 0.05 eq, 0.75 mmol), NaOtBu (1.44 g, 1 eq, 14.98 mmol), toluene (164 ml), N,N-(4-biphenyl)-[4-(1-naphthalenyl)phenyl]yl)amine (6.12 g, 1.1 eq, 16.48 mmol) and tBu$_3$P (0.61 g, 0.2 eq, 3.0 mmol) were added in order, followed by heating, refluxing and stirring for about 6 hours. After cooling to room temperature in the air, water was added to a reaction solvent, and the organic layer was separated. The aqueous layer was extracted with toluene. The combined organic layers were collected and then washed with a saline solution and dried with MgSO$_4$. MgSO$_4$ was filtered and removed, and the filtrate was concentrated to obtain a crude product. The crude product was separated by silica gel column chromatography to obtain Intermediate A15 (6.8 g, yield 70%) as a white solid.

The molecular ion peak (m/z) of Intermediate A15 measured by a FAB-MS measurement method was 652.

1-3. Synthesis of Compound A45

Polycyclic Compound A45 of an embodiment may be synthesized, for example, by the following Scheme 3:

Scheme 3

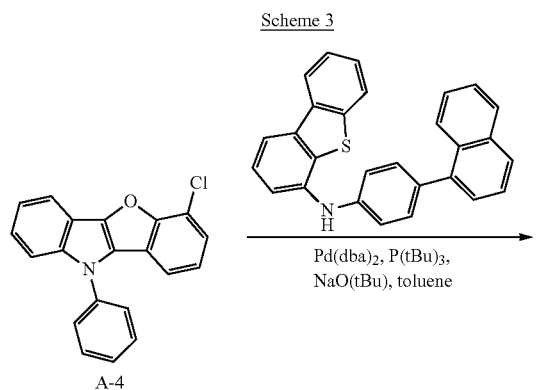

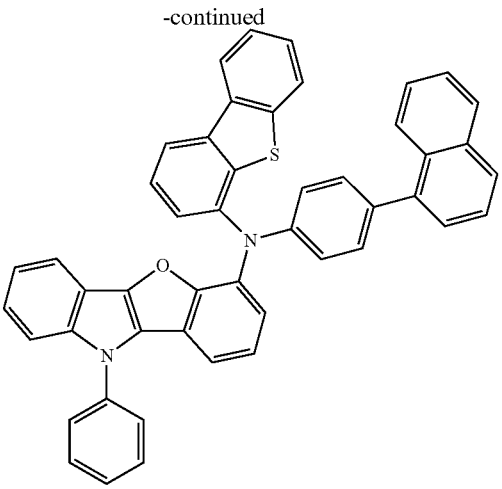

A45

Synthesis of Compound A45

Compound A45 was synthesized by the same method as the synthetic method of Compound A15 except for using N,N-[4-(1-naphthalenyl)phenyl]-4-dibenzothiophenyl-4-amine instead of N,N-(4-biphenyl)-[4-(1-naphthalenyl)phenyl]yl)amine.

The molecular ion peak (m/z) of Intermediate A45 measured by a FAB-MS measurement method was 682.

1-4. Synthesis of Intermediate B-4

Intermediate B-4 for synthesizing the compound of an embodiment may be synthesized, for example, by the following Scheme 4:

Scheme 4

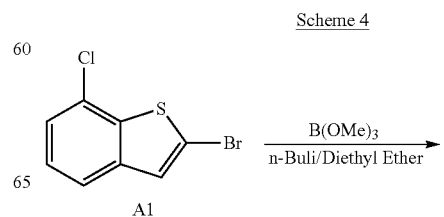

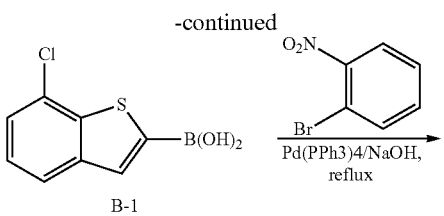

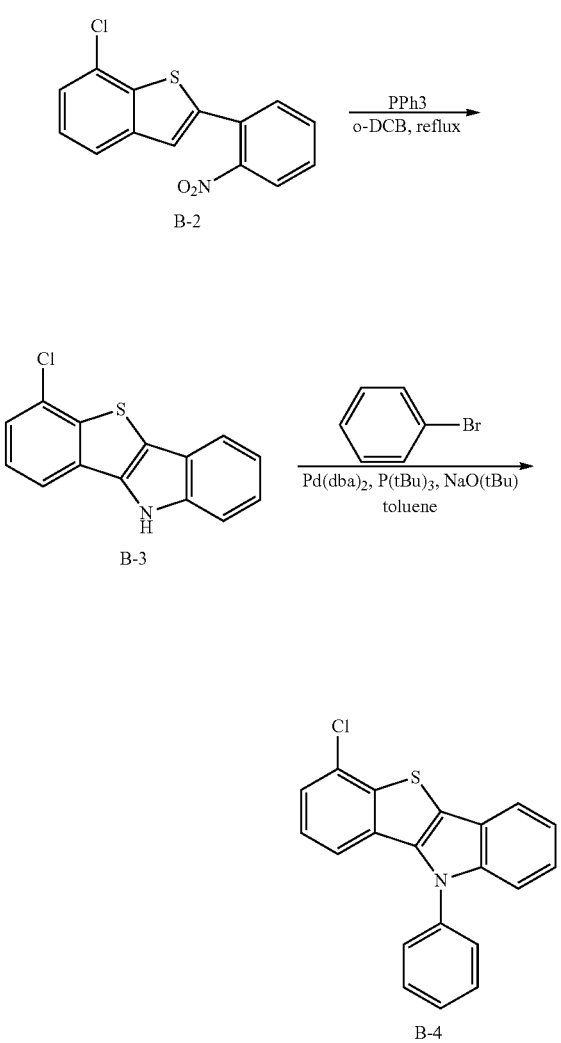

Synthesis of Intermediate B-1

Under an argon atmosphere, to a 500 ml, three-neck flask, Reactant A1 (12.37 g, 50 mmol), and diethyl ether (250 ml) were added, and the temperature was decreased to about −78° C. Then, n-BuLi (74.07 g, 120 mmol) was added thereto dropwise and stirred for about 1 hour. After that, B(OMe)$_3$ (15.59 g, 150 mmol) was added thereto dropwise, and the reaction temperature was elevated back to room temperature, followed by stirring for about 3 hours. Then, the reaction solution was neutralized with 1 M HC, extracted with CH$_2$Cl$_2$, dried with MgSO$_4$, and concentrated. The crude product thus obtained was separated by silica gel column chromatography to obtain a white solid compound (7.65 g, yield 72%).

The molecular ion peak (m/z) of Intermediate B-1 measured by a FAB-MS measurement method was 212.

Synthesis of Intermediate B-2

Under an argon atmosphere, to a 500 ml, three-neck flask, 2-nitrobromobenzene (7.0 g, 34.6 mmol), Intermediate B-1 (7.36 g, 41.6 mmol), K$_3$PO$_4$ (14.7 g, 69.3 mmol), toluene (138.6 ml), ethanol (69.3 ml), and H$_2$O (34.6 ml) were added in order and then completely mixed. Then, Pd(PPh$_3$)$_4$ (1.2 g, 1.07 mmol) was added thereto, followed by heating and stirring at about 80° C. for about 4 hours. After cooling to room temperature in the air, reaction solvents were removed by distillation. The crude product thus obtained was separated by silica gel column chromatography to obtain Intermediate B-2 (7.8 g, yield 78%) as a white solid.

The molecular ion peak (m/z) of Intermediate B-2 measured by a FAB-MS measurement method was 289.

Synthesis of Intermediate B-3

Under an argon atmosphere, to a 500 ml, three-neck flask, B-2 (7.5 g, 25.9 mmol), PPh$_3$ (6.8 g, 25.9 mmol), and o-dichlorobenzene (105 ml) were added, followed by refluxing and stirring for about 24 hours. After cooling to room temperature in the air, the reaction product was filtered. The filtrate was concentrated and separated by silica gel column chromatography to obtain Intermediate B-3 (5.3 g, yield 79%).

The molecular ion peak (m/z) of Intermediate B-3 measured by a FAB-MS measurement method was 257.

Synthesis of Intermediate B-4

Under an argon atmosphere, to a 500 ml, three-neck flask, Intermediate B-3 (5.0 g, 19.4 mmol), Pd(dba)$_2$ (0.56 g, 0.05 eq, 0.97 mmol), NaOtBu (1.86 g, 1 eq, 19.40 mmol), toluene (194 ml), bromobenzene (3.05 g, 1.1 eq, 21.34 mmol) and tBu$_3$P (0.79 g, 0.2 eq, 4.14 mmol) were added in order, followed by heating, refluxing and stirring for about 6 hours. After cooling in the air to room temperature, water was added to the reaction solvent, and the organic layer separated. The aqueous layer was extracted with toluene. The combined organic layers were washed with a saline solution and dried with MgSO$_4$. MgSO$_4$ was filtered and removed, and the filtrate was concentrated to obtain a crude product. The crude product thus obtained was separated by silica gel column chromatography to obtain Intermediate B-4 (5.6 g, yield 87%) as a white solid.

The molecular ion peak (m/z) of Intermediate B-4 measured by a FAB-MS measurement method was 333.

1-5. Synthesis of Compound B4

Polycyclic Compound B4 of an embodiment may be synthesized, for example, by the following Scheme 5:

Scheme 5

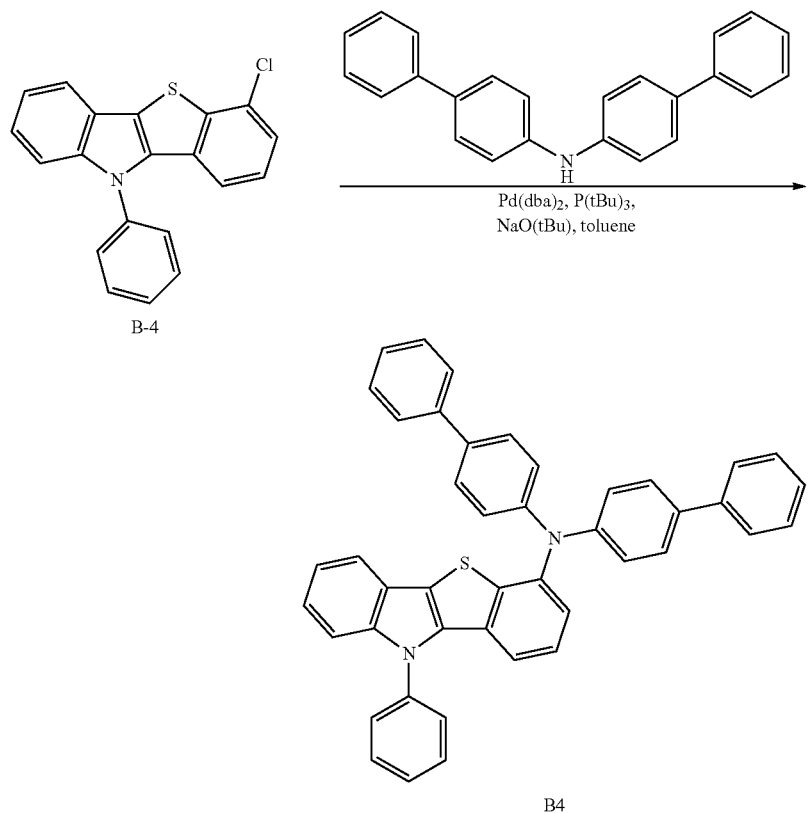

Synthesis of Compound B4

Under an argon atmosphere, to a 300 ml, three-neck flask, Intermediate B-4 (5.0 g, 14.98 mmol), Pd(dba)$_2$ (0.43 g, 0.05 eq, 0.75 mmol), NaOtBu (1.44 g, 1 eq, 14.98 mmol), toluene (164 ml), N,N'-dibiphenylamine (5.30 g, 1.1 eq, 16.48 mmol) and tBu$_3$P (0.61 g, 0.2 eq, 3.0 mmol) were added in order, followed by heating, refluxing and stirring for about 6 hours. After cooling to room temperature in the air, water was added to a reaction solvent, and the organic layer was separated. Then aqueous layer was extracted with toluene. The combined organic layers were washed with a saline solution and dried with MgSO$_4$. MgSO$_4$ was filtered and removed, and the filtrate was concentrated to obtain a crude product. The crude product thus obtained was separated by silica gel column chromatography to obtain Compound B4 (6.5 g, yield 70%) as a white solid.

The molecular ion peak (m/z) of Compound B4 measured by a FAB-MS measurement method was 618.

1-6. Synthesis of Compound B15

Polycyclic Compound B15 of an embodiment may be synthesized, for example, by the following Scheme 6:

Scheme 6

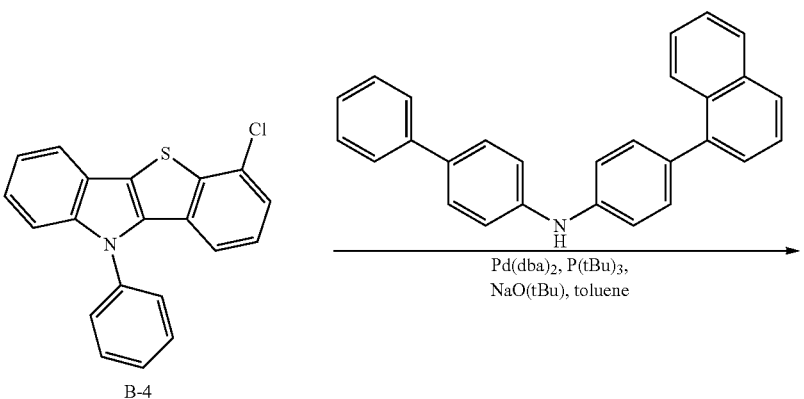

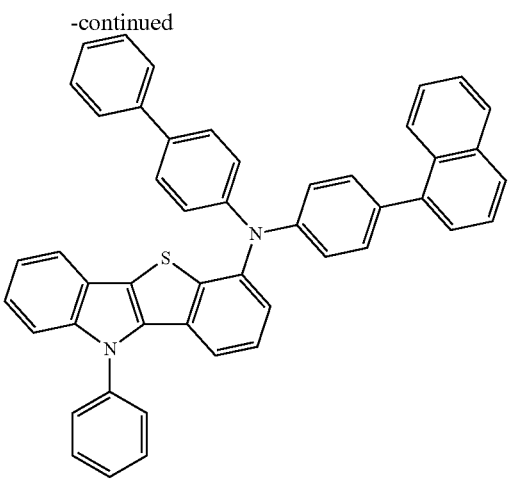

B15

Synthesis of Compound B15

Compound B15 was synthesized by the same method as the synthetic method of Compound B4 except for using N,N-[4-(biphenyl)-]-4-(1-naphthalenyl)phenyl)amine instead of N,N'-dibiphenylamine.

The molecular ion peak (m/z) of Compound B15 measured by a FAB-MS measurement method was 668.

1-7. Synthesis of Compound B44

Polycyclic Compound B44 of an embodiment may be synthesized, for example, by the following Scheme 7:

Scheme 7

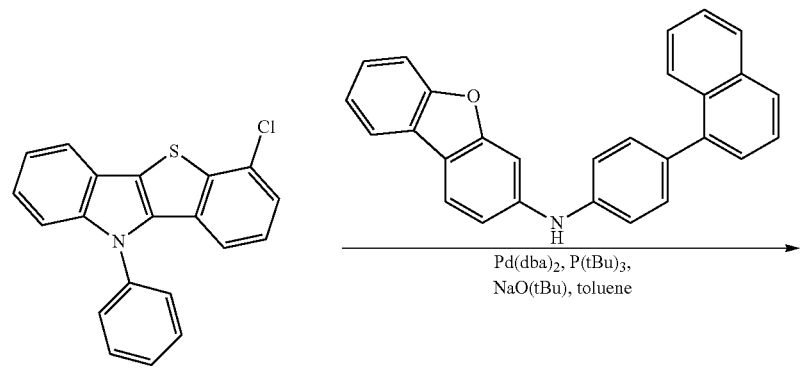

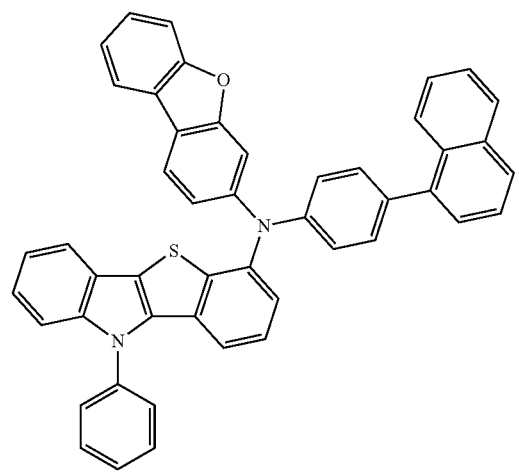

B44

Synthesis of Compound B44

Compound B44 was synthesized by the same method as the synthetic method of Compound B4 except for using N,N-[4-(1-naphthalenyl)phenyl]-3-dibenzofuranphenyl-4-amine instead of N,N'-dibiphenylamine.

The molecular ion peak (m/z) of Compound B44 measured by a FAB-MS measurement method was 682.

1-8. Synthesis of Compound B45

Polycyclic Compound B45 of an embodiment may be synthesized, for example, by the following Scheme 8:

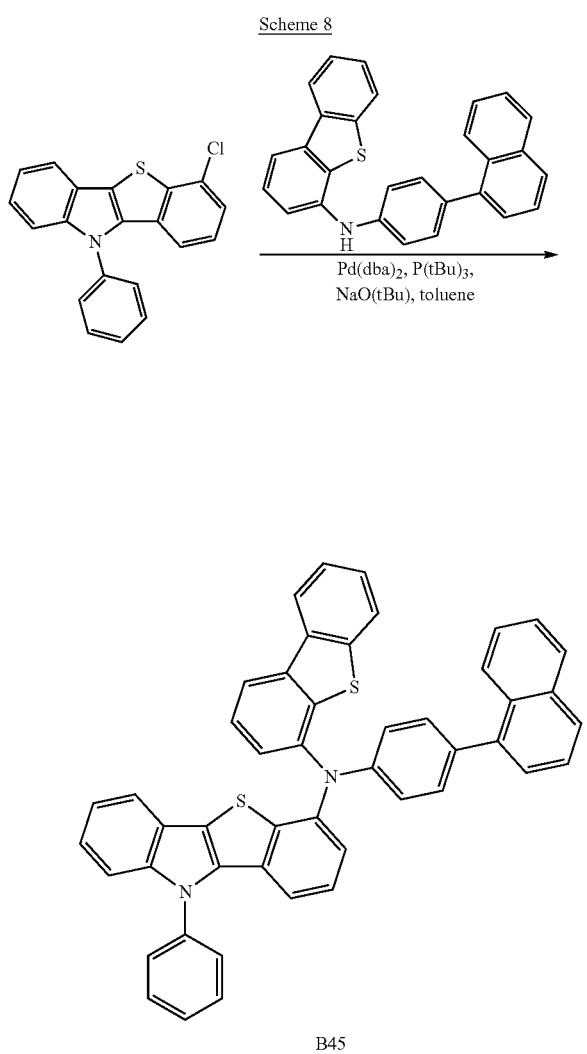

B45

Synthesis of Compound B45

Compound B45 was synthesized by the same method as the synthetic method of Compound B4 except for using N,N-[4-(1-naphthalenyl)phenyl]-4-dibenzothiophenyl-4-amine instead of N,N'-dibiphenylamine.

The molecular ion peak (m/z) of Compound B45 measured by a FAB-MS measurement method was 698.

1-9. Synthesis of Compound B53

Polycyclic Compound B53 of an embodiment may be synthesized, for example, by the following Scheme 9:

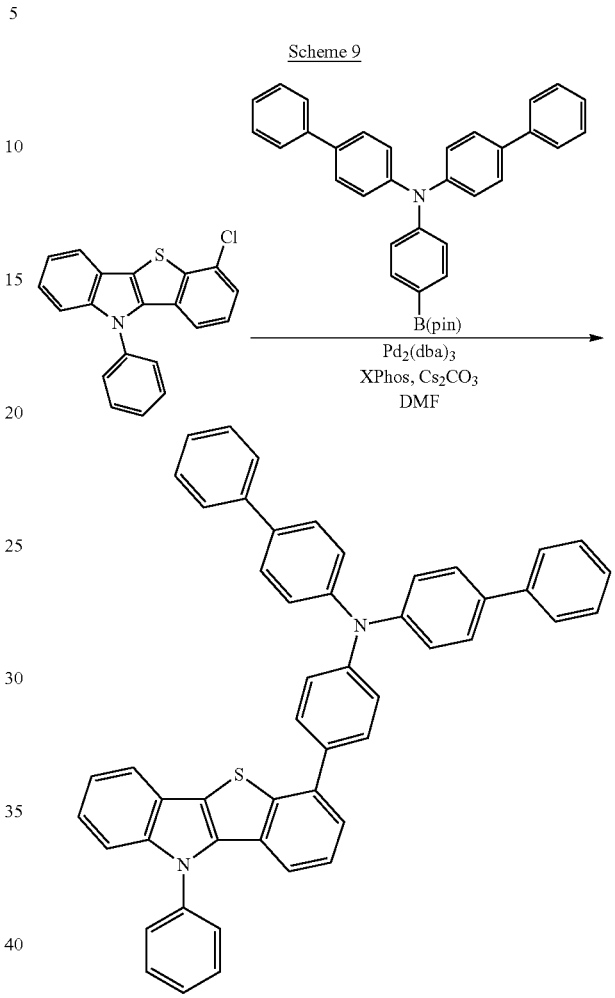

(Synthesis of Compound B53)

Under an argon atmosphere, to a 300 ml, three-neck flask, Intermediate B-4 (5.0 g, 14.98 mmol), N,N-di(4-biphenyl)-4-(4,4,5,5-tetramethyl-1,3,2-dioxaborolan-2-yl)aniline (6.53 g, 1.1 eq, 16.5 mmol), Pd(dba)$_2$ (0.55 g, 0.04 eq, 0.6 mmol), Cs$_2$CO$_3$ (14.64 g, 3 eq, 44.94 mmol), 2-dicyclohexylphosphino-2',4',6'-triisopropylbiphenyl (XPhos, 0.86 g, 0.12 eq, 1.8 mmol), and N,N-dimethylformamide (DMF, 100 ml) were added in order, followed by heating, refluxing and stirring at about 130° C. for about 6 hours. After cooling to room temperature in the air, water was added to a reaction mixture, and an organic layer was separated. Toluene was added to an aqueous layer, and organic layers were additionally extracted by adding CH$_2$Cl$_2$. The combined organic layers were washed with a saline solution and dried with MgSO$_4$. MgSO$_4$ was filtered and removed, and an organic layer was concentrated to obtain a crude product. The crude product thus obtained was separated by silica gel column chromatography to obtain Compound B53 (7.7 g, yield 68%) as a white solid.

The molecular ion peak (m/z) of Compound B53 measured by a FAB-MS measurement method was 694.

1-10. Synthesis of Compound B72

Polycyclic Compound B72 of an embodiment may be synthesized, for example, by the following Scheme 10:

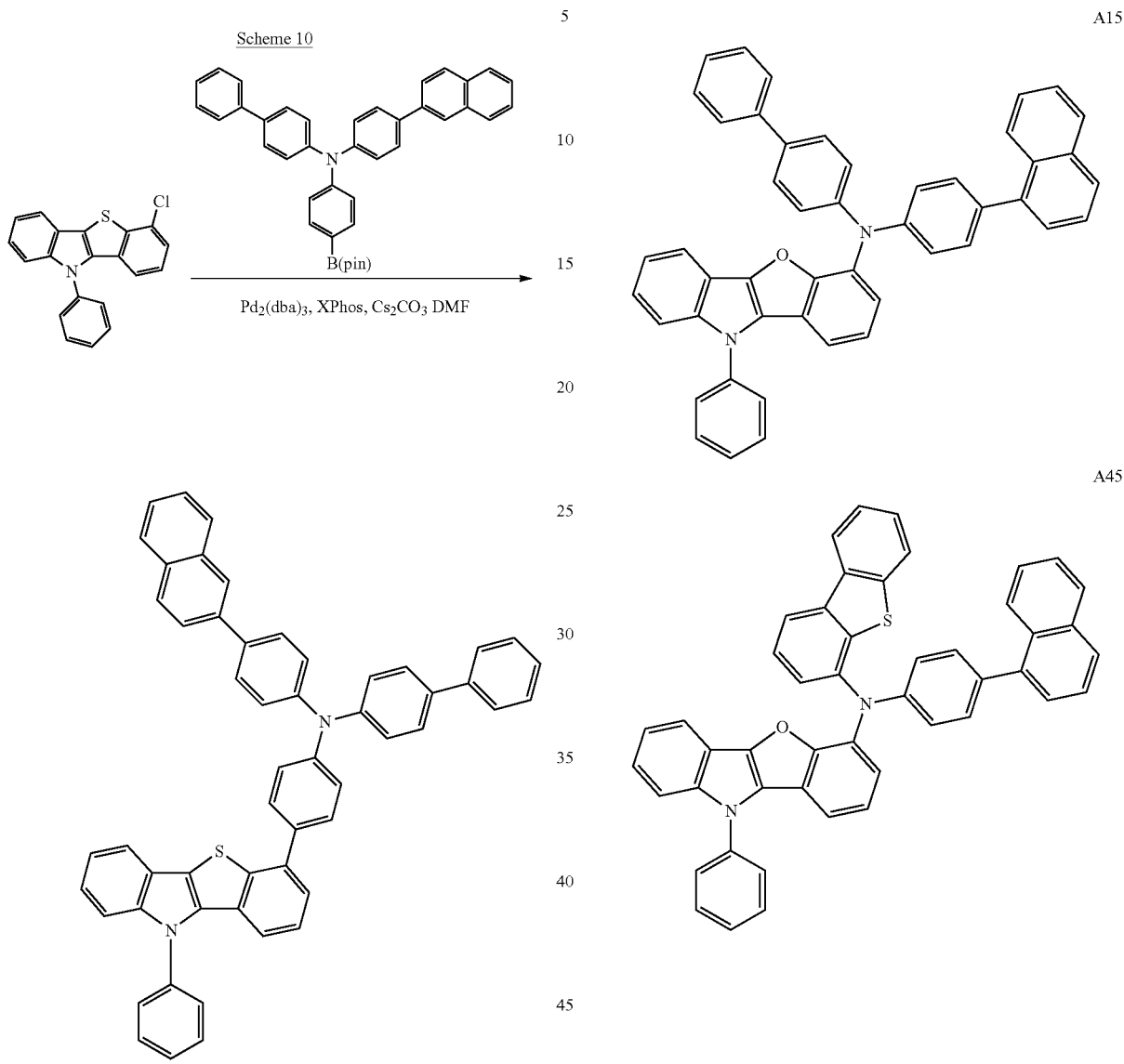

Synthesis of Compound B72

Compound B72 was synthesized by the same method as the synthetic method of Compound B53 except for using N,N-[4-(biphenylyl)-4-(2-naphthyl)phenyldioxaborolan-2-yl]aniline instead of N,N-di(4-biphenyl)-4-(4,4,5,5-tetramethyl-1,3,2-dioxaborolan-2-yl)aniline.

The molecular ion peak (m/z) of Compound B72 measured by a FAB-MS measurement method was 744.

2. Manufacture and Evaluation of Luminescence Device Including Polycyclic Compound 2-1. Example of Luminescence Device Including Polycyclic Compound Luminescence devices of Examples 1 to 6, and Comparative Examples 1 to 4 were manufactured using Example Compounds A15, A45, B4, B15, B44, B45, B53, and B71, and Comparative Compounds C1 to C6 as materials for a hole transport layer.

Example Compounds

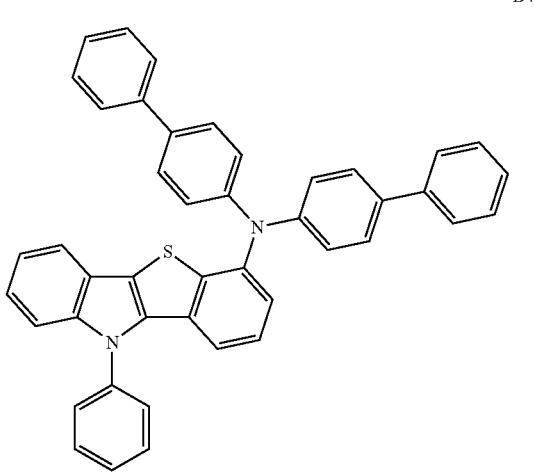

B15
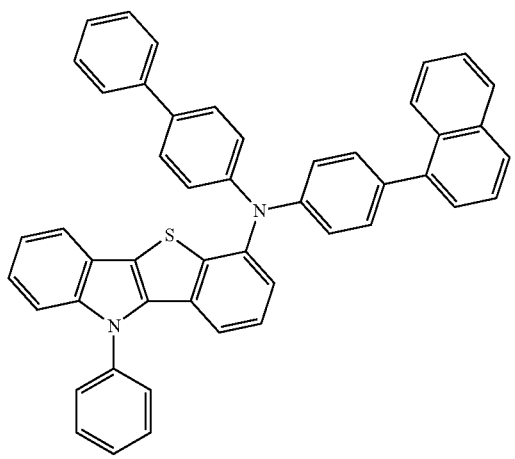
B44
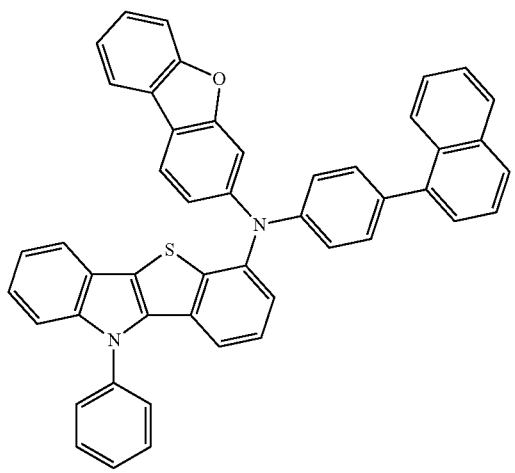
B45
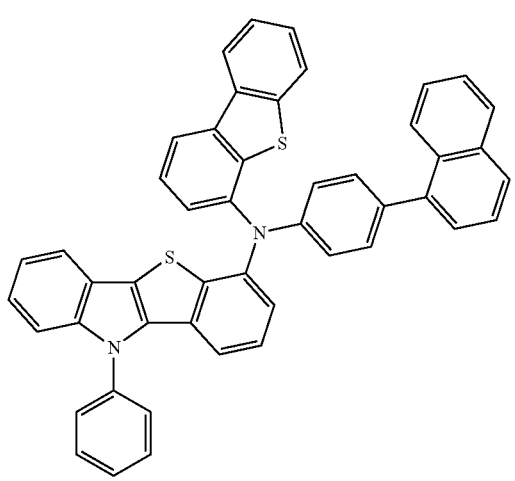
B53
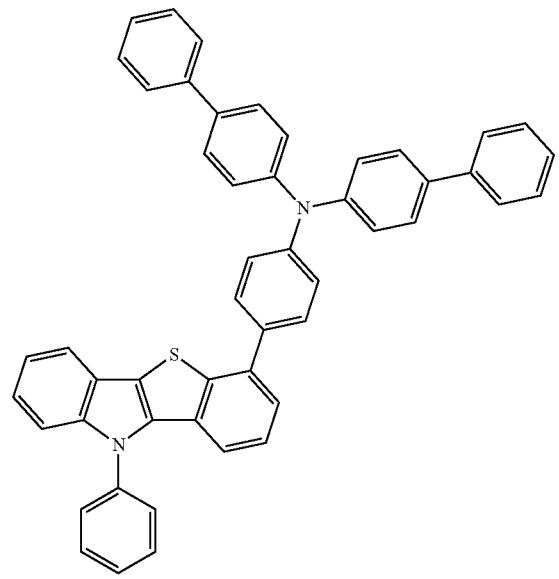
B72
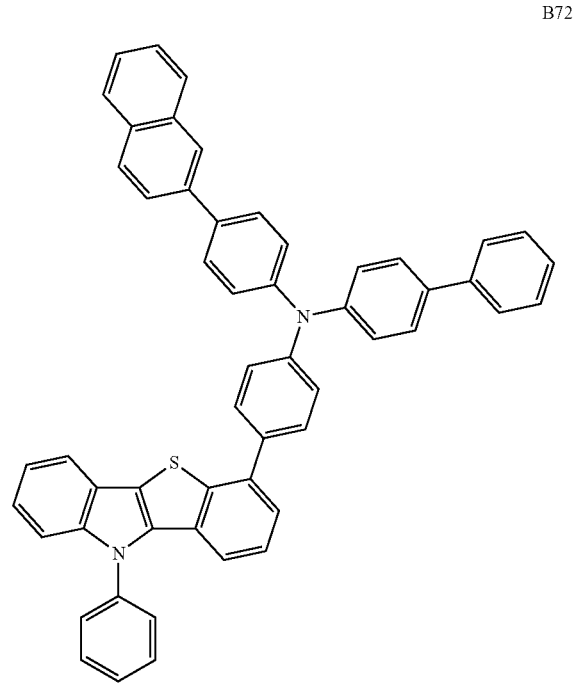

Comparative Compounds

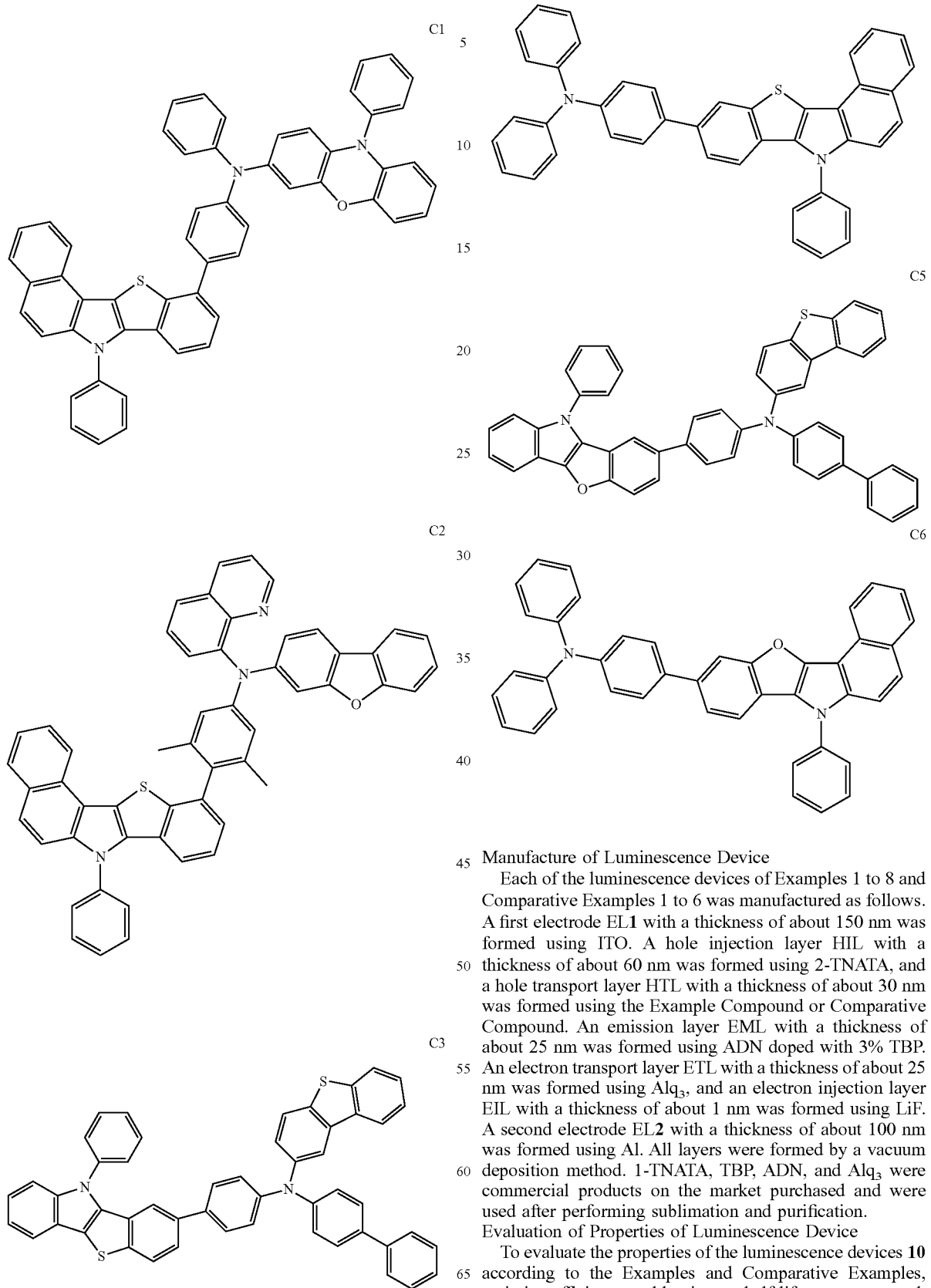

Manufacture of Luminescence Device

Each of the luminescence devices of Examples 1 to 8 and Comparative Examples 1 to 6 was manufactured as follows. A first electrode EL1 with a thickness of about 150 nm was formed using ITO. A hole injection layer HIL with a thickness of about 60 nm was formed using 2-TNATA, and a hole transport layer HTL with a thickness of about 30 nm was formed using the Example Compound or Comparative Compound. An emission layer EML with a thickness of about 25 nm was formed using ADN doped with 3% TBP. An electron transport layer ETL with a thickness of about 25 nm was formed using $Alq_3$, and an electron injection layer EIL with a thickness of about 1 nm was formed using LiF. A second electrode EL2 with a thickness of about 100 nm was formed using Al. All layers were formed by a vacuum deposition method. 1-TNATA, TBP, ADN, and $Alq_3$ were commercial products on the market purchased and were used after performing sublimation and purification.

Evaluation of Properties of Luminescence Device

To evaluate the properties of the luminescence devices 10 according to the Examples and Comparative Examples, emission efficiency and luminance half-life were measured. The emission efficiency was a value on a current density of about 10 mA/cm². The luminance half-life was represented based on a time period required for decreasing luminescence of about 1,000 cd/m² by 50%. The luminance half-life was measured by continuously driving at a current density of about 1.0 mA/cm². For the evaluation of emission properties of the luminescence devices 10 manufactured, a current density, a driving voltage, and emission efficiency were measured using Source Meter of 2400 Series of Keithley Instruments Co., a luminance colorimeter, CS-200 which is a product of Konica Minolta Co., and LabVIEW8.2 PC program for measurement, which is a product of Japanese National Instruments Co.

TABLE 1

| Device manufacturing example | Hole transport layer material | Driving voltage (V) | Current density (cd/A) | Luminance half-life |
|---|---|---|---|---|
| Example 1 | Example Compound A15 | 5.6 | 8.1 | 2200 |
| Example 2 | Example Compound A45 | 5.5 | 8.3 | 2000 |
| Example 3 | Example Compound B4 | 5.7 | 8.1 | 2100 |
| Example 4 | Example Compound B15 | 5.8 | 8.5 | 2000 |
| Example 5 | Example Compound B44 | 5.6 | 8.4 | 2250 |
| Example 6 | Example Compound B45 | 5.7 | 8.8 | 2200 |
| Example 7 | Example Compound B53 | 5.6 | 8.3 | 2200 |
| Example 8 | Example Compound B72 | 5.8 | 8.0 | 2300 |
| Comparative Example 1 | Comparative Compound C1 | 6.0 | 6.2 | 1700 |
| Comparative Example 2 | Comparative Compound C2 | 6.0 | 6.0 | 1500 |
| Comparative Example 3 | Comparative Compound C3 | 5.9 | 7.4 | 1800 |
| Comparative Example 4 | Comparative Compound C4 | 6.1 | 7.5 | 1900 |
| Comparative Example 5 | Comparative Compound C5 | 6.2 | 6.3 | 1600 |
| Comparative Example 6 | Comparative Compound C6 | 5.9 | 7.2 | 1300 |

Referring to the results of Table 1, it could be found that if the polycyclic compound according to an embodiment of the inventive concept was applied to a luminescence device as a material for a hole transport layer, a low driving voltage, high efficiency and long life could be achieved. Particularly, it was confirmed that Example 1 to Example 8 achieved a lower driving voltage, higher efficiency and longer life when compared with Comparative Example 1 to Comparative Example 4.

When compared with Comparative Compounds C1 and C2, in which a benzene ring is additionally condensed to a benzofuranoindole skeleton or benzothienoindole skeleton, a benzene ring is not additionally condensed in the Example Compounds. Accordingly, improved hole transport capacity could be achieved due to different structural and electrical properties from those of the Comparative Compounds C1 and C2. Accordingly, the Example Compounds are considered to achieve the low driving voltage, high efficiency, and long life of a device.

The compounds of the Examples have different substitution positions of an aryl amine group from Comparative Compounds C3 to C6. Accordingly, improved hole transport capacity could be achieved due to different structural and electrical properties from those of the Comparative Compounds C3 to C6. Accordingly, the Example Compounds are considered to have achieved a low driving voltage, high efficiency, and long life of a device.

The luminescence device of an embodiment includes the polycyclic compound represented by Formula 1. Accordingly, the luminescence device of an embodiment may achieve a low driving voltage, high efficiency and long life.

By applying the polycyclic compound of an embodiment to a luminescence device, a low driving voltage, a high efficiency and a long life of a device may be achieved.

The luminescence device according to an embodiment of the inventive concept may achieve a low driving voltage, a high efficiency, and a long life.

The polycyclic compound according to an embodiment may be applied to a luminescence device to achieve a low driving voltage, a high efficiency, and a long life.

Although the exemplary embodiments of the present invention have been described, it is understood that the present invention should not be limited to these exemplary embodiments, but various changes and modifications can be made by one ordinary skilled in the art within the spirit and scope of the present invention as hereinafter claimed.

What is claimed is:
1. A luminescence device, comprising:
a first electrode;
a second electrode disposed on the first electrode; and
at least one functional layer disposed between the first electrode and the second electrode,
wherein the at least one functional layer comprises a polycyclic compound represented by Formula 1:

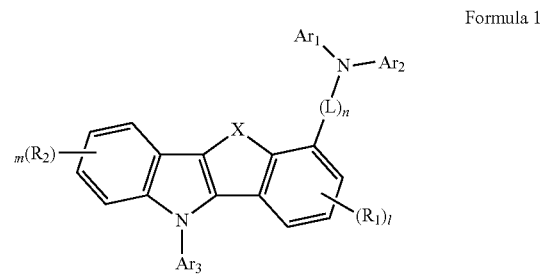

Formula 1 wherein in Formula 1,
X is O, or S,
$R_1$ and $R_2$ are each independently a hydrogen atom, a deuterium atom, a halogen atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms,
$Ar_1$ and $Ar_2$ are each independently represented by Formula 2:

$$*-(Ar_{11})_p-Ar_{12} \quad \text{Formula 2}$$

wherein in Formula 2,
$Ar_{11}$ is a substituted or unsubstituted phenylene group, a substituted or unsubstituted divalent biphenyl group, a substituted or unsubstituted divalent terphenyl group, a substituted or unsubstituted phenanthrylene group, a substituted or unsubstituted fluorenylene group, a substituted or unsubstituted naphthylene group, a substituted or unsubstituted carbazolylene group, a substituted or unsubstituted dibenzofuranylene group, or a substituted or unsubstituted dibenzothiophenylene group,
$Ar_{12}$ is a substituted or unsubstituted phenyl group, a substituted or unsubstituted biphenyl group, a substituted or unsubstituted terphenyl group, a substituted or unsubstituted phenanthryl group, a substituted or unsubstituted fluorenyl group, a substituted or unsubstituted naphthyl group, a substituted or unsubstituted carbazolyl group, a substituted or unsubstituted dibenzofuranyl group, or a substituted or unsubstituted dibenzothiophenyl group, and p is 0 or 1, provided that i) when n is 1 and *—(Ar$_{11}$)$_p$Ar$_{12}$ of Ar$_1$ is an unsubstituted biphenylene group, then *—(Ar$_{11}$)$_p$Ar$_{12}$ of Ar$_2$ is not an unsubstituted dibenzothiophenylene group, and ii) when n is 1 and *—(Ar$_{11}$)$_p$Ar$_{12}$ of Ar$_2$ is an unsubstituted biphenylene group, then *—(Ar$_{11}$)$_p$Ar$_{12}$ of Ar$_1$ is not an unsubstituted dibenzothiophenylene group, wherein in Formula 1, Ar$_3$ is a substituted or unsubstituted aryl group of 6 to 30 ring carbon atoms, or a substituted or unsubstituted heteroaryl group of 2 to 30 ring carbon atoms, L is a direct linkage, a substituted or unsubstituted arylene group of 6 to 30 ring carbon atoms, or a substituted or unsubstituted heteroarylene group of 2 to 30 ring carbon atoms, l is an integer of 0 to 3, m is an integer of 0 to 4, and n is an integer of 0 to 3.

2. The luminescence device of claim 1, wherein the at least one functional layer comprises:

a hole transport region disposed on the first electrode;

an emission layer disposed on the hole transport region; and an electron transport region disposed on the emission layer, wherein the hole transport region comprises the polycyclic compound.

3. The luminescence device of claim 2, wherein the hole transport region comprises:

a hole injection layer disposed on the first electrode; and a hole transport layer disposed between the hole injection layer and the emission layer, wherein the hole transport layer comprises the polycyclic compound.

4. The luminescence device of claim 1, wherein the polycyclic compound comprises one acyclic amine.

5. The luminescence device of claim 1, wherein Formula 1 is represented by Formula 1-1 or Formula 1-2:

Formula 1-1

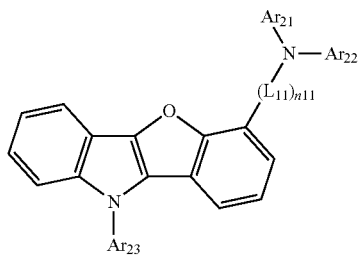

Formula 1-2

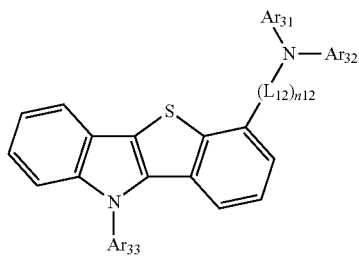

wherein in Formula 1-1 and Formula 1-2,

Ar$_{21}$, Ar$_{22}$, Ar$_{31}$, and Ar$_{32}$ are each independently represented by Formula 2, Ar$_{23}$ and Ar$_{33}$ are each independently a substituted or unsubstituted aryl group of 6 to 30 ring carbon atoms, or a substituted or unsubstituted heteroaryl group of 2 to 30 ring carbon atoms, L$_{11}$, and L$_{12}$ are each independently a direct linkage, a substituted or unsubstituted arylene group of 6 to 30 ring carbon atoms, or a substituted or unsubstituted heteroarylene group of 2 to 30 ring carbon atoms, and n11, and n12 are each independently an integer of 0 to 3.

6. The luminescence device of claim 1, wherein Formula 1 is represented by Formula 1-3:

Formula 1-3

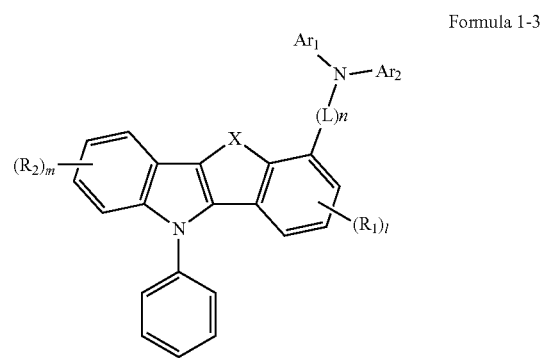

wherein in Formula 1-3,

X, R$_1$, R$_2$, Ar$_1$, Ar$_2$, L, and l to n are the same as defined in Formula 1.

7. The luminescence device of claim 1, wherein Formula 1 is represented by Formula 1-4:

Formula 1-4

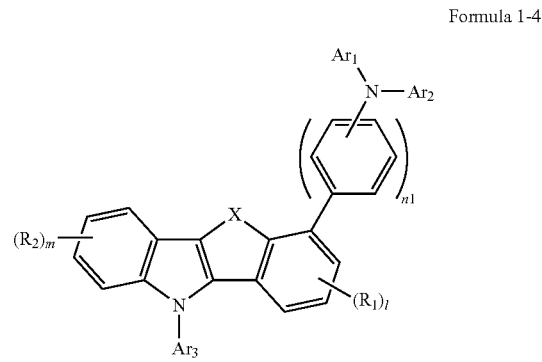

wherein in Formula 1-4, n1 is 0 or 1, and

X, R$_1$, R$_2$, Ar$_1$ to Ar$_3$, l, and m are the same as defined in Formula 1.

8. The luminescence device of claim 1, wherein Ar$_1$ and Ar$_2$ are each independently represented by Formulae 1-1 to 1-10:

1-1

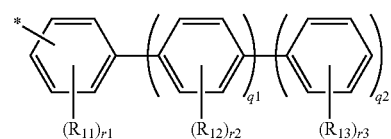

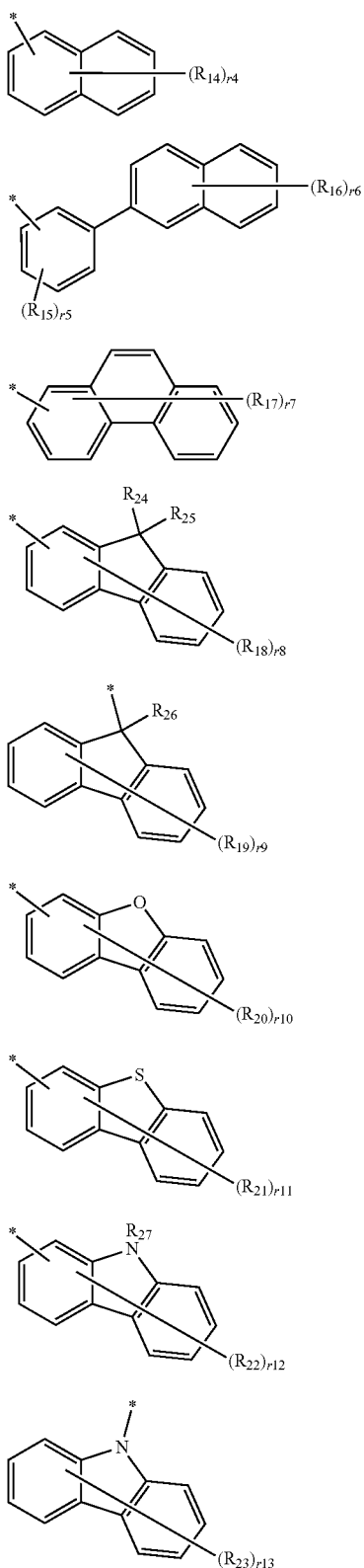

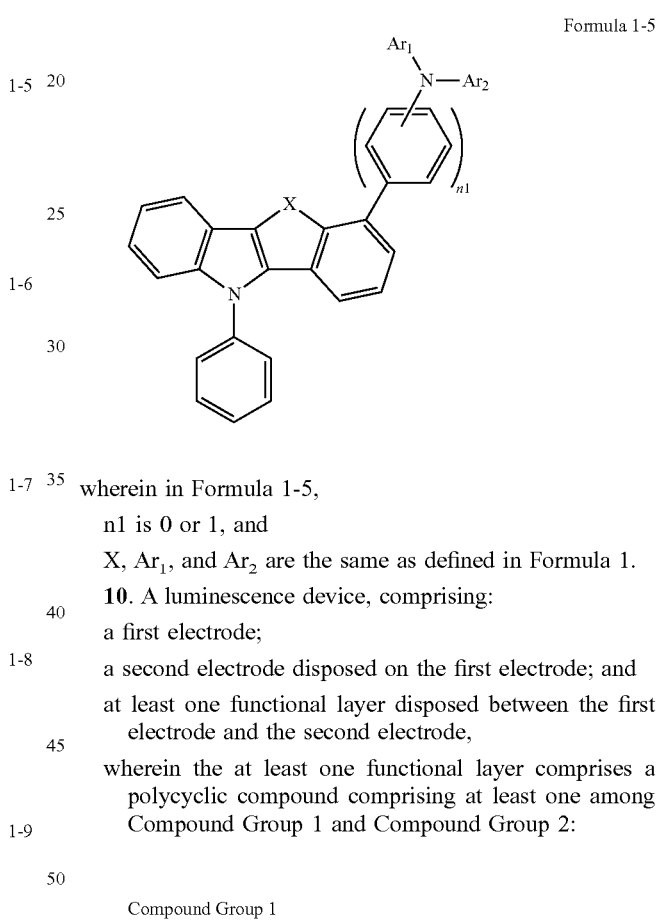

wherein in Formulae 1-1 to 1-10,

R$_{11}$ to R$_{27}$ are each independently a hydrogen atom, a deuterium atom, a halogen atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms, r1, r2, and r5 are each independently an integer of 0 to 4, r3 is an integer of 0 to 5, r4, r6, r8, and r10 to r12 are each independently an integer of 0 to 7, r7 is an integer of 0 to 9, r9 and r13 are each independently an integer of 0 to 8, and q1 and q2 are each independently 0 or 1.

9. The luminescence device of claim 1, wherein Formula 1 is represented by Formula 1-5:

Formula 1-5 wherein in Formula 1-5, n1 is 0 or 1, and

X, Ar$_1$, and Ar$_2$ are the same as defined in Formula 1.

10. A luminescence device, comprising:

a first electrode;

a second electrode disposed on the first electrode; and at least one functional layer disposed between the first electrode and the second electrode, wherein the at least one functional layer comprises a polycyclic compound comprising at least one among Compound Group 1 and Compound Group 2:

Compound Group 1

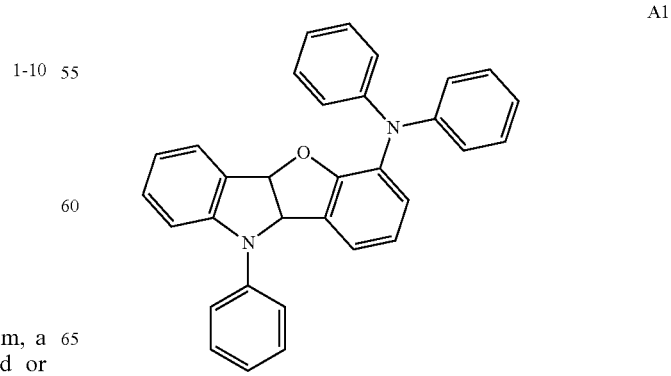

A1

A2
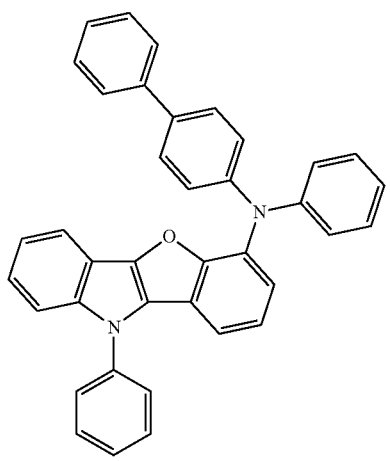
A3
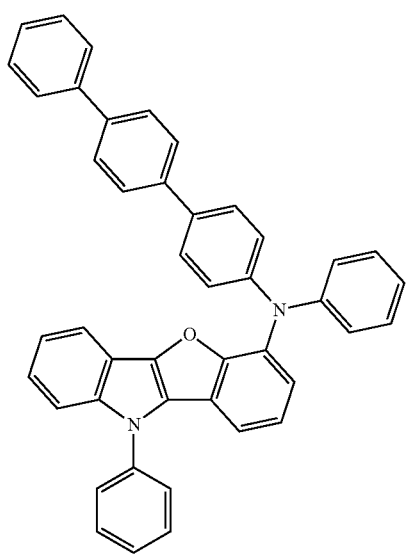
A4
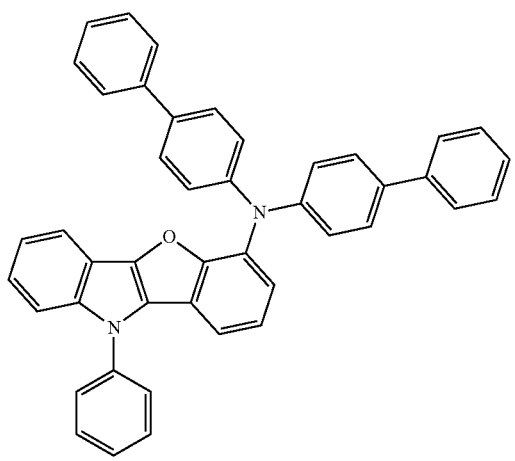
A5
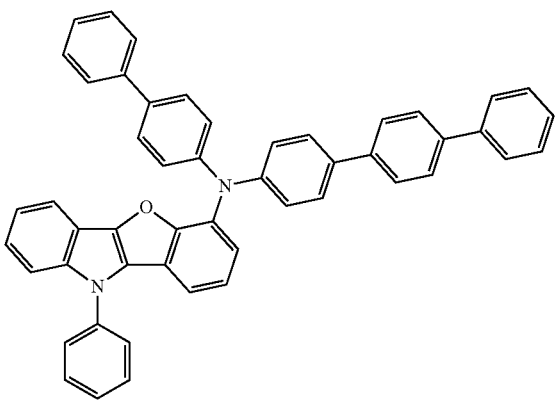
A6
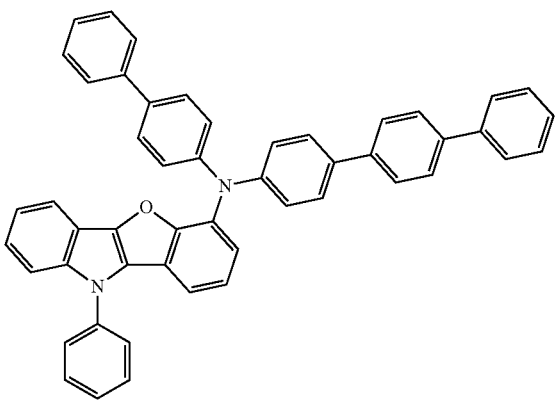
A7
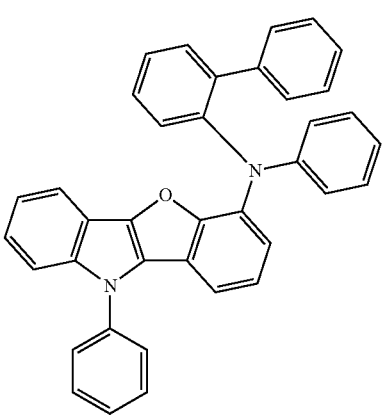

A8
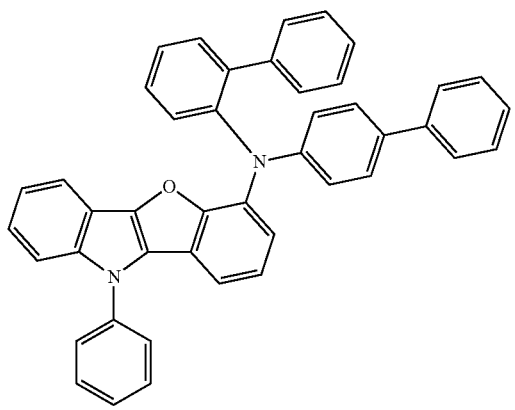
A9
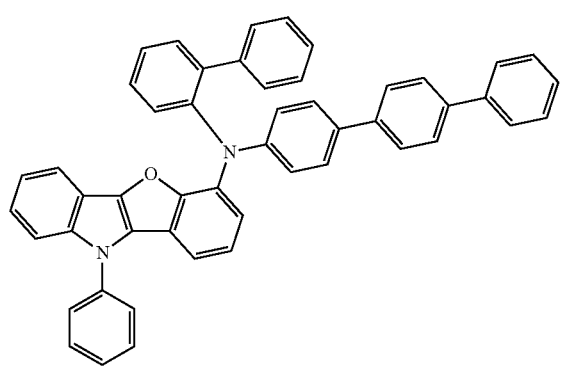
A10
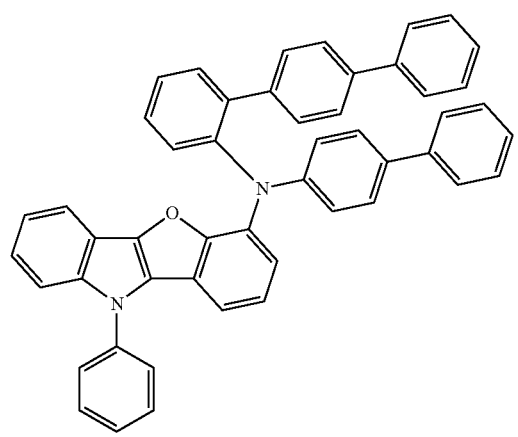
A11
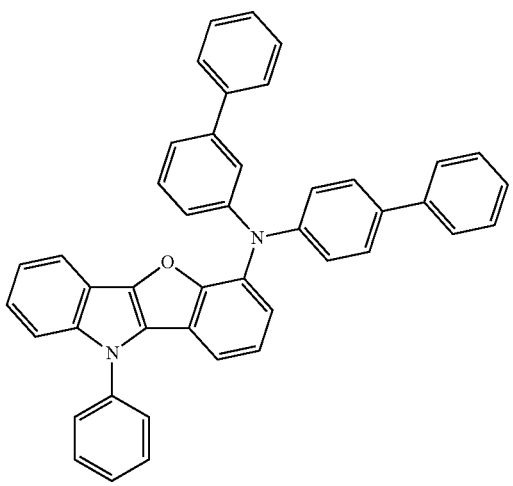
A12
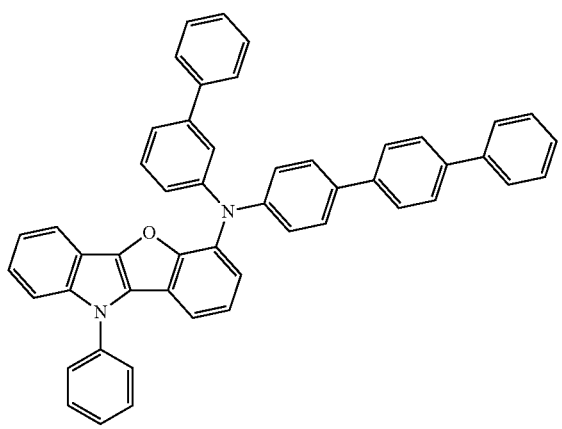
A13
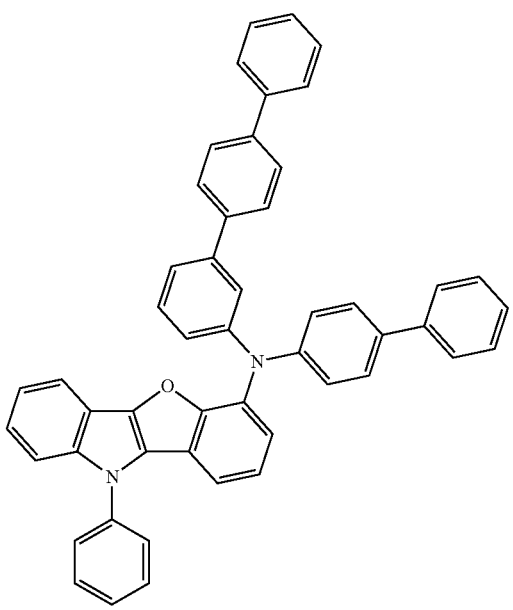

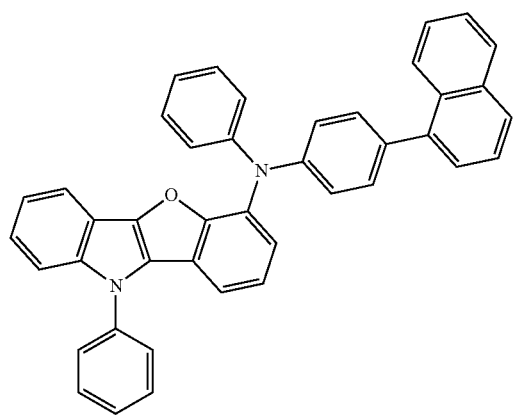
A14
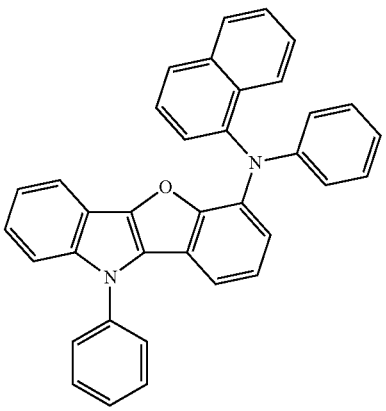
A17
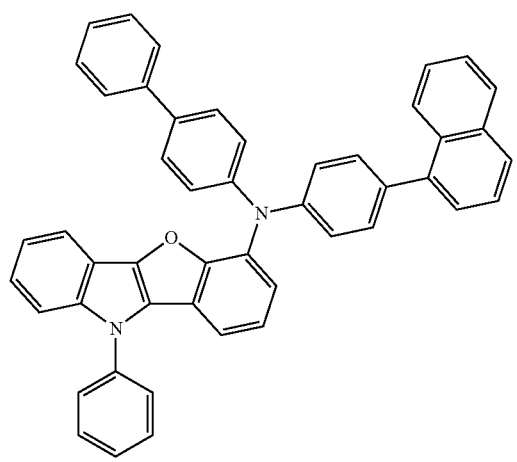
A15
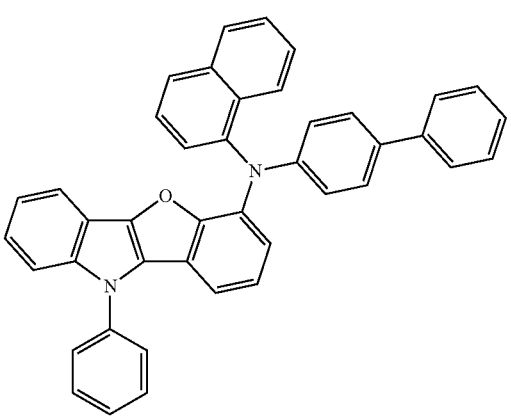
A18
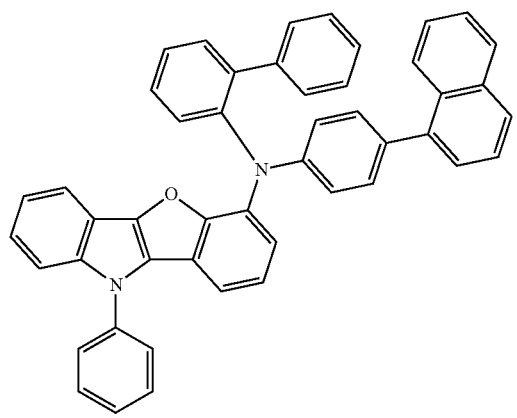
A16
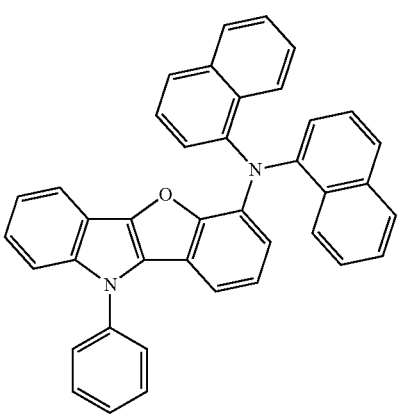
A19

A20
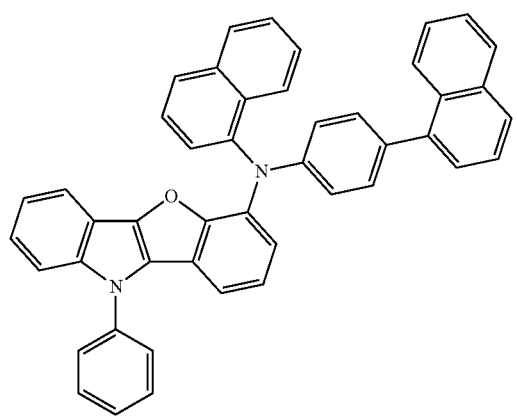
A23
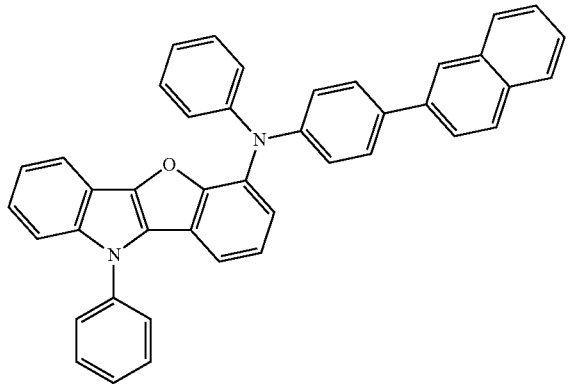
A21
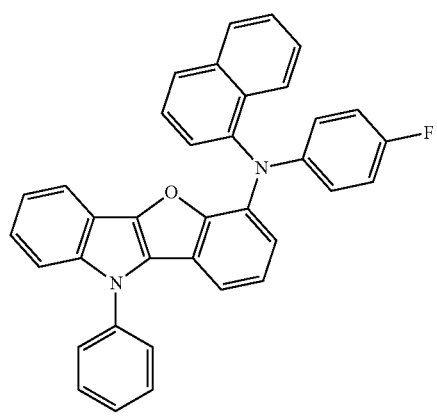
A24
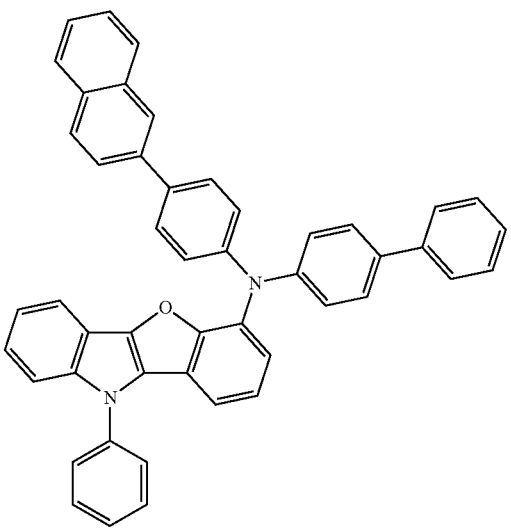
A22
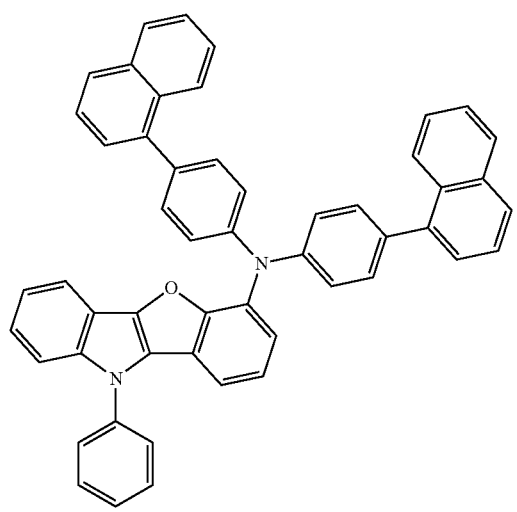
A25
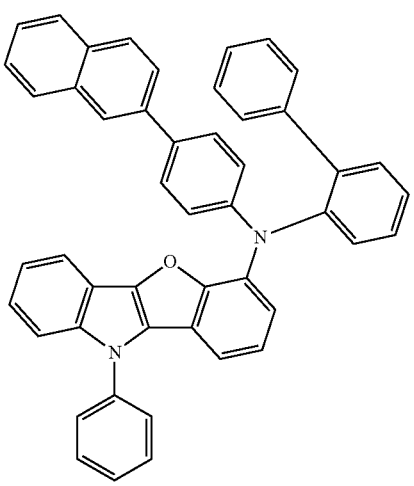

A26
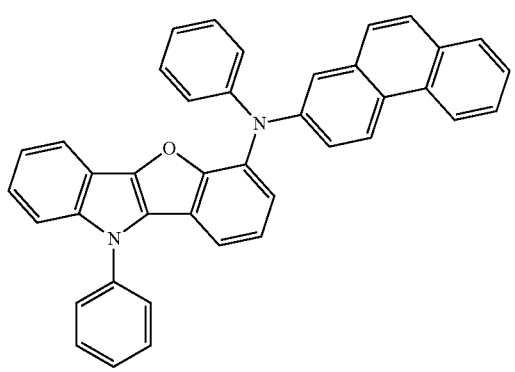
A27
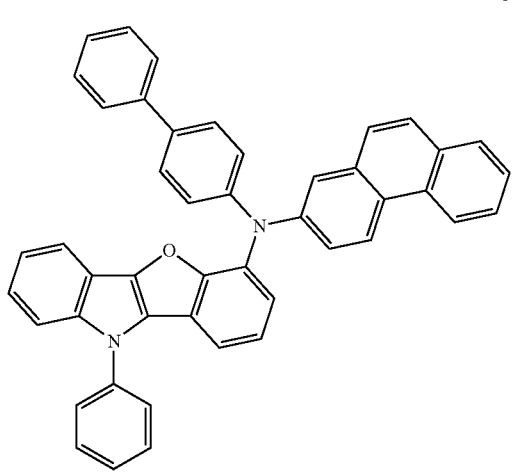
A28
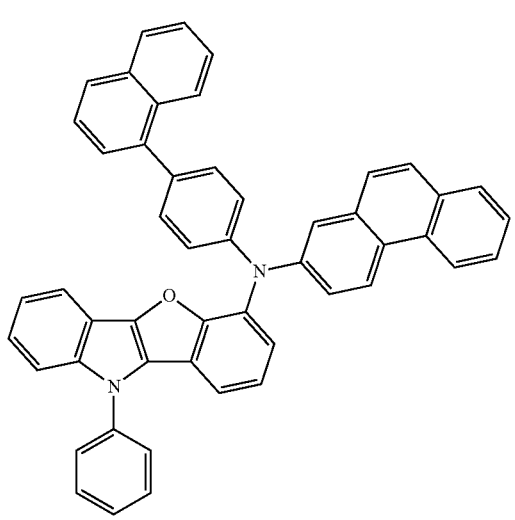
A29
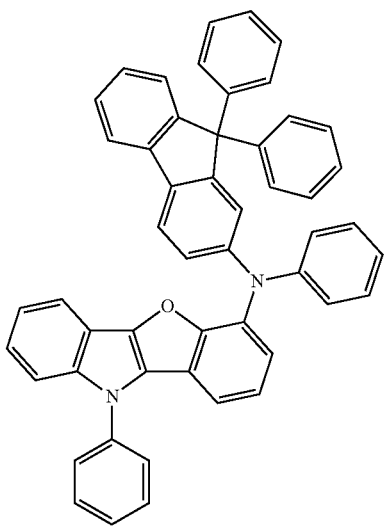
A30

A31
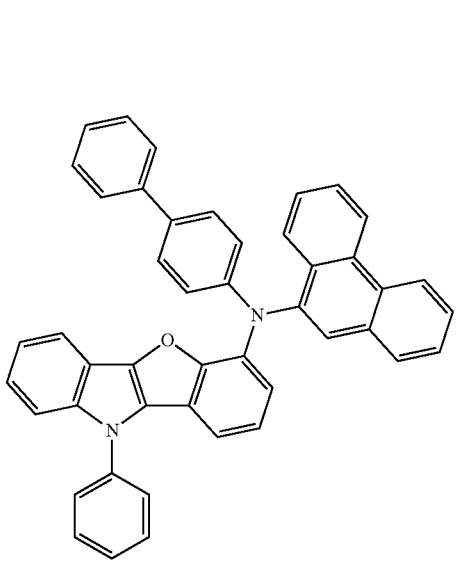

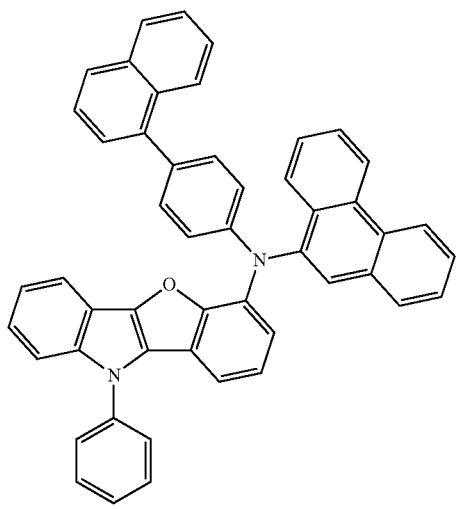
A32
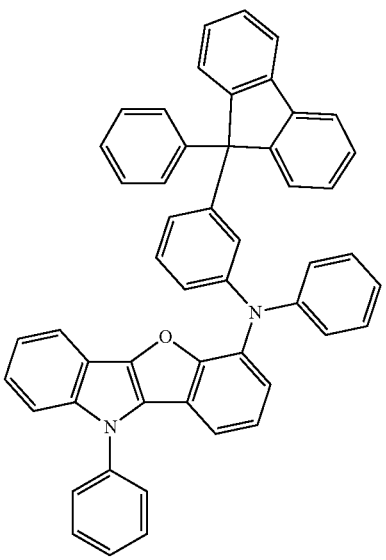
A35
A33
A34
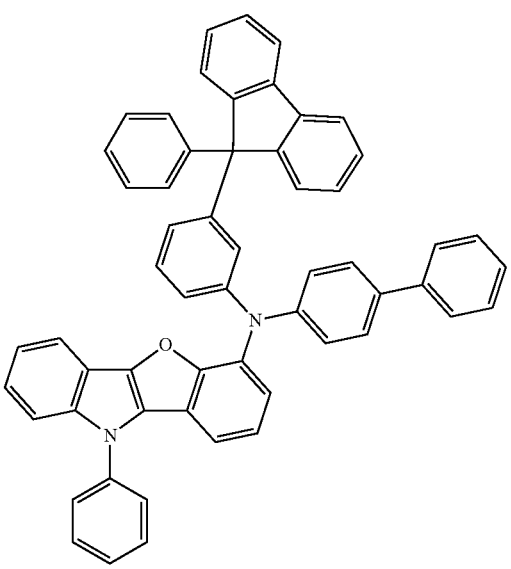
A36

-continued
A37
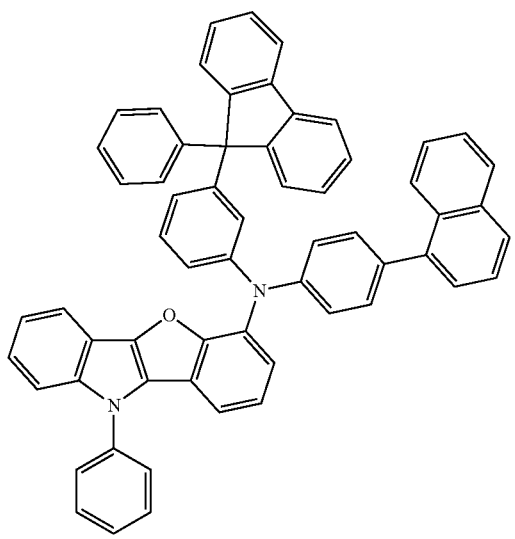
A38
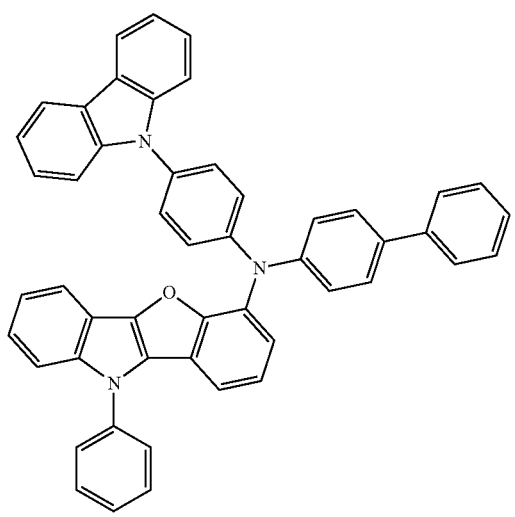
A39
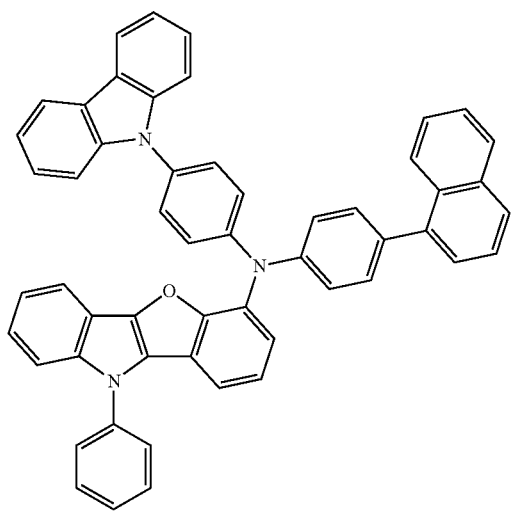
-continued
A40
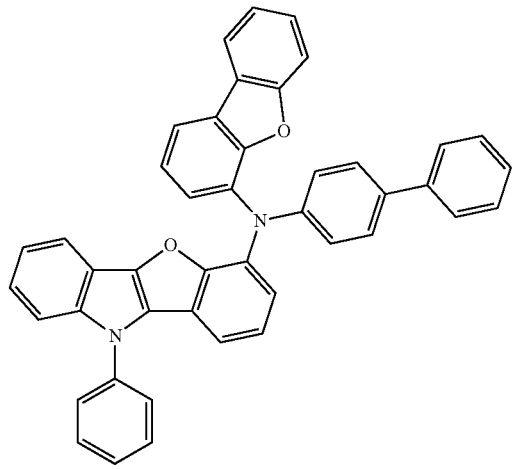
A41
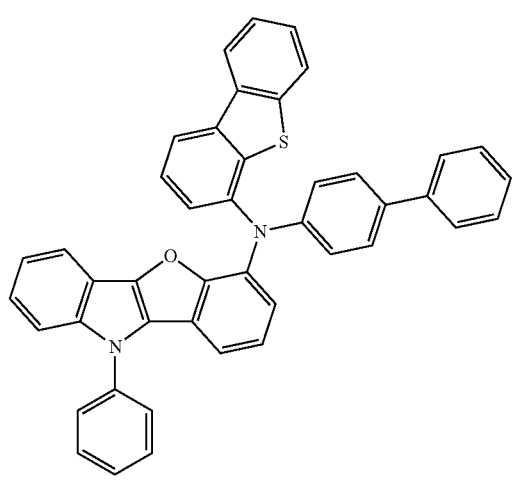
A42
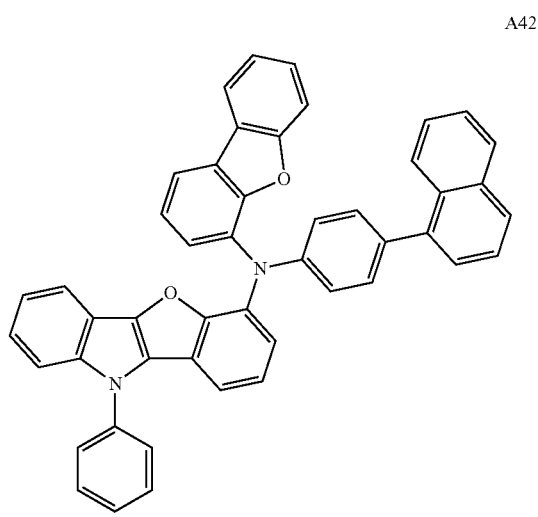

A43
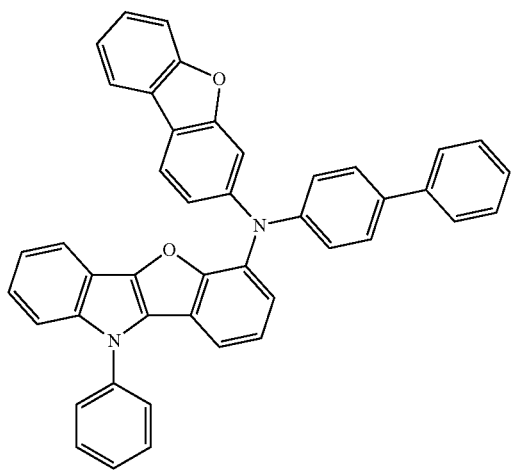
A44
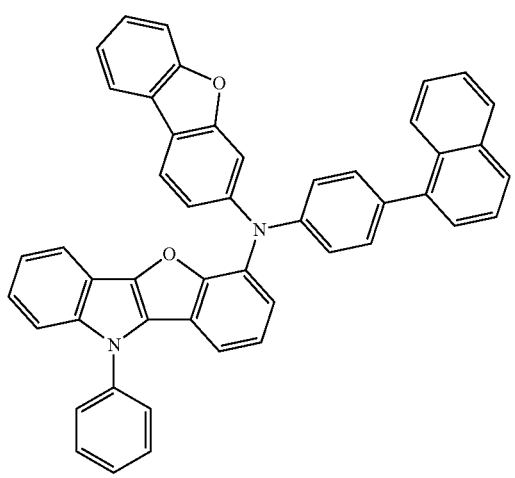
A45
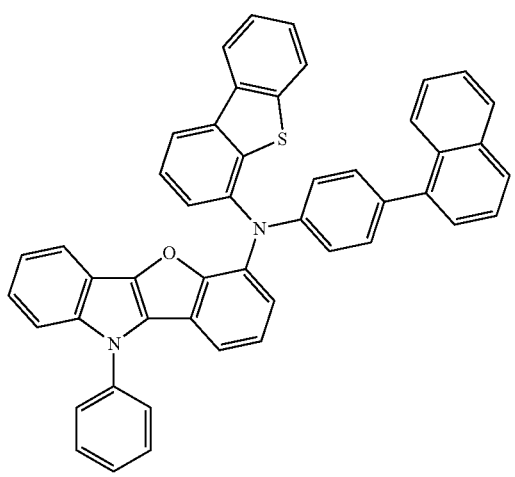
A46
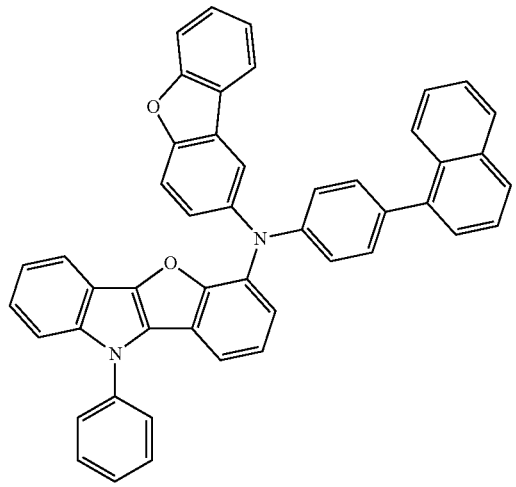
A47
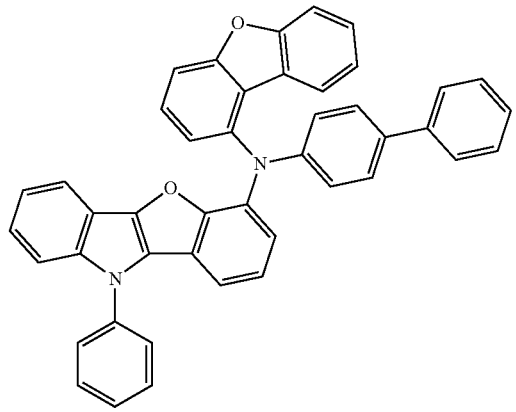
A48
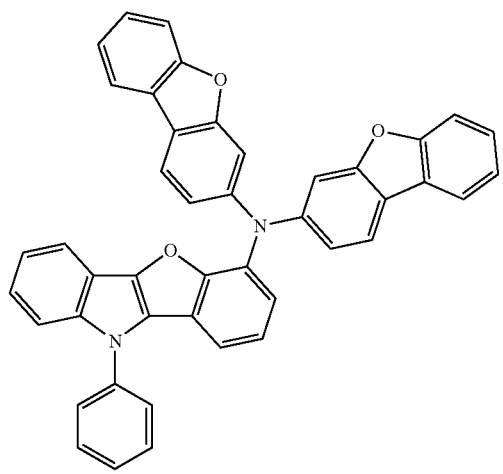

A49
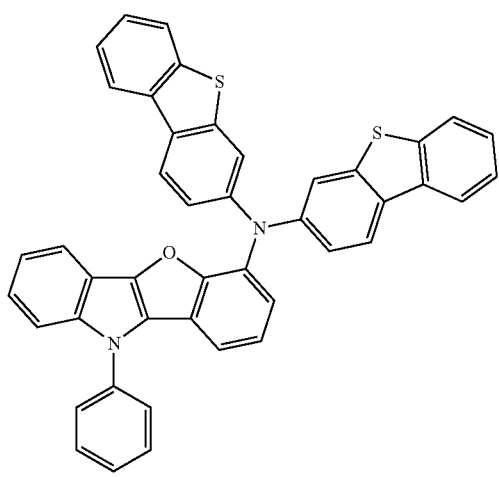
A50
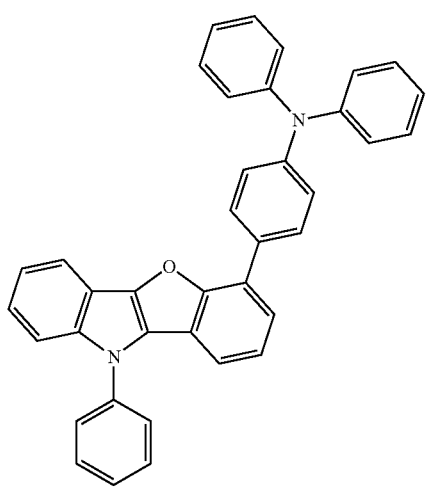
A51
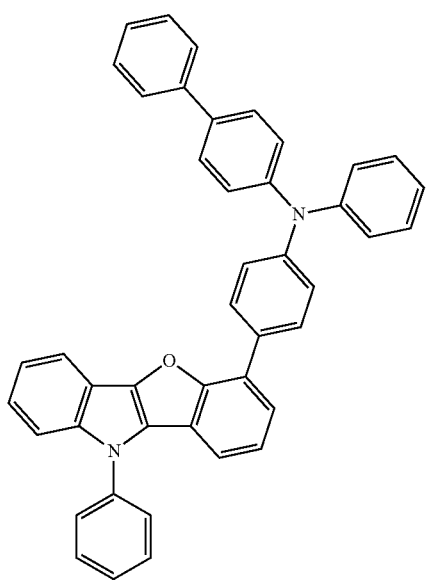
A52
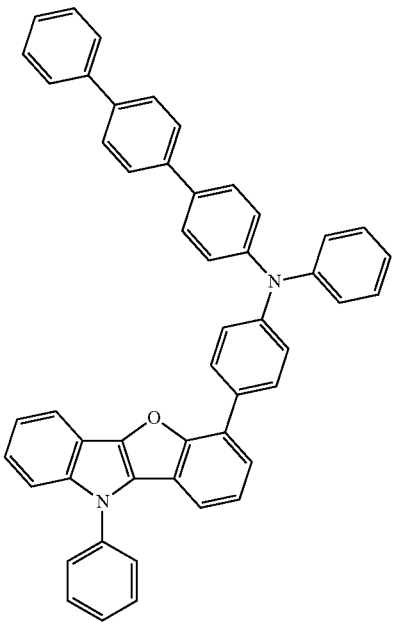
A53
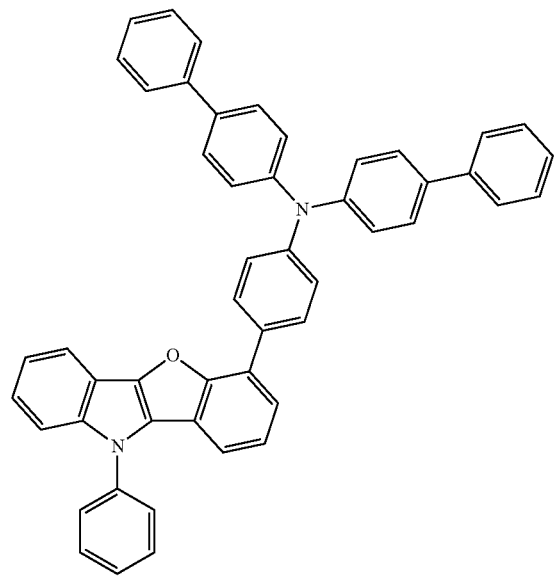

A54
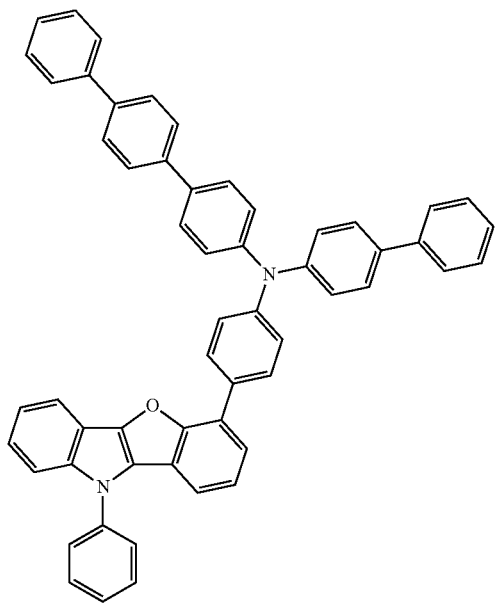
A55
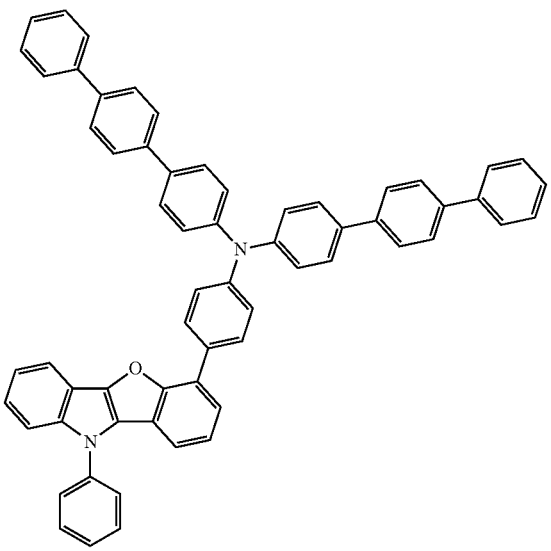
A56
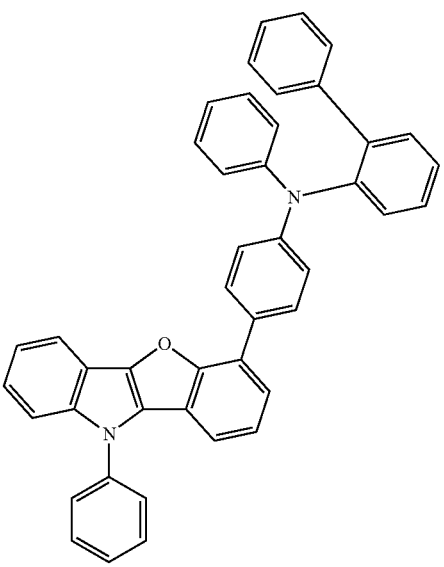
A57
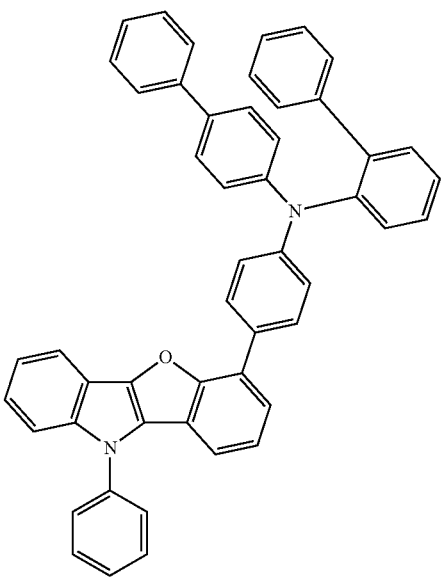
A58
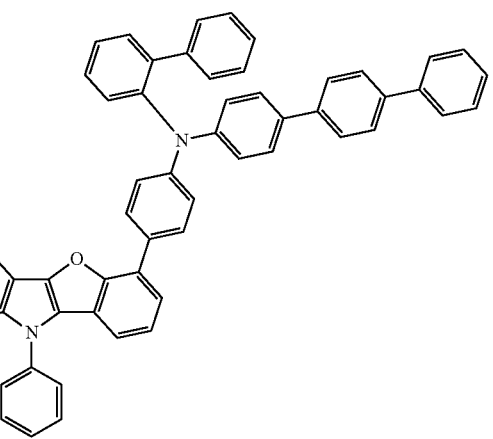

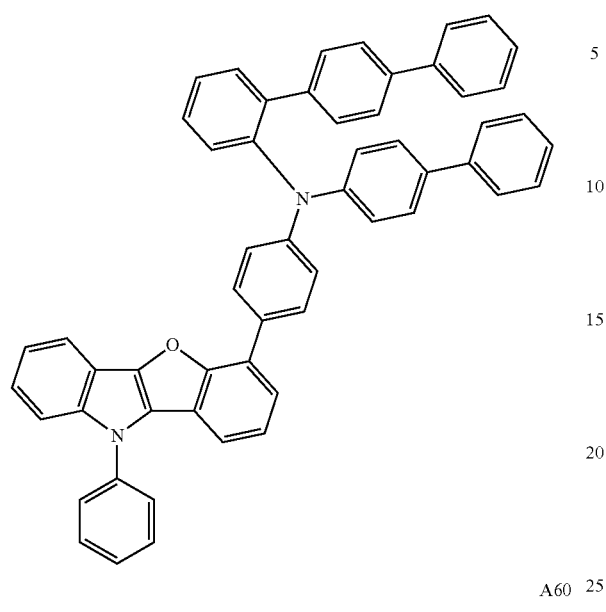
A59
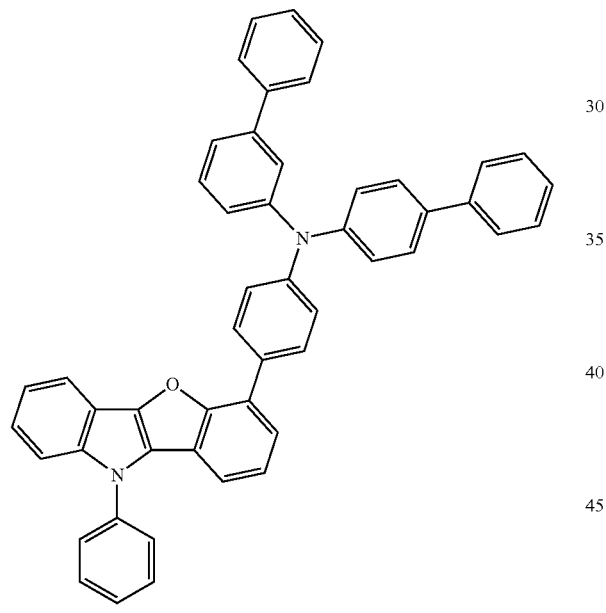
A60
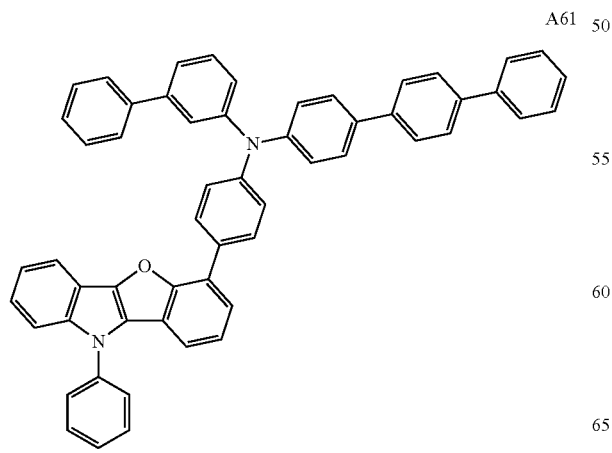
A61
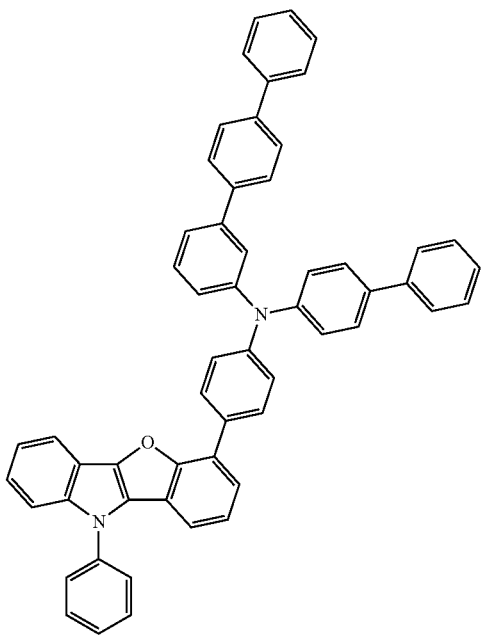
A62
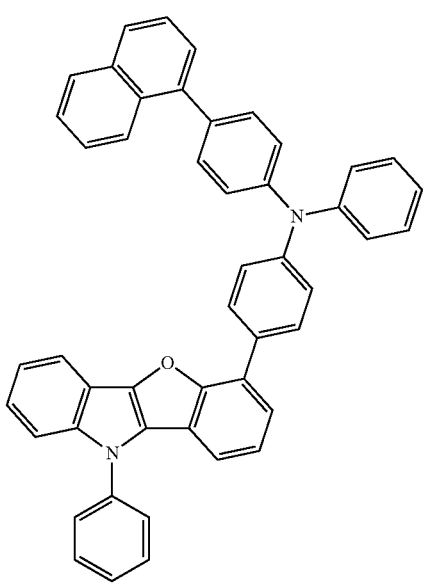
A63

-continued

A64

A66

A67

A65

A68

A69
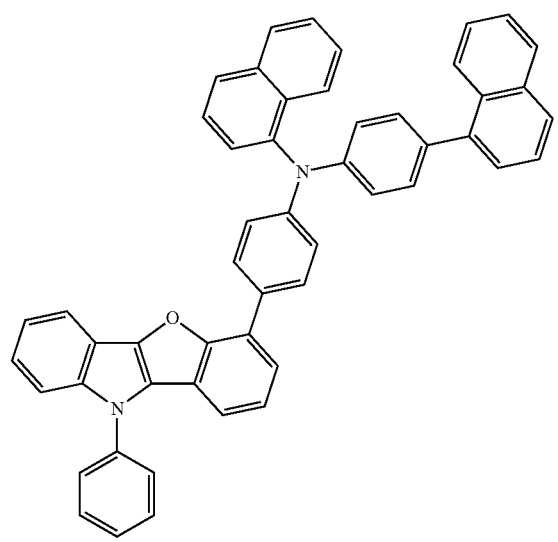
A71
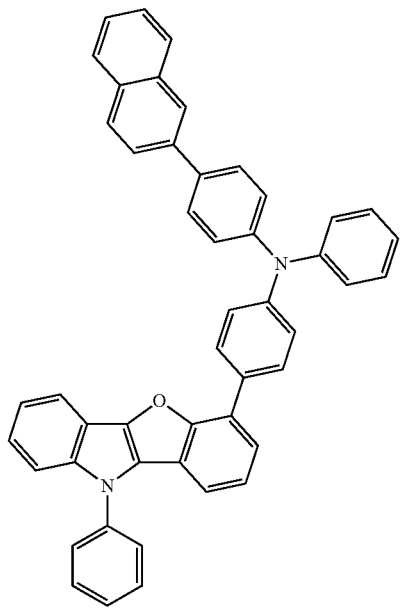
A70
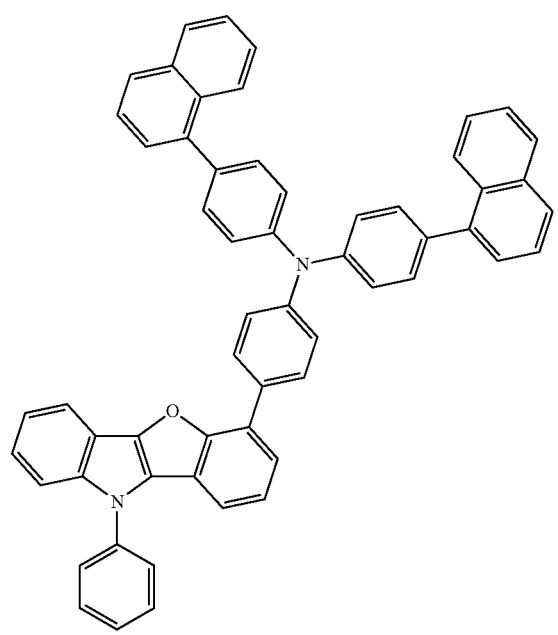
A72
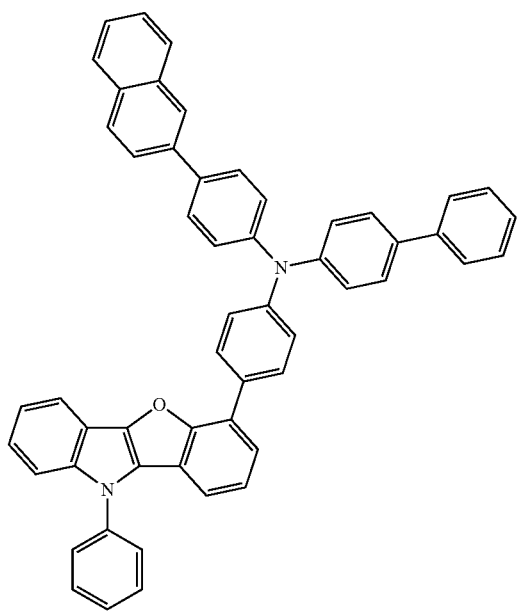

A73
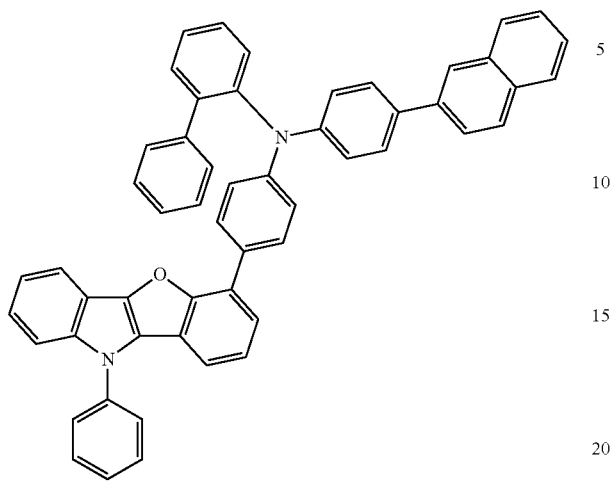
A74
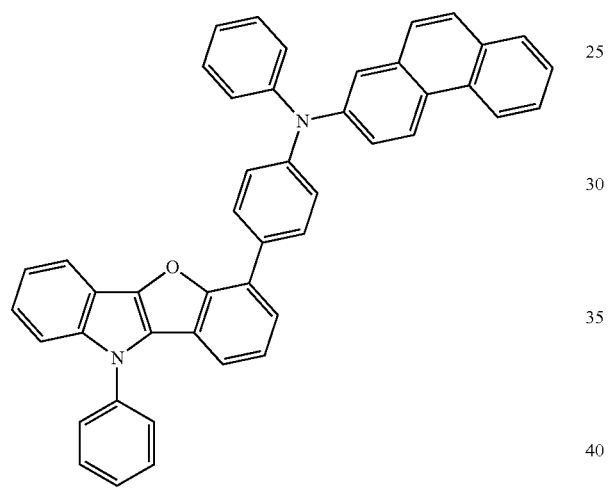
A75
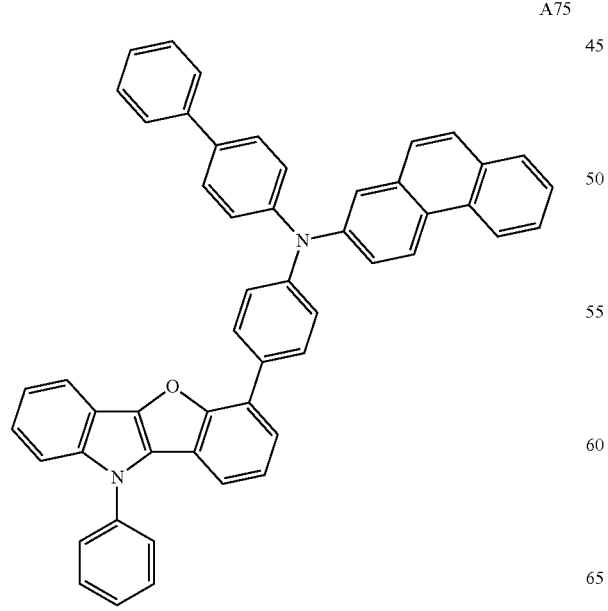
A76
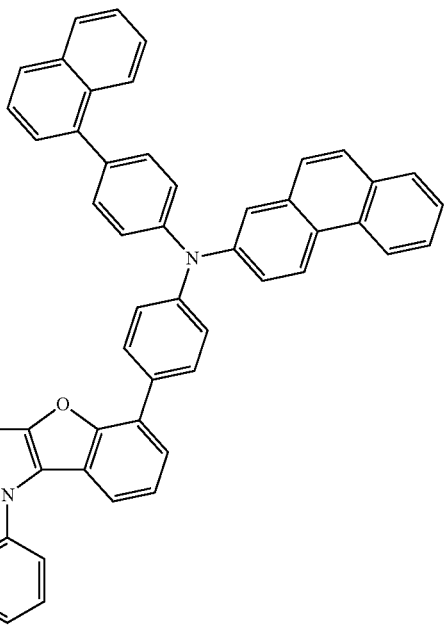
A77
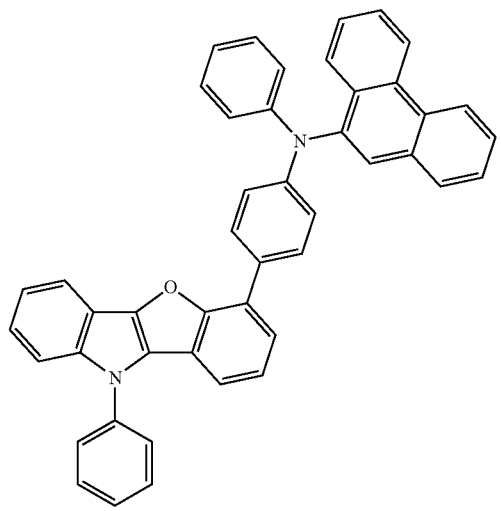

A78
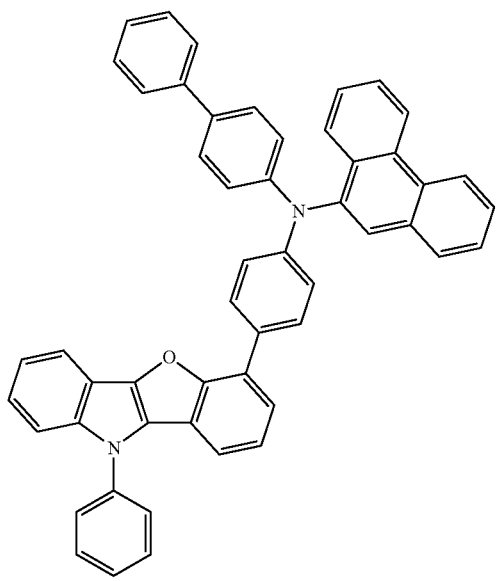
A80
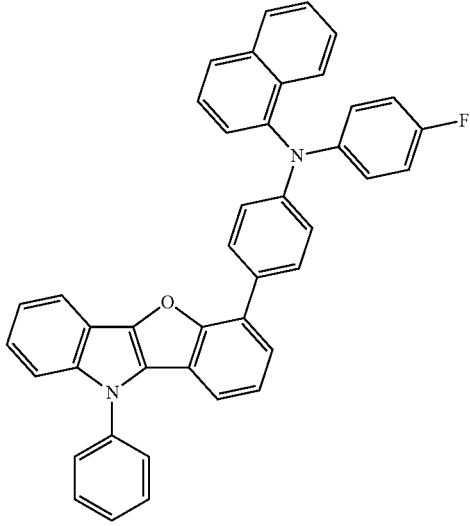
A79
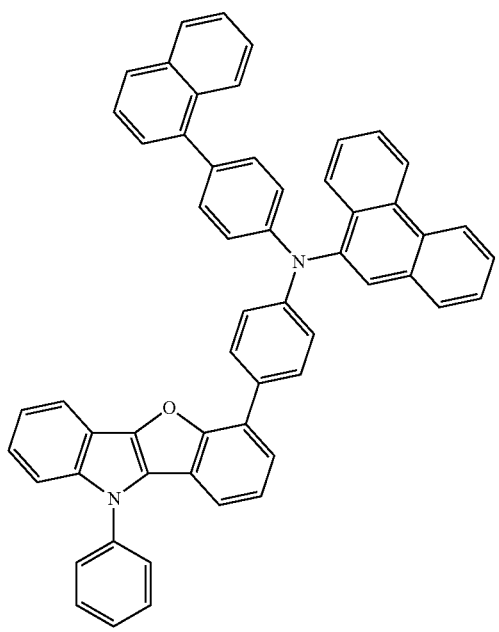
A81
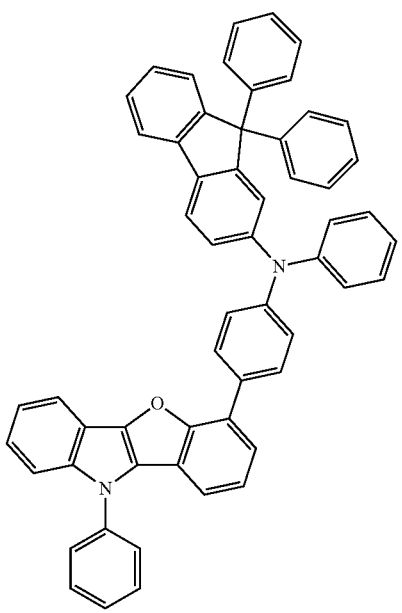

-continued
A82
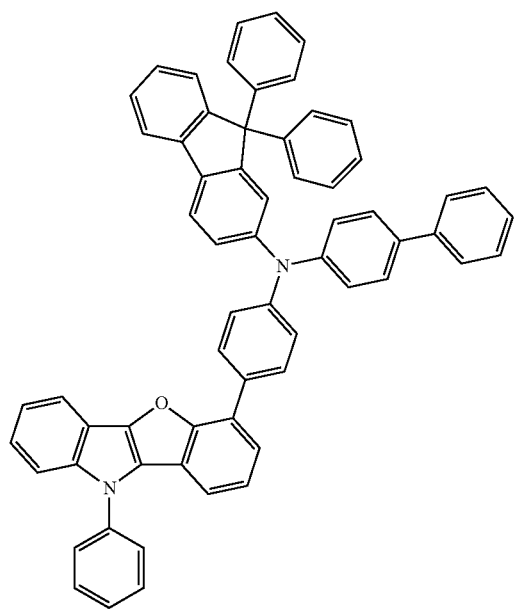
A84
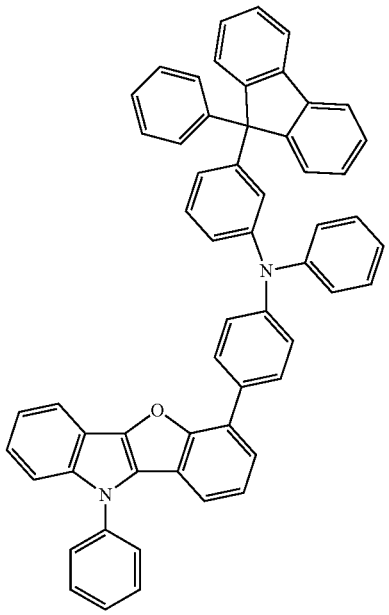
A83
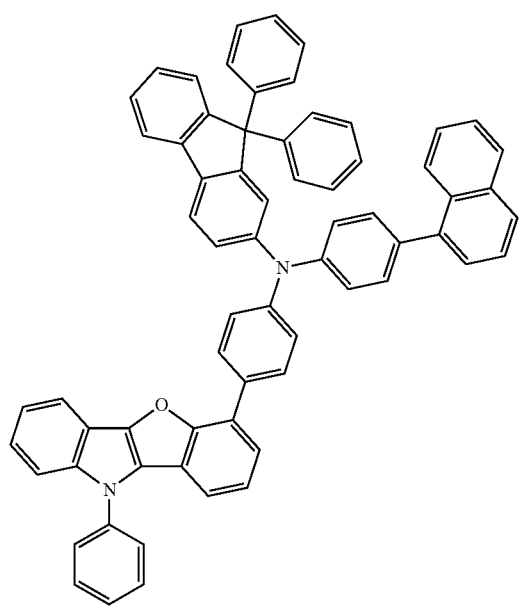
A85

-continued
A86
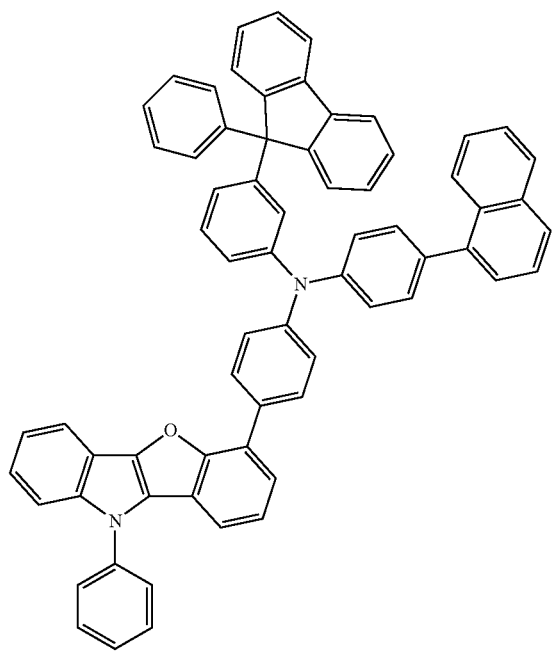
A87
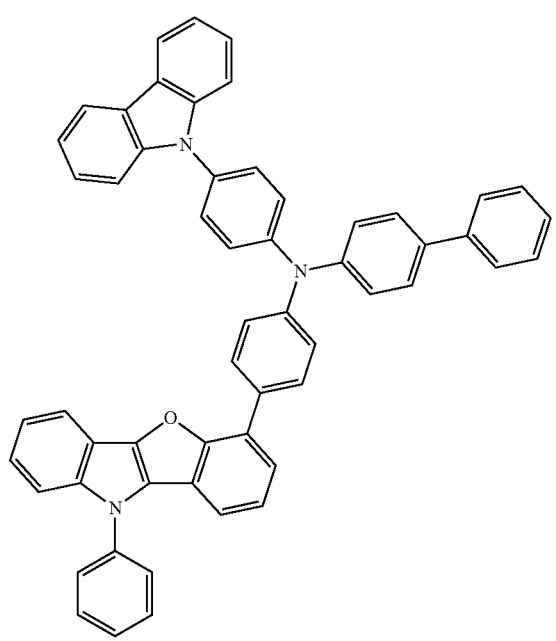
A88
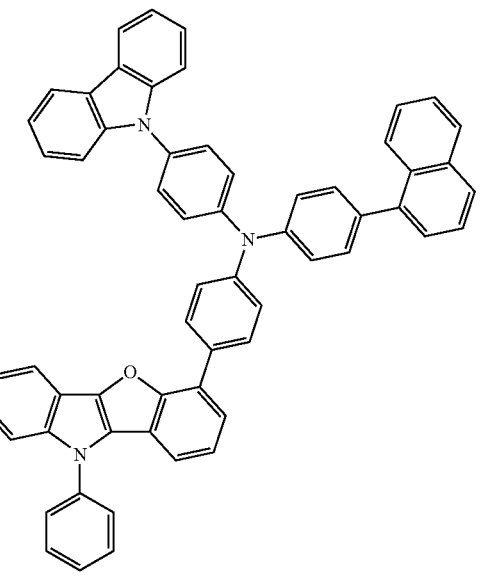
A89
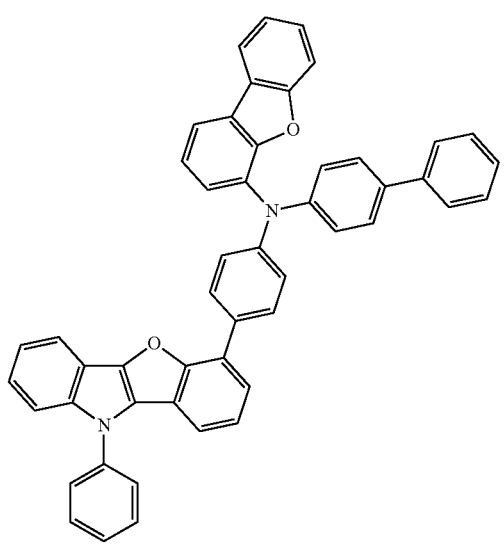

-continued
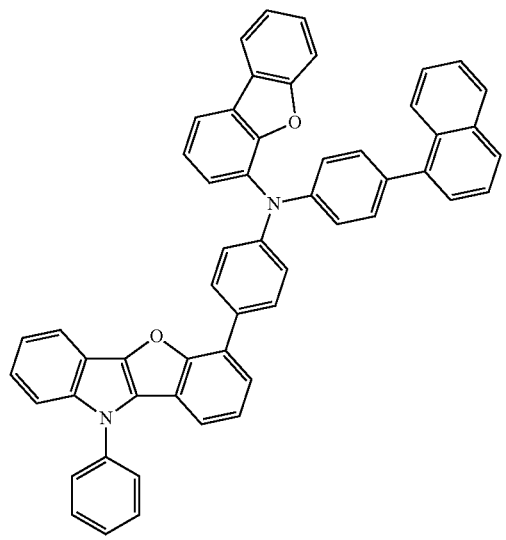
A90
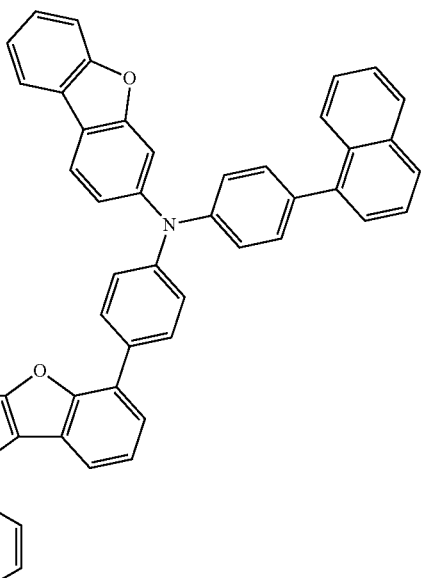
A92
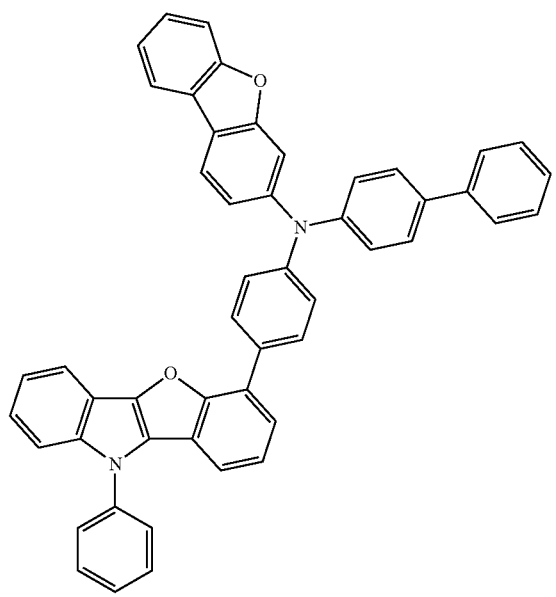
A91
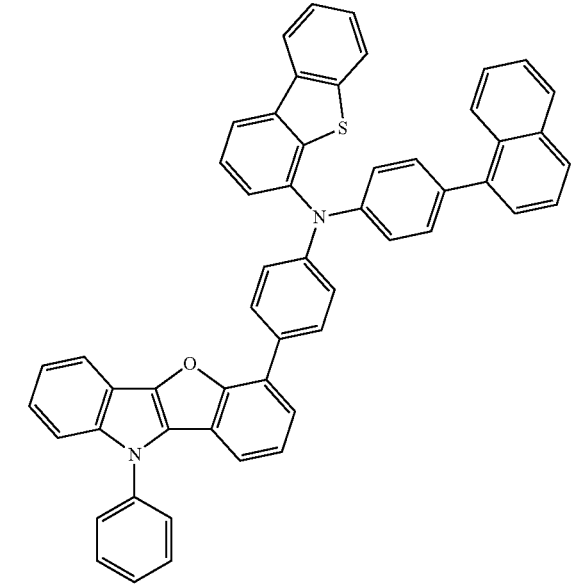
A93

-continued
A94
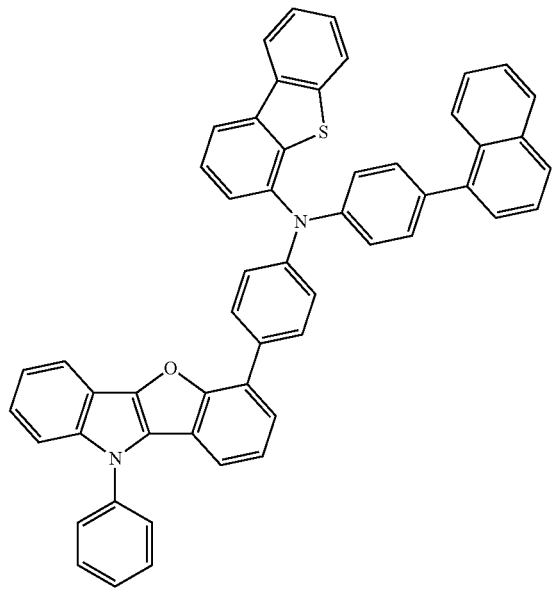
A96
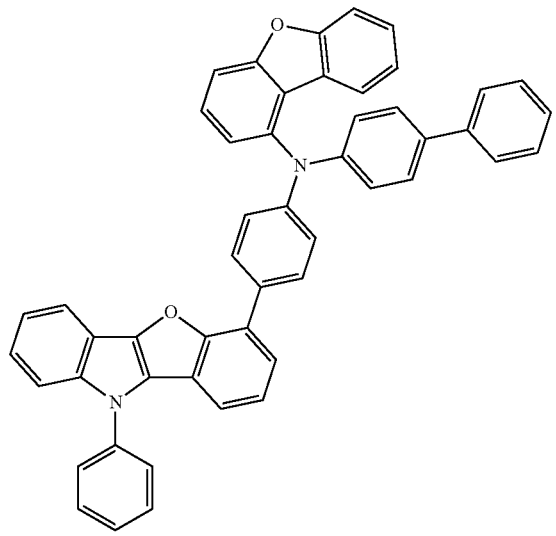
A95
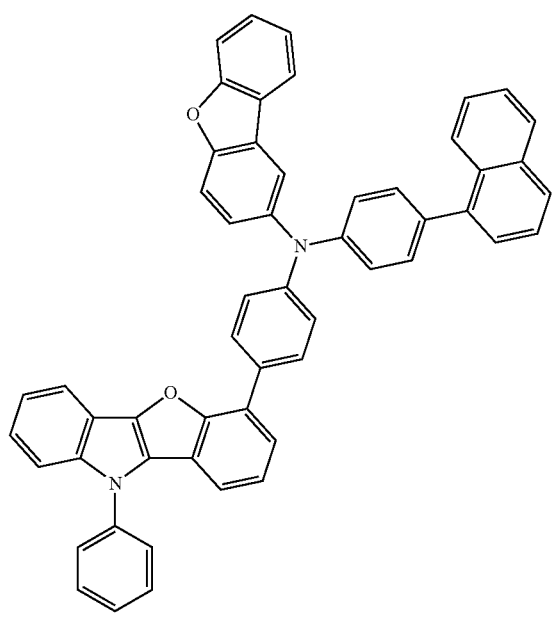
A97
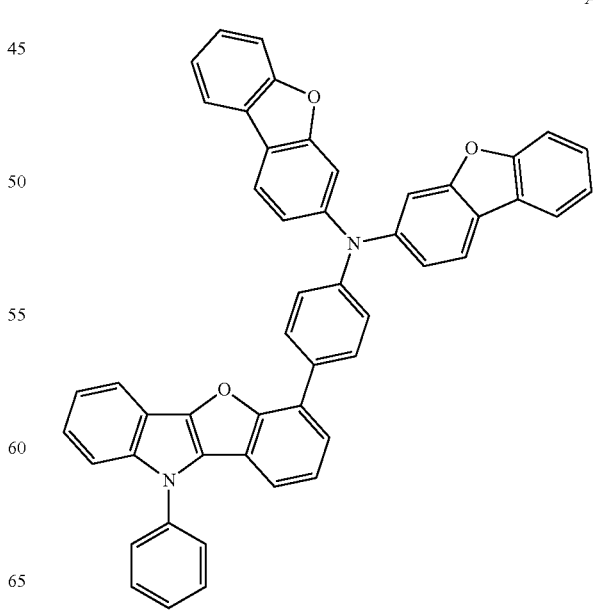

A98
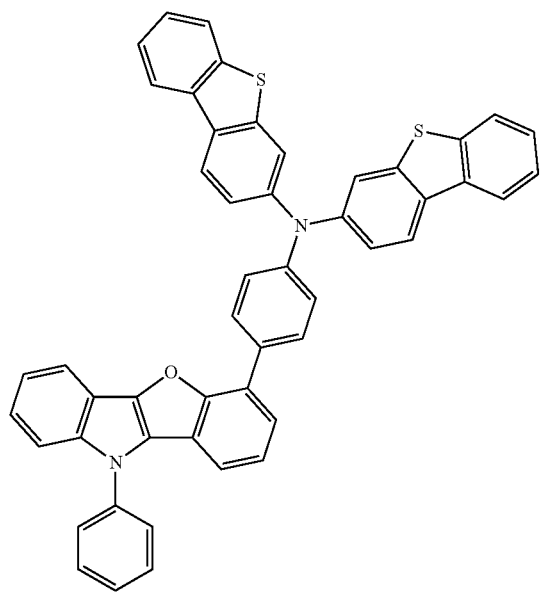
A99
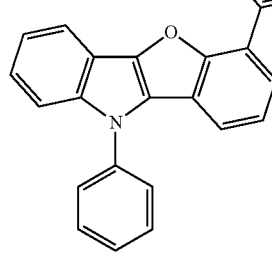
A100
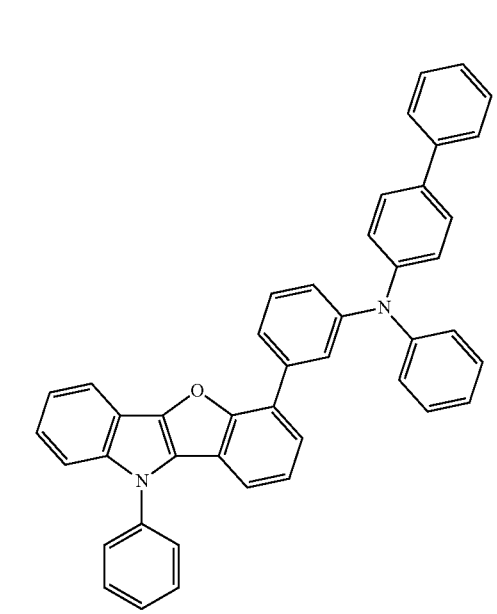
A101
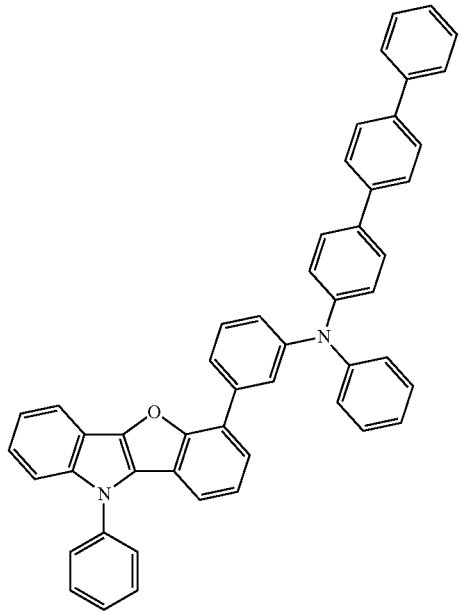
A102
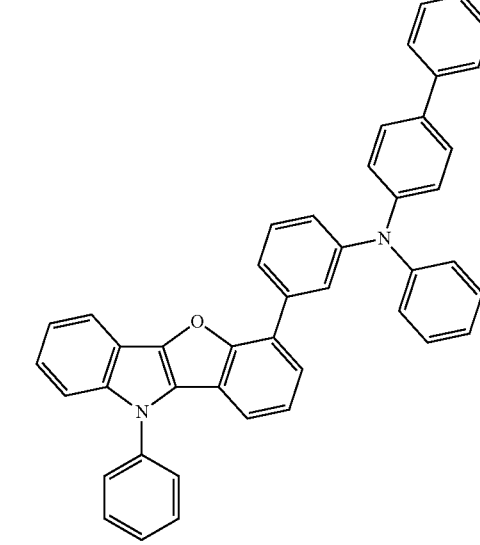

A103
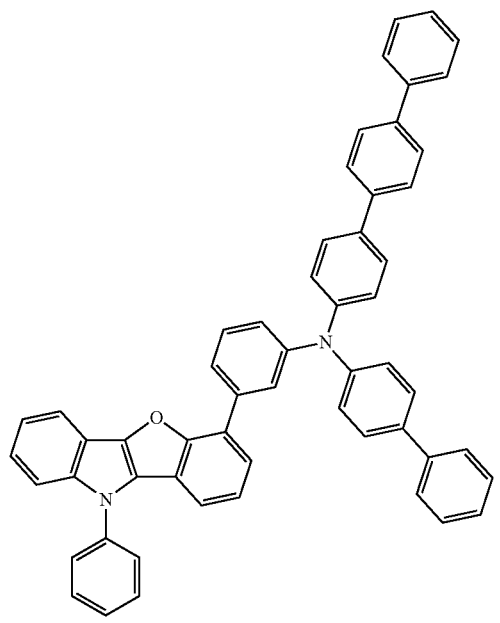
A104
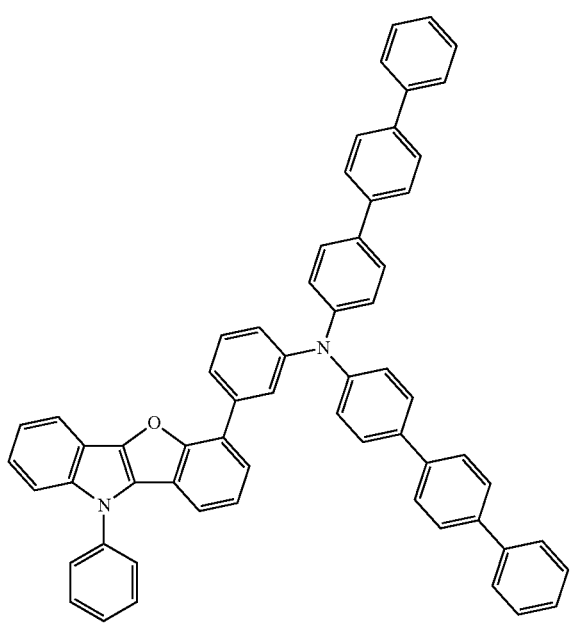
A105
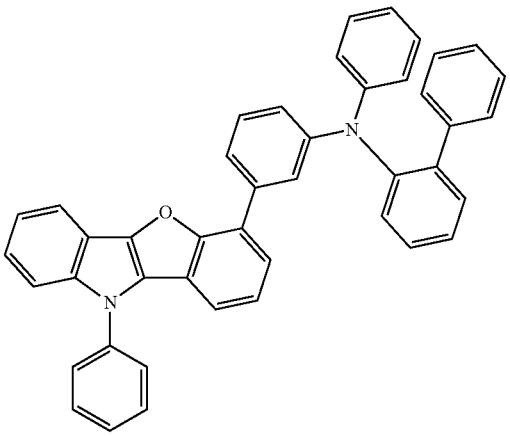
A106
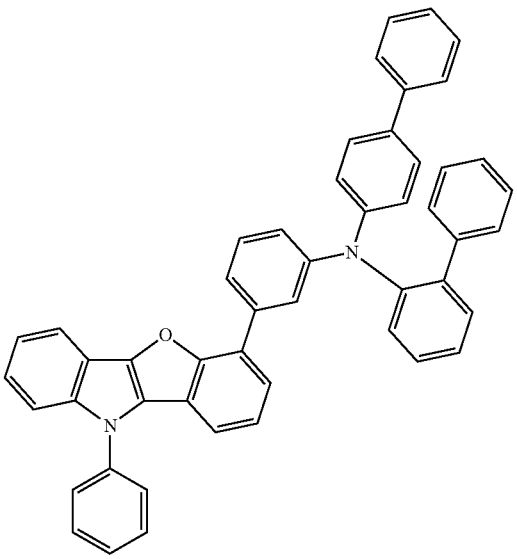
A107
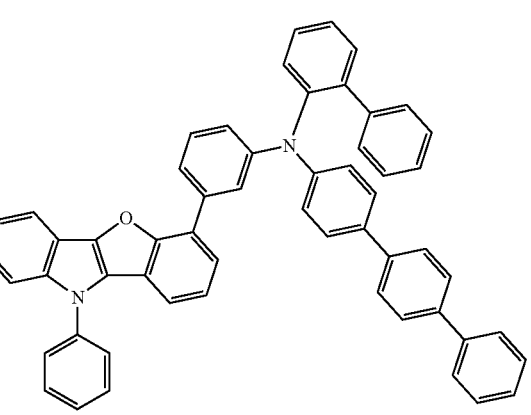

A108
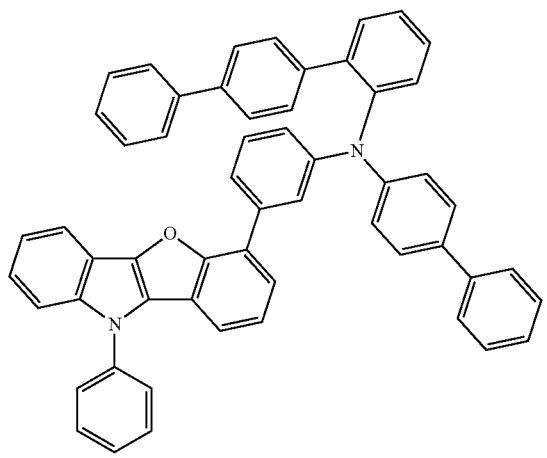
A109
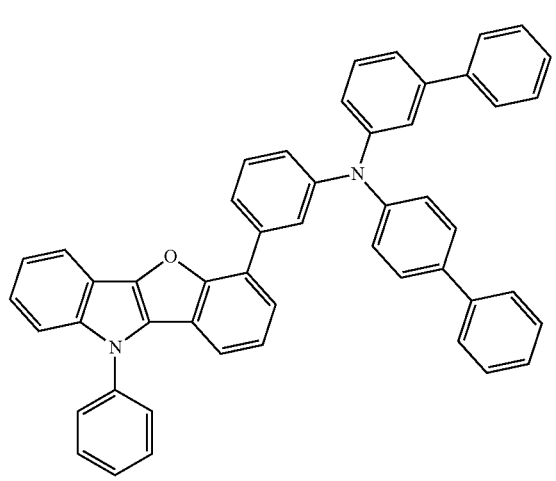
A110
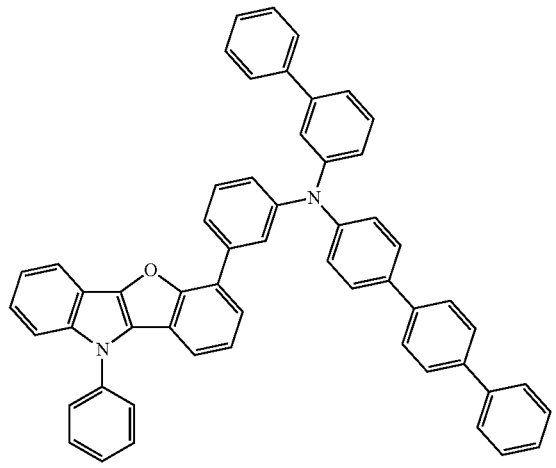
A111
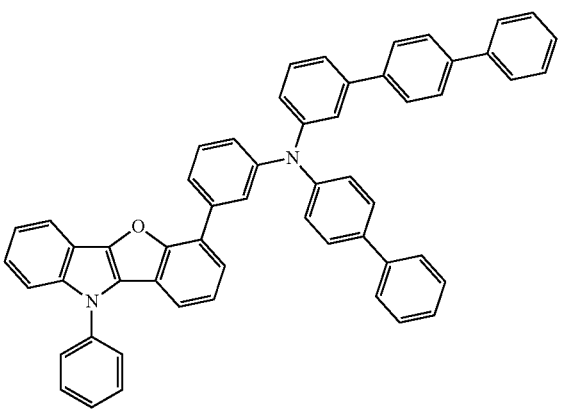
A112
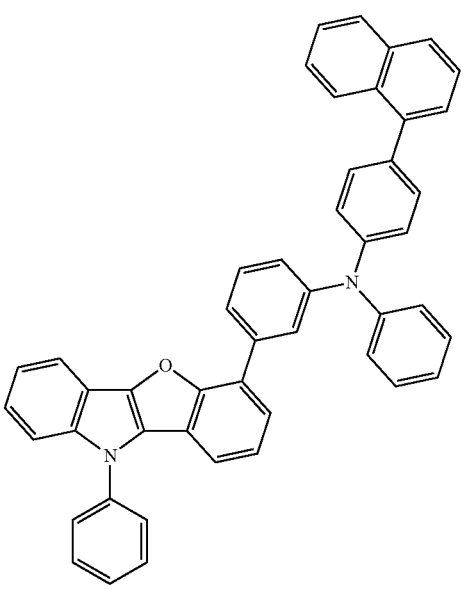
A113
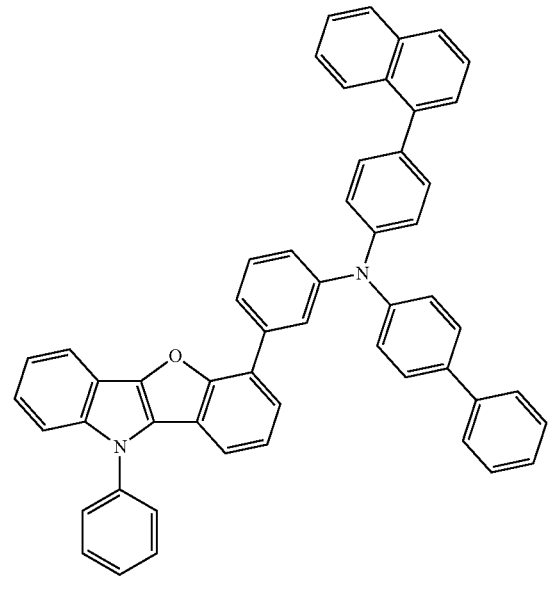

-continued
A114
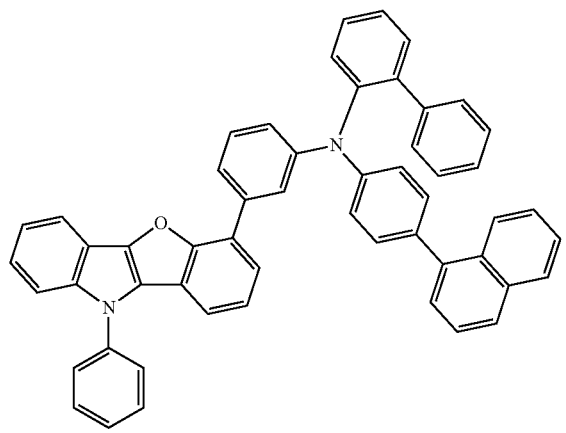
A115
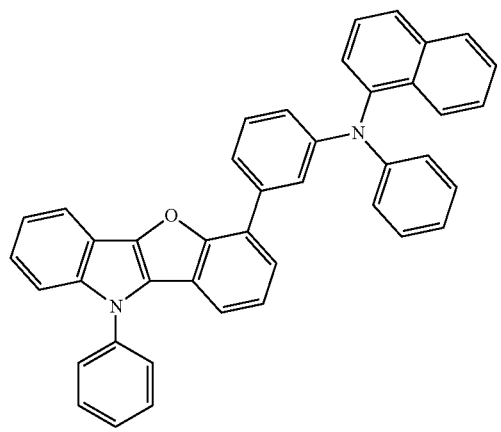
A116
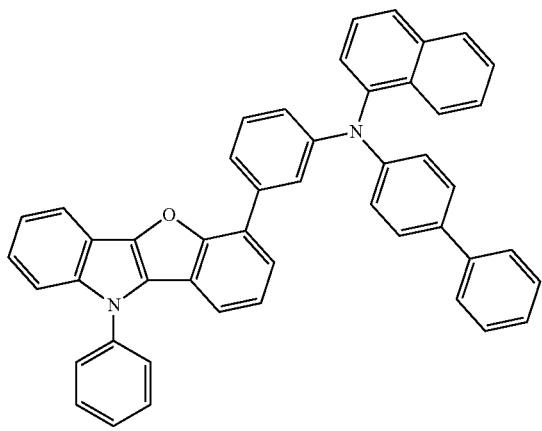
-continued
A117
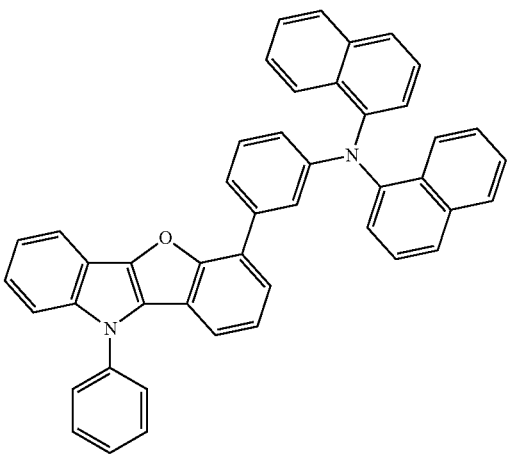
A118
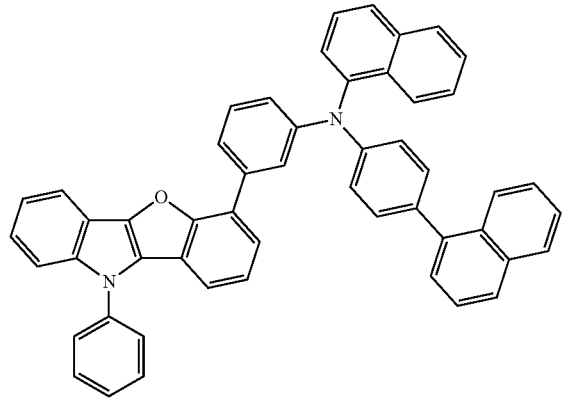
A119
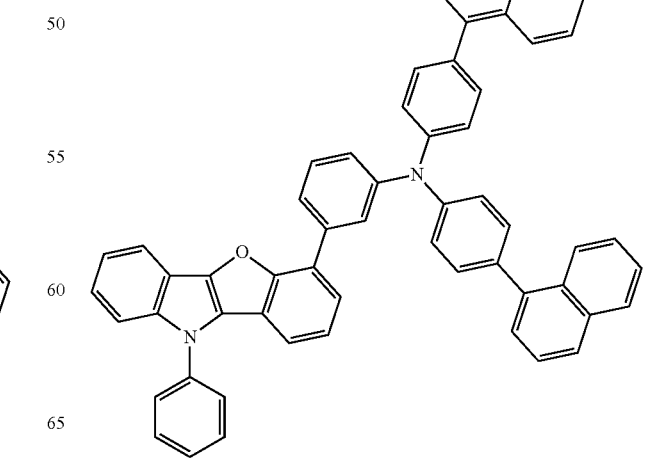

A120
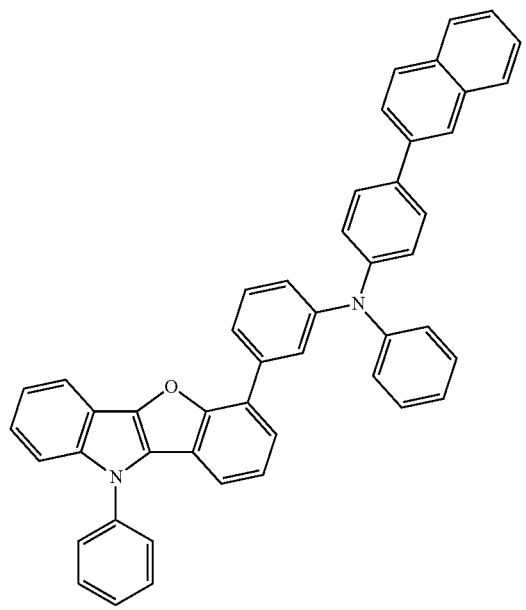
A121
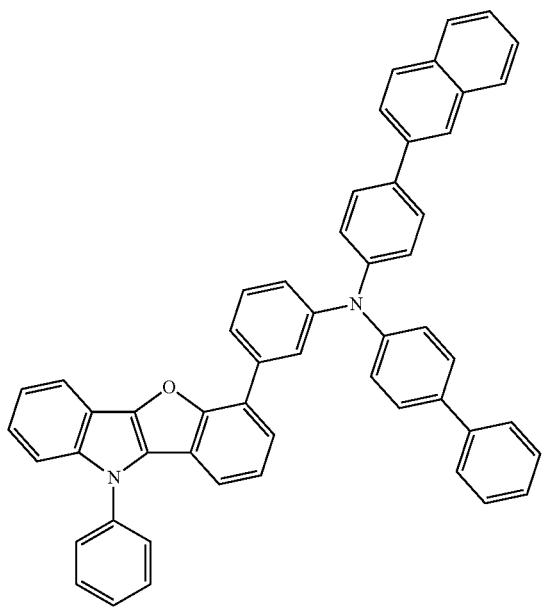
A122
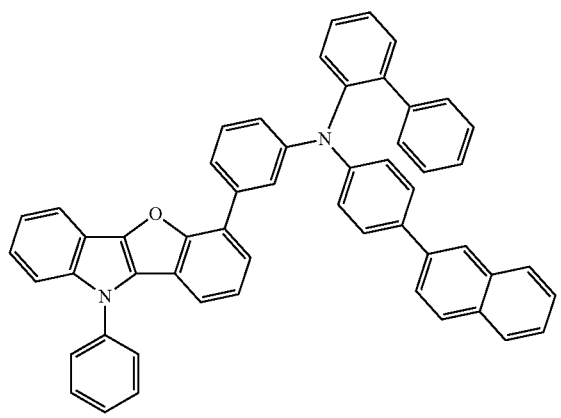
A123
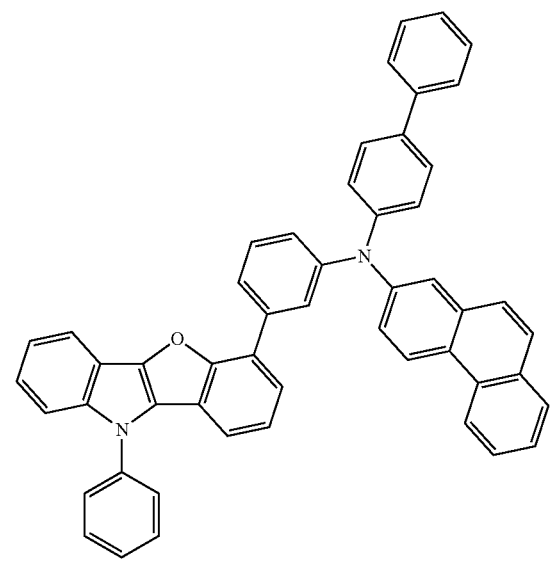
A124

A125
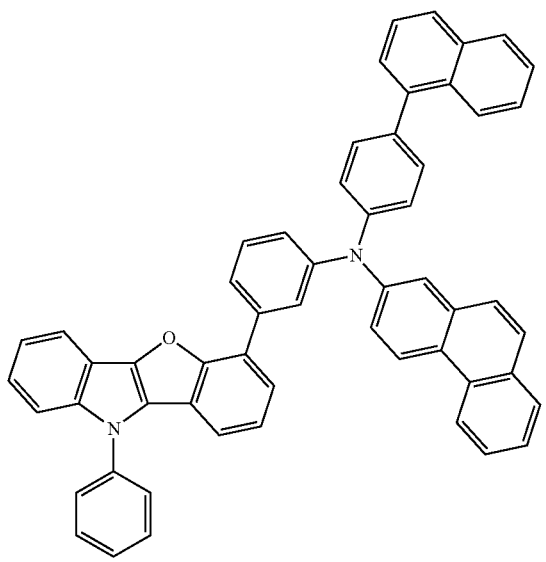
A126
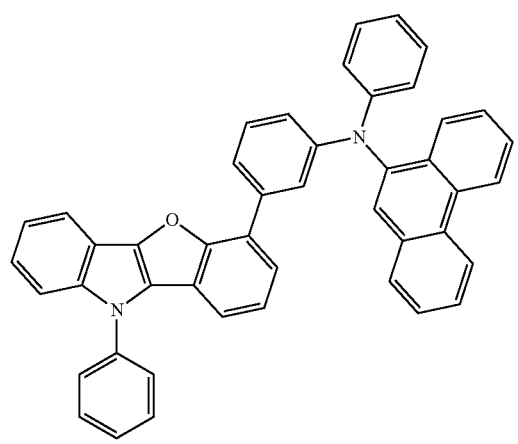
A127
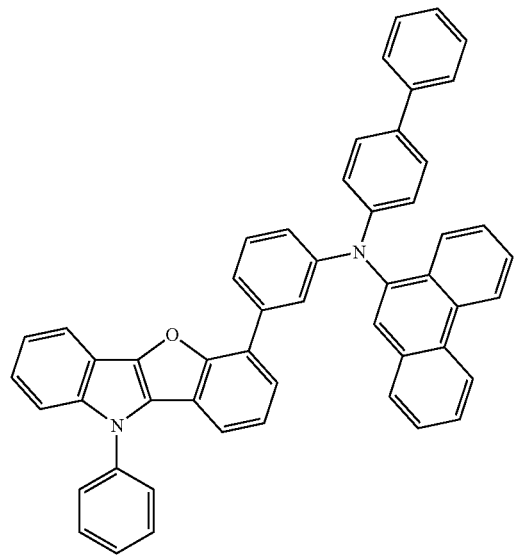
A128
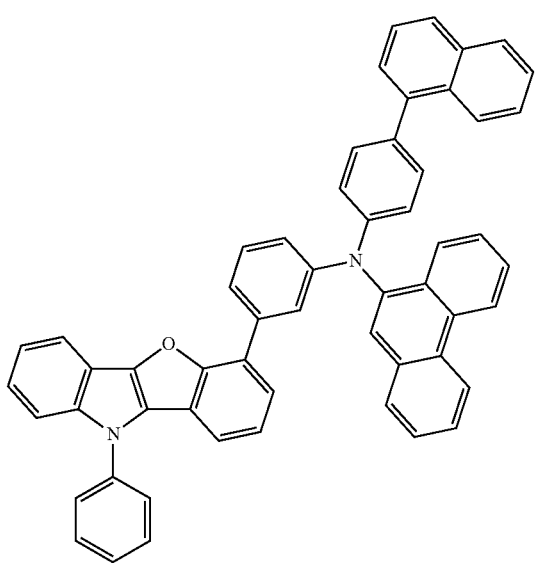
A129
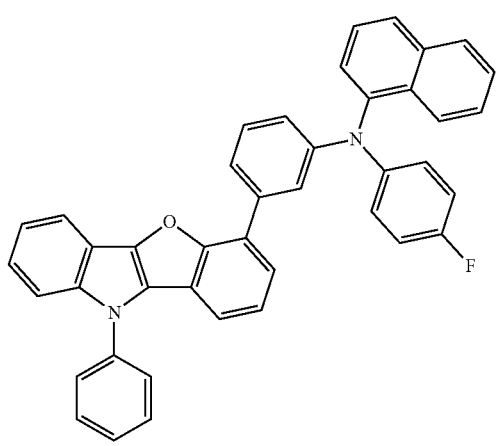
A130
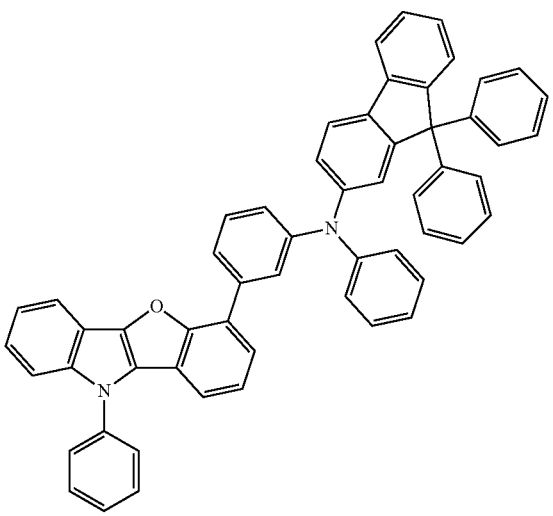

A131
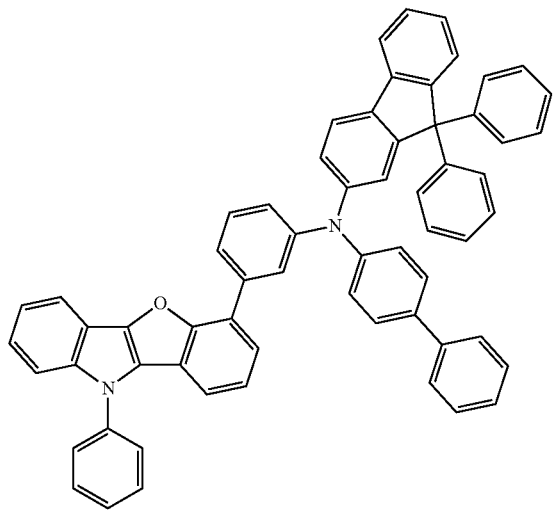
A132
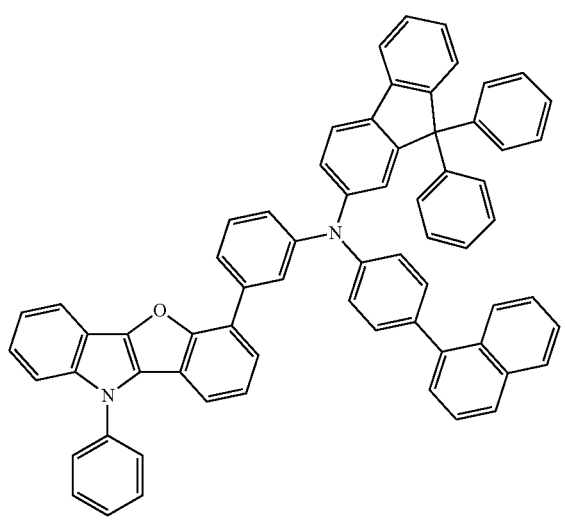
A133
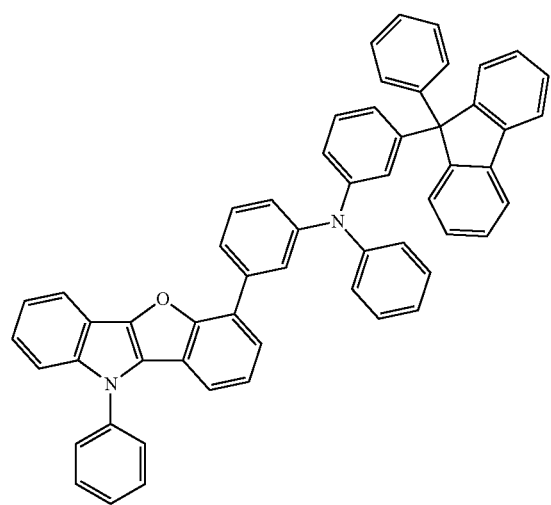
A134
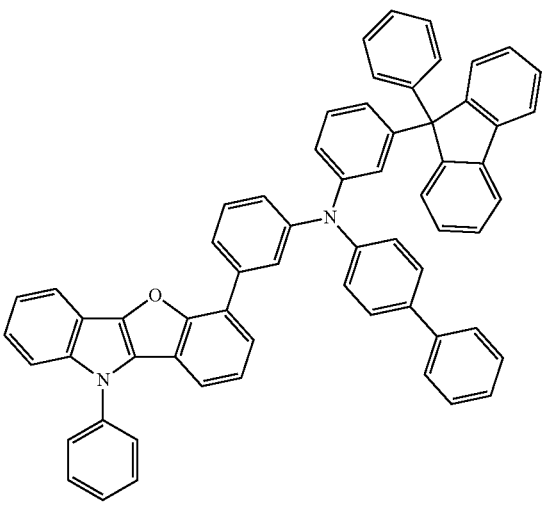
A135
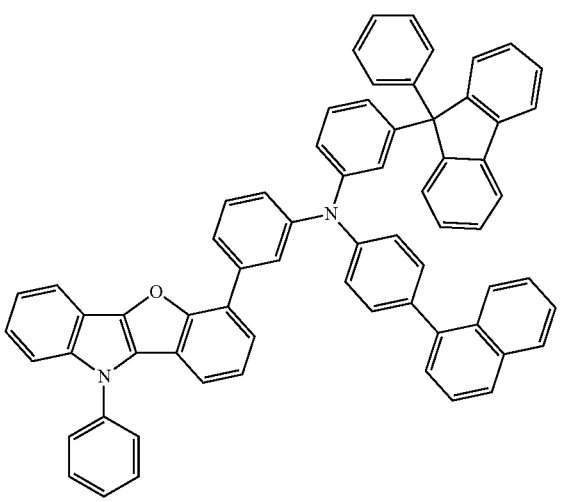
A136
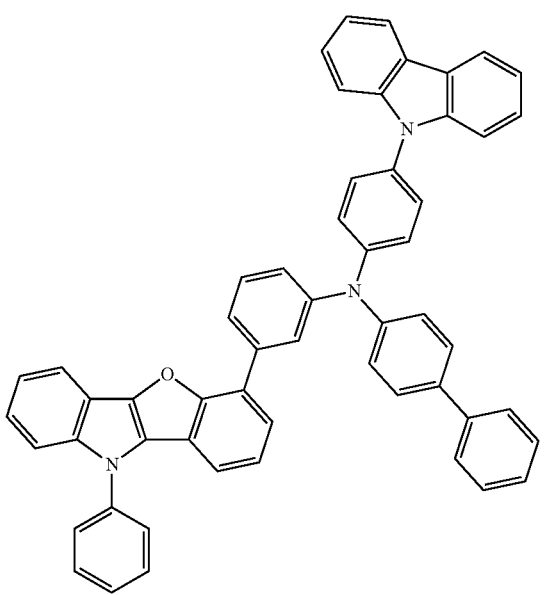

-continued
A137
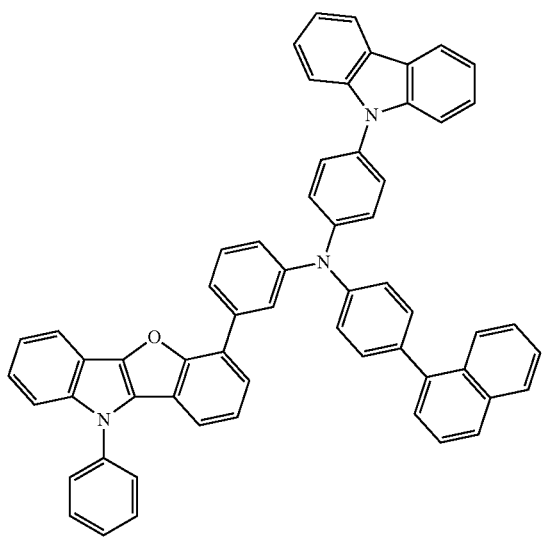
A138
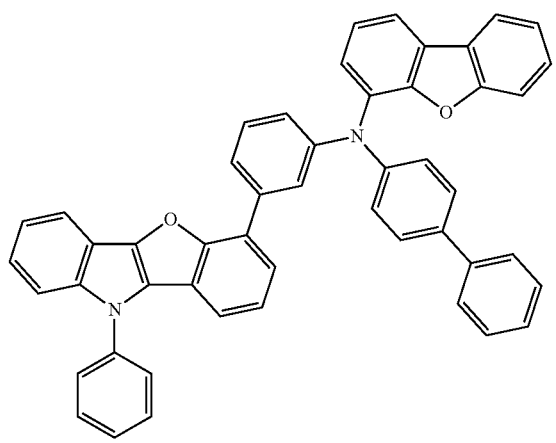
A139
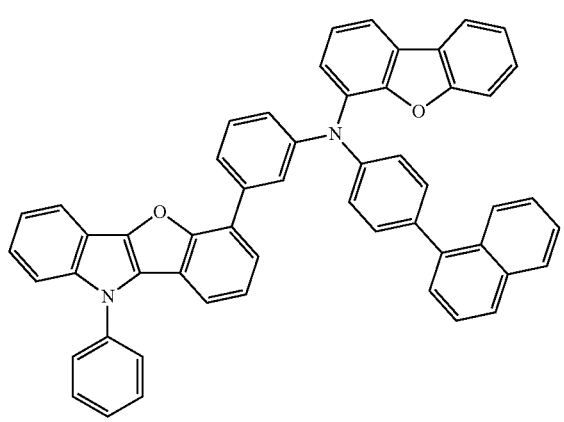
A140
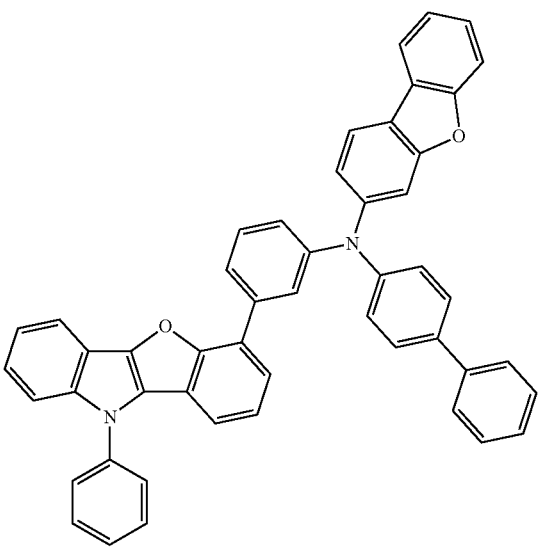
A141
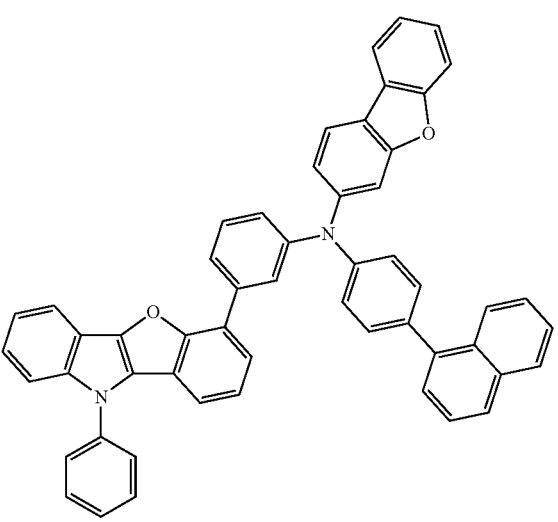
A142
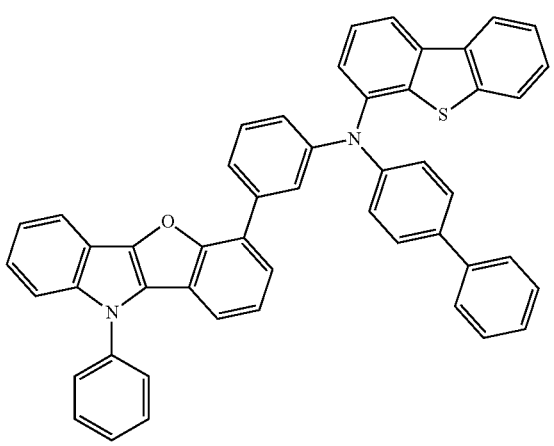

A143
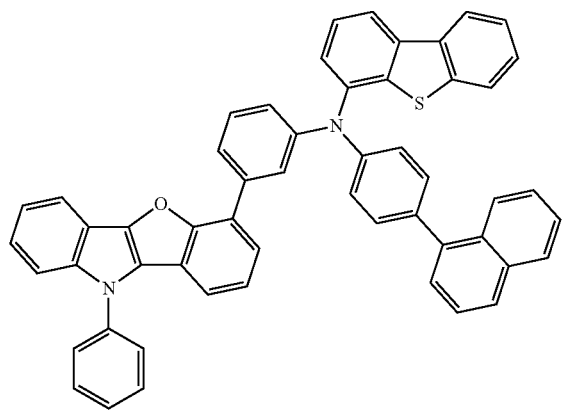
A144
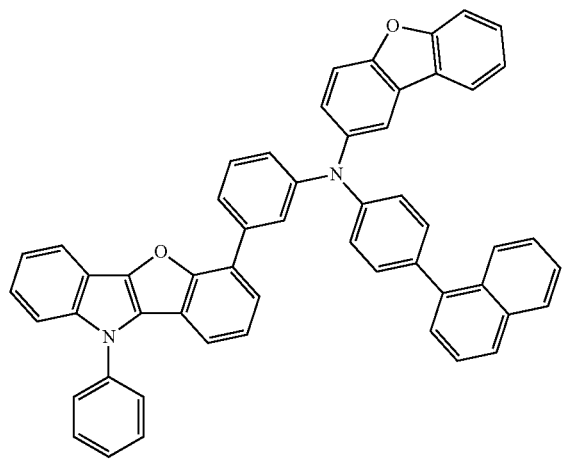
A145
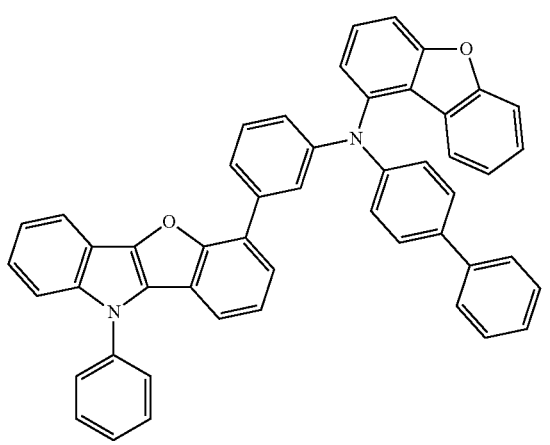
A146
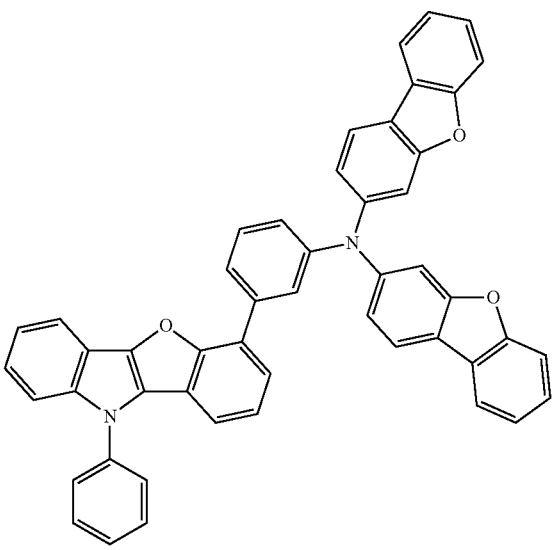
A147
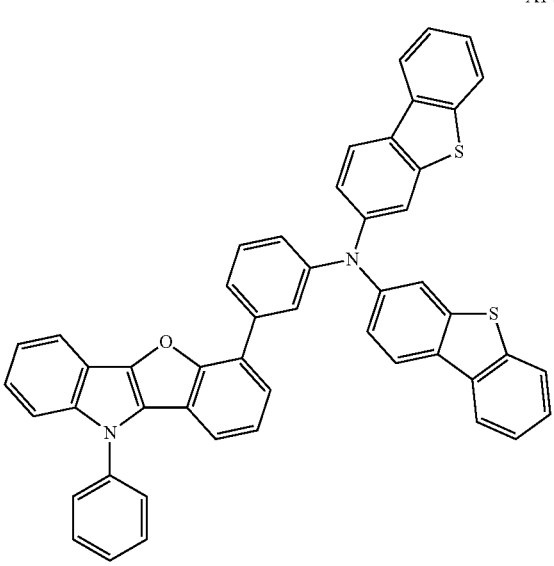
A148
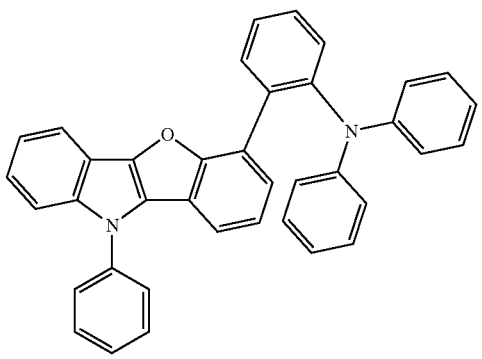

A149
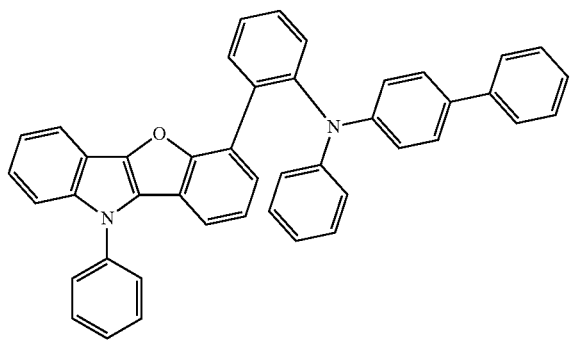
A150
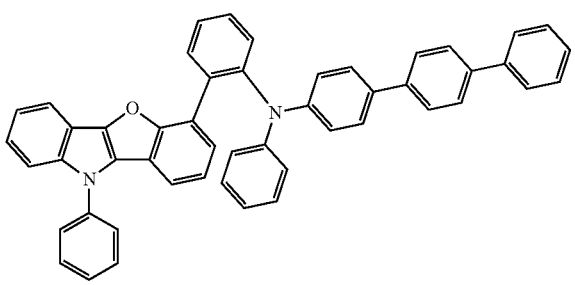
A151
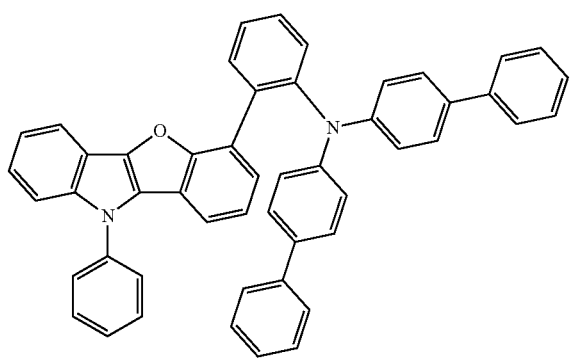
A152
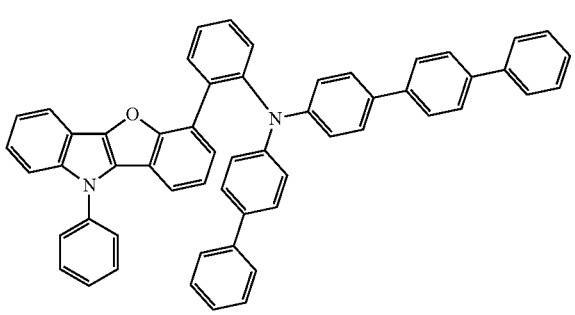
A153
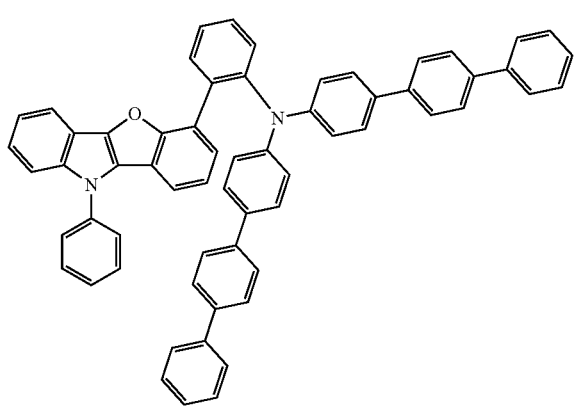
A154
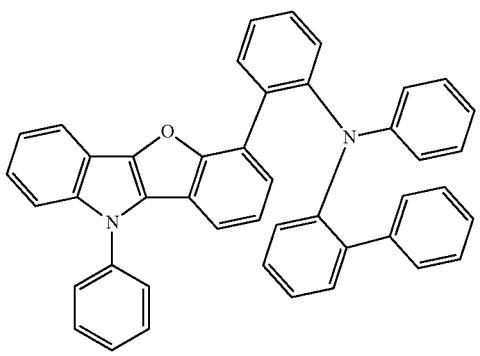
A155
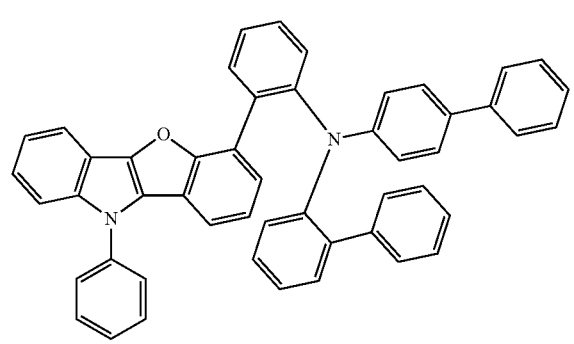

A156
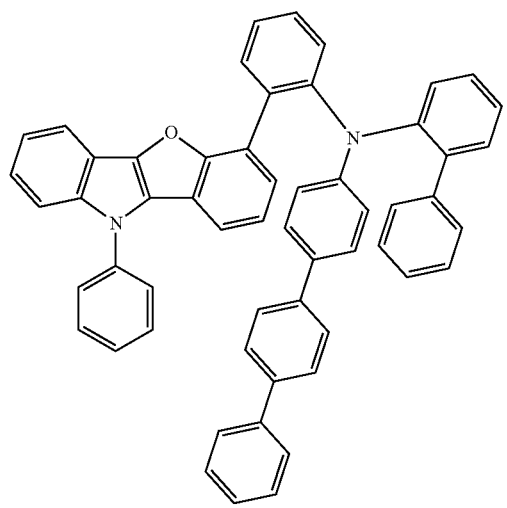
A157
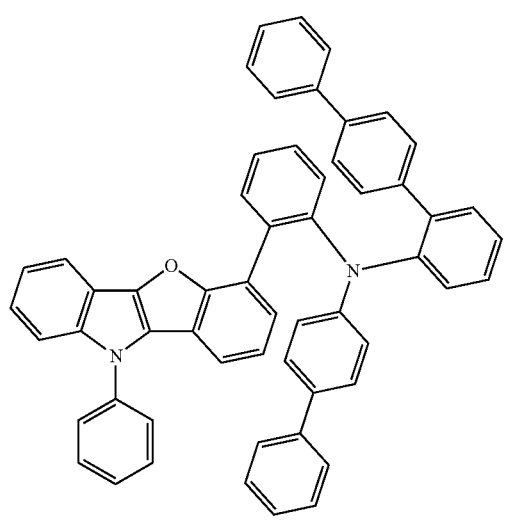
A158
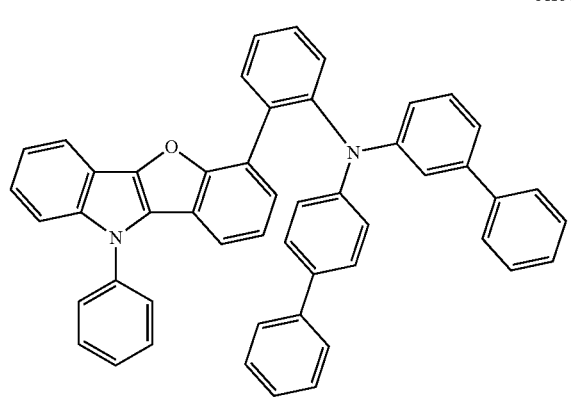
A159
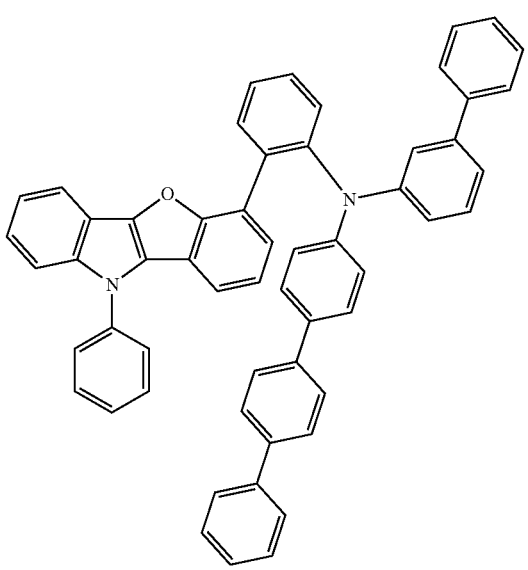
A160
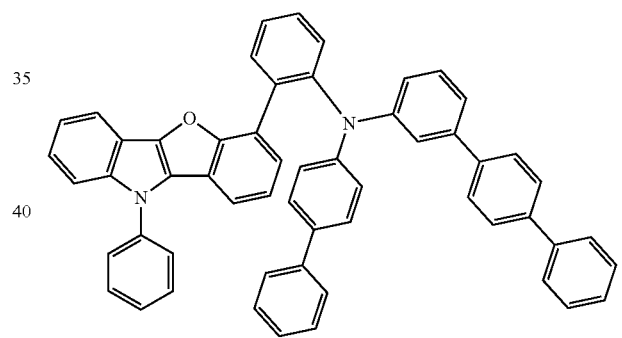
A161
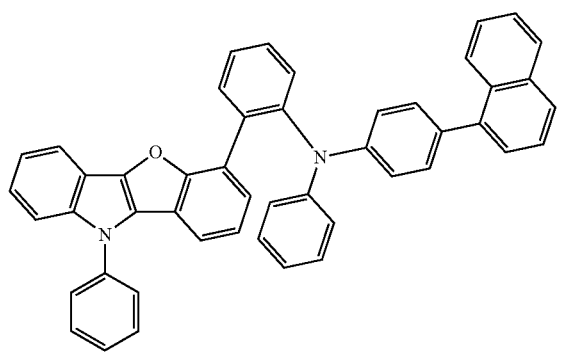

A162
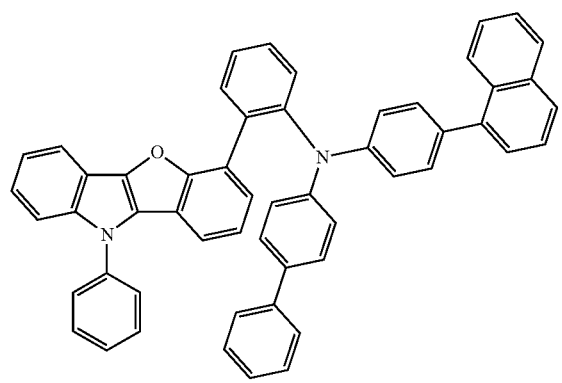
A163
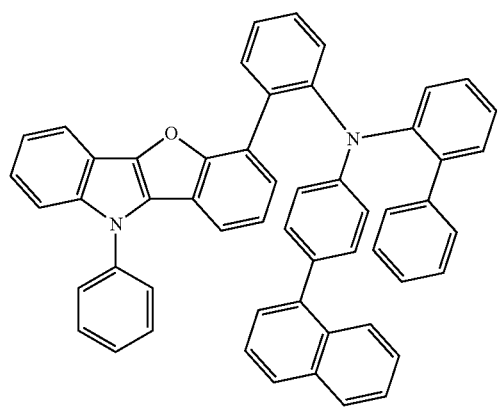
A164
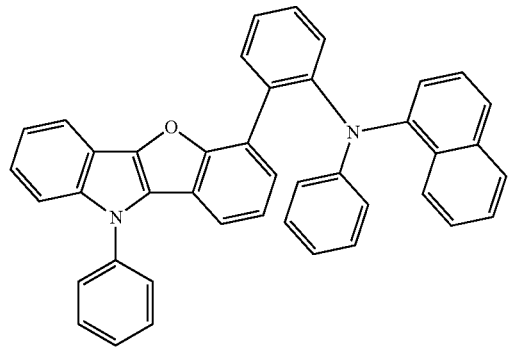
A165
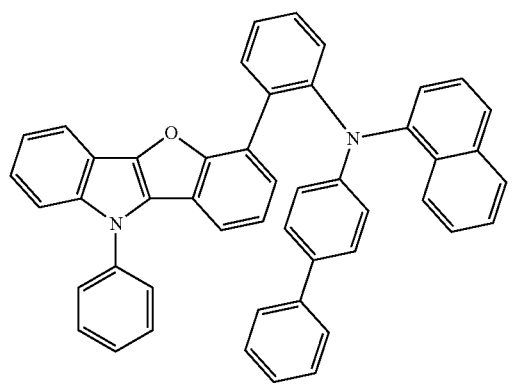
A166
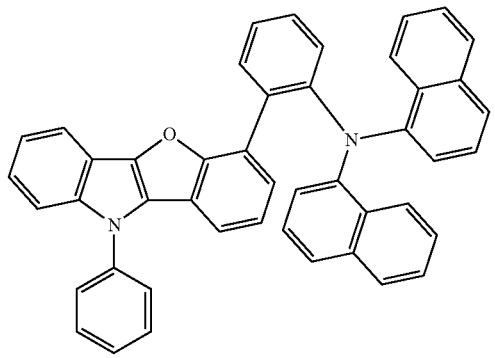
A167
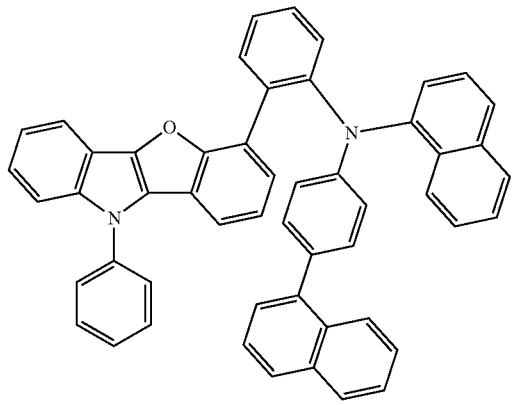
A168
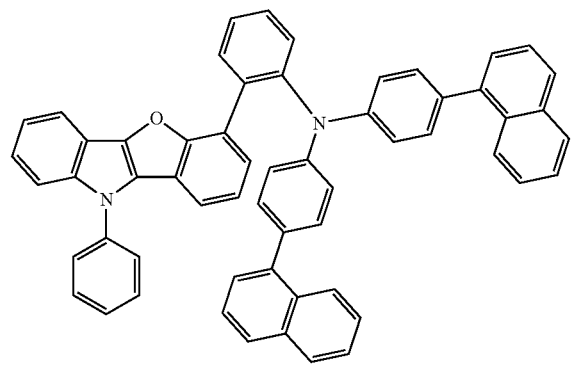
A169
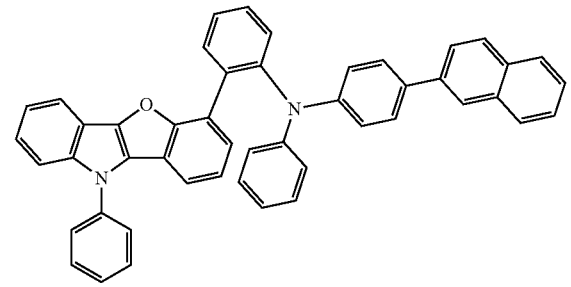

A170
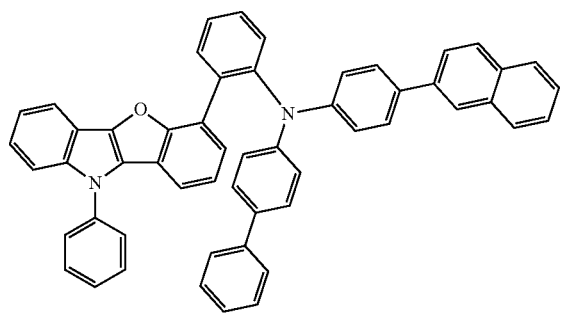
A171
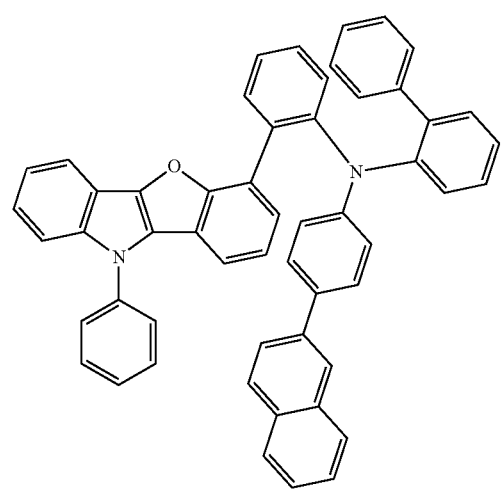
A172
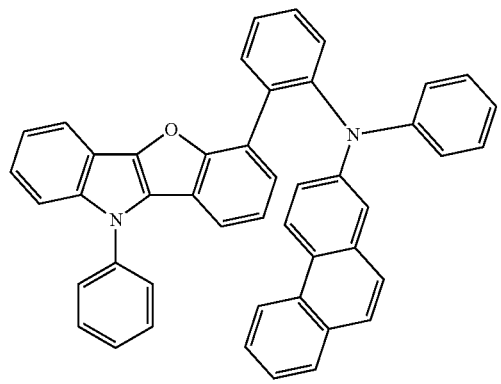
A173
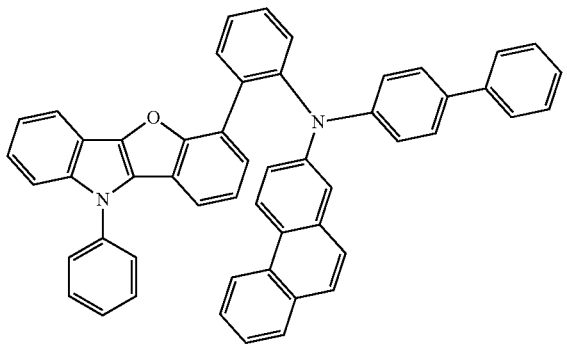
A174
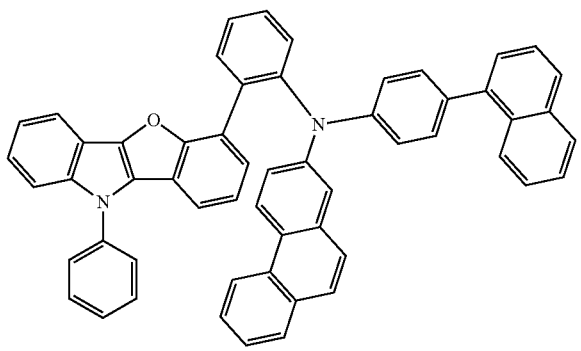
A175
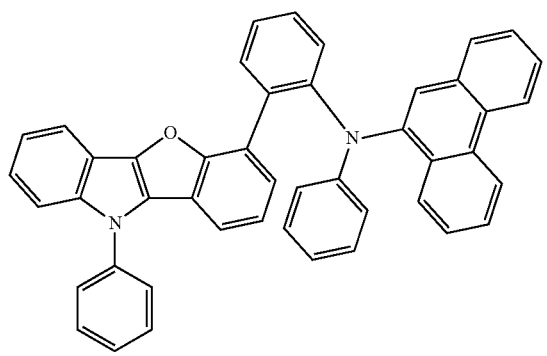
A176
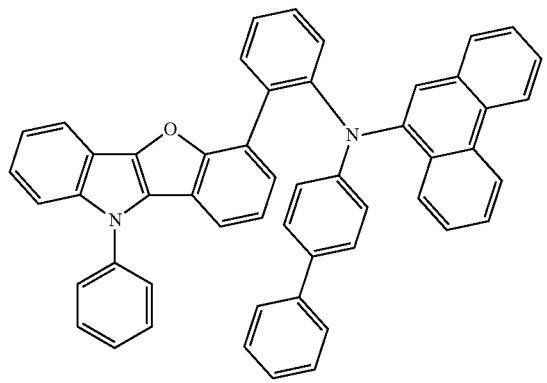
A177
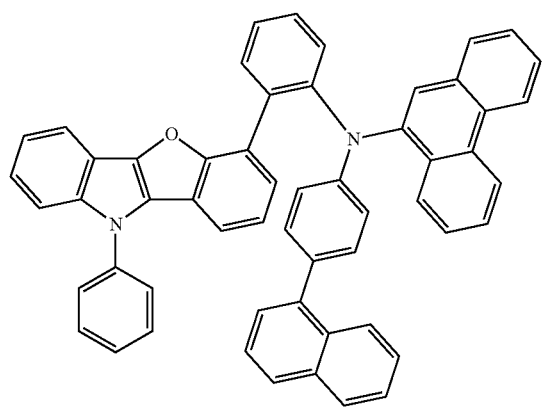

A178
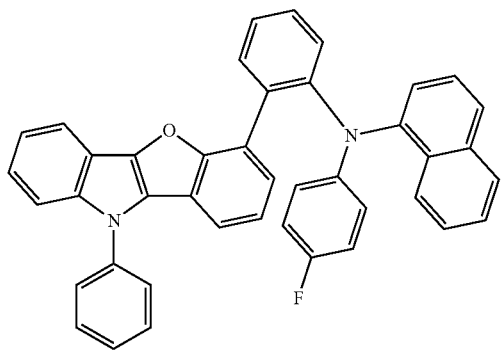
A182
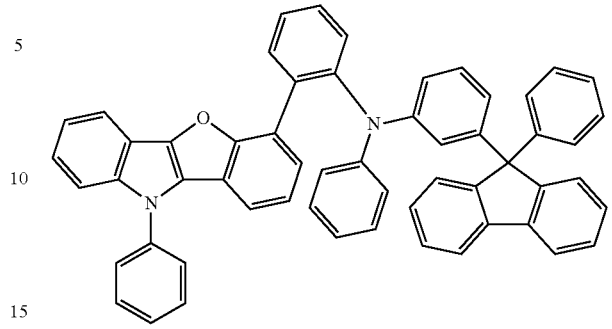
A179
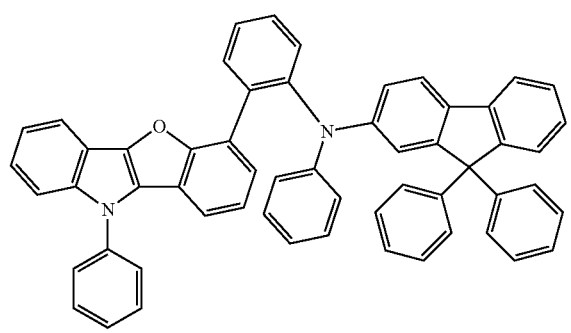
A183
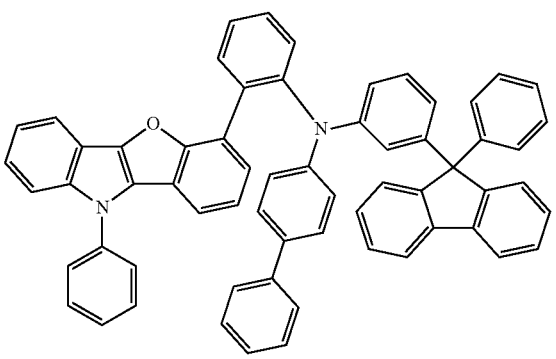
A180
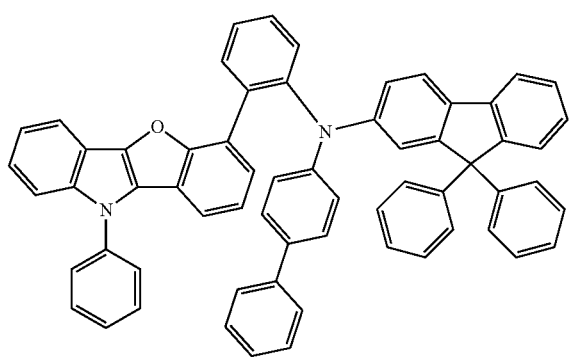
A184
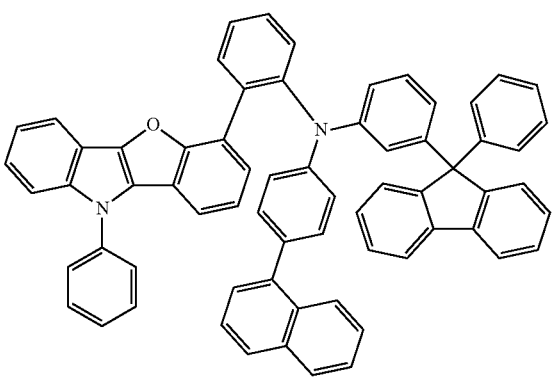
A181
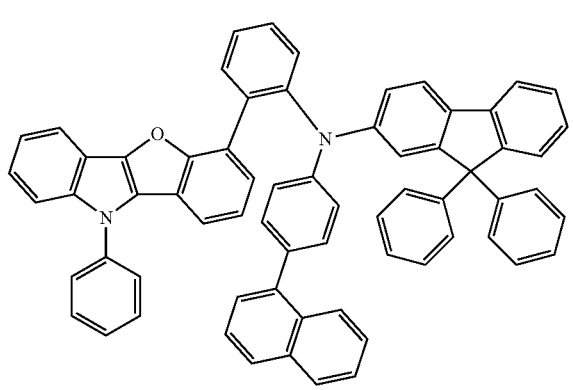
A185
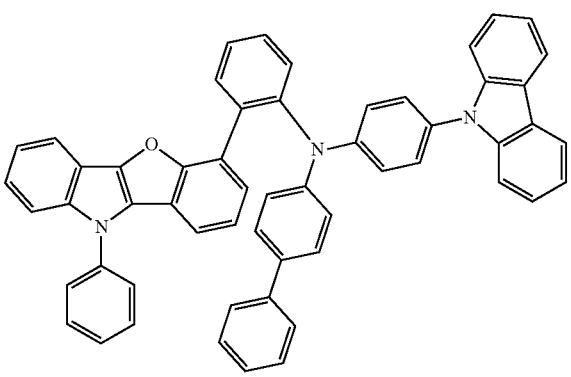

A186
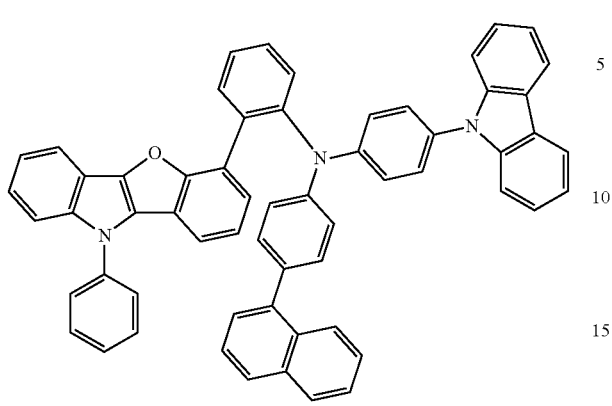
A187
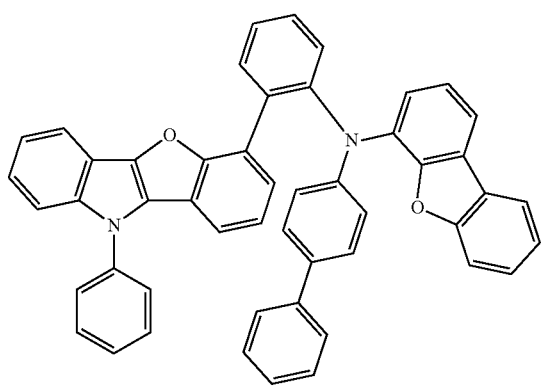
A188
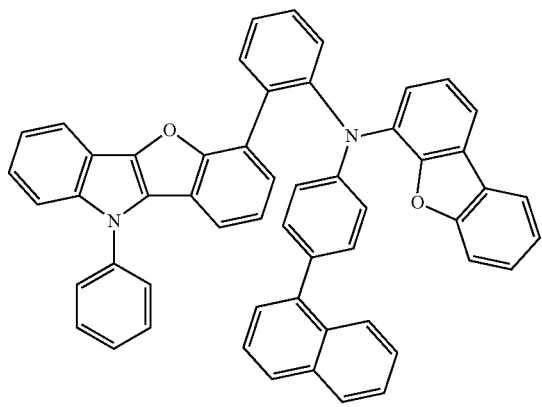
A189
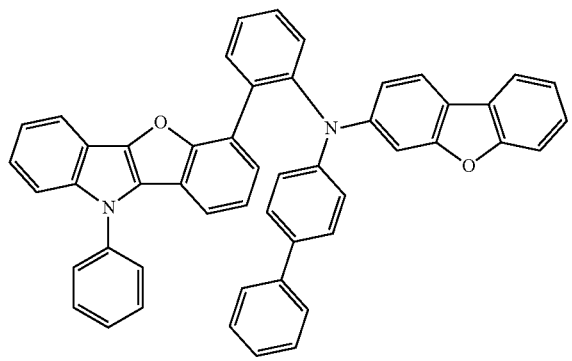
A190
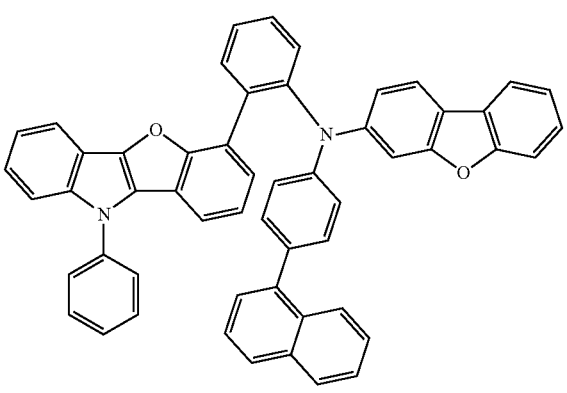
A191
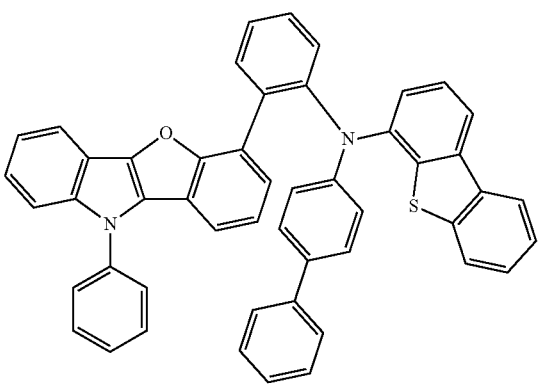
A192
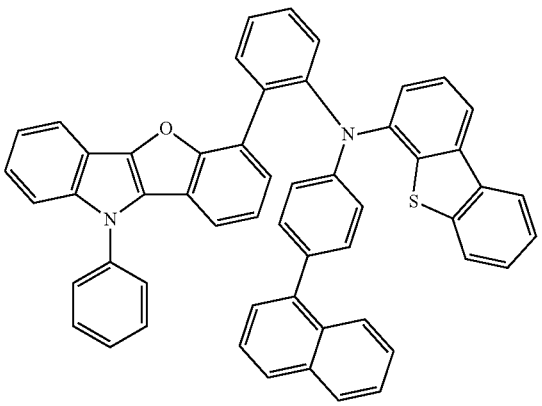
A193
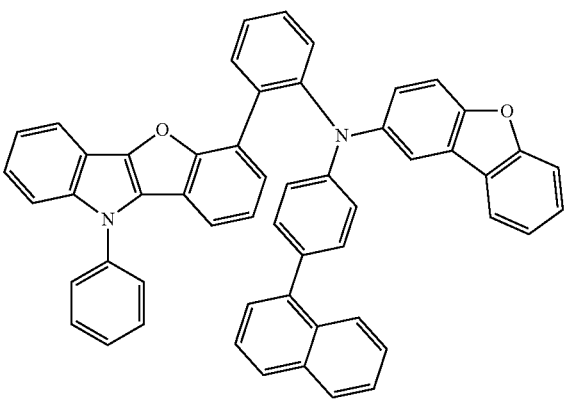

A194
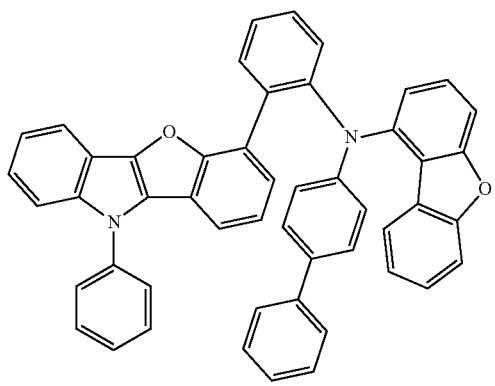
A195
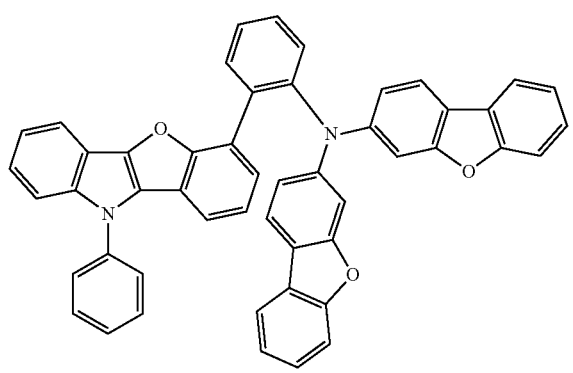
A196
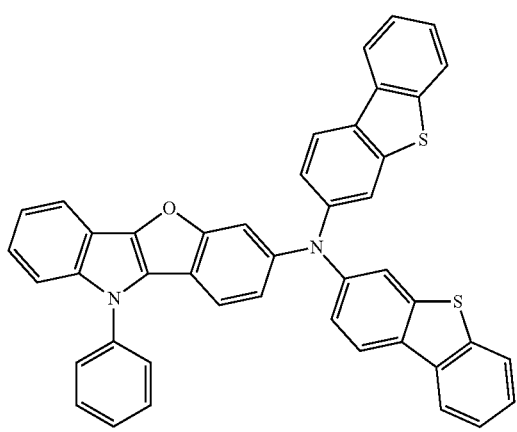
A197
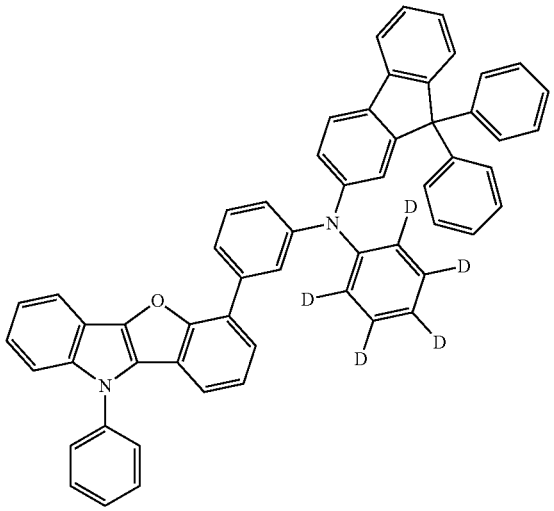
A198
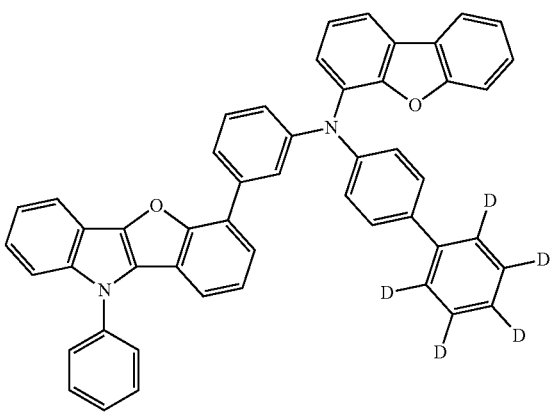
A199
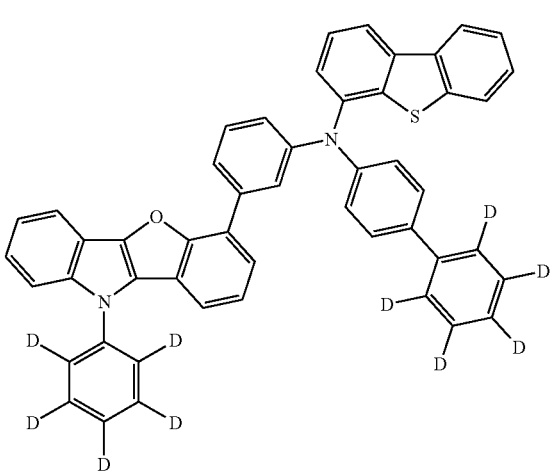

A200
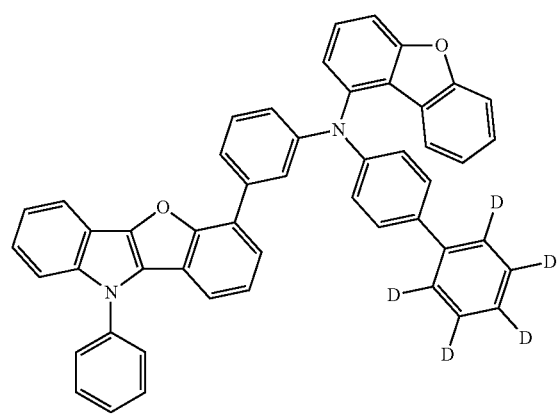
A201
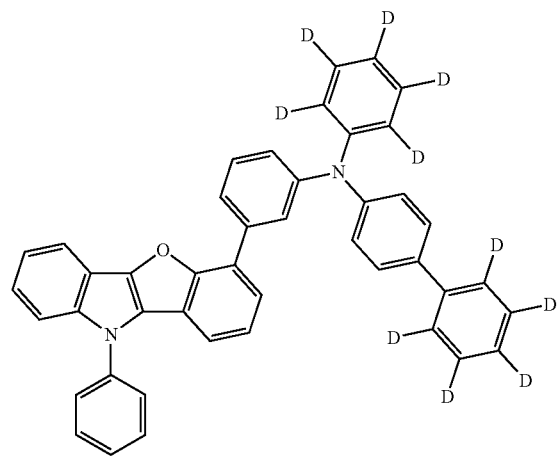
Compound Group 2
B1
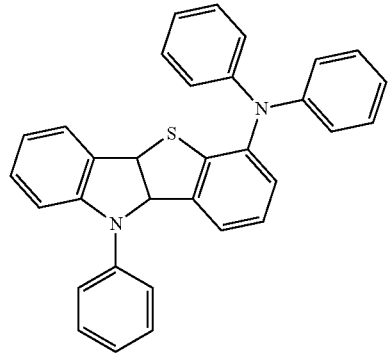
B2
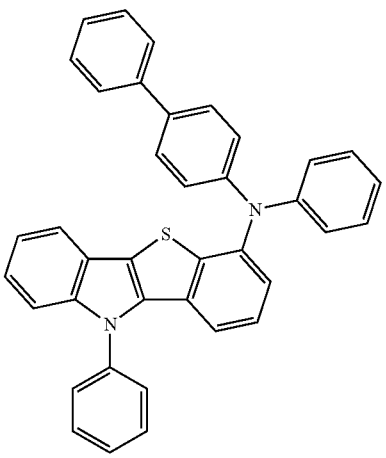
B3
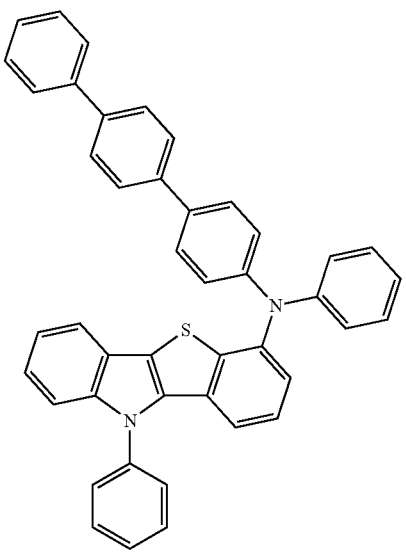
B4
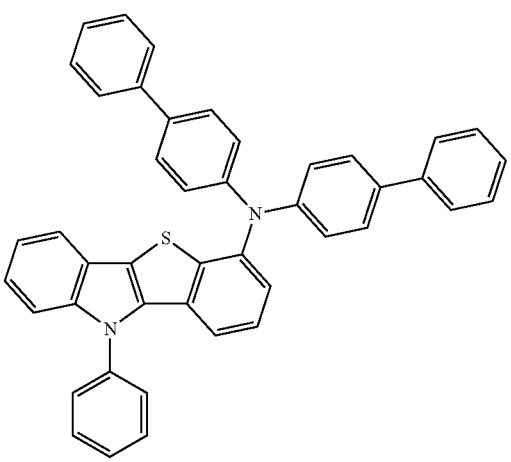

B5
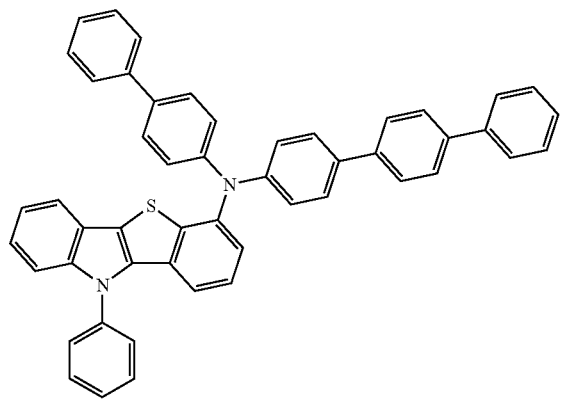
B6
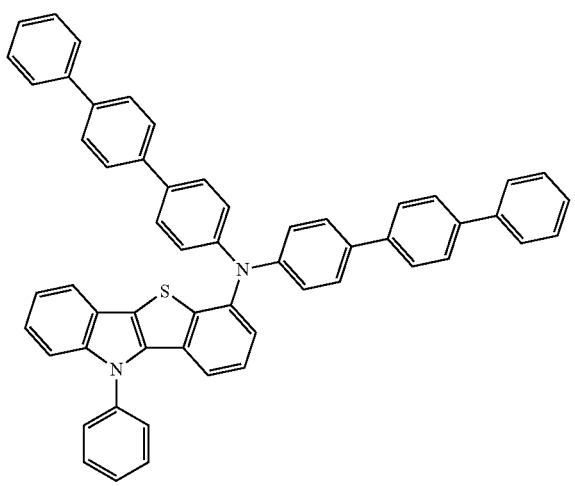
B7
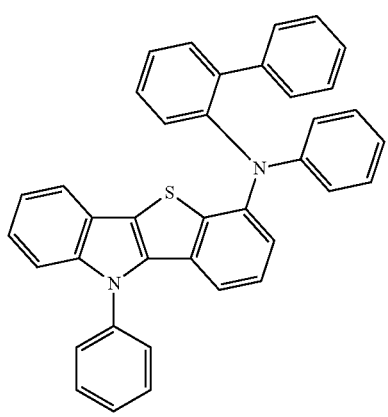
B8
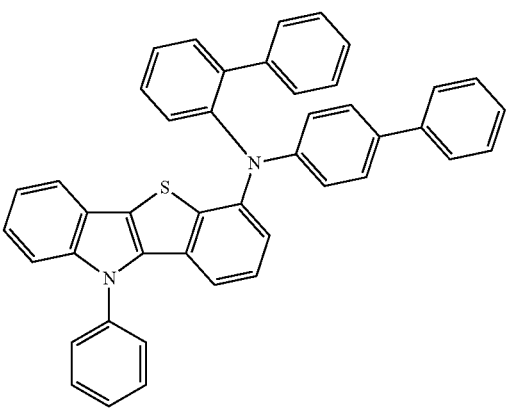
B9
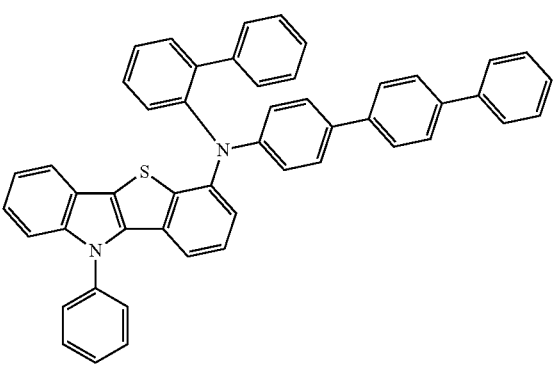
B10
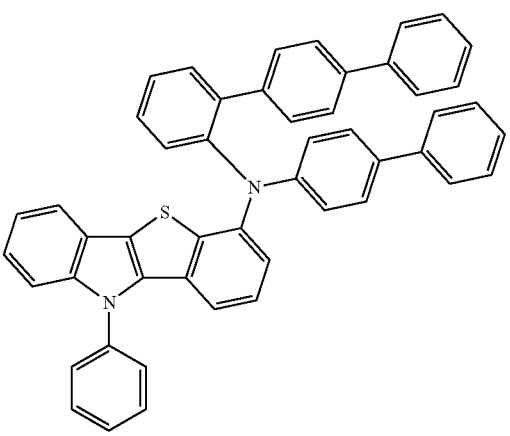

B11
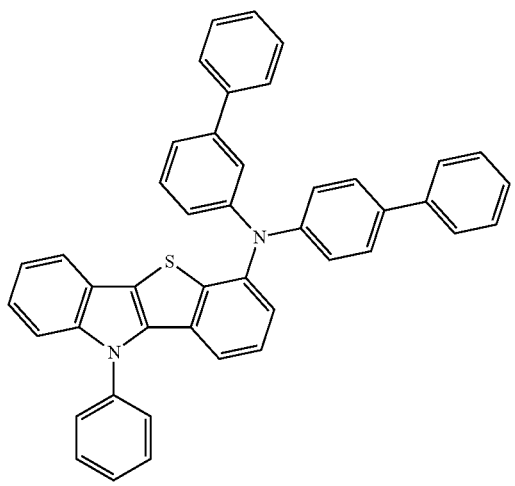
B12
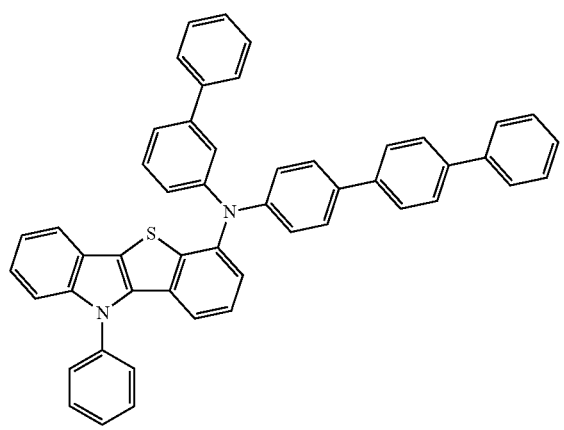
B13
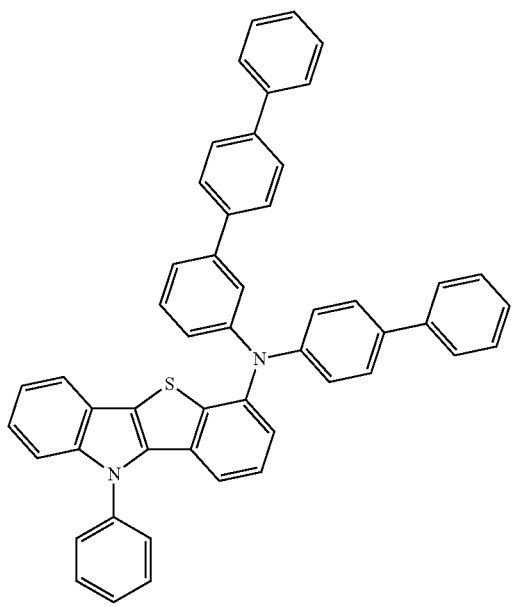
B14
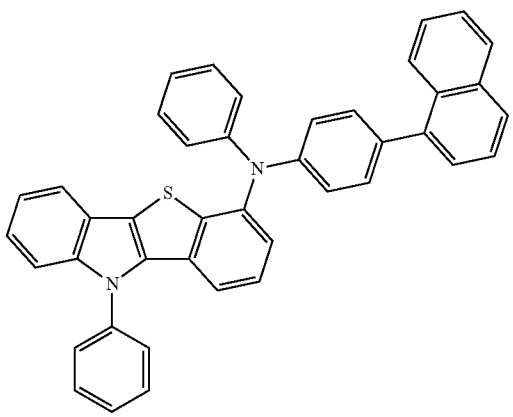
B15
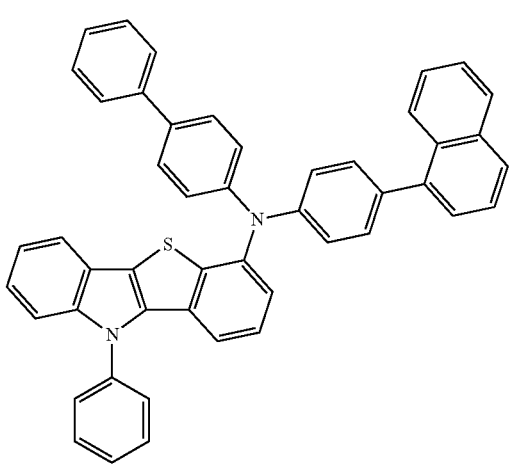
B16
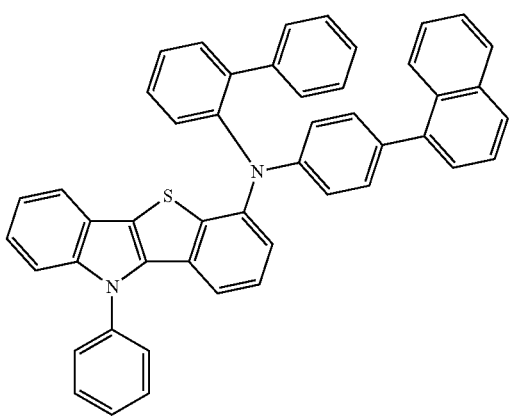

-continued
B17
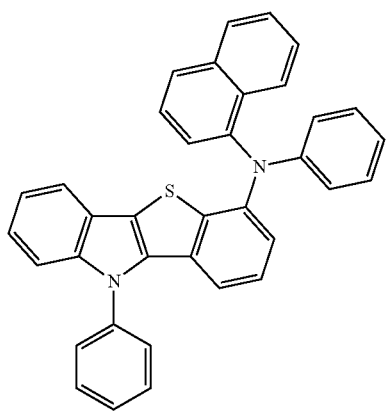
B18
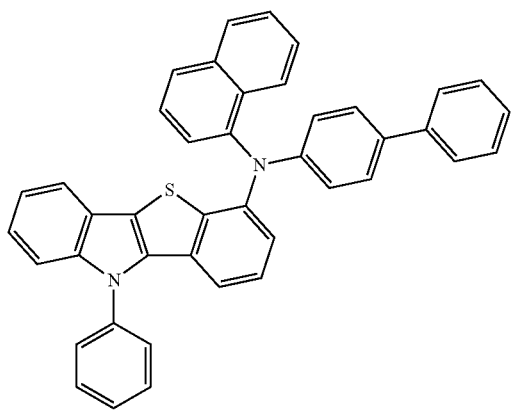
B19
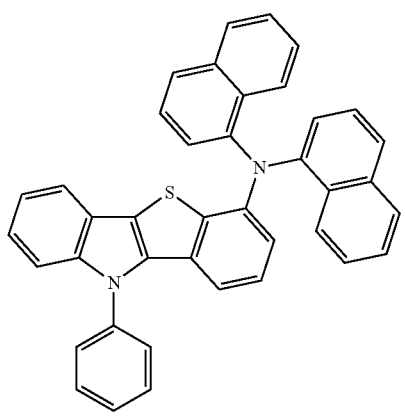
-continued
B20
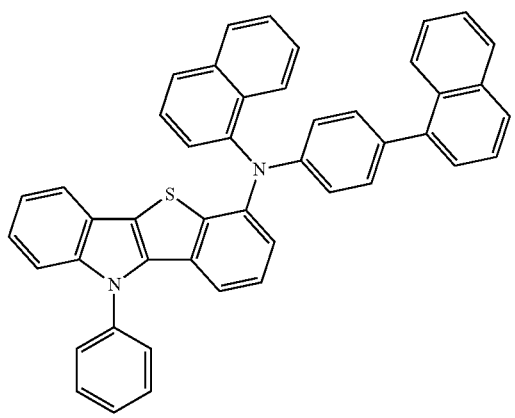
B21
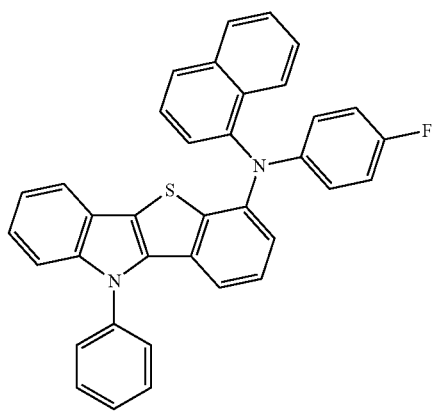
B22
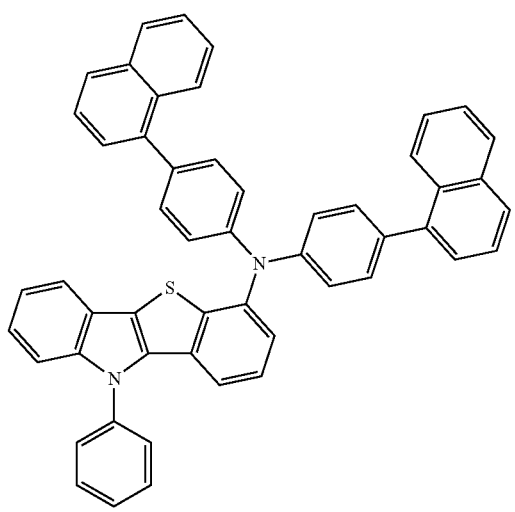

B23
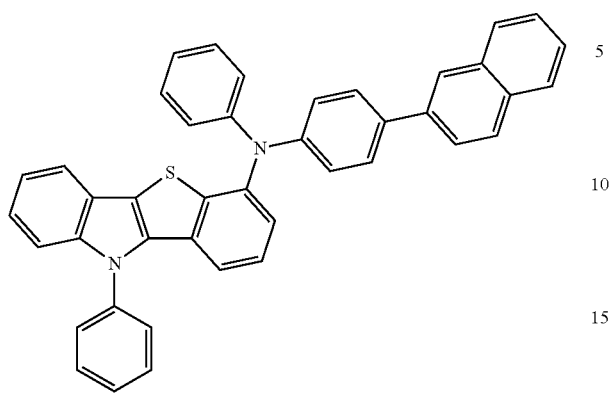
B26
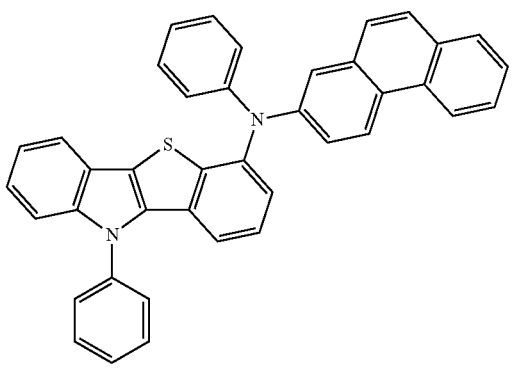
B24
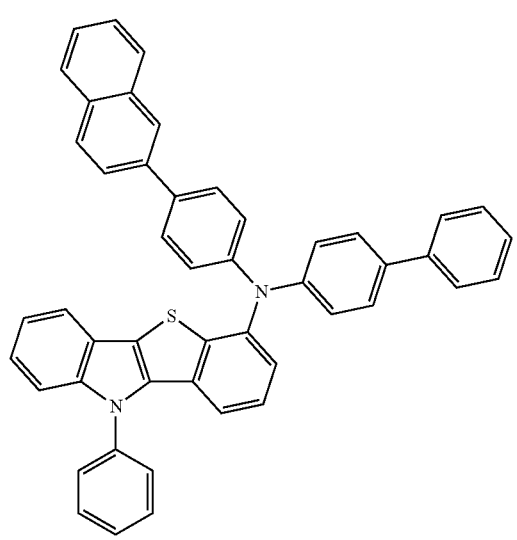
B27
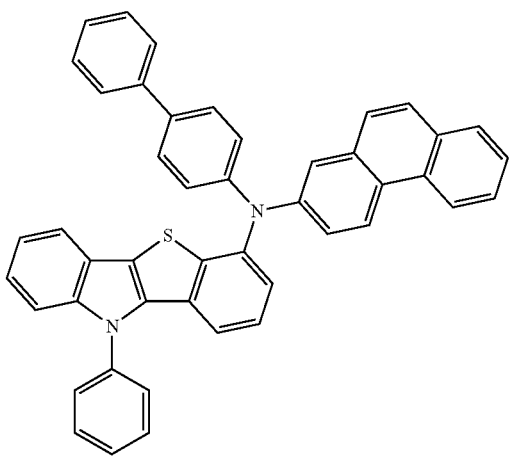
B25
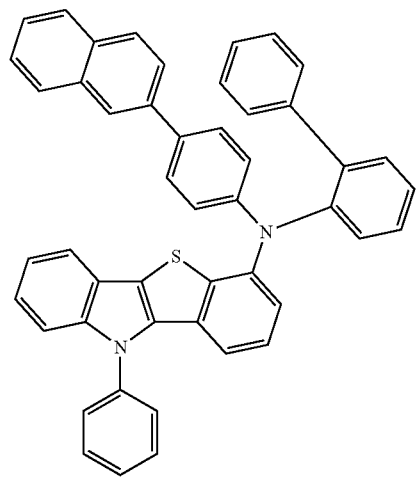
B28
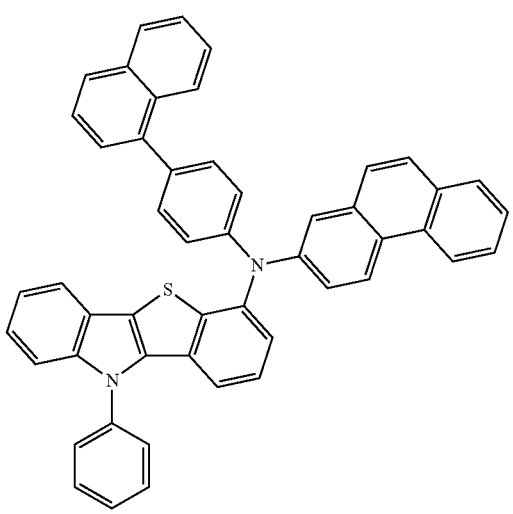

B29
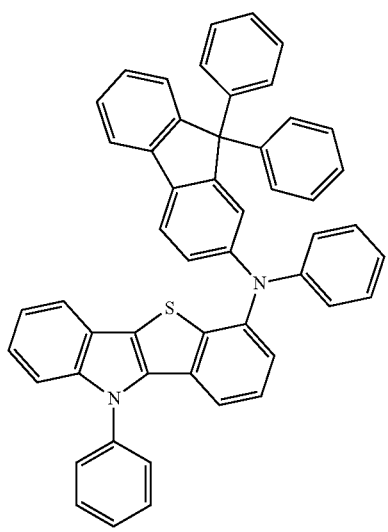
B30
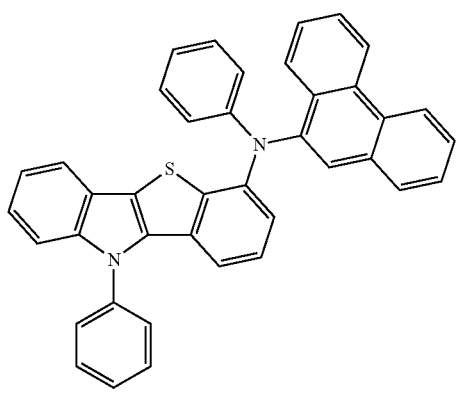
B31
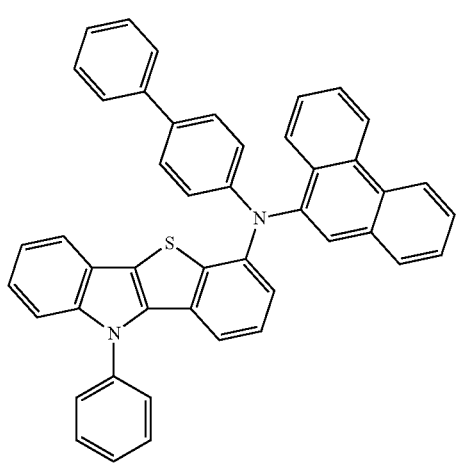
B32
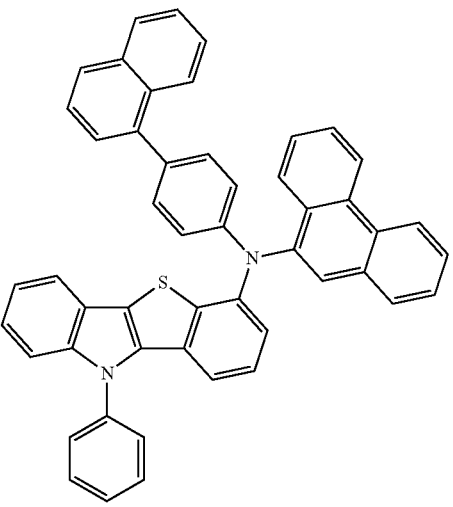
B33
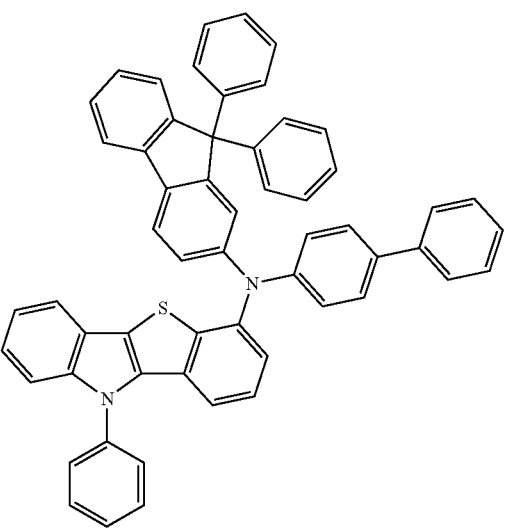
B34
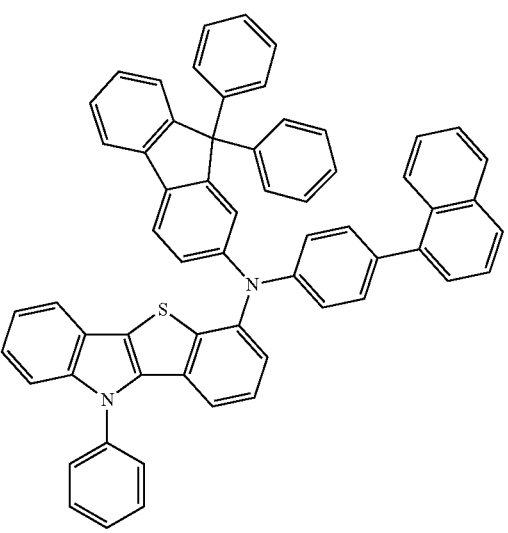

B35
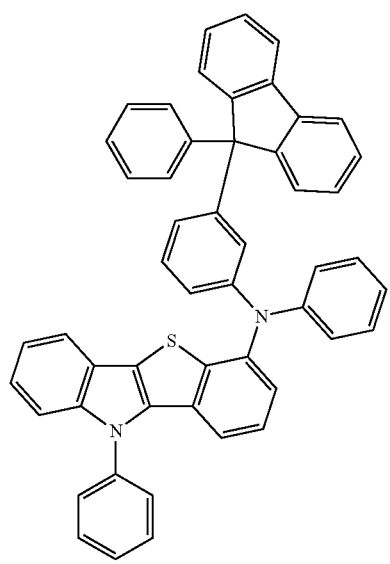
B37
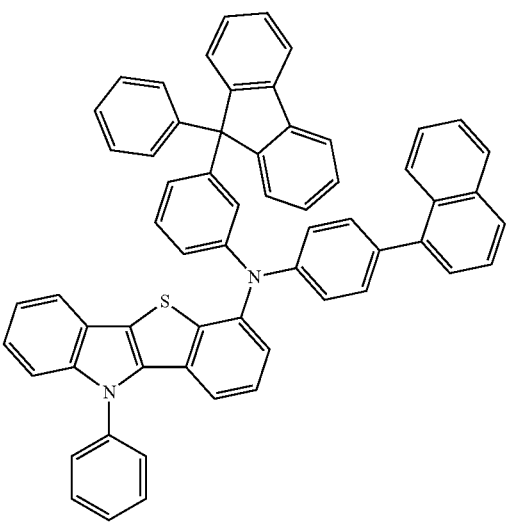
B38
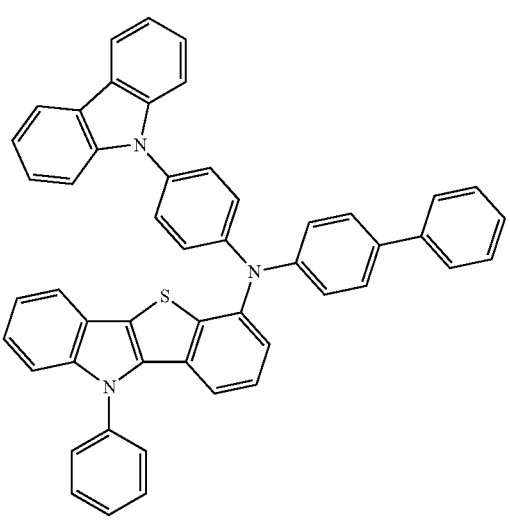
B36
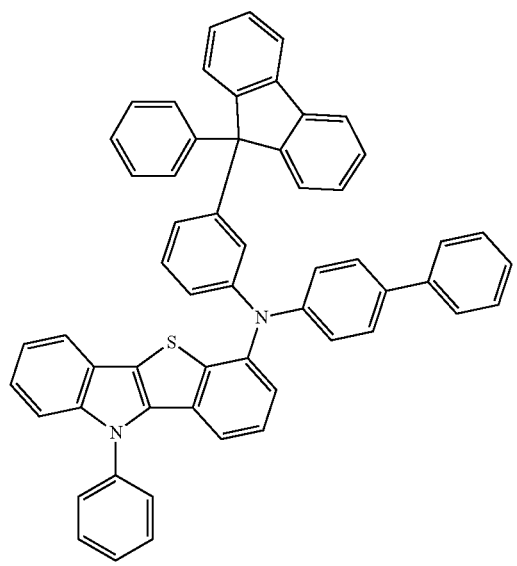
B39
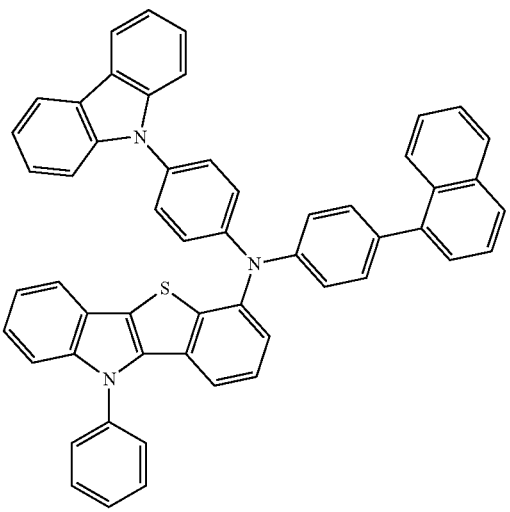

B40
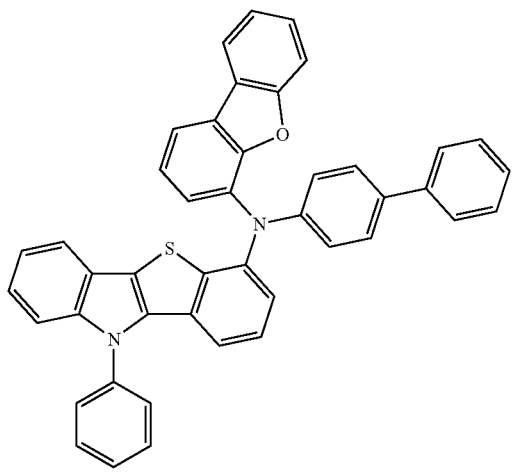
B41
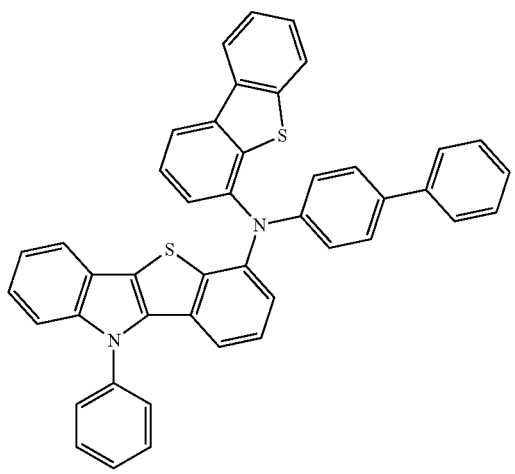
B42
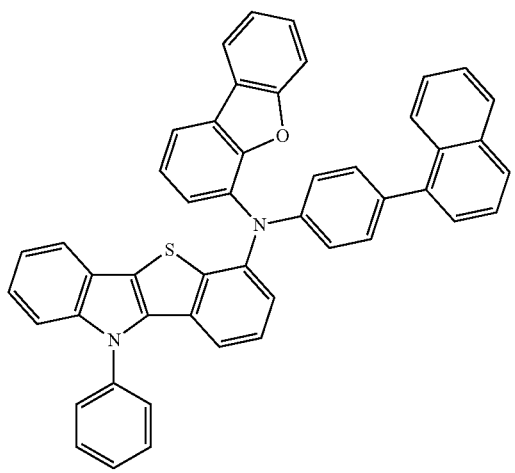
B43
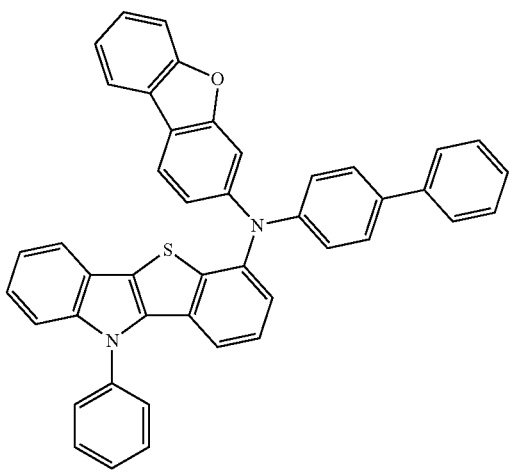
B44
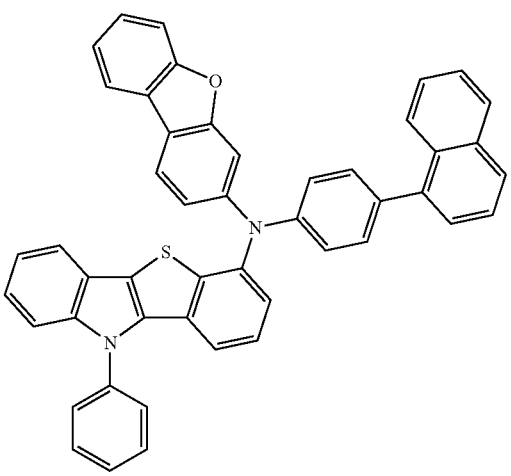
B45
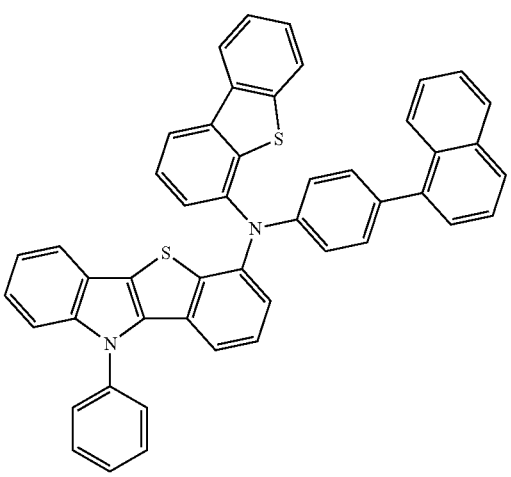

B46
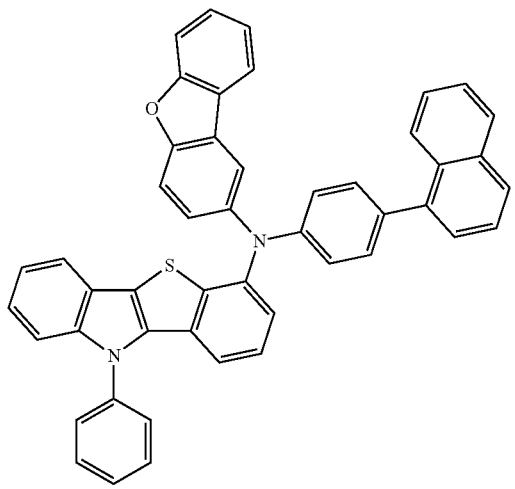
B47
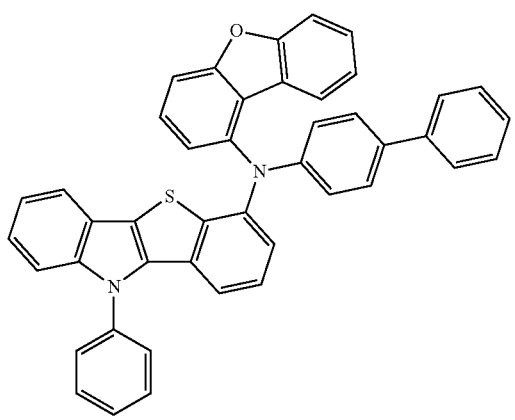
B48
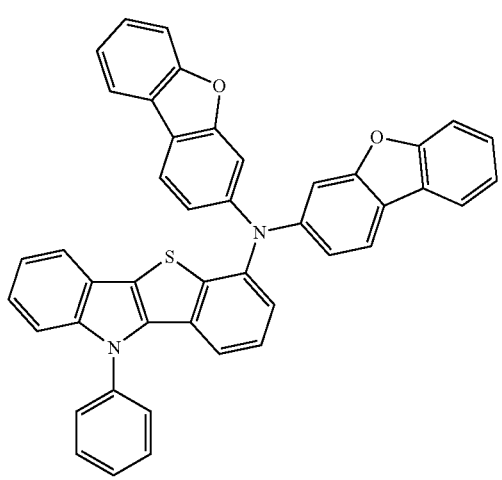
B49
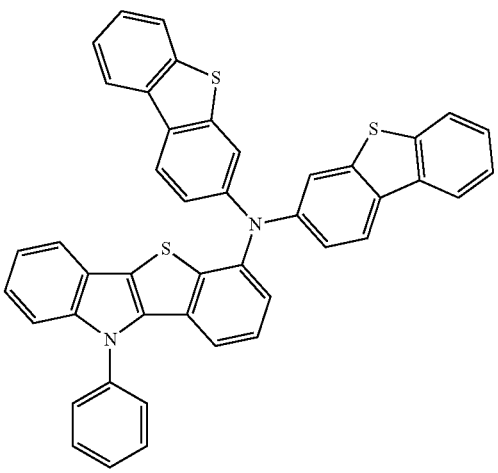
B50
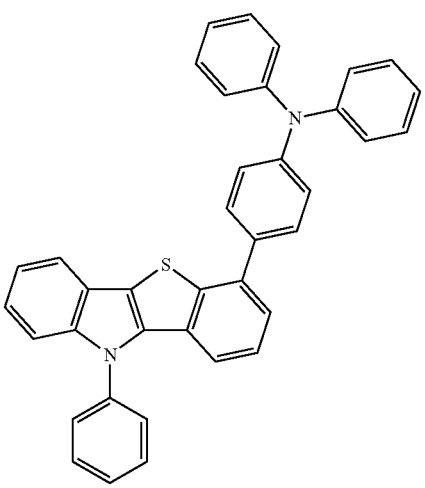
B51
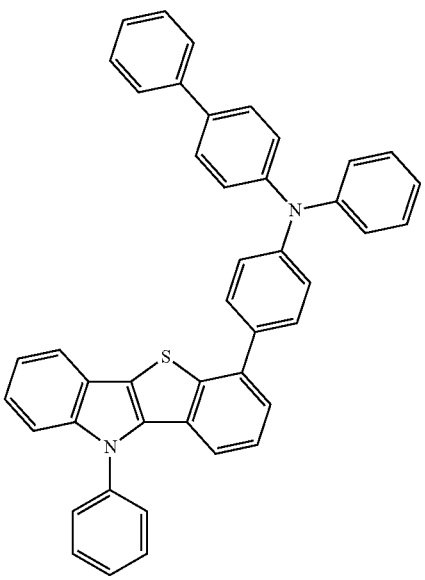

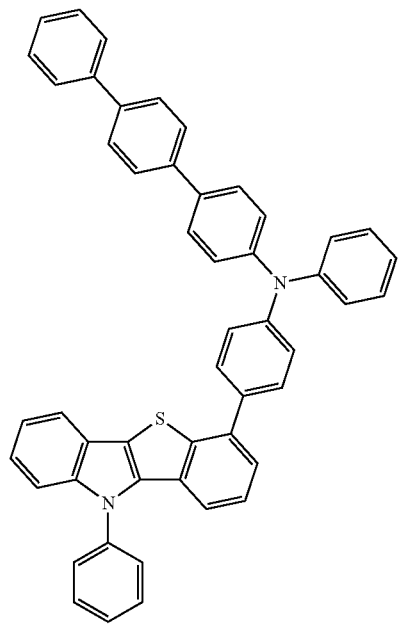
B52
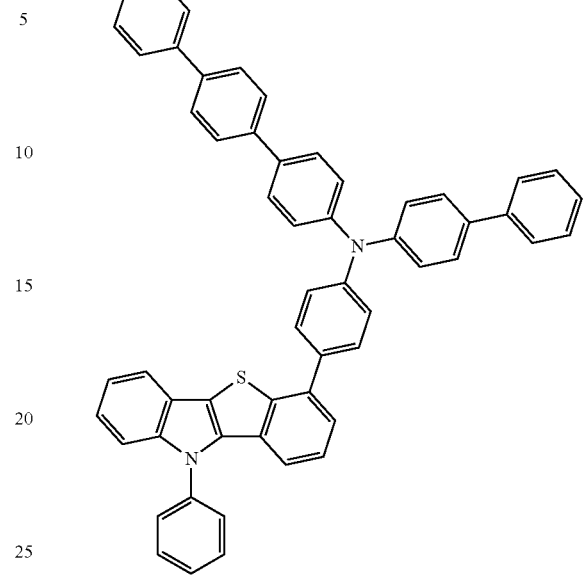
B54
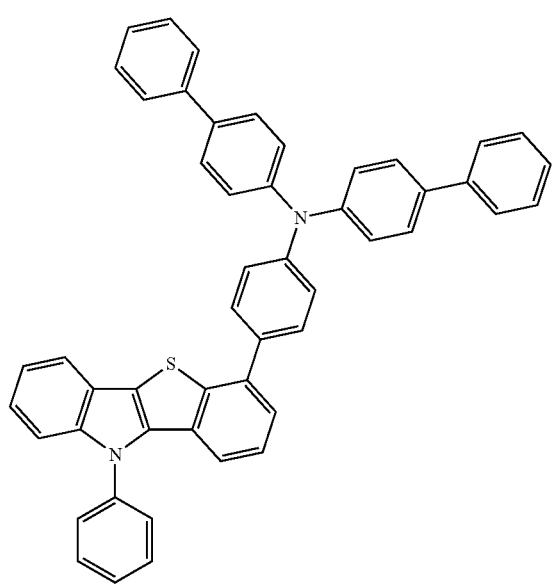
B53
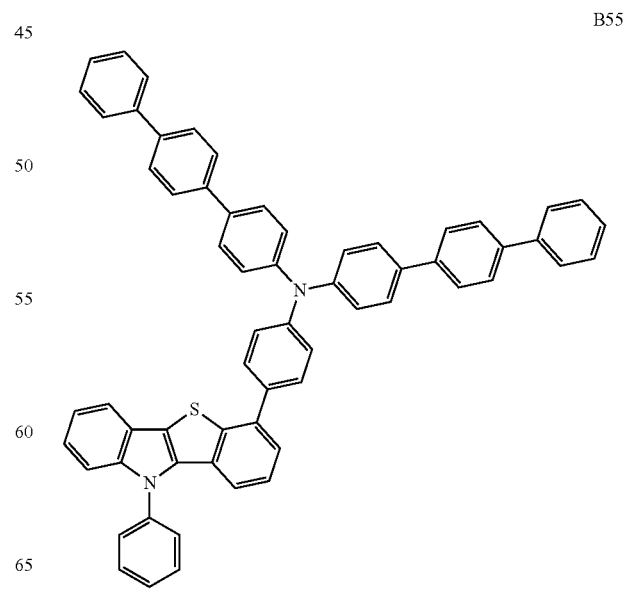
B55

-continued
B56
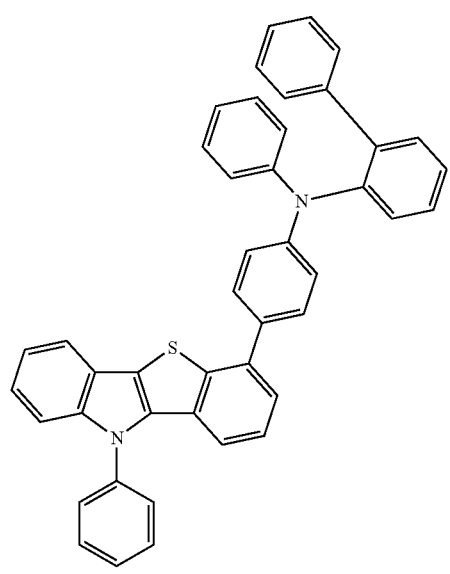
B57
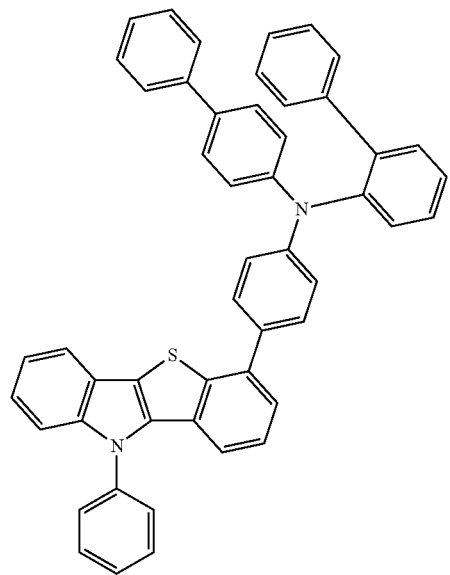
B58
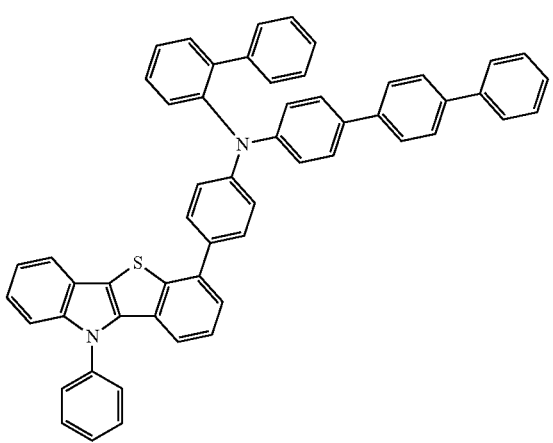
-continued
B59
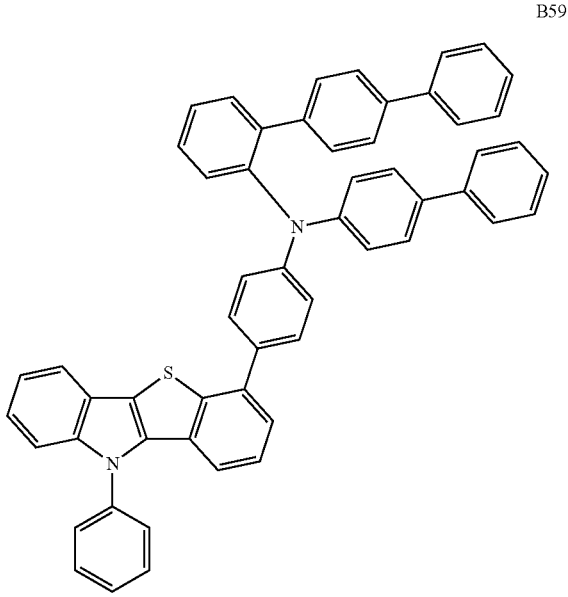
B60
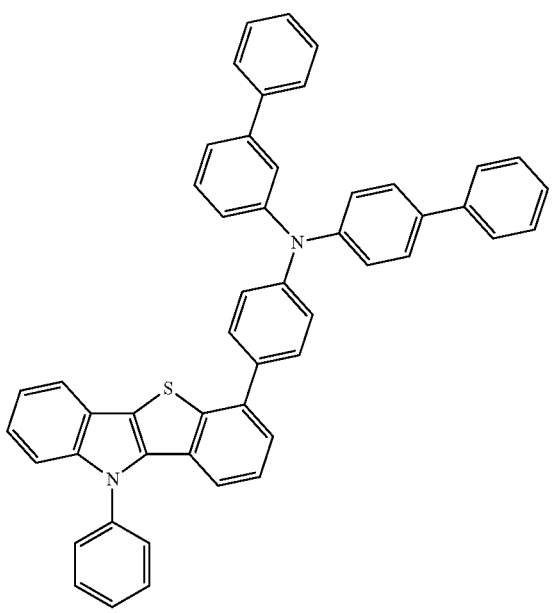
B61
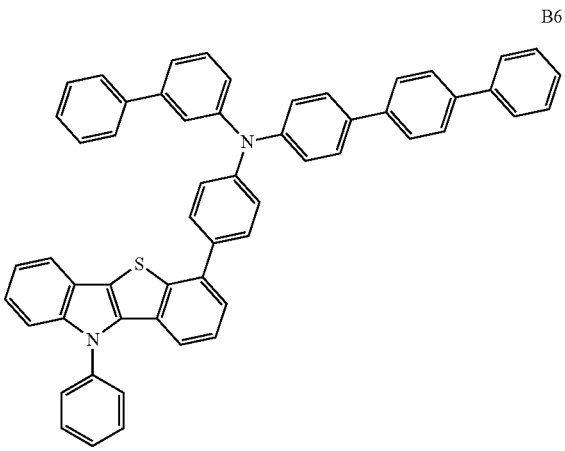

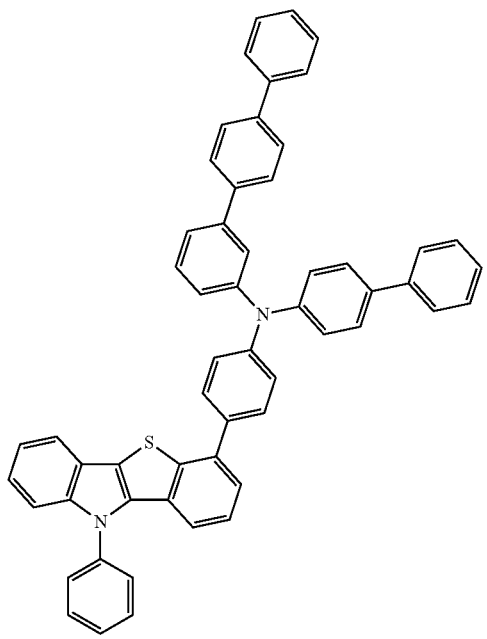
B62
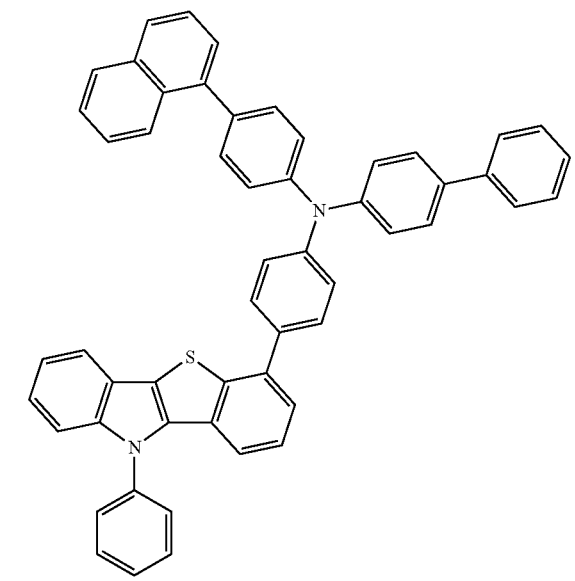
B64
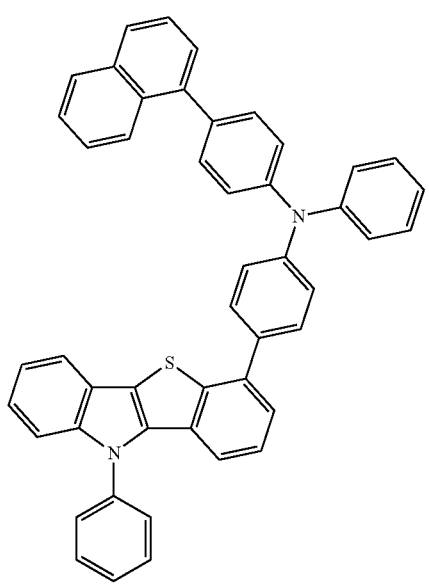
B63
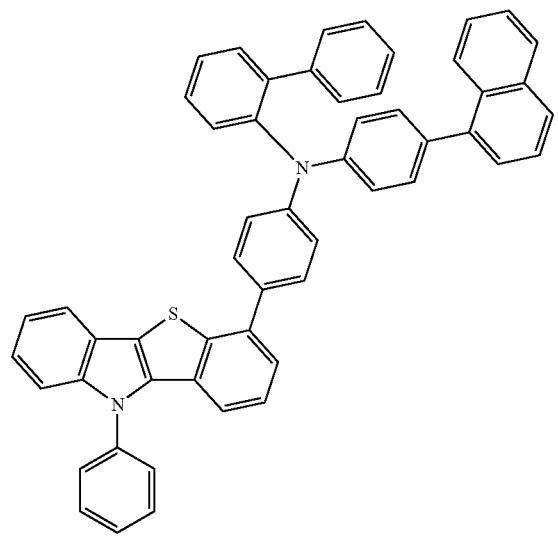
B65

-continued
B66
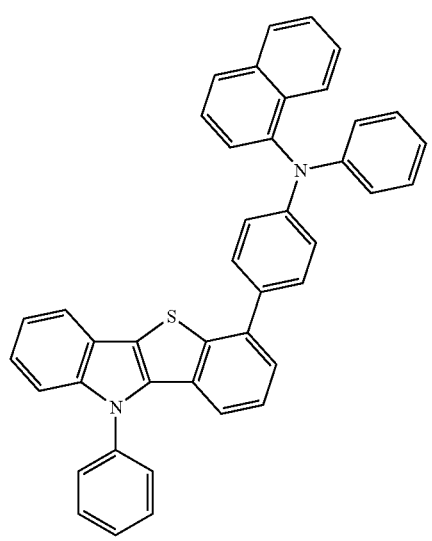
B67
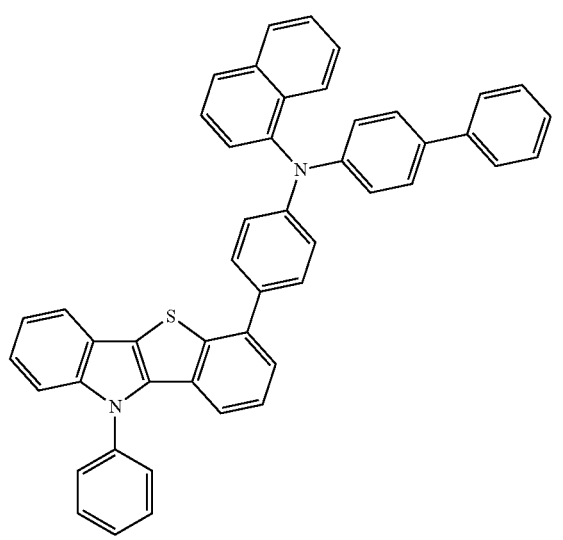
B69
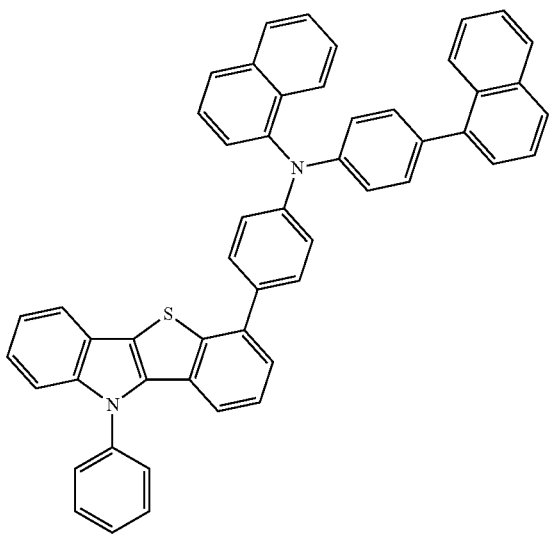
B68
B70
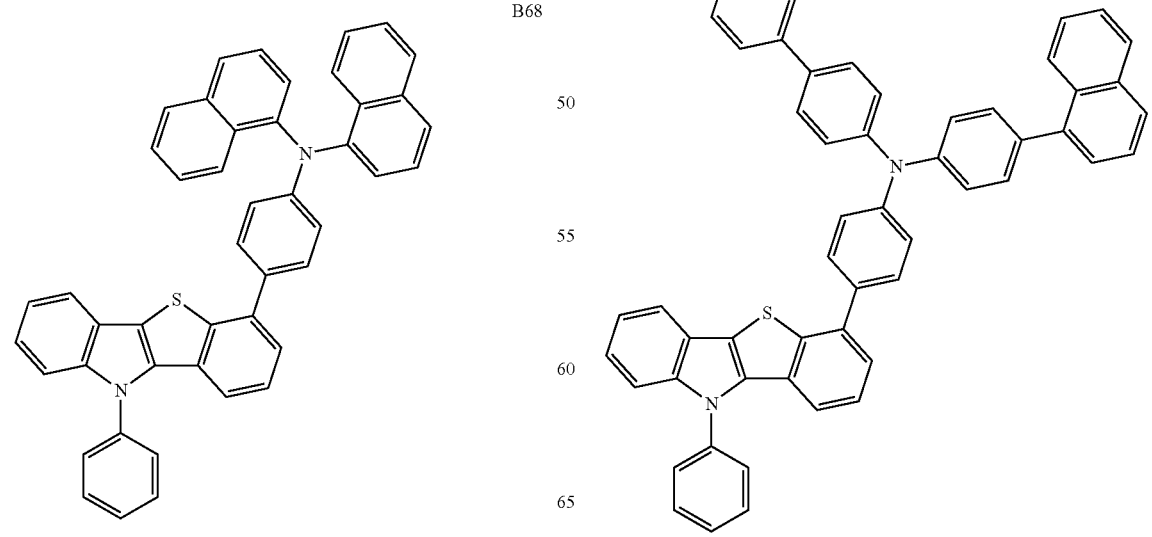

-continued
B71
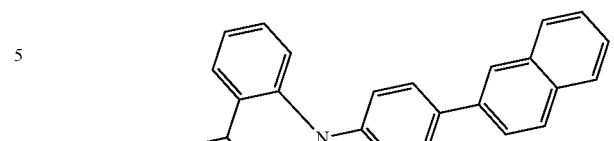
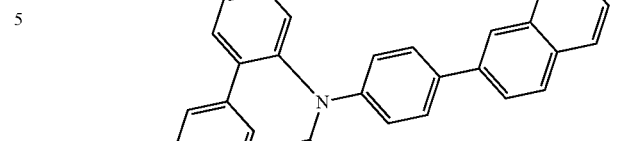
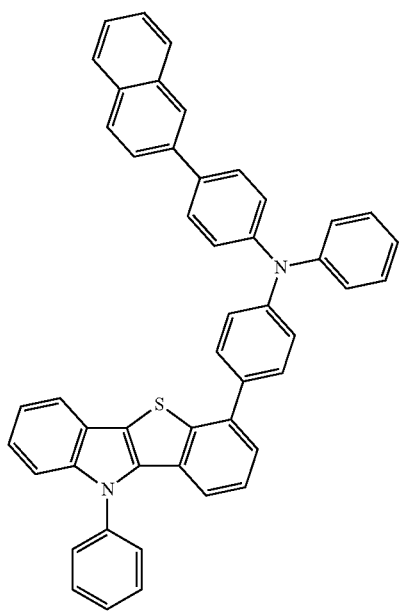
B73
B74
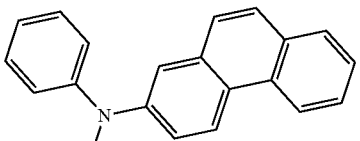
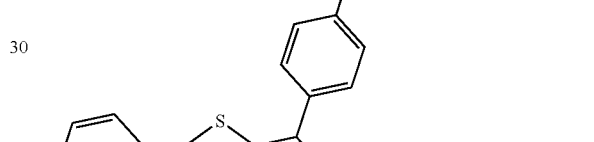
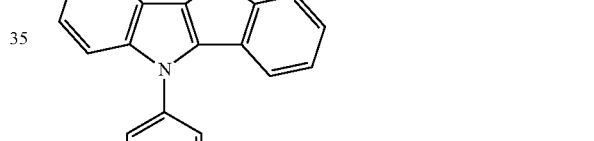
B72
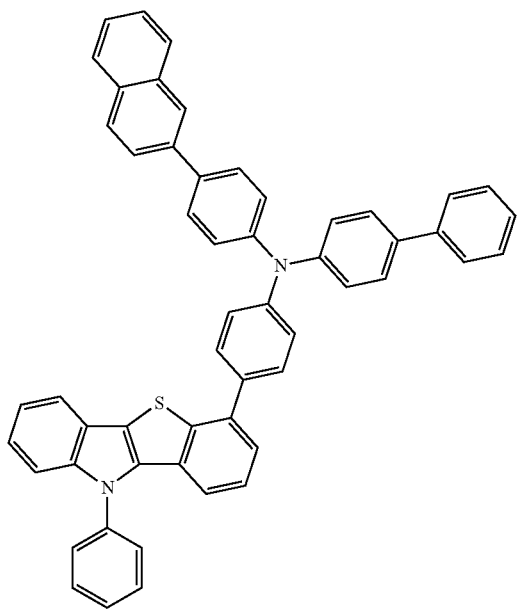
B75
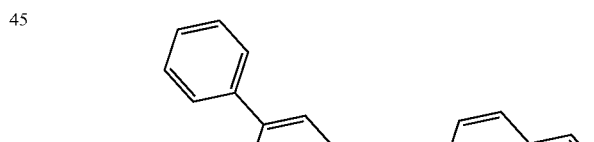
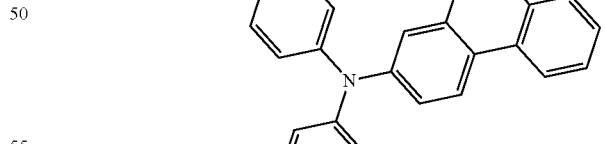
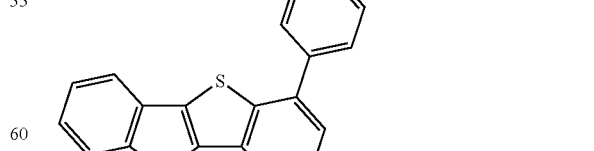
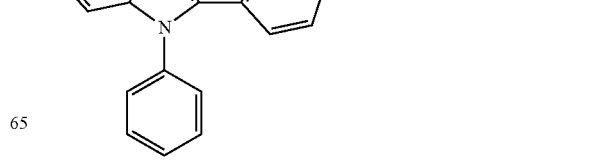

B76
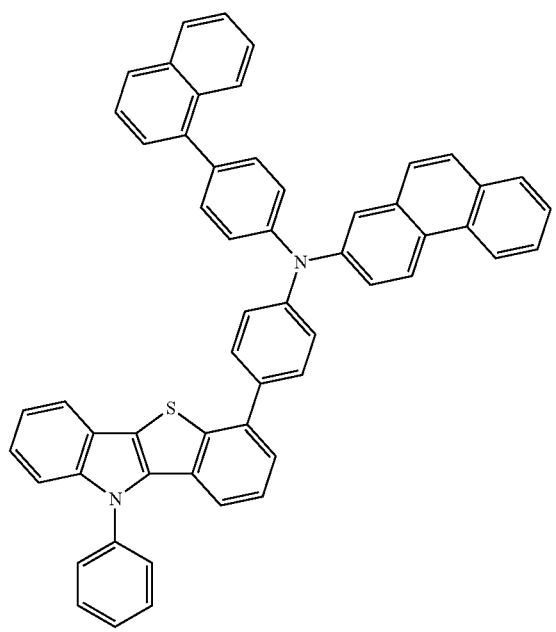
B77
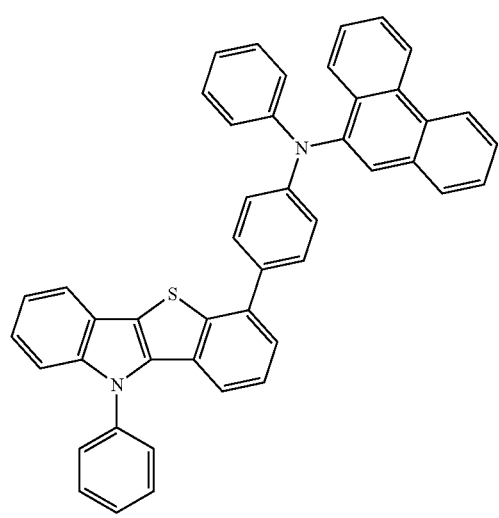
B78
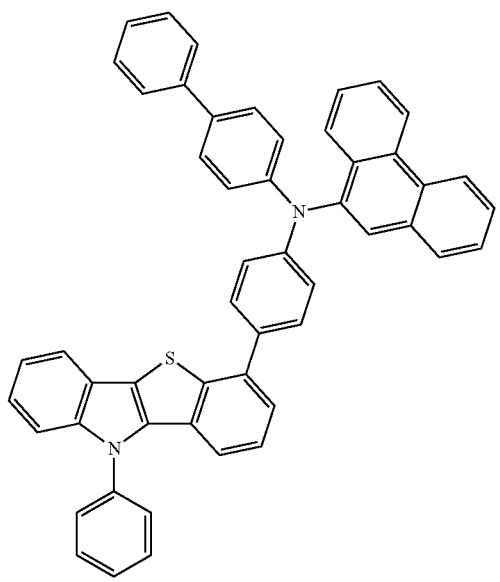
B79
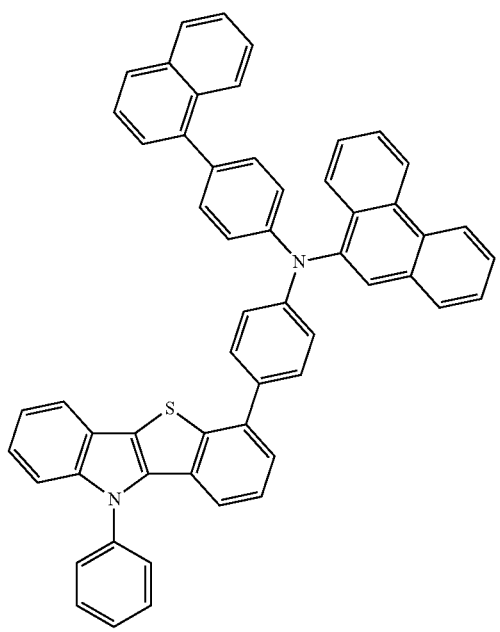

B80
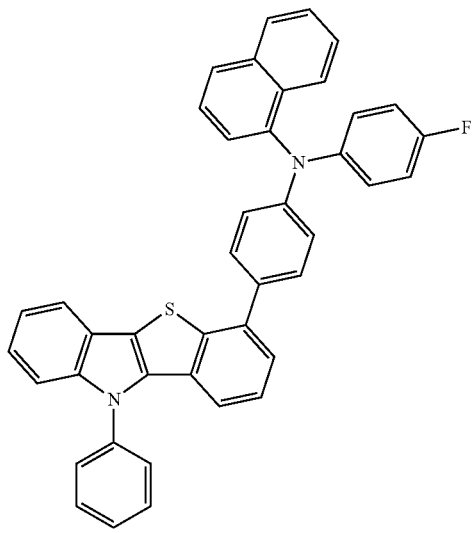
B81
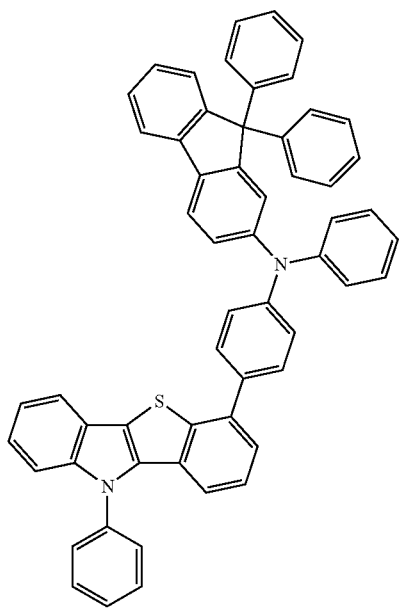
B82
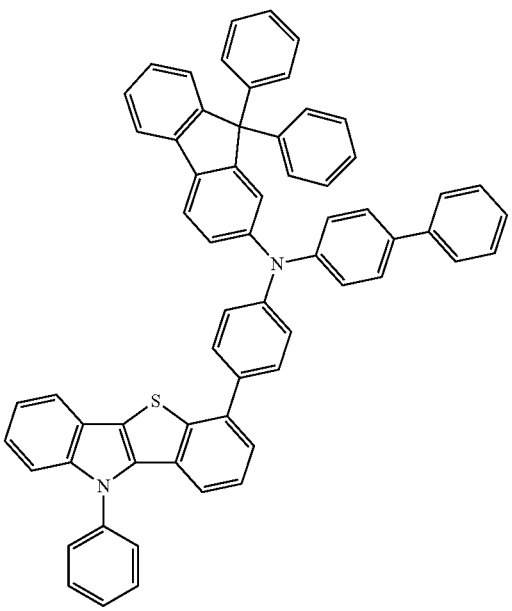
B83
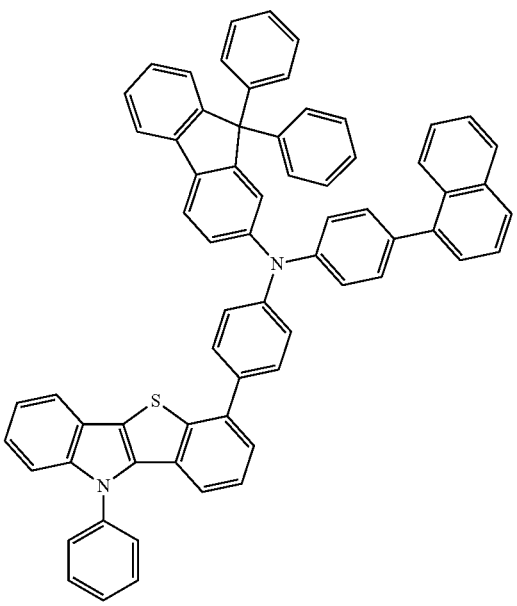

B84
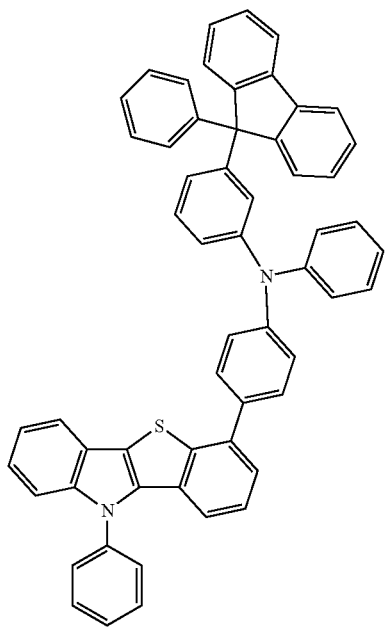
B86
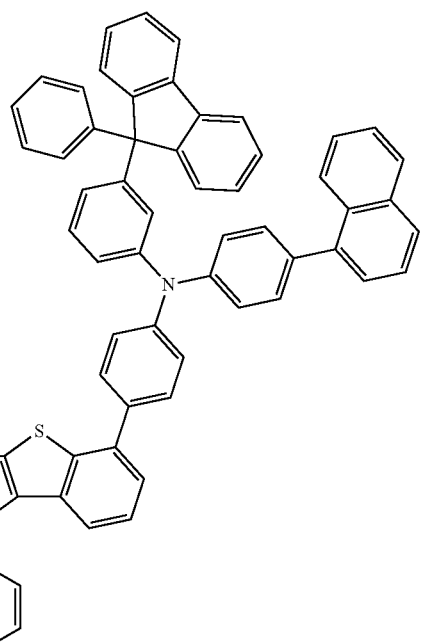
B85
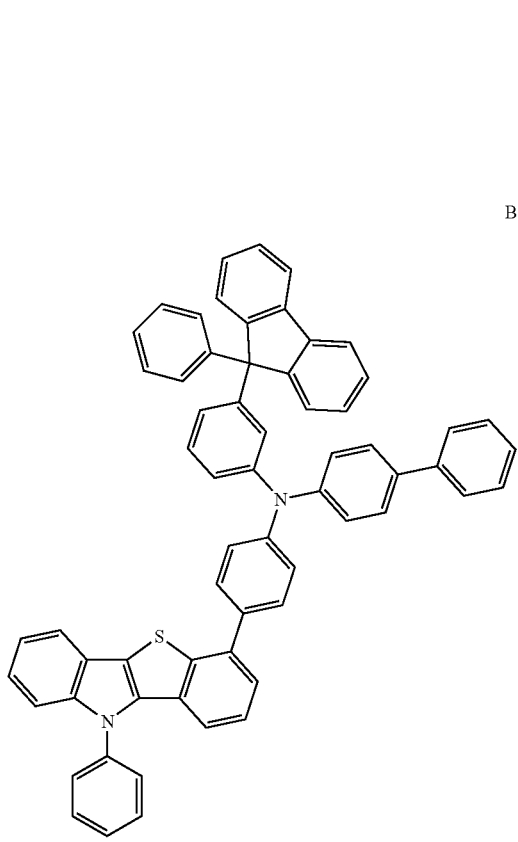
B87
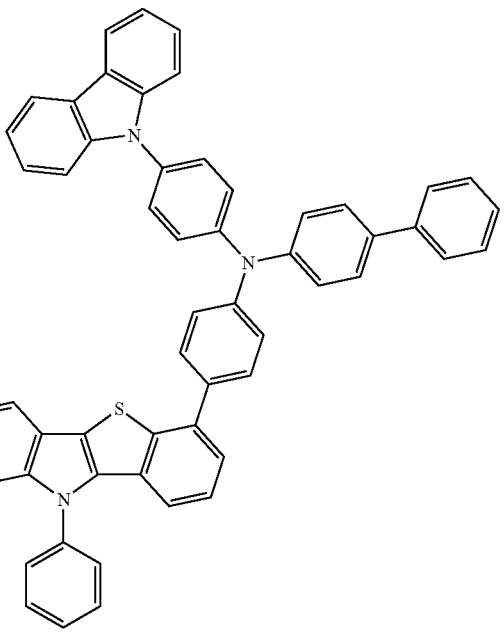

B88
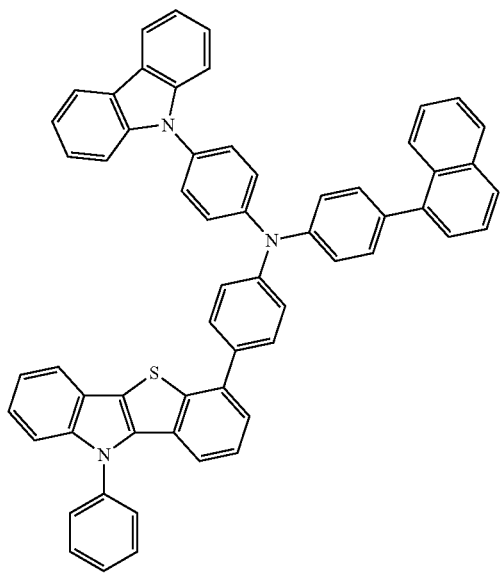
B89
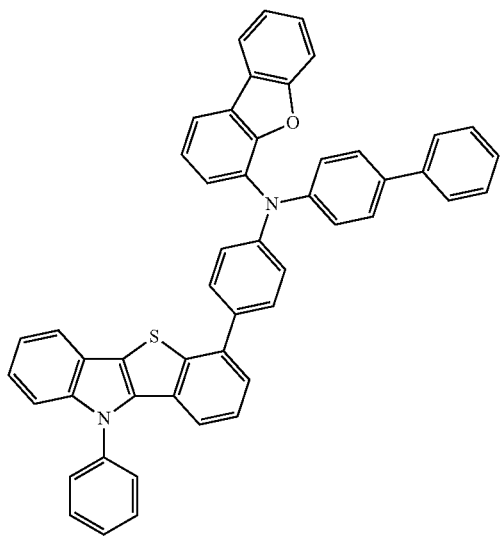
B90
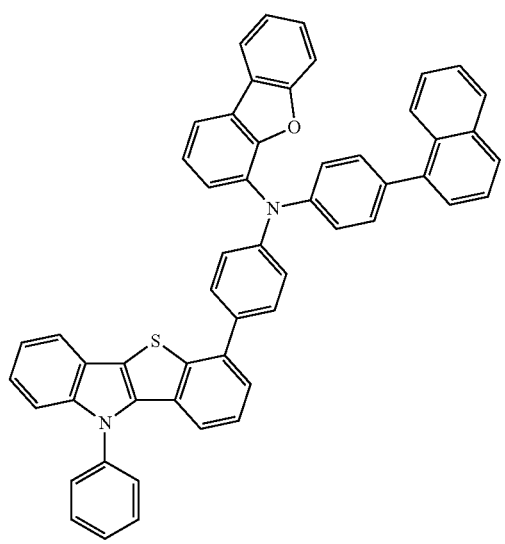
B91
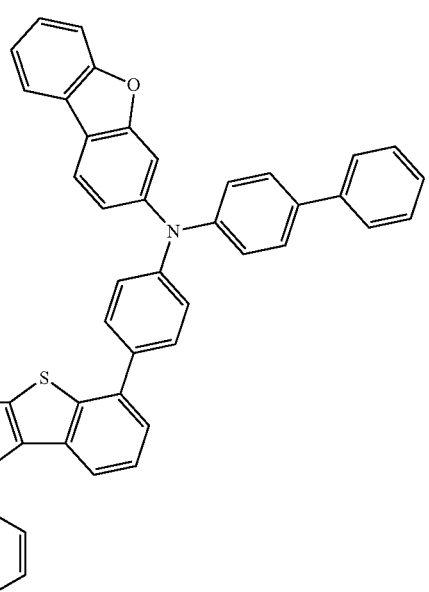

B92
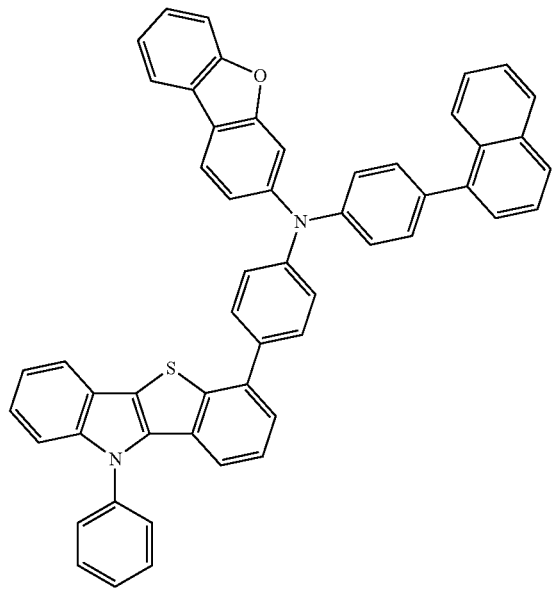
B94
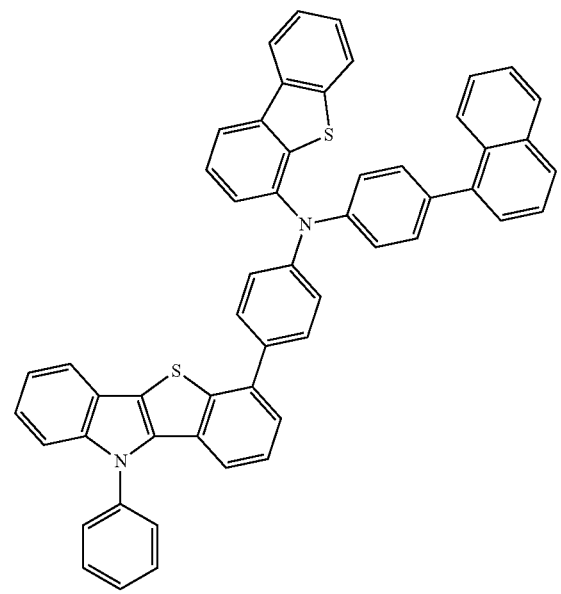
B93
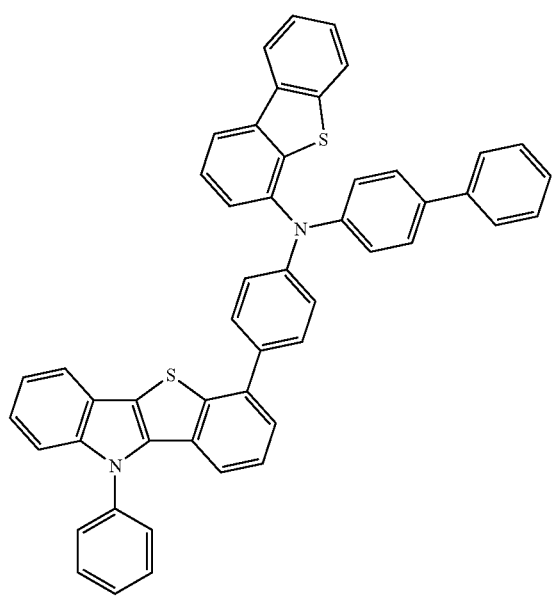
B95
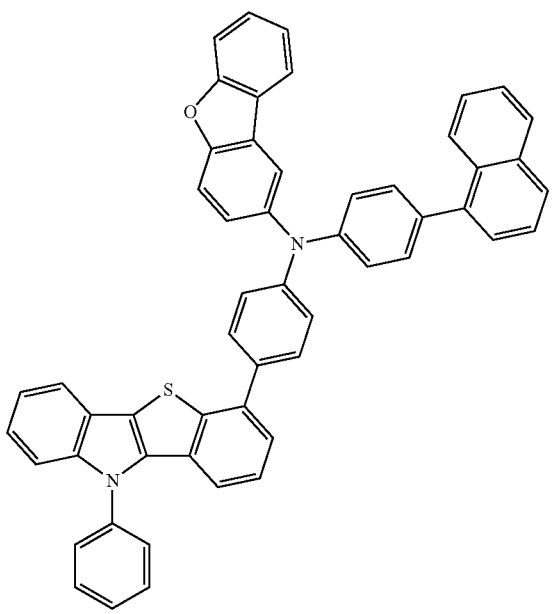

-continued
B96
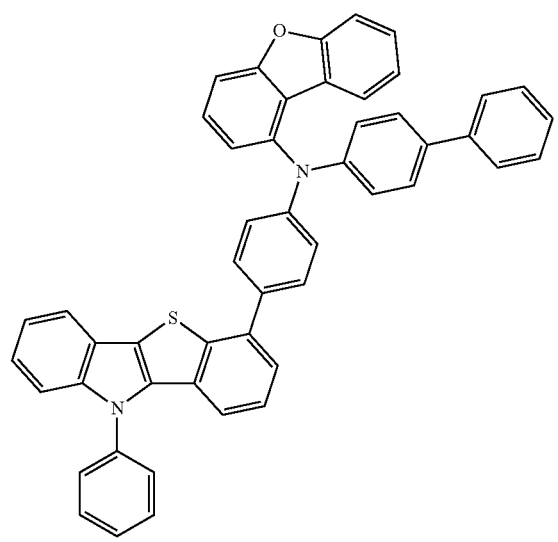
B97
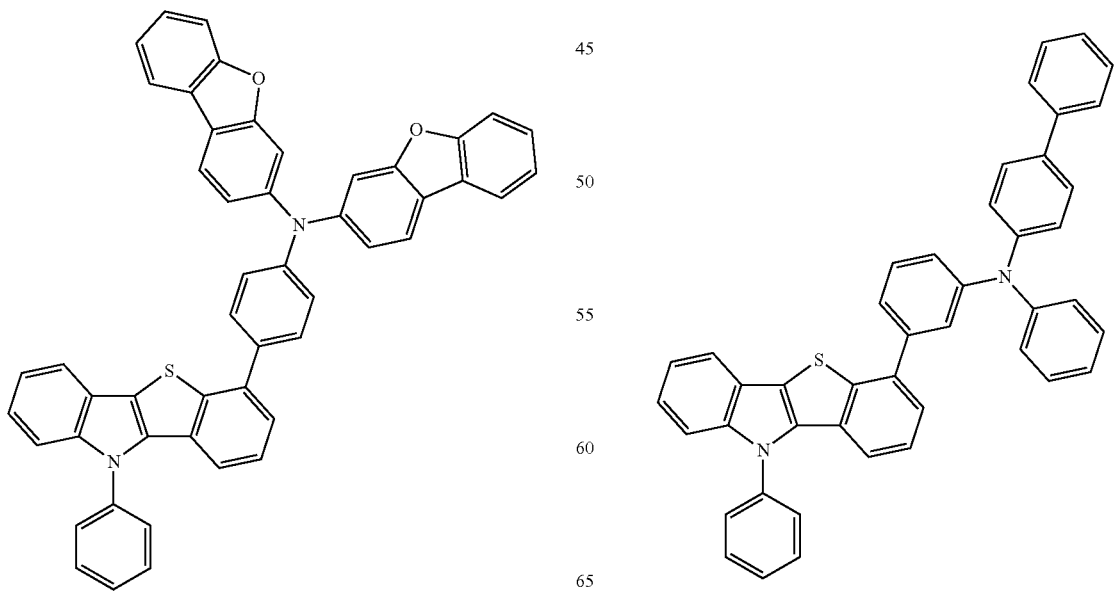
B98
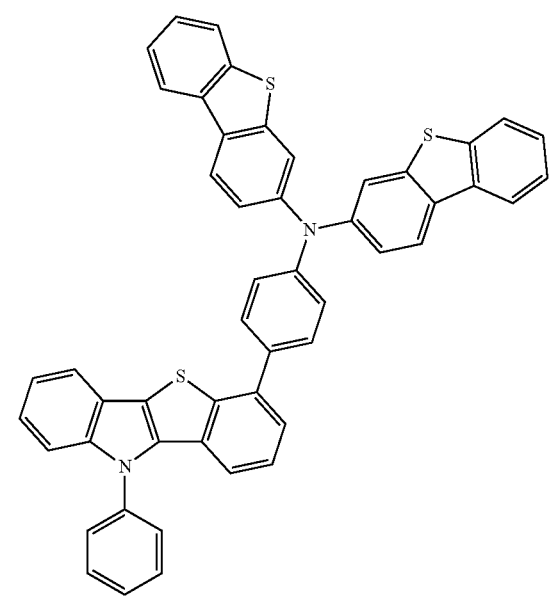
B99
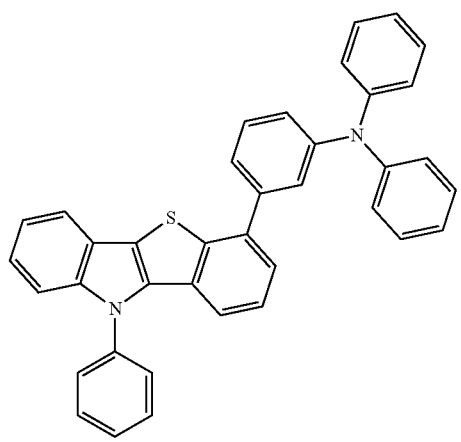
B100

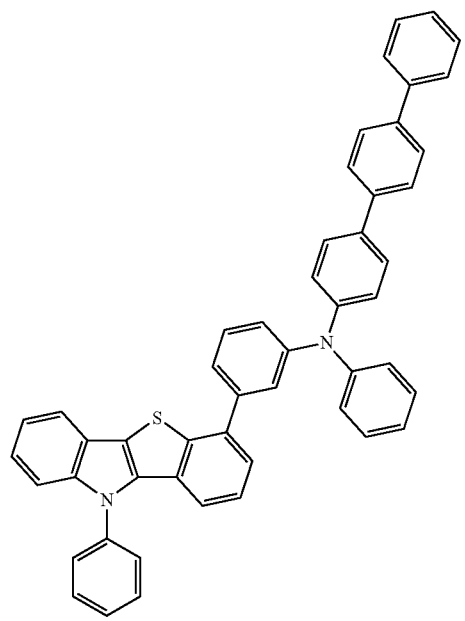
B101
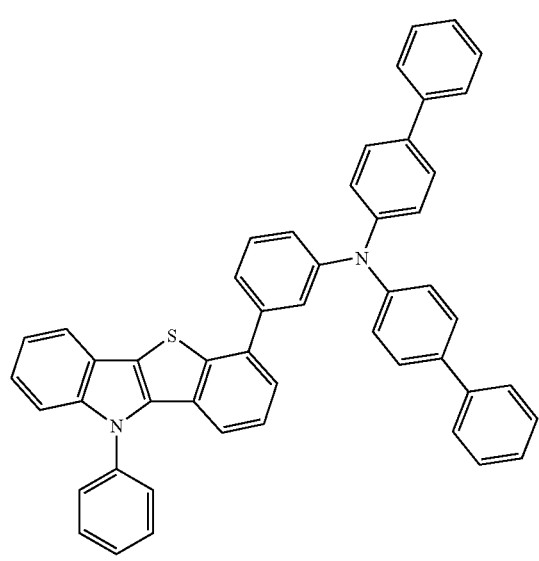
B102
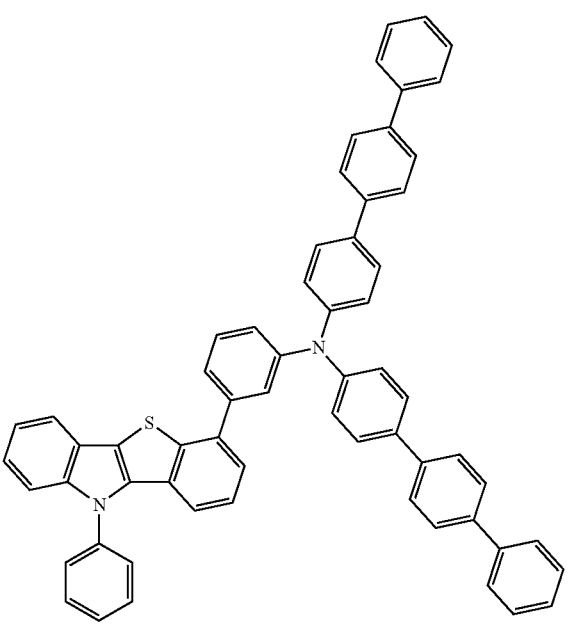
B103
B104

B105
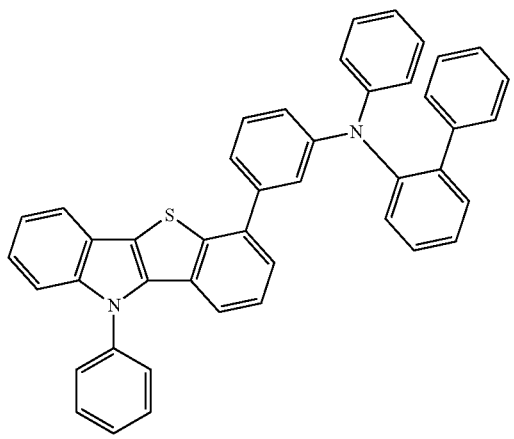
B108
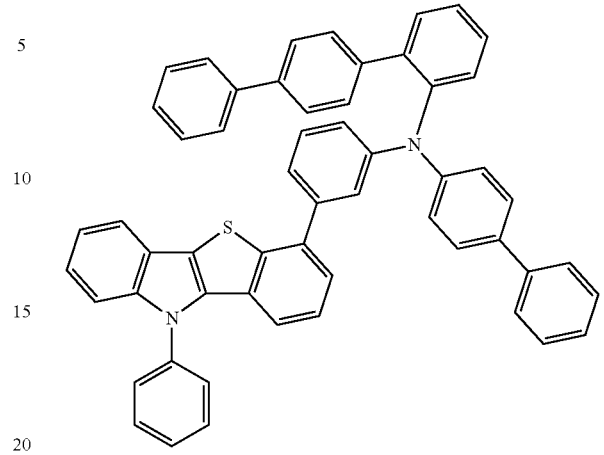
B106
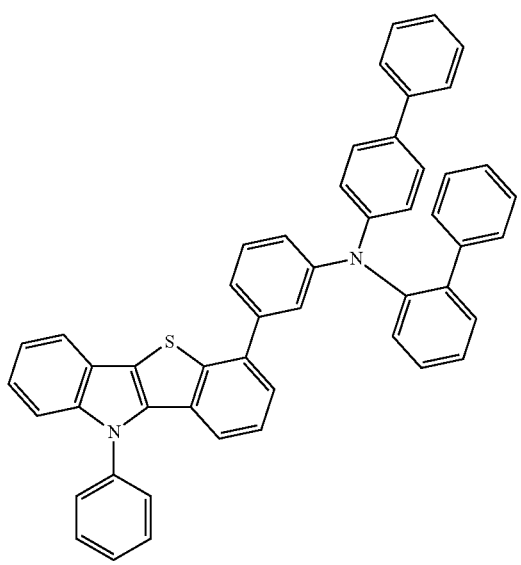
B109
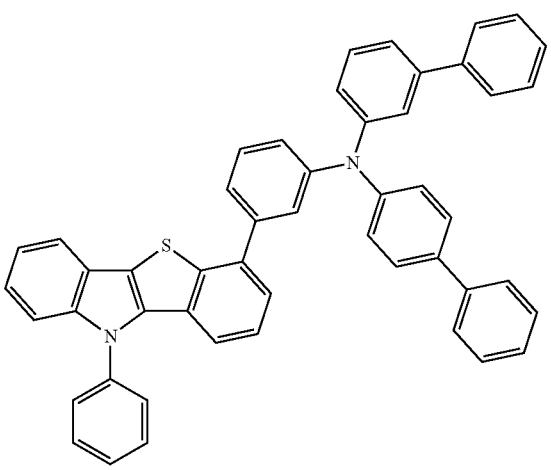
B107
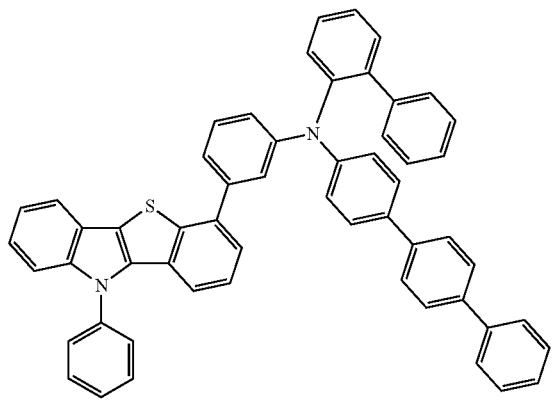
B110
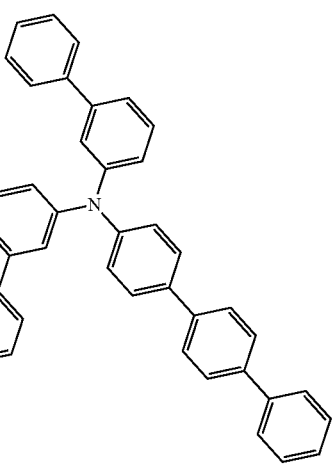

B111
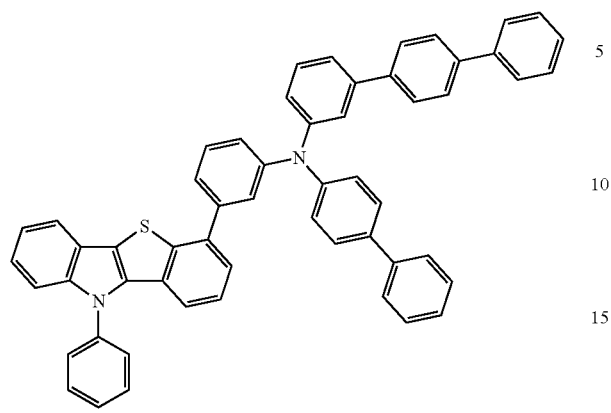
B112
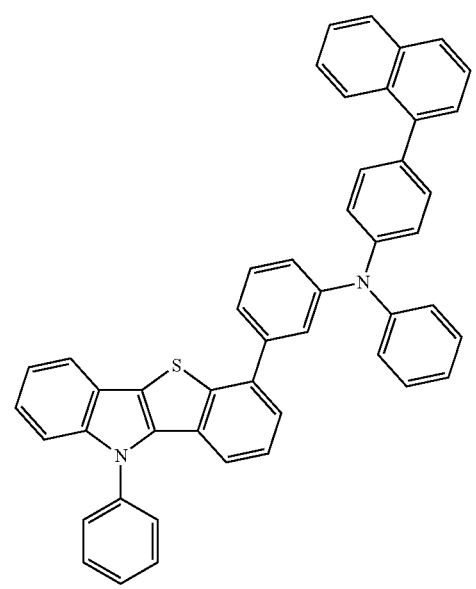
B113
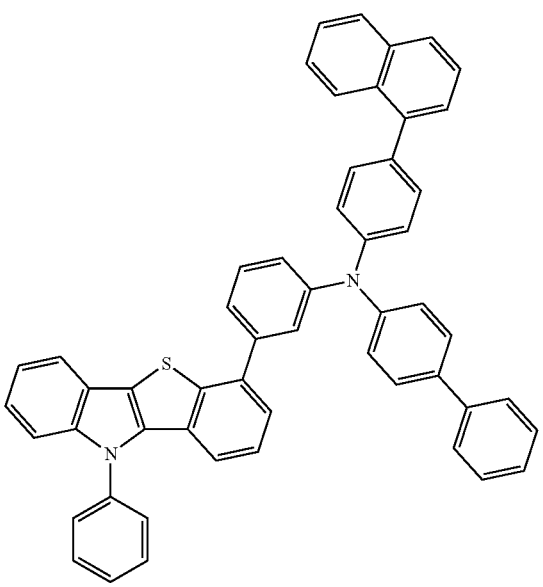
B114
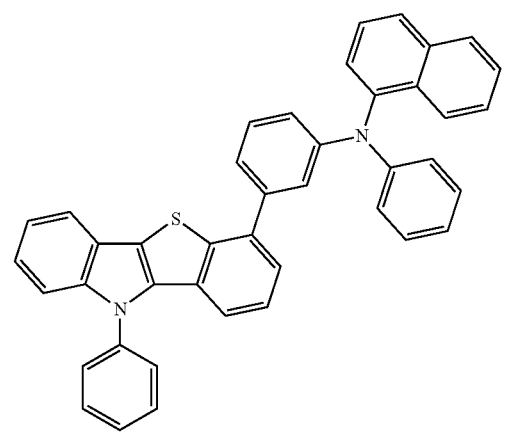
B115
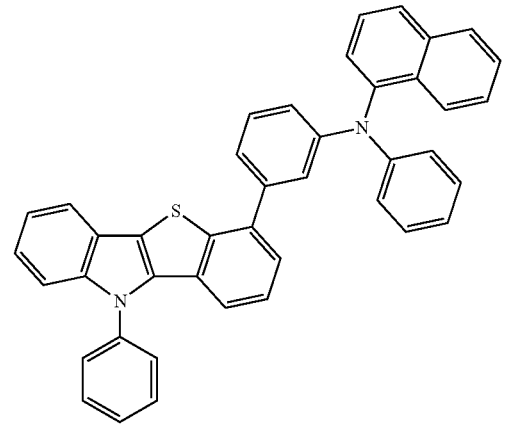
B116
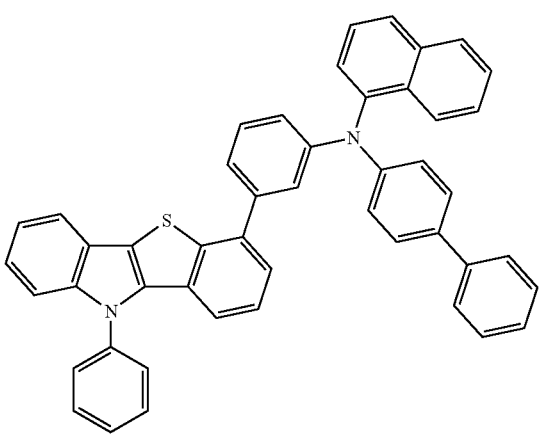

B117
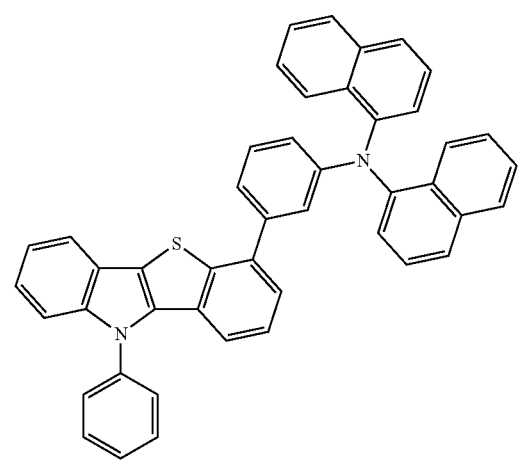
B118
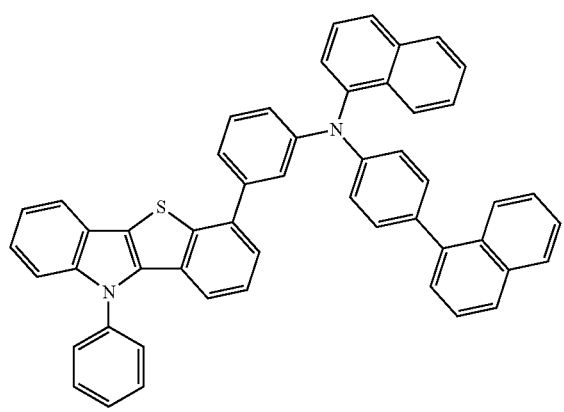
B119
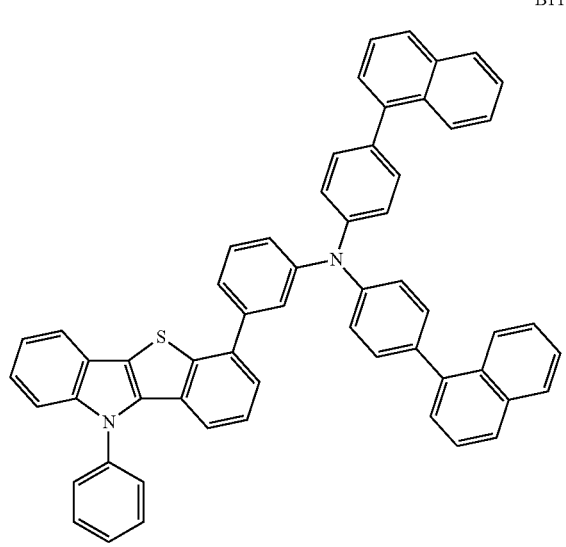
B120
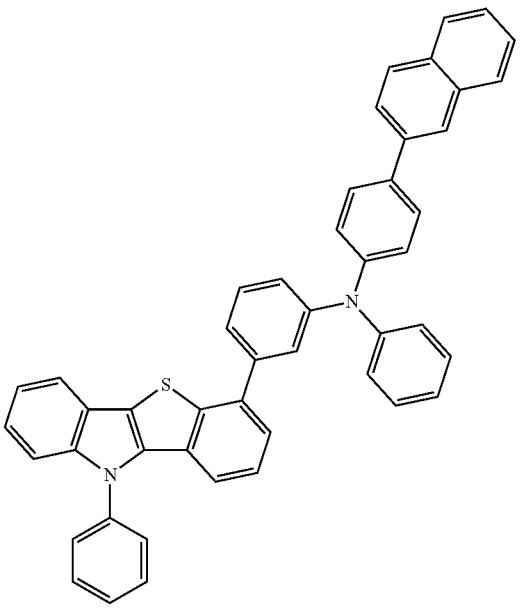
B121
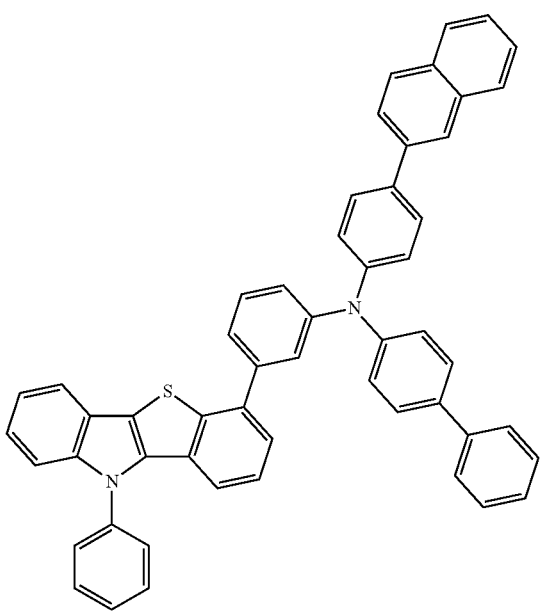

-continued
B122
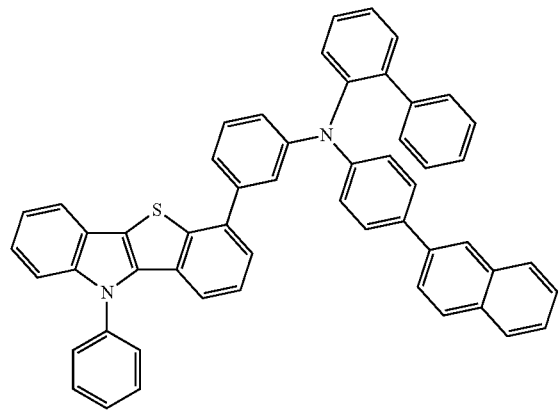
B123
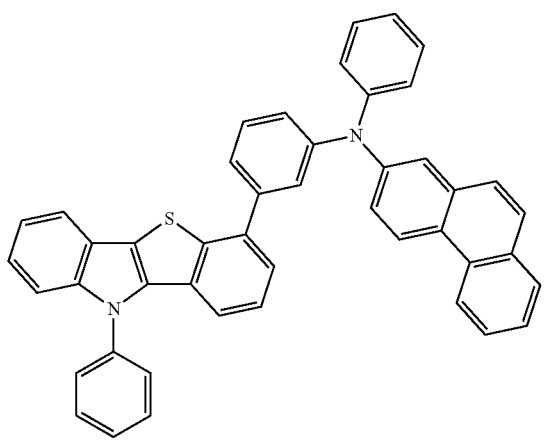
B124
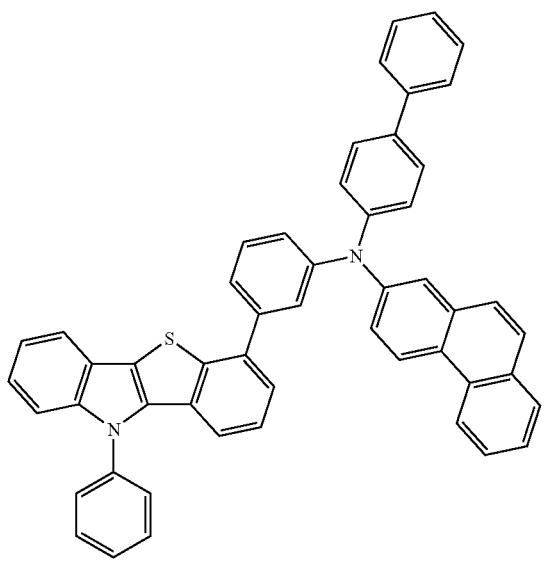
-continued
B125
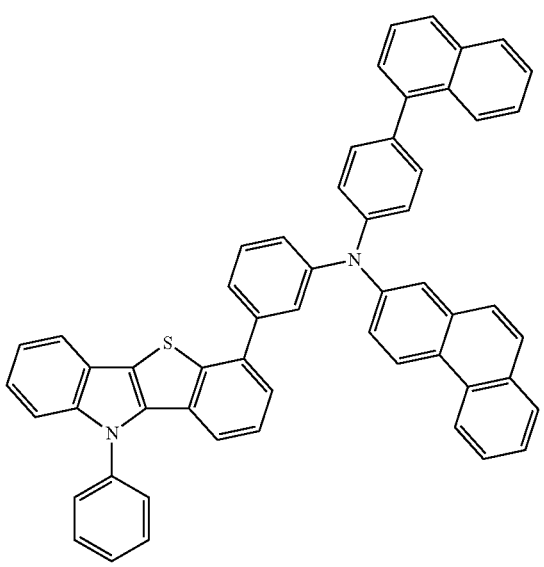
B126
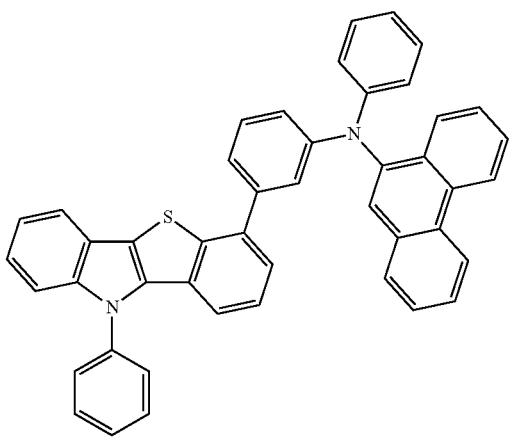
B127
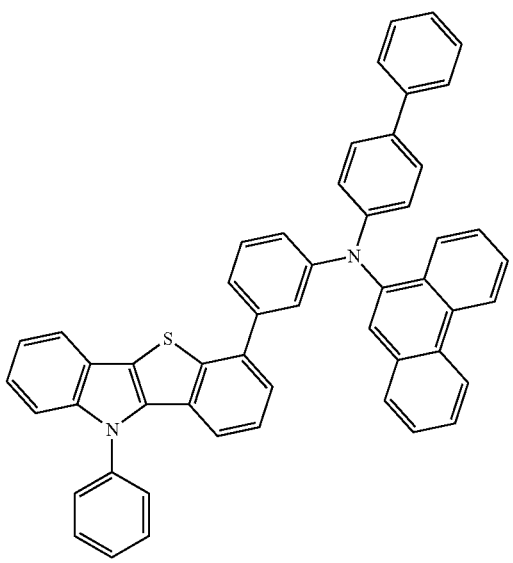

-continued
B128
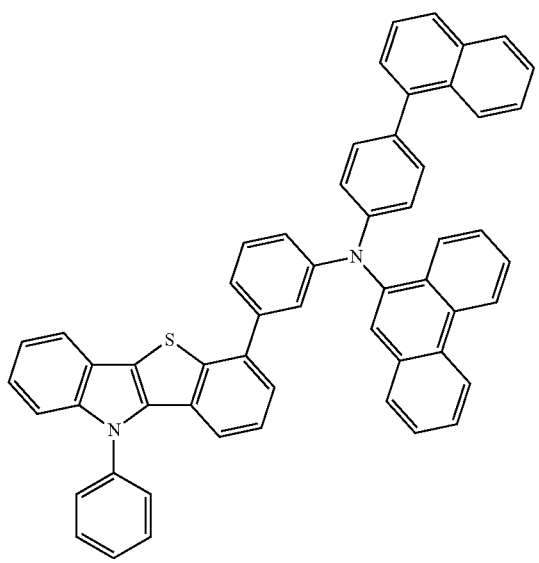
B129
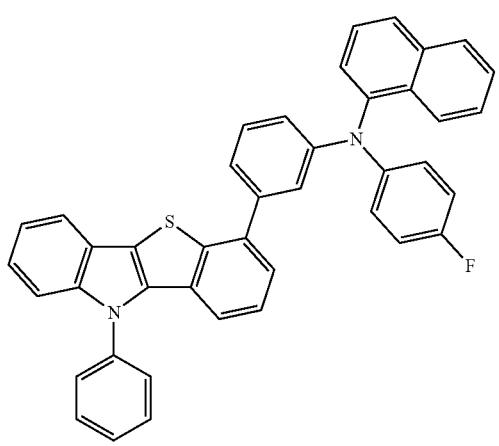
B130
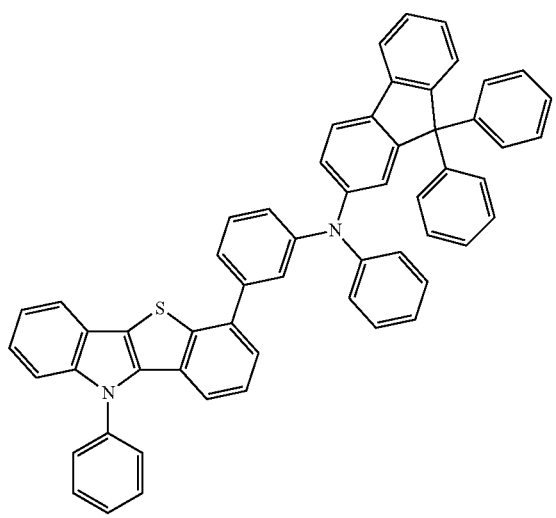
-continued
B131
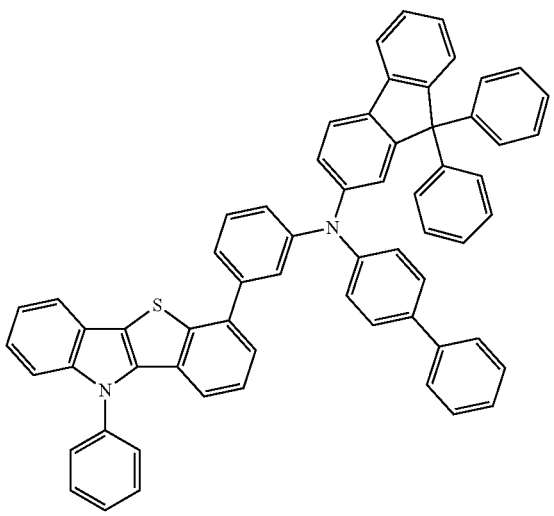
B132
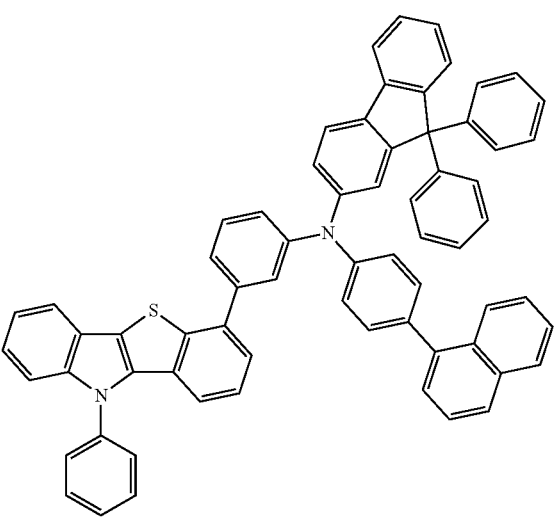
B133
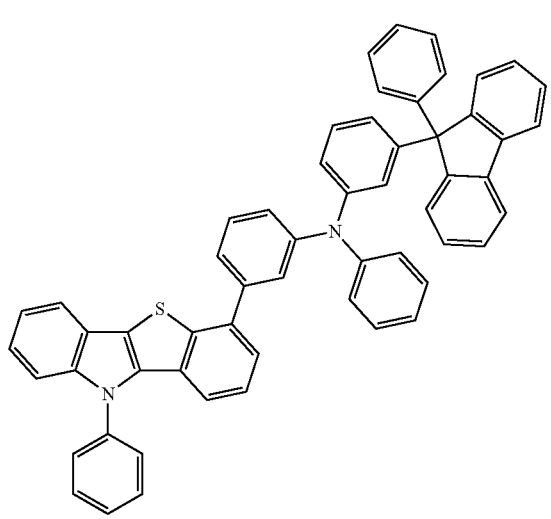

B134
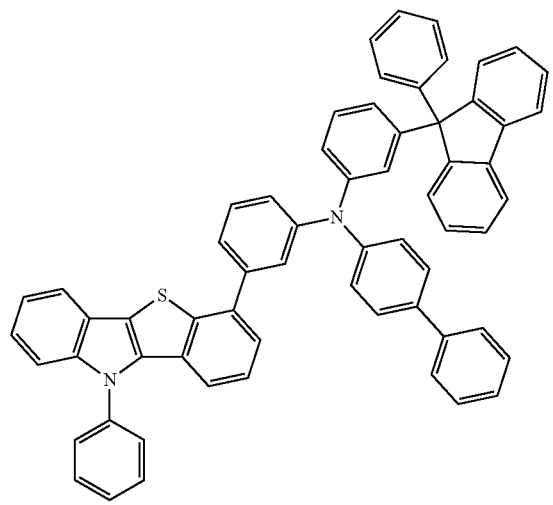
B135
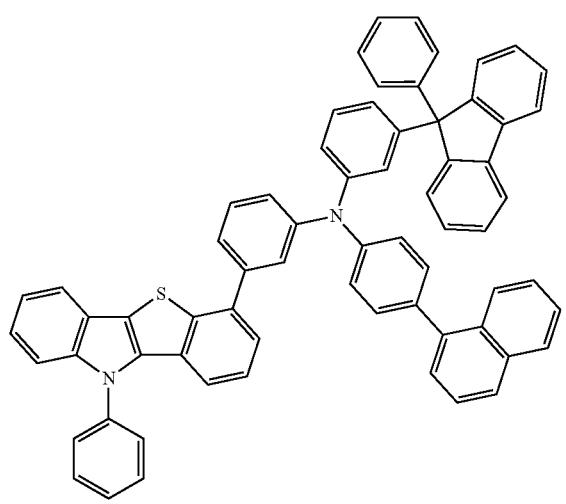
B136
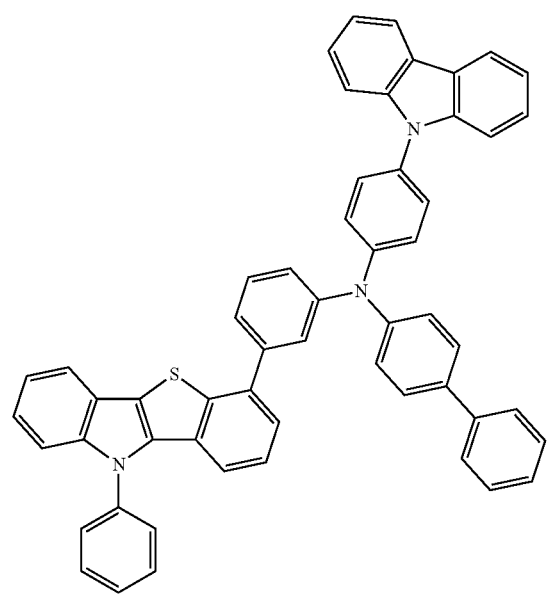
B137
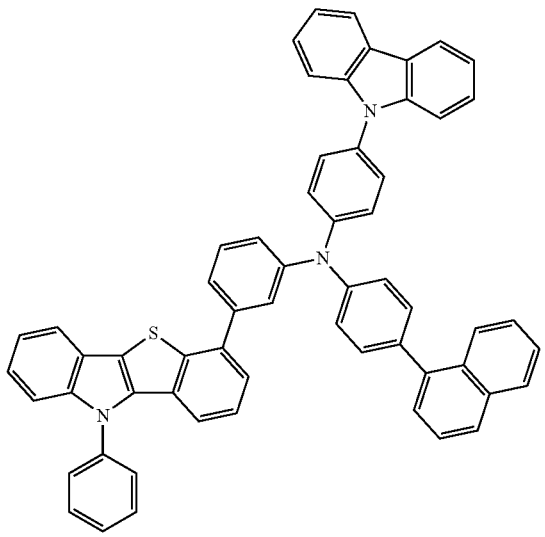
B138
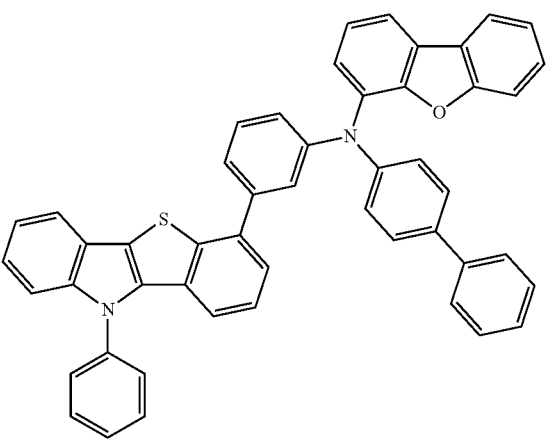
B139
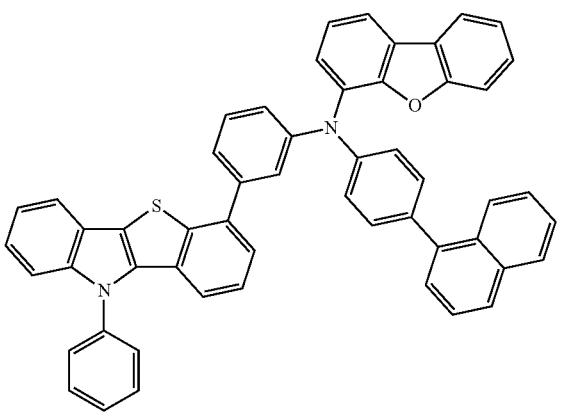

-continued
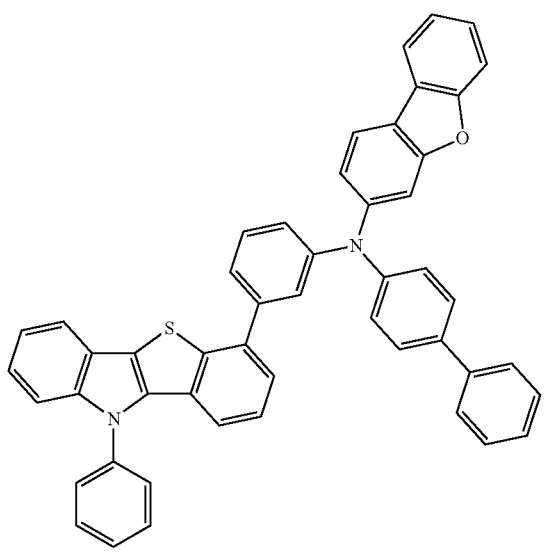
B140
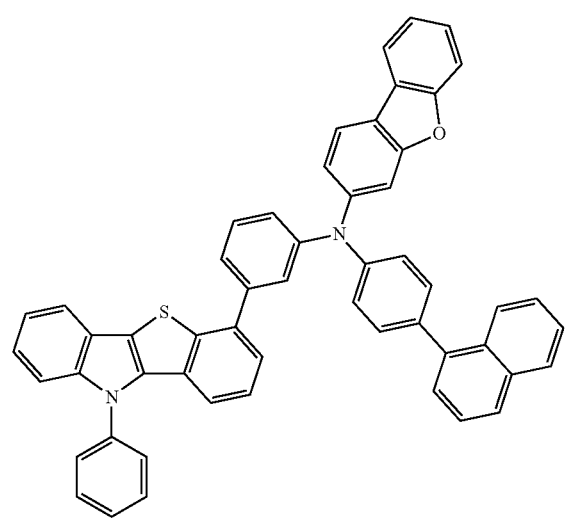
B141
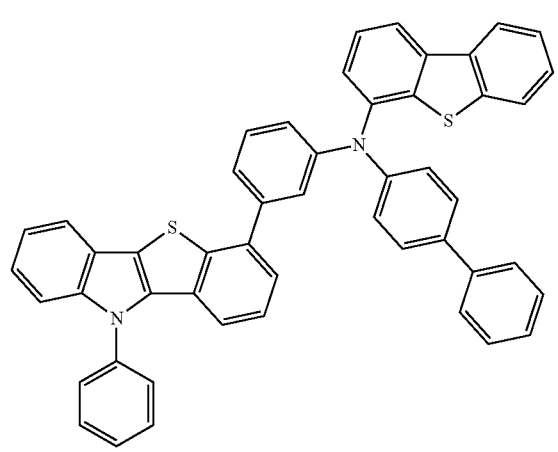
B142
-continued
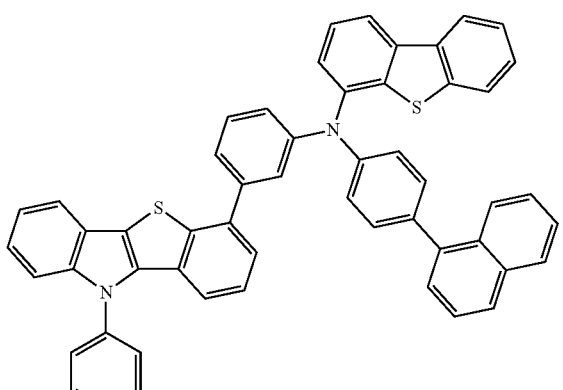
B143
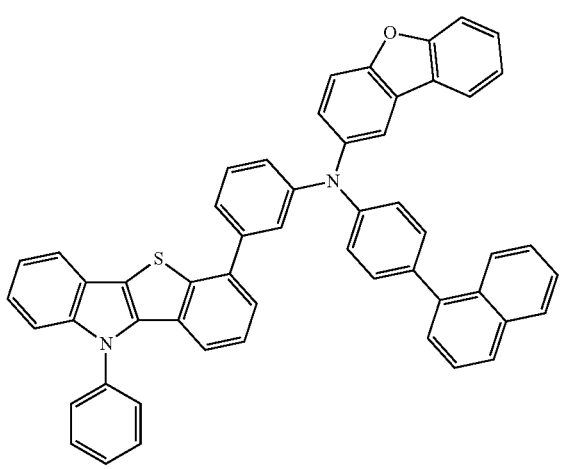
B144
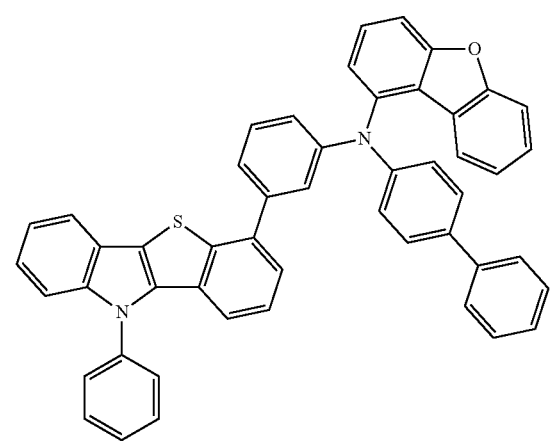
B145

B146
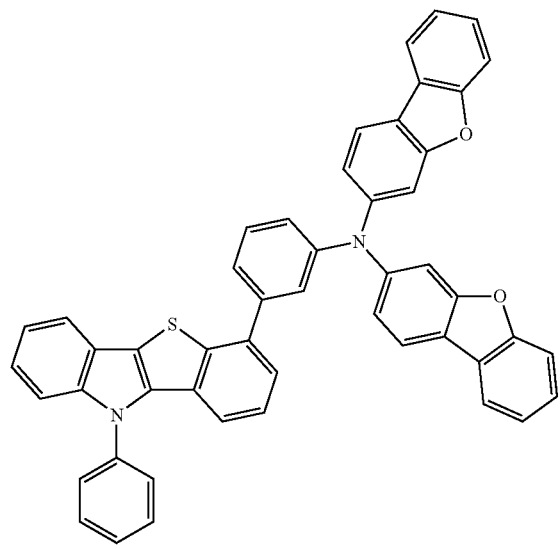
B147
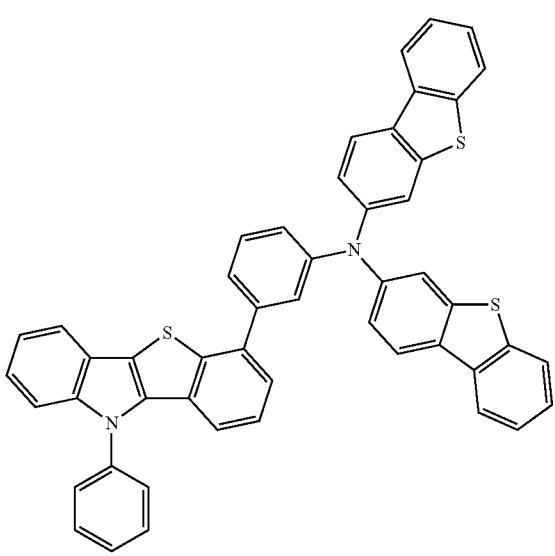
B148
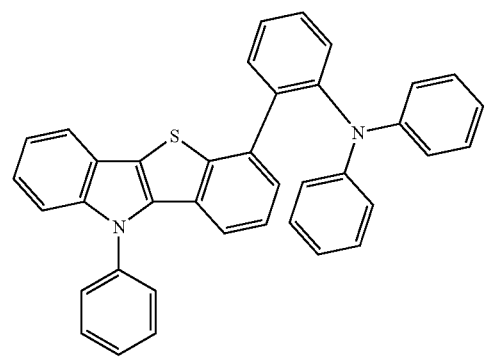
B149
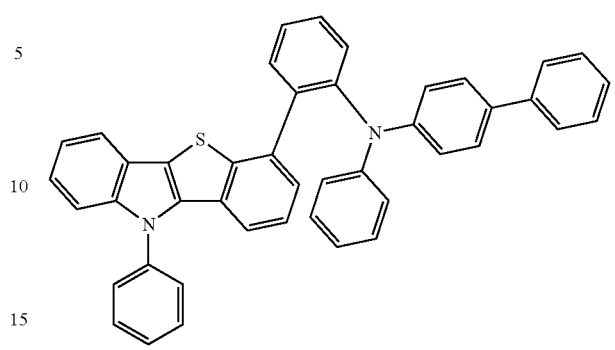
B150
B151
B152
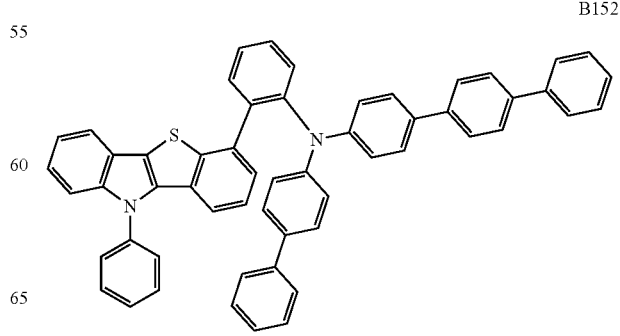

B153
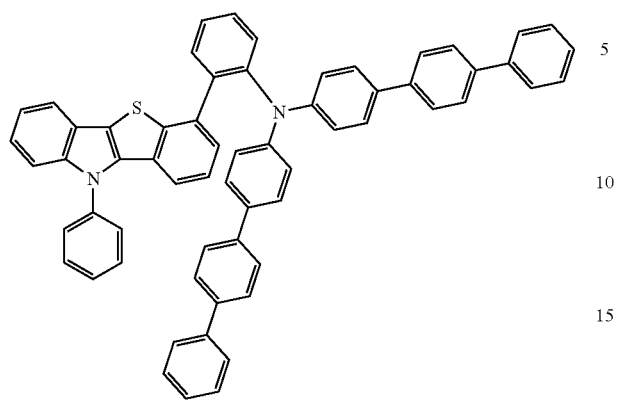
B156
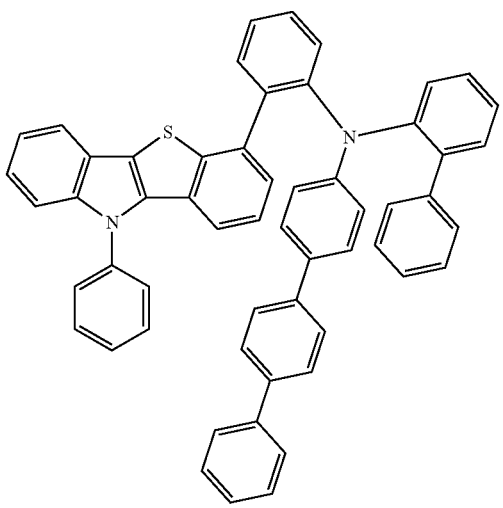
B154
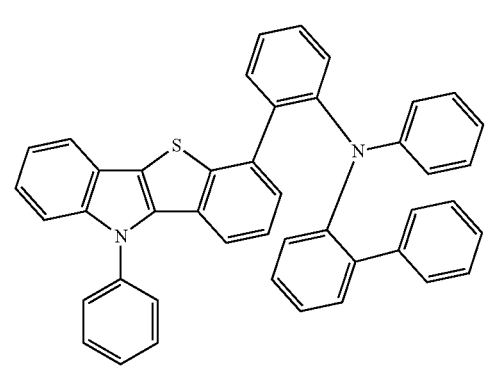
B157
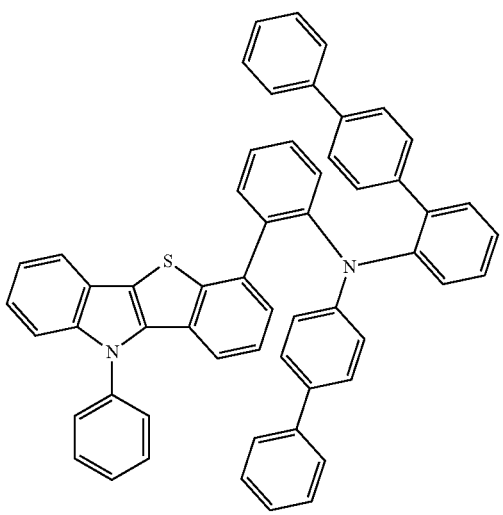
B155
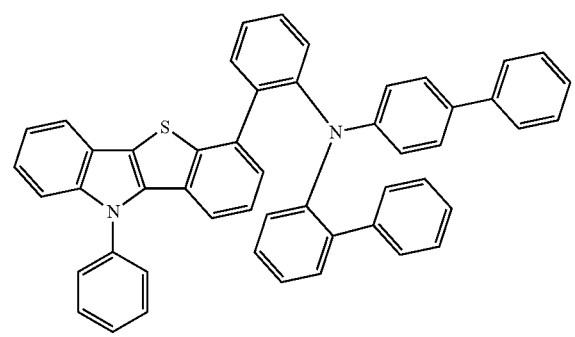
B158
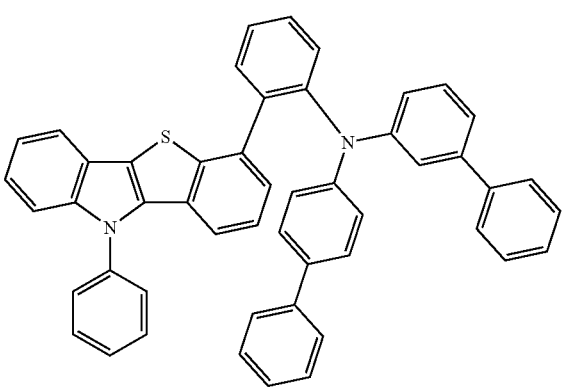

B159
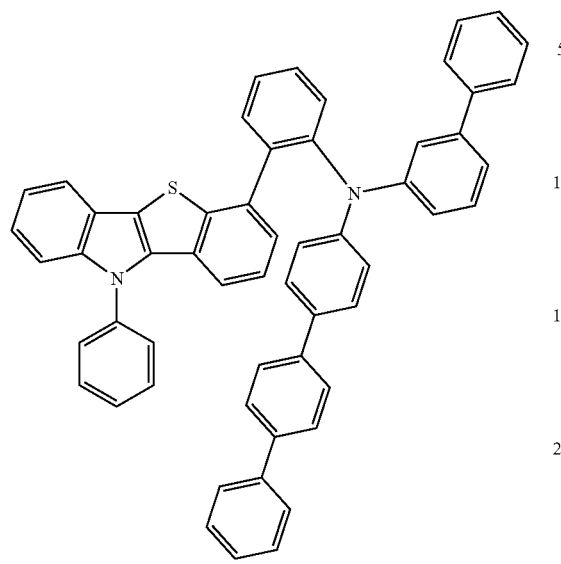
B160
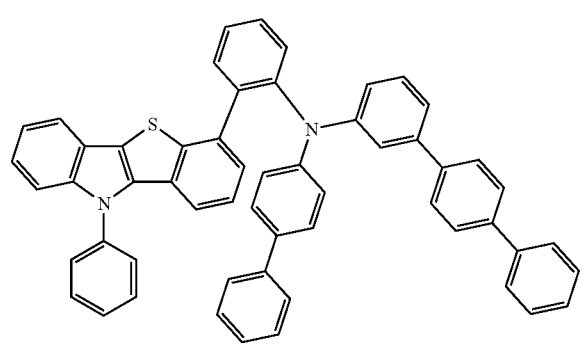
B161
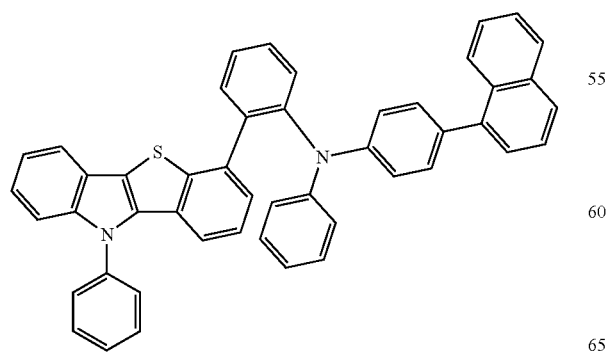
B162
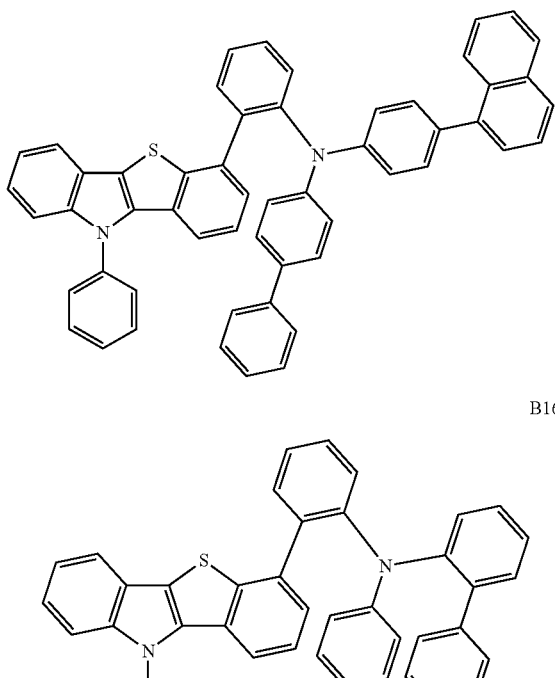
B163
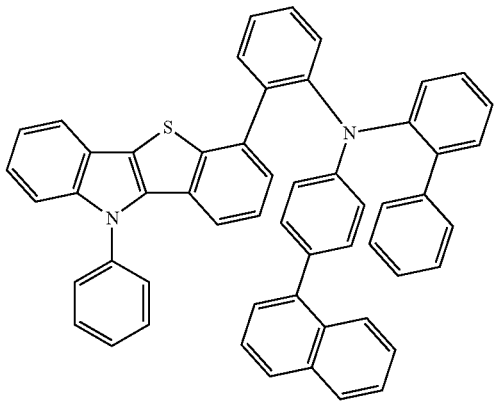
B164
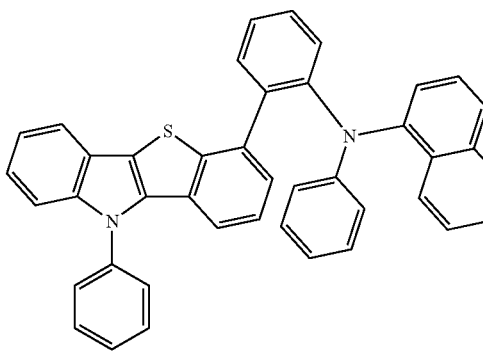
B165
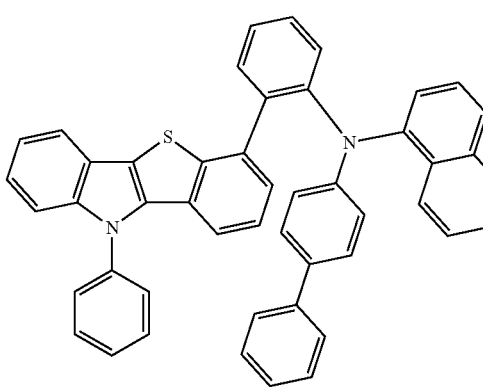

B166
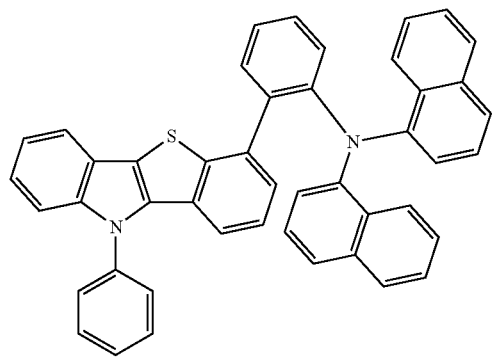
B167
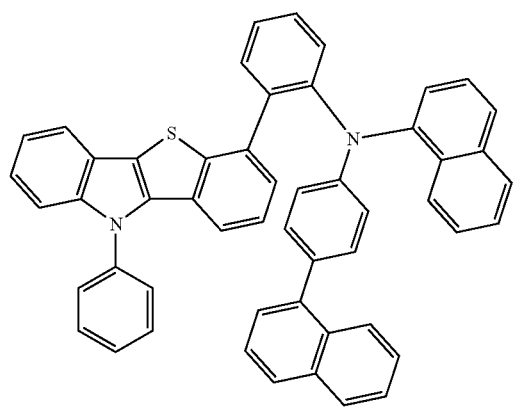
B168
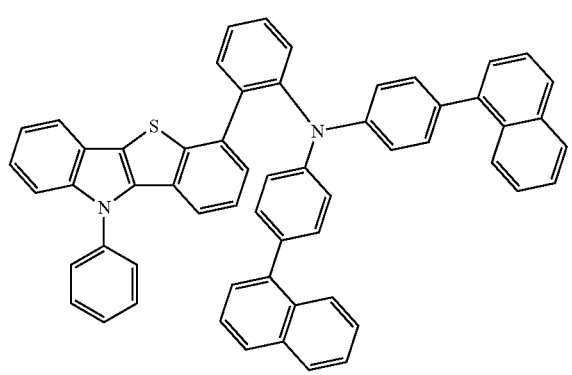
B169
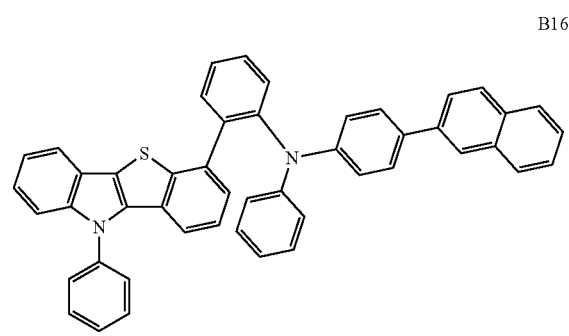
B170
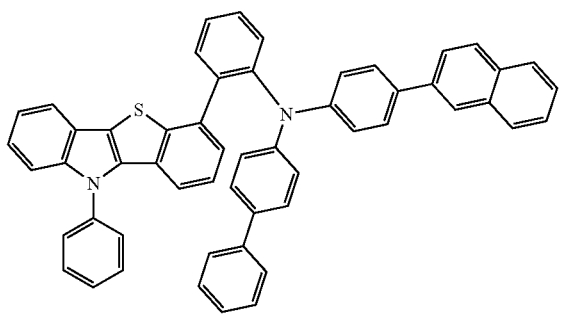
B171
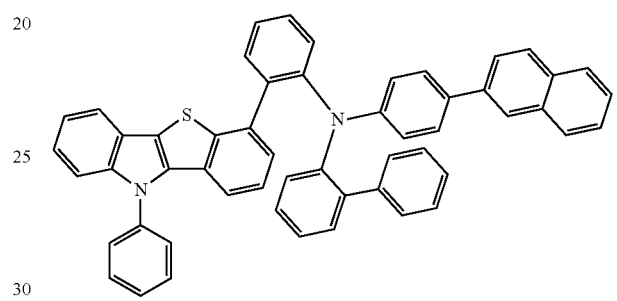
B172
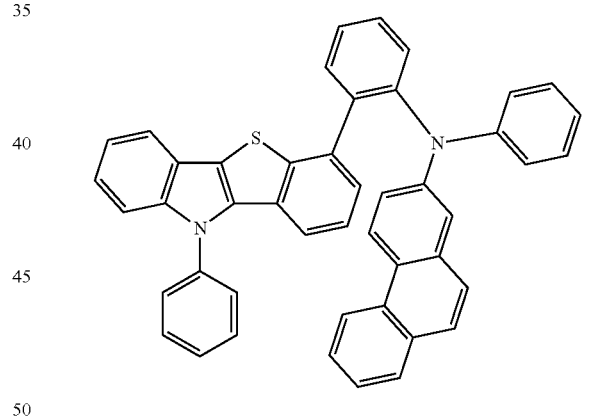
B173
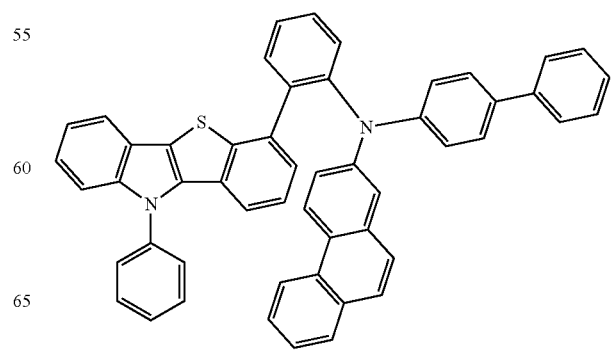

B174
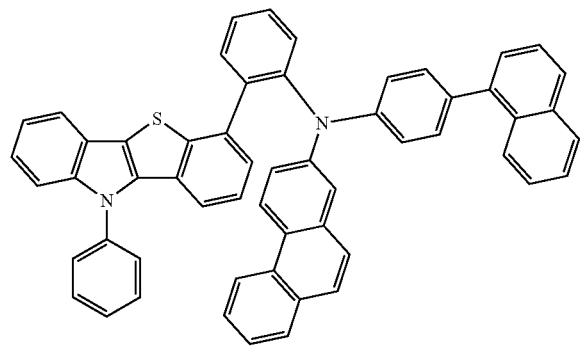
B175
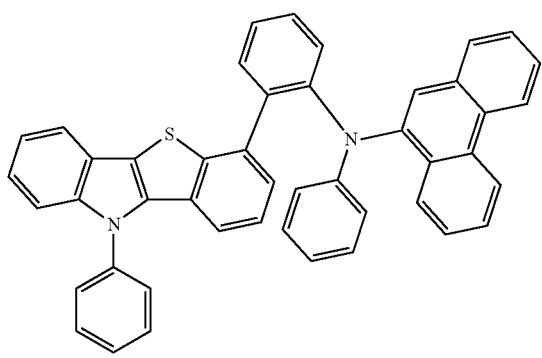
B176
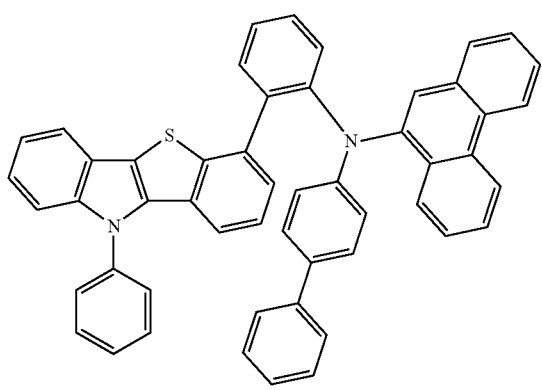
B177
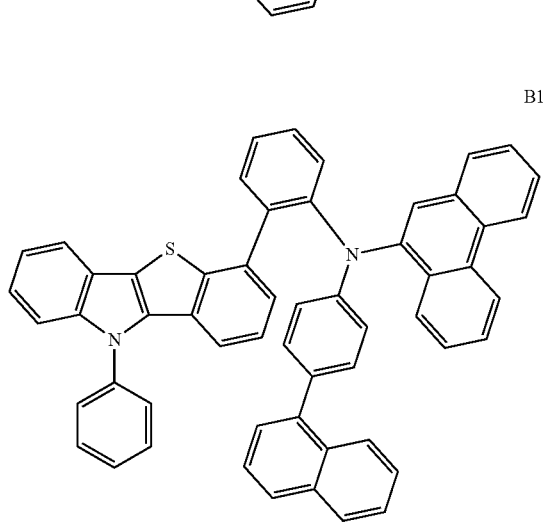
B178
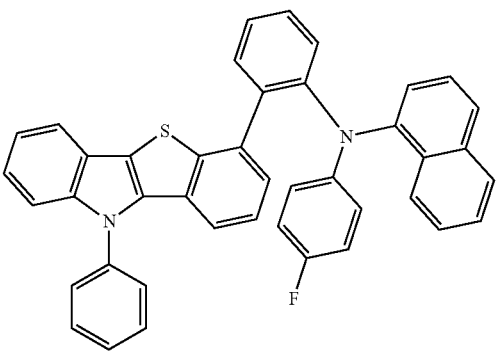
B179
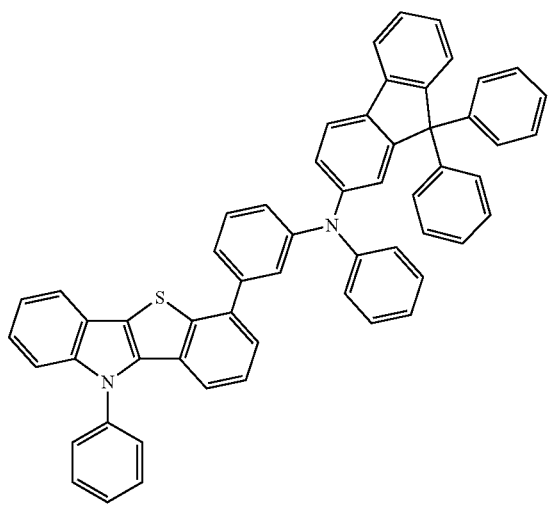
B180
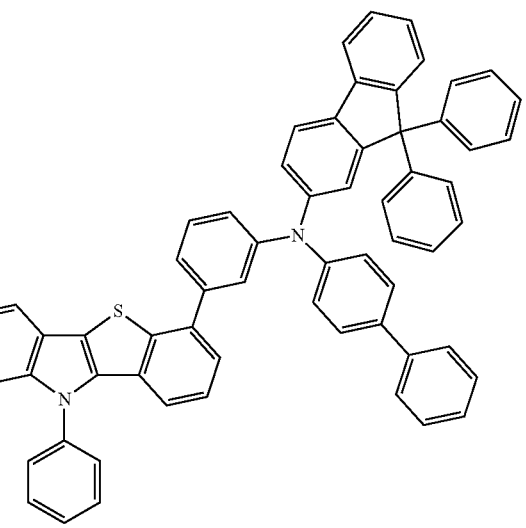

325
-continued
B181
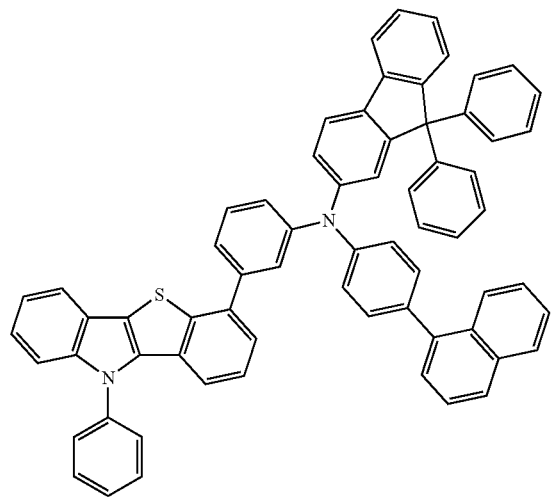
B182
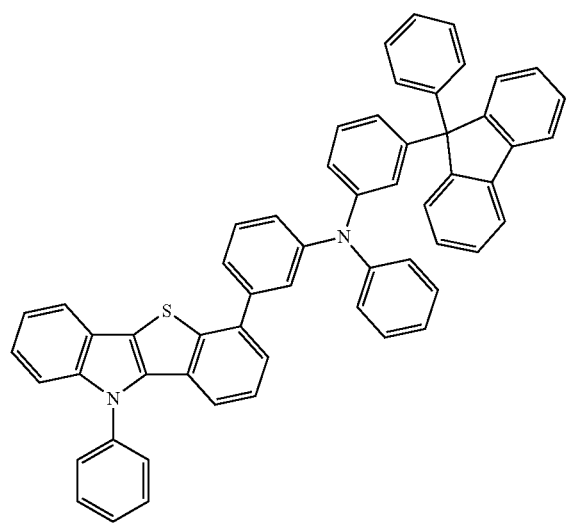
B183
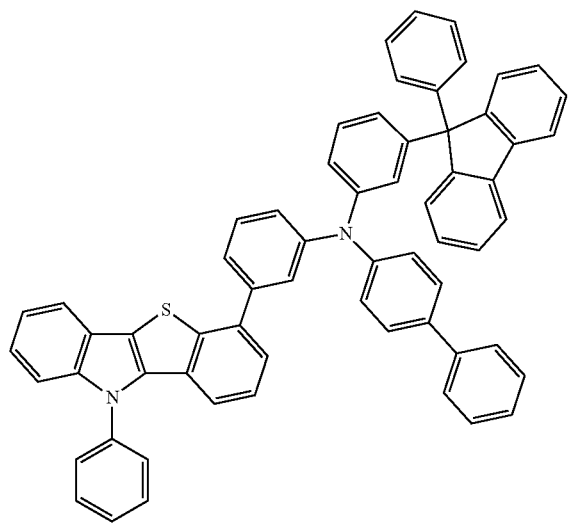
326
-continued
B184
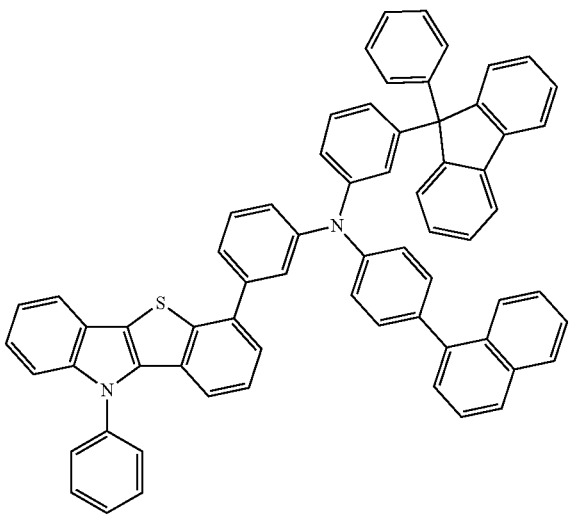
B185
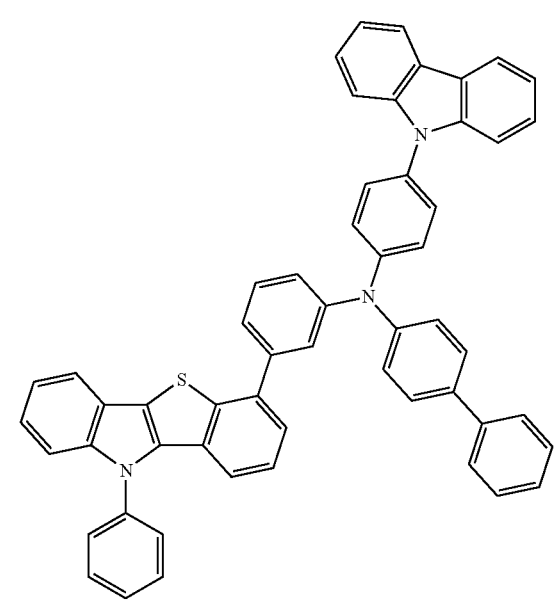

B186
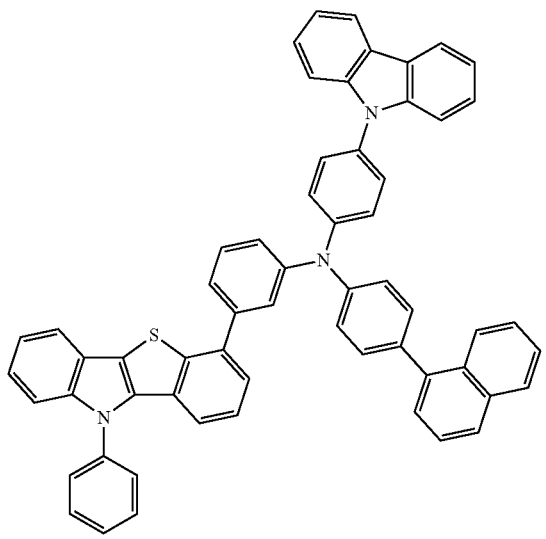
B187
B188
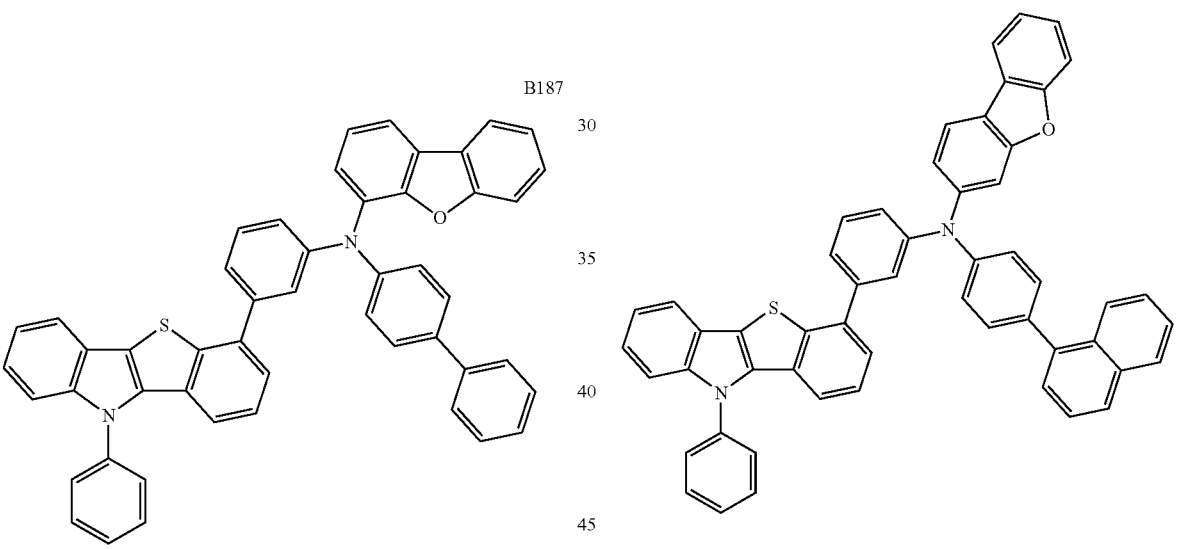
B189
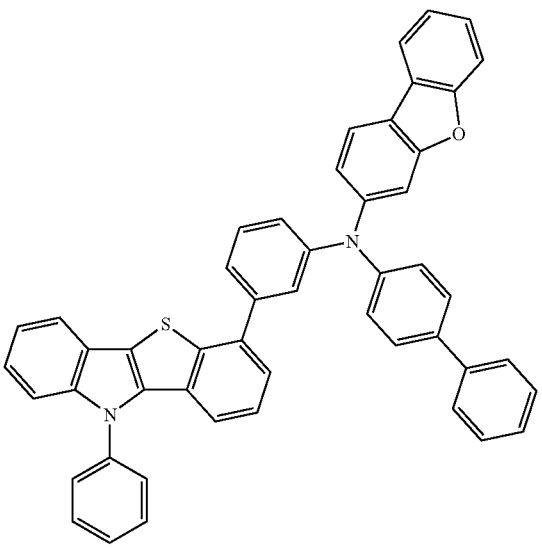
B190
B191
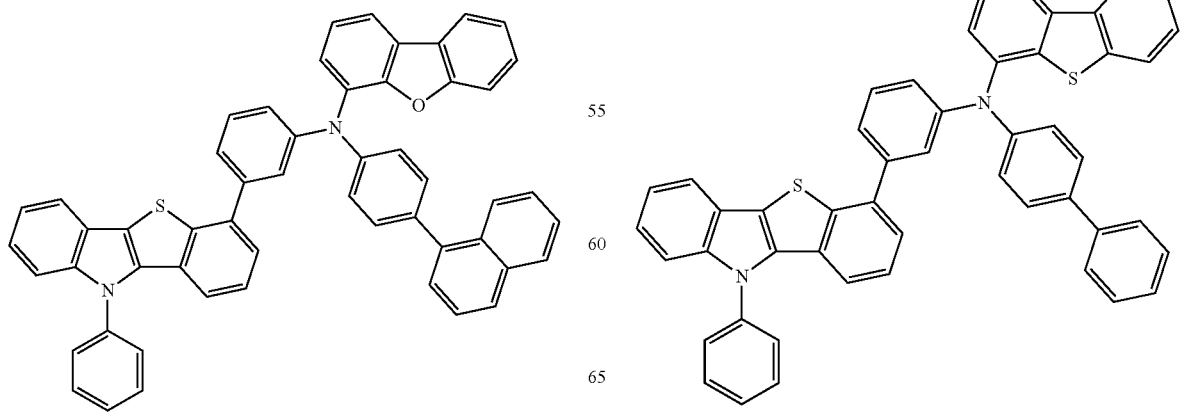

B192
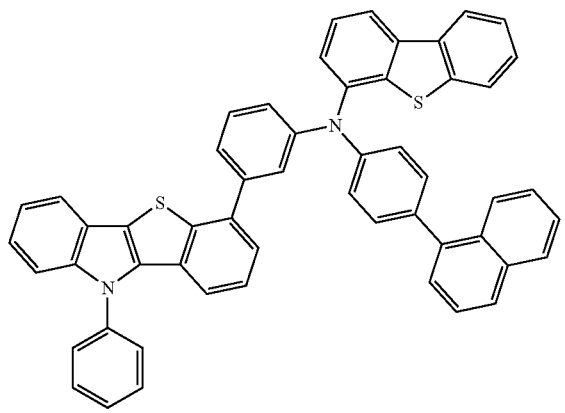
B193
B194
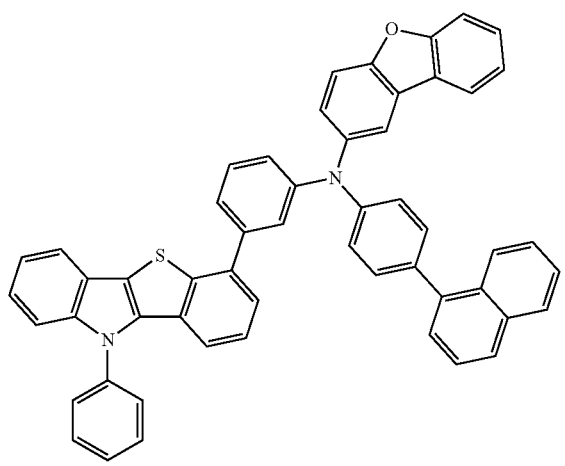
B195
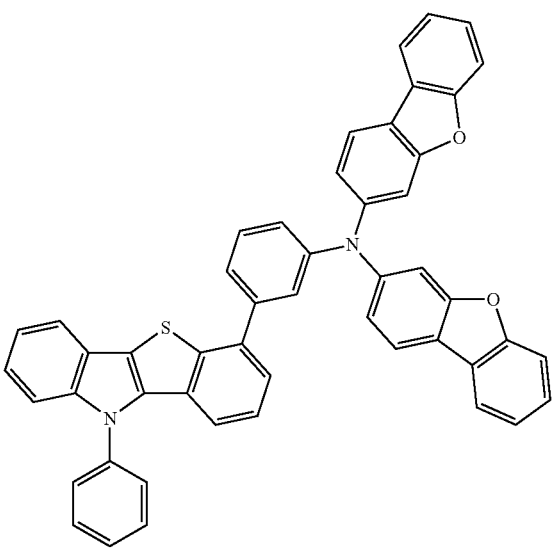
B196
B197
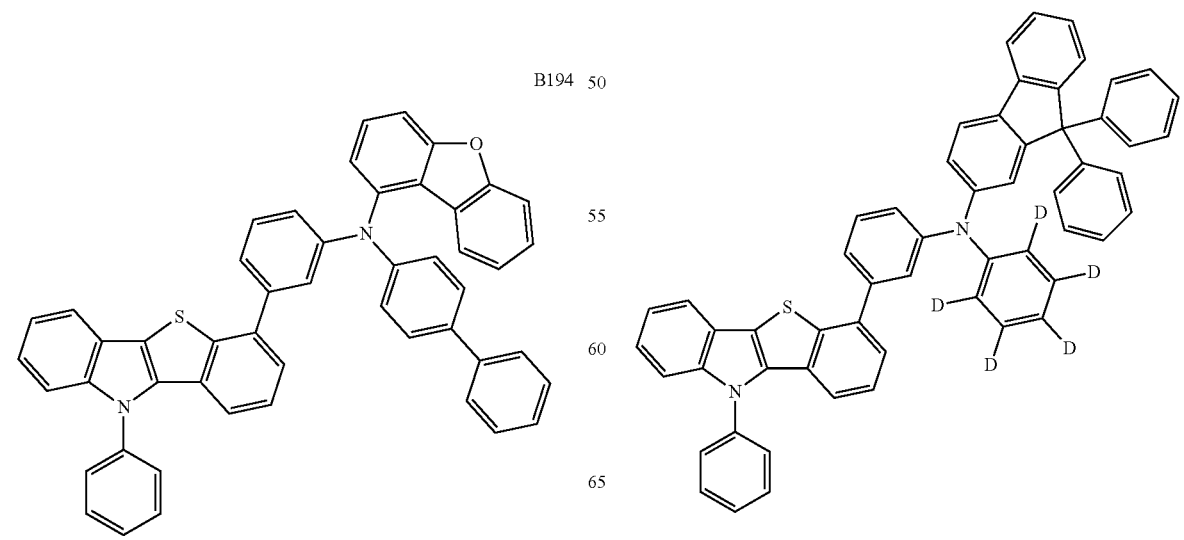

331
-continued

B198

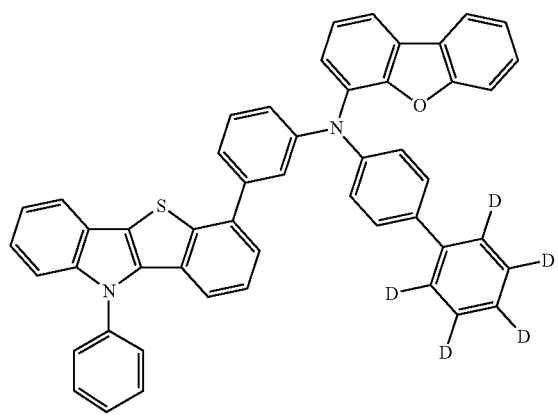

B199

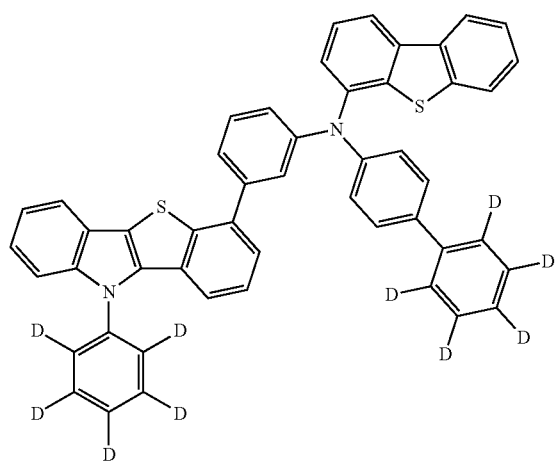

B200

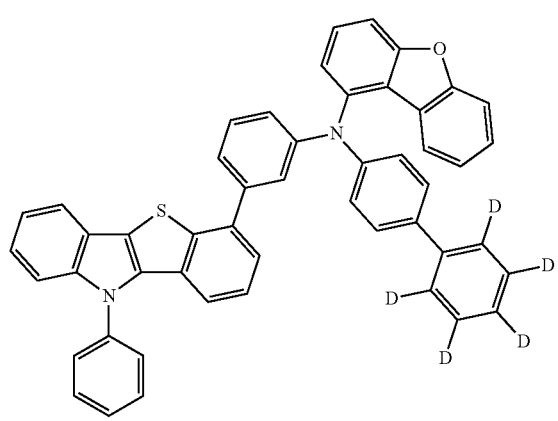

332
-continued

B201

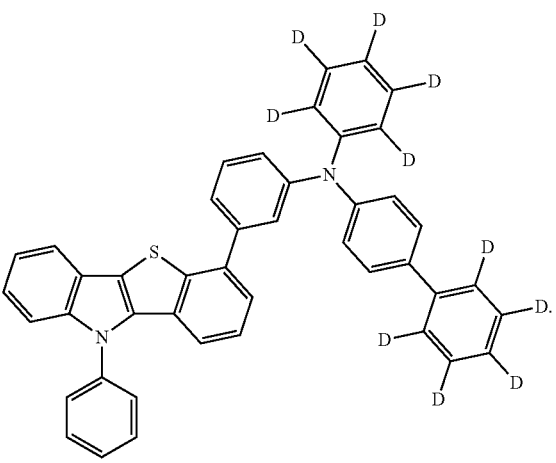

11. A polycyclic compound represented by the following Formula 1:

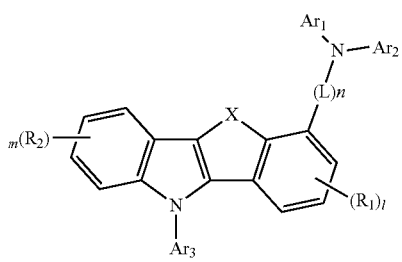

Formula 1 in Formula 1,
X is O, or S,
$R_1$ and $R_2$ are each independently a hydrogen atom, a deuterium atom, a halogen atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms,
$Ar_1$ and $Ar_2$ are each independently represented by Formula 2:

$$*-(Ar_{11})_p-Ar_{12} \quad \text{Formula 2}$$

wherein in Formula 2,
$Ar_{11}$ is a substituted or unsubstituted phenylene group, a substituted or unsubstituted divalent biphenyl group, a substituted or unsubstituted divalent terphenyl group, a substituted or unsubstituted phenanthrylene group, a substituted or unsubstituted fluorenylene group, a substituted or unsubstituted naphthylene group, a substituted or unsubstituted carbazolylene group, a substituted or unsubstituted dibenzofuranylene group, or a substituted or unsubstituted dibenzothiophenylene group,
$Ar_{12}$ is a substituted or unsubstituted phenyl group, a substituted or unsubstituted biphenyl group, a substituted or unsubstituted terphenyl group, a substituted or unsubstituted phenanthryl group, a substituted or unsubstituted fluorenyl group, a substituted or unsubstituted naphthyl group, a substituted or unsubstituted carbazolyl group, a substituted or unsubstituted dibenzofuranyl group, or a substituted or unsubstituted dibenzothiophenyl group, and p is 0 or 1, provided that i) when n is 1 and *—(Ar$_{11}$)$_p$Ar$_{12}$ of Ar$_1$ is an unsubstituted biphenylene group, then *—(Ar$_{11}$)$_p$Ar$_{12}$ of Ar$_2$ is not an unsubstituted dibenzothiophenylene group, and ii) when n is 1 and *—(Ar$_{11}$)$_p$Ar$_{12}$ of Ar$_2$ is an unsubstituted biphenylene group, then *—(Ar$_{11}$)$_p$Ar$_{12}$ of Ar$_1$ is not an unsubstituted dibenzothiophenylene group, wherein in Formula 1, Ar$_3$ is a substituted or unsubstituted aryl group of 6 to 30 ring carbon atoms, or a substituted or unsubstituted heteroaryl group of 2 to 30 ring carbon atoms, L is a direct linkage, a substituted or unsubstituted arylene group of 6 to 30 ring carbon atoms, or a substituted or unsubstituted heteroarylene group of 2 to 30 ring carbon atoms, l is an integer of 0 to 3, m is an integer of 0 to 4, and n is an integer of 0 to 3.

12. The polycyclic compound of claim 11, wherein the polycyclic compound comprises one acyclic amine.

13. The polycyclic compound of claim 11, wherein Formula 1 is represented by the following Formula 1-1 or Formula 1-2:

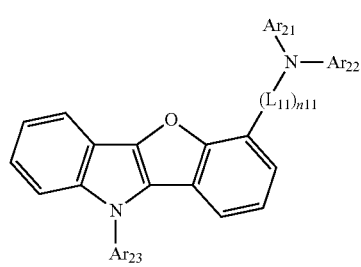

Formula 1-1

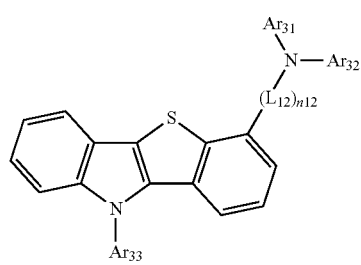

Formula 1-2 in Formula 1-1 and Formula 1-2,

Ar$_{21}$, Ar$_{22}$, Ar$_{31}$, and Ar$_{32}$ are each independently represented by Formula 2, Ar$_{23}$ and Ar$_{33}$ are each independently a substituted or unsubstituted aryl group of 6 to 30 ring carbon atoms, or a substituted or unsubstituted heteroaryl group of 2 to 30 ring carbon atoms, L$_{11}$, and L$_{12}$ are each independently a direct linkage, a substituted or unsubstituted arylene group of 6 to 30 ring carbon atoms, or a substituted or unsubstituted heteroarylene group of 2 to 30 ring carbon atoms, and n11, and n12 are each independently an integer of 0 to 3.

14. The polycyclic compound of claim 11, wherein Formula 1 is represented by the following Formula 1-3:

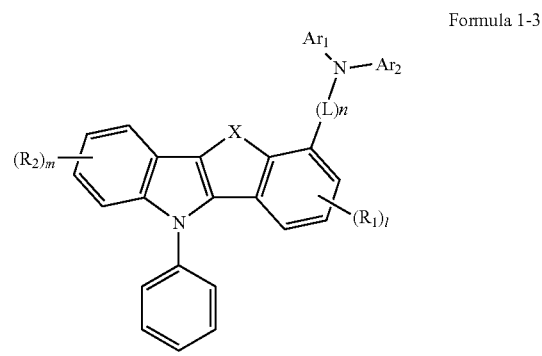

Formula 1-3 wherein in Formula 1-3,

X, R$_1$, R$_2$, Ar$_1$, Ar$_2$, L, and l to n are the same as defined in Formula 1.

15. The polycyclic compound of claim 11, wherein Formula 1 is represented by the following Formula 1-4:

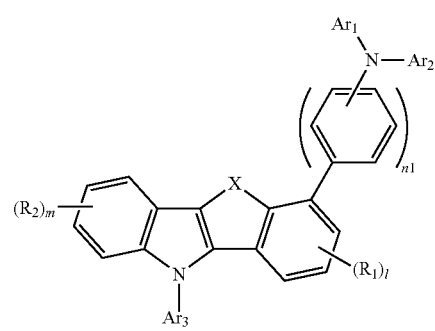

Formula 1-4 wherein in Formula 1-4, n1 is 0 or 1, and

X, R$_1$, R$_2$, Ar$_1$ to Ar$_3$, l, and m are the same as defined in Formula 1.

16. The polycyclic compound of claim 11, wherein Ar$_1$ and Ar$_2$ are each independently represented by the following 1-1 to 1-10:

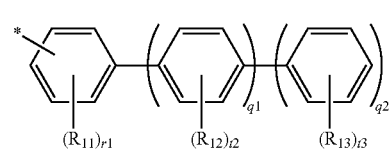

1-1

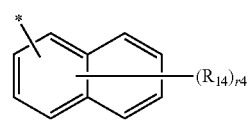

1-2

-continued 1-3
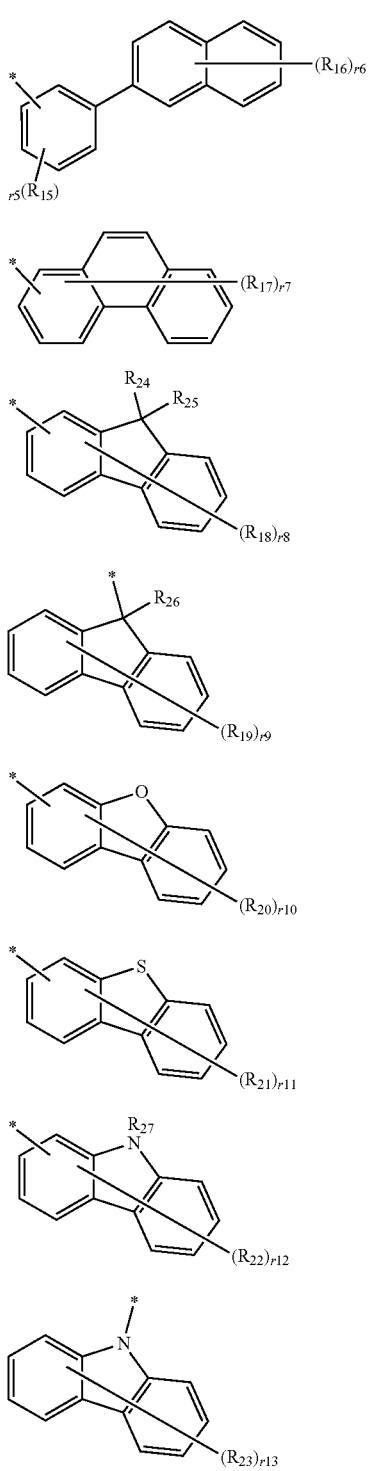
1-4
1-5
1-6
1-7
1-8
1-9
1-10 wherein in 1-1 to 1-10,
R$_{11}$ to R$_{27}$ are each independently a hydrogen atom, a deuterium atom, a halogen atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms,
r1, r2, and r5 are each independently an integer of 0 to 4,
r3 is an integer of 0 to 5,
r4, r6, r8, and r10 to r12 are each independently an integer of 0 to 7,
r7 is an integer of 0 to 9,
r9 and r13 are each independently an integer of 0 to 8, and
q1 and q2 are each independently 0 or 1.

17. The polycyclic compound of claim 11, wherein Formula 1 is represented by the following Formula 1-5:

Formula 1-5

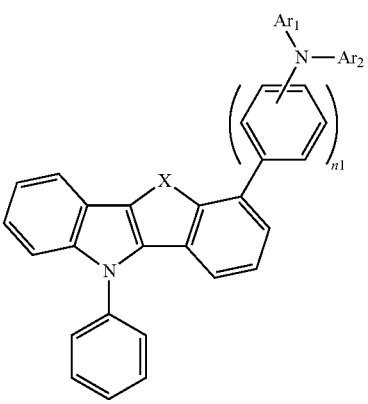

in Formula 1-5,
n1 is 0 or 1, and
X, Ar$_1$, and Ar$_2$ are the same as defined in Formula 1.

18. A polycyclic compound selected from Compound Group 1 or Compound Group 2:

Compound Group 1

A1
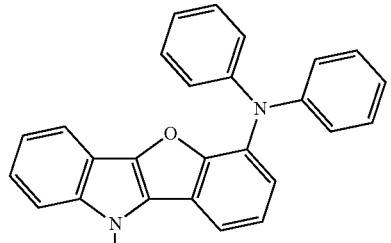

A2
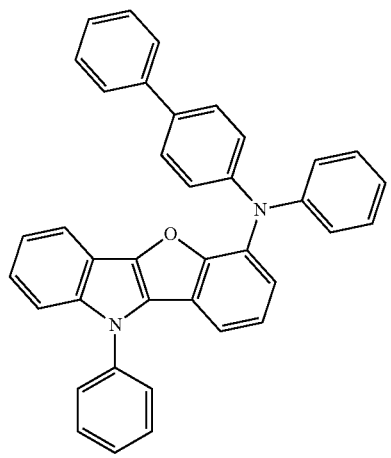

A3
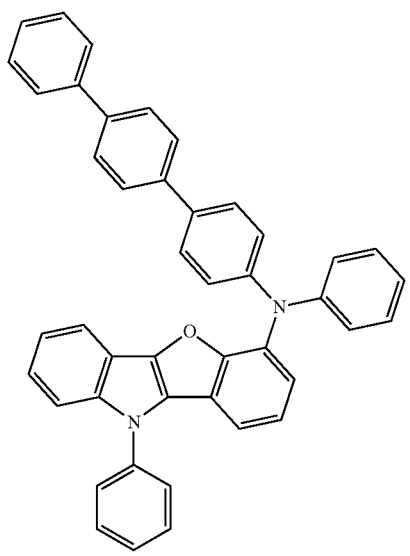
A6
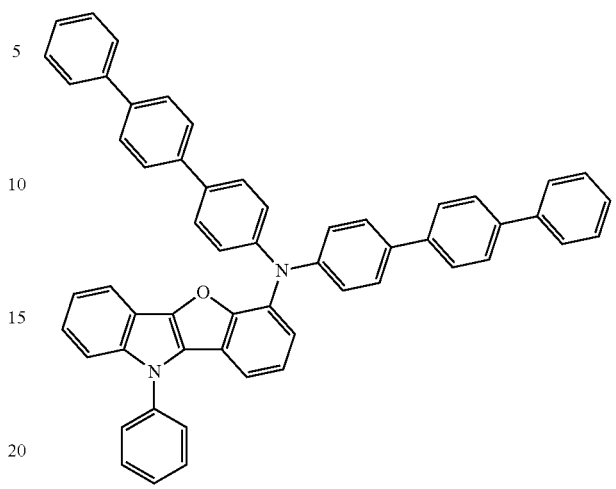
A4
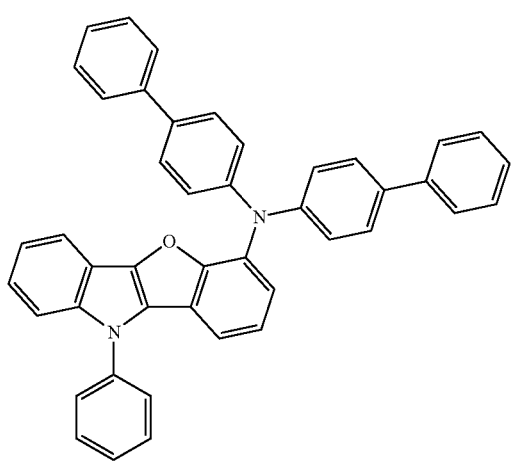
A7
A5
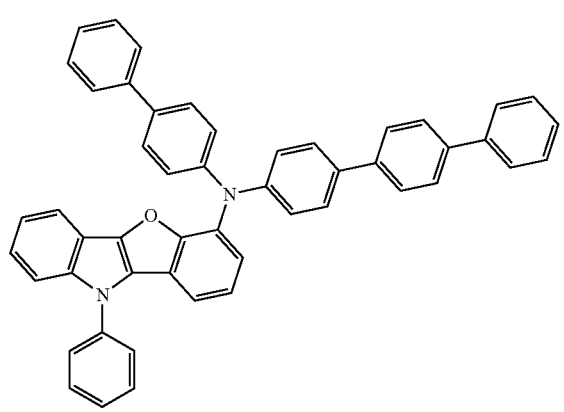
A8
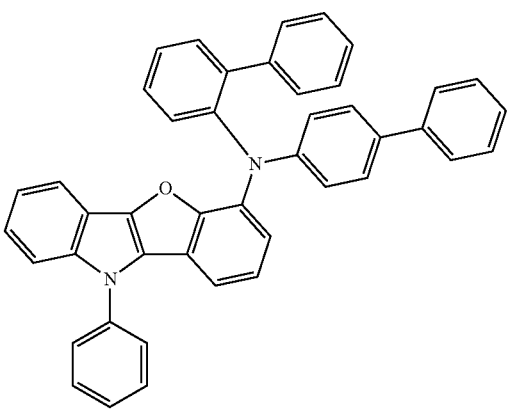

-continued
A9
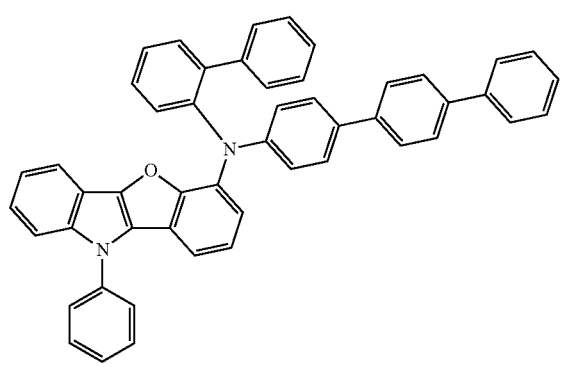
A10
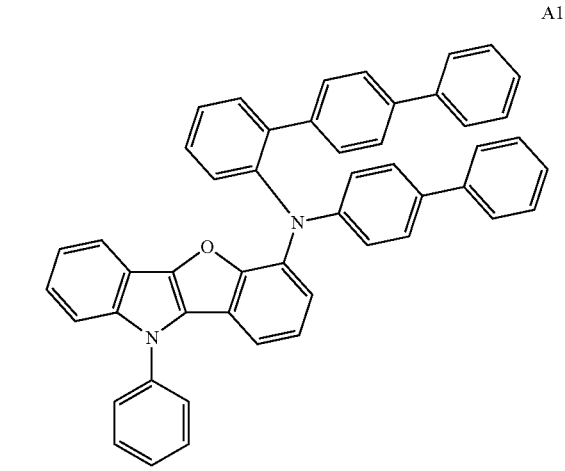
A11
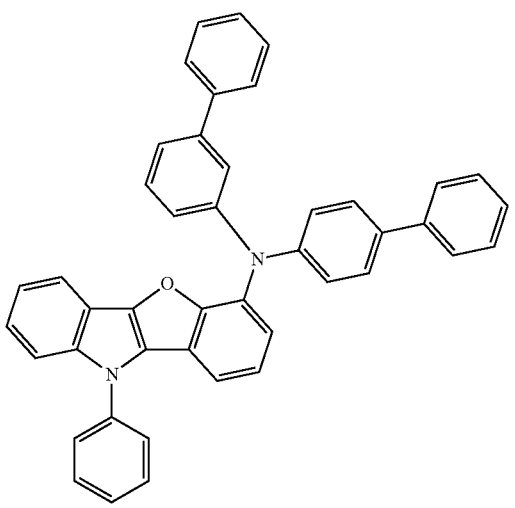
-continued
A12
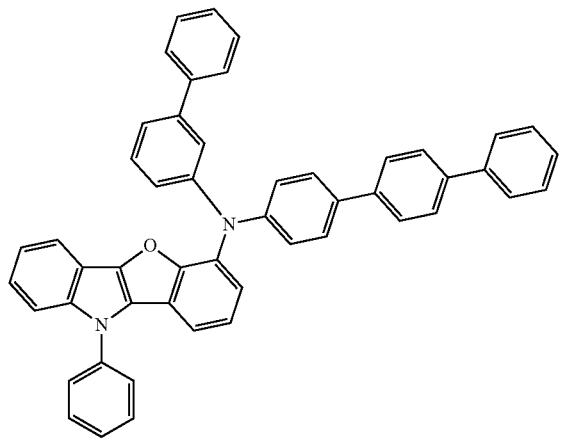
A13
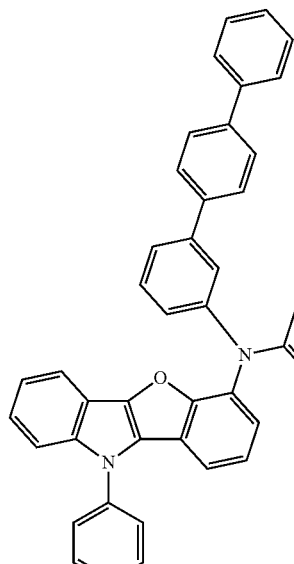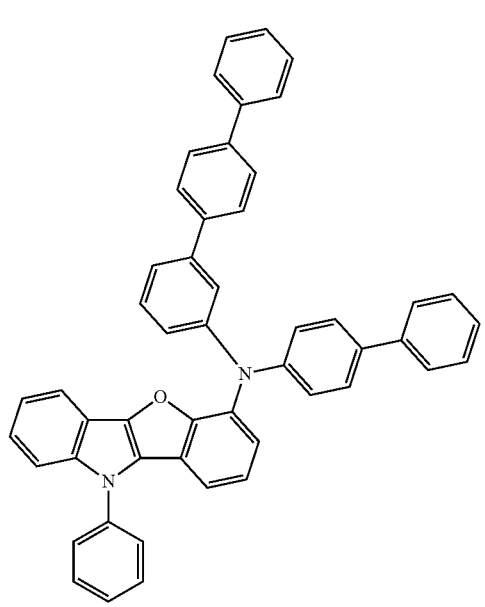
A14
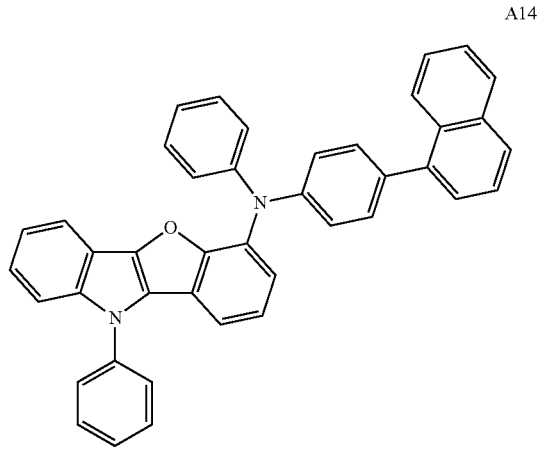

A15
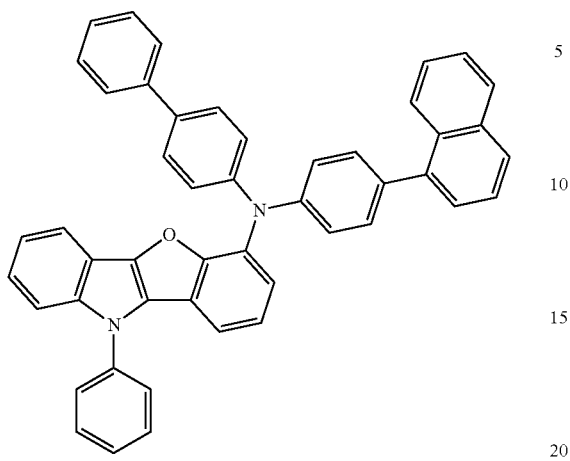
A18
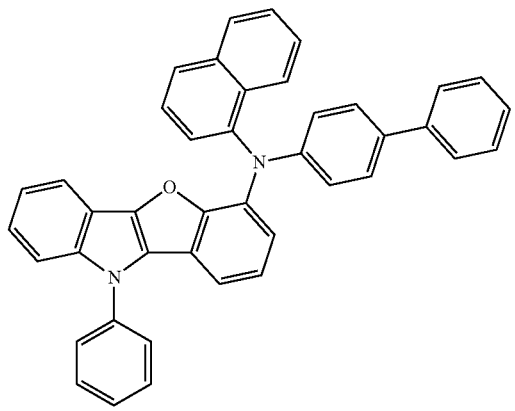
A16
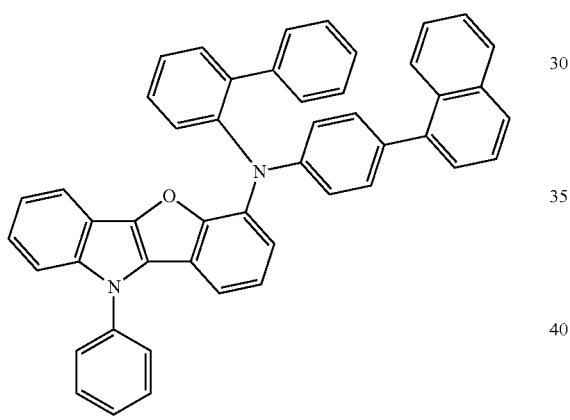
A19
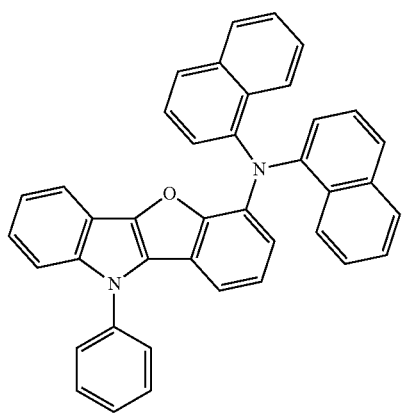
A17
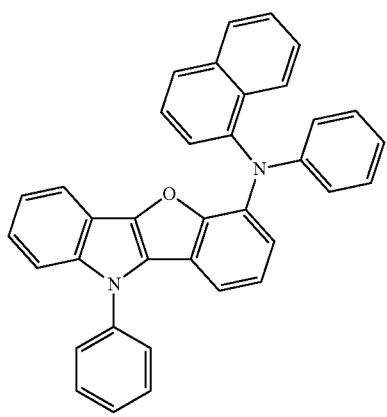
A20
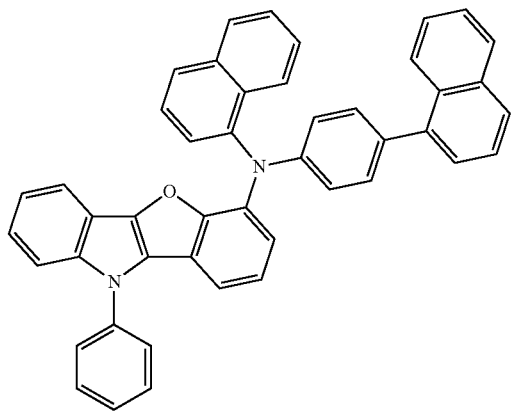

-continued
A21
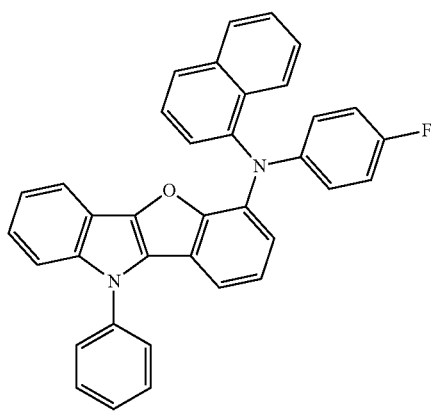
A22
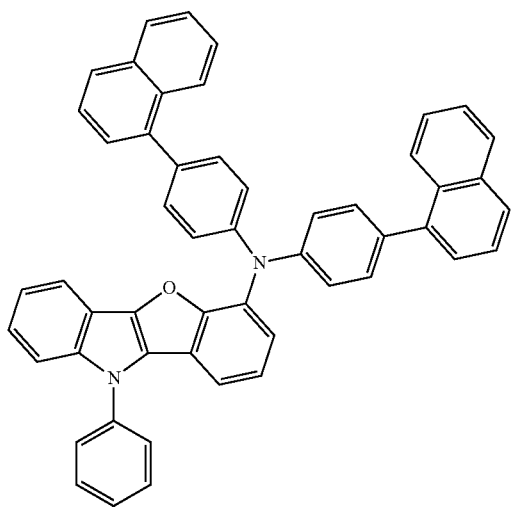
A23
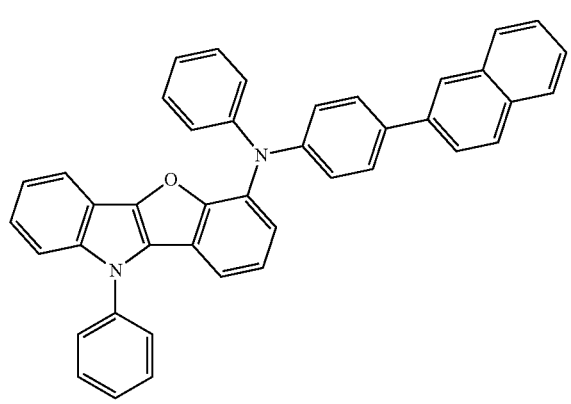
-continued
A24
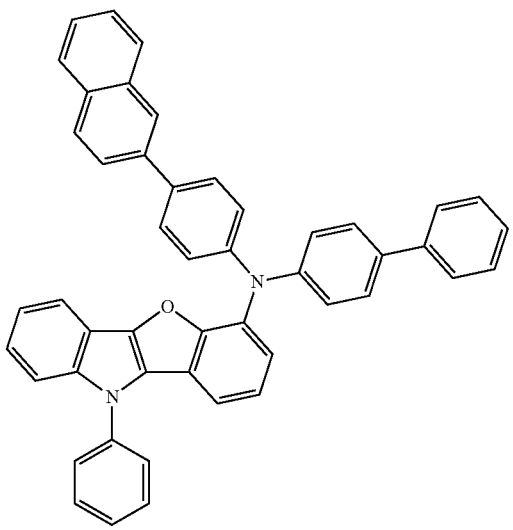
A25
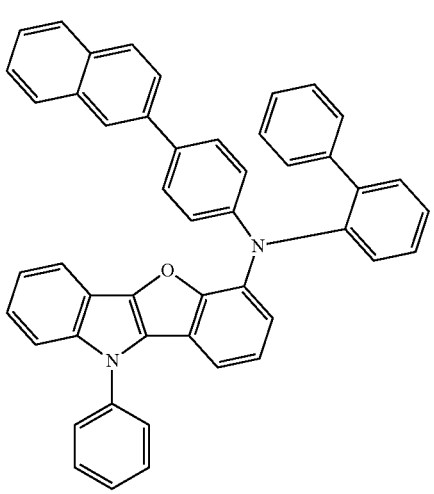
A26
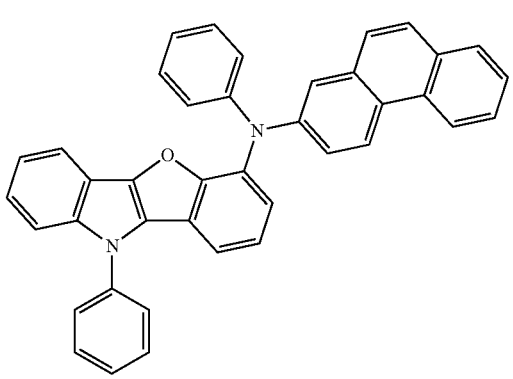

-continued
A27
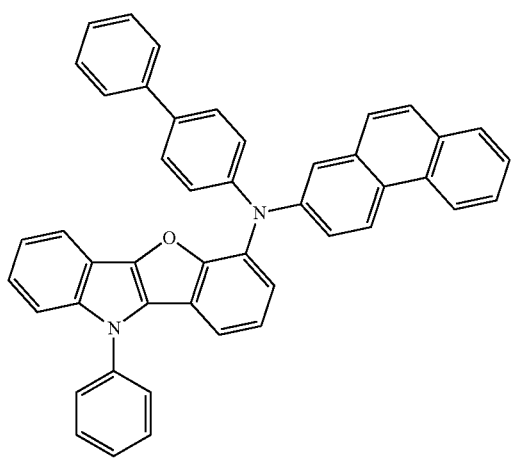
A28
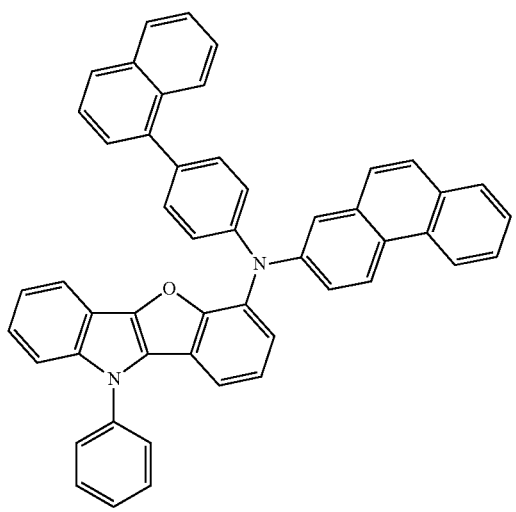
A29
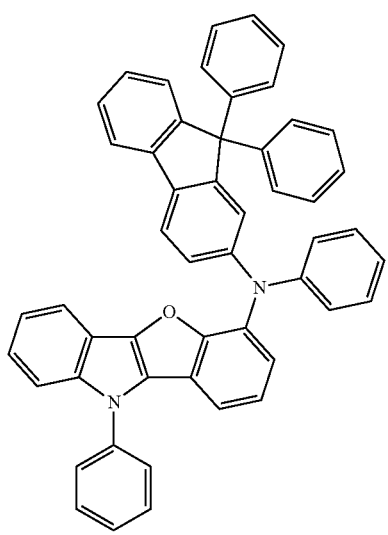
-continued
A30
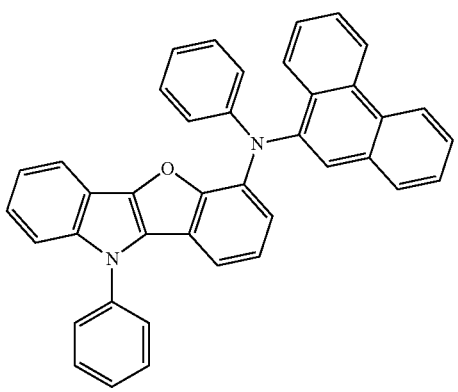
A31
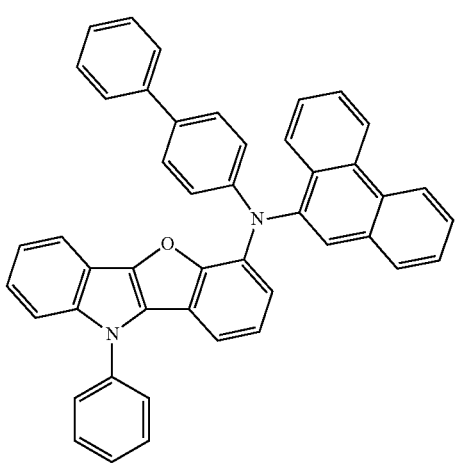
A32
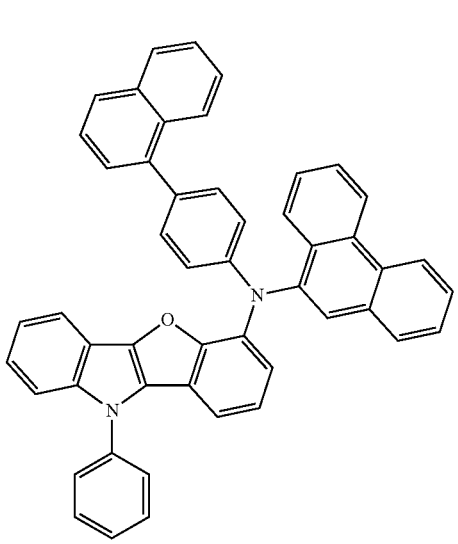

A33
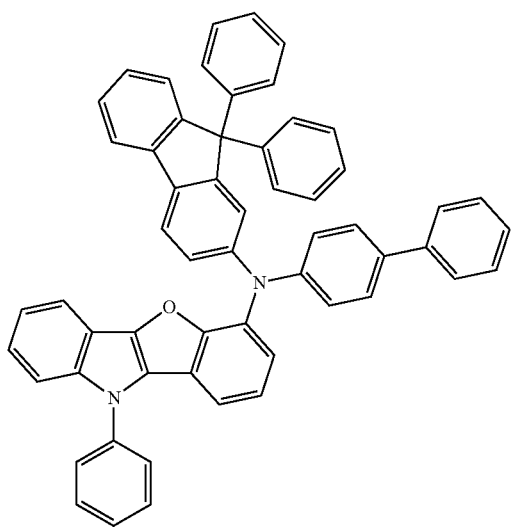
A34
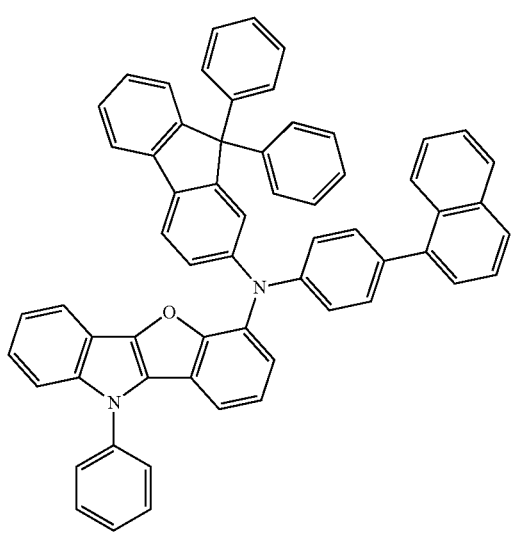
A35
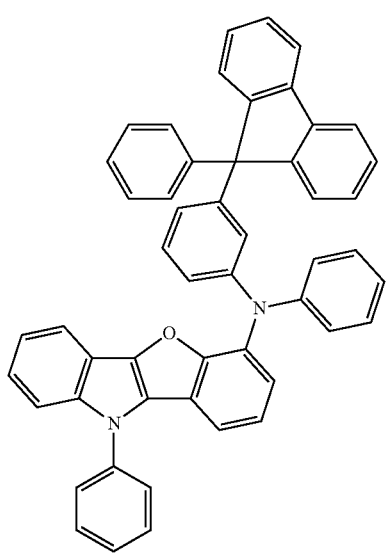
A36
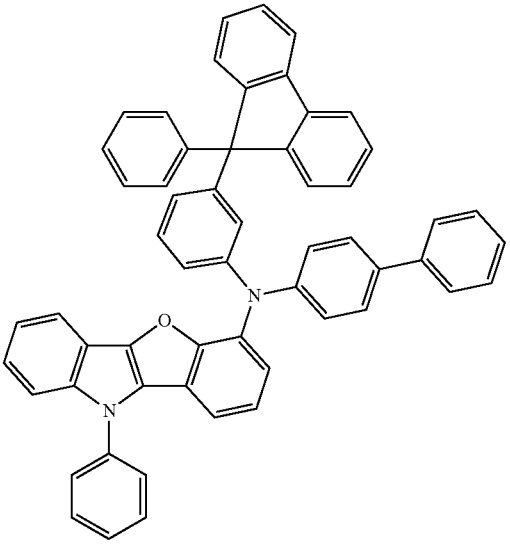
A37
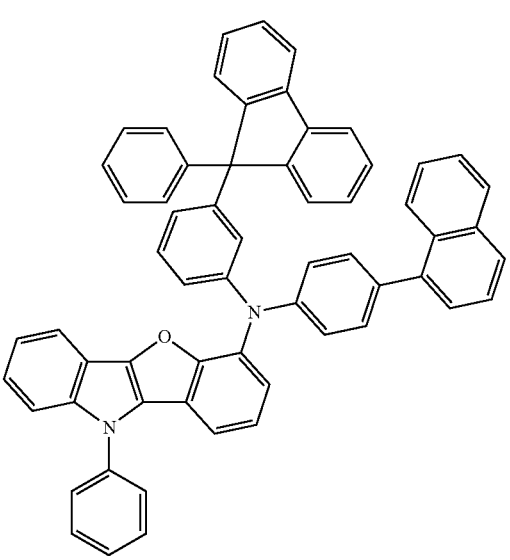
A38
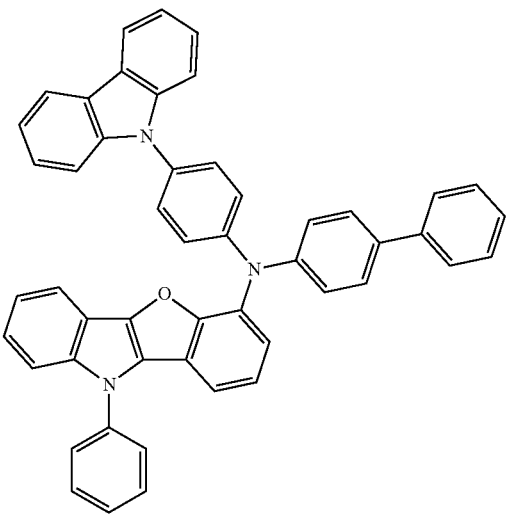

-continued
A39
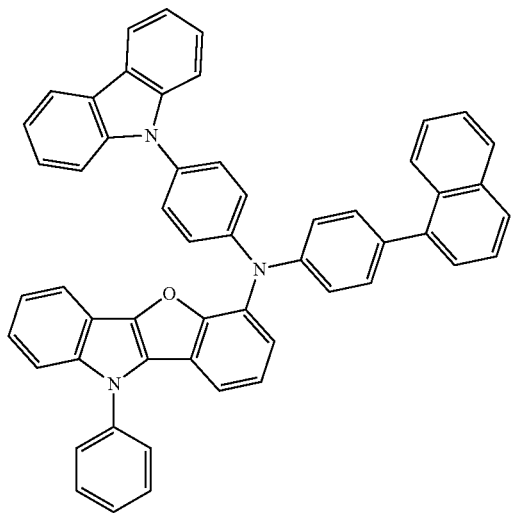
A40
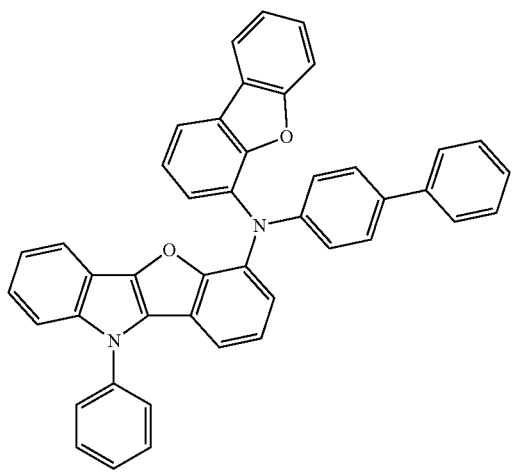
A41
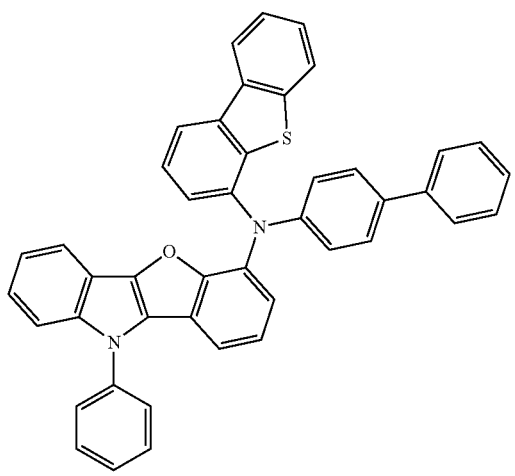
-continued
A42
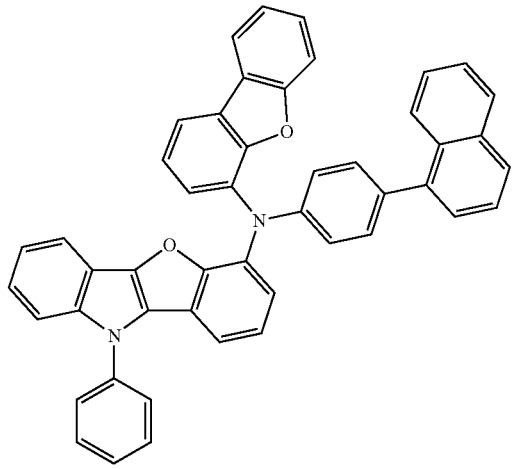
A43
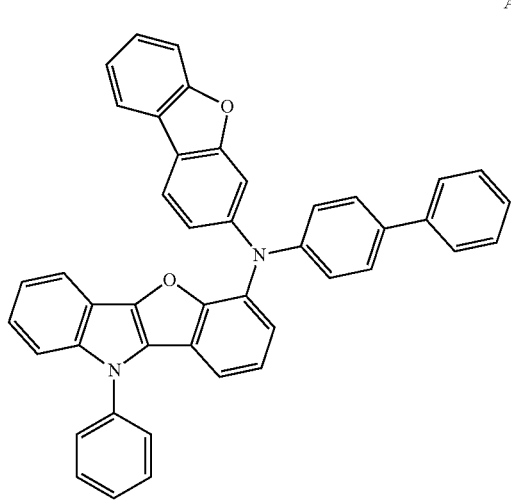
A44
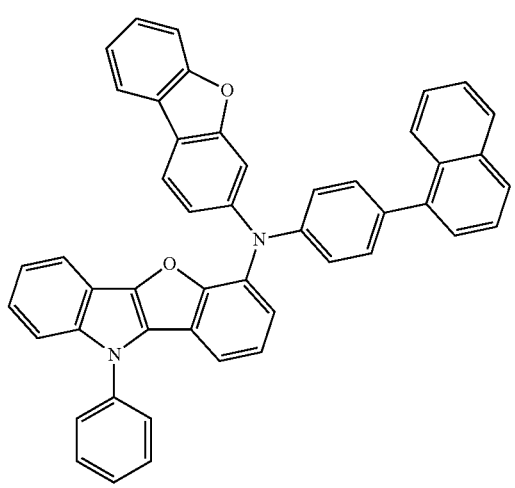

A45
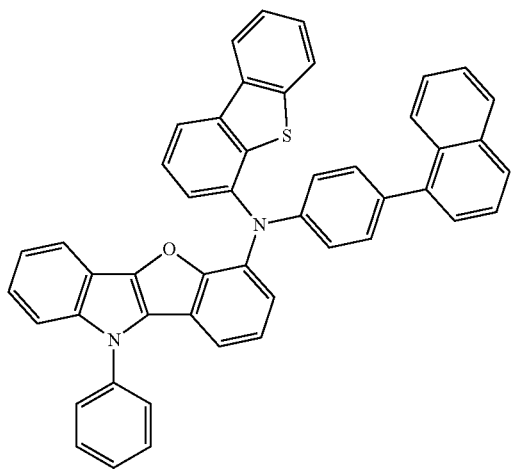
A46
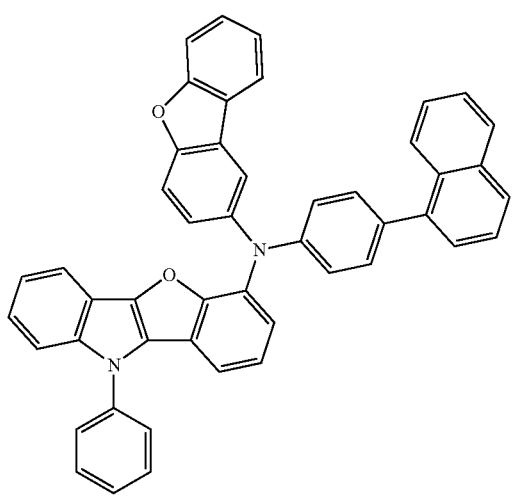
A47
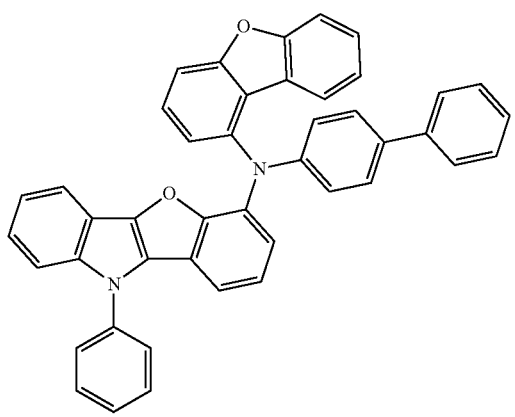
A48
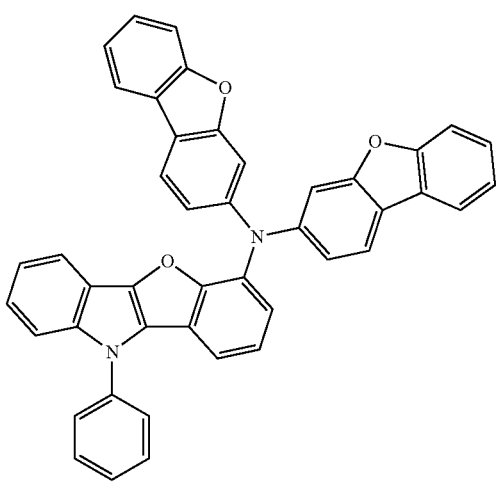
A49
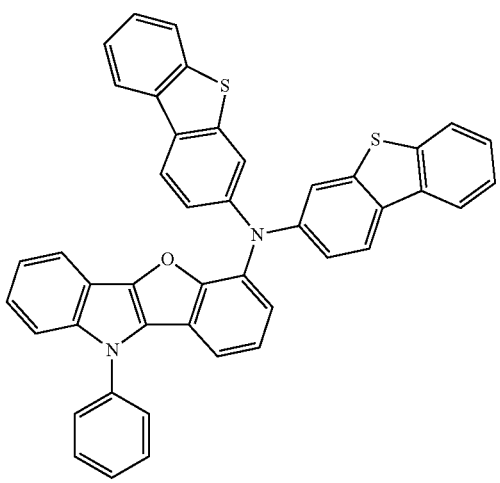
A50
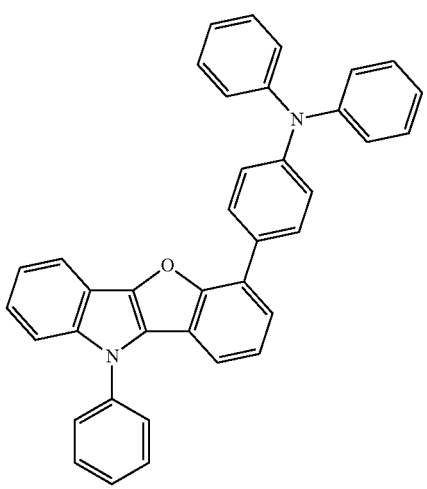

353
-continued
A51
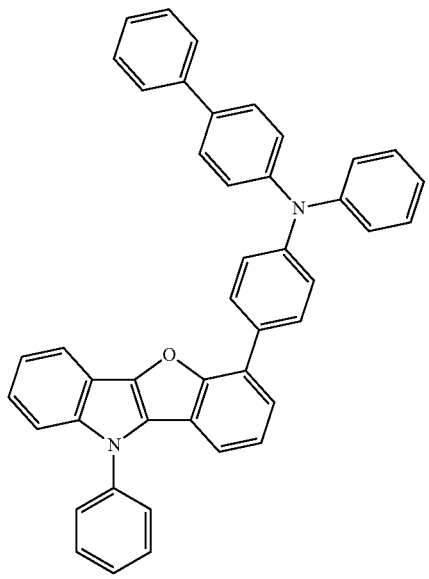
A52
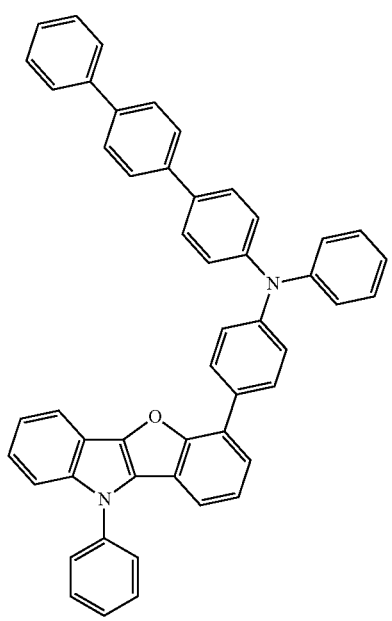
354
-continued
A53
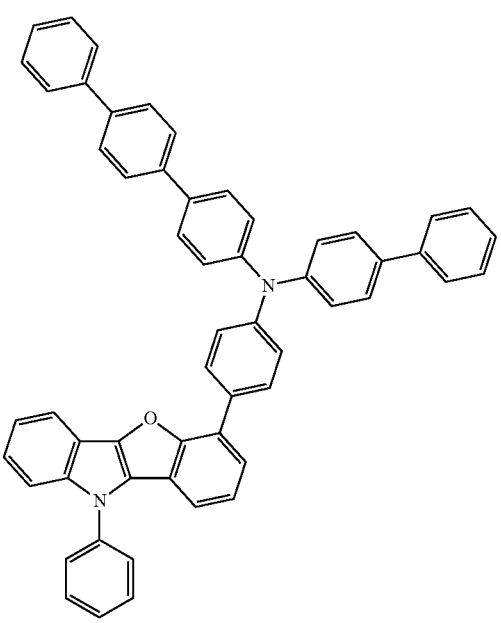
A54

A55
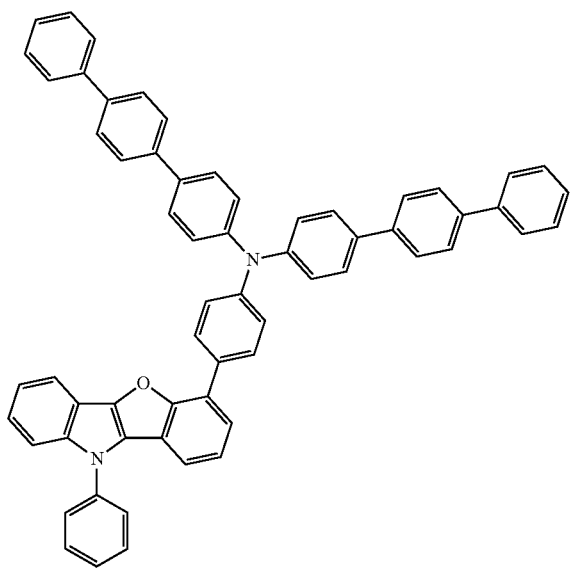
A56
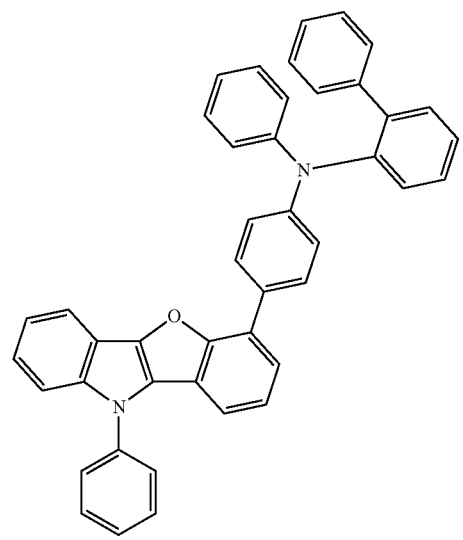
A57
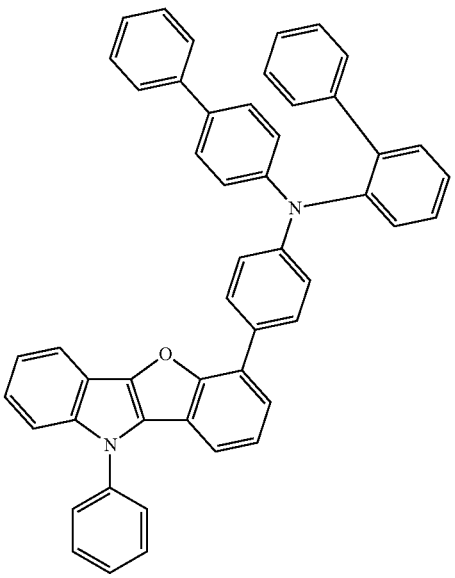
A58
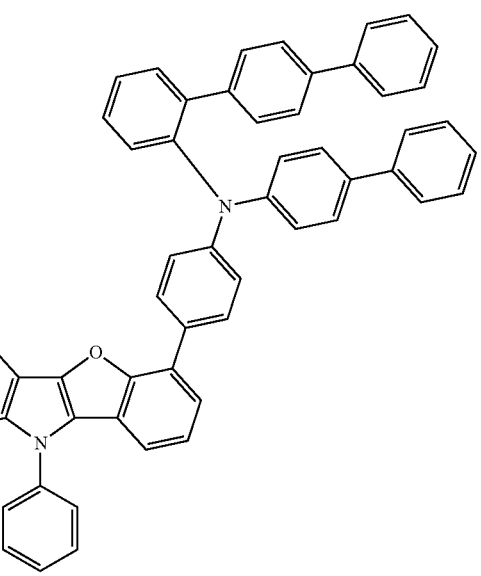
A59

A60
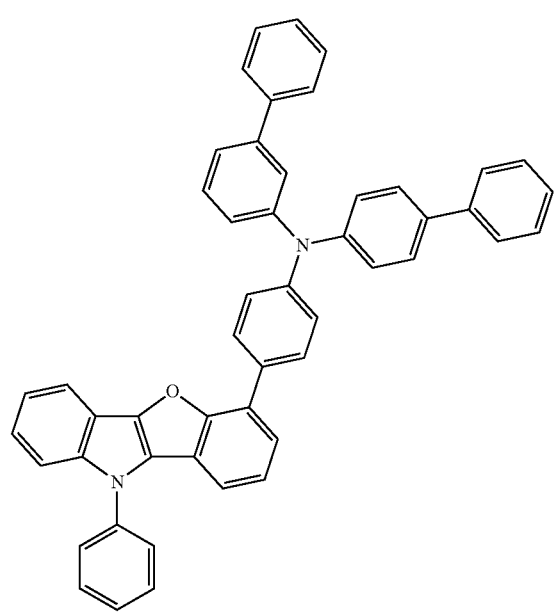
A61
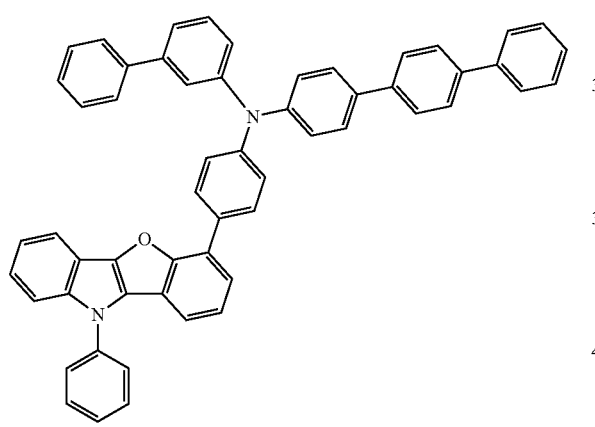
A62
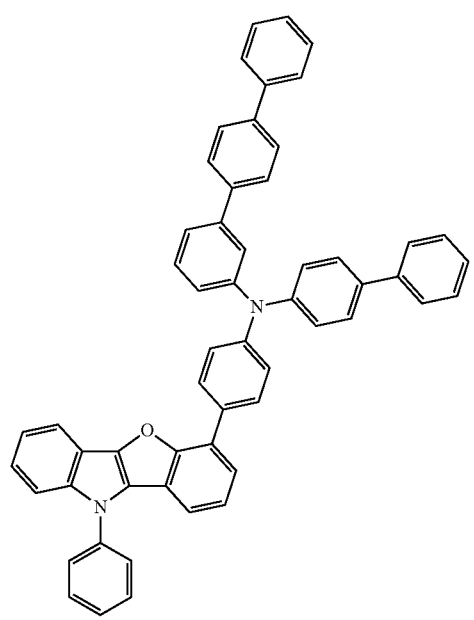
A63
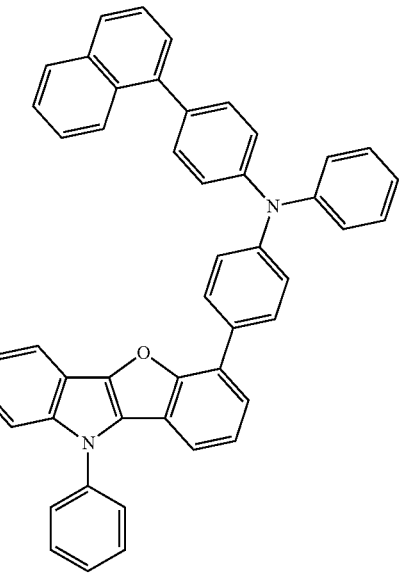
A64
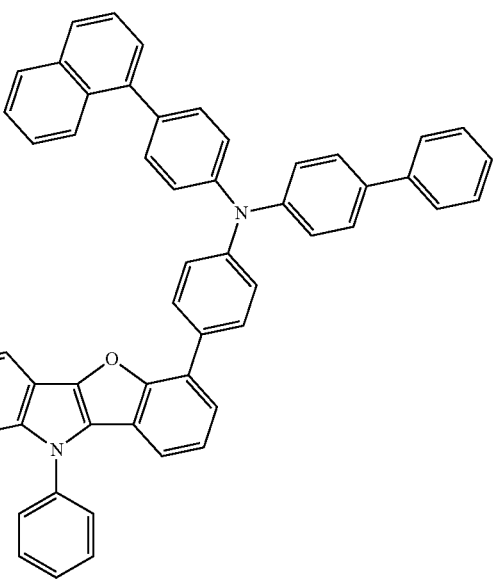

-continued
A65
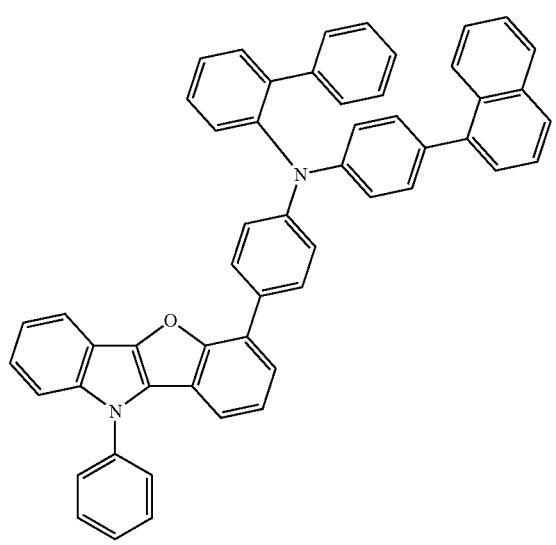
A66
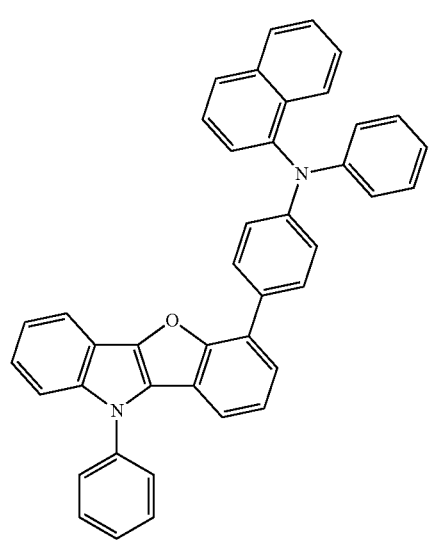
A67
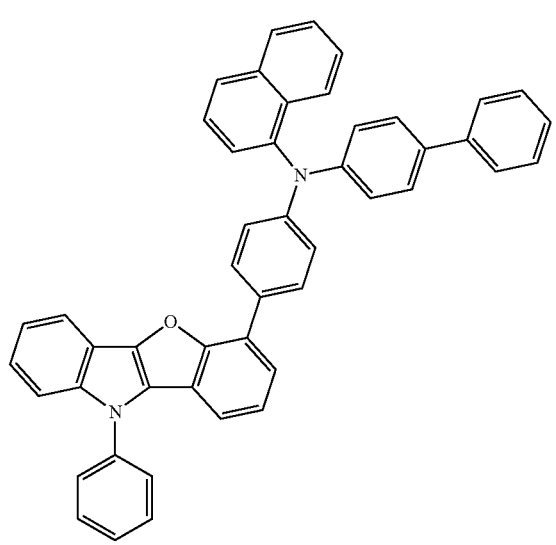
-continued
A68
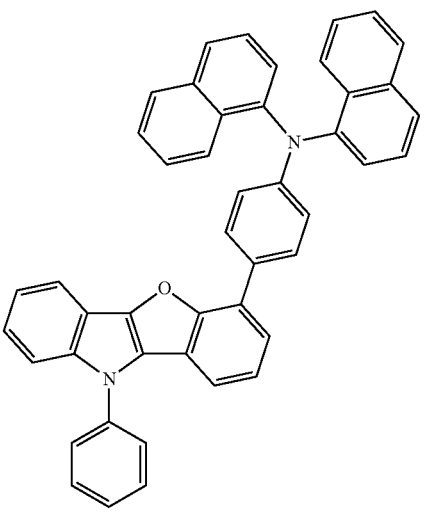
A69
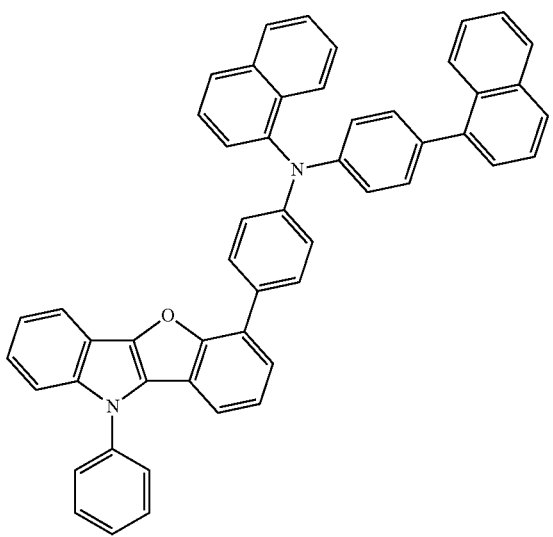

A70
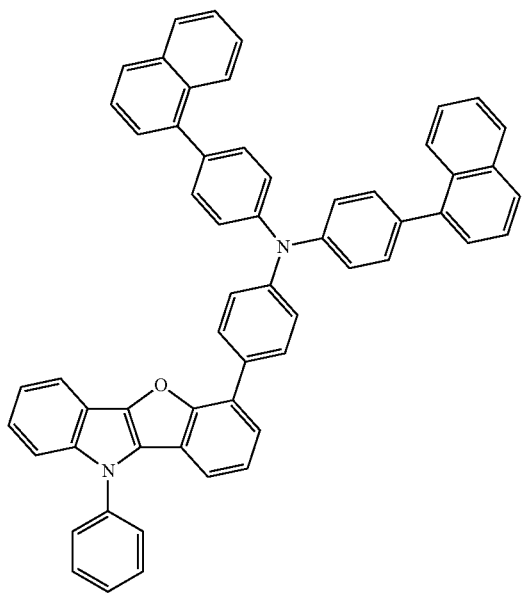
A71
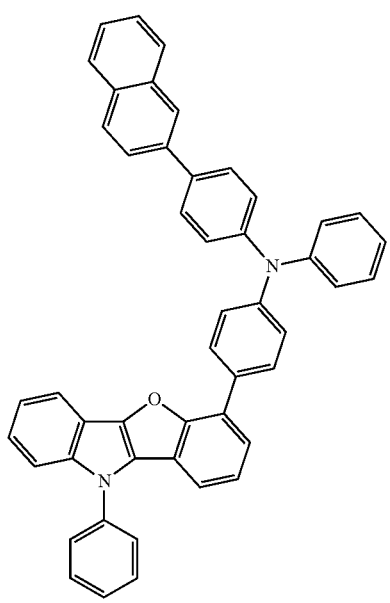
A72
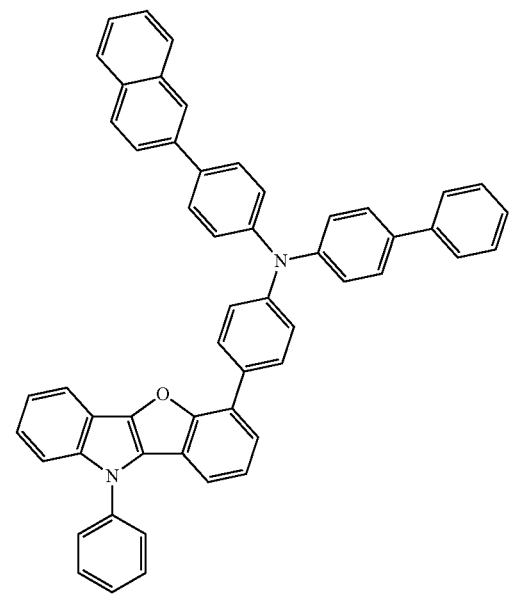
A73
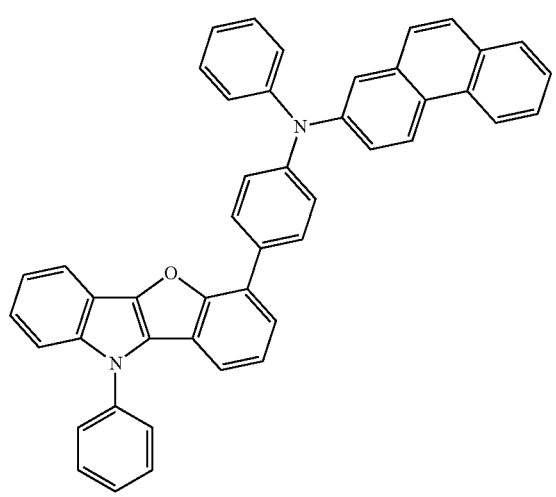
A74

A75
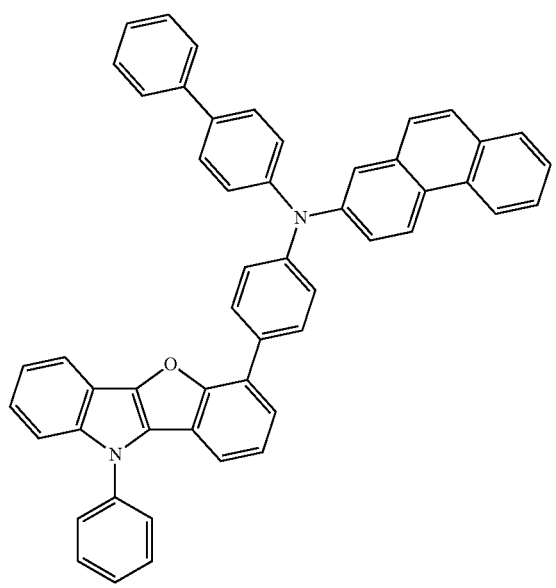
A76
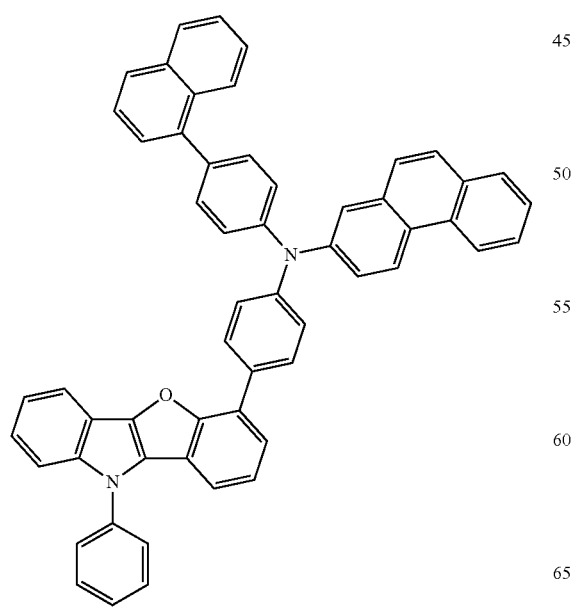
A77
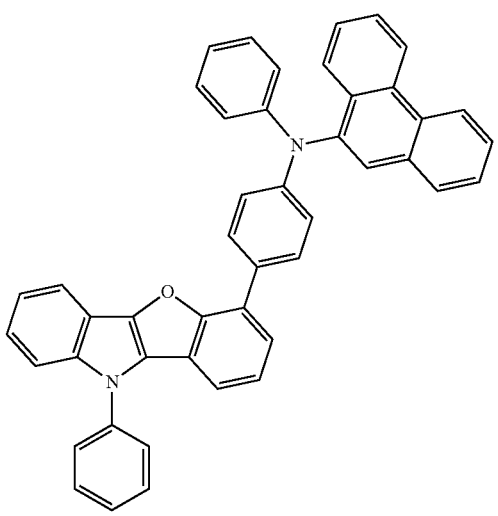
A78
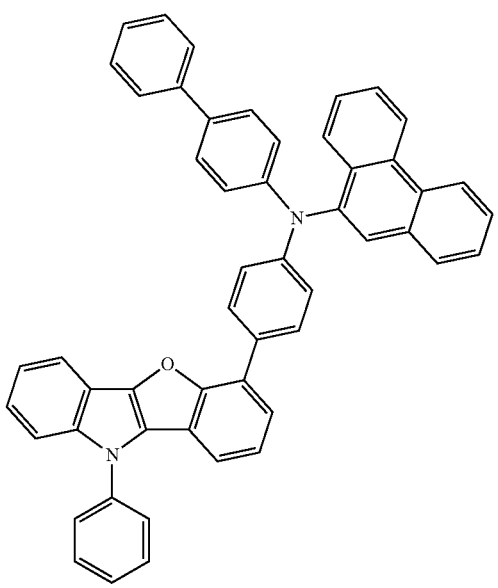

-continued
A79
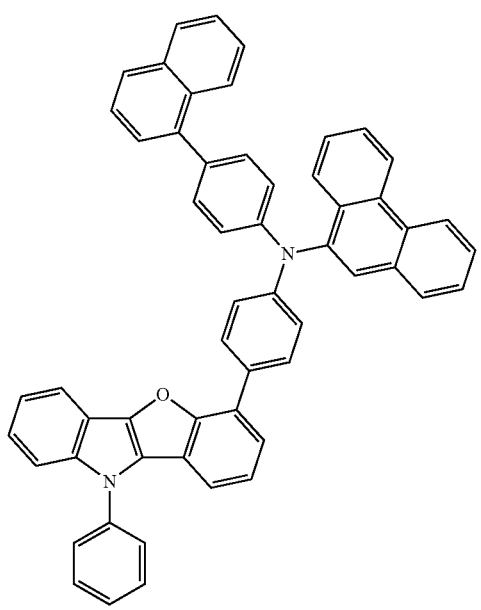
A80
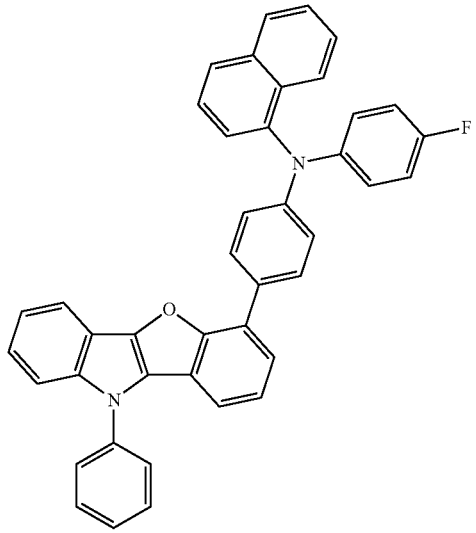
A81
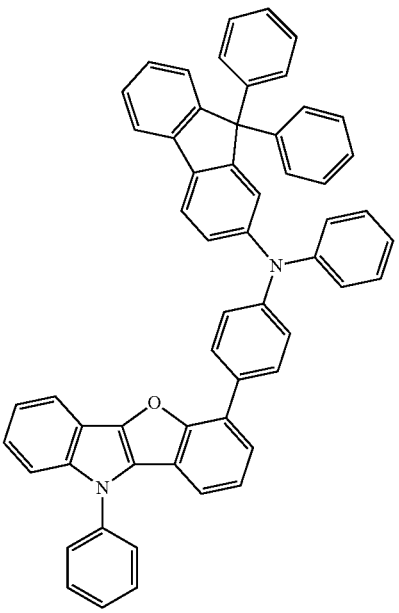
A82
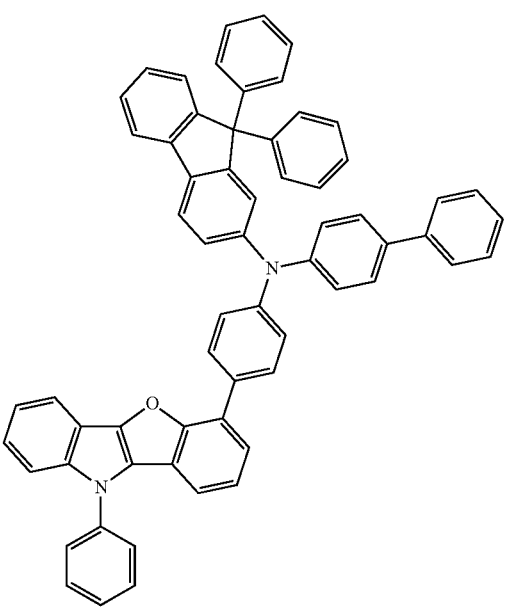

-continued
A83
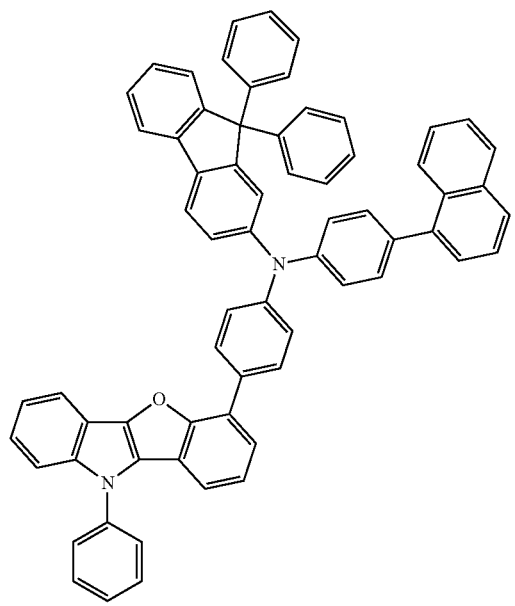
A84
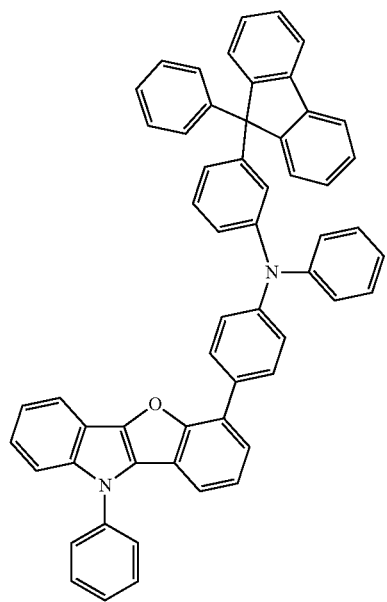
-continued
A85
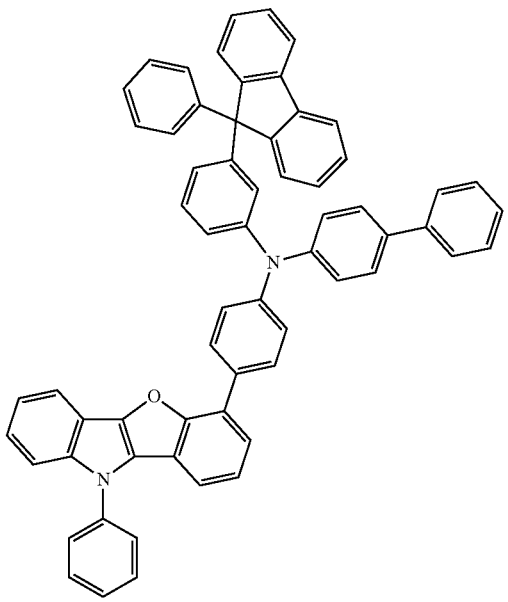
A86
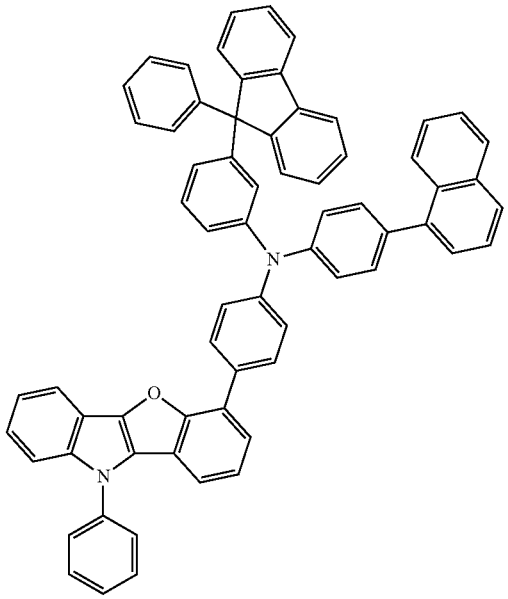

-continued
A87
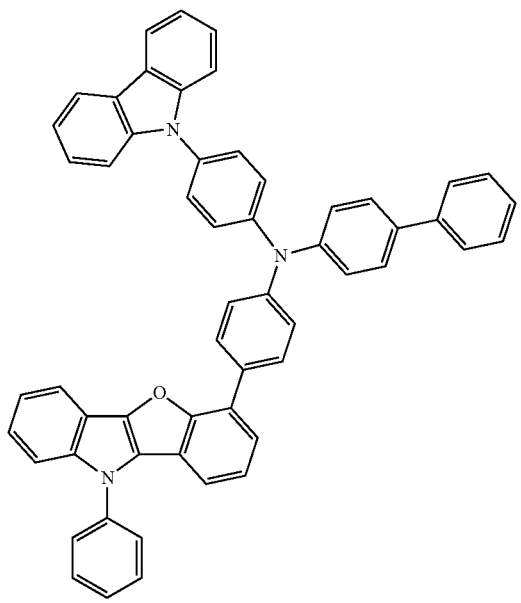
A89
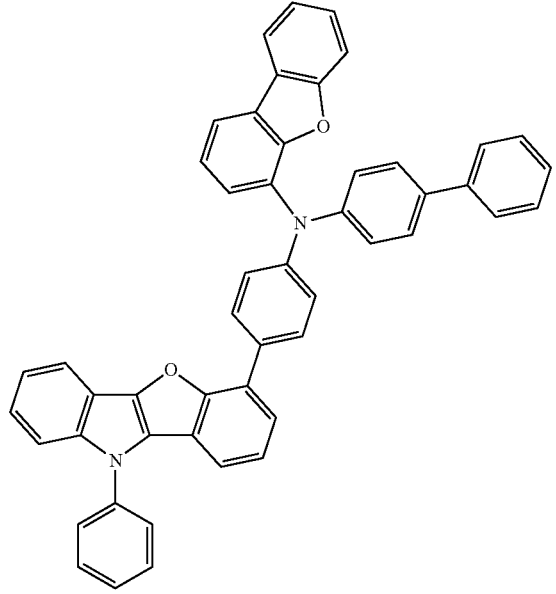
A88
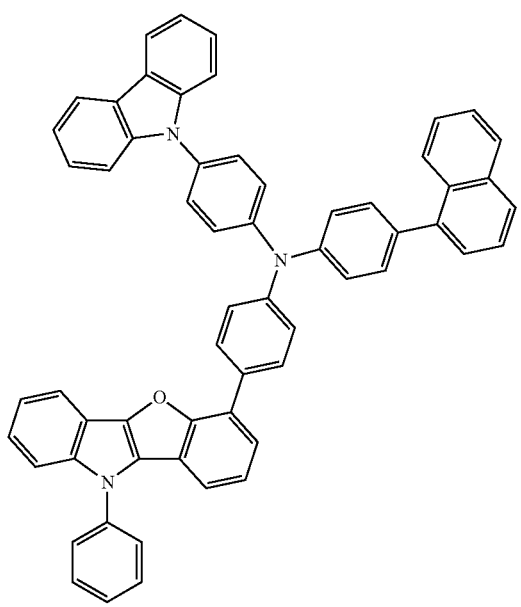
A90
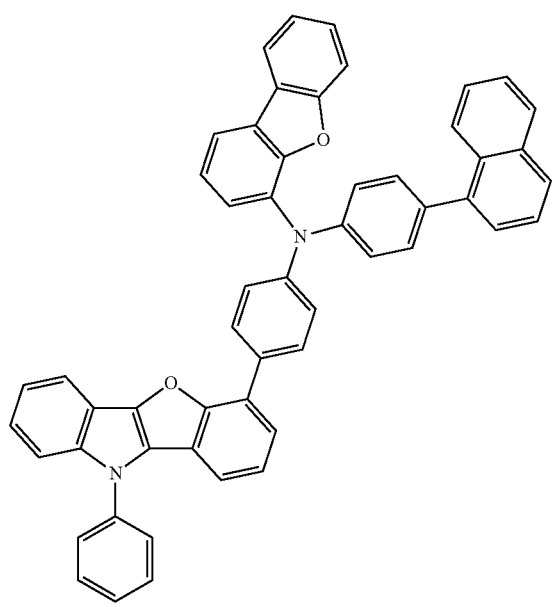

-continued
A91
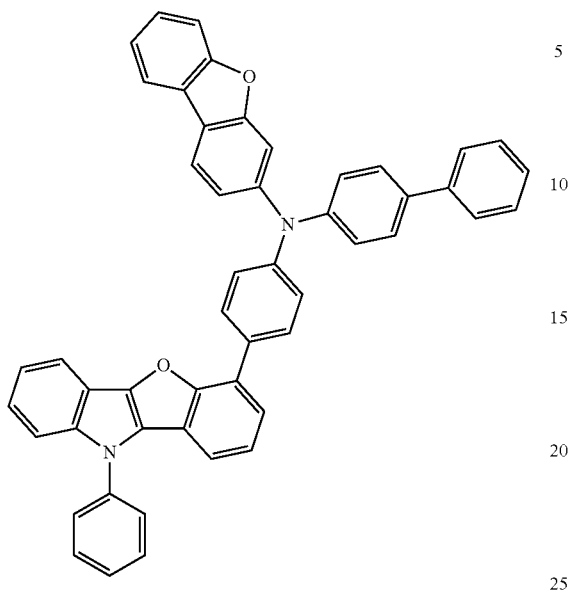
A92
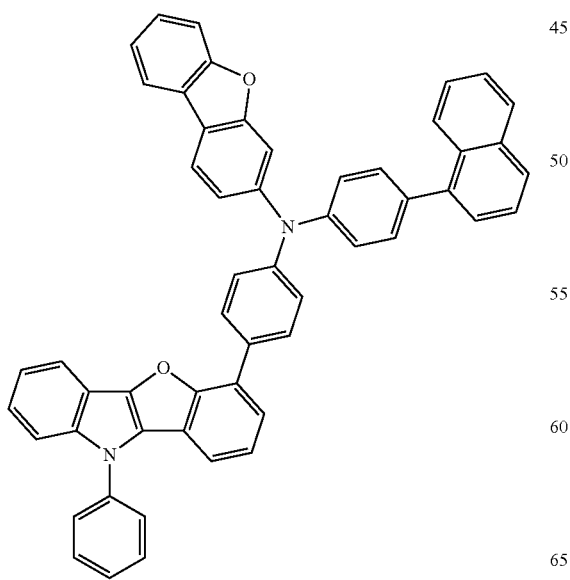
A93
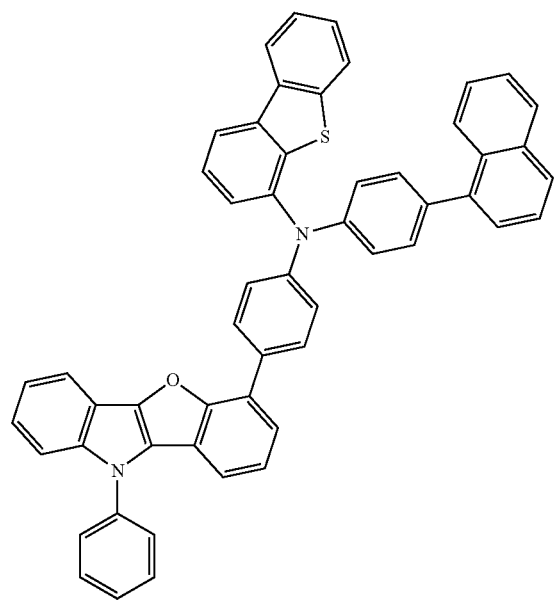
A94
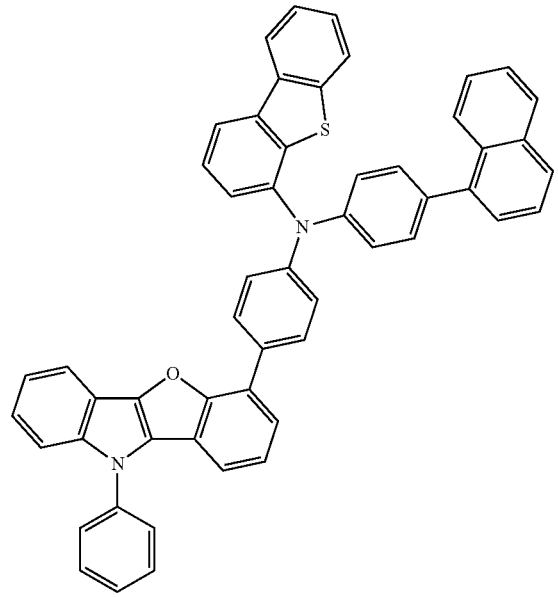

-continued
A95
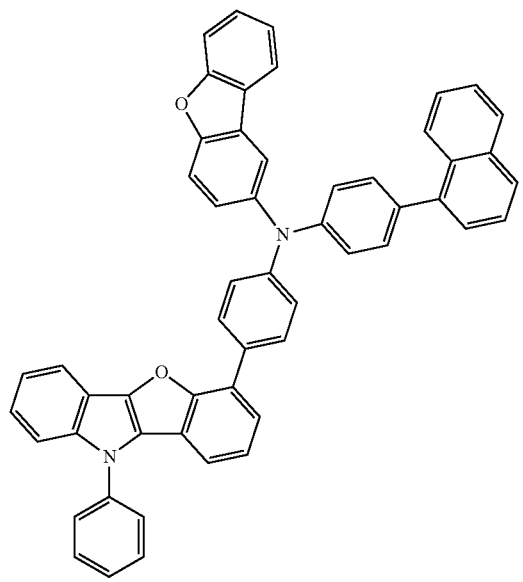
A96
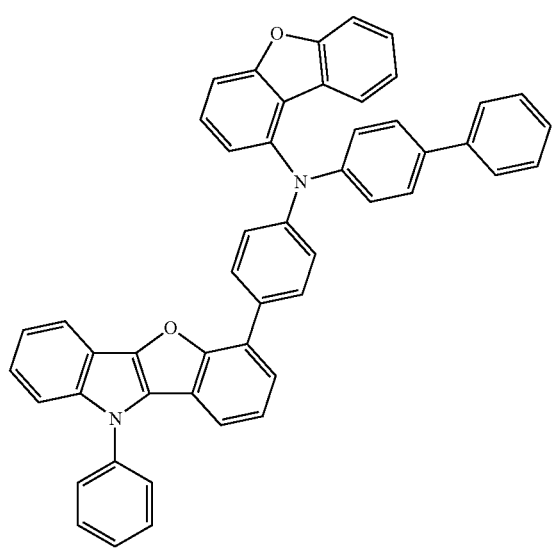
A97
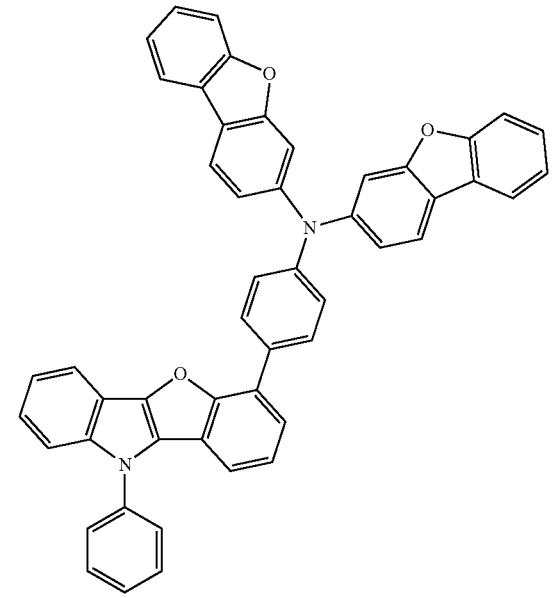
A98
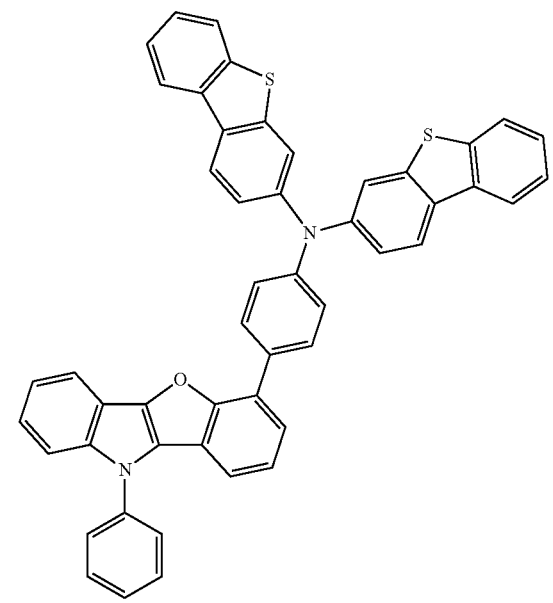
A99
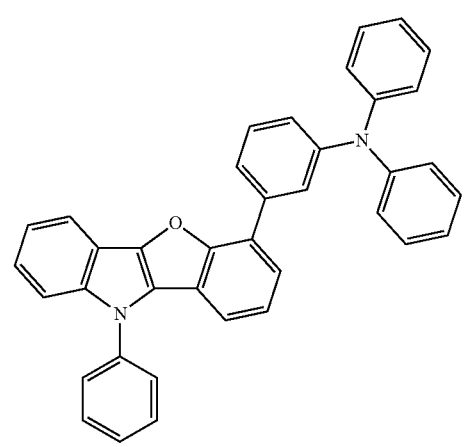

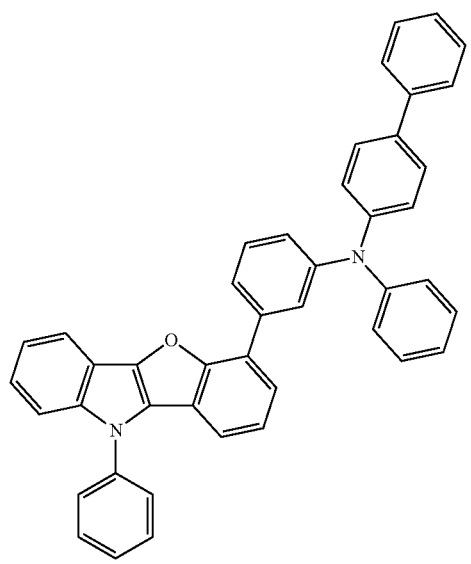
A100
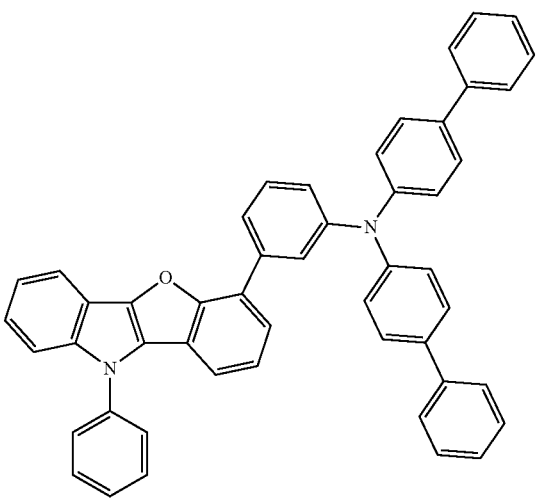
A102
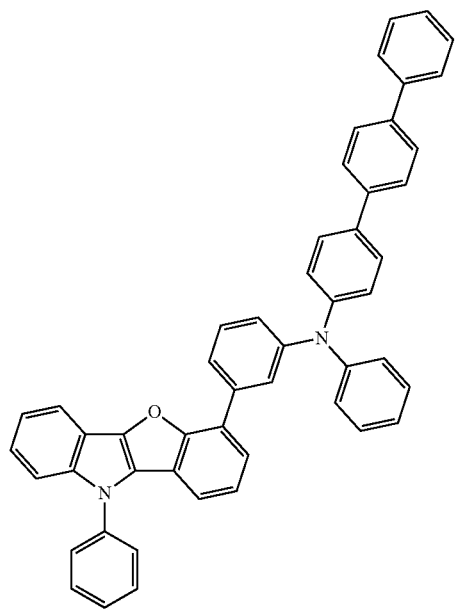
A101
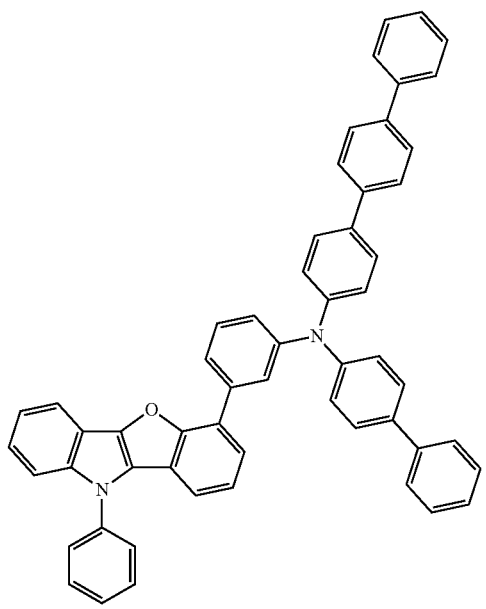
A103

-continued
A104
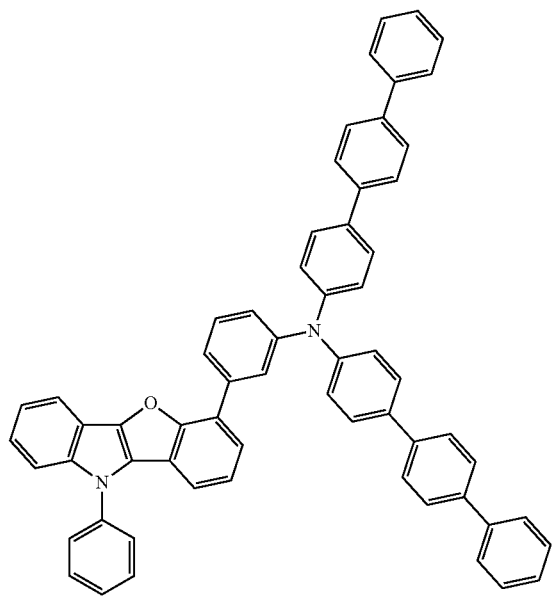
A105
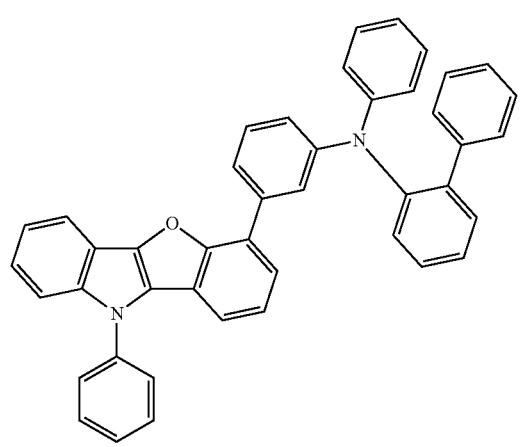
A106
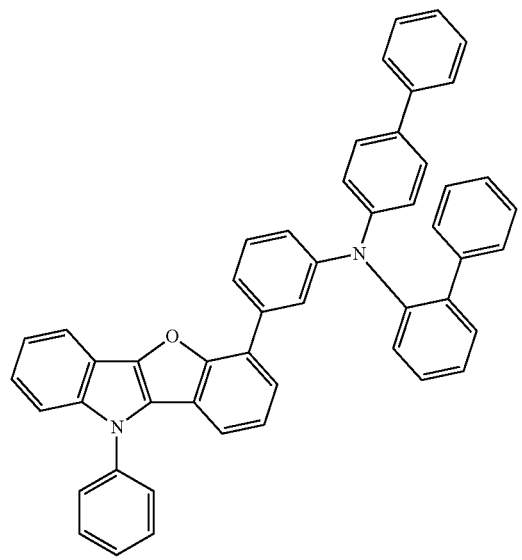
-continued
A107
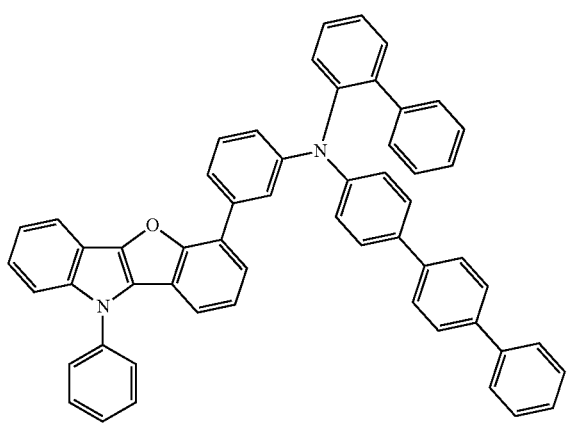
A108
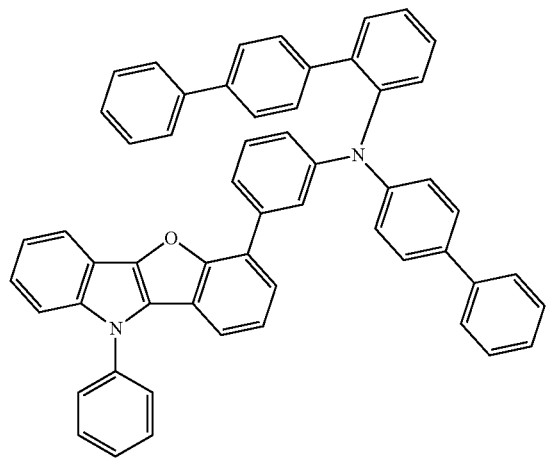
A109
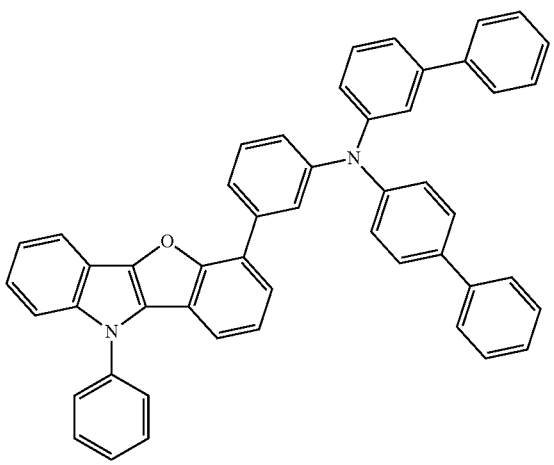

A110
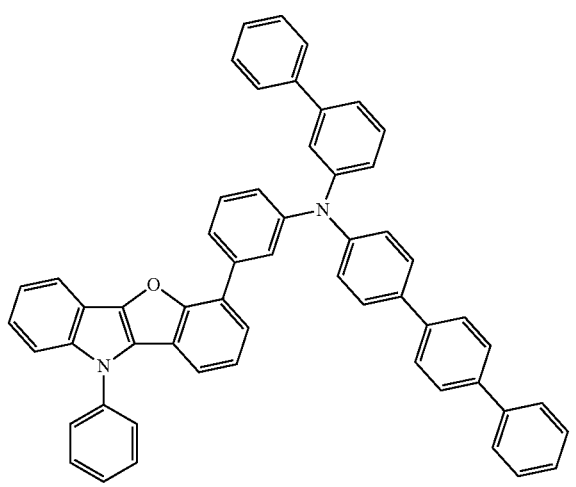
A111
A113
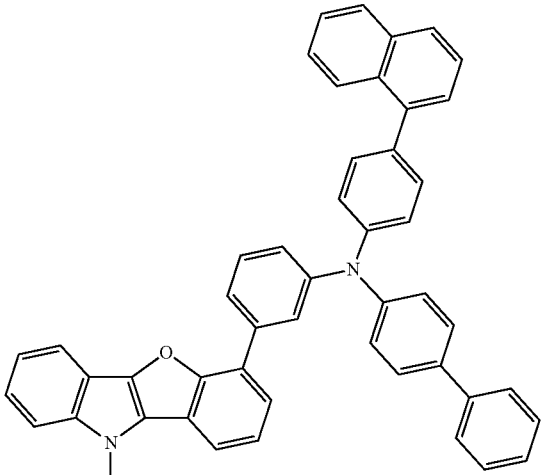
A114
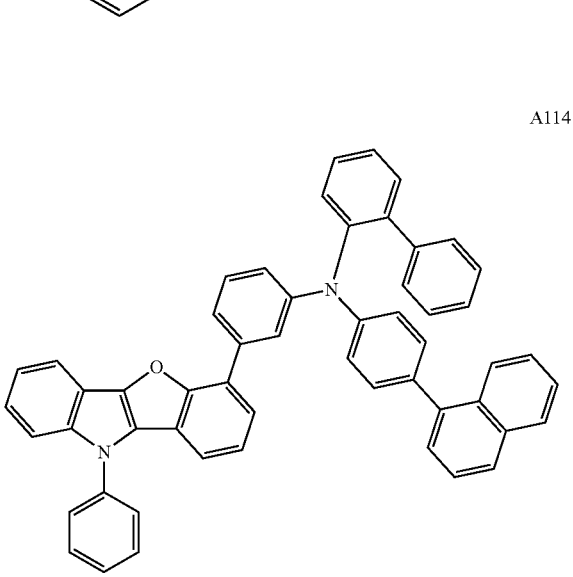
A112
A115
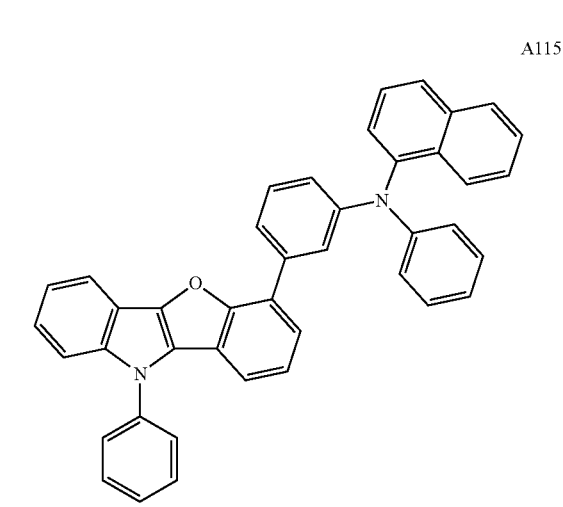

-continued
A116
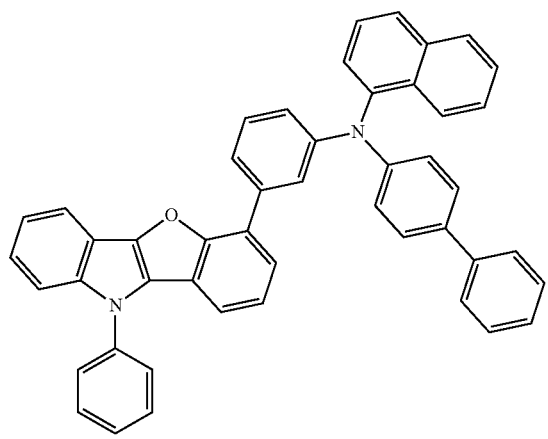
A117
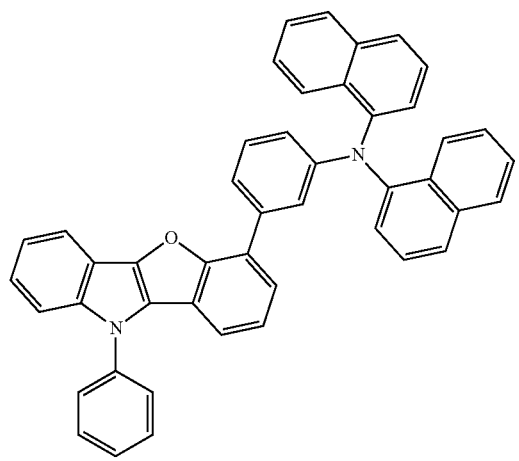
A118
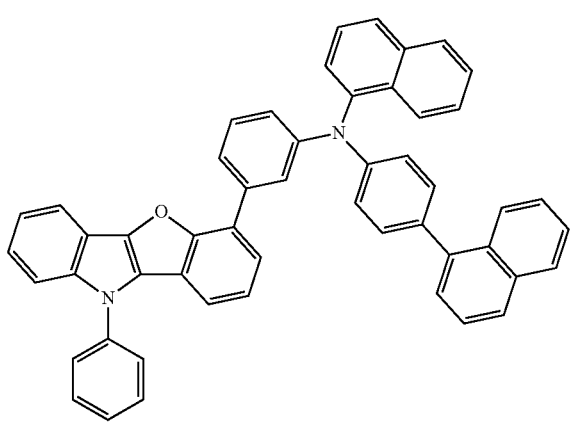
-continued
A119
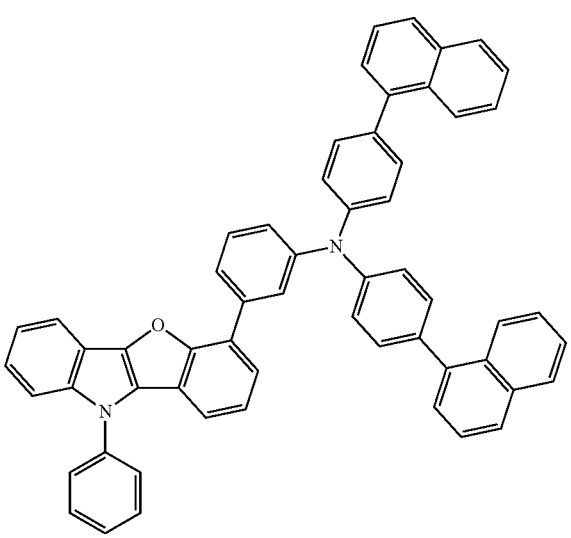
A120
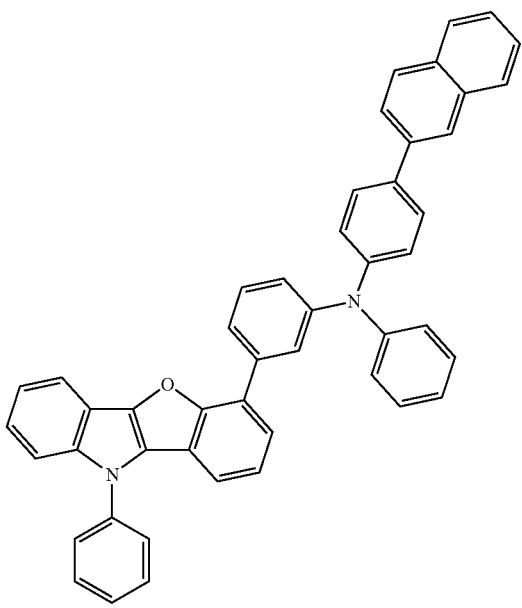

A121
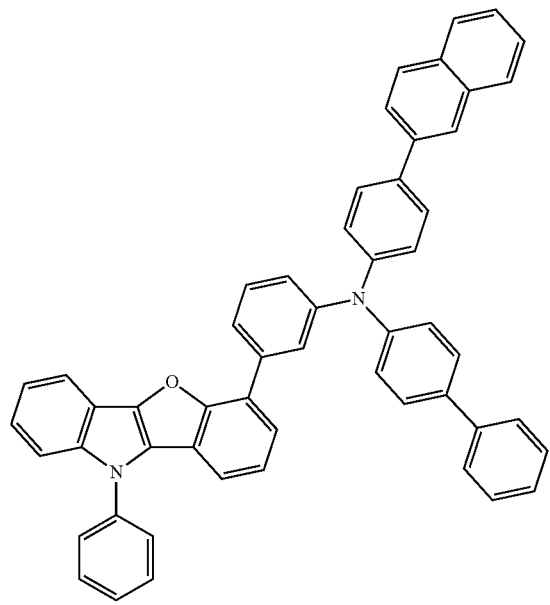
A122
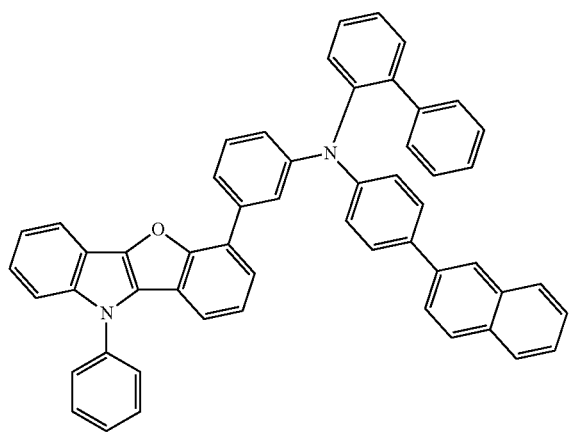
A123
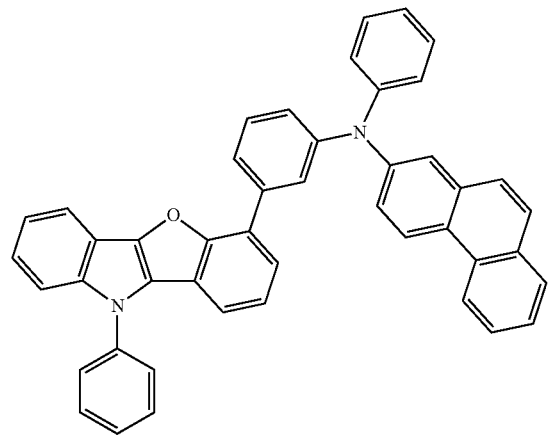
A124
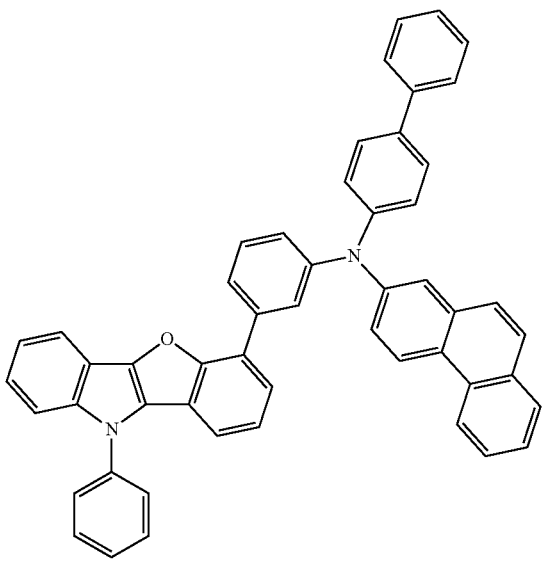
A125
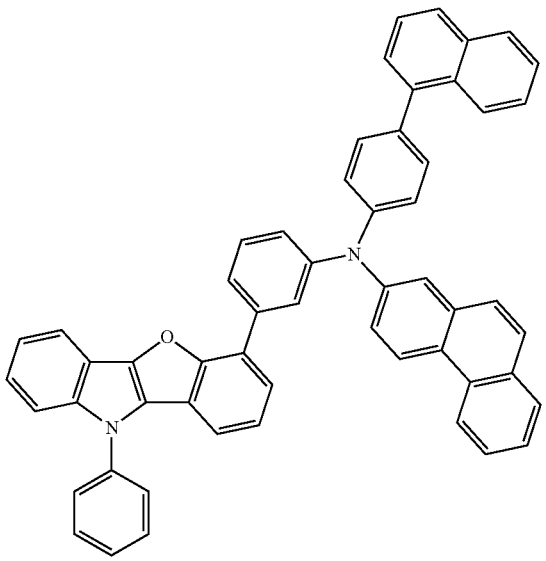
A126
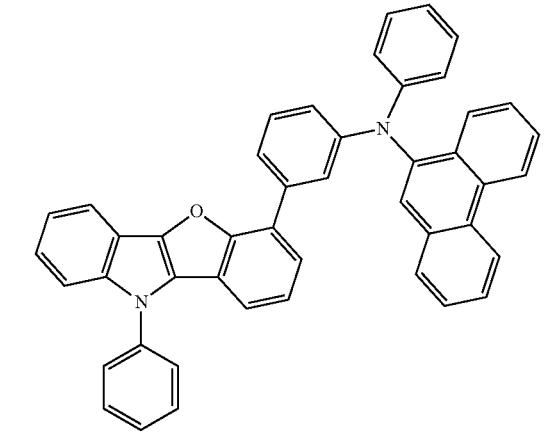

A127
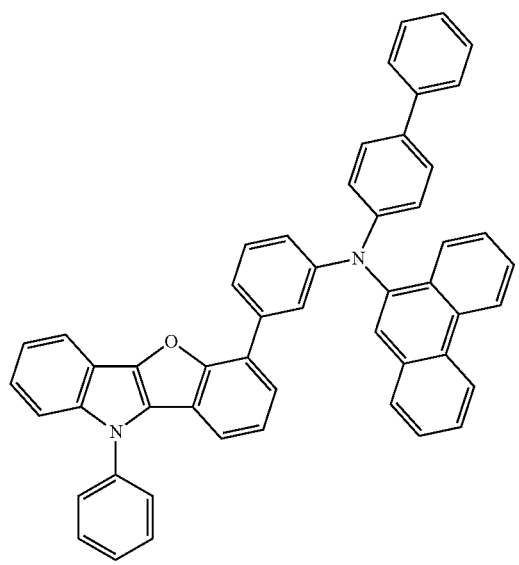
A128
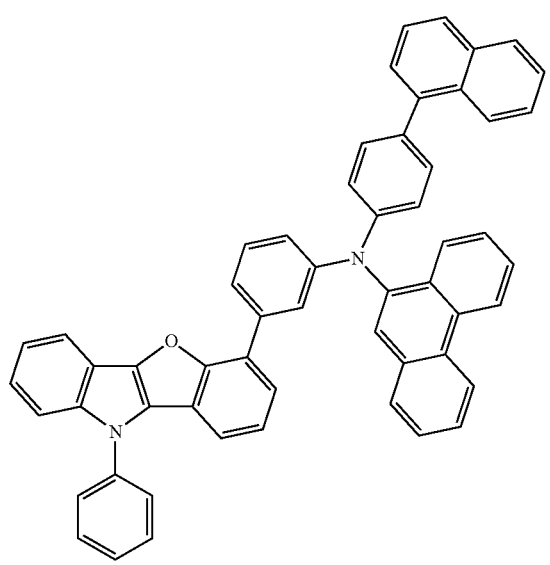
A129
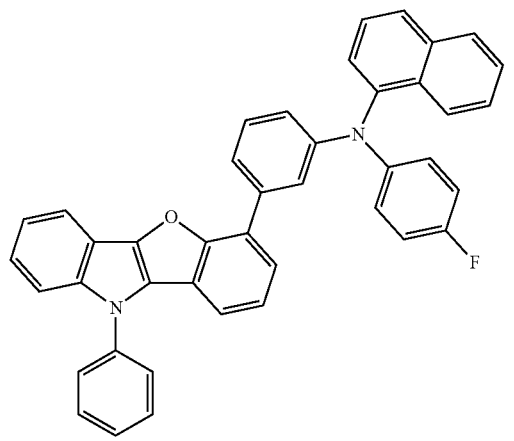
A130
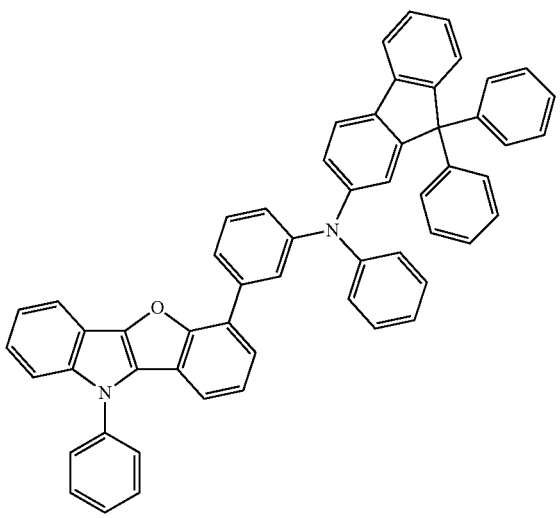
A131
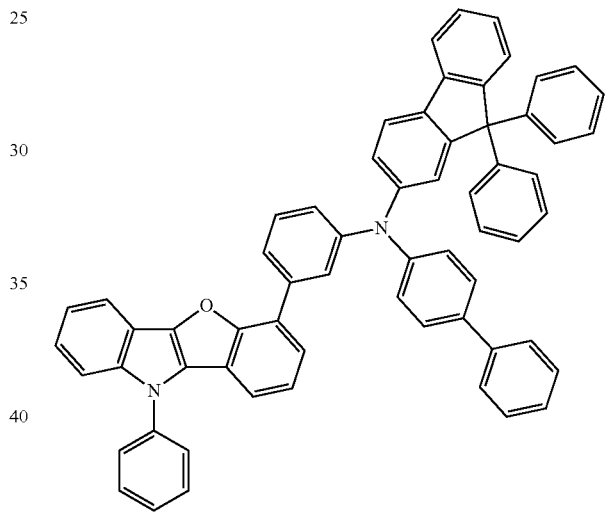
A132
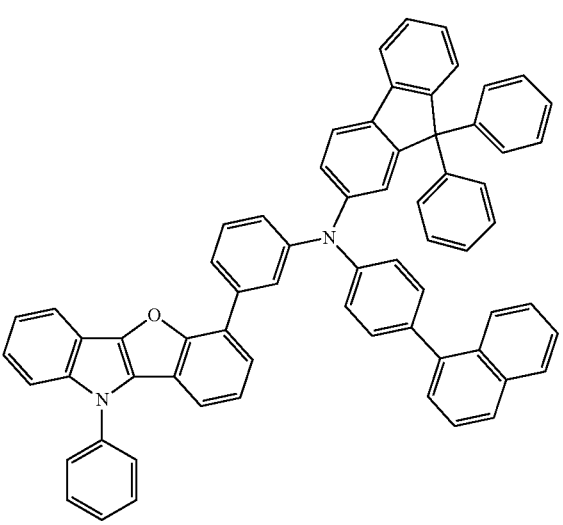

-continued
A133
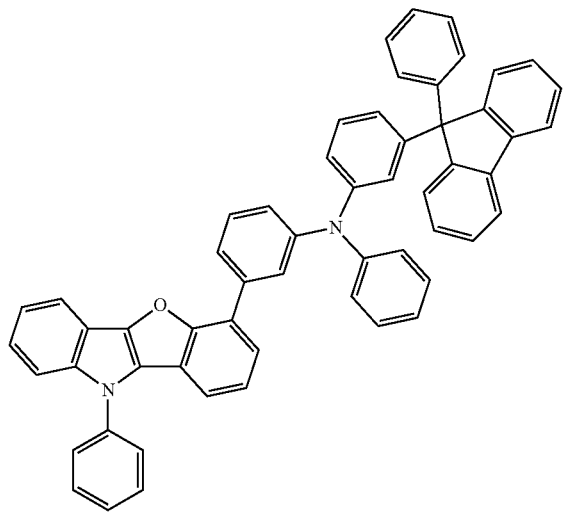
A134
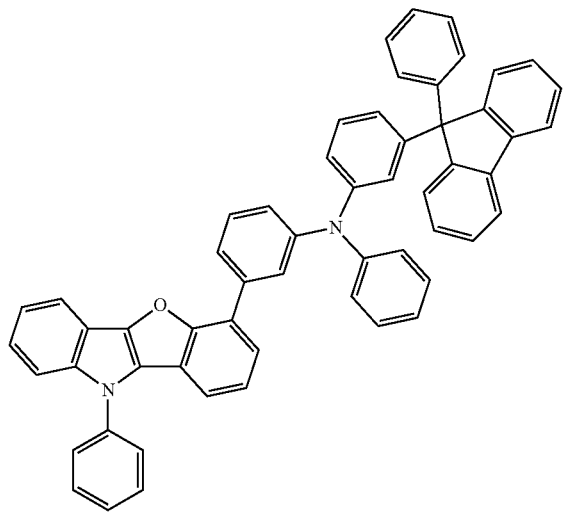
A135
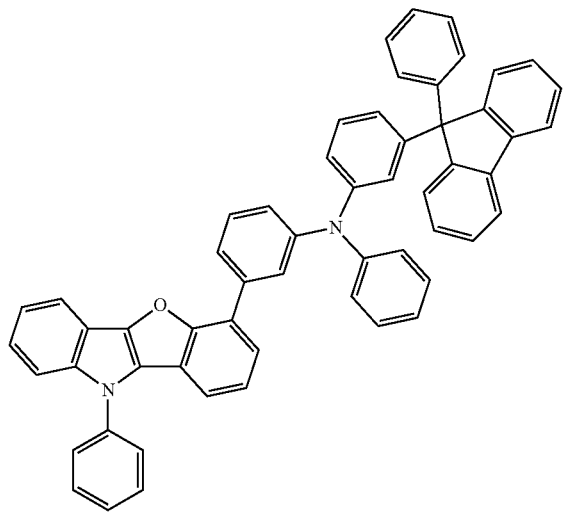
-continued
A136
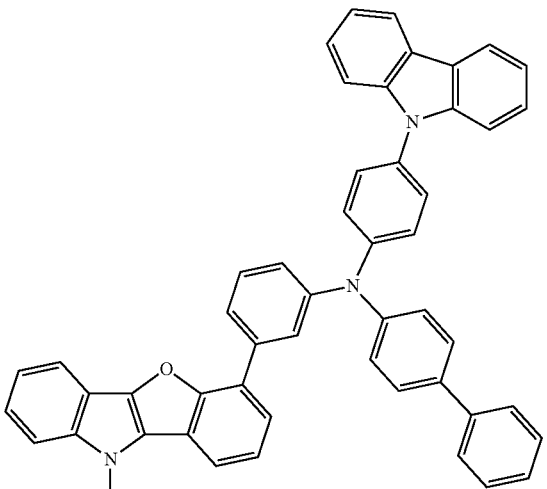
A137
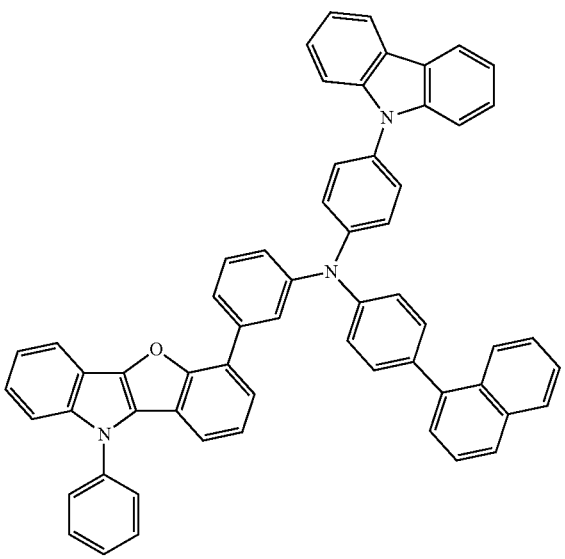
A138
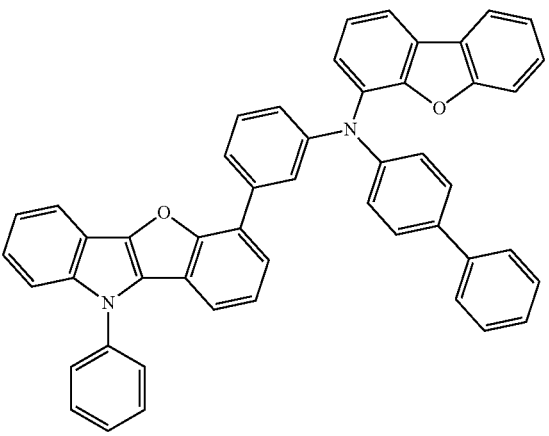

A139
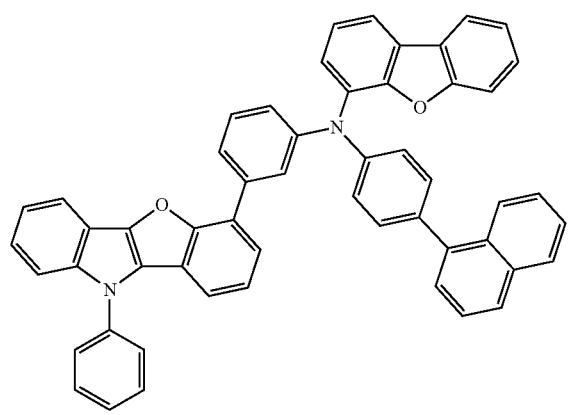
A140
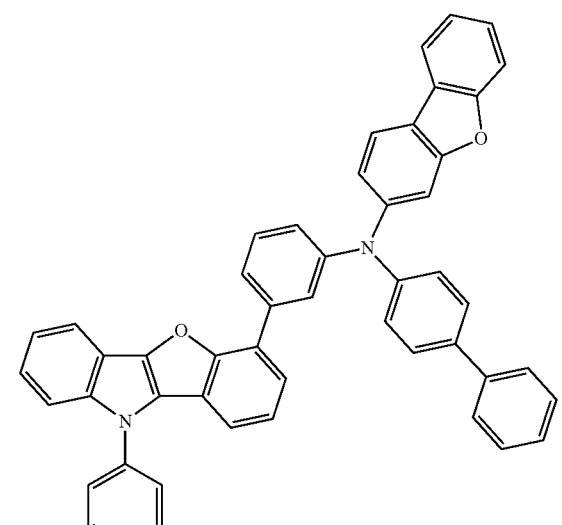
A141
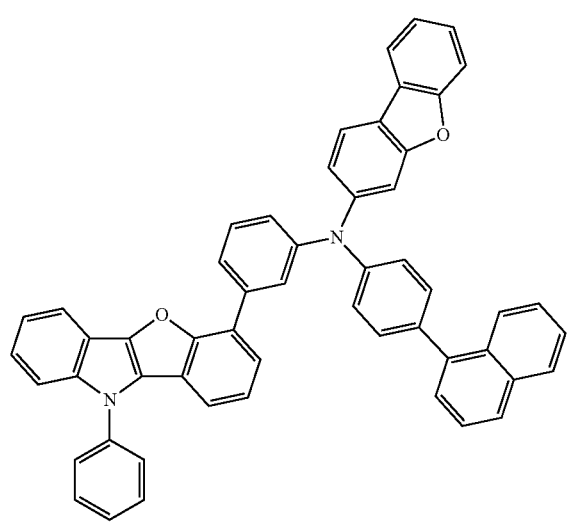
A142
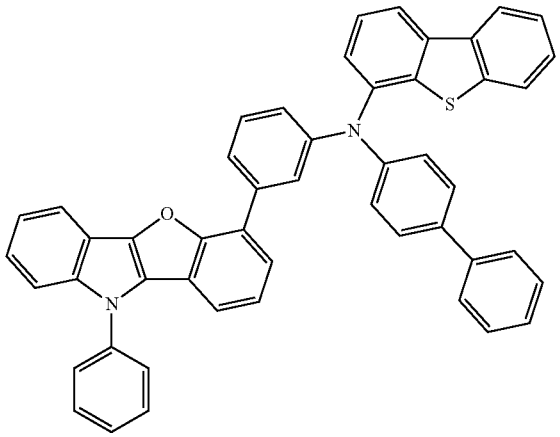
A143
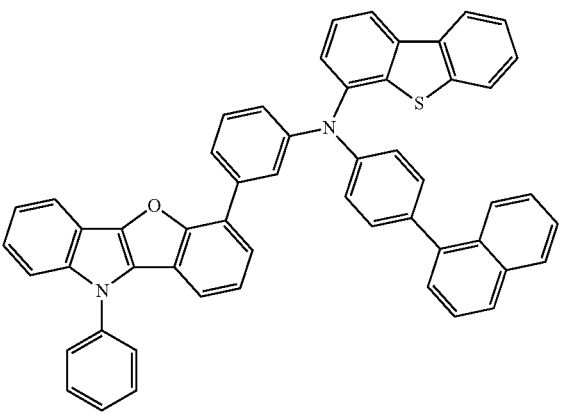
A144
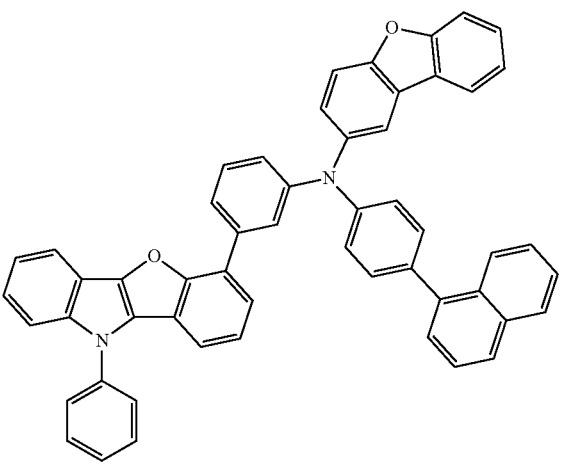

A145
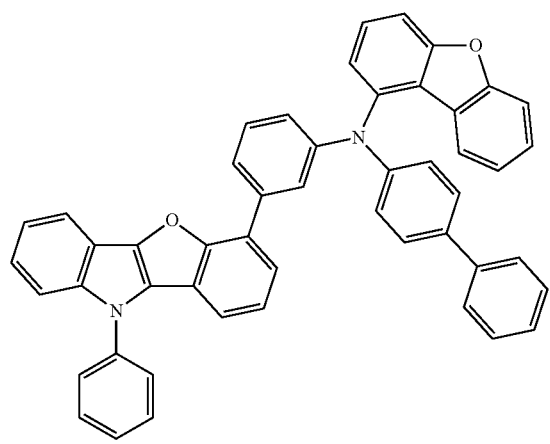
A146
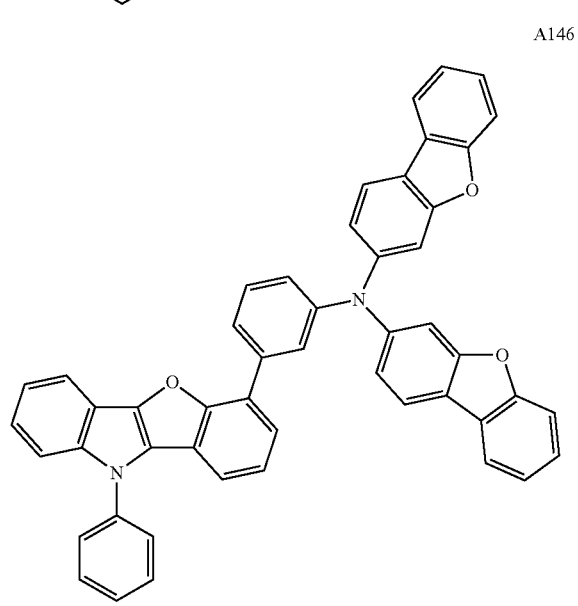
A147
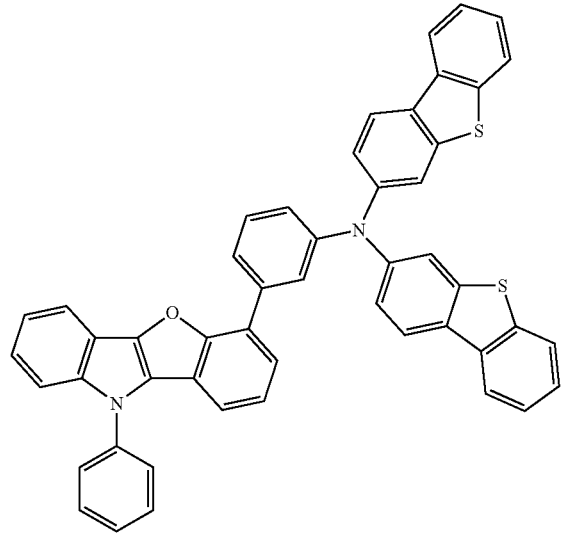
A148
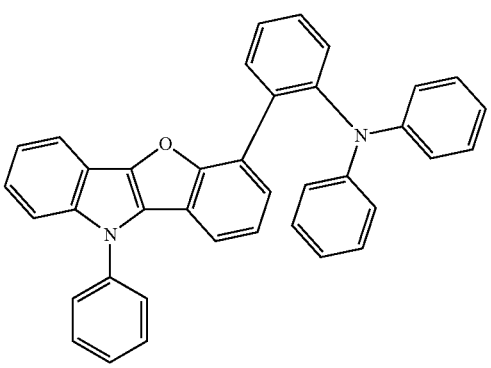
A149
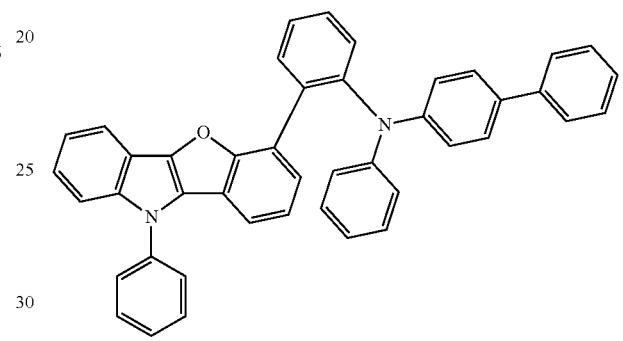
A150
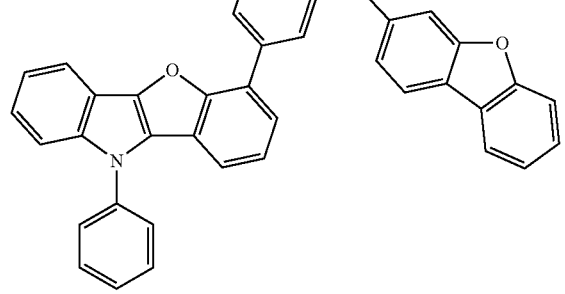
A151
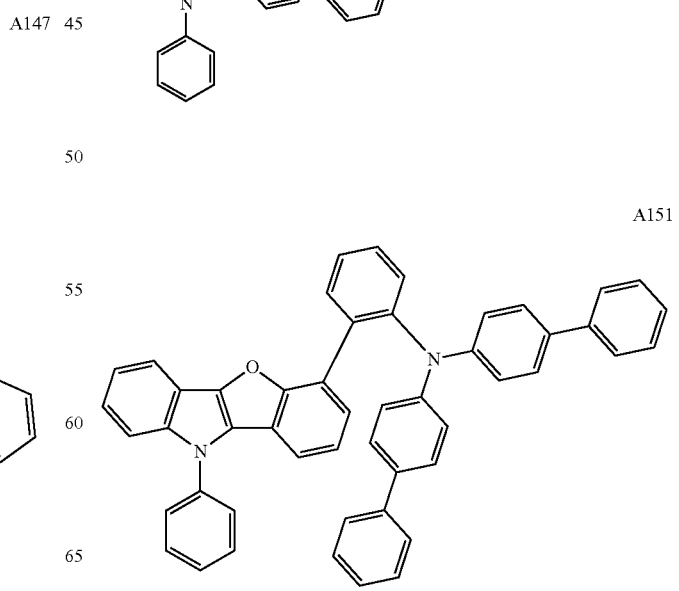

A152
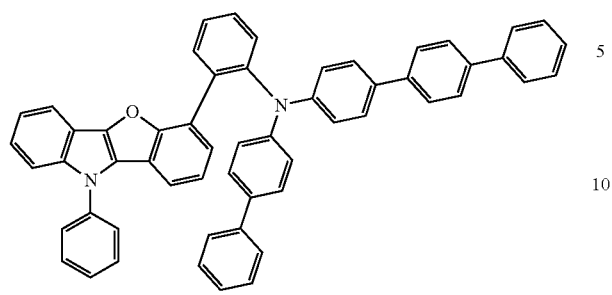
A153
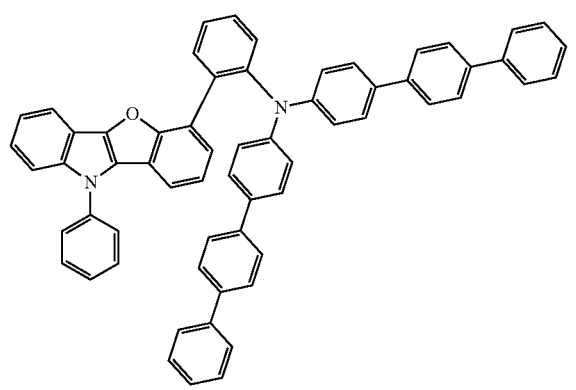
A154
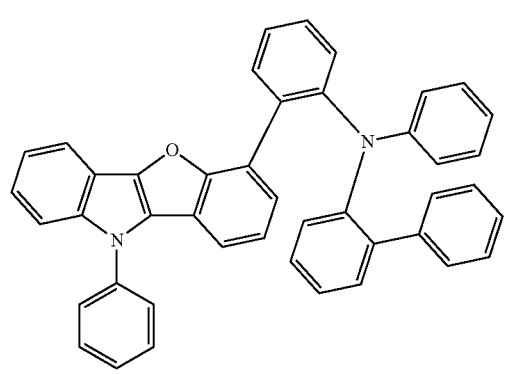
A155
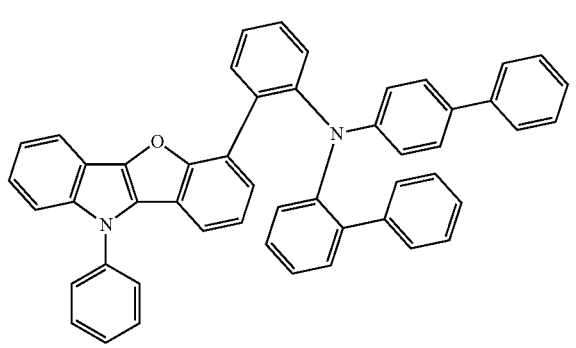
A156
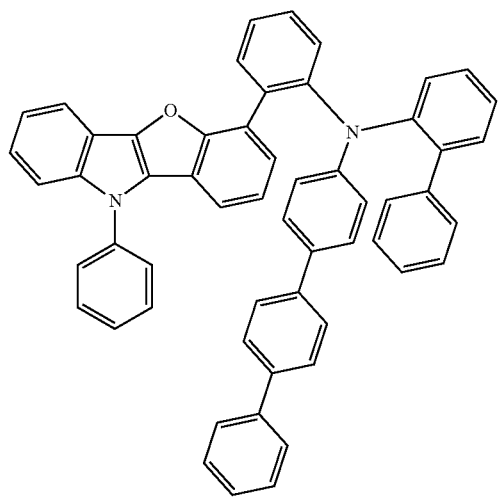
A157
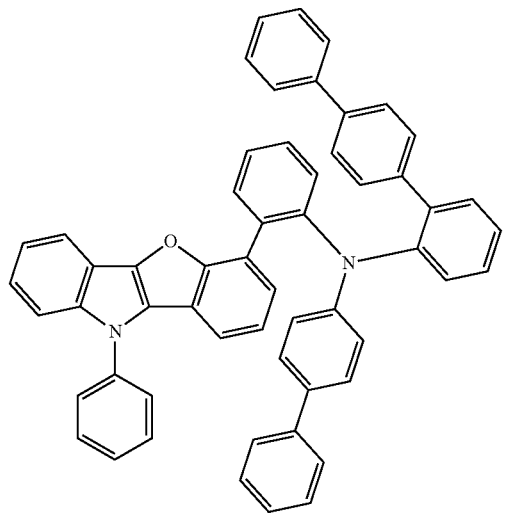
A158
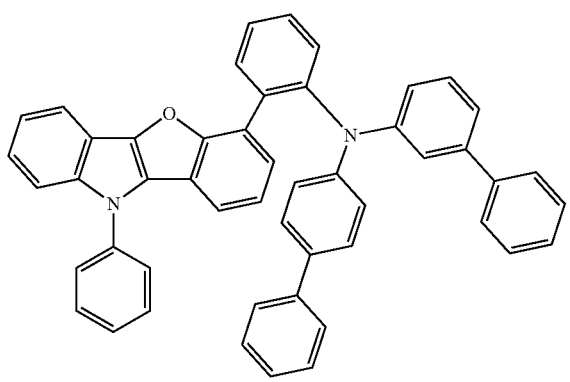

-continued
A159
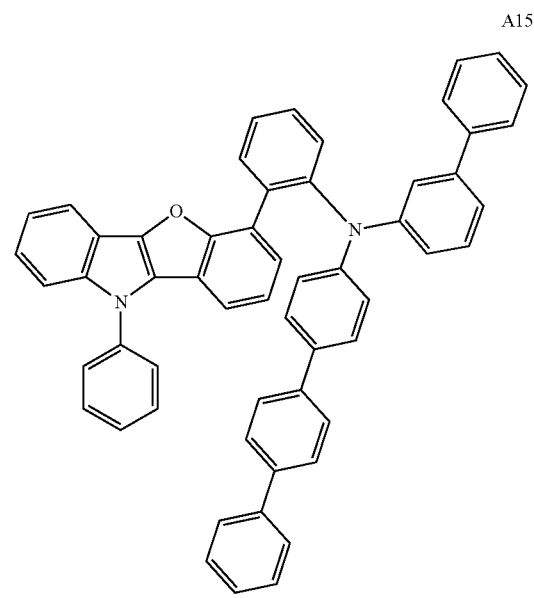
A160
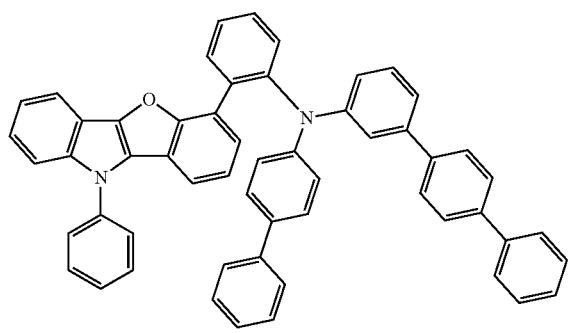
A161
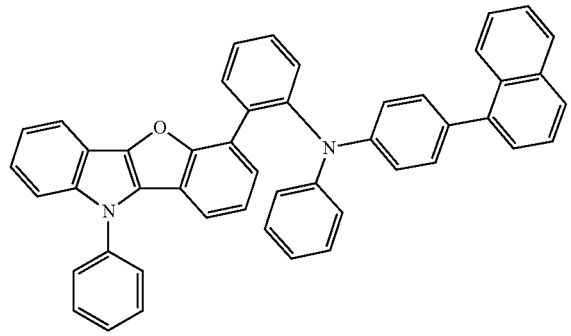
-continued
A162
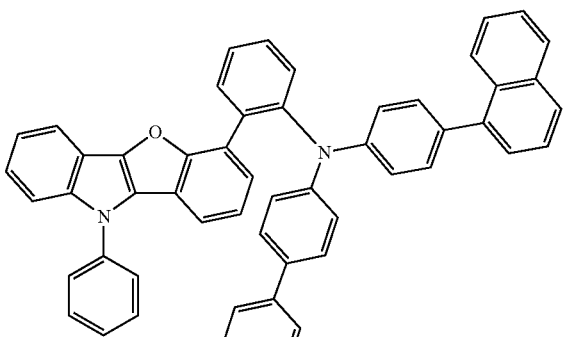
A163
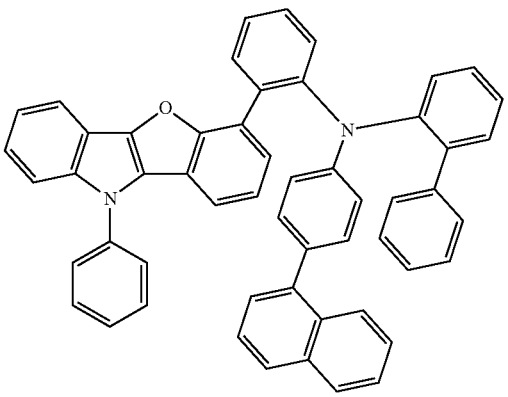
A164
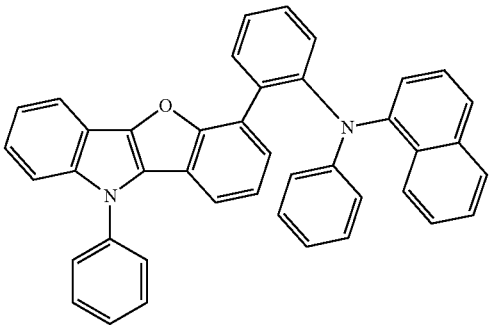
A165
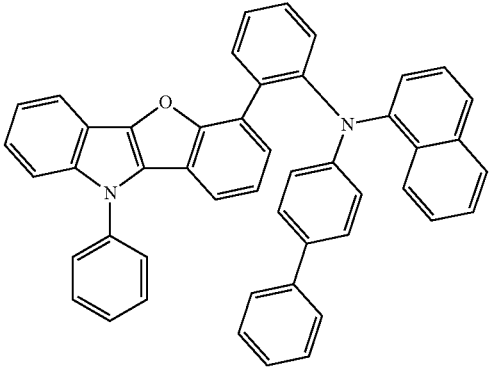

A166
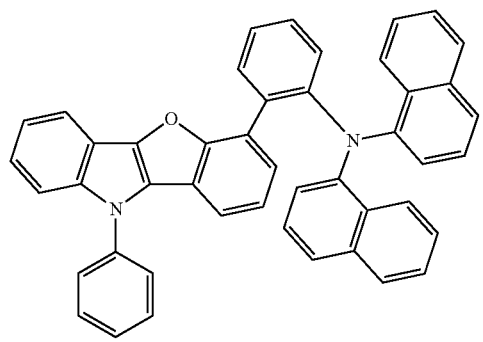
A167
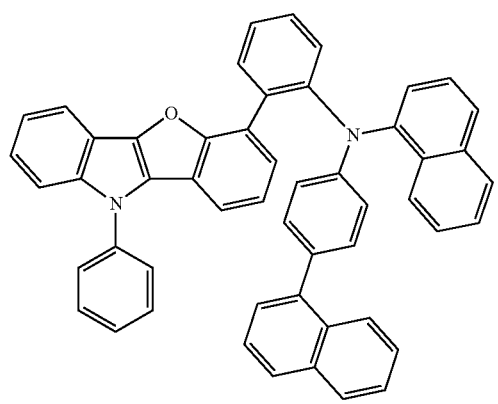
A168
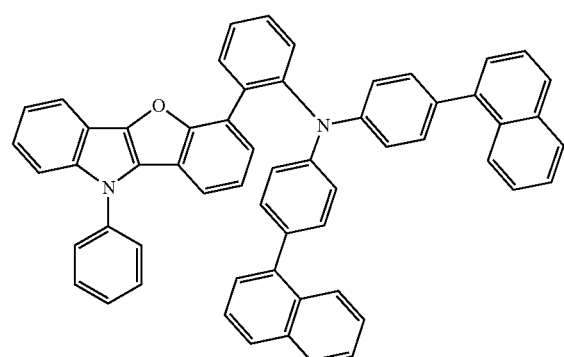
A169
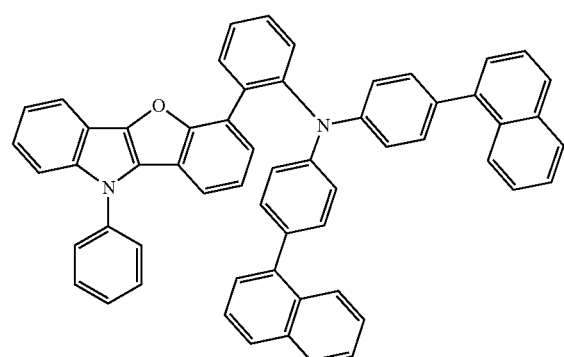
A170
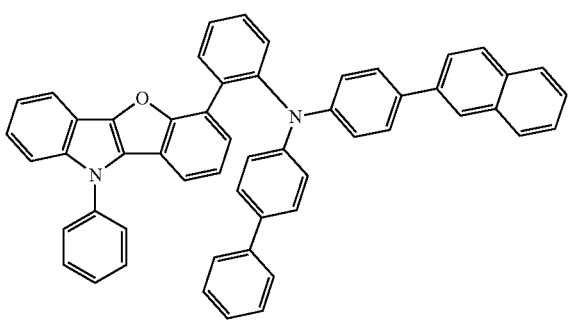
A171
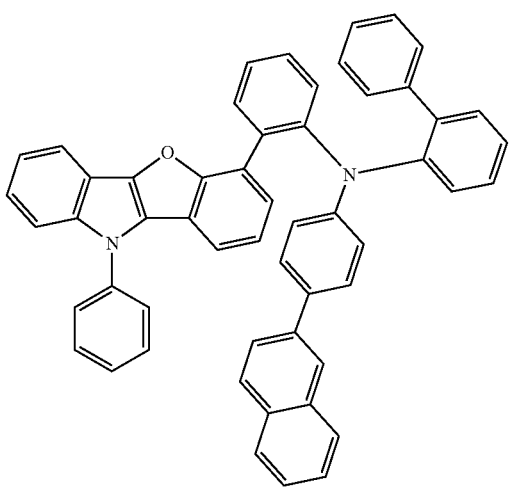
A172
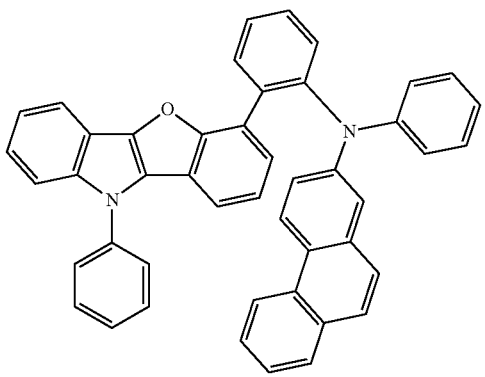
A173
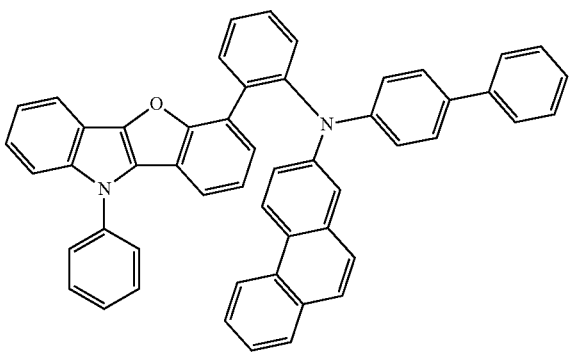

A174
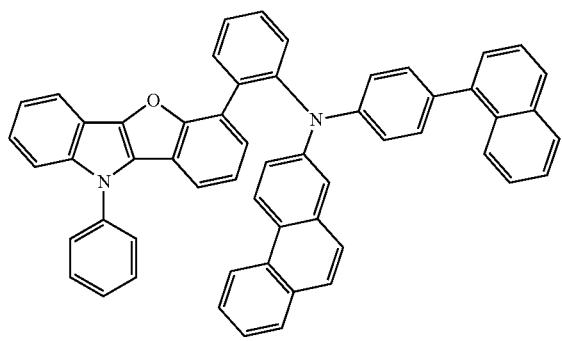
A175
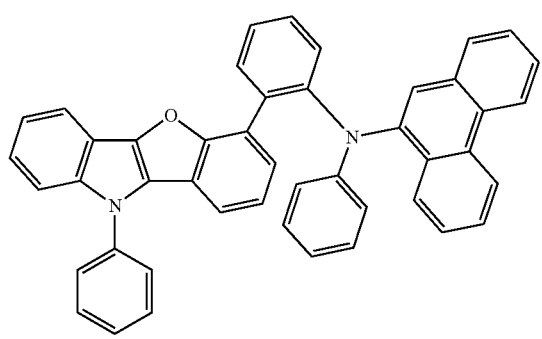
A176
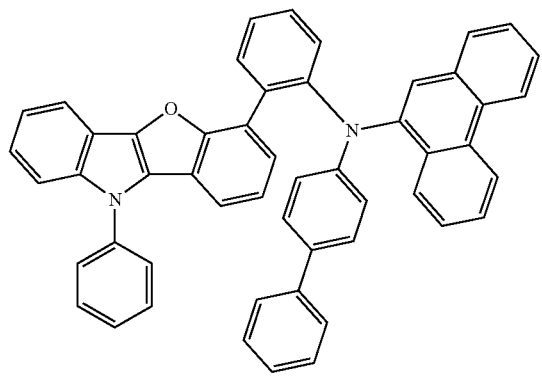
A177
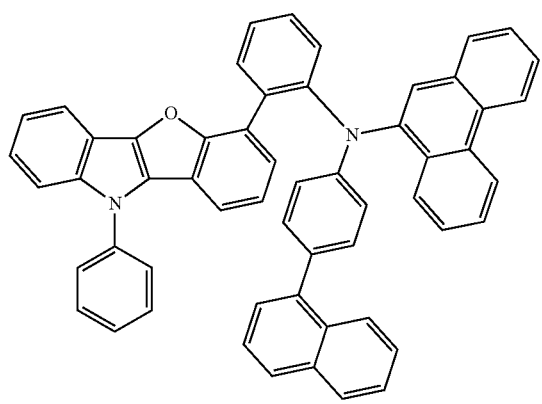
A178
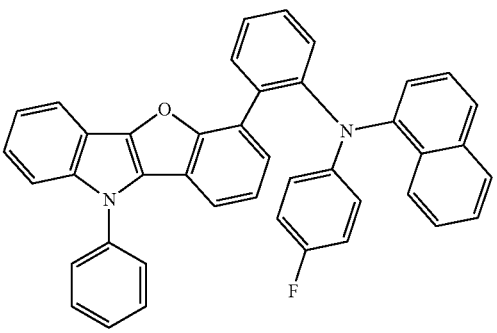
A179
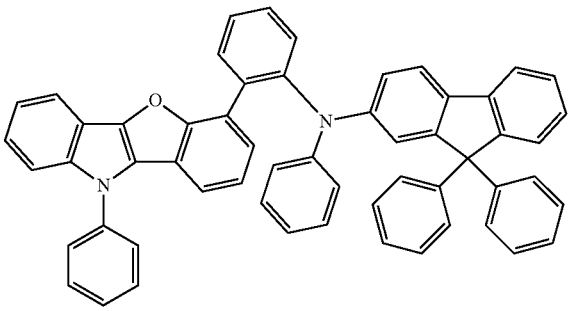
A180
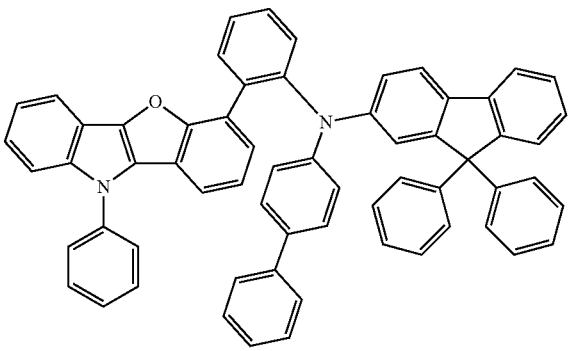
A181
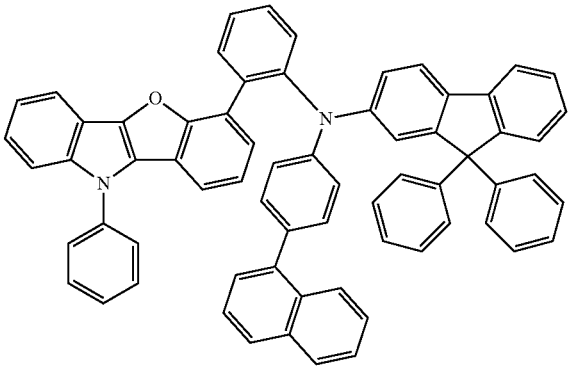

-continued
A182
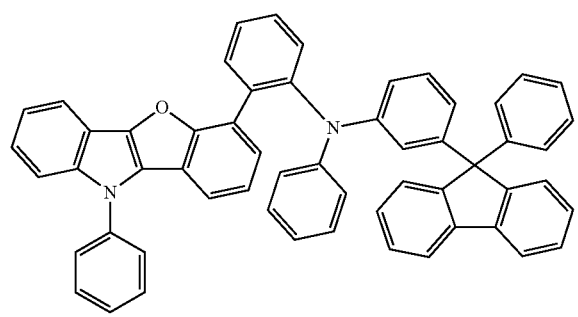
A183
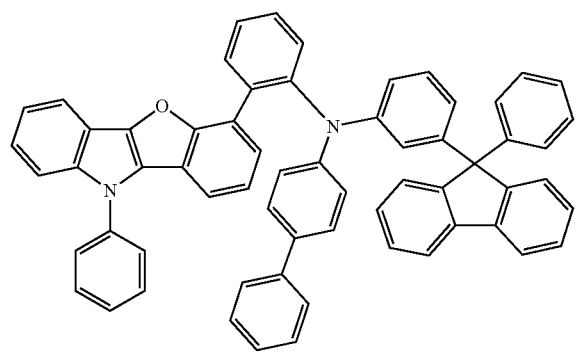
A184
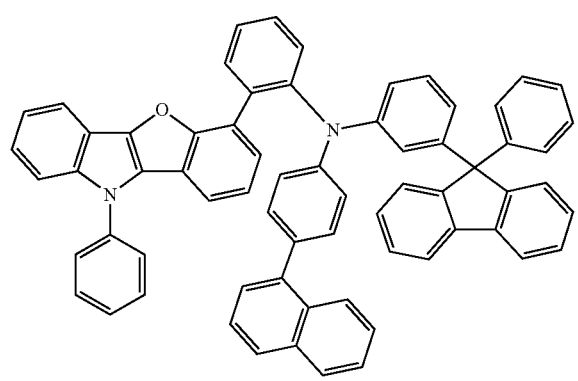
A185
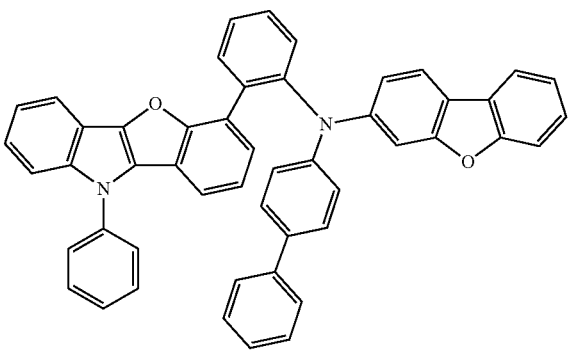
-continued
A186
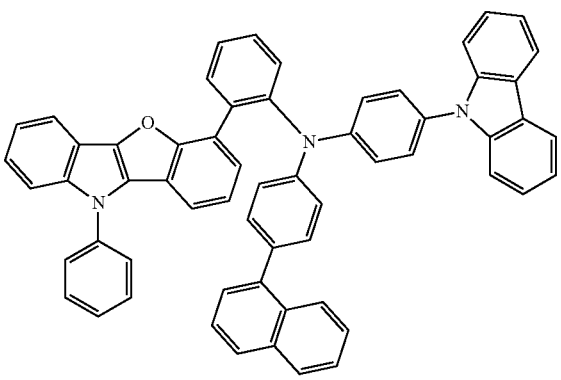
A187
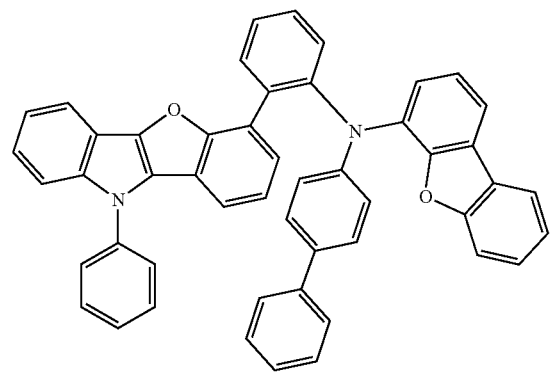
A188
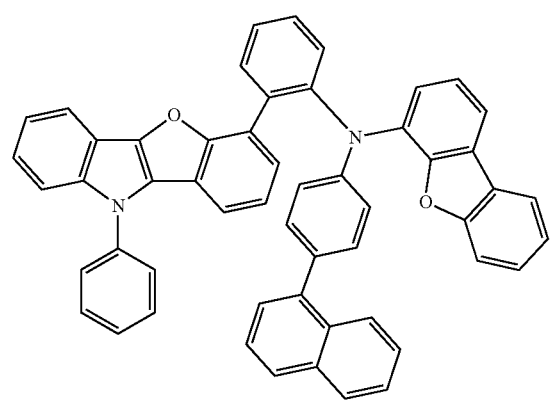
A189

403
-continued
A190
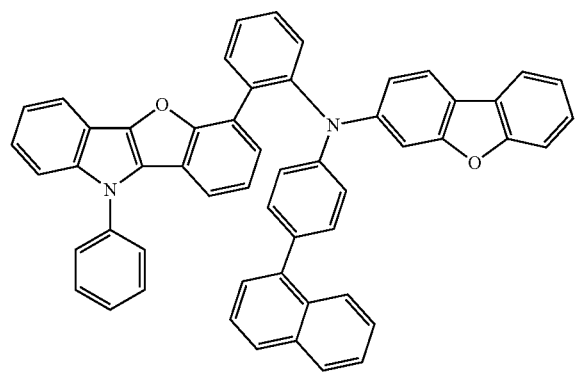
A191
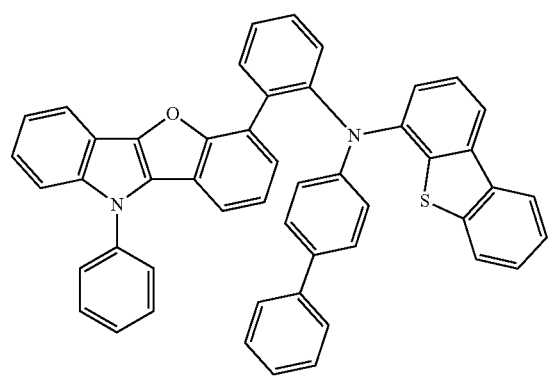
A192
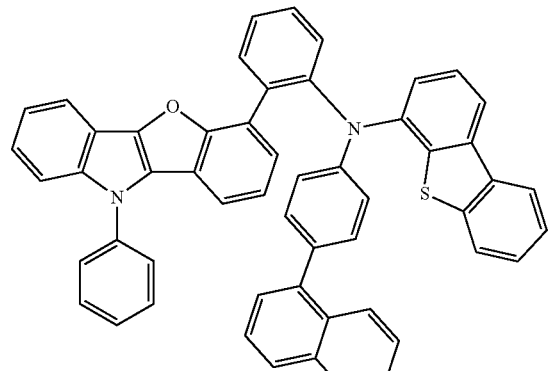
A193
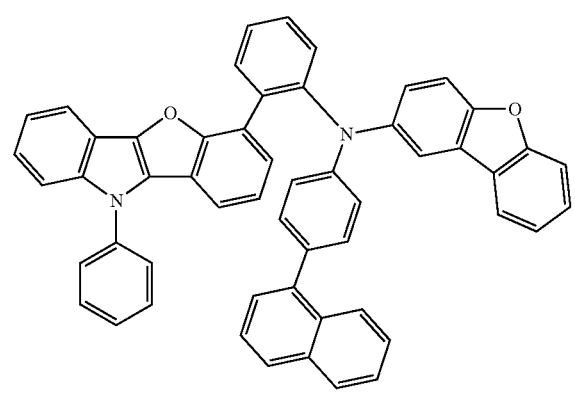
404
-continued
A194
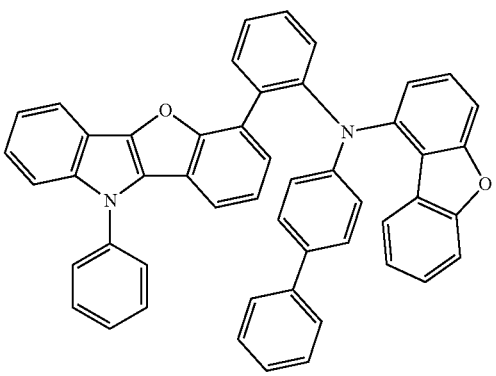
A195
A196
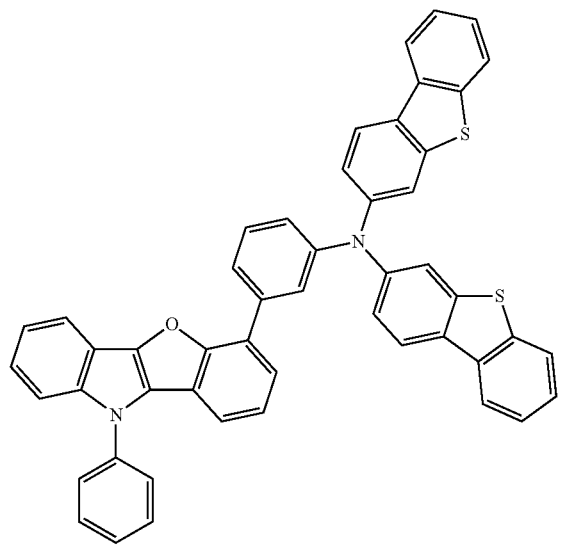

A197
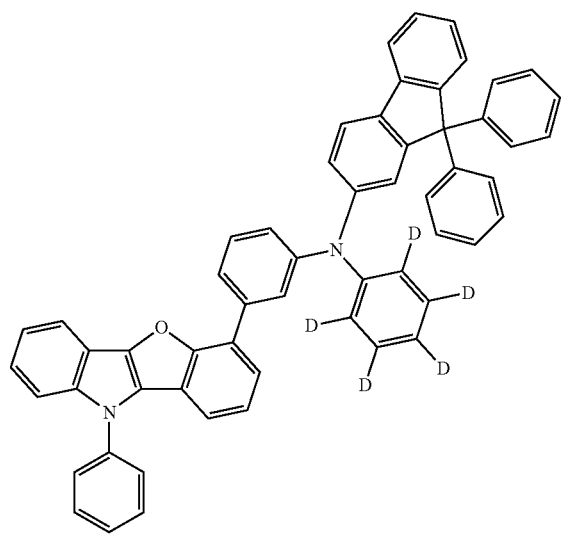
A198
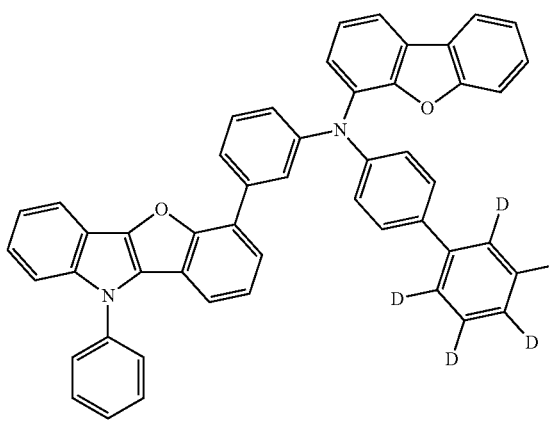
A199
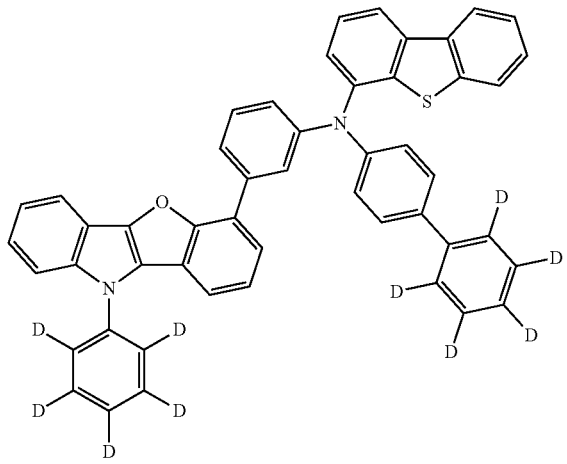
A200
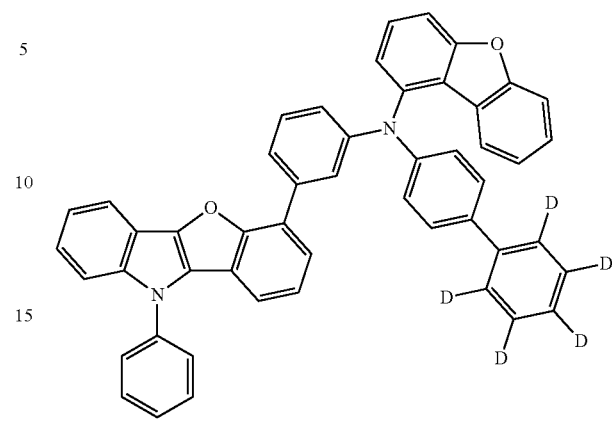
A201
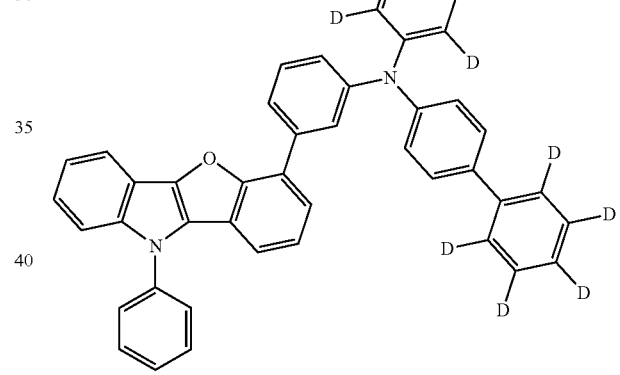
Compound Group 2
B1
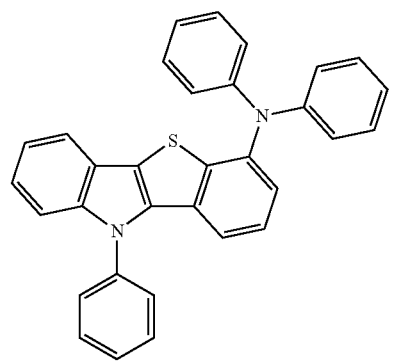

B2
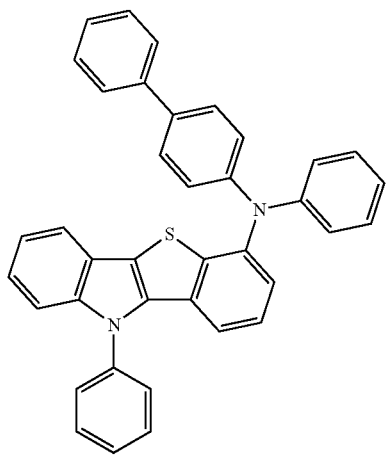
B3
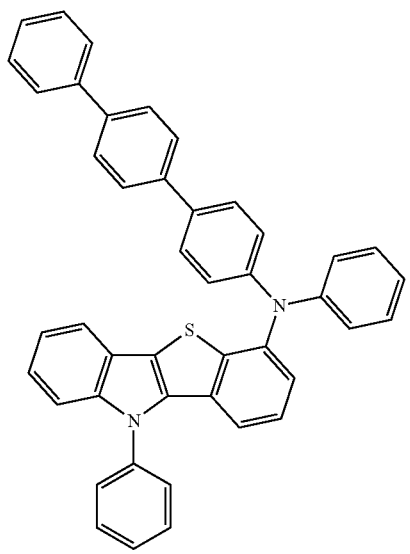
B4
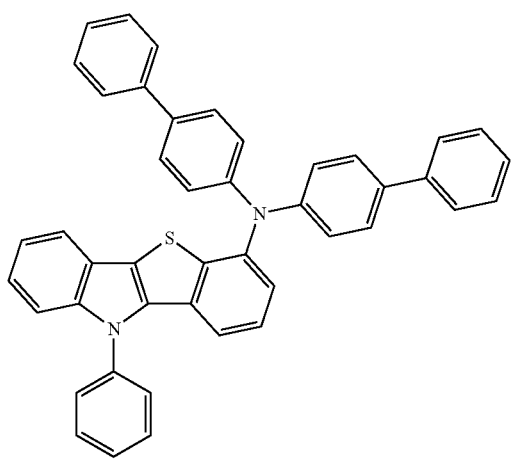
B5
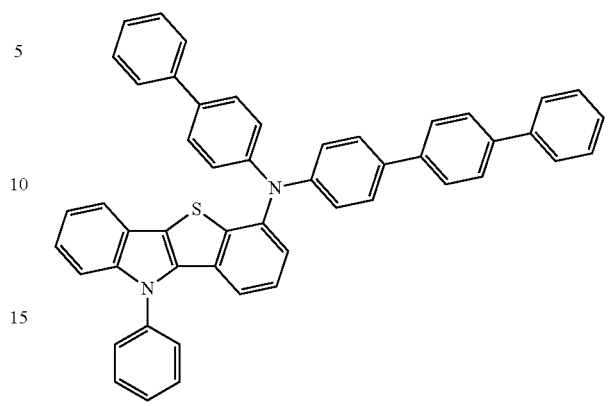
B6
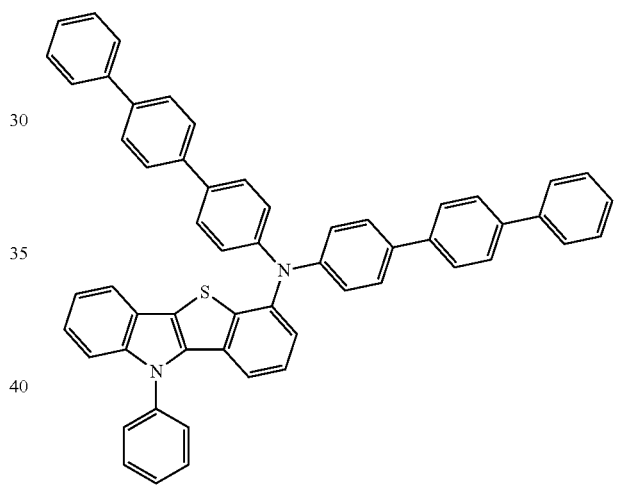
B7
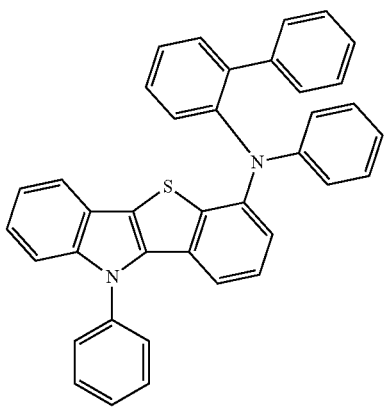

B8
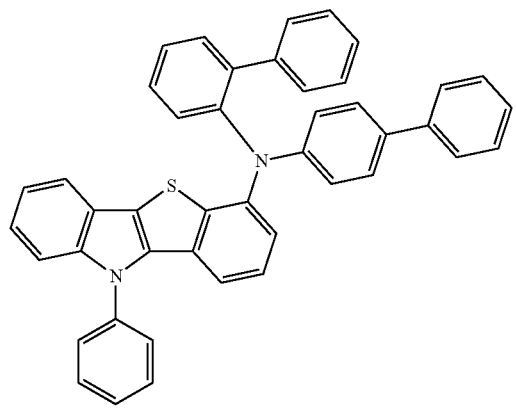
B9
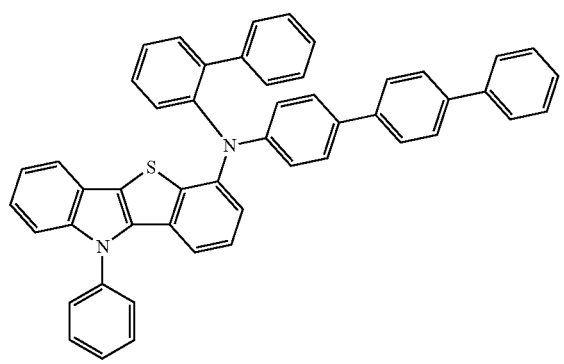
B10
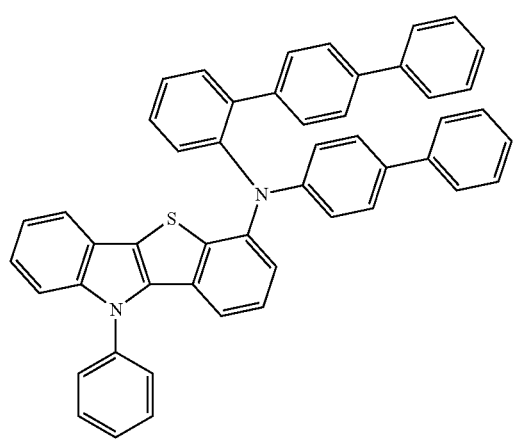
B11
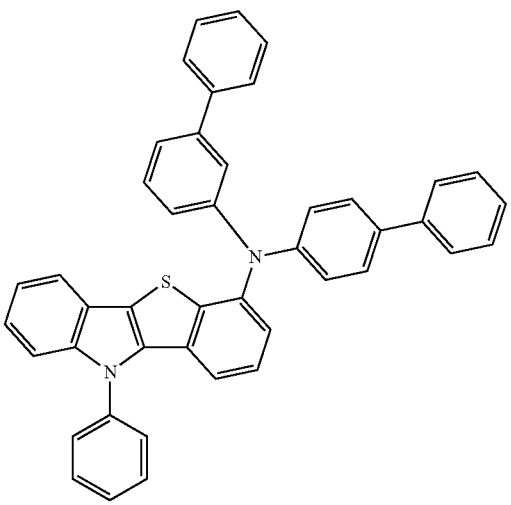
B12
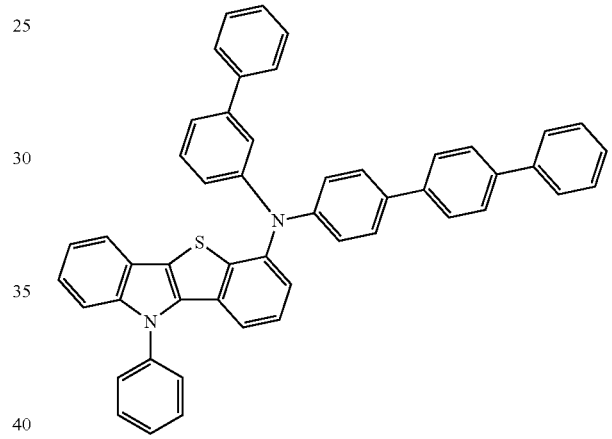
B13
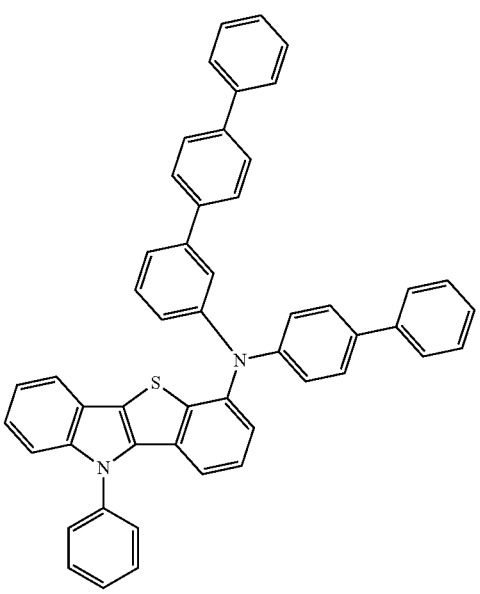

B14
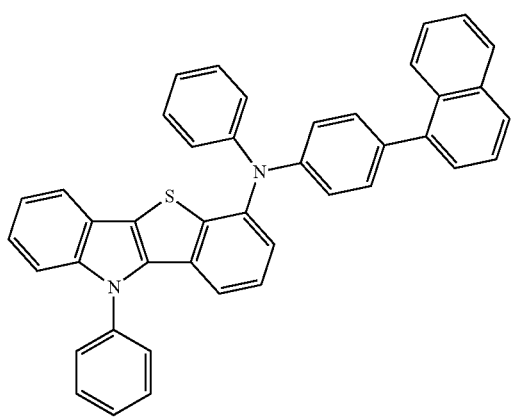
B15
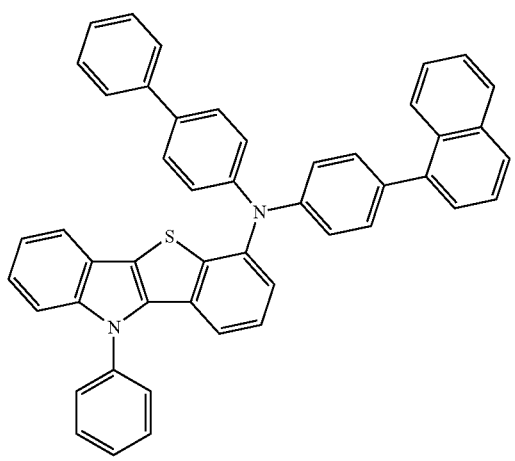
B16
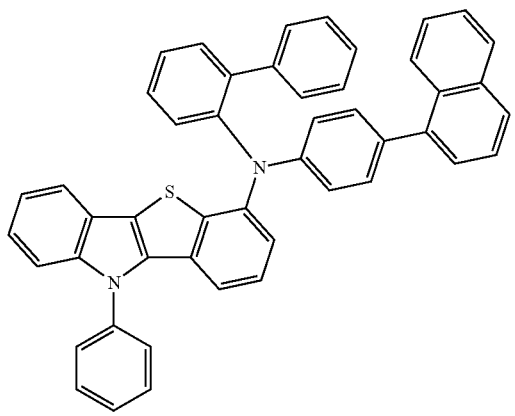
B17
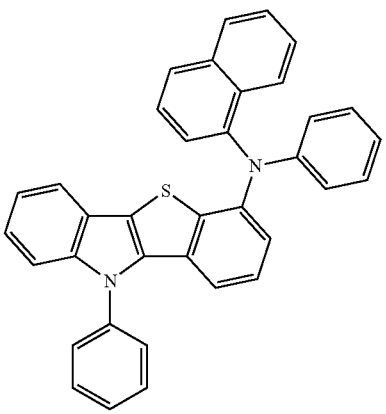
B18
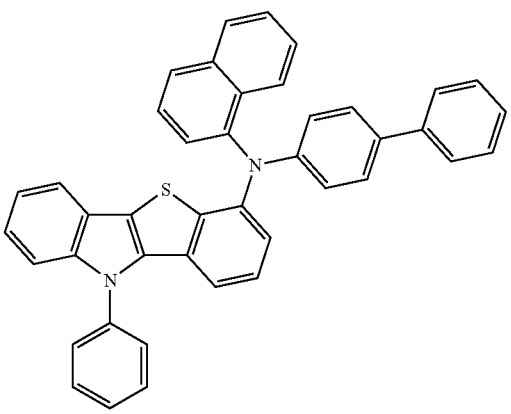
B19
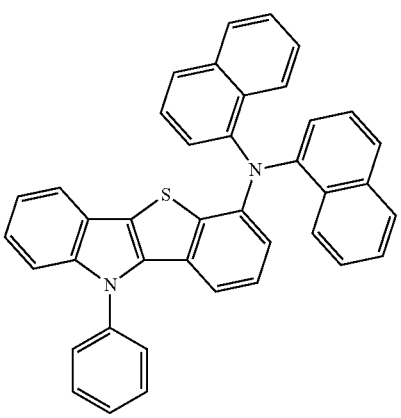

B20
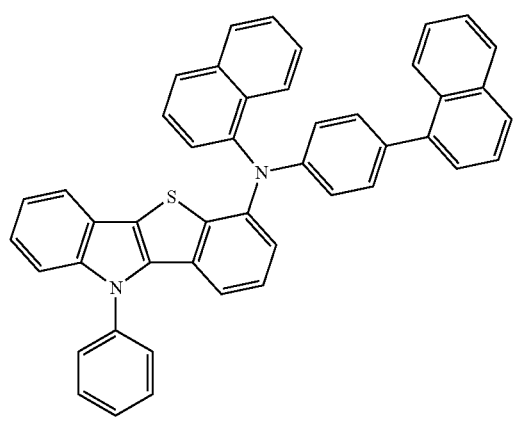
B21
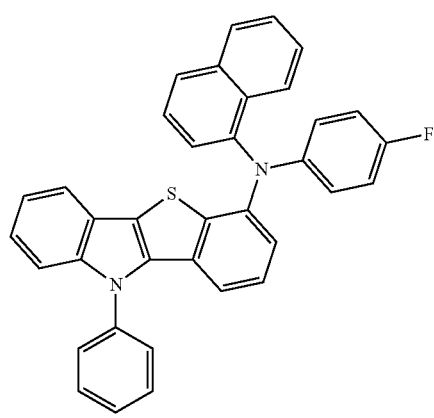
B22
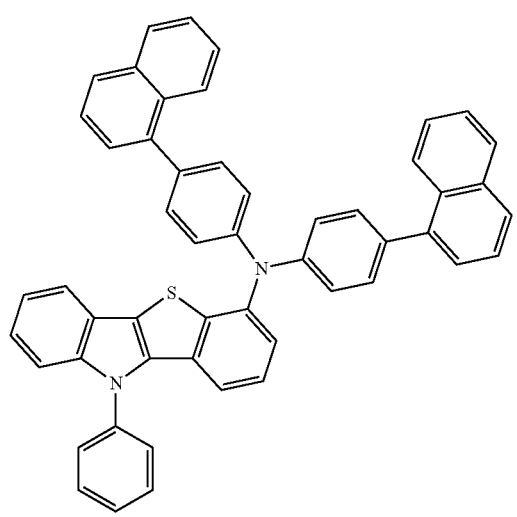
B23
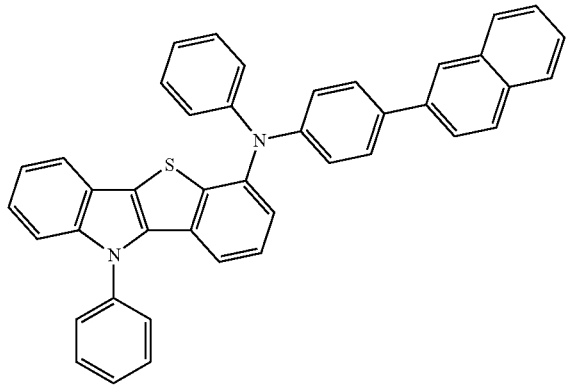
B24
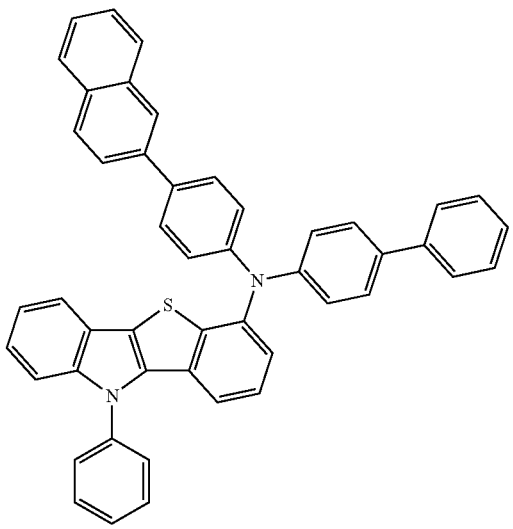
B25
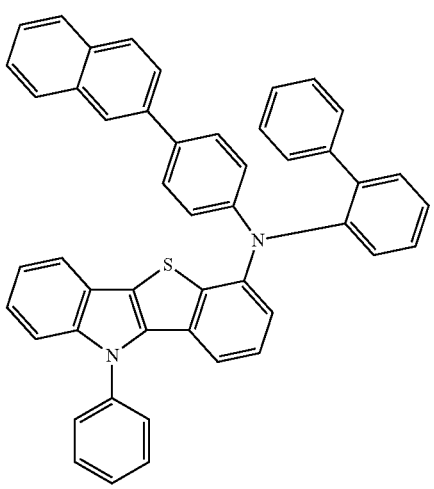

B26
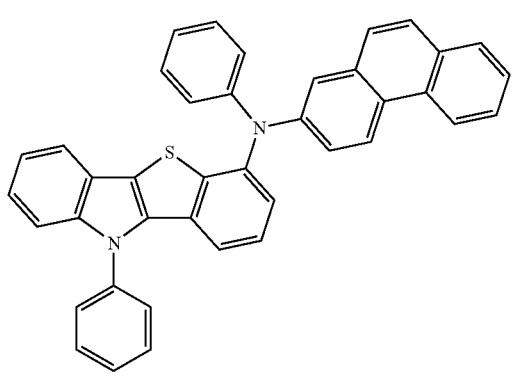
B27
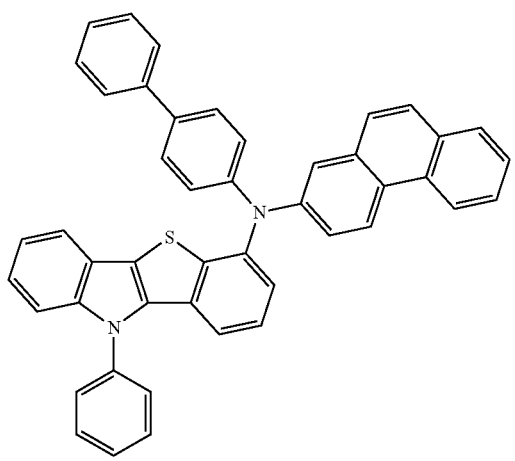
B28
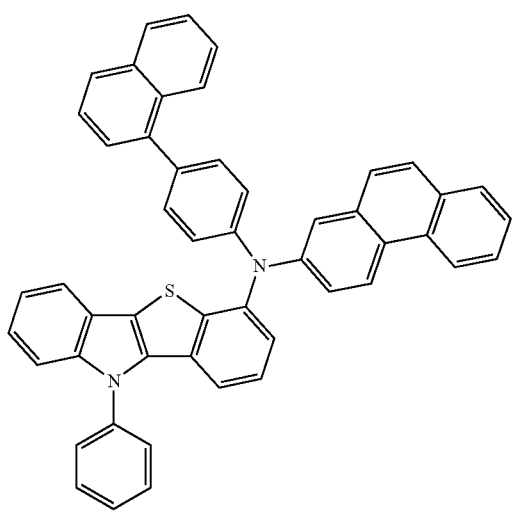
B29
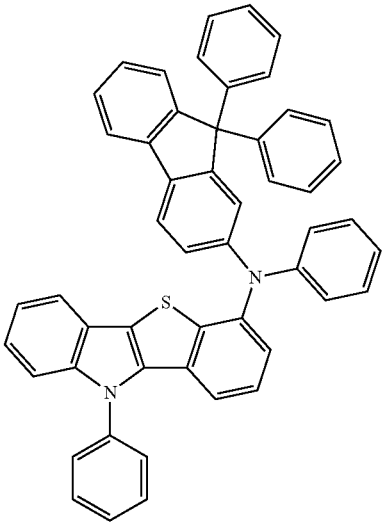
B30
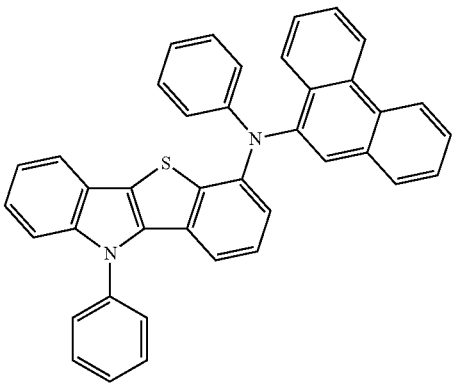
B31
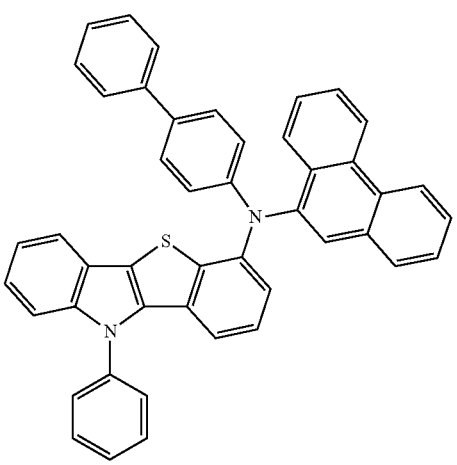

B32
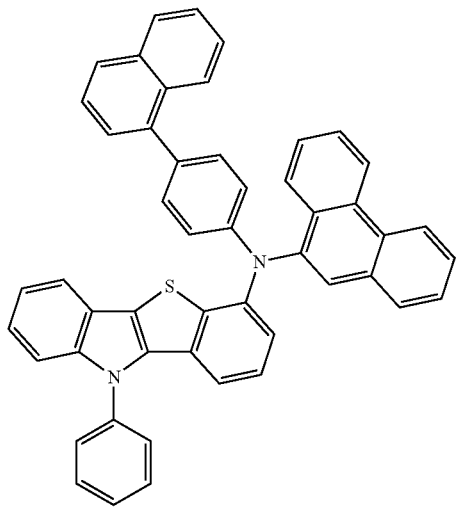
B33
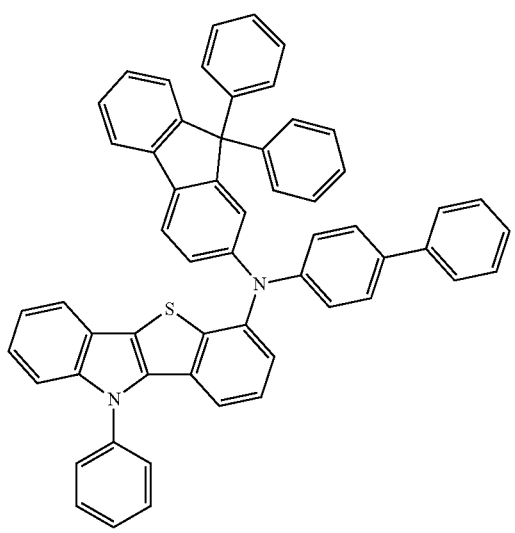
B34
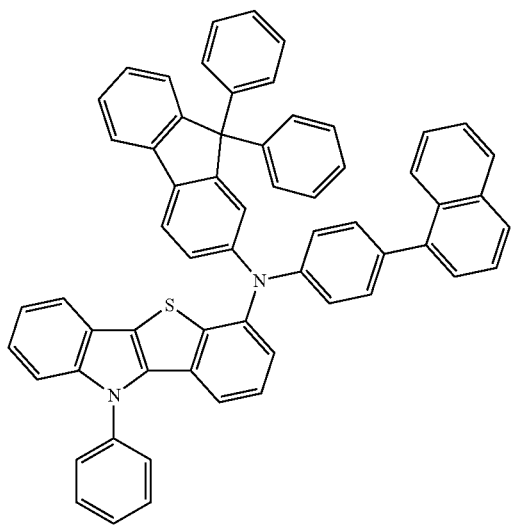
B35
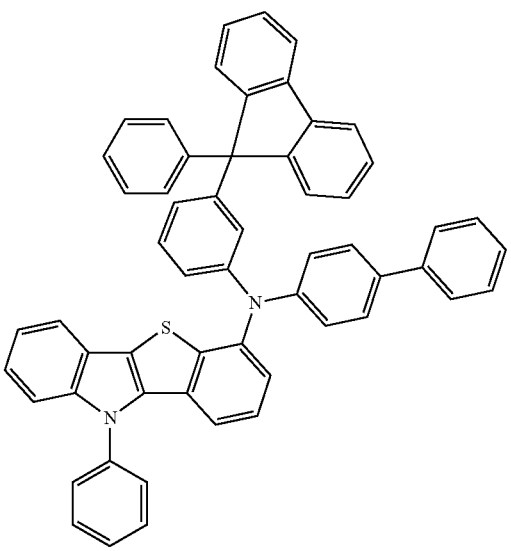
B36

B37
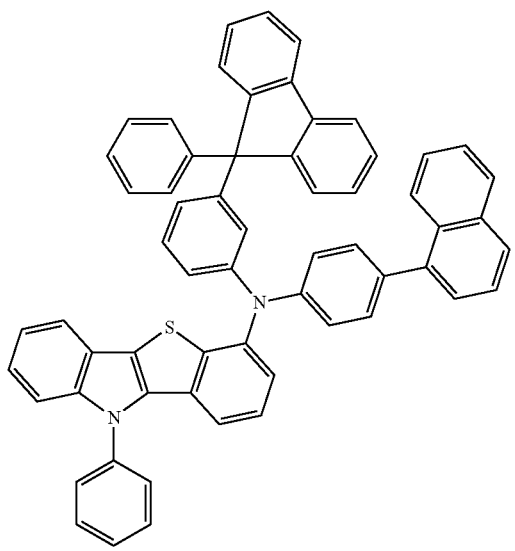
B38
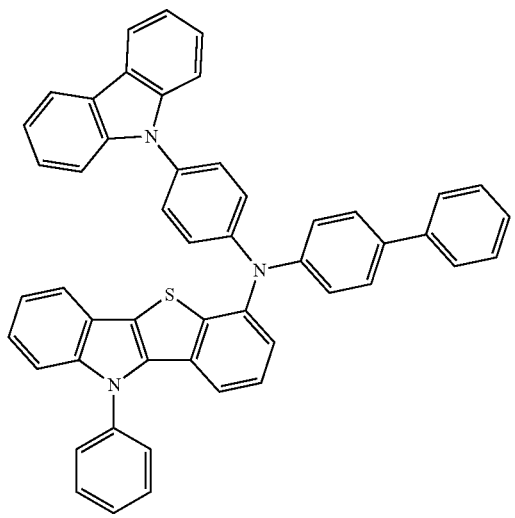
B39
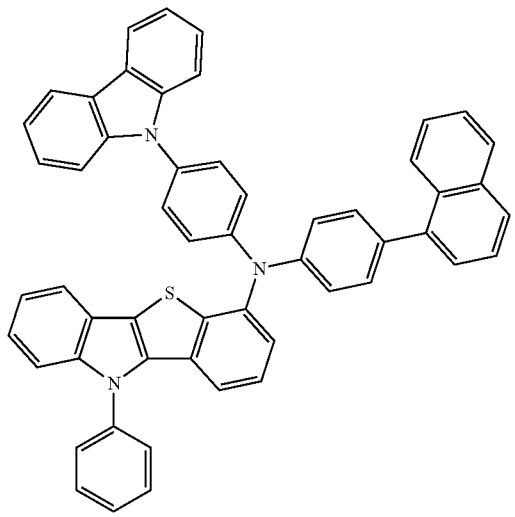
B40
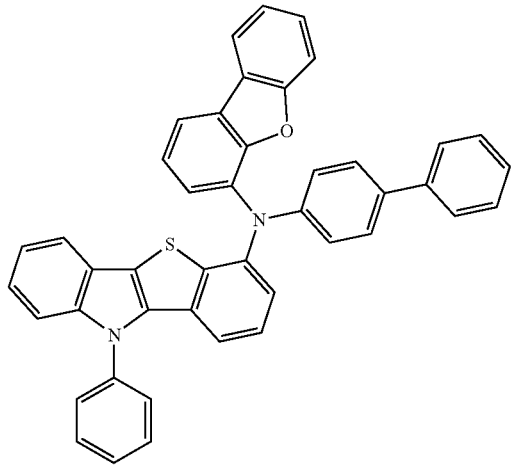
B41
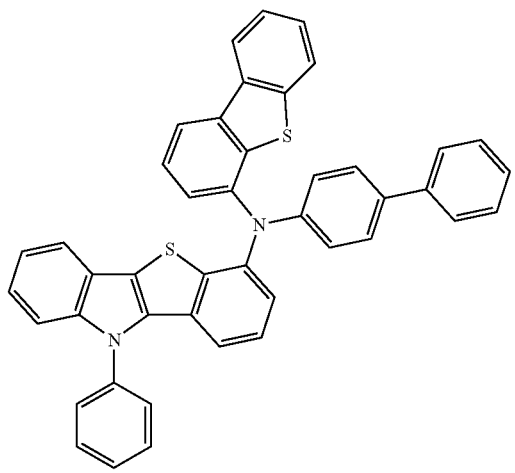
B42
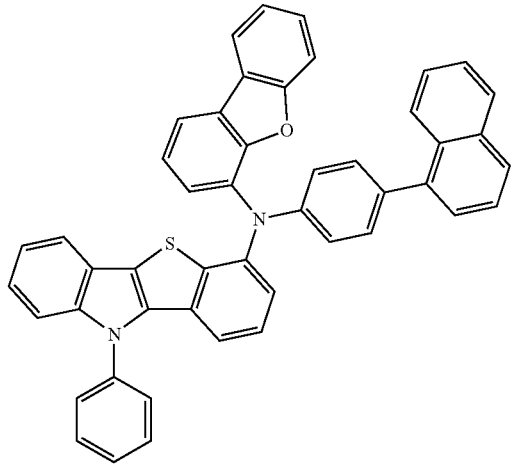

-continued
B43
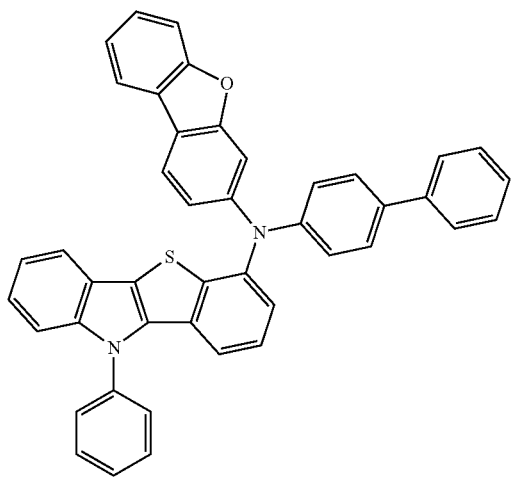
B44
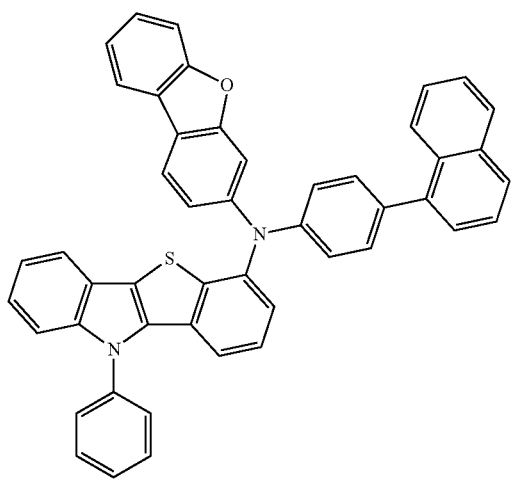
B45
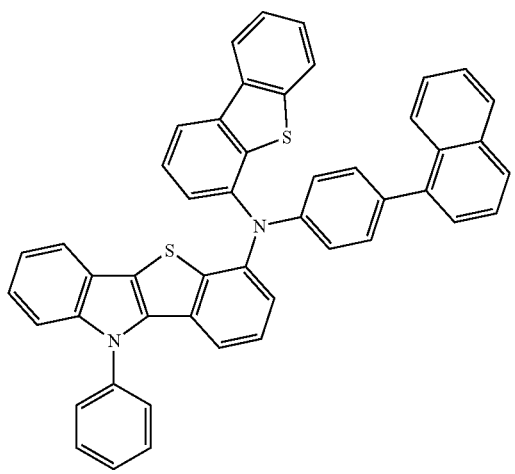
-continued
B46
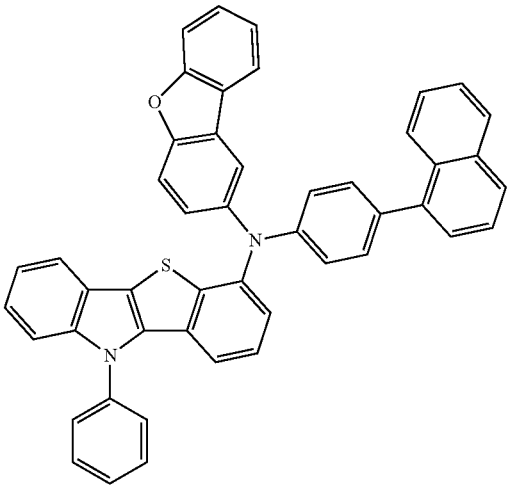
B47
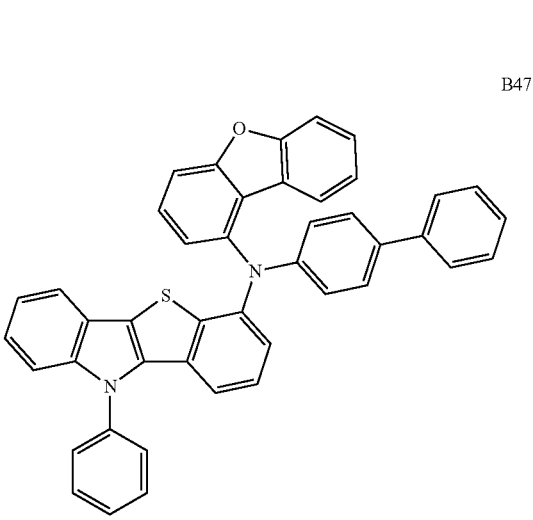
B48
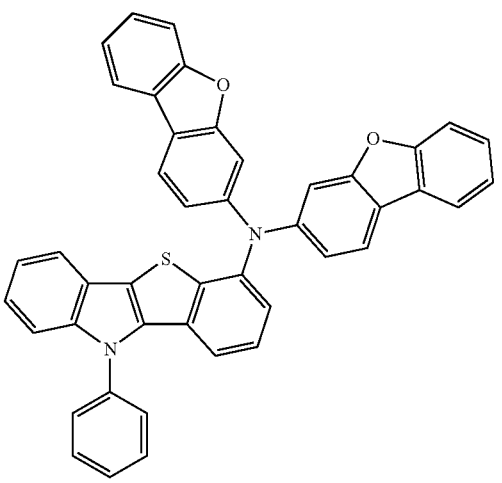

-continued
B49
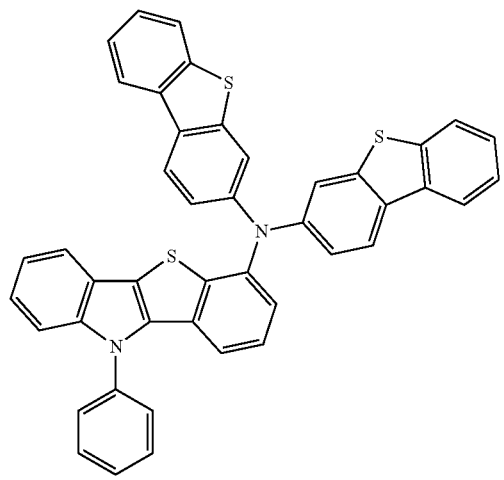
B50
B51
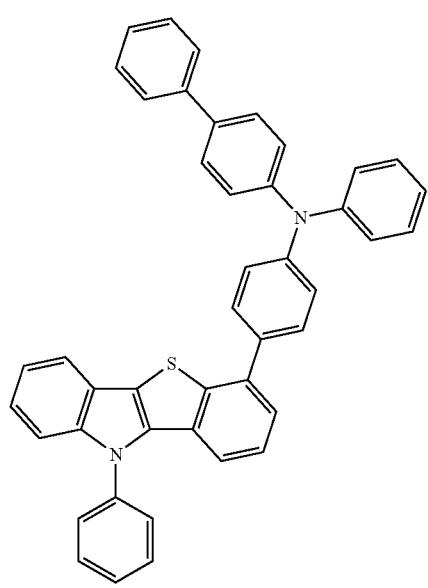
B52
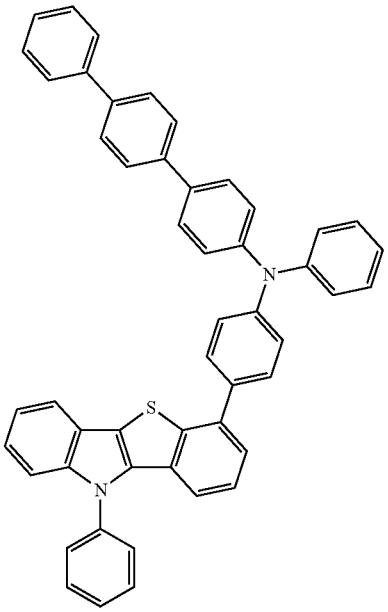
B53

B54
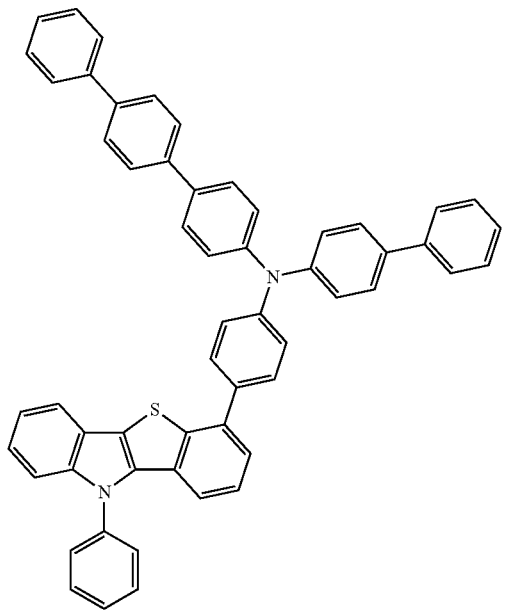
B55
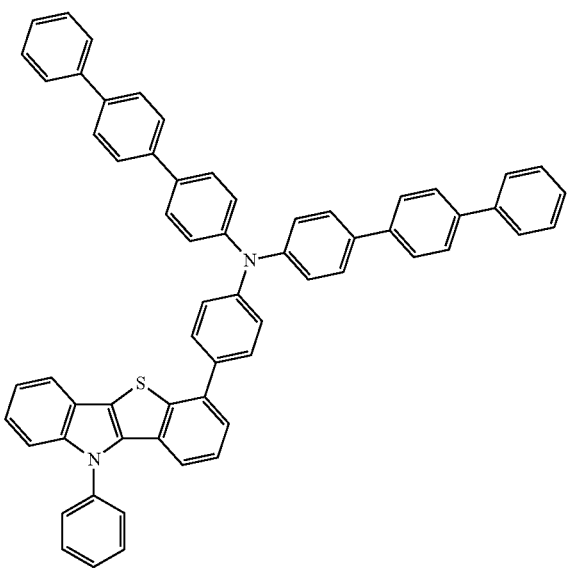
B56
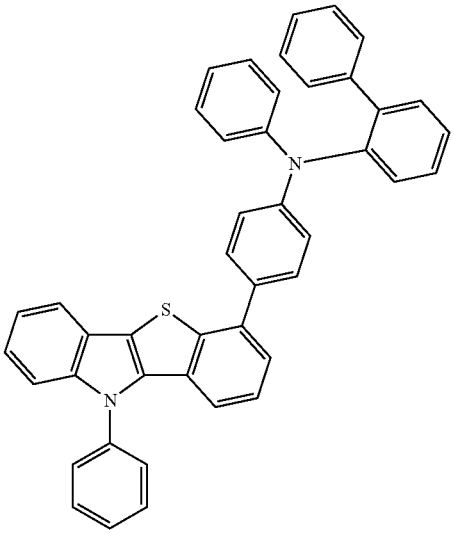
B57
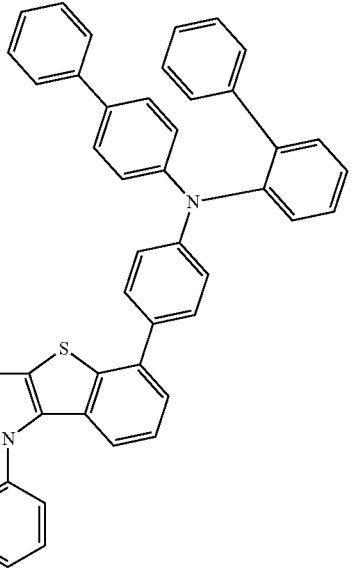
B58
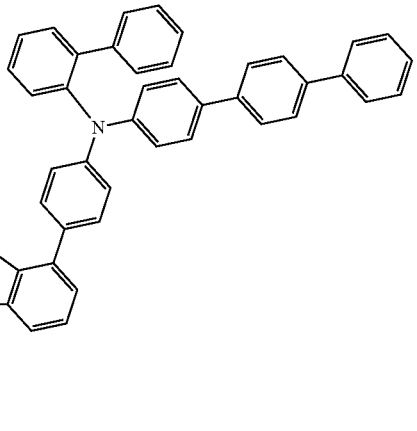

427
-continued
B59
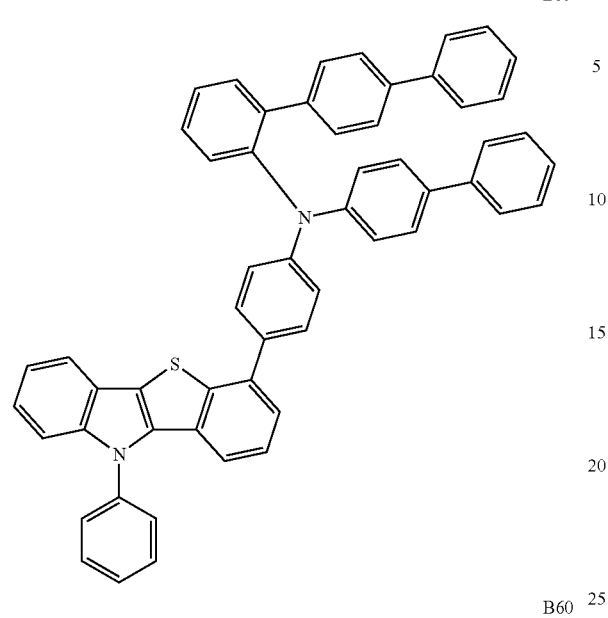
B60
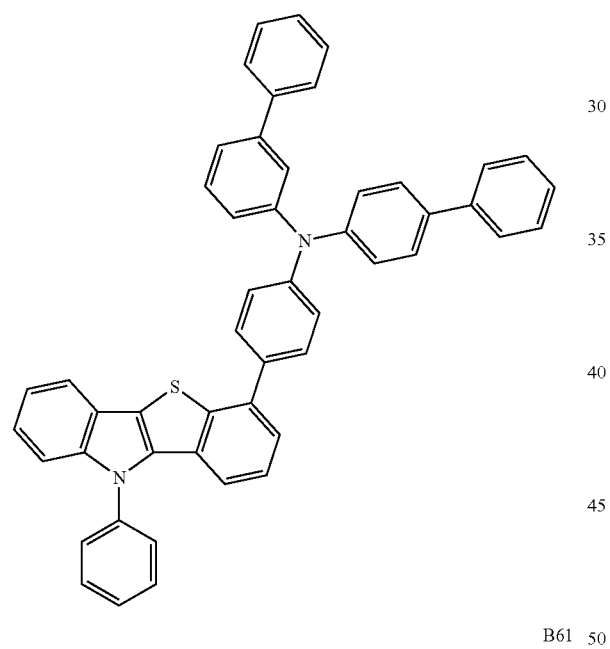
B61
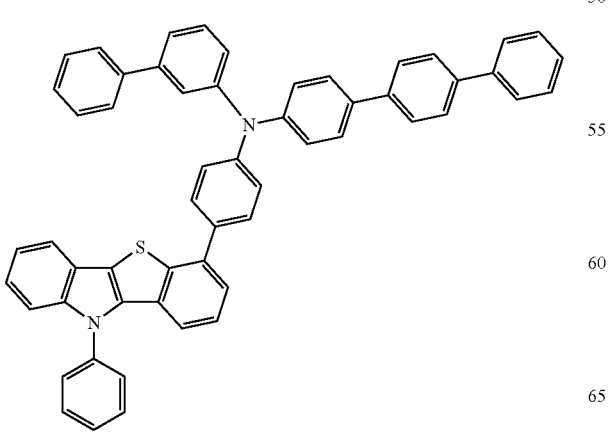
428
-continued
B62
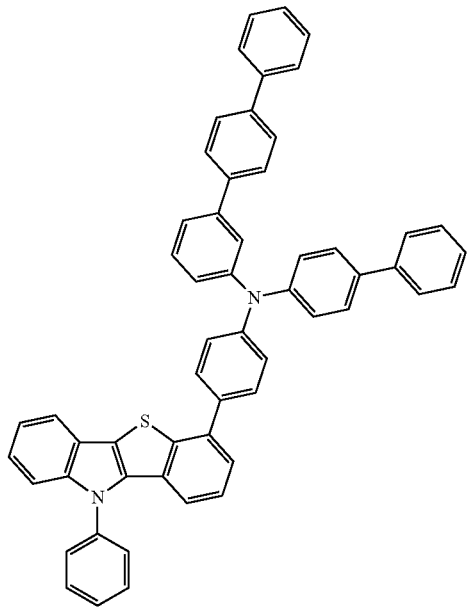
B63
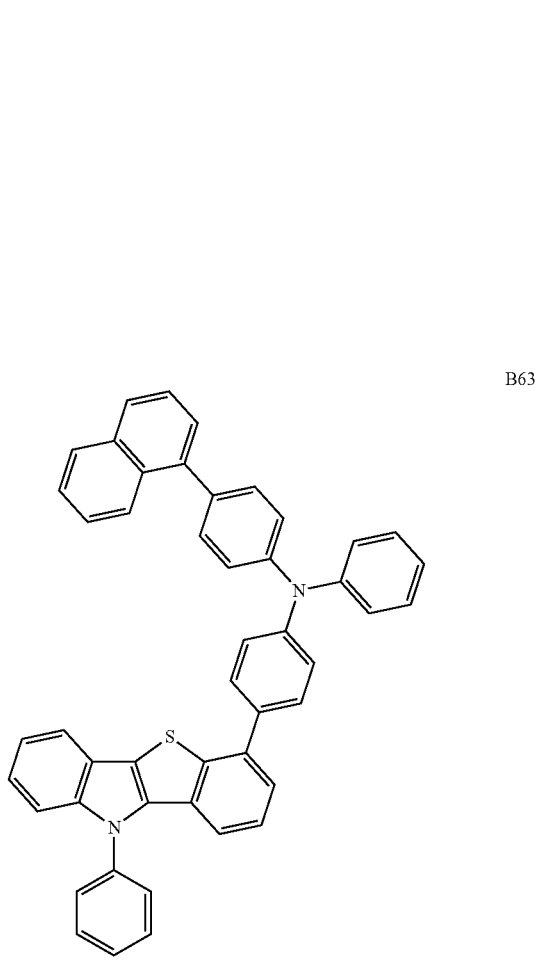

B64
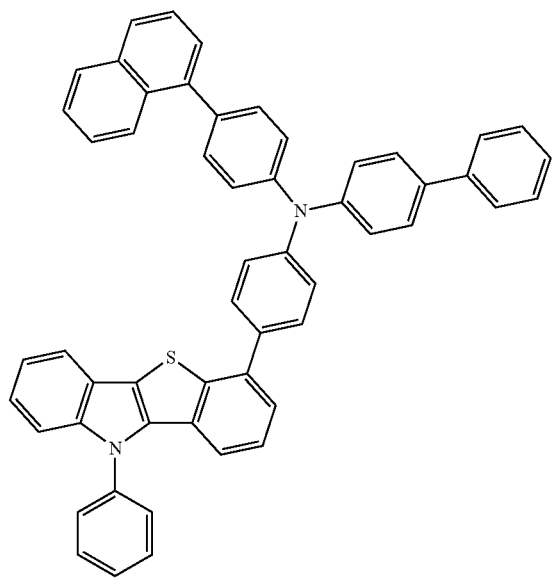
B65
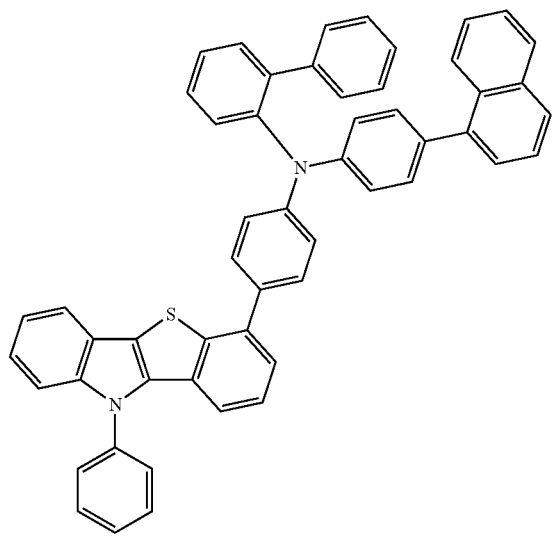
B66
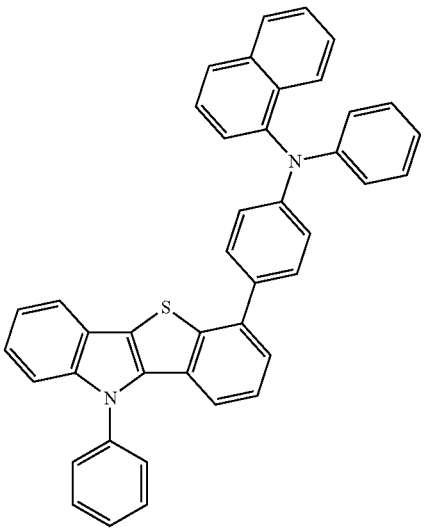
B67
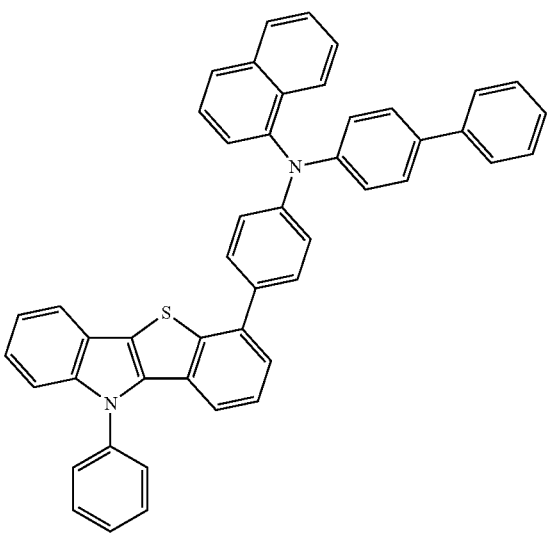
B68
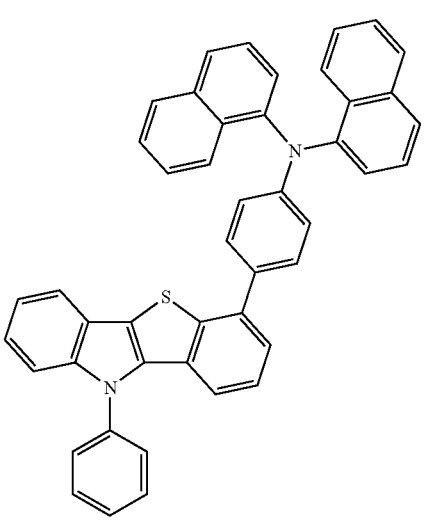

431
-continued
B69
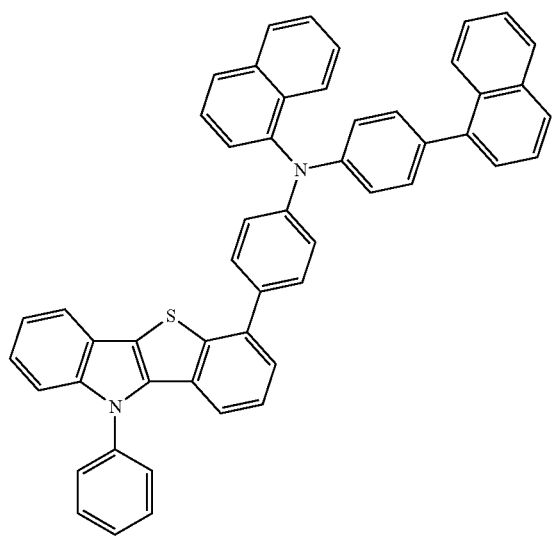
B70
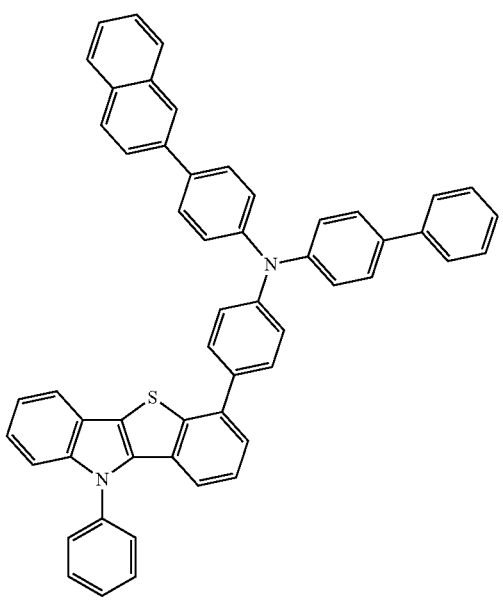
432
-continued
B71
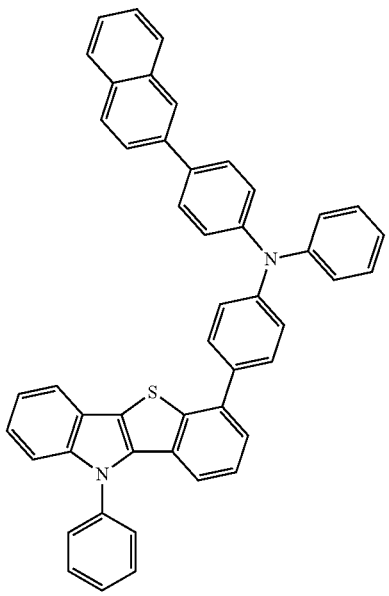
B72

B73
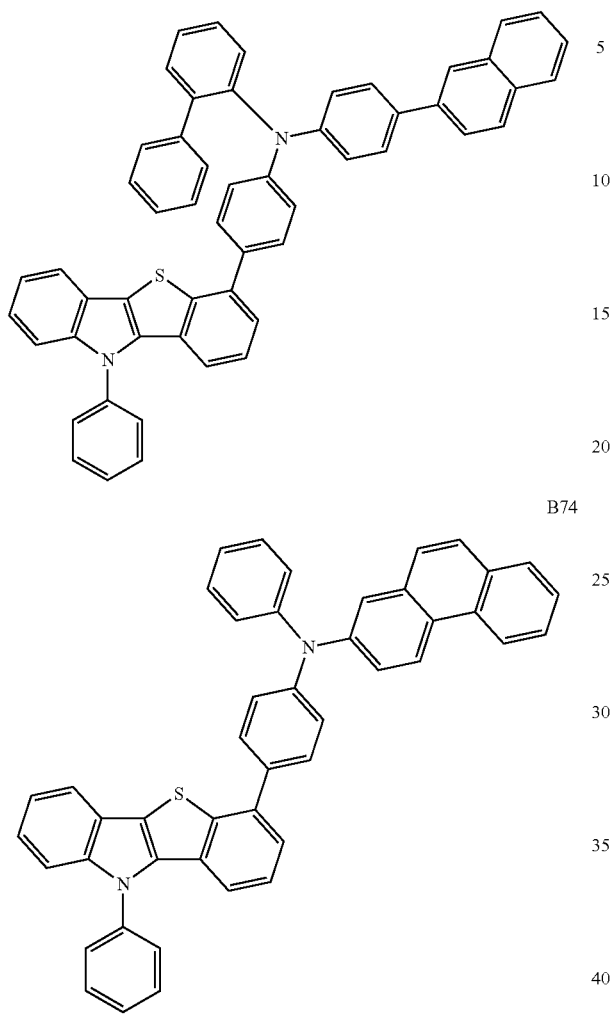
B74
B76
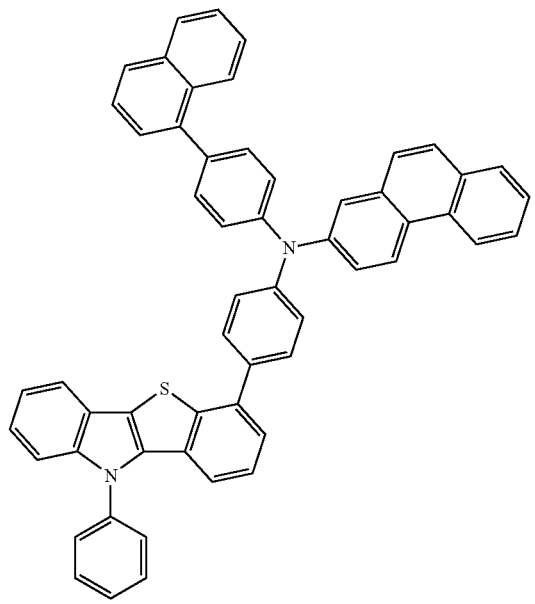
B75
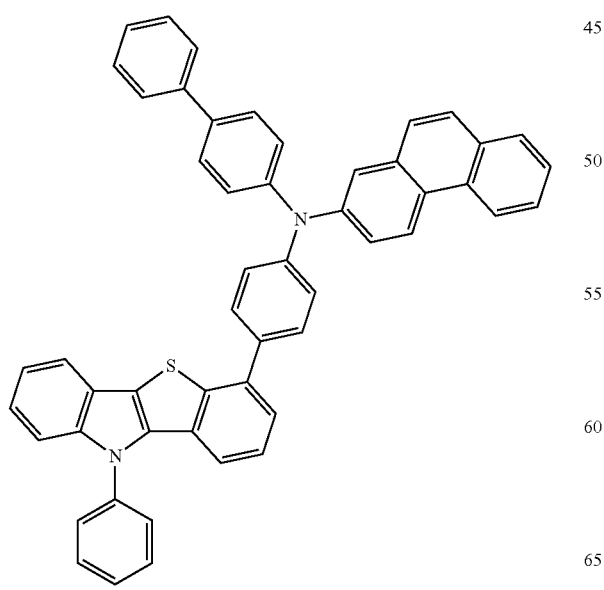
B77
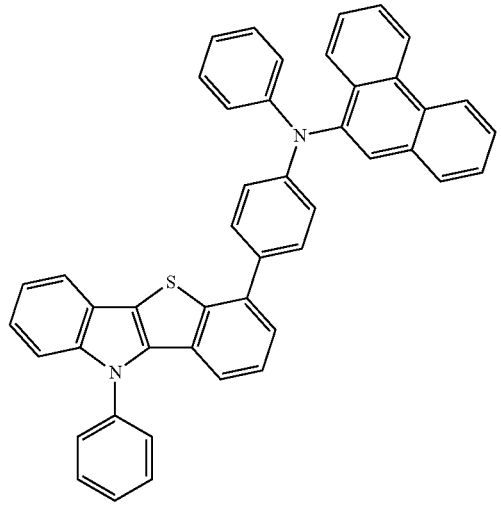

B78
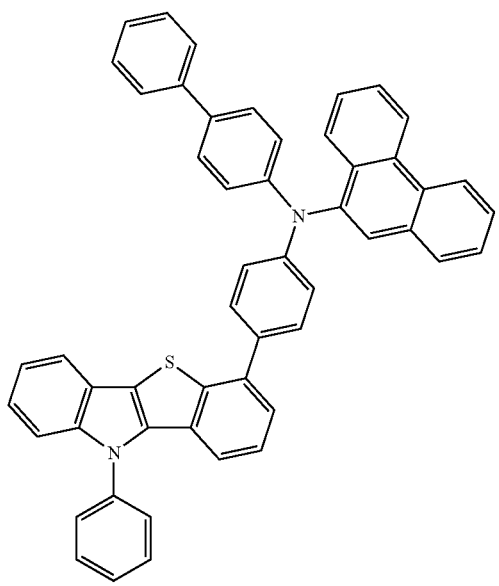
B80
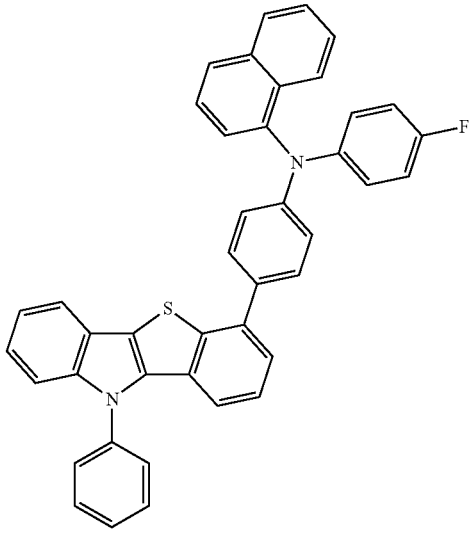
B79
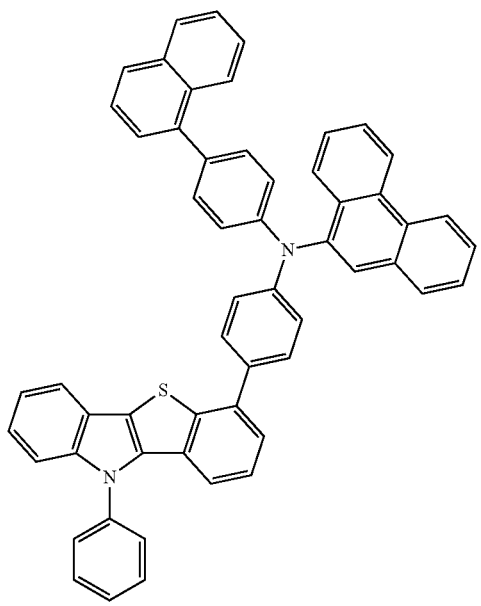
B81
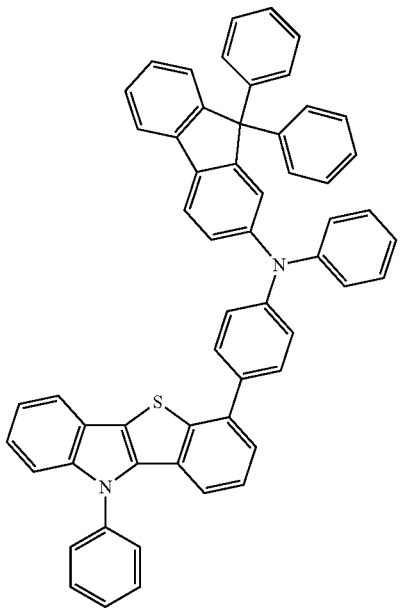

-continued
B82
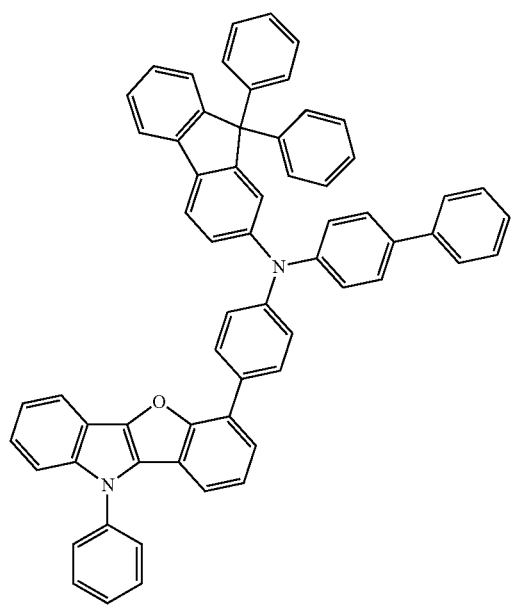
B83
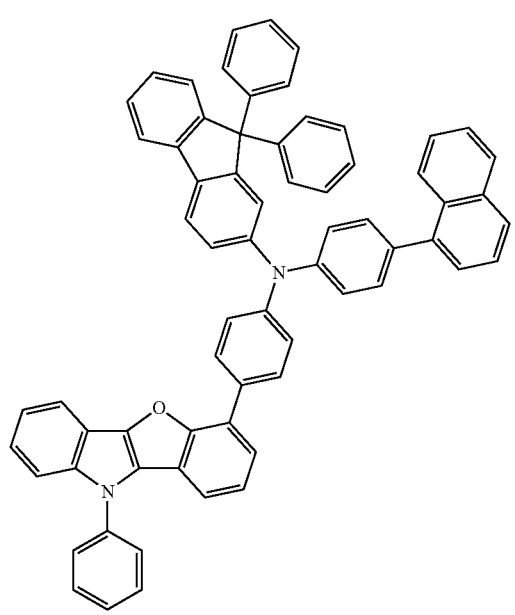
-continued
B84
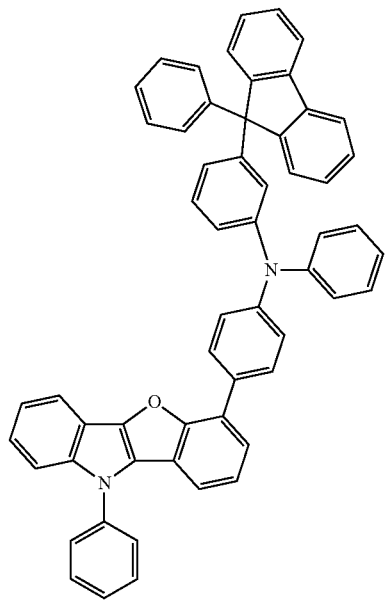
B85
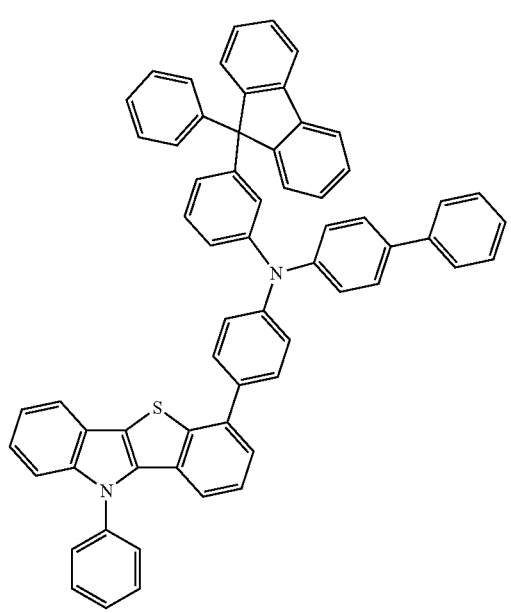

B86
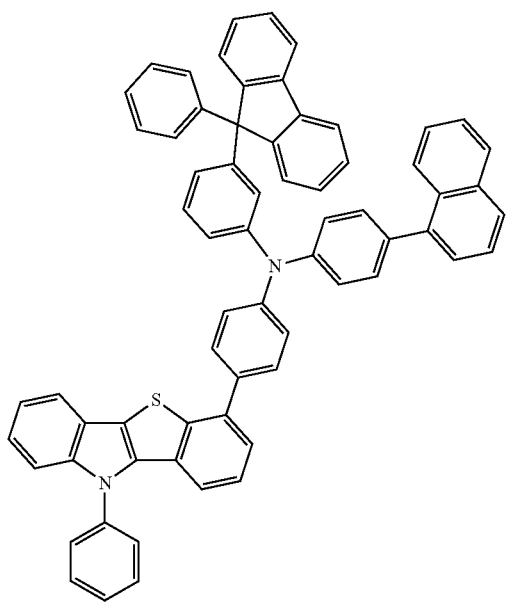
B88
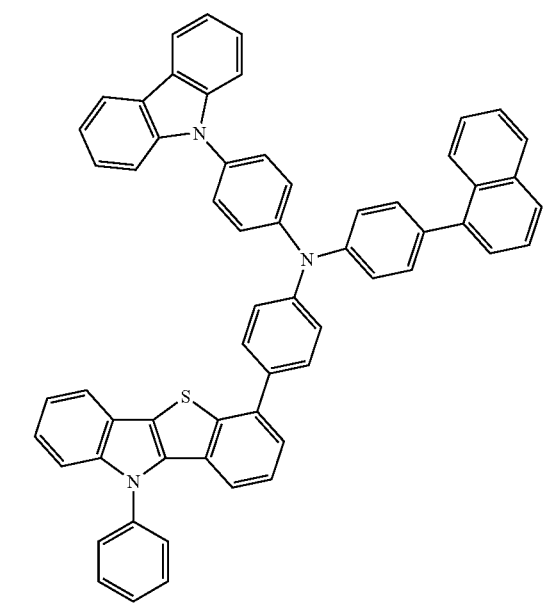
B87
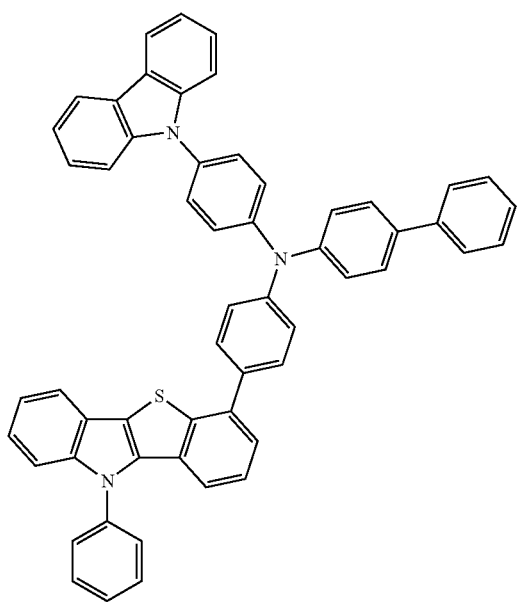
B89
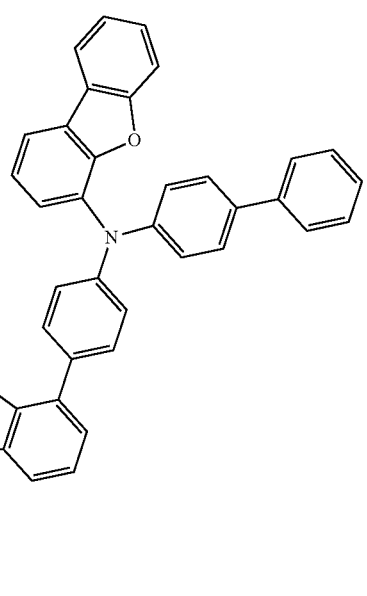

-continued
B90
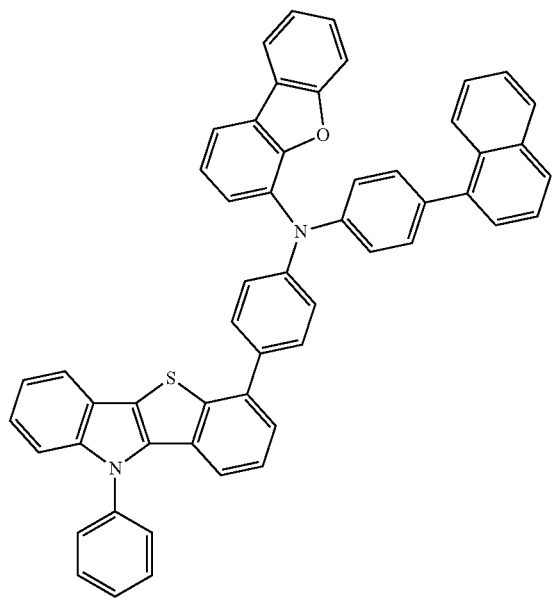
B91
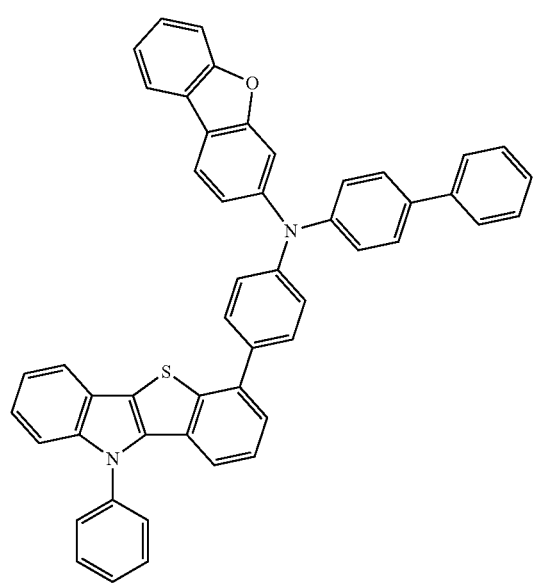
-continued
B92
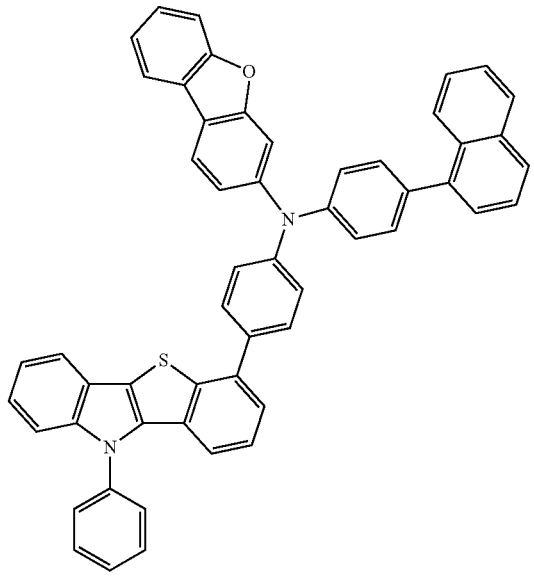
B93
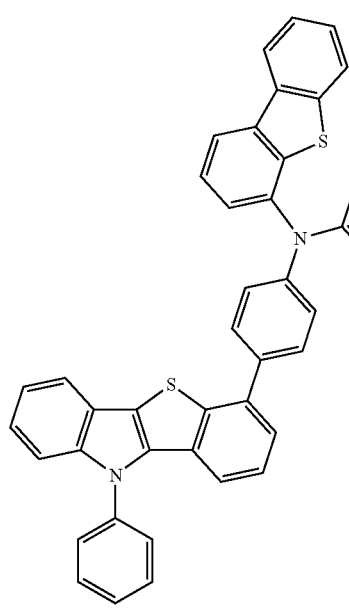

B94
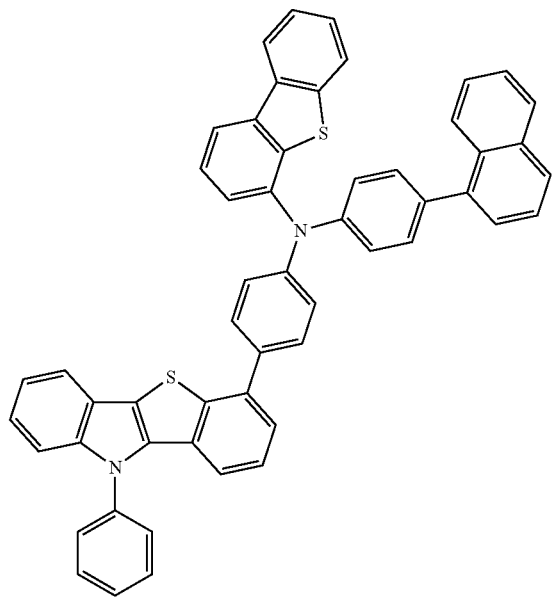
B96
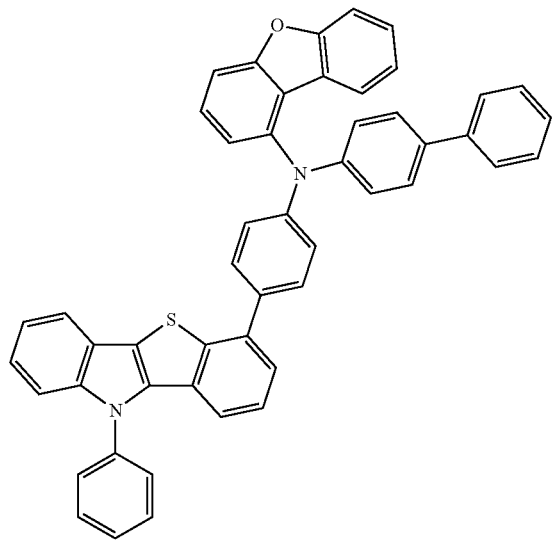
B95
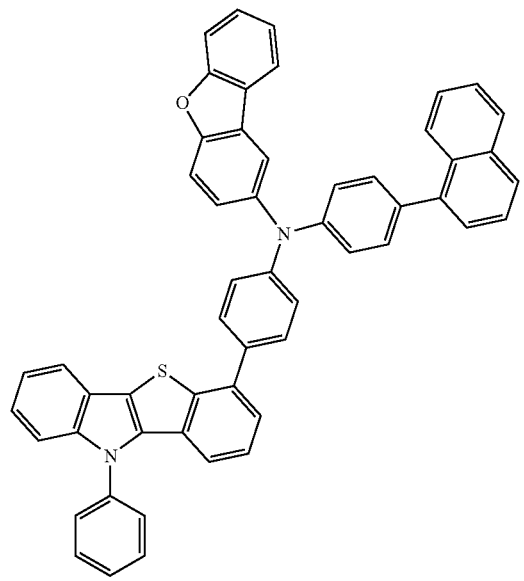
B97
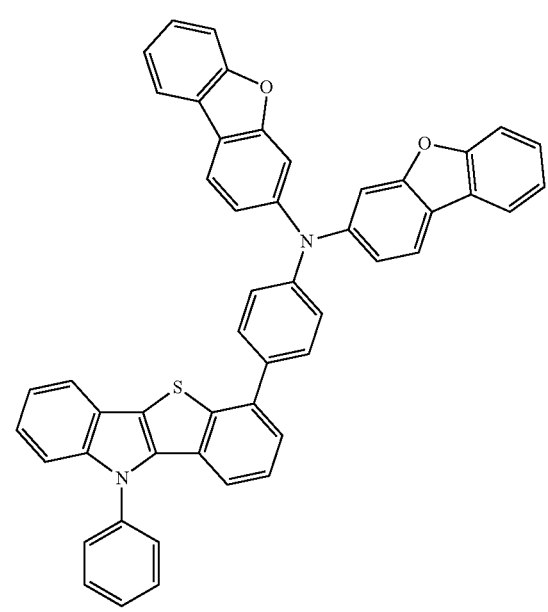

B98
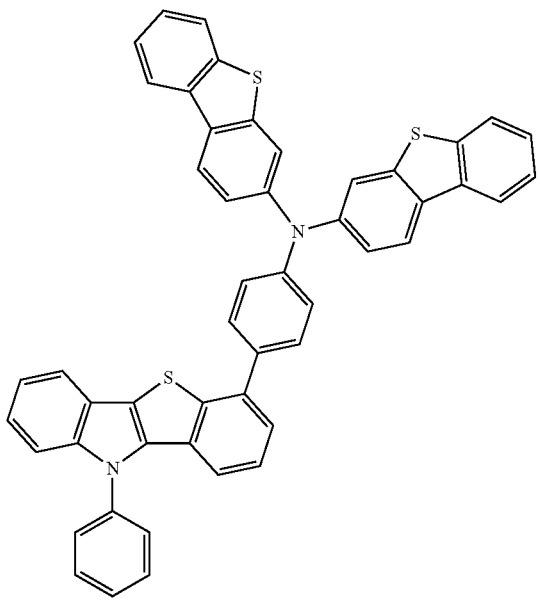
B99
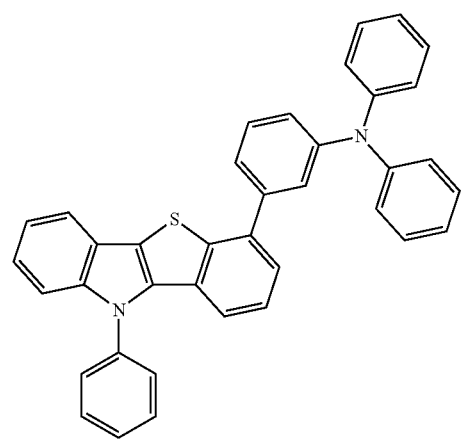
B100
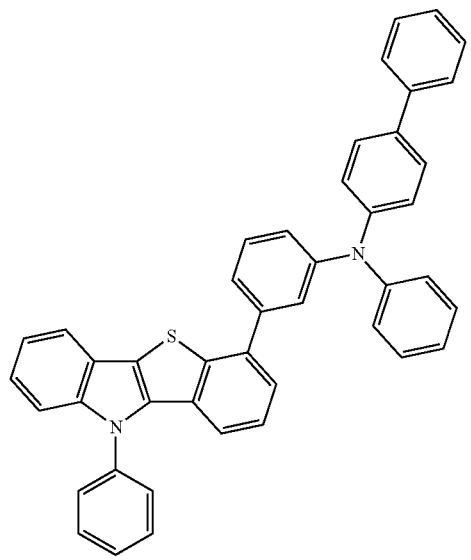
B101
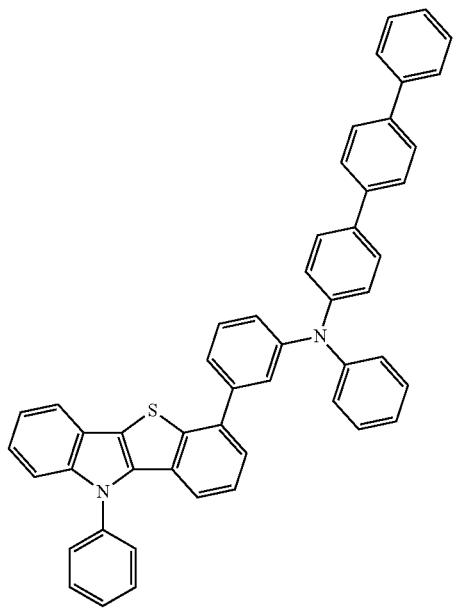
B102
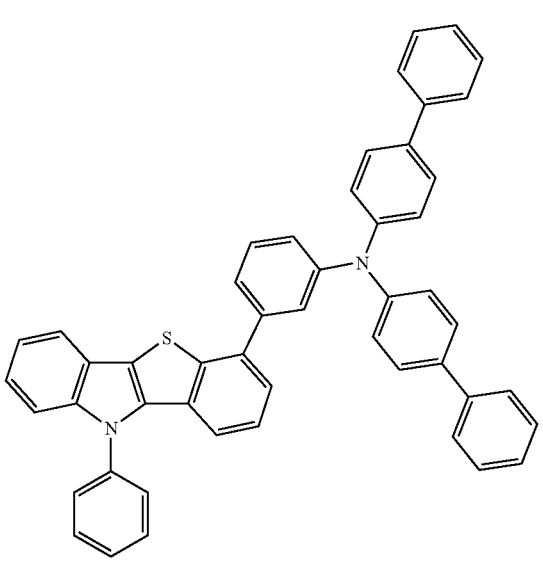

B103
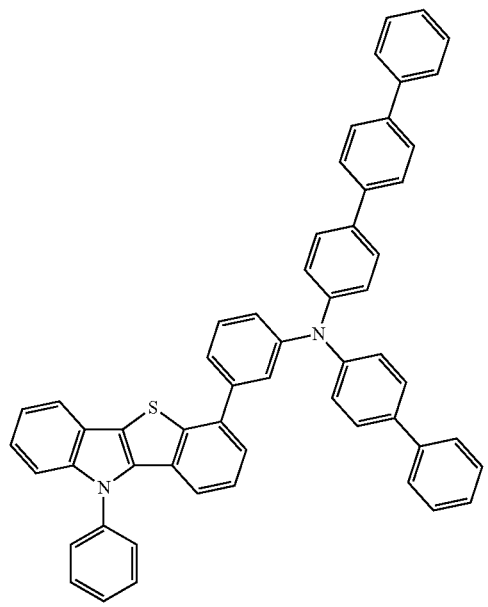
B105
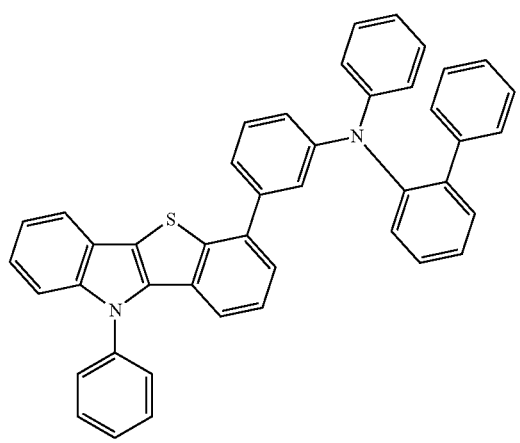
B106
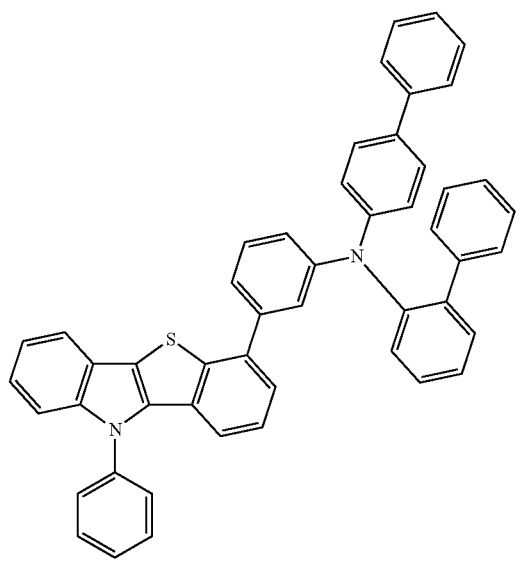
B104
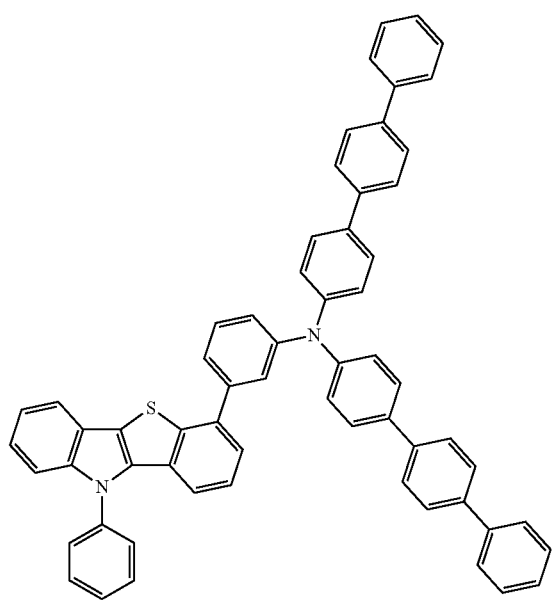
B107

449
-continued
B108
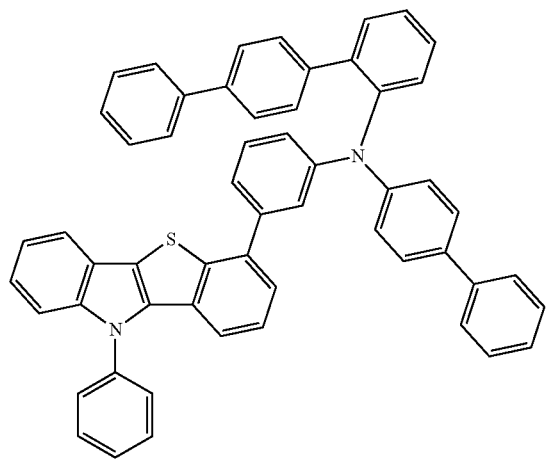
B109
B110
450
-continued
B111
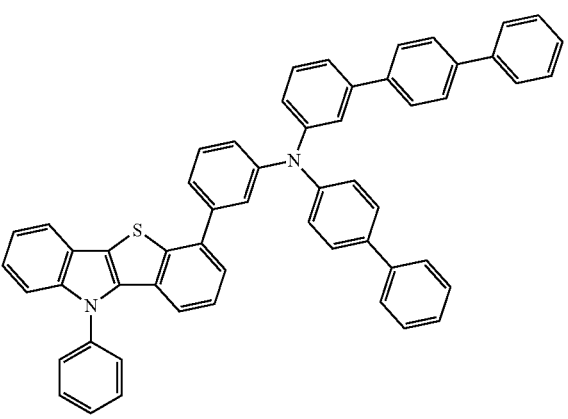
B112
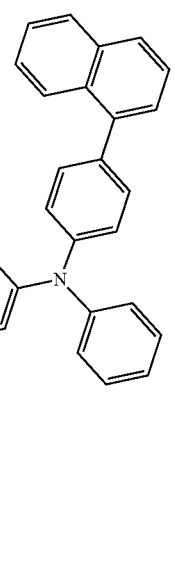
B113
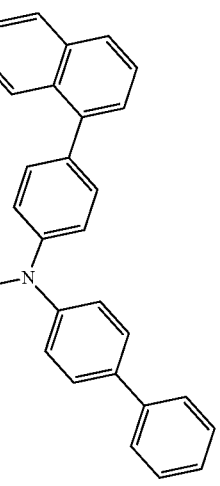

B114
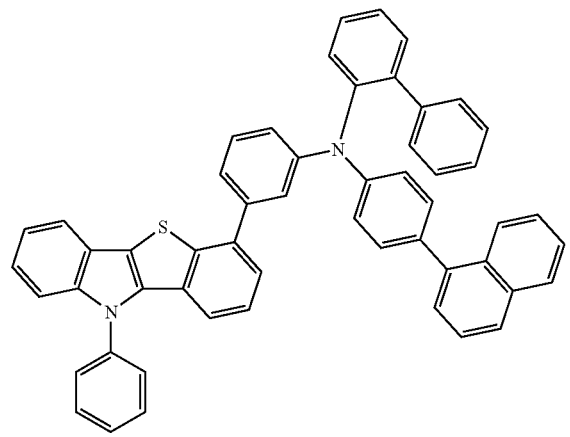
B115
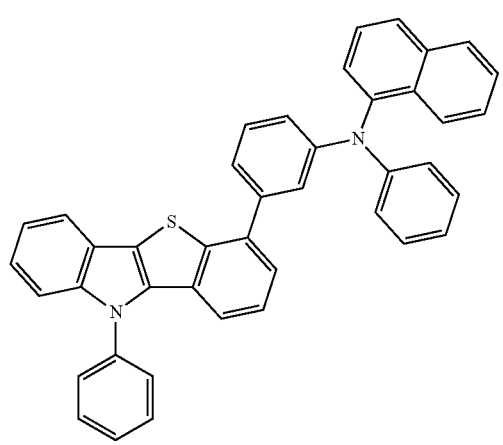
B116
B117
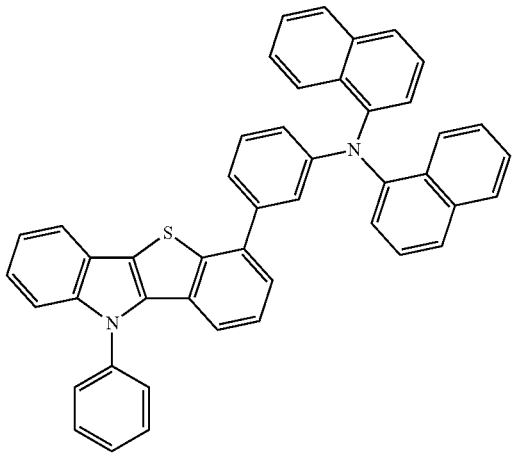
B118
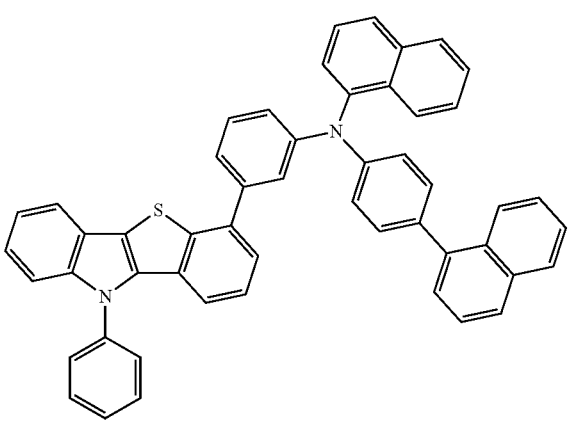
B119
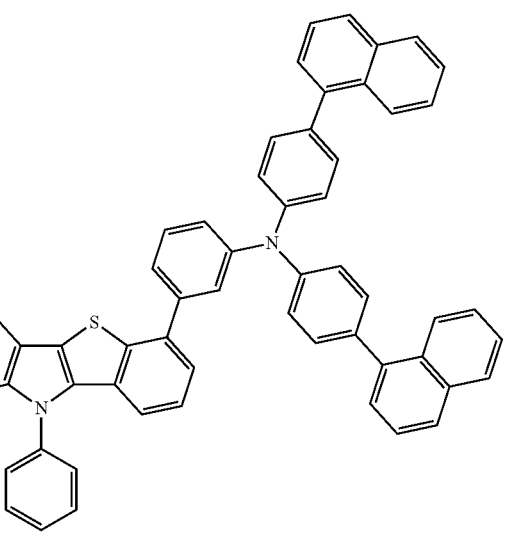

B120
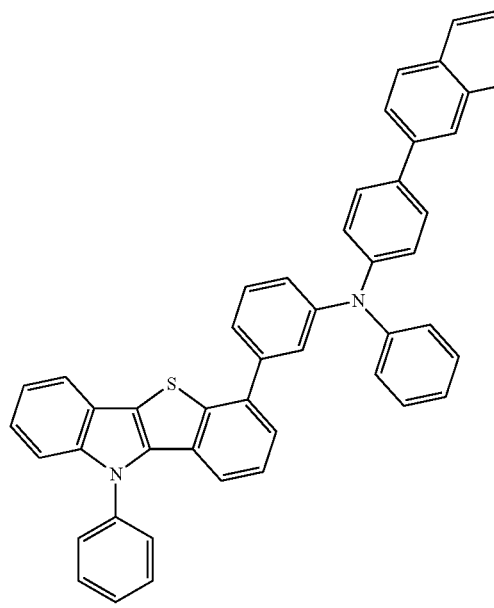
B122
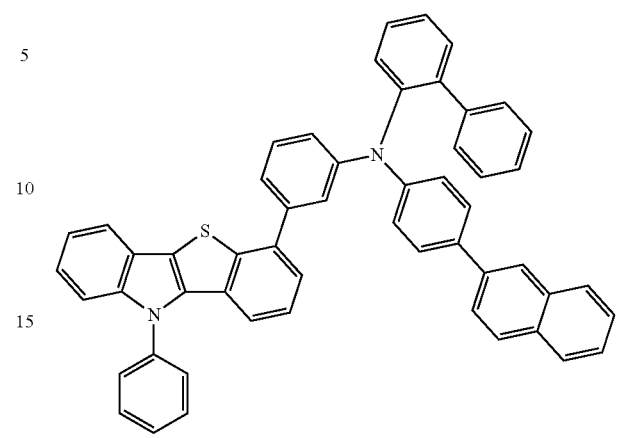
B123
B121
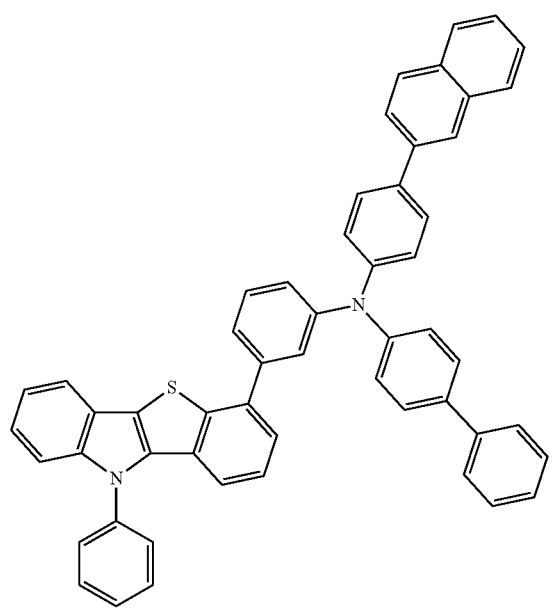
B124
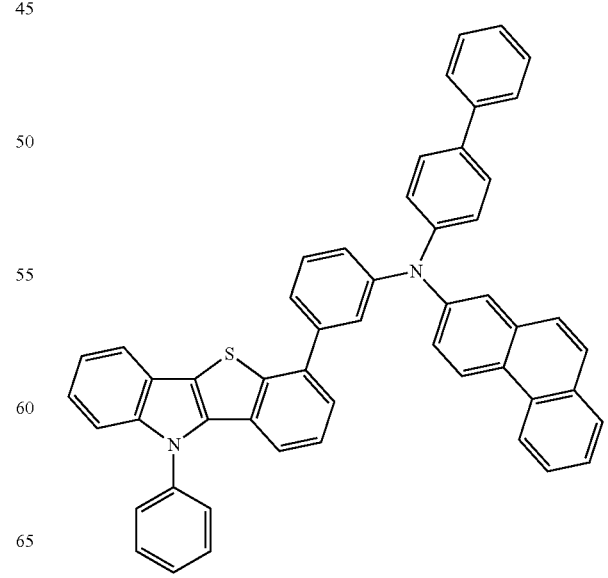

-continued
B125
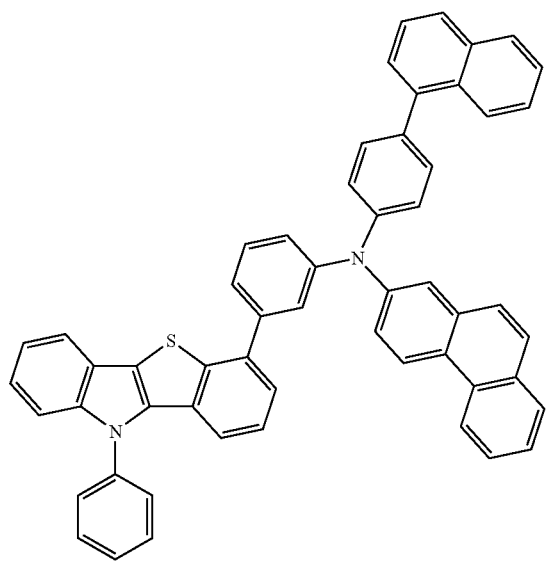
B126
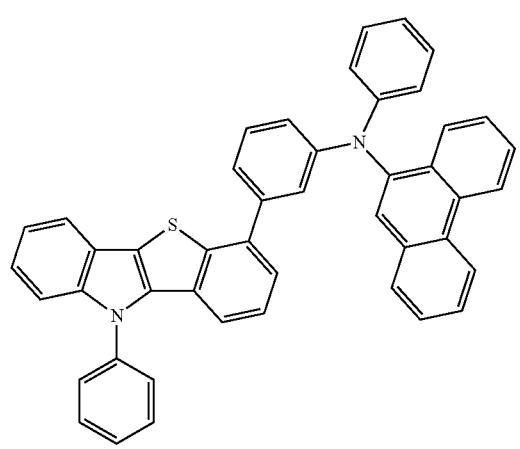
B127
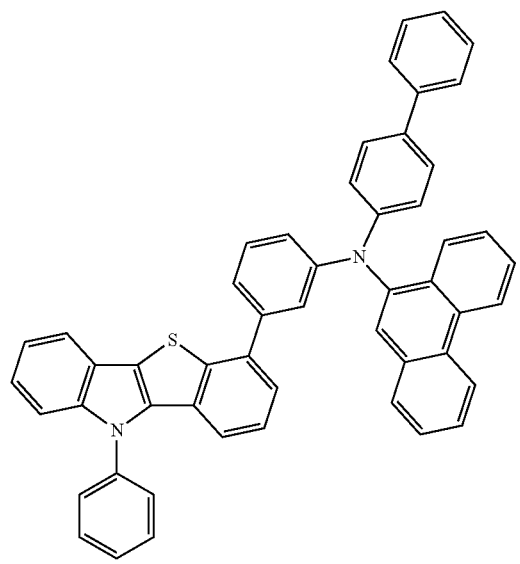
-continued
B128
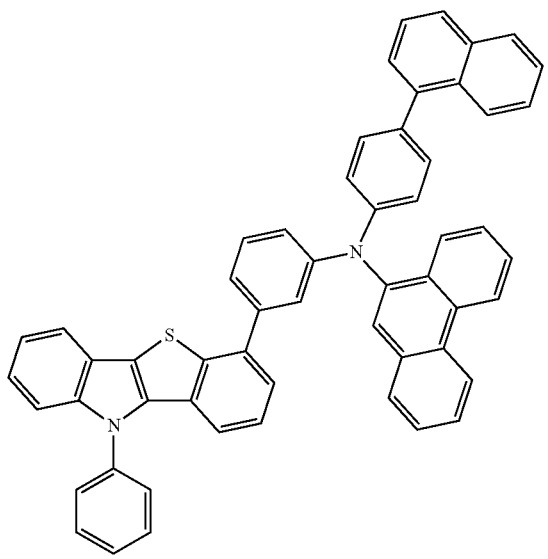
B129
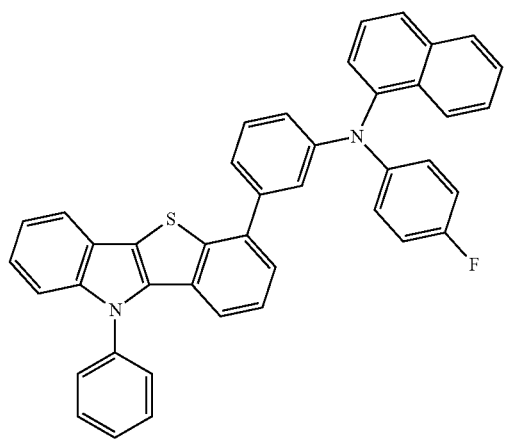
B130
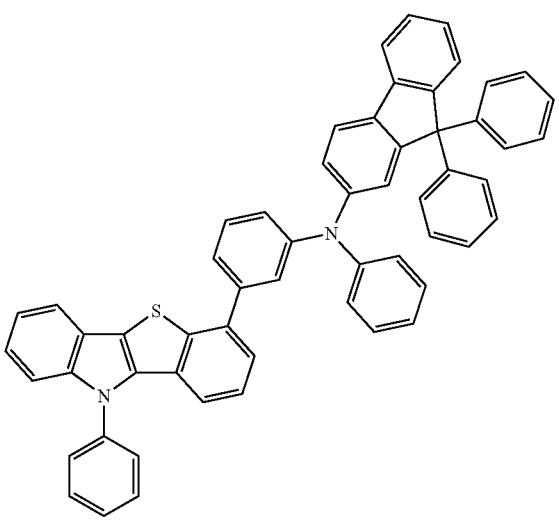

-continued
B131
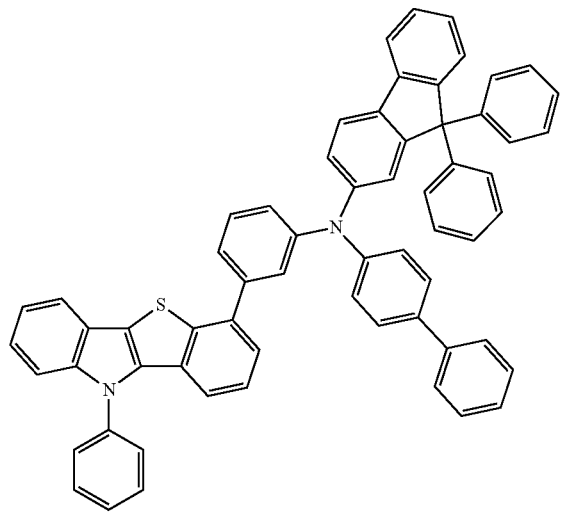
B134
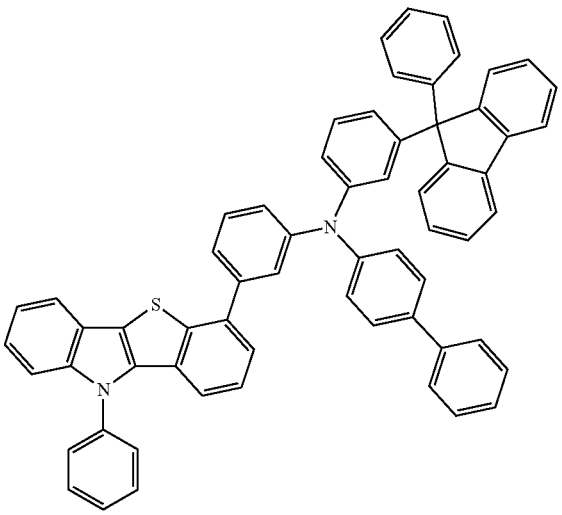
B132
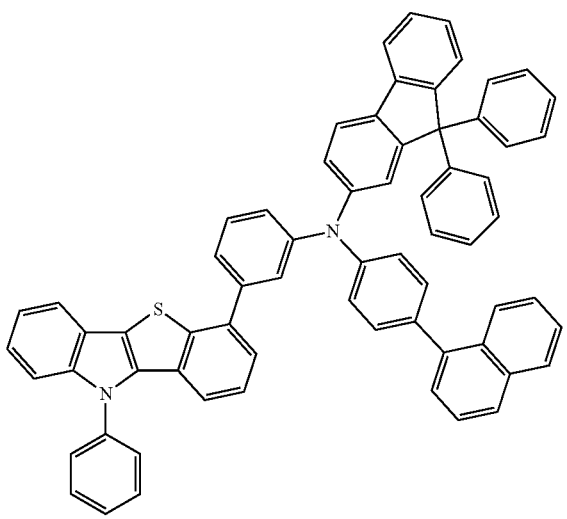
B135
B133
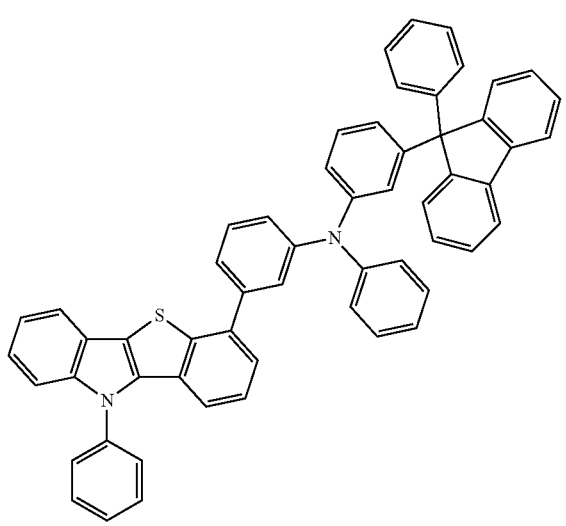
B136
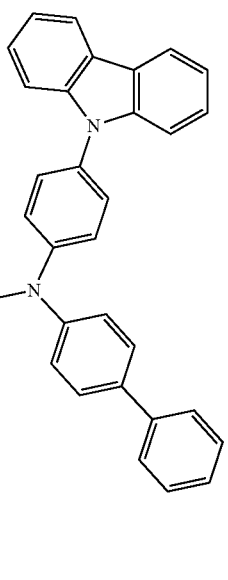

-continued
B137
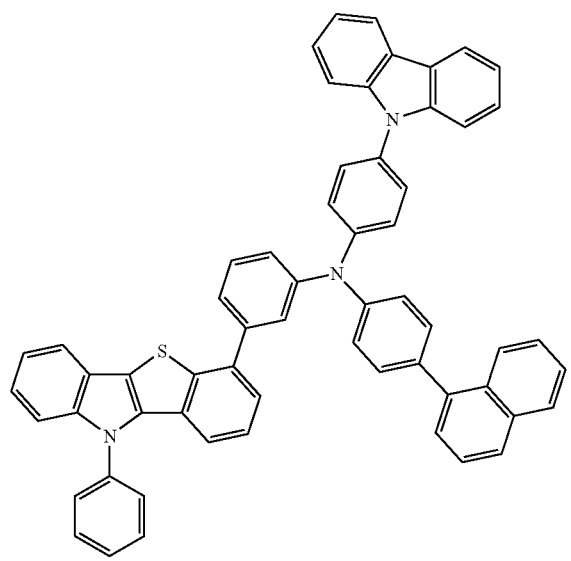
B138
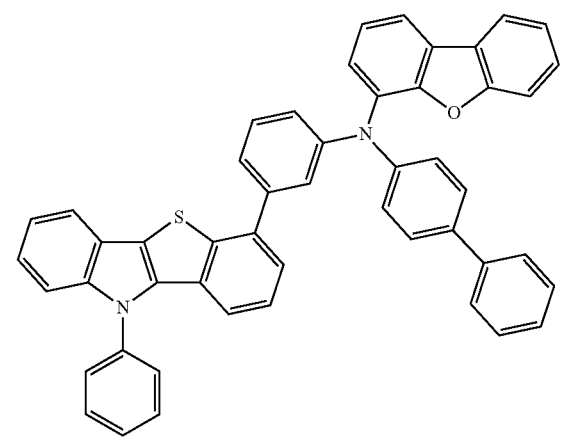
B139
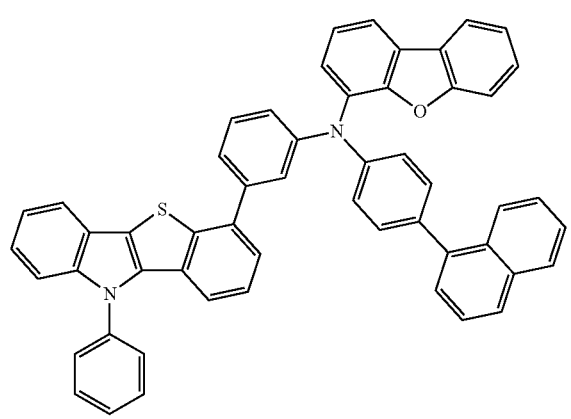
-continued
B140
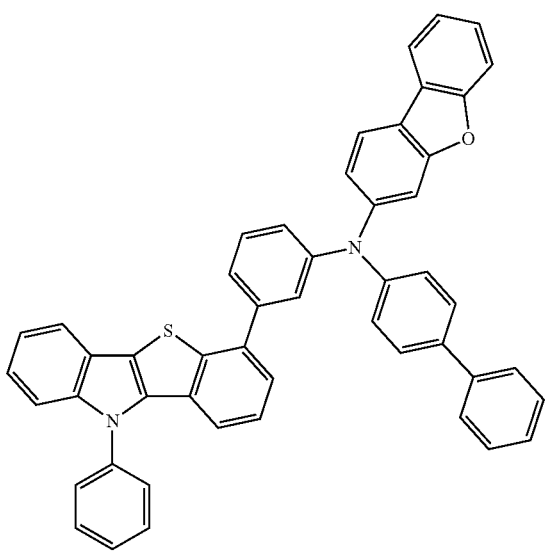
B141
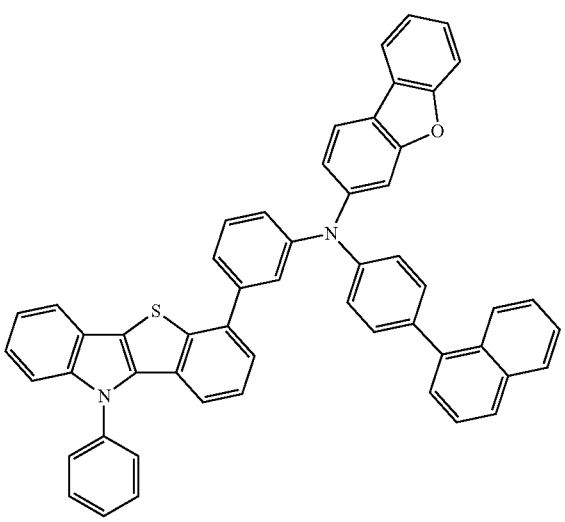
B142
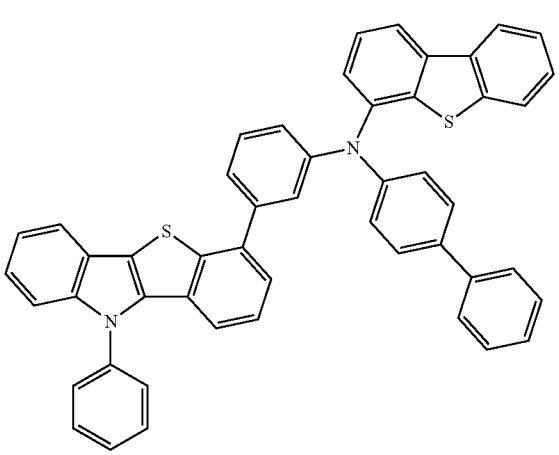

-continued
B143
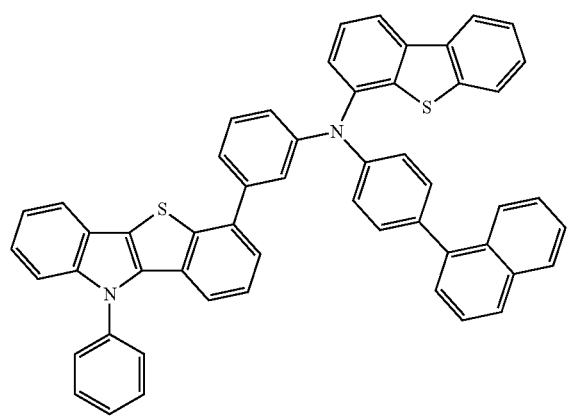
B144
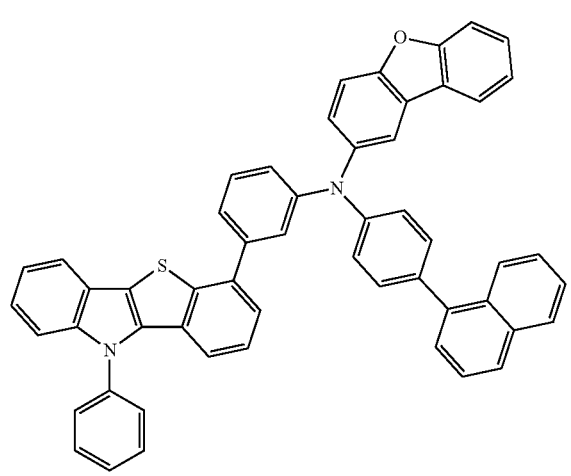
B145
B146
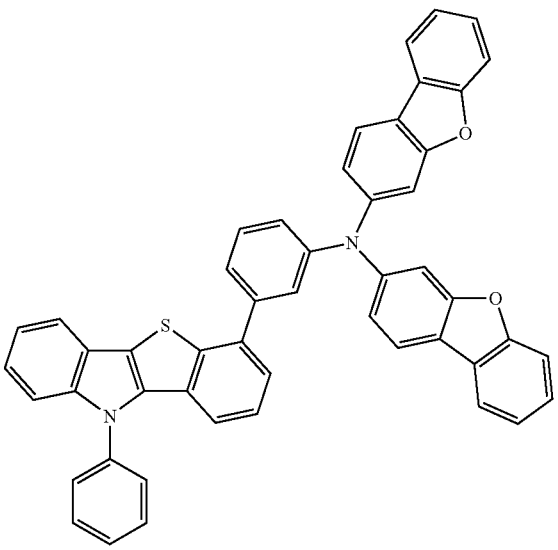
B147
B148
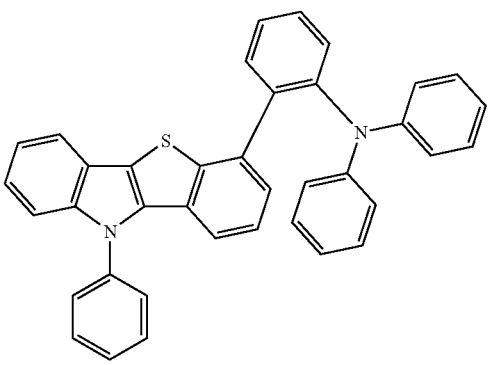

B149
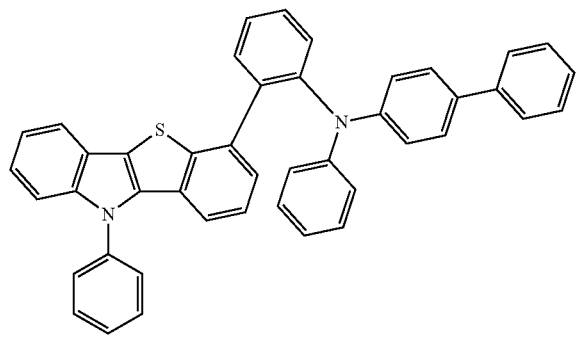
B150
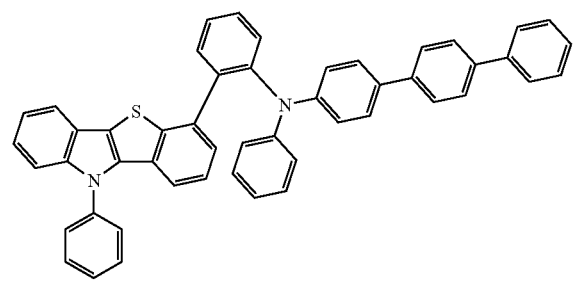
B151
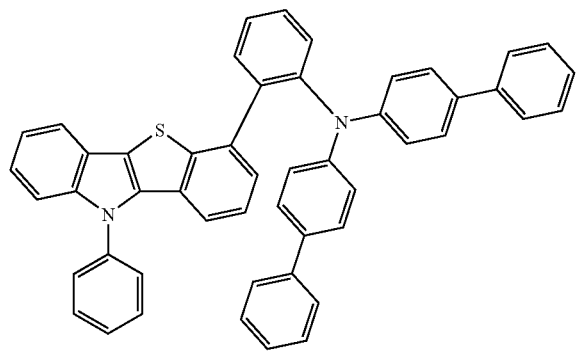
B152
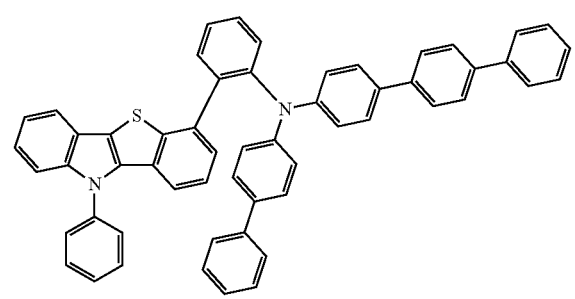
B153
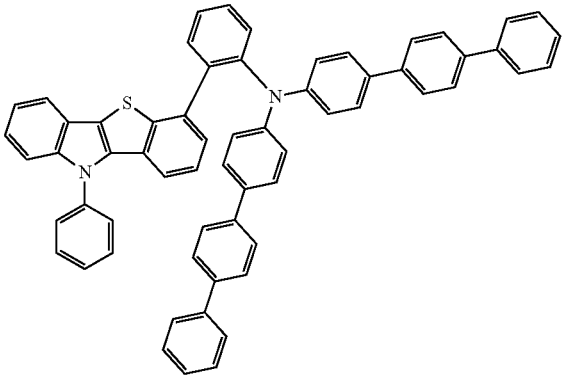
B154
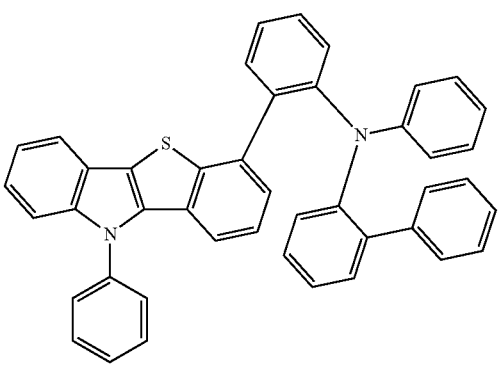
B155
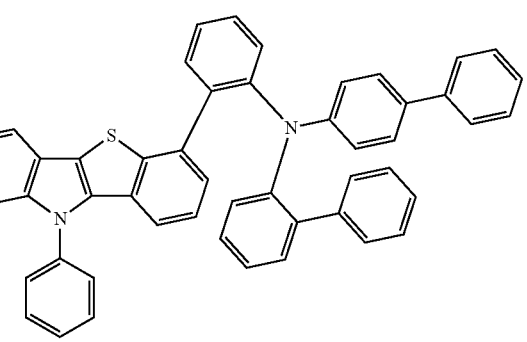
B156
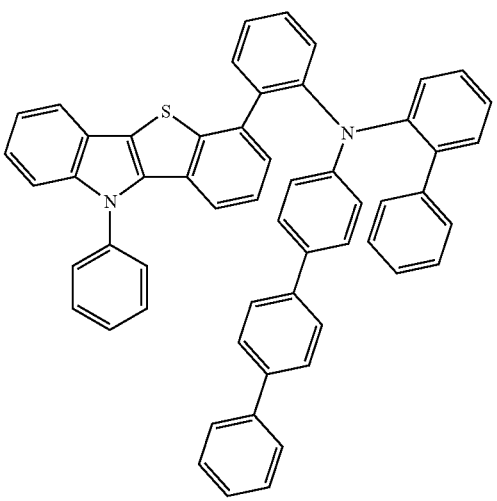

-continued
B157
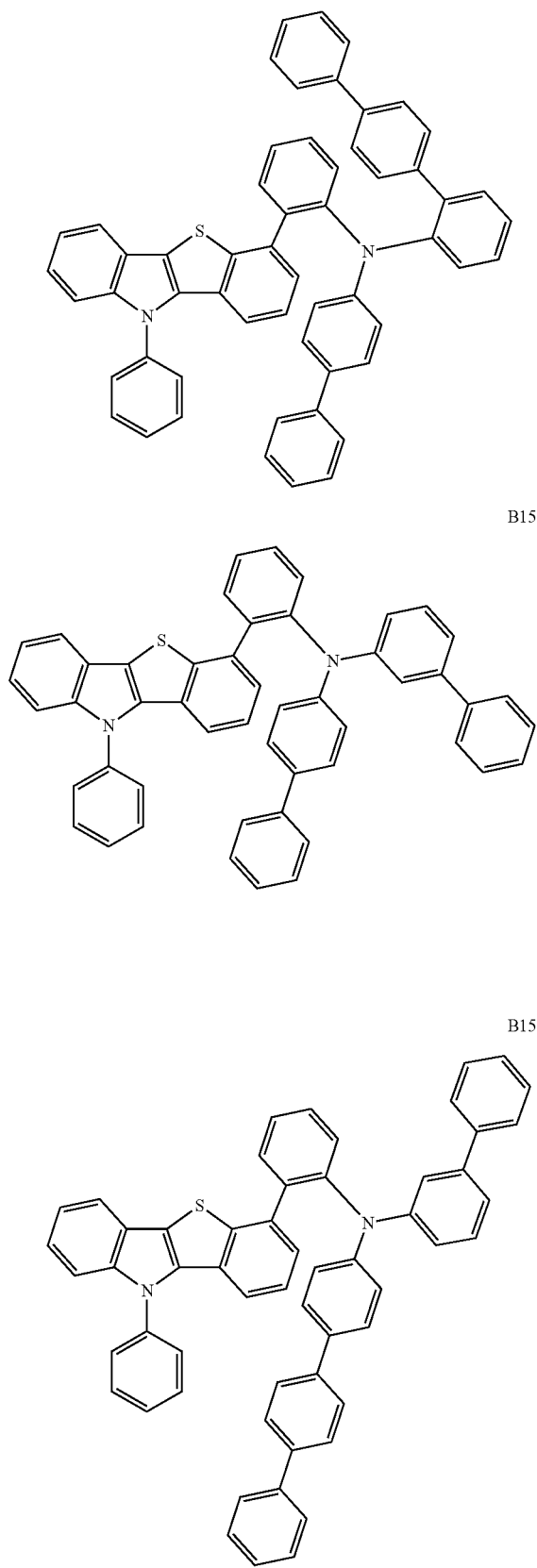
B158
B159
-continued
B160
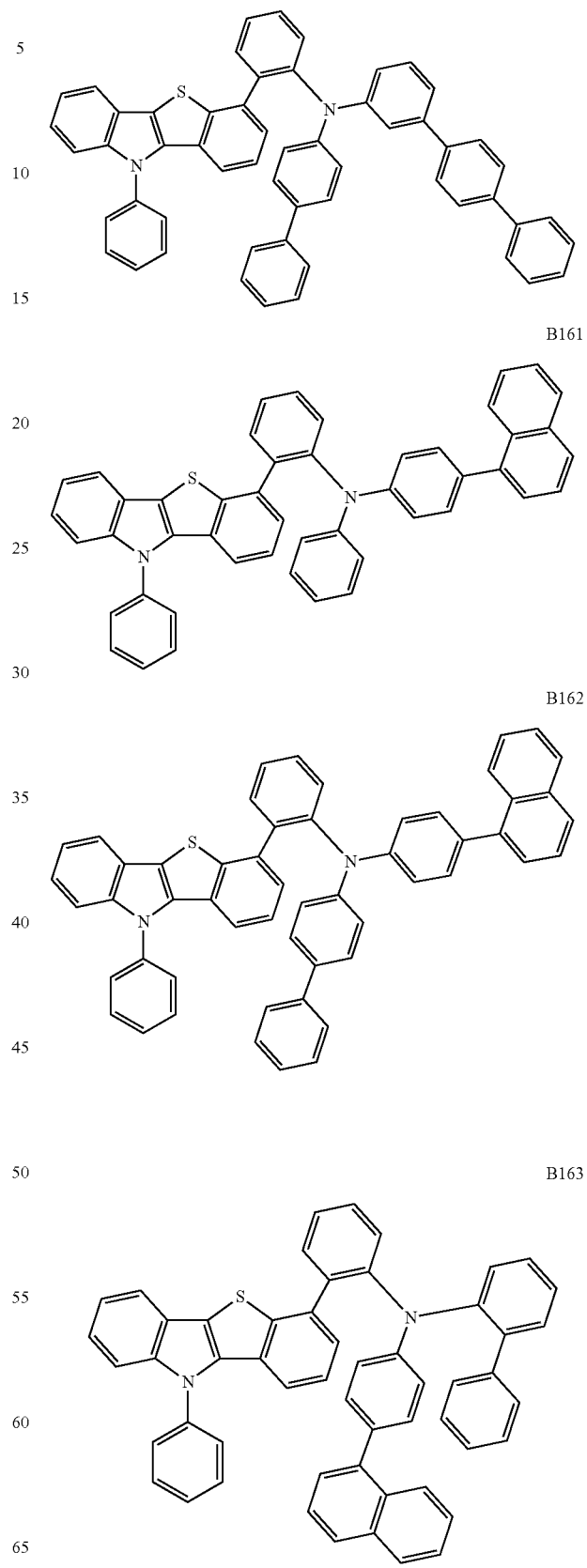
B161
B162
B163

B164
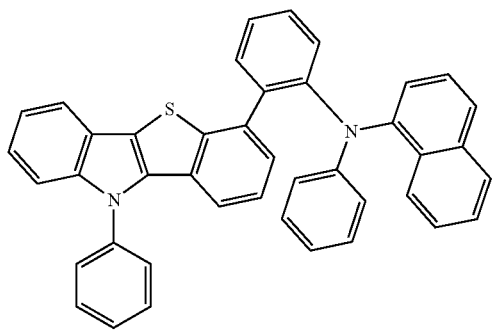
B165
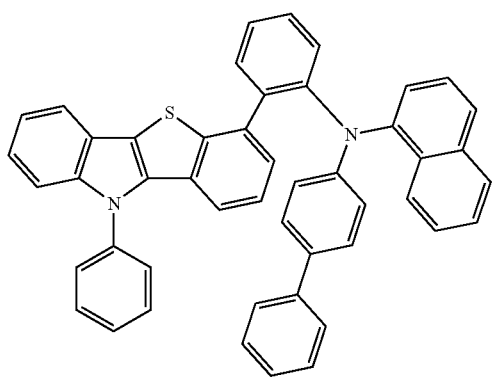
B166
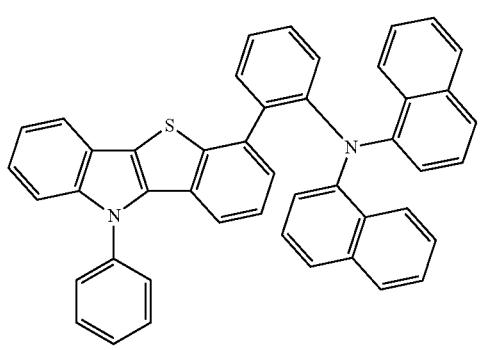
B167
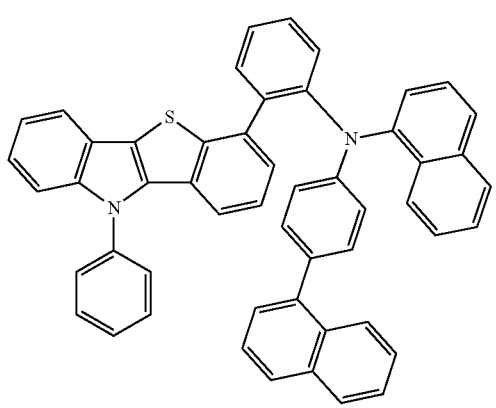
B168
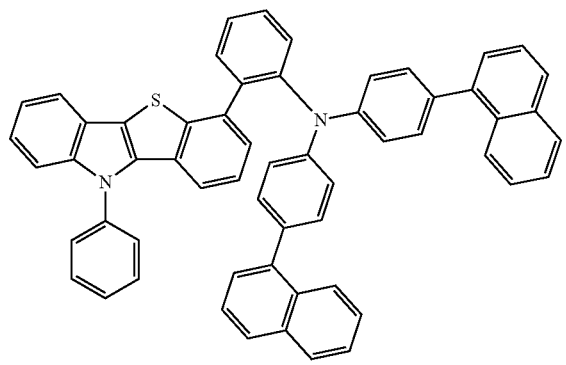
B169
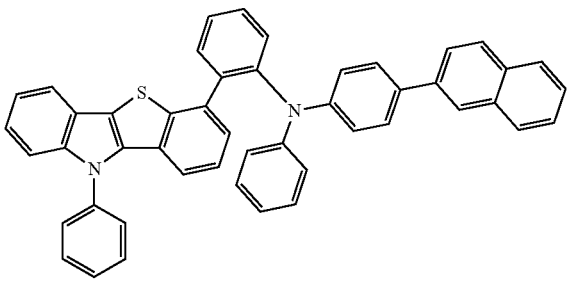
B170
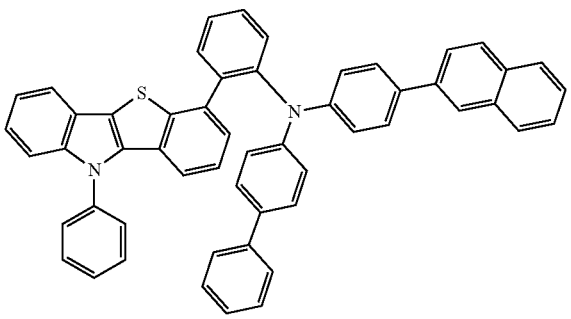
B171
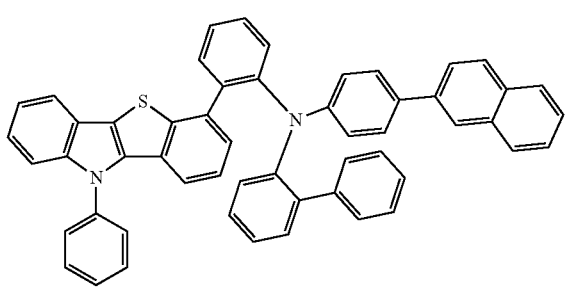

B172
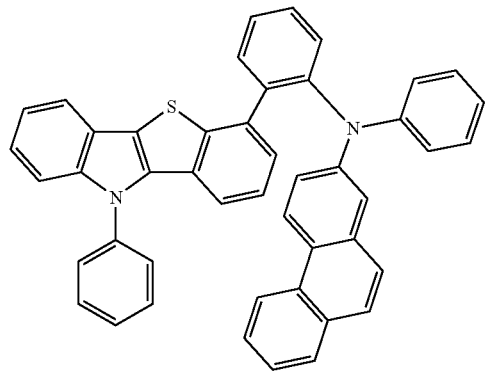
B173
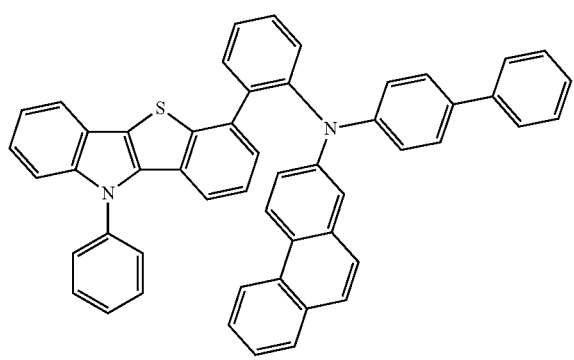
B174
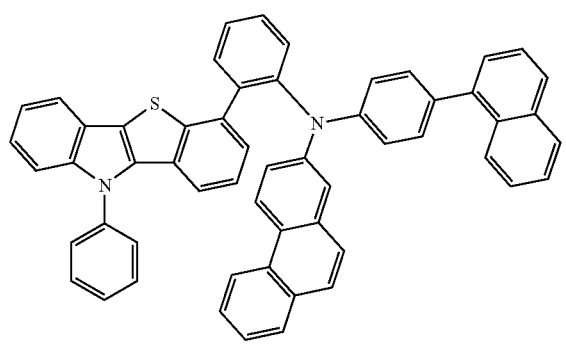
B175
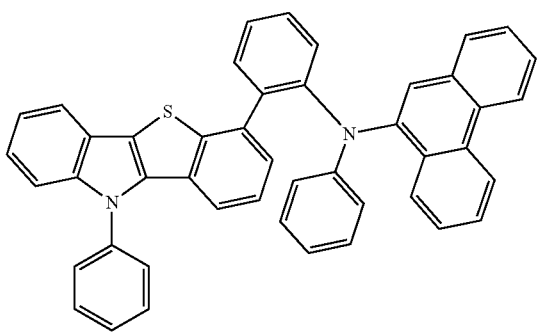
B176
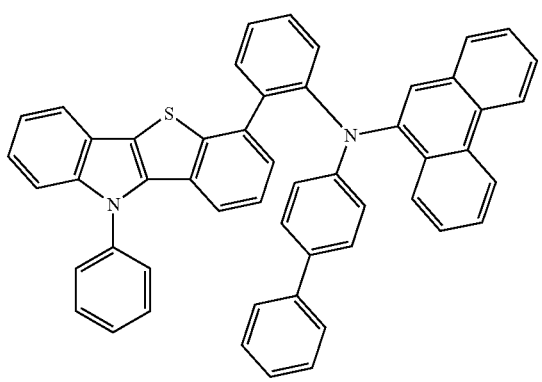
B177
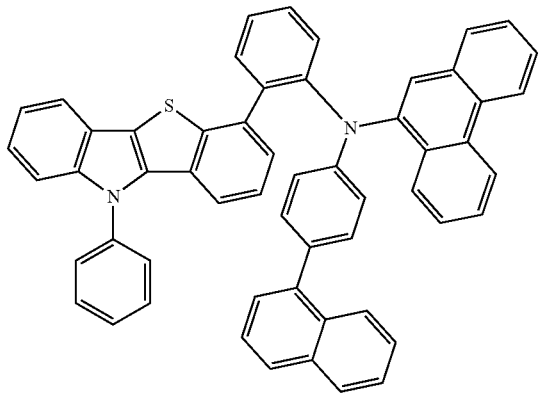
B178
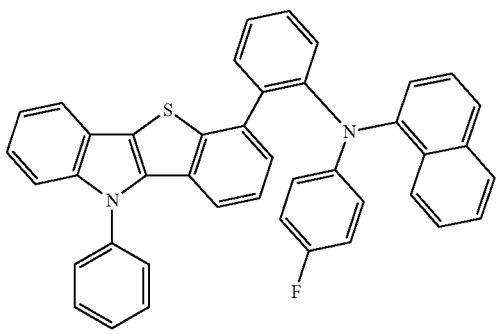

B179
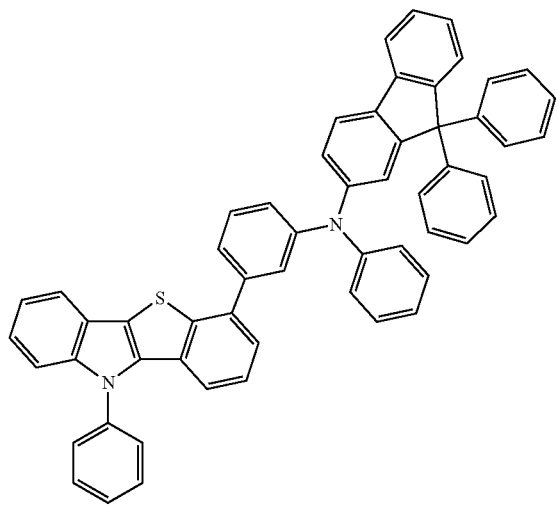
B180
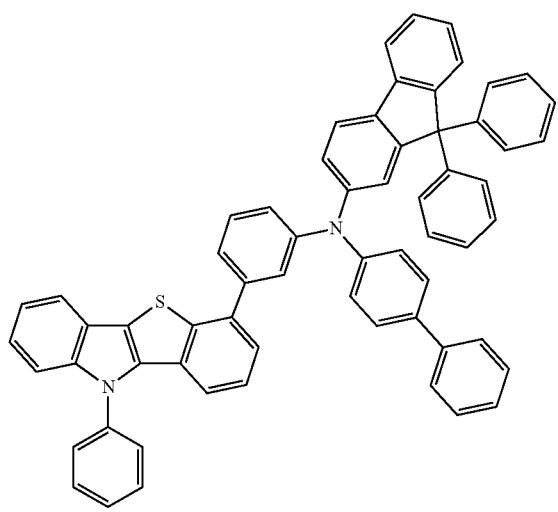
B181
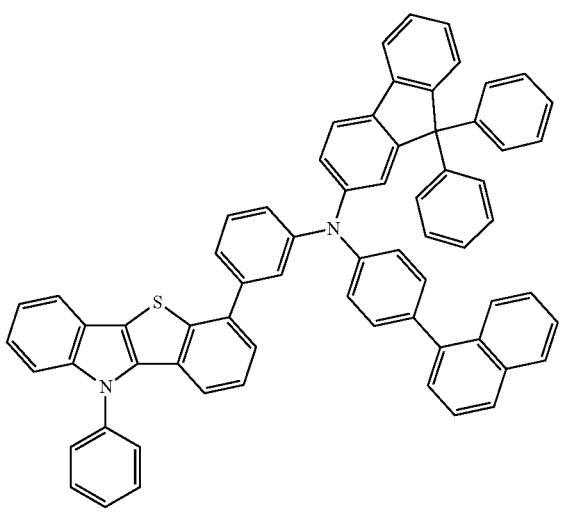
B182
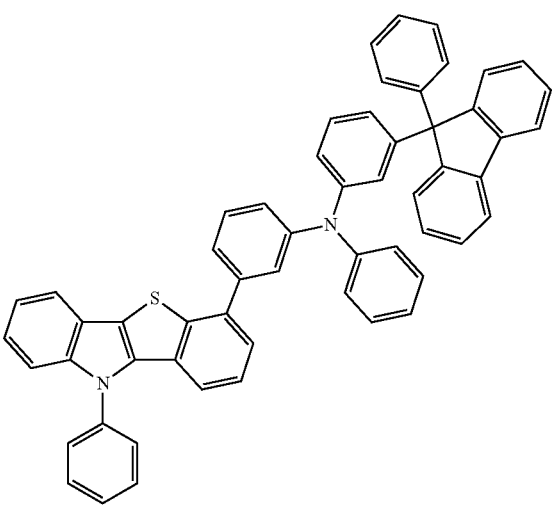
B183
B184
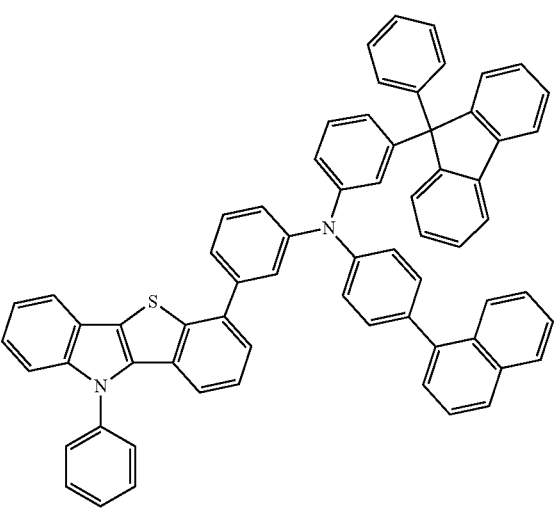

B185
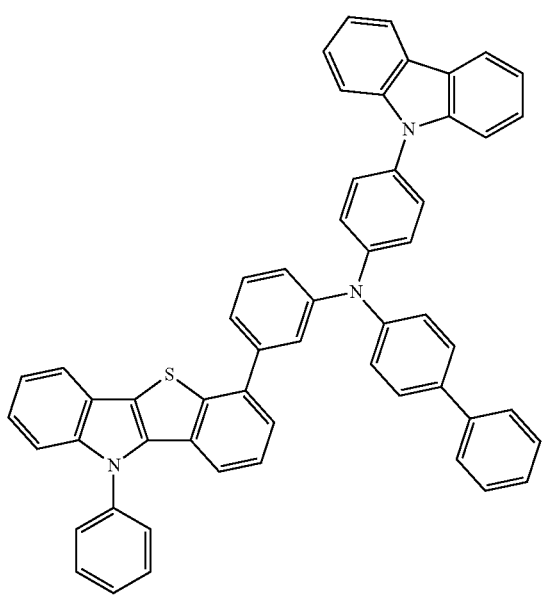
B186
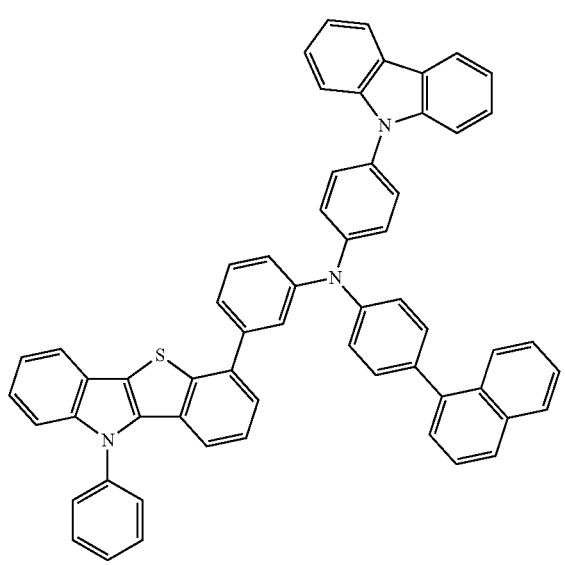
B187
B188
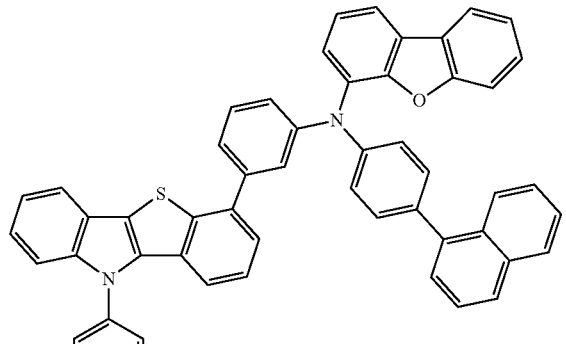
B189
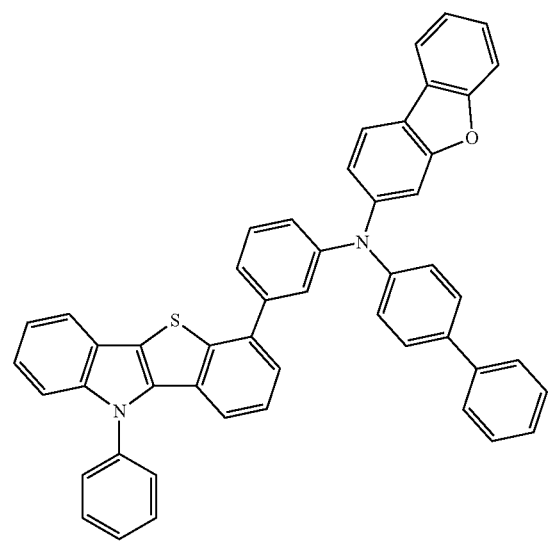
B190
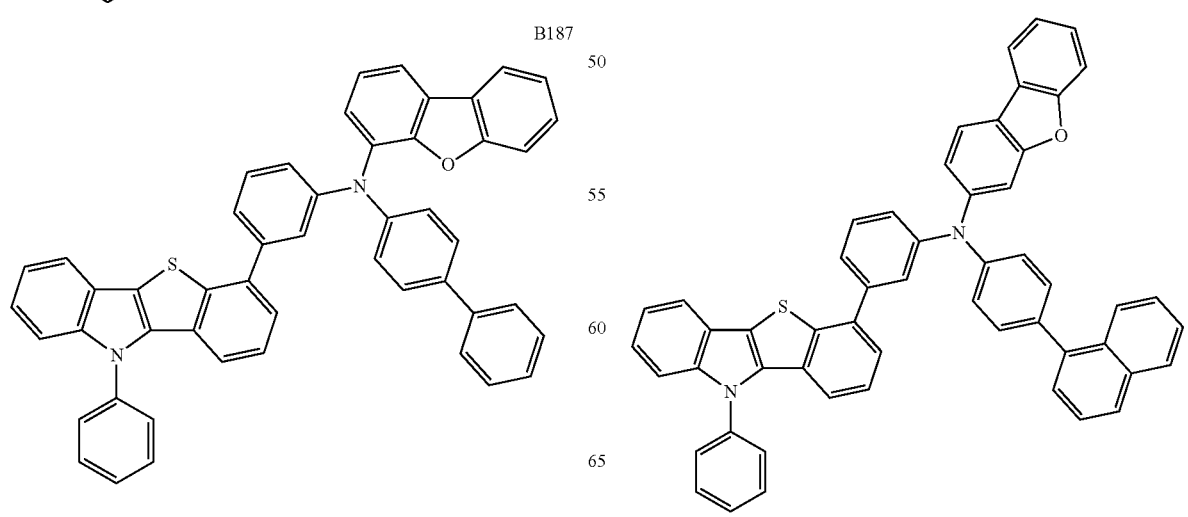

-continued
B191
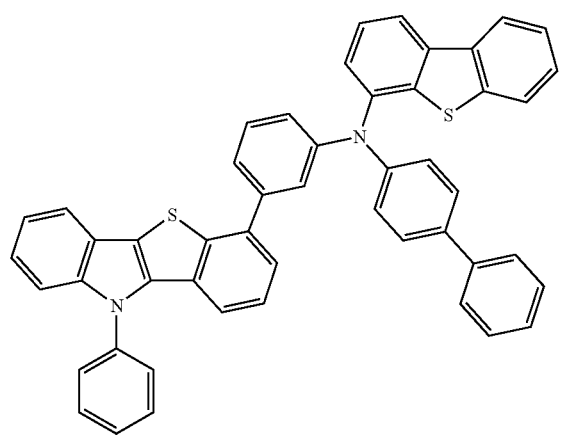
B192
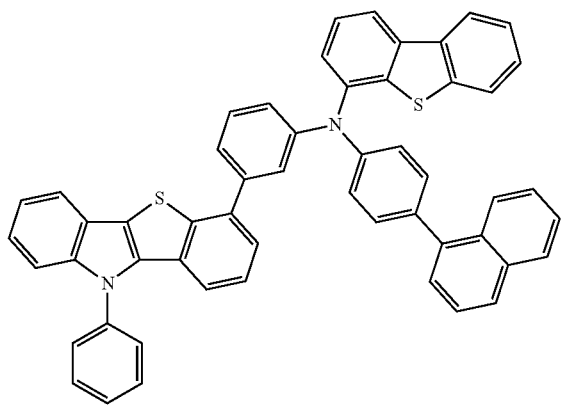
B193
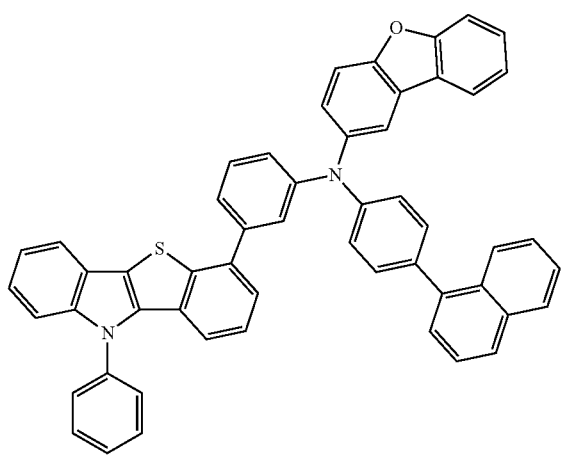
-continued
B194
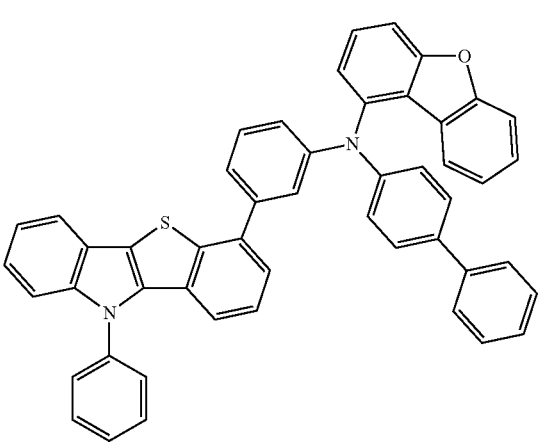
B195
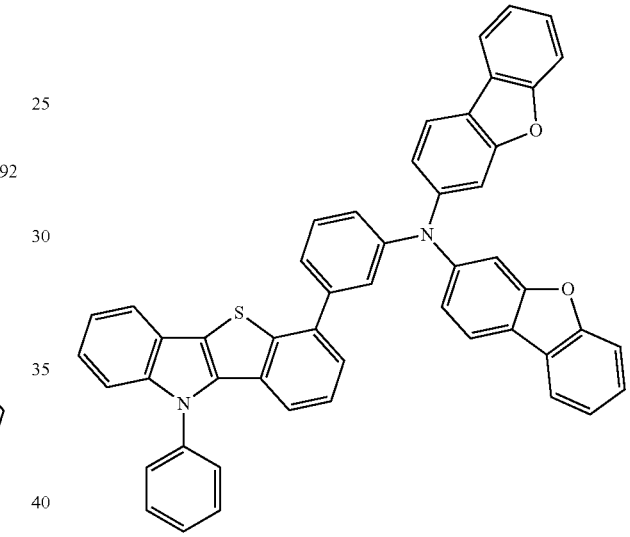
B196
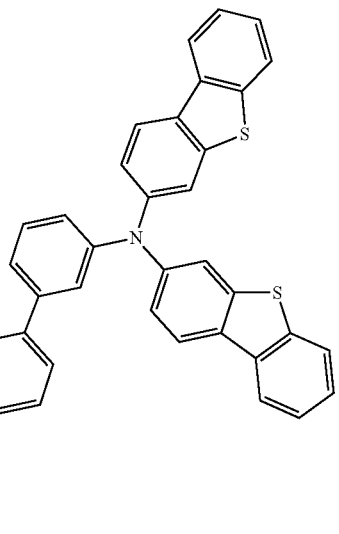

477
-continued
B197
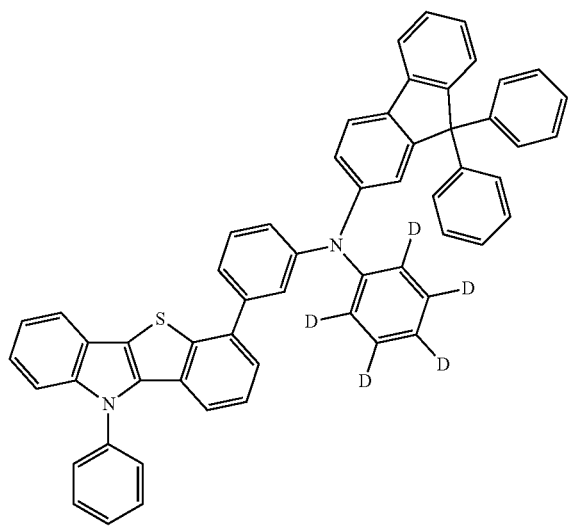
B198
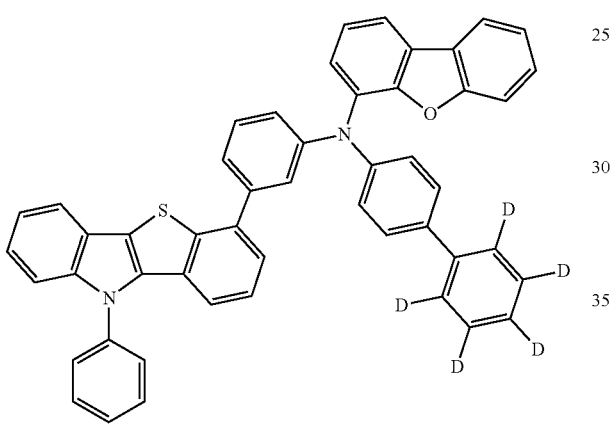
478
-continued
B200
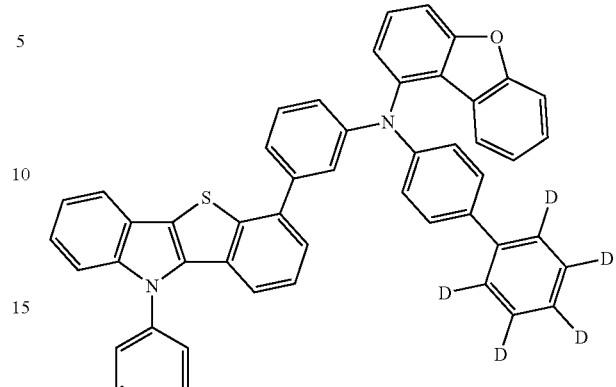
B199
B201
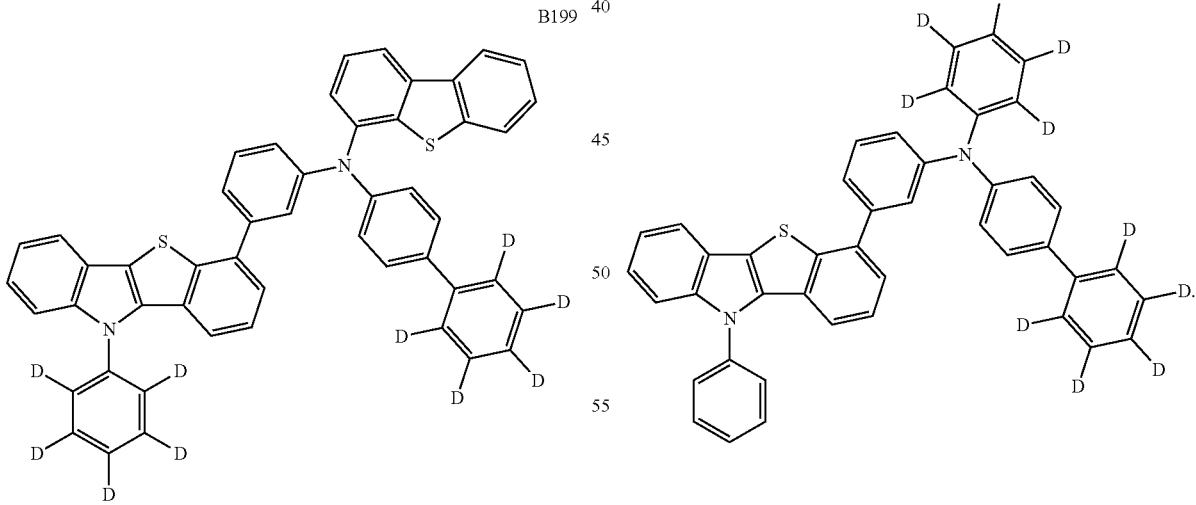
* * * * *